(12) United States Patent
Fukunaga et al.

(10) Patent No.: US 8,569,294 B2
(45) Date of Patent: Oct. 29, 2013

(54) 2-(CYCLIC AMINO)-PYRIMIDONE DERIVATIVES

(75) Inventors: Kenji Fukunaga, Kanagawa (JP); Toshiyuki Kohara, Kanagawa (JP); Kazutoshi Watanabe, Kanagawa (JP); Yoshihiro Usui, Ibaraki (JP); Fumiaki Uehara, Kanagawa (JP); Satoshi Yokoshima, Tokyo (JP); Daiki Sakai, Cambridge (GB); Shin-ichi Kusaka, Kanagawa (JP); Kazuki Nakayama, Kanagawa (JP)

(73) Assignees: Mitsubishi Tanabe Pharma Corporation, Osaka (JP); Sanofi, Paris (FR)

( * ) Notice: Subject to any disclaimer, the term of this patent is extended or adjusted under 35 U.S.C. 154(b) by 867 days.

(21) Appl. No.: 12/282,396

(22) PCT Filed: Mar. 14, 2007

(86) PCT No.: PCT/JP2007/055787
§ 371 (c)(1),
(2), (4) Date: Jan. 5, 2009

(87) PCT Pub. No.: WO2007/119463
PCT Pub. Date: Oct. 25, 2007

(65) Prior Publication Data
US 2009/0233918 A1 Sep. 17, 2009

(30) Foreign Application Priority Data
Mar. 15, 2006 (JP) ................................. 2006-110242

(51) Int. Cl.
*A61K 31/535* (2006.01)
(52) U.S. Cl.
USPC .................... 514/230.5; 514/235.8; 514/273; 544/105; 544/123; 544/320
(58) Field of Classification Search
USPC .................... 544/101, 296, 295, 320
See application file for complete search history.

(56) References Cited

U.S. PATENT DOCUMENTS

| | | | |
|---|---|---|---|
| 5,140,029 A | 8/1992 | Kennis et al. | |
| 5,256,659 A | 10/1993 | Kennis et al. | |
| 5,284,854 A | 2/1994 | Kennis et al. | |
| 6,610,698 B2 * | 8/2003 | Spohr et al. | 514/269 |
| 7,256,199 B1 | 8/2007 | Watanabe et al. | |
| 7,427,615 B2 * | 9/2008 | Uehara et al. | 514/229.5 |
| 7,504,411 B2 * | 3/2009 | Watanabe et al. | 514/273 |
| 7,572,793 B2 * | 8/2009 | Uehara et al. | 514/235.8 |
| 7,994,315 B2 * | 8/2011 | Okuyama et al. | 544/106 |
| 8,106,045 B2 * | 1/2012 | Watanabe et al. | 514/231.5 |
| 8,129,377 B2 * | 3/2012 | Watanabe et al. | 514/235.8 |
| 8,198,437 B2 * | 6/2012 | Fukunaga et al. | 544/123 |
| 8,288,383 B2 * | 10/2012 | Sakai et al. | 514/235.8 |
| 2003/0187004 A1 | 10/2003 | Almario Garcia et al. | |
| 2005/0130967 A1 | 6/2005 | Uehara et al. | |
| 2005/0130998 A1 | 6/2005 | Almario Garcia et al. | |
| 2006/0252768 A1 | 11/2006 | Watanabe et al. | |
| 2007/0142409 A1 | 6/2007 | Usui et al. | |
| 2009/0124618 A1 | 5/2009 | Watanabe et al. | |
| 2009/0239864 A1 * | 9/2009 | Watanabe et al. | 514/235.8 |
| 2010/0113775 A1 * | 5/2010 | Watanabe et al. | 544/123 |
| 2011/0251385 A1 | 10/2011 | Okuyama et al. | |

(Continued)

FOREIGN PATENT DOCUMENTS

| | | |
|---|---|---|
| EP | 0616 032 | 9/1994 |
| EP | 1 136 482 | 9/2001 |

(Continued)

OTHER PUBLICATIONS

Scarpini et al., Lancet Neurol. 2(9), 539-47 (2003).*
J.H. Poupaert, Drug Design: Basic Principles and Applications, in 2 Encyclopedia of Pharmaceutical Technology 1362-1369, 1367 (James Swarbrick ed., 3rd ed., 2007).*
B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*

(Continued)

*Primary Examiner* — James O Wilson
*Assistant Examiner* — Alexander R Pagano
(74) *Attorney, Agent, or Firm* — Greenblum & Bernstein, P.L.C.

(57) ABSTRACT

A compound represented by the formula (I), an optically active isomer thereof, or a pharmaceutical acceptable salt thereof:

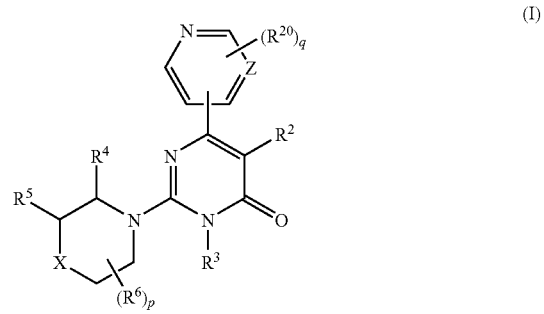

wherein $R^2$ represents a hydrogen or the like; $R^3$ represents methyl group or the like; $R^{20}$ represents a halogen atom or the like; q represents an integer of 0 to 3; Z represent nitrogen atom, CH, or the like; $R^4$ represents hydrogen or the like; $R^5$ represents hydrogen or the like; $R^6$ represents a substituted alkyloxy and the like; p represents an integer of 0 to 3; X represents bond, $CH_2$, oxygen atom, NH, or the like; any one or more of $R^5$ and $R^6$, $R^5$ and $R^4$, $R^6$ and $R^4$, X and $R^5$, X and $R^4$, X and $R^6$, and $R^6$ and $R^6$ may combine to each other to form a ring, which is used for preventive and/or therapeutic treatment of a disease caused by tau protein kinase 1 hyperactivity such as a neurodegenerative diseases (e.g. Alzheimer disease).

8 Claims, No Drawings

(56) References Cited

U.S. PATENT DOCUMENTS

| | | |
|---|---|---|
| 2011/0257392 A1 | 10/2011 | Okuyama et al. |
| 2012/0059165 A1 * | 3/2012 | Furuya et al. ............... 544/123 |
| 2012/0220591 A1 * | 8/2012 | Sakai et al. ............... 514/236.2 |

FOREIGN PATENT DOCUMENTS

| | | |
|---|---|---|
| EP | 1 136 493 | 9/2001 |
| EP | 1136482 A1 * | 9/2001 |
| EP | 1454910 A1 * | 9/2004 |
| EP | 2078717 | 7/2009 |
| JP | 49 035634 | 9/1974 |
| JP | 2002-525366 | 8/2002 |
| JP | 2003-528095 | 9/2003 |
| JP | 2006-519813 | 8/2006 |
| JP | 2006-521370 | 9/2006 |
| JP | 2007-517904 | 7/2007 |
| RU | 2028297 | 2/1995 |
| WO | 00/18758 | 4/2000 |
| WO | WO 0018758 A1 * | 4/2000 |
| WO | 01/70729 | 9/2001 |
| WO | WO 0170728 A1 * | 9/2001 |
| WO | 03/027080 | 4/2003 |
| WO | WO 03027080 A1 * | 4/2003 |
| WO | 03/037888 | 5/2003 |
| WO | 2004/055007 | 7/2004 |
| WO | 2004/078759 | 9/2004 |
| WO | WO 2004085408 A1 * | 10/2004 |
| WO | 2005/070934 | 8/2005 |
| WO | 2006/028290 | 3/2006 |
| WO | 2006/036015 | 4/2006 |
| WO | 2007/011065 | 1/2007 |
| WO | 2008/078837 | 7/2008 |

OTHER PUBLICATIONS

Masters et al., "Amyloid Plaque Core Protein in Alzheimer Disease and Down Syndrome," Proceedings of the National Academy of Sciences USA, vol. 82, pp. 4245-4249, 1985.

Wischik et al., "Isolation of a Fragment of tau derived from the Core of the paired helical Filament of Alzheimer Disease," Proceedings of the National Academy of Sciences USA, vol. 85, pp. 4506-4510, 1988.

Tomita et al., "The Presenilin 2 Mutation (N141I) linked to familial Alzheimer Disease (Volga German Families) increases the Secretion of Amyloid β Protein ending at the $42^{nd}$ (or $43^{rd}$) Residue," Proceedings of the National Academy of Sciences USA, vol. 94, pp. 2025-2030, 1987.

Siman, et al., "Proteolytic Processing of β-Amyloid Precursor by Calpain I," The Journal of Neuroscience, vol. 10, No. 7, pp. 2400-2411, 1990.

Grundke-Iqbal et al., "Abnormal Phosphorylation of the Microtubule-Associated Protein τ (tau) in Alzheimer Cytoskeletal Pathology," Proceedings of the National Academy of Sciences USA, vol. 83, pp. 4913-4917, 1986.

Ishiguro et al., "Tau Protein Kinase I converts Normal Tau Protein into A68-like Component of Paired Helical Filaments," The Journal of Biological Chemistry, vol. 267, No. 15, pp. 10897-10901, 1992.

Takashima et al., "Tau Protein Kinase I is essential for Amyloid β-Protein-Induced Neurotoxicity," Proceedings of the National Academy of Sciences USA, vol. 90, pp. 7789-7793, 1993.

U.S. Appl. No. 09/787,426 to Watanabe et al., filed Sep. 24, 1999, entitled "Pyrimidone Derivatives."

U.S. Appl. No. 10/489,606 to Uehara et al., filed Sep. 20, 2002, entitled "3-substituted-4-pyrimidone derivatives."

U.S. Appl. No. 10/489,607 to Uehara et al., filed Sep. 20, 2002, entitled "3-substituted-4-pyrimidone derivatives".

U.S. Appl. No. 10/538,766 to Usui et al., filed Dec. 12, 2003, entitled "3-substituted-4-pyrimidone derivatives."

U.S. Appl. No. 10/550,299 to Watanabe et al., filed Mar. 26, 2004, entitled "2,3,6-Trisubstituted-4-pyrimidone derivatives".

U.S. Appl. No. 11/573,476 to Fukunaga et al., filed Feb. 9, 2007, and entitled "2-Morpholino-4-Pyrimidone Compound."

U.S. Appl. No. 11/576,062 to Fukunaga et al., filed Mar. 27, 2007, and entitled "6-(Pyridinyl) -4- Pyrimidone Derivates as Tau Protein Kinase I Inhibitors."

Partial European Search Report for European Application No. 11189865.6 dated Dec. 19, 2011.

Japanese Office Action issued with respect to patent family member Japanese Application No. 2008-543334, mailed Aug. 14, 2012.

CA Registry No. 794489-55-7, indexed in Registry file on STN on Dec. 8, 2004.

CA Registry No. 794489-54-6, indexed in Registry file on STN on Dec. 8, 2004.

European Office Action issued with respect to counterpart European Application No. 07 739 230.6, dated Mar. 18, 2013.

Extended European Search Report issued with respect to related European Application No. 11189865.6, dated May 16, 2012.

European Office Action for European Appl. No. 11189865.6, dated Jul. 25, 2013.

* cited by examiner

2-(CYCLIC AMINO)-PYRIMIDONE DERIVATIVES

TECHNICAL FIELD

The present invention relates to compounds that are useful as an active ingredient of a medicament for preventive and/or therapeutic treatment of diseases mainly caused by abnormal activity of tau protein kinase 1, such as neurodegenerative diseases (e.g. Alzheimer disease).

BACKGROUND ART

Alzheimer disease is progressive senile dementia, in which marked cerebral cortical atrophy is observed due to degeneration of nerve cells and decrease of nerve cell number. Pathologically, numerous senile plaques and neurofibrillary tangles are observed in brain. The number of patients has been increased with the increment of aged population, and the disease arises a serious social problem. Although various theories have been proposed, a cause of the disease has not yet been elucidated. Early resolution of the cause has been desired.

It has been known that the degree of appearance of two characteristic pathological changes of Alzheimer disease well correlates to the degree of intellectual dysfunction. Therefore, researches have been conducted from early 1980's to reveal the cause of the disease through molecular level investigations of components of the two pathological changes. Senile plaques accumulate extracellularly, and β amyloid protein has been elucidated as their main component (abbreviated as "Aβ" hereinafter in the specification: Biochem. Biophys. Res. Commun., 120, 885 (1984); EMBO J., 4, 2757 (1985); Proc. Natl. Acad. Sci. USA, 82, 4245 (1985)). In the other pathological change, i.e., the neurofibrillary tangles, a double-helical filamentous substance called paired helical filament (abbreviated as "PHF" hereinafter in the specification) accumulate intracellularly, and tau protein, which is a kind of microtubule-associated protein specific for brain, has been revealed as its main component (Proc. Natl. Acad. Sci. USA, 85, 4506 (1988); Neuron, 1, 827 (1988)).

Furthermore, on the basis of genetic investigations, presenilins 1 and 2 were found as causative genes of familial Alzheimer disease (Nature, 375, 754 (1995); Science, 269, 973 (1995); Nature. 376, 775 (1995)), and it has been revealed that presence of mutants of presenilins 1 and 2 promotes the secretion of Aβ (Neuron, 17, 1005 (1996); Proc. Natl. Acad. Sci. USA, 94, 2025 (1997)). From these results, it is considered that, in Alzheimer disease, Aβ abnormally accumulates and agglomerates due to a certain reason, which engages with the formation of PHF to cause death of nerve cells. It is also expected that extracellular outflow of glutamic acid and activation of glutamate receptor responding to the outflow may possibly be important factors in an early process of the nerve cell death caused by ischemic cerebrovascular accidents.

It has been reported that kainic acid treatment that stimulates the AMPA receptor, one of glutamate receptor, increases mRNA of the amyloid precursor protein (abbreviated as "APP" hereinafter in the specification) as a precursor of Aβ (Society for Neuroscience Abstracts, 17, 1445 (1991)), and also promotes metabolism of APP (The Journal of Neuroscience, 10, 2400 (1990)). Therefore, it has been strongly suggested that the accumulation of Aβ is involved in cellular death due to ischemic cerebrovascular disorders. Other diseases in which abnormal accumulation and agglomeration of Aβ are observed include, for example, Down syndrome, cerebral bleeding due to solitary cerebral amyloid angiopathy, Lewy body disease and the like. Furthermore, as diseases showing neurofibrillary tangles due to the PHF accumulation, examples include progressive supranuclear palsy, subacute sclerosing panencephalitic parkinsonism, postencephalitic parkinsonism, pugilistic encephalitis, Guam parkinsonism-dementia complex, Lewy body disease and the like.

The tau protein is generally composed of a group of related proteins that forms several bands at molecular weights of 48-65 kDa in SDS-polyacrylamide gel electrophoresis, and it promotes the formation of microtubules. It has been verified that tau protein incorporated in the PHF in the brain suffering from Alzheimer disease is abnormally phosphorylated compared with usual tau protein (J. Biochem., 99, 1807 (1986); Proc. Natl. Acad. Sci. USA, 83, 4913 (1986)). An enzyme catalyzing the abnormal phosphorylation has been isolated. The protein was named as tau protein kinase 1 (abbreviated as "TPK1" hereinafter in the specification), and its physicochemical properties have been elucidated (J. Biol. Chem., 267, 10897 (1992)). Moreover, cDNA of rat TPK1 was cloned from a rat cerebral cortex cDNA library based on a partial amino acid sequence of TPK1, and its nucleotide sequence was determined and an amino acid sequence was deduced. As a result, it has been revealed that the primary structure of the rat TPK1 corresponds to that of the enzyme known as rat GSK-3 β (glycogen synthase kinase 3β, FEBS Lett., 325, 167 (1993)).

It has been reported that Aβ, the main component of senile plaques, is neurotoxic (Science, 250, 279 (1990)). However, various theories have been proposed as for the reason why Aβ causes the cell death, and any authentic theory has not yet been established. Takashima et al. observed that the cell death was caused by Aβ treatment of fetal rat hippocampus primary culture system, and then found that the TPK1 activity was increased by Aβ treatment and the cell death by Aβ was inhibited by antisense of TPK1 (Proc. Natl. Acad. Sci. USA, 90, 7789 (1993); EP616032).

In view of the foregoing, compounds which inhibit the TPK1 activity may possibly suppress the neurotoxicity of Aβ and the formation of PHF and inhibit the nerve cell death in the Alzheimer disease, thereby cease or defer the progress of the disease. The compounds may also be possibly used as a medicament for therapeutic treatment of ischemic cerebrovascular disorder, Down syndrome, cerebral amyloid angiopathy, cerebral bleeding due to Lewy body disease and the like by suppressing the cytotoxicity of Aβ. Furthermore, the compounds may possibly be used as a medicament for therapeutic treatment of neurodegenerative diseases such as progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration and frontotemporal dementia, vascular dementia, traumatic injuries, brain and spinal cord trauma, peripheral neuropathies, retinopathies and glaucoma, as well as other diseases such as non-insulin dependent diabetes, obesity, manic depressive illness, schizophrenia, alopecia, breast cancer, non-small cell lung carcinoma, thyroid cancer, T or B-cell leukemia, and several virus-induced tumors.

As structurally similar compounds to the compounds of the present invention represented by formula (I) described later, the compounds disclosed in the International Publication Nos. WO01/70729, WO03/037888 and WO03/027080 are known. However, these compounds are not enough as medicament in the pharmacokinetics and so on.

DISCLOSURE OF THE INVENTION

An object of the present invention is to provide compounds useful as an active ingredient of a medicament for preventive and/or therapeutic treatment of diseases such as Alzheimer disease. More specifically, the object is to provide novel compounds useful as an active ingredient of a medicament that enables radical prevention and/or treatment of the neurodegenerative diseases such as Alzheimer disease by inhibiting the TPK1 activity to suppress the neurotoxicity of Aβ and the formation of the PHF and by inhibiting the death of nerve cells.

In order to achieve the foregoing object, the inventors of the present invention conducted screenings of various compounds having inhibitory activity against the phosphorylation of TPK1. As a result, they found that compounds represented by the following formula (I) had the desired activity and were useful as an active ingredient of a medicament for preventive and/or therapeutic treatment of the aforementioned diseases. The present invention was achieved on the basis of these findings.

The present invention thus provides;

1. A compound represented by the formula (I), an optically active isomer thereof, or a pharmaceutically acceptable salt thereof:

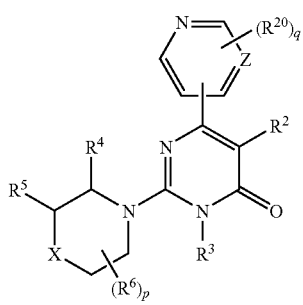

wherein each symbol is defined as below:

$R^4$ may be the same or different and represents cyano group or a group represented by the following formula (II):

$$A^{14}\text{-}A^{13}\text{-}A^{12}\text{-} \quad (II)$$

wherein $A^{14}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, a heterocyclic group which may be substituted, $A^{13}$ represents bond, oxygen atom or a group represented by the following formula (II-a):

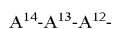

wherein $A^{15}$ represents bond, C=O, C=S or S(=O)$_2$,
$A^{16}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ group cycloalkenyl which may be substituted, a $C_6$-$C_{10}$ aryl group which may be substituted, or a heterocyclic group which may be substituted, $A^{12}$ represents bond, a $C_1$-$C_3$ methylene group, a sulfur atom, C=O, C=S or S(=O)$_2$, and $A^{14}$ and $A^{13}$ may combine to each other to form a 5 to 7 membered heterocyclic ring;

X represents bond, oxygen atom, sulfur atom, S=O, S(=O)$_2$, CH$_2$, CHR$^6$, CR$^6{}_2$, or a group represented by the following formula (III):

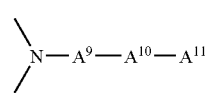

wherein $A^9$ represents bond, C=O, C=S, or S(=O)$_2$,
$A^{10}$ represents bond, oxygen atom or a group represented by the following formula (III-a):

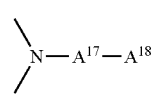

wherein $A^{17}$ represents bond, C=O, C=S, or S(=O)$_2$,
$A^{18}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ group cycloalkenyl which may be substituted, a $C_6$-$C_{10}$ aryl group which may be substituted, or a heterocyclic group which may be substituted, $A^{11}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ group cycloalkenyl which may be substituted, or a group represented by following formula (III-b):

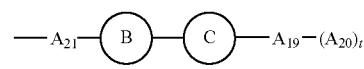

$A_{20}$ may be the same or different and represents a hydrogen atom, a halogen atom, nitro group, cyano group, or a group represented by the following formula (III-c):

$$C^{34}\text{—}C^{33}\text{—}C^{32}\text{—}C^{31}\text{—} \quad (III\text{-}c)$$

wherein $C^{34}$ represents hydrogen atom (except when all of $C^{33}$, $C^{32}$, and $C^{31}$ represent bond), a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted,
a $C_6$-$C_{10}$ aryl group which may be substituted, a heterocyclic group which may be substituted, $C^{33}$ represents bond, oxygen atom, sulfur atom or a group represented by the following formula (III-d):

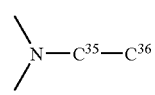

wherein $C^{35}$ represents bond, C=O, C=S, or S(=O)$_2$,
$C^{36}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted,
$C^{32}$ represents bond, C=O, C=S, or S(=O)$_2$,
$C^{31}$ represents bond, a $C_1$-$C_3$ alkyl group, oxygen atom, sulfur atom or a group represented by the following formula (III-e):

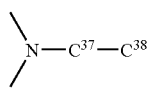
(III-e)

wherein $C^{37}$ represents bond, C=O, C=S, or S(=O)$_2$,
$C^{38}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted,
and $C^{34}$ and $C^{33}$, $C^{34}$ and $C^{31}$, $C^{33}$ and $C^{31}$ may combine to each other to form 5 to 7 membered heterocyclic ring,
t represents an integer of 1 to 5,
$A_{19}$ represents bond, a $C_1$-$C_6$ alkylene group,
B represents a $C_6$-$C_{10}$ aryl group, or a heterocyclic group,
C represents bond, a $C_6$-$C_{10}$ aryl group, or a heterocyclic group,
$A_{21}$ represents bond or a $C_1$-$C_6$ alkyl group;
$R^5$ may be the same or different and represents a hydrogen atom, a $C_1$-$C_6$ alkyl group which may be substituted, or a group represented by the following formula (IV):

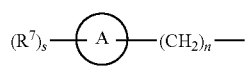
(IV)

wherein n represents 0 or integer of 1 to 3,
A represents a $C_6$-$C_{10}$ aryl group or a heterocyclic group,
$R^7$ may be the same or different and represents a halogen atom, nitro group, cyano group, or a group represented by the following formula (IV-a):

(IV-a)

wherein $C^4$ represents hydrogen atom (except when all of $C^3$, $C^2$, and $C^1$ represent bond), a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, a heterocyclic group which may be substituted,
$C^3$ represents bond, oxygen atom, sulfur atom or a group represented by the following formula (IV-b):

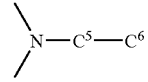
(IV-b)

wherein $C^5$ represents bond, C=O, C=S, or S(=O)$_2$,
$C^6$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted,
$C^2$ represents bond, C=O, C=S, or S(=O)$_2$,
$C^1$ represents bond, a $C_1$-$C_3$ alkyl group, oxygen atom, sulfur atom or a group represented by the following formula (IV-c):

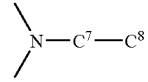
(IV-c)

wherein $C^7$ represents bond, C=O, C=S, or S(=O)$_2$,
$C^8$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted,
and $C^4$ and $C^3$, $C^4$ and $C^1$, $C^3$ and $C^1$ may combine to each other to form 5 to 7 membered heterocyclic ring,
s represents 0 or an integer of 1 to 5,
$R^6$ may be the same or different and represents a halogen atom, nitro group, cyano group, or a group represented by the following formula (V):

(V)

wherein $B^{14}$ represents hydrogen atom (except when all of $B^{13}$, $B^{12}$, $B^{11}$ represent bond), a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, a heterocyclic group which may be substituted,
$B^{13}$ represents bond, oxygen atom, sulfur atom or a group represented by the following formula (V-a):

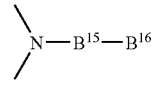
(V-a)

wherein $B^{15}$ represents bond, C=O, C=S or S(=O)$_2$,
$B^{16}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted, $B^{12}$ represents bond, C=O, C=S, or S(=O)$_2$, $B^{11}$ represents bond, a $C_1$-$C_3$ methylene group, oxygen atom, sulfur atom or a group represented by the following formula (V-b):

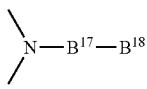
(V-b)

wherein $B^{17}$ represents bond, C=O, C=S or S(=O)$_2$;

$B^{18}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted;

and $B^{14}$ and $B^{13}$, $B^{14}$ and $B^{11}$, $B^{13}$ and $B^{11}$ may combine to each other to form a 5 to 7 membered heterocyclic ring, or any two $R^6$, or $R^5$ and $R^6$ may combine to each other to form carbonyl group together with the carbon atom which the two $R^6$ or $R^5$ and $R^6$ bind to;

p represents an integer of 0 to 6;

Z represents nitrogen atom, C—H or C—$R^{20}$;

$R^{20}$ may be the same or different and represents a halogen atom, nitro group, cyano group, or a group represented by the following formula (VI):

$$D^4\text{-}D^3\text{-}D^2\text{-}D^1\text{-} \quad (VI)$$

wherein $D^4$ represents hydrogen atom (except when all of $D^3$, $D^2$, and $D^1$ represent bond), a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, a heterocyclic group which may be substituted, $D^3$ represents bond, oxygen atom, sulfur atom or a group represented by the following formula (VI-a):

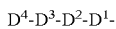
(VI-a)

wherein $D^5$ represents bond, C=O, C=S or S(=O)$_2$, $D^6$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted, $D^2$ represents bond, C=O, C=S or S(=O)$_2$, $D^1$ represents bond, a $C_1$-$C_3$ methylene group, oxygen atom, sulfur atom, or a group represented by the following formula (VI-b):

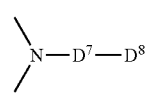
(VI-b)

wherein $D^7$ represents bond, C=O, C=S or S(=O)$_2$, $D^8$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted, and $D^4$ and $D^3$, $D^4$ and $D^1$, $D^3$ and $D^1$ may combine to each other to form 5 to 7 membered heterocyclic ring, q represents 0 or an integer of 1 to 3;

$R^2$ represents hydrogen atom, a halogen atom or a $C_1$-$C_6$ alkyl group which may be substituted;

$R^3$ represents a hydrogen atom, a $C_1$-$C_{12}$ alkyl group which may be substituted, a $C_2$-$C_{12}$ alkenyl group which may be substituted, a $C_2$-$C_{12}$ alkynyl group which may be substituted, a $C_3$-$C_{12}$ cycloalkyl group which may be substituted, a $C_3$-$C_{12}$ cycloalkenyl group which may be substituted, a $C_6$-$C_{10}$ aryl group which may be substituted, or a heterocyclic group which may be substituted;

any one or more of $R^5$ and $R^6$, $R^5$ and $R^4$, $R^6$ and $R^4$, X and $R^5$, X and $R^4$, X and $R^6$, and $R^6$ and $R^6$ may combine to each other to form a fused or spiro, carbocyclic or heterocyclic ring, together with the ring which contains X, and $R^5$, $R^4$ and $R^6$ bind to;

and each symbol satisfies the following provisos (1) to (5):

(1) when $R^4$ represents a hydrogen atom, X represents bond, or at least one of $R^5$ and $R^6$, $R^5$ and $R^4$, $R^6$ and $R^4$, X and $R^5$, X and $R^4$, X and $R^6$, and $R^6$ and $R^6$ combine to each other to form a fused or spiro, carbocyclic or heterocyclic ring, together with the ring which contains X, and $R^5$, $R^4$ and $R^6$ bind to;

(2) when X represents a group represented by the formula (III), $R^4$ and $R^6$ do not combine to each other;

(3) when Z represents C—$R^{20}$ and $R^3$ does not represents a hydrogen atom, or when Z represents C—H or C—$R^{20}$, q represent an integer of 1 to 3, and $R^3$ does not represent a hydrogen atom, X represents bond, or at least one of $R^5$ and $R^6$, X and $R^6$, and $R^6$ and $R^6$ combine to each other to form a fused or spiro, carbocyclic of heterocyclic ring, together with the ring which contains X, and $R^5$, $R^4$ $R^6$ bind to;

(4) when q represents 0, X represents an oxygen atom, and $R^3$ does not represents a hydrogen atom, a spiro ring does not attach the carbon atom adjacent to X; and (5) when q represents 0 and X represents $CH_2$, $CHR^6$, $CR^6_2$ or formula (III), $R^4$ represents a hydrogen atom and at least one of $R^5$ and $R^6$, X and $R^5$, X and $R^6$, and $R^6$ and $R^6$ combine to each other to form a fused, carbocyclic or heterocyclic ring, together with the ring which contains X, and $R^5$, $R^4$ and $R^6$ bind to.

2. A compound represented by the formula (I), an optically active isomer thereof, or a pharmaceutically acceptable salt thereof:

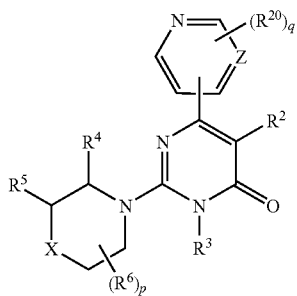
(I)

wherein each symbol is defined as below:

$R^4$ may be the same or different and represents cyano group or a group represented by the following formula (II):

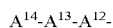
(I)

wherein $A^{14}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, a heterocyclic group which may be substituted, $A^{13}$ represents bond, oxygen atom or a group represented by the following formula (II-a):

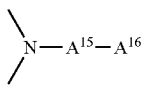
(II-a)

wherein $A^{15}$ represents bond, C=O, C=S or S(=O)$_2$, $A^{16}$ represents a hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted, $A^{12}$ represents bond, a $C_1$-$C_3$ methylene group, a sulfur atom, C=O, C=S or S(=O)$_2$, and $A^{14}$ and $A^{13}$ may combine to each other to form a 5 to 7 membered heterocyclic ring;

X represents a bond, an oxygen atom, sulfur atom, S=O, S(=O)$_2$, CH$_2$, CHR$^6$, CR$^6_2$, or a group represented by the following formula (III):

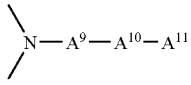
(III)

wherein $A^9$ represents bond, C=O, C=S, or S(=O)$_2$, $A^{10}$ represents bond, oxygen atom or a group represented by the following formula (III-a):

(III-a)

wherein $A^{17}$ represents bond, C=O, C=S, or S(=O)$_2$, $A^{18}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ group cycloalkenyl which may be substituted, a $C_6$-$C_{10}$ aryl group which may be substituted, or a heterocyclic group which may be substituted, $A^{11}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ group cycloalkenyl which may be substituted, a $C_6$-$C_{10}$ aryl group which may be substituted, or a heterocyclic group which may be substituted;

$R^5$ may be the same or different and represents a hydrogen atom or a group represented by the following formula (IV):

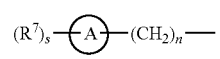
(IV)

wherein n represents 0 or integer of 1 to 3,

A represents a $C_6$-$C_{10}$ aryl group or a heterocyclic group, $R^7$ may be the same or different and represents a halogen atom, nitro group, cyano group, or a group represented by the following formula (IV-a):

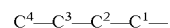
(IV-a)

wherein $C^4$ represents hydrogen atom (except when all of $C^3$, $C^2$, and $C^1$ represent bond), a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, a heterocyclic group which may be substituted, $C^3$ represents bond, oxygen atom, sulfur atom or a group represented by the following formula (IV-b):

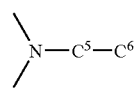
(IV-b)

wherein $C^5$ represents bond, C=O, C=S or S(=O)$_2$, $C^6$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted, $C^2$ represents bond, C=O, C=S, or S(=O)$_2$, $C^1$ represents bond, a $C_1$-$C_3$ alkyl group, oxygen atom, sulfur atom or a group represented by the following formula (IV-c):

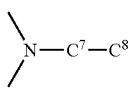
(IV-c)

wherein $C^7$ represents bond, C=O, C=S, or S(=O)$_2$,
$C^8$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted,
and $C^4$ and $C^3$, $C^4$ and $C^1$, $C^3$ and $C^1$ may combine to each other to form 5 to 7 membered heterocyclic ring,
s represents 0 or an integer of 1 to 5;
$R^6$ may be the same or different and represents a halogen atom, nitro group, cyano group, or a group represented by the following formula (V):

(V)

wherein $B^{14}$ represents hydrogen atom (except when all of $B^{13}$, $B^{12}$, and $B^{11}$ represent bond), a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, a heterocyclic group which may be substituted,
$B^{13}$ represents bond, oxygen atom, sulfur atom or a group represented by the following formula (V-a):

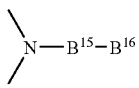
(V-a)

wherein $B^{15}$ represents bond, C=O, C=S or S(=O)$_2$,
$B^{16}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted,
or a heterocyclic group which may be substituted,
$B^{12}$ represents bond, C=O, C=S, or S(=O)$_2$,
$B^{11}$ represents bond, a $C_1$-$C_3$ methylene group, oxygen atom, sulfur atom or a group represented by the following formula (V-b):

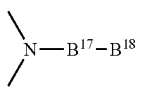
(V-b)

wherein $B^{17}$ represents bond, C=O, C=S or S(=O)$_2$;
$B^{18}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted;

and $B^{14}$ and $B^{13}$, $B^{14}$ and $B^{11}$, $B^{13}$ and $B^{11}$ may combine to each other to form a 5 to 7 membered heterocyclic ring,
or two of $R^6$ may combine together to form carbonyl group;
p represents an integer of 0 to 6;
Z represents nitrogen atom, C—H or C—$R^{20}$;
$R^{20}$ may be the same or different and represents a halogen atom, nitro group, cyano group, or a group represented by the following formula (VI):

(VI)

wherein $D^4$ represents hydrogen atom (except when all of $D^3$, $D^2$, and $D^1$ represent bond), a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, a heterocyclic group which may be substituted,
$D^3$ represents bond, oxygen atom, sulfur atom or a group represented by the following formula (VI-a):

(VI-a)

wherein $D^5$ represents bond, C=O, C=S or S(=O)$_2$,
$D^6$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted,
$D^2$ represents bond, C=O, C=S or S(=O)$_2$,
$D^1$ represents bond, a $C_1$-$C_3$ methylene group, oxygen atom, sulfur atom, or a group represented by the following formula (VI-b):

(VI-b)

wherein $D^7$ represents bond, C=O, C=S or S(=O)$_2$,
$D^8$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted,
and $D^4$ and $D^3$, $D^4$ and $D^1$, $D^3$ and $D^1$ may combine to each other to form 5 to 7 membered heterocyclic ring,
q represents 0 or an integer of 1 to 3;
$R^2$ represents hydrogen atom, a halogen atom or a $C_1$-$C_6$ alkyl group which may be substituted;
$R^3$ represents a hydrogen atom, a $C_1$-$C_{12}$ alkyl group which may be substituted, a $C_2$-$C_{12}$ alkenyl group which may be substituted, a $C_2$-$C_{12}$ alkynyl group which may be substituted, a $C_3$-$C_{12}$ cycloalkyl group which may be substituted, a $C_3$-$C_{12}$ cycloalkenyl group which may be substituted, a $C_6$-$C_{10}$ aryl group which may be substituted, or a heterocyclic group which may be substituted;

any one or more of $R^5$ and $R^6$, $R^5$ and $R^4$, $R^6$ and $R^4$, X and $R^5$, X and $R^4$, X and $R^6$, and $R^6$ and $R^6$ may combine to each other to form a fused or spiro, carbocyclic or heterocyclic ring, together with the ring which contains X, and $R^5$, $R^4$ and $R^6$ bind to;

and each symbol satisfies the following provisos (1) to (5):

(1) when $R^4$ represents a hydrogen atom, X represents bond, or at least one of $R^5$ and $R^6$, $R^5$ and $R^4$, $R^6$ and $R^4$, X and $R^5$, X and $R^4$, X and $R^6$, and $R^6$ and $R^6$ combine to each other to form a fused or spiro, carbocyclic or heterocyclic ring, together with the ring which contains X, and $R^5$, $R^4$ and $R^6$ bind to;

(2) when X represents a group represented by the formula (III), $R^4$ and $R^6$ do not combine to each other;

(3) when Z represents C—$R^{20}$ and $R^3$ does not represents a hydrogen atom, or when Z represents C—H or C—$R^{20}$, q represent an integer of 1 to 3, and $R^3$ does not represent a hydrogen atom, X represents bond, or at least one of $R^5$ and $R^6$, X and $R^6$, and $R^6$ and $R^6$ combine to each other to form a fused or spiro, carbocyclic of heterocyclic ring, together with the ring which contains X, and $R^5$, $R^4$ and $R^6$ bind to;

(4) when q represents 0, X represents an oxygen atom, and $R^3$ does not represents a hydrogen atom, a spiro ring does not attach the carbon atom adjacent to X; and (5) when q represents 0 and X represents $CH_2$, $CHR^6$, $CR^6_2$ or formula (III), $R^4$ represents a hydrogen atom and at least one of $R^5$ and $R^6$, X and $R^5$, X and $R^6$, and $R^6$ and $R^6$ combine to each other to form a fused, carbocyclic or heterocyclic ring, together with the ring which contains X, and $R^5$, $R^4$ and $R^6$ bind to.

3. The compound, an optically active isomer thereof, or a pharmaceutical acceptable salt thereof according to the above 2, wherein the formula (VI), (V), and (IV-a) each independently represents a group represented by the following formula (IIa):

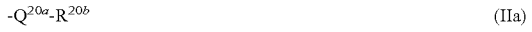

$R^{20b}$ represents a hydrogen atom (except when $Q^{20a}$ represents a bond), a $C_1$-$C_{12}$ alky group, a $C_2$-$C_{12}$ alkenyl group, a $C_2$-$C_{12}$ alkynyl group, a $C_3$-$C_{12}$ cycloalkyl group, a $C_3$-$C_{12}$ cycloalkenyl group, a $C_1$-$C_{12}$ alkyl-$C_3$-$C_{12}$ cycloalkyl group, a $C_1$-$C_{12}$ alkyl-$C_3$-$C_{12}$ cycloalkenyl group, a $C_1$-$C_{12}$ alkyl-$C_6$-$C_{10}$ aryl group, a $C_1$-$C_{12}$ alkyl-heterocyclic group, a $C_3$-$C_{12}$ cycloalkyl-$C_1$-$C_{12}$ alkyl group, a $C_3$-$C_{12}$ cycloalkyl-$C_3$-$C_{12}$ cycloalkyl group, a $C_3$-$C_{12}$ cycloalkyl-$C_6$-$C_{10}$ aryl group, a $C_3$-$C_{12}$ cycloalkyl-heterocyclic group, a $C_6$-$C_{10}$ aryl-$C_1$-$C_{12}$ alkyl group, a $C_6$-$C_{10}$ aryl-$C_3$-$C_{12}$ cycloalkyl group, a $C_6$-$C_{10}$ aryl-$C_6$-$C_{10}$ aryl group, a $C_6$-$C_{10}$ aryl-heterocyclic group, a —$C_1$-$C_{12}$ alkyl group substituted with a heterocyclic group, a $C_3$-$C_{12}$ cycloalkyl group substituted with a heterocyclic group, a $C_6$-$C_{10}$ aryl group substituted with a heterocyclic group or a heterocyclic group substituted with a heterocyclic group, and each of said groups may be substituted with a halogen atom, cyano group, nitro group, hydroxyl group, a $C_1$-$C_{12}$ alkyloxy, a $C_6$-$C_{10}$ aryloxy, amino group, a $C_1$-$C_{12}$ alkylamino group, a $C_3$-$C_{12}$ cycloalkylamino group, a di($C_1$-$C_{12}$ alkyl) amino group, or a heterocyclic group;

$Q^{20a}$ represents a bond, an oxygen atom, a sulfur atom, N—$R^{20b}$, C=O, $SO_2$, O—C(=O), C(=O)—O, C(=O)—N($R^{20b}$), N($R^{20b}$)—C(=O), N($R^{20b}$)—$SO_2$, $SO_2$—N($R^{20b}$), O—C(=O)—N($R^{20b}$), N($R^{20b}$)—C(=O)—O, N($R^{20b}$)—C(=O)—N($R^{20b}$);

the formula (II) represents a group represented by the following formula (Va):


wherein $Q^{4a}$ represents bond, oxygen atom, sulfur atom, N—$R^{20b}$, C=O, $SO_2$, O—C(=O), N($R^{20b}$)—C(=O), or N($R^{20b}$)—$SO_2$;

X is bond, oxygen atom, sulfur atom, —S(=O)$_2$—, —$CH_2$—. —$CHR^6$—, —C($R^6$)$_2$—, —NH—, or —$NR^4$— (wherein $R^4$ is not cyano group);

n in the formula (IV) is 0 or 1

A in the formula (IV) is phenyl group, naphthyl group, a heteroaryl group;

and when any one or more of $R^5$ and $R^6$, $R^5$ and $R^4$, $R^6$ and $R^4$, X and $R^5$, X and $R^4$, X and $R^6$, and $R^6$ and $R^6$ combine to each other to form a fused or spiro, carbocyclic or heterocyclic ring, together with the ring which contains X, and $R^5$, $R^4$ and $R^6$ bind to, the one or more of $R^5$ and $R^6$, $R^5$ and $R^4$, $R^6$ and $R^4$, X and $R^5$, X and $R^4$, X and $R^6$, and $R^6$ and $R^6$ are a part of an optionally substituted 5 to 7 membered ring optionally containing 1 or 2 hetero atoms selected from the group consisting of nitrogen atoms, oxygen atoms and sulfur atoms, and said 5 to 7 membered ring may be substituted and/or be condensed with a $C_6$-$C_{10}$ aryl group which may be substituted or a heterocyclic group which may be substituted.

4. The compound, an optically active isomer thereof, or a pharmaceutical acceptable salt thereof according to the above 2 or 3, wherein $R^2$ is hydrogen atom.

5. The compound, an optically active isomer thereof, or a pharmaceutical acceptable salt thereof according to any one of the above 2 to 4, wherein, $R^3$ is hydrogen atom, or a $C_1$-$C_{12}$ alkyl group which may be substituted.

6. The compound, an optically active isomer thereof, or a pharmaceutical acceptable salt thereof according to any one of the above 2 to 4, wherein $R^3$ is methyl group.

7. The compound, an optically active isomer thereof, or a pharmaceutical acceptable salt thereof according to any one of the above 2 to 6, wherein X is bond.

8. The compound, an optically active isomer thereof, or a pharmaceutical acceptable salt thereof according to the above 7, wherein $R^4$ is hydrogen atom, $R^5$ is hydrogen atom, p is 1, and $R^6$ binds to the carbon not adjacent to the nitrogen atom.

9. The compound, an optically active isomer thereof, or a pharmaceutical acceptable salt thereof according to the above 7, wherein $R^4$ is hydrogen atom, p is 1, $R^6$ binds to the carbon adjacent via X to the carbon which $R^5$ binds to, and $R^5$ and $R^6$ combine together to form a pyrrolidine ring which may be substituted or chroman ring together with the two carbon atoms which have X as bond.

10. The compound, an optically active isomer thereof, or a pharmaceutical acceptable salt thereof according to the above 7, wherein $R^4$ is not hydrogen atom, $R^5$ is hydrogen atom, and p is 0, 11. The compound, an optically active isomer thereof, or a pharmaceutical acceptable salt thereof according to any one of the above 2 to 6, wherein, X is oxygen atom, $CH_2$, or a group represented by the formula (III) wherein $A^9$ represents bond, $A^{10}$ represents bond and $A^{11}$ represents hydrogen atom or a $C_1$-$C_6$ alkyl group which may be substituted.

12. The compound, an optically active isomer thereof, or a pharmaceutical acceptable salt thereof according to the above 11, wherein $R^4$ is not hydrogen atom, $R^5$ is hydrogen atom, and p is 0, 13. The compound, an optically active isomer thereof, or a pharmaceutical acceptable salt thereof according to the above 12, wherein $R^4$ is phenyl group, phenylmethyl group, an unsubstituted $C_1$-$C_6$ alkyl group, or a $C_1$-$C_6$ alkyloxycarbonyl group ($A^{14}$ is a $C_1$-$C_6$ alkyl group, $A^3$ is oxygen atom, and $A^{12}$ is C=O).

14. The compound, an optically active isomer thereof, or a pharmaceutical acceptable salt thereof according to the above 11, wherein p is 0, and $R^4$ and $R^5$ combine together to form a 1,2,3,4-tetrahydronaphthalene which may be substituted, a chroman ring which may be substituted, or a cyclohexane ring which may be substituted, together with the two carbon atoms to which $R^4$ and $R^5$ bind to.

15. The compound, an optically active isomer thereof, or a pharmaceutical acceptable salt thereof according to the above 11, wherein p is 1, and $R^4$ and $R^6$ combine together to form dimethylene group.

16. The compound, an optically active isomer thereof, or a pharmaceutical acceptable salt thereof according to any one of the above 2 to 6, wherein X and $R^5$ combine together to form a cyclohexane ring which may be substituted, a pyrrolidine ring which may be substituted, or a 1,2,3,4-tetrahydroisoquinoline ring which may be substituted, together with the carbon atom which $R^5$ binds to.

17. The compound, an optically active isomer thereof, or a pharmaceutical acceptable salt thereof according to the above 16, wherein $R^4$ is hydrogen atom, 18. The compound, an optically active isomer thereof, or a pharmaceutical acceptable salt thereof according to the above 16 or 17, wherein p is 0, 19. The compound, an optically active isomer thereof, or a pharmaceutical acceptable salt thereof according to the above 16, wherein p is 1, and $R^4$ and $R^6$ combine to form dimethylene group.

20. A compound according to the above 2 selected from the group consisting of:
6-(3-Fluoro-pyridin-4-yl)-2-[5-(3-methoxy-phenyl)-(3aRS, 6aSR)-cis-hexahydro-pyrrolo[3,4-c]pyrrol-2-yl]-3-methyl-3H-pyrimidin-4-one;
2-[5-(2-Methoxy-phenyl)-(3aRS,6aSR)-cis-hexahydro-pyrrolo[3,4-c]pyrrol-2-yl]-3-methyl-6-pyridin-4-yl-3H-pyrimidin-4-one;
2-[5-(2-Methoxy-phenyl)-(3aRS,6aSR)-cis-hexahydro-pyrrolo[3,4-c]pyrrol-2-yl]-1-methyl-1H-[4,4']bipyrimidinyl-6-one;
6-(3-Fluoro-pyridin-4-yl)-2-[5-(2-methoxy-phenyl)-(3aRS, 6aSR)-cis-hexahydro-pyrrolo[3,4-c]pyrrol-2-yl]-3-methyl-3H-pyrimidin-4-one;
3-Methyl-6-pyridin-4-yl-2-((3aRS,9bRS)-cis-1,3a,4,9b-tetrahydro-3H-5-oxa-2-aza-cyclopenta[a]naphthalen-2-yl)-3H-pyrimidin-4-one;
6-(3-Fluoro-pyridin-4-yl)-3-methyl-2-((3aRS,9bRS)-cis-1, 3a,4,9b-tetrahydro-3H-5-oxa-2-aza-cyclopenta[a]naphthalen-2-yl)-3H-pyrimidin-4-one;
2-((3S)-3-Benzylamino-pyrrolidin-1-yl)-3-methyl-6-pyridin-4-yl-3H-pyrimidin-4-one;
2-((3S)-3-Benzylamino-pyrrolidin-1-yl)-1-methyl-1H-[4,4'] bipyrimidinyl-6-one;
2-((3S)-3-Benzylamino-pyrrolidin-1-yl)-6-(3-fluoro-pyridin-4-yl)-3-methyl-3H-pyrimidin-4-one;
2-((3S)-3-Amino-pyrrolidin-1-yl)-1-methyl-1H-[4,4']bipyrimidinyl-6-one;
N-[1-(1-Methyl-6-oxo-1,6-dihydro-[4,4']bipyrimidinyl-2-yl)-pyrrolidin-(3S)-3-yl]-benzamide;
2-[(3S)-3-(4-Fluoro-phenylamino)-pyrrolidin-1-yl]-1-methyl-1H-[4,4']bipyrimidinyl-6-one;
2-((3R)-3-Benzylamino-pyrrolidin-1-yl)-6-(3-fluoro-pyridin-4-yl)-3-methyl-3H-pyrimidin-4-one;
2-((3R)-3-Benzylamino-pyrrolidin-1-yl)-3-methyl-6-pyridin-4-yl-3H-pyrimidin-4-one;
2-((3R)-3-Benzylamino-pyrrolidin-1-yl)-1-methyl-1H-[4, 4']bipyrimidinyl-6-one;
2-((3R)-3-Amino-pyrrolidin-1-yl)-6-(3-fluoro-pyridin-4-yl)-3-methyl-3H-pyrimidin-4-one;
2-((3R)-3-Amino-pyrrolidin-1-yl)-1-methyl-1H-[4,4']bipyrimidinyl-6-one;
2-[(3R)-3-(4-Fluoro-phenylamino)-pyrrolidin-1-yl]-1-methyl-1H-[4,4']bipyrimidinyl-6-one;
2-[(3R)-3-(4-Fluoro-phenylamino)-pyrrolidin-1-yl]-3-methyl-6-pyridin-4-yl-3H-pyrimidin-4-one;
2-((3R)-3-Amino-pyrrolidin-1-yl)-3-methyl-6-pyridin-4-yl-3H-pyrimidin-4-one;
2-[(3R)-3-(2-Fluoro-phenylamino)-pyrrolidin-1-yl]-3-methyl-6-pyridin-4-yl-3H-pyrimidin-4-one,
2-[3-((3R)-3-Fluoro-phenylamino)-pyrrolidin-1-yl]-3-methyl-6-pyridin-4-yl-3H-pyrimidin-4-one;
2-[(3R)-3-(2-Methoxy-phenylamino)-pyrrolidin-1-yl]-3-methyl-6-pyridin-4-yl-3H-pyrimidin-4-one;
2-[(3R)-3-(3-Methoxy-phenylamino)-pyrrolidin-1-yl]-3-methyl-6-pyridin-4-yl-3H-pyrimidin-4-one;
3-Methyl-2-(2-methyl-pyrrolidin-1-yl)-6-pyridin-4-yl-3H-pyrimidin-4-one;
1-Methyl-2-(2-methyl-pyrrolidin-1-yl)-1H-[4,4']bipyrimidinyl-6-one;
6-(3-Fluoro-pyridin-4-yl)-3-methyl-2-(2-methyl-pyrrolidin-1-yl)-3H-pyrimidin-4-one;
2-[(3R)-3-(2-Fluoro-phenylamino)-pyrrolidin-1-yl]-1-methyl-1H-[4,4']bipyrimidinyl-6-one;
2-[(3R)-3-(2-Methoxy-phenylamino)-pyrrolidin-1-yl]-1-methyl-1H-[4,4']bipyrimidinyl-6-one;
2-[(3R)-3-(3-Methoxy-phenylamino)-pyrrolidin-1-yl]-1-methyl-1H-[4,4']bipyrimidinyl-6-one;
2-[(3R)-3-(4-Methoxy-phenylamino)-pyrrolidin-1-yl]-1-methyl-1H-[4,4']bipyrimidinyl-6-one;
3-Methyl-2-((3R)-3-phenylamino-pyrrolidin-1-yl)-6-pyridin-4-yl-3H-pyrimidin-4-one;
1-Methyl-2-((3R)-3-phenylamino-pyrrolidin-1-yl)-1H-[4,4'] bipyrimidinyl-6-one; and
6-(3-Fluoro-pyridin-4-yl)-2-[(3R)-3-(2-methoxy-phenylamino)-pyrrolidin-1-yl]-3-methyl-3H-pyrimidin-4-one,
an optically active isomer thereof, or a pharmaceutically acceptable salt thereof.

21. A compound according to the above 2 selected from the group consisting of:
2-((3S)-3-Benzyl-morpholin-4-yl)-1-methyl-1H-[4,4']bipyrimidinyl-6-one;
2-((4aRS,10bRS)-trans-2,3,4a,5,6,10b-Hexahydro-naphtho [1,2-b][1,4]oxazin-4-yl)-3-methyl-6-pyridin-4-yl-3H-pyrimidin-4-one;
6-(3-Fluoro-pyridin-4-yl)-2-((4aRS,10bRS)-trans-2,3,4a,5, 6,10b-hexahydro-naphtho[1,2-b][1,4]oxazin-4-yl)-3-methyl-3H-pyrimidin-4-one;
2-((4aRS,10bRS)-trans-3,4,4a,5,6,10b-Hexahydro-2H-naphtho[1,2-b][1,4]oxazin-4-yl)-3-methyl-6-(pyrimidin-4-yl)-3H-pyrimidin-4-one;
3-Methyl-2-(4-phenyl-4,8-diaza-tricyclo[5.2.2.0$^{2,6}$]undec-8-yl)-6-pyridin-4-yl-3H-pyrimidin-4-one;
3-Methyl-6-pyridin-4-yl-2-[6-(4-pyrrolidin-1-yl-phenyl)-2-aza-bicyclo[2.2.2]oct-2-yl]-3H-pyrimidin-4-one;
2-[3-(2-Methoxy-phenylamino)-8-aza-bicyclo[3.2.1]oct-8-yl]-3-methyl-6-pyridin-4-yl-3H-pyrimidin-4-one;
6-(3-Fluoro-pyridin-4-yl)-2-[3-(2-methoxy-phenylamino)-8-aza-bicyclo[3.2.1]oct-8-yl]-3-methyl-3H-pyrimidin-4-one;
2-[3-(4-Methoxy-phenylamino)-8-aza-bicyclo[3.2.1]oct-8-yl]-3-methyl-6-pyridin-4-yl-3H-pyrimidin-4-one;
6-(3-Fluoro-pyridin-4-yl)-2-[3-(4-methoxy-phenylamino)-8-aza-bicyclo[3.2.1]oct-8-yl]-3-methyl-3H-pyrimidin-4-one;

2-(8-Methoxy-(4aRS,10bRS)-trans-2,3,4a,5,6,10b-hexahydro-naphtho[1,2-b][1,4]oxazin-4-yl)-3-methyl-6-pyridin-4-yl-3H-pyrimidin-4-one;

6-(3-Fluoro-pyridin-4-yl)-2-(8-methoxy-(4aRS,10bRS)-trans-2,3,4a,5,6,10b-hexahydro-naphtho[1,2-b][1,4]oxazin-4-yl)-3-methyl-3H-pyrimidin-4-one;

2-(8-Methoxy-(4aRS,10bRS)-trans-2,3,4a,5,6,10b-hexahydro-naphtho[1,2-b][1,4]oxazin-4-yl)-1-methyl-1H-[4,4']bipyrimidinyl-6-one;

2-(7-Methoxy-(4aRS,10bRS)-trans-2,3,4a,5,6,10b-hexahydro-naphtho[1,2-b][1,4]oxazin-4-yl)-3-methyl-6-pyridin-4-yl-3H-pyrimidin-4-one;

6-(3-Fluoro-pyridin-4-yl)-2-(7-methoxy-(4aRS,10bRS)-trans-2,3,4a,5,6,10b-hexahydro-naphtho[1,2-b][1,4]oxazin-4-yl)-3-methyl-3H-pyrimidin-4-one;

2-(7-Methoxy-(4aRS,10bRS)-trans-2,3,4a,5,6,10b-hexahydro-naphtho[1,2-b][1,4]oxazin-4-yl)-1-methyl-1H-[4,4']bipyrimidinyl-6-one;

2-(9-Methoxy-(4aRS,10bRS)-trans-2,3,4a,5,6,10b-hexahydro-naphtho[1,2-b][1,4]oxazin-4-yl)-3-methyl-6-pyridin-4-yl-3H-pyrimidin-4-one;

6-(3-Fluoro-pyridin-4-yl)-2-(9-methoxy-(4aRS,10bRS)-trans-2,3,4a,5,6,10b-hexahydro-naphtho[1,2-b][1,4]oxazin-4-yl)-3-methyl-3H-pyrimidin-4-one;

2-(9-Methoxy-(4aRS,10bRS)-trans-2,3,4a,5,6,10b-hexahydro-naphtho[1,2-b][1,4]oxazin-4-yl)-1-methyl-1H-[4,4']bipyrimidinyl-6-one;

2-((4aRS,10bSR)-cis-2,3,4a,5,6,10b-Hexahydro-naphtho[1,2-b][1,4]oxazin-4-yl)-3-methyl-6-pyridin-4-yl-3H-pyrimidin-4-one;

6-(3-Fluoro-pyridin-4-yl)-2-((4aRS,10bSR)-cis-2,3,4a,5,6,10b-hexahydro-naphtho[1,2-b][1,4]oxazin-4-yl)-3-methyl-3H-pyrimidin-4-one;

2-((4aRS,10bSR)-cis-2,3,4a,5,6,10b-Hexahydro-naphtho[1,2-b][1,4]oxazin-4-yl)-1-methyl-1H-[4,4']bipyrimidinyl-6-one;

6-(3-Fluoro-pyridin-4-yl)-3-methyl-2-((4aRS,10bRS)-trans-2,3,10,10a-tetrahydro-4-aH-4,9-dioxa-1-aza-phenanthren-1-yl)-3H-pyrimidin-4-one;

6-(3-Fluoro-pyridin-4-yl)-2-(8-methoxy-(4aRS,10bSR)-cis-2,3,4a,5,6,10b-hexahydro-naphtho[1,2-b][1,4]oxazin-4-yl)-3-methyl-3H-pyrimidin-4-one;

6-(3-Fluoro-pyridin-4-yl)-2-(6-methoxy-(4aRS,10aRS)-trans-2,3,10,10a-tetrahydro-4-aH-4,9-dioxa-1-aza-phenanthren-1-yl)-3-methyl-3H-pyrimidin-4-one;

2-(9-Methoxy-(4aRS,10bSR)-cis-2,3,4a,5,6,10b-hexahydro-naphtho[1,2-b][1,4]oxazin-4-yl)-3-methyl-6-pyridin-4-yl-3H-pyrimidin-4-one;

6-(3-Fluoro-pyridin-4-yl)-2-(9-methoxy-(4aRS,10bSR)-cis-2,3,4a,5,6,10b-hexahydro-naphtho[1,2-b][1,4]oxazin-4-yl)-3-methyl-3H-pyrimidin-4-one;

2-(9-Methoxy-(4aRS,10bSR)-cis-2,3,4a,5,6,10b-hexahydro-naphtho[1,2-b][1,4]oxazin-4-yl)-1-methyl-1H-[4,4']bipyrimidinyl-6-one;

2-(7-Methoxy-(4aRS,10bSR)-cis-2,3,4a,5,6,10b-hexahydro-naphtho[1,2-b][1,4]oxazin-4-yl)-3-methyl-6-pyridin-4-yl-3H-pyrimidin-4-one;

6-(3-Fluoro-pyridin-4-yl)-2-(7-methoxy-(4aRS,10bSR)-cis-2,3,4a,5,6,10b-hexahydro-naphtho[1,2-b][1,4]oxazin-4-yl)-3-methyl-3H-pyrimidin-4-one;

2-(7-Methoxy-(4aRS,10bSR)-cis-2,3,4a,5,6,10b-hexahydro-naphtho[1,2-b][1,4]oxazin-4-yl)-1-methyl-1H-[4,4']bipyrimidinyl-6-one;

6-(3-Fluoro-pyridin-4-yl)-2-((4aRS,10aRS)-trans-2,3,4a,5,6,10b-hexahydro-1H-benzo[f]quinolin-4-yl)-3-methyl-3H-pyrimidin-4-one;

2-(8-Methoxy-(4aRS,10aRS)-trans-2,3,4a,5,6,10b-hexahydro-1H-benzo[f]quinolin-4-yl)-3-methyl-6-pyridin-4-yl-3H-pyrimidin-4-one;

6-(3-Fluoro-pyridin-4-yl)-2-(8-methoxy-(4aRS,10aRS)-trans-2,3,4a,5,6,10b-hexahydro-1H-benzo[f]quinolin-4-yl)-3-methyl-3H-pyrimidin-4-one;

2-(8-Methoxy-(4aRS,10aRS)-trans-2,3,4a,5,6,10b-hexahydro-1H-benzo[f]quinolin-4-yl)-1-methyl-1H-[4,4']bipyrimidinyl-6-one;

3-Methyl-6-pyridin-4-yl-2-((4aRS,10aRS)-cis-2,3,10,10a-tetrahydro-4-aH-4,9-dioxa-1-aza-phenanthren-1-yl)-3H-pyrimidin-4-one;

6-(3-Fluoro-pyridin-4-yl)-3-methyl-2-((4aRS,10aRS)-cis-2,3,10,10a-tetrahydro-4-aH-4,9-dioxa-1-aza-phenanthren-1-yl)-3H-pyrimidin-4-one;

1-Methyl-2-((4aRS,10aRS)-cis-2,3,10,10a-tetrahydro-4-aH-4,9-dioxa-1-aza-phenanthren-1-yl)-1H-[4,4']bipyrimidinyl-6-one;

6-(3-Fluoro-pyridin-4-yl)-2-(6-methoxy-(4aRS,10aRS)-cis-2,3,10,10a-tetrahydro-4-aH-4,9-dioxa-1-aza-phenanthren-1-yl)-3-methyl-3H-pyrimidin-4-one;

2-(6-Methoxy-(4aRS,10aRS)-cis-2,3,10,10a-tetrahydro-4-aH-4,9-dioxa-1-aza-phenanthren-1-yl)-1-methyl-1H-[4,4']bipyrimidinyl-6-one;

2-(9-Fluoro-(4aRS,10bRS)-trans-2,3,4a,5,6,10b-hexahydro-naphtho[1,2-b][1,4]oxazin-4-yl)-3-methyl-6-pyridin-4-yl-3H-pyrimidin-4-one;

2-(9-Fluoro-(4aRS,10bRS)-trans-2,3,4a,5,6,10b-hexahydro-naphtho[1,2-b][1,4]oxazin-4-yl)-6-(3-fluoro-pyridin-4-yl)-3-methyl-3H-pyrimidin-4-one;

2-(9-Fluoro-(4aRS,10bRS)-trans-2,3,4a,5,6,10b-hexahydro-naphtho[1,2-b][1,4]oxazin-4-yl)-1-methyl-1H-[4,4']bipyrimidinyl-6-one;

2-(9-Fluoro-(4aRS,10bSR)-cis-2,3,4a,5,6,10b-hexahydro-naphtho[1,2-b][1,4]oxazin-4-yl)-3-methyl-6-pyridin-4-yl-3H-pyrimidin-4-one;

2-(9-Fluoro-(4aRS,10bSR)-cis-2,3,4a,5,6,10b-hexahydro-naphtho[1,2-b][1,4]oxazin-4-yl)-6-(3-fluoro-pyridin-4-yl)-3-methyl-3H-pyrimidin-4-one;

2-(9-Fluoro-(4aRS,10bSR)-cis-2,3,4a,5,6,10b-hexahydro-naphtho[1,2-b][1,4]oxazin-4-yl)-1-methyl-1H-[4,4']bipyrimidinyl-6-one;

3-Methyl-2-((3R)-3-methyl-morpholin-4-yl)-6-pyridin-4-yl-3H-pyrimidin-4-one;

6-(3-Fluoro-pyridin-4-yl)-3-methyl-2-((3R)-3-methyl-morpholin-4-yl)-3H-pyrimidin-4-one;

1-Methyl-2-((3R)-3-methyl-morpholin-4-yl)-1H-[4,4']bipyrimidinyl-6-one;

6-(3-Fluoro-pyridin-4-yl)-3-methyl-2-((3S)-3-methyl-morpholin-4-yl)-3H-pyrimidin-4-one;

3-Methyl-2-(2-methyl-piperidin-1-yl)-6-pyridin-4-yl-3H-pyrimidin-4-one;

1-Methyl-2-(2-methyl-piperidin-1-yl)-1H-[4,4']bipyrimidinyl-6-one;

6-(3-Fluoro-pyridin-4-yl)-3-methyl-2-(2-methyl-piperidin-1-yl)-3H-pyrimidin-4-one;

4-[4-(3-Fluoro-pyridin-4-yl)-1-methyl-6-oxo-1,6-dihydro-pyrimidin-2-yl]-(3R)-3-methyl-piperazine-1-carboxylic acid benzyl ester;

4-[4-(3-Fluoro-pyridin-4-yl)-1-methyl-6-oxo-1,6-dihydro-pyrimidin-2-yl]-(3S)-3-methyl-piperazine-1-carboxylic acid benzyl ester;

6-(3-Fluoro-pyridin-4-yl)-3-methyl-2-((2S)-2-methyl-piperazin-1-yl)-3H-pyrimidin-4-one;

6-(3-Fluoro-pyridin-4-yl)-3-methyl-2-((2R)-2-methyl-piperazin-1-yl)-3H-pyrimidin-4-one;

1-[4-(3-Fluoro-pyridin-4-yl)-1-methyl-6-oxo-1,6-dihydro-pyrimidin-2-yl]-piperidine-2-carboxylic acid ethyl ester;
2-((2SR,4RS)-2,4-Dimethyl-piperidin-1-yl)-6-(3-fluoro-pyridin-4-yl)-3-methyl-3H-pyrimidin-4-one;
2-((2RS,4RS)-2,4-Dimethyl-piperidin-1-yl)-6-(3-fluoro-pyridin-4-yl)-3-methyl-3H-pyrimidin-4-one;
3-Methyl-2-((4aRS,8aRS)-trans-octahydro-benzo[1,4]oxazin-4-yl)-6-pyridin-4-yl-3H-pyrimidin-4-one;
6-(3-Fluoro-pyridin-4-yl)-3-methyl-2-((4aRS,8aRS)-trans-octahydro-benzo[1,4]oxazin-4-yl)-3H-pyrimidin-4-one;
1-Methyl-2-((4aRS,8aRS)-trans-octahydro-benzo[1,4]oxazin-4-yl)-1H-[4,4']bipyrimidinyl-6-one;
2-((3R)-3-Ethyl-morpholin-4-yl)-6-(3-fluoro-pyridin-4-yl)-3-methyl-3H-pyrimidin-4-one;
2-((3R)-3-Ethyl-morpholin-4-yl)-1-methyl-1H-[4,4']bipyrimidinyl-6-one;
2-(8-Aza-bicyclo[3.2.1]oct-8-yl)-6-(3-fluoro-pyridin-4-yl)-3-methyl-3H-pyrimidin-4-one;
2-(8-Aza-bicyclo[3.2.1]oct-8-yl)-1-methyl-1H-[4,4']bipyrimidinyl-6-one;
6-(3-Fluoro-pyridin-4-yl)-2-((3R)-3-isopropyl-morpholin-4-yl)-3-methyl-3H-pyrimidin-4-one;
6-(3-Fluoro-pyridin-4-yl)-2-((3R)-3-isobutyl-morpholin-4-yl)-3-methyl-3H-pyrimidin-4-one;
4-[4-(3-Fluoro-pyridin-4-yl)-1-methyl-6-oxo-1,6-dihydro-pyrimidin-2-yl]-morpholine-3-carboxylic acid ethyl ester;
6-(3-Fluoro-pyridin-4-yl)-3-methyl-2-((3R)-3-phenyl-morpholin-4-yl)-3H-pyrimidin-4-one;
1-Methyl-2-((3R)-3-phenyl-morpholin-4-yl)-1H-[4,4']bipyrimidinyl-6-one;
3-Methyl-2-(octahydro-quinolin-1-yl)-6-pyridin-4-yl-3H-pyrimidin-4-one;
1-Methyl-2-(octahydro-quinolin-1-yl)-1H-[4,4']bipyrimidinyl-6-one;
6-(3-Fluoro-pyridin-4-yl)-3-methyl-2-(octahydro-quinolin-1-yl)-3H-pyrimidin-4-one; and
3-Methyl-2-(4-phenyl-4,8-diaza-tricyclo[5.2.2.0$^{2,6}$]undec-8-yl)-6-pyridin-4-yl-3H-pyrimidin-4-one,
an optically active isomer thereof, or a pharmaceutically acceptable salt thereof.

22. A compound according to the above 2 selected from the group consisting of:
3-Methyl-2-((1RS,4SR,6RS)-6-phenyl-2-aza-bicyclo[2.2.2]oct-2-yl)-6-pyridin-4-yl-3H-pyrimidin-4-one;
2-(1,3,4,6,7,11b-Hexahydro-pyrazino[2,1-a]isoquinolin-2-yl)-3-methyl-6-pyridin-4-yl-3H-pyrimidin-4-one;
6-(3-Fluoro-pyridin-4-yl)-2-(1,3,4,6,7,11b-hexahydro-pyrazino[2,1-a]isoquinolin-2-yl)-3-methyl-3H-pyrimidin-4-one; and
2-(1,3,4,6,7,11b-Hexahydro-pyrazino[2,1-a]isoquinolin-2-yl)-1-methyl-1H-[4,4']bipyrimidinyl-6-one
an optically active isomer thereof, or a pharmaceutically acceptable salt thereof.

23. A compound according to the above 2 selected from the group consisting of:
3-Methyl-2-((4aR,8aR)-octahydro-benzo[1,4]oxazin-4-yl)-6-pyridin-4-yl-3H-pyrimidin-4-one;
6-(3-Fluoro-pyridin-4-yl)-3-methyl-2-((4aR,8aR)-octahydro-benzo[1,4]oxazin-4-yl)-3H-pyrimidin-4-one;
1-Methyl-2-((4aR,8aR)-octahydro-benzo[1,4]oxazin-4-yl)-1H-[4,4']bipyrimidinyl-6-one;
2-((4aR,7aR)-Hexahydro-cyclopenta[1,4]oxazin-4-yl)-3-methyl-6-pyridin-4-yl-3H-pyrimidin-4-one;
6-(3-Fluoro-pyridin-4-yl)-2-((4aR,7aR)-hexahydro-cyclopenta[1,4]oxazin-4-yl)-3-methyl-3H-pyrimidin-4-one;
2-((4aR,7aR)-Hexahydro-cyclopenta[1,4]oxazin-4-yl)-1-methyl-1H-[4,4']bipyrimidinyl-6-one;
6-(3-Fluoro-pyridin-4-yl)-3-methyl-2-((3RS)-2,2,3-trimethyl-morpholin-4-yl)-3H-pyrimidin-4-one;
2-((2RS,3RS)-2,3-Dimethyl-morpholin-4-yl)-6-(3-fluoro-pyridin-4-yl)-3-methyl-3H-pyrimidin-4-one;
2-((2RS,3RS)-2,3-Dimethyl-morpholin-4-yl)-1-methyl-1H-[4,4']bipyrimidinyl-6-one;
2-((2RS,3SR)-2,3-Dimethyl-morpholin-4-yl)-6-(3-fluoro-pyridin-4-yl)-3-methyl-3H-pyrimidin-4-one;
2-((2R,3SR)-2,3-Dimethyl-morpholin-4-yl)-6-(3-fluoro-pyridin-4-yl)-3-methyl-3H-pyrimidin-4-one;
2-((2S,3SR)-2,3-Dimethyl-morpholin-4-yl)-6-(3-fluoro-pyridin-4-yl)-3-methyl-3H-pyrimidin-4-one;
2-((2R,3R)-2,3-Dimethyl-morpholin-4-yl)-1-methyl-1H-[4,4']bipyrimidinyl-6-one;
2-((2R,3R)-2,3-Dimethyl-morpholin-4-yl)-6-(3-fluoro-pyridin-4-yl)-3-methyl-3H-pyrimidin-4-one;
1-Methyl-2-((3RS)-2,2,3-trimethyl-morpholin-4-yl)-1H-[4,4']bipyrimidinyl-6-one;
1-Methyl-2-((3R)-2,2,3-trimethyl-morpholin-4-yl)-1H-[4,4']bipyrimidinyl-6-one;
1-Methyl-2-((3S)-2,2,3-trimethyl-morpholin-4-yl)-1H-[4,4']bipyrimidinyl-6-one;
2-((3aS,7aR)-Hexahydro-2,4-dioxa-7-aza-inden-7-yl)-1-methyl-1H-[4,4']bipyrimidinyl-6-one;
6-((3aS,7aR)-3-Fluoro-pyridin-4-yl)-2-(hexahydro-2,4-dioxa-7-aza-inden-7-yl)-3-methyl-3H-pyrimidin-4-one;
2-((3RS)-3-Fluoromethyl-morpholin-4-yl)-1-methyl-1H-[4,4']bipyrimidinyl-6-one;
2-((3R)-3-Fluoromethyl-morpholin-4-yl)-1-methyl-1H-[4,4']bipyrimidinyl-6-one;
2-((3S)-3-Fluoromethyl-morpholin-4-yl)-1-methyl-1H-[4,4']bipyrimidinyl-6-one;
2-((3RS)-3-Fluoromethyl-morpholin-4-yl)-6-(3-fluoro-pyridin-4-yl)-3-methyl-3H-pyrimidin-4-one;
2-((3R)-3-Fluoromethyl-morpholin-4-yl)-6-(3-fluoro-pyridin-4-yl)-3-methyl-3H-pyrimidin-4-one; and
2-((3S)-3-Fluoromethyl-morpholin-4-yl)-6-(3-fluoro-pyridin-4-yl)-3-methyl-3H-pyrimidin-4-one,
an optically active isomer thereof, or a pharmaceutically acceptable salt thereof.

24. A compound according to the above 2 selected from the group consisting of:
6-(3-Fluoro-pyridin-4-yl)-3-methyl-2-((4aR,8aR)-octahydro-benzo[1,4]oxazin-4-yl)-3H-pyrimidin-4-one;
1-Methyl-2-((4aR,8aR)-octahydro-benzo[1,4]oxazin-4-yl)-1H-[4,4']bipyrimidinyl-6-one;
6-(3-Fluoro-pyridin-4-yl)-2-((4aR,7aR)-hexahydro-cyclopenta[1,4]oxazin-4-yl)-3-methyl-3H-pyrimidin-4-one;
2-((4aR,7aR)-Hexahydro-cyclopenta[1,4]oxazin-4-yl)-1-methyl-1H-[4,4']bipyrimidinyl-6-one;
6-(3-Fluoro-pyridin-4-yl)-3-methyl-2-((3RS)-2,2,3-trimethyl-morpholin-4-yl)-3H-pyrimidin-4-one;
2-((2RS,3RS)-2,3-Dimethyl-morpholin-4-yl)-6-(3-fluoro-pyridin-4-yl)-3-methyl-3H-pyrimidin-4-one;
2-((2RS,3RS)-2,3-Dimethyl-morpholin-4-yl)-1-methyl-1H-[4,4']bipyrimidinyl-6-one;
2-((2R,3SR)-2,3-Dimethyl-morpholin-4-yl)-6-(3-fluoro-pyridin-4-yl)-3-methyl-3H-pyrimidin-4-one;
2-((2S,3SR)-2,3-Dimethyl-morpholin-4-yl)-6-(3-fluoro-pyridin-4-yl)-3-methyl-3H-pyrimidin-4-one;
2-((2R,3R)-2,3-Dimethyl-morpholin-4-yl)-1-methyl-1H-[4,4']bipyrimidinyl-6-one;
2-((2R,3R)-2,3-Dimethyl-morpholin-4-yl)-6-(3-fluoro-pyridin-4-yl)-3-methyl-3H-pyrimidin-4-one;
1-Methyl-2-((3R)-2,2,3-trimethyl-morpholin-4-yl)-1H-[4,4']bipyrimidinyl-6-one;

1-Methyl-2-((3S)-2,2,3-trimethyl-morpholin-4-yl)-1H-[4, 4']bipyrimidinyl-6-one;
2-((3aR,7aS)-Hexahydro-2,4-dioxa-7-aza-inden-7-yl)-1-methyl-1H-[4,4']bipyrimidinyl-6-one;
6-((3aR,7aS)-3-Fluoro-pyridin-4-yl)-2-(hexahydro-2,4-dioxa-7-aza-inden-7-yl)-3-methyl-3H-pyrimidin-4-one;
2-((3RS)-3-Fluoromethyl-morpholin-4-yl)-1-methyl-1H-[4, 4']bipyrimidinyl-6-one;
2-((3R)-3-Fluoromethyl-morpholin-4-yl)-1-methyl-1H-[4, 4']bipyrimidinyl-6-one;
2-((3S)-3-Fluoromethyl-morpholin-4-yl)-1-methyl-1H-[4, 4']bipyrimidinyl-6-one;
2-((3RS)-3-Fluoromethyl-morpholin-4-yl)-6-(3-fluoro-pyridin-4-yl)-3-methyl-3H-pyrimidin-4-one;
2-((3R)-3-Fluoromethyl-morpholin-4-yl)-6-(3-fluoro-pyridin-4-yl)-3-methyl-3H-pyrimidin-4-one; and
2-((3S)-3-Fluoromethyl-morpholin-4-yl)-6-(3-fluoro-pyridin-4-yl)-3-methyl-3H-pyrimidin-4-one,
an optically active isomer thereof, or a pharmaceutically acceptable salt thereof.

25. A compound according to the above 2 selected from the group consisting of:
6-(3-Fluoro-pyridin-4-yl)-3-methyl-2-((2R)-2-methyl-pyrrolidin-1-yl)-3H-pyrimidin-4-one;
1-Methyl-2-((4aSR,8aRS)-octahydro-quinolin-1-yl)-1H-[4, 4']bipyrimidinyl-6-one;
1-Methyl-2-((4aS,8aR)-octahydro-quinolin-1-yl)-1H-[4,4'] bipyrimidinyl-6-one;
1-Methyl-2-((4aR,8aS)-octahydro-quinolin-1-yl)-1H-[4,4'] bipyrimidinyl-6-one;
6-(3-Fluoro-pyridin-4-yl)-3-methyl-2-((4aSR,8aRS)-octahydro-quinolin-1-yl)-3H-pyrimidin-4-one;
6-(3-Fluoro-pyridin-4-yl)-3-methyl-2-((4aS,8aR)-octahydro-quinolin-1-yl)-3H-pyrimidin-4-one;
6-(3-Fluoro-pyridin-4-yl)-3-methyl-2-((4aR,8aS)-octahydro-quinolin-1-yl)-3H-pyrimidin-4-one;
2-((2R,4R)-2,4-Dimethyl-piperidin-1-yl)-1-methyl-1H-[4, 4']bipyrimidinyl-6-one;
(2S)-2-[4-(3-Fluoro-pyridin-4-yl)-1-methyl-6-oxo-1,6-dihydro-pyrimidin-2-yl]-cyclopentanecarbonitrile;
2-((2RS)-2-Butyl-pyrrolidin-1-yl)-1-methyl-1H-[4,4']bipyrimidinyl-6-one;
2-((2RS)-2-Benzyl-pyrrolidin-1-yl)-1-methyl-1H-[4,4']bipyrimidinyl-6-one;
2-((2RS)-2-Benzyl-pyrrolidin-1-yl)-6-(3-fluoro-pyridin-4-yl)-3-methyl-3H-pyrimidin-4-one;
2-((2R)-2-Benzyl-pyrrolidin-1-yl)-6-(3-fluoro-pyridin-4-yl)-3-methyl-3H-pyrimidin-4-one;
2-((2S)-2-Benzyl-pyrrolidin-1-yl)-6-(3-fluoro-pyridin-4-yl)-3-methyl-3H-pyrimidin-4-one; and
6-(3-Fluoro-pyridin-4-yl)-2-[(3R)-3-(3-methoxy-phenylamino)-pyrrolidin-1-yl]-3-methyl-3H-pyrimidin-4-one,
an optically active isomer thereof, or a pharmaceutically acceptable salt thereof.

26. A compound according to the above 2 selected from the group consisting of:
1-Methyl-2-((4aSR,8aRS)-octahydro-quinolin-1-yl)-1H-[4, 4']bipyrimidinyl-6-one;
1-Methyl-2-((4aS,8aR)-octahydro-quinolin-1-yl)-1H-[4,4'] bipyrimidinyl-6-one;
1-Methyl-2-((4aR,8aS)-octahydro-quinolin-1-yl)-1H-[4,4'] bipyrimidinyl-6-one;
6-(3-Fluoro-pyridin-4-yl)-3-methyl-2-((4aSR,8aRS)-octahydro-quinolin-1-yl)-3H-pyrimidin-4-one;
6-(3-Fluoro-pyridin-4-yl)-3-methyl-2-((4aS,8aR)-octahydro-quinolin-1-yl)-3H-pyrimidin-4-one;
6-(3-Fluoro-pyridin-4-yl)-3-methyl-2-((4aR,8aS)-octahydro-quinolin-1-yl)-3H-pyrimidin-4-one;
2-((2R,4R)-2,4-Dimethyl-piperidin-1-yl)-1-methyl-1H-[4, 4']bipyrimidinyl-6-one;
(2S)-2-[4-(3-Fluoro-pyridin-4-yl)-1-methyl-6-oxo-1,6-dihydro-pyrimidin-2-yl]-cyclopentanecarbonitrile;
2-((2RS)-2-Benzyl-pyrrolidin-1-yl)-6-(3-fluoro-pyridin-4-yl)-3-methyl-3H-pyrimidin-4-one;
2-((2R)-2-Benzyl-pyrrolidin-1-yl)-6-(3-fluoro-pyridin-4-yl)-3-methyl-3H-pyrimidin-4-one;
2-((2S)-2-Benzyl-pyrrolidin-1-yl)-6-(3-fluoro-pyridin-4-yl)-3-methyl-3H-pyrimidin-4-one; and
6-(3-Fluoro-pyridin-4-yl)-2-[(3R)-3-(3-methoxy-phenylamino)-pyrrolidin-1-yl]-3-methyl-3H-pyrimidin-4-one,
an optically active isomer thereof, or a pharmaceutically acceptable salt thereof.

27. A compound according to the above 1 selected from the group consisting of:
2-((2R)-2,4-Dimethyl-piperazin-1-yl)-6-(3-fluoro-pyridin-4-yl)-3-methyl-3H-pyrimidin-4-one;
(3R)-6-(3-Fluoro-pyridin-4-yl)-3-methyl-2-(2-methyl-piperazin-1-yl)-3H-pyrimidin-4-one;
2-((2R)-4-Benzyl-2-methyl-piperazin-1-yl)-1-methyl-1H-[4,4']bipyrimidinyl-6-one;
1-Methyl-2-((2R)-2-methyl-4-phenyl-piperazin-1-yl)-1H-[4,4']bipyrimidinyl-6-one;
2-[(2R)-4-(2-Fluoro-phenyl)-2-methyl-piperazin-1-yl]-1-methyl-1H-[4,4']bipyrimidinyl-6-one;
2-[(2R)-4-(3-Fluoro-phenyl)-2-methyl-piperazin-1-yl]-1-methyl-1H-[4,4']bipyrimidinyl-6-one;
2-[(2R)-4-(4-Fluoro-phenyl)-2-methyl-piperazin-1-yl]-1-methyl-1H-[4,4']bipyrimidinyl-6-one;
2-[(2R)-4-(2-Methoxy-phenyl)-2-methyl-piperazin-1-yl]-1-methyl-1H-[4,4']bipyrimidinyl-6-one;
2-[(2R)-4-(3-Methoxy-phenyl)-2-methyl-piperazin-1-yl]-1-methyl-1H-[4,4']bipyrimidinyl-6-one;
2-[(2R)-4-(4-Methoxy-phenyl)-2-methyl-piperazin-1-yl]-1-methyl-1H-[4,4']bipyrimidinyl-6-one;
2-((2R)-4-Isopropyl-2-methyl-piperazin-1-yl)-1-methyl-1H-[4,4']bipyrimidinyl-6-one;
5-[(3R)-3-Methyl-4-(1-methyl-6-oxo-1,6-dihydro-[4,4']bipyrimidinyl-2-yl)-piperazin-1-yl]-thiophene-2-carboxylic acid ethyl ester;
1-Methyl-2-[(2R)-2-methyl-4-(5-methyl-thiophen-2-yl)-piperazin-1-yl]-1H-[4,4']bipyrimidinyl-6-one;
2-[(2R)-2-Ethyl-4-(4-methoxy-phenyl)-piperazin-1-yl]-1-methyl-1H-[4,4']bipyrimidinyl-6-one;
2-[(2R)-2-Ethyl-4-(4-methoxy-phenyl)-piperazin-1-yl]-6-(3-fluoro-pyridin-4-yl)-3-methyl-3H-pyrimidin-4-one;
1-Methyl-2-[(2R)-2-methyl-4-(pyridine-3-carbonyl)-piperazin-1-yl]-1H-[4,4']bipyrimidinyl-6-one;
4-[(2S)-2-Methyl-4-(1-methyl-6-oxo-1,6-dihydro-[4,4']bipyrimidinyl-2-yl)-piperazin-1-yl]-benzonitrile;
4-[(3R)-3-Methyl-4-(1-methyl-6-oxo-1,6-dihydro-[4,4']bipyrimidinyl-2-yl)-piperazin-1-yl]-benzonitrile;
3-Methyl-2-((2R)-2-methyl-4-pyrimidin-2-yl-piperazin-1-yl)-6-pyridin-4-yl-3H-pyrimidin-4-one;
6-(3-Fluoro-pyridin-4-yl)-3-methyl-2-((2R)-2-methyl-4-pyrimidin-2-yl-piperazin-1-yl)-3H-pyrimidin-4-one;
1-Methyl-2-{(2R)-2-methyl-4-[4-(5-methyl-[1,2,4]oxadiazol-3-yl)-benzoyl]-piperazin-1-yl}-1H-[4,4']bipyrimidinyl-6-one;
1-Methyl-2-{(2R)-2-methyl-4-[4-(5-methyl-[1,2,4]oxadiazol-3-yl)-benzyl]-piperazin-1-yl}-1H-[4,4']bipyrimidinyl-6-one;
1-Methyl-2-[(2R)-2-methyl-4-(pyridine-2-carbonyl)-piperazin-1-yl]-1H-[4,4']bipyrimidinyl-6-one;

2-[(2R)-4-(4-Fluoro-benzoyl)-2-methyl-piperidin-1-yl]-1-methyl-1H-[4,4']bipyrimidinyl-6-one;
2-[(2R)-4-(4-Chloro-benzoyl)-2-methyl-piperidin-1-yl]-1-methyl-1H-[4,4']bipyrimidinyl-6-one;
2-[(2R)-4-(3,4-Dichloro-benzoyl)-2-methyl-piperidin-1-yl]-1-methyl-1H-[4,4']bipyrimidinyl-6-one;
2-[(2R)-4-(4-tert-Butyl-benzoyl)-2-methyl-piperazin-1-yl]-1-methyl-1H-[4,4']bipyrimidinyl-6-one;
4-[(3R)-3-Methyl-4-(1-methyl-6-oxo-1,6-dihydro-[4,4']bipyrimidinyl-2-yl)-piperazine-1-carbonyl]-benzonitrile;
1-Methyl-2-[(2R)-2-methyl-4-(4-trifluoromethoxy-benzoyl)-piperazin-1-yl]-1H-[4,4']bipyrimidinyl-6-one;
4-[(3R)-3-Methyl-4-(1-methyl-6-oxo-1,6-dihydro-[4,4']bipyrimidinyl-2-yl)-piperazine-1-carbonyl]-benzoic acid methyl ester;
1-Methyl-2-[(2R)-2-methyl-4-(4-methyl-benzoyl)-piperazin-1-yl]-1H-[4,4']bipyrimidinyl-6-one;
1-Methyl-2-[(2R)-2-methyl-4-(4-trifluoromethyl-benzoyl)-piperazin-1-yl]-1H-[4,4']bipyrimidinyl-6-one;
2-[(2R)-4-(4-Dimethylamino-benzoyl)-2-methyl-piperazin-1-yl]-1-methyl-1H-[4,4']bipyrimidinyl-6-one;
2-[(2R)-4-(4-Methoxy-benzoyl)-2-methyl-piperazin-1-yl]-1-methyl-1H-[4,4']bipyrimidinyl-6-one;
1-Methyl-2-[(2R)-2-methyl-4-(naphthalene-2-carbonyl)-piperazin-1-yl]-1H-[4,4']bipyrimidinyl-6-one;
2-[(2R)-4-(Benzo[1,3]dioxole-5-carbonyl)-2-methyl-piperazin-1-yl]-1-methyl-1H-[4,4']bipyrimidinyl-6-one;
1-Methyl-2-[(2R)-2-methyl-4-(quinoline-2-carbonyl)-piperazin-1-yl]-1H-[4,4']bipyrimidinyl-6-one;
2-[(3R)-3-Methyl-4-(1-methyl-6-oxo-1,6-dihydro-[4,4']bipyrimidinyl-2-yl)-piperazin-1-yl]-benzoic acid methyl ester;
3-[(3R)-3-Methyl-4-(1-methyl-6-oxo-1,6-dihydro-[4,4']bipyrimidinyl-2-yl)-piperazin-1-yl]-benzonitrile;
2-[(3R)-3-Methyl-4-(1-methyl-6-oxo-1,6-dihydro-[4,4']bipyrimidinyl-2-yl)-piperazin-1-yl]-benzonitrile;
1-Methyl-2-((2R)-2-methyl-4-pyrimidin-5-yl-piperazin-1-yl)-1H-[4,4']bipyrimidinyl-6-one;
1-Methyl-2-((3R)-3-methyl-2,3,5,6-tetrahydro-[1,2']bipyrazinyl-4-yl)-1H-[4,4']bipyrimidinyl-6-one;
1-Methyl-2-((2R)-2-methyl-4-pyridin-4-yl-piperazin-1-yl)-1H-[4,4']bipyrimidinyl-6-one;
1-Methyl-2-((2R)-2-methyl-4-pyridin-3-yl-piperazin-1-yl)-1H-[4,4']bipyrimidinyl-6-one;
1-Methyl-2-((2R)-2-methyl-4-pyridin-2-yl-piperazin-1-yl)-1H-[4,4']bipyrimidinyl-6-one;
4-[(3R)-3-Methyl-4-(1-methyl-6-oxo-1,6-dihydro-[4,4']bipyrimidinyl-2-yl)-piperazin-1-yl]-benzoic acid tert-butyl ester;
2-[(2R)-4-(4-Chloro-phenyl)-2-methyl-piperazin-1-yl]-1-methyl-1H-[4,4']bipyrimidinyl-6-one;
1-Methyl-2-((2R)-2-methyl-4-quinolin-3-yl-piperazin-1-yl)-1H-[4,4']bipyrimidinyl-6-one;
2-[(2R)-4-(4-Hydroxy-phenyl)-2-methyl-piperazin-1-yl]-1-methyl-1H-[4,4']bipyrimidinyl-6-one;
4-[(3R)-3-Methyl-4-(1-methyl-6-oxo-1,6-dihydro-[4,4']bipyrimidinyl-2-yl)-piperazin-1-yl]-benzoic acid;
4-{(3R)-4-[4-(3-Fluoro-pyridin-4-yl)-1-methyl-6-oxo-1,6-dihydro-pyrimidin-2-yl]-3-methyl-piperazin-1-yl}-benzoic acid methyl ester;
3-{(3R)-4-[4-(3-Fluoro-pyridin-4-yl)-1-methyl-6-oxo-1,6-dihydro-pyrimidin-2-yl]-3-methyl-piperazin-1-yl}-benzoic acid methyl ester;
4-{(3R)-4-[4-(3-Fluoro-pyridin-4-yl)-1-methyl-6-oxo-1,6-dihydro-pyrimidin-2-yl]-3-methyl-piperazin-1-yl}-benzonitrile;
3-{(3R)-4-[4-(3-Fluoro-pyridin-4-yl)-1-methyl-6-oxo-1,6-dihydro-pyrimidin-2-yl]-3-methyl-piperazin-1-yl}-benzonitrile;
2-{(3R)-4-[4-(3-Fluoro-pyridin-4-yl)-1-methyl-6-oxo-1,6-dihydro-pyrimidin-2-yl]-3-methyl-piperazin-1-yl}-benzonitrile;
6-(3-Fluoro-pyridin-4-yl)-3-methyl-2-((2R)-2-methyl-4-pyrimidin-5-yl-piperazin-1-yl)-3H-pyrimidin-4-one;
6-(3-Fluoro-pyridin-4-yl)-3-methyl-2-((3R)-3-methyl-2,3,5,6-tetrahydro-[1,2']bipyrazinyl-4-yl)-3H-pyrimidin-4-one;
6-(3-Fluoro-pyridin-4-yl)-3-methyl-2-((2R)-2-methyl-4-pyridin-4-yl-piperazin-1-yl)-3H-pyrimidin-4-one;
6-(3-Fluoro-pyridin-4-yl)-3-methyl-2-((2R)-2-methyl-4-pyridin-3-yl-piperazin-1-yl)-3H-pyrimidin-4-one;
6-(3-Fluoro-pyridin-4-yl)-3-methyl-2-((2R)-2-methyl-4-pyridin-2-yl-piperazin-1-yl)-3H-pyrimidin-4-one;
4-{(3R)-4-[4-(3-Fluoro-pyridin-4-yl)-1-methyl-6-oxo-1,6-dihydro-pyrimidin-2-yl]-3-methyl-piperazin-1-yl}-benzoic acid tert-butyl ester;
6-(3-Fluoro-pyridin-4-yl)-3-methyl-2-{(2R)-2-methyl-4-[4-(5-methyl-[1,2,4]oxadiazol-3-yl)-phenyl]-piperazin-1-yl}-3H-pyrimidin-4-one;
2-[(2R)-4-(4-Chloro-phenyl)-2-methyl-piperazin-1-yl]-6-(3-fluoro-pyridin-4-yl)-3-methyl-3H-pyrimidin-4-one;
6-(3-Fluoro-pyridin-4-yl)-3-methyl-2-((2R)-2-methyl-4-quinolin-3-yl-piperazin-1-yl)-3H-pyrimidin-4-one;
6-(3-Fluoro-pyridin-4-yl)-3-methyl-2-((2R)-2-methyl-4-quinolin-6-yl-piperazin-1-yl)-3H-pyrimidin-4-one;
6-(3-Fluoro-pyridin-4-yl)-2-[(2R)-4-(4-hydroxy-phenyl)-2-methyl-piperazin-1-yl]-3-methyl-3H-pyrimidin-4-one;
4-{(3R)-4-[4-(3-Fluoro-pyridin-4-yl)-1-methyl-6-oxo-1,6-dihydro-pyrimidin-2-yl]-3-methyl-piperazin-1-yl}-benzoic acid;
4-[(3R)-3-Methyl-4-(1-methyl-6-oxo-4-pyridin-4-yl-1,6-dihydro-pyrimidin-2-yl)-piperazin-1-yl]-benzoic acid methyl ester;
3-[(3R)-3-Methyl-4-(1-methyl-6-oxo-4-pyridin-4-yl-1,6-dihydro-pyrimidin-2-yl)-piperazin-1-yl]-benzoic acid methyl ester;
4-[(3R)-3-Methyl-4-(1-methyl-6-oxo-4-pyridin-4-yl-1,6-dihydro-pyrimidin-2-yl)-piperazin-1-yl]-benzonitrile;
3-[(3R)-3-Methyl-4-(1-methyl-6-oxo-4-pyridin-4-yl-1,6-dihydro-pyrimidin-2-yl)-piperazin-1-yl]-benzonitrile;
3-Methyl-2-((3R)-3-methyl-2,3,5,6-tetrahydro-[1,2']bipyrazinyl-4-yl)-6-pyridin-4-yl-3H-pyrimidin-4-one;
3-Methyl-2-((2R)-2-methyl-4-pyridin-4-yl-piperazin-1-yl)-6-pyridin-4-yl-3H-pyrimidin-4-one;
3-Methyl-2-((2R)-2-methyl-4-pyridin-3-yl-piperazin-1-yl)-6-pyridin-4-yl-3H-pyrimidin-4-one;
4-[(3R)-3-Methyl-4-(1-methyl-6-oxo-4-pyridin-4-yl-1,6-dihydro-pyrimidin-2-yl)-piperazin-1-yl]-benzoic acid tert-butyl ester;
3-Methyl-2-{(2R)-2-methyl-4-[4-(5-methyl-[1,2,4]oxadiazol-3-yl)-phenyl]-piperazin-1-yl}-6-pyridin-4-yl-3H-pyrimidin-4-one;
2-[(2R)-4-(4-Chloro-phenyl)-2-methyl-piperazin-1-yl]-3-methyl-6-pyridin-4-yl-3H-pyrimidin-4-one;
3-Methyl-2-((2R)-2-methyl-4-quinolin-3-yl-piperazin-1-yl)-6-pyridin-4-yl-3H-pyrimidin-4-one;
3-Methyl-2-((2R)-2-methyl-4-quinolin-6-yl-piperazin-1-yl)-6-pyridin-4-yl-3H-pyrimidin-4-one;
2-[(2R)-4-(4-Hydroxy-phenyl)-2-methyl-piperazin-1-yl]-3-methyl-6-pyridin-4-yl-3H-pyrimidin-4-one;
4-[(3R)-3-Methyl-4-(1-methyl-6-oxo-4-pyridin-4-yl-1,6-dihydro-pyrimidin-2-yl)-piperazin-1-yl]-benzoic acid;

1-Methyl-2-{(2R)-2-methyl-4-[4-(5-propyl-[1,2,4]oxadiazol-3-yl)-phenyl]-piperazin-1-yl}-1H-[4,4']bipyrimidinyl-6-one;

2-{(2R)-4-[4-(5-Methoxymethyl-[1,2,4]oxadiazol-3-yl)-phenyl]-2-methyl-piperazin-1-yl}-1-methyl-1H-[4,4']bipyrimidinyl-6-one;

2-{(2R)-4-[4-(5-tert-Butyl-[1,2,4]oxadiazol-3-yl)-phenyl]-2-methyl-piperazin-1-yl}-1-methyl-1H-[4,4']bipyrimidinyl-6-one;

1-Methyl-2-{(2R)-2-methyl-4-[4-(5-pyridin-2-yl-[1,2,4]oxadiazol-3-yl)-phenyl]-piperazin-1-yl}-1H-[4,4']bipyrimidinyl-6-one;

2-{(2R)-4-[4-(5-Aminomethyl-[1,2,4]oxadiazol-3-yl)-phenyl]-2-methyl-piperazin-1-yl}-1-methyl-1H-[4,4']bipyrimidinyl-6-one;

2-((2R)-4-{4-[5-((1S)-1-Amino-ethyl)-[1,2,4]oxadiazol-3-yl]-phenyl}-2-methyl-piperazin-1-yl)-1-methyl-1H-[4,4']bipyrimidinyl-6-one;

2-((2R)-4-{4-[5-(1-Amino-1-methyl-ethyl)-[1,2,4]oxadiazol-3-yl]-phenyl}-2-methyl-piperazin-1-yl)-1-methyl-1H-[4,4']bipyrimidinyl-6-one;

1-Methyl-2-{(2R)-2-methyl-4-[4-((2RS)-5-pyrrolidin-2-yl-[1,2,4]oxadiazol-3-yl)-phenyl]-piperazin-1-yl}-1H-[4,4']bipyrimidinyl-6-one;

2-[(2R)-4-(4-{5-[(S)-1-Amino-2-(3H-imidazol-4-yl)-ethyl]-[1,2,4]oxadiazol-3-yl}-phenyl)-2-methyl-piperazin-1-yl]-1-methyl-1H-[4,4']bipyrimidinyl-6-one;

1-Methyl-2-{(2R)-2-methyl-4-[4-(5-phenyl-[1,2,4]oxadiazol-3-yl)-phenyl]-piperazin-1-yl}-1H-[4,4']bipyrimidinyl-6-one;

6-(3-Fluoro-pyridin-4-yl)-3-methyl-2-{(2R)-2-methyl-4-[4-(5-propyl-[1,2,4]oxadiazol-3-yl)-phenyl]-piperazin-1-yl}-3H-pyrimidin-4-one;

6-(3-Fluoro-pyridin-4-yl)-2-{(2R)-4-[4-(5-methoxymethyl-[1,2,4]oxadiazol-3-yl)-phenyl]-2-methyl-piperazin-1-yl}-3-methyl-3H-pyrimidin-4-one;

2-{(2R)-4-[4-(5-tert-Butyl-[1,2,4]oxadiazol-3-yl)-phenyl]-2-methyl-piperazin-1-yl}-6-(3-fluoro-pyridin-4-yl)-3-methyl-3H-pyrimidin-4-one;

6-(3-Fluoro-pyridin-4-yl)-3-methyl-2-{(2R)-2-methyl-4-[4-(5-pyridin-4-yl-[1,2,4]oxadiazol-3-yl)-phenyl]-piperazin-1-yl}-3H-pyrimidin-4-one;

6-(3-Fluoro-pyridin-4-yl)-3-methyl-2-{(2R)-2-methyl-4-[4-(5-pyridin-2-yl-[1,2,4]oxadiazol-3-yl)-phenyl]-piperazin-1-yl}-3H-pyrimidin-4-one;

2-{(2R)-4-[4-(5-Aminomethyl-[1,2,4]oxadiazol-3-yl)-phenyl]-2-methyl-piperazin-1-yl}-6-(3-fluoro-pyridin-4-yl)-3-methyl-3H-pyrimidin-4-one;

2-((2R)-4-{4-[5-((1S)-1-Amino-ethyl)-[1,2,4]oxadiazol-3-yl]-phenyl}-2-methyl-piperazin-1-yl)-6-(3-fluoro-pyridin-4-yl)-3-methyl-3H-pyrimidin-4-one;

2-((2R)-4-{4-[5-(1-Amino-1-methyl-ethyl)-[1,2,4]oxadiazol-3-yl]-phenyl}-2-methyl-piperazin-1-yl)-6-(3-fluoro-pyridin-4-yl)-3-methyl-3H-pyrimidin-4-one;

6-(3-Fluoro-pyridin-4-yl)-3-methyl-2-{(2R)-2-methyl-4-[4-((2RS)-5-pyrrolidin-2-yl-[1,2,4]oxadiazol-3-yl)-phenyl]-piperazin-1-yl}-3H-pyrimidin-4-one;

2-[(2R)-4-(4-{5-[(1S)-1-Amino-2-(3H-imidazol-4-yl)-ethyl]-[1,2,4]oxadiazol-3-yl}-phenyl)-2-methyl-piperazin-1-yl]-6-(3-fluoro-pyridin-4-yl)-3-methyl-3H-pyrimidin-4-one;

6-(3-Fluoro-pyridin-4-yl)-3-methyl-2-{(2R)-2-methyl-4-[4-(5-phenyl-[1,2,4]oxadiazol-3-yl)-phenyl]-piperazin-1-yl}-3H-pyrimidin-4-one;

2-((2R)-4-{4-[5-((1R)-Amino-phenyl-methyl)-[1,2,4]oxadiazol-3-yl]-phenyl}-2-methyl-piperazin-1-yl)-6-(3-fluoro-pyridin-4-yl)-3-methyl-3H-pyrimidin-4-one;

2-((2R)-4-{4-[5-((1R)-1-Amino-ethyl)-[1,2,4]oxadiazol-3-yl]-phenyl}-2-methyl-piperazin-1-yl)-6-(3-fluoro-pyridin-4-yl)-3-methyl-3H-pyrimidin-4-one;

3-Methyl-2-{(2R)-2-methyl-4-[4-(5-propyl-[1,2,4]oxadiazol-3-yl)-phenyl]-piperazin-1-yl}-6-pyridin-4-yl-3H-pyrimidin-4-one;

2-{(2R)-4-[4-(5-Methoxymethyl-[1,2,4]oxadiazol-3-yl)-phenyl]-2-methyl-piperazin-1-yl}-3-methyl-6-pyridin-4-yl-3H-pyrimidin-4-one;

2-{(2R)-4-[4-(5-tert-Butyl-[1,2,4]oxadiazol-3-yl)-phenyl]-2-methyl-piperazin-1-yl}-3-methyl-6-pyridin-4-yl-3H-pyrimidin-4-one;

3-Methyl-2-{(2R)-2-methyl-4-[4-(5-pyridin-2-yl-[1,2,4]oxadiazol-3-yl)-phenyl]-piperazin-1-yl}-6-pyridin-4-yl-3H-pyrimidin-4-one;

2-{(2R)-4-[4-(5-Aminomethyl-[1,2,4]oxadiazol-3-yl)-phenyl]-2-methyl-piperazin-1-yl}-3-methyl-6-pyridin-4-yl-3H-pyrimidin-4-one;

2-((2R)-4-{4-[5-((1S)-1-Amino-ethyl)-[1,2,4]oxadiazol-3-yl]-phenyl}-2-methyl-piperazin-1-yl)-3-methyl-6-pyridin-4-yl-3H-pyrimidin-4-one;

2-((2R)-4-{4-[5-(1-Amino-1-methyl-ethyl)-[1,2,4]oxadiazol-3-yl]-phenyl}-2-methyl-piperazin-1-yl)-3-methyl-6-pyridin-4-yl-3H-pyrimidin-4-one;

3-Methyl-2-{(2R)-2-methyl-4-[4-((2RS)-5-pyrrolidin-2-yl-[1,2,4]oxadiazol-3-yl)-phenyl]-piperazin-1-yl}-6-pyridin-4-yl-3H-pyrimidin-4-one;

2-[(2R)-4-(4-{5-[(1S)-1-Amino-2-(3H-imidazol-4-yl)-ethyl]-[1,2,4]oxadiazol-3-yl}-phenyl)-2-methyl-piperazin-1-yl]-3-methyl-6-pyridin-4-yl-3H-pyrimidin-4-one;

2-((2R)-4-{4-[5-((1R)-1-Amino-ethyl)-[1,2,4]oxadiazol-3-yl]-phenyl}-2-methyl-piperazin-1-yl)-3-methyl-6-pyridin-4-yl-3H-pyrimidin-4-one;

3-Methyl-2-{(2R)-2-methyl-4-[4-(5-pyridin-4-yl-[1,2,4]oxadiazol-3-yl)-phenyl]-piperazin-1-yl}-6-pyridin-4-yl-3H-pyrimidin-4-one; and 2-[(2R)-4-(3-Hydroxy-phenyl)-2-methyl-piperazin-1-yl]-3-methyl-6-pyridin-4-yl-3H-pyrimidin-4-one, an optically active isomer thereof, or a pharmaceutically acceptable salt thereof.

28. A compound according to the above 2 selected from the group consisting of:

(3R)-6-(3-Fluoro-pyridin-4-yl)-3-methyl-2-(2-methyl-piperazin-1-yl)-3H-pyrimidin-4-one;

2-((2R)-4-Benzyl-2-methyl-piperazin-1-yl)-1-methyl-1H-[4,4']bipyrimidinyl-6-one;

1-Methyl-2-((2R)-2-methyl-4-phenyl-piperazin-1-yl)-1H-[4,4']bipyrimidinyl-6-one;

2-[(2R)-4-(2-Fluoro-phenyl)-2-methyl-piperazin-1-yl]-1-methyl-1H-[4,4']bipyrimidinyl-6-one;

2-[(2R)-4-(3-Fluoro-phenyl)-2-methyl-piperazin-1-yl]-1-methyl-1H-[4,4']bipyrimidinyl-6-one;

2-[(2R)-4-(4-Fluoro-phenyl)-2-methyl-piperazin-1-yl]-1-methyl-1H-[4,4']bipyrimidinyl-6-one;

2-[(2R)-4-(2-Methoxy-phenyl)-2-methyl-piperazin-1-yl]-1-methyl-1H-[4,4']bipyrimidinyl-6-one;

2-[(2R)-4-(3-Methoxy-phenyl)-2-methyl-piperazin-1-yl]-1-methyl-1H-[4,4']bipyrimidinyl-6-one;

2-[(2R)-4-(4-Methoxy-phenyl)-2-methyl-piperazin-1-yl]-1-methyl-1H-[4,4']bipyrimidinyl-6-one;

5-[(3R)-3-Methyl-4-(1-methyl-6-oxo-1,6-dihydro-[4,4']bipyrimidinyl-2-yl)-piperazin-1-yl]-thiophene-2-carboxylic acid ethyl ester;

1-Methyl-2-[(2R)-2-methyl-4-(5-methyl-thiophen-2-yl)-piperazin-1-yl]-1H-[4,4']bipyrimidinyl-6-one;

2-[(2R)-2-Ethyl-4-(4-methoxy-phenyl)-piperazin-1-yl]-1-methyl-1H-[4,4']bipyrimidinyl-6-one;

2-[(2R)-2-Ethyl-4-(4-methoxy-phenyl)-piperazin-1-yl]-6-(3-fluoro-pyridin-4-yl)-3-methyl-3H-pyrimidin-4-one;
4-[(2S)-2-Methyl-4-(1-methyl-6-oxo-1,6-dihydro-[4,4']bipyrimidinyl-2-yl)-piperazin-1-yl]-benzonitrile;
4-[(3R)-3-Methyl-4-(1-methyl-6-oxo-1,6-dihydro-[4,4']bipyrimidinyl-2-yl)-piperazin-1-yl]-benzonitrile;
6-(3-Fluoro-pyridin-4-yl)-3-methyl-2-((2R)-2-methyl-4-pyrimidin-2-yl-piperazin-1-yl)-3H-pyrimidin-4-one;
1-Methyl-2-{(2R)-2-methyl-4-[4-(5-methyl-[1,2,4]oxadiazol-3-yl)-benzoyl]-piperazin-1-yl}-1H-[4,4']bipyrimidinyl-6-one;
1-Methyl-2-{(2R)-2-methyl-4-[4-(5-methyl-[1,2,4]oxadiazol-3-yl)-benzyl]-piperazin-1-yl}-1H-[4,4']bipyrimidinyl-6-one;
2-[(2R)-4-(4-Fluoro-benzoyl)-2-methyl-piperidin-1-yl]-1-methyl-1H-[4,4']bipyrimidinyl-6-one;
2-[(2R)-4-(4-Chloro-benzoyl)-2-methyl-piperidin-1-yl]-1-methyl-1H-[4,4']bipyrimidinyl-6-one;
2-[(2R)-4-(3,4-Dichloro-benzoyl)-2-methyl-piperidin-1-yl]-1-methyl-1H-[4,4']bipyrimidinyl-6-one;
2-[(2R)-4-(4-tert-Butyl-benzoyl)-2-methyl-piperazin-1-yl]-1-methyl-1H-[4,4']bipyrimidinyl-6-one;
4-[(3R)-3-Methyl-4-(1-methyl-6-oxo-1,6-dihydro-[4,4']bipyrimidinyl-2-yl)-piperazine-1-carbonyl]-benzonitrile;
1-Methyl-2-[(2R)-2-methyl-4-(4-trifluoromethoxy-benzoyl)-piperazin-1-yl]-1H-[4,4']bipyrimidinyl-6-one;
4-[(3R)-3-Methyl-4-(1-methyl-6-oxo-1,6-dihydro-[4,4']bipyrimidinyl-2-yl)-piperazine-1-carbonyl]-benzoic acid methyl ester;
1-Methyl-2-[(2R)-2-methyl-4-(4-methyl-benzoyl)-piperazin-1-yl]-1H-[4,4']bipyrimidinyl-6-one;
2-[(2R)-4-(4-Dimethylamino-benzoyl)-2-methyl-piperazin-1-yl]-1-methyl-1H-[4,4']bipyrimidinyl-6-one;
2-[(2R)-4-(4-Methoxy-benzoyl)-2-methyl-piperazin-1-yl]-1-methyl-1H-[4,4']bipyrimidinyl-6-one;
1-Methyl-2-[(2R)-2-methyl-4-(naphthalene-2-carbonyl)-piperazin-1-yl]-1H-[4,4']bipyrimidinyl-6-one;
2-[(2R)-4-(Benzo[1,3]dioxole-5-carbonyl)-2-methyl-piperazin-1-yl]-1-methyl-1H-[4,4']bipyrimidinyl-6-one;
1-Methyl-2-[(2R)-2-methyl-4-(quinoline-2-carbonyl)-piperazin-1-yl]-1H-[4,4']bipyrimidinyl-6-one;
3-[(3R)-3-Methyl-4-(1-methyl-6-oxo-1,6-dihydro-[4,4']bipyrimidinyl-2-yl)-piperazin-1-yl]-benzonitrile;
2-[(3R)-3-Methyl-4-(1-methyl-6-oxo-1,6-dihydro-[4,4']bipyrimidinyl-2-yl)-piperazin-1-yl]-benzonitrile;
1-Methyl-2-((3R)-3-methyl-2,3,5,6-tetrahydro-[1,2']bipyrazinyl-4-yl)-1H-[4,4']bipyrimidinyl-6-one;
1-Methyl-2-((2R)-2-methyl-4-pyridin-4-yl-piperazin-1-yl)-1H-[4,4']bipyrimidinyl-6-one;
1-Methyl-2-((2R)-2-methyl-4-pyridin-3-yl-piperazin-1-yl)-1H-[4,4']bipyrimidinyl-6-one;
1-Methyl-2-((2R)-2-methyl-4-pyridin-2-yl-piperazin-1-yl)-1H-[4,4']bipyrimidinyl-6-one;
4-[(3R)-3-Methyl-4-(1-methyl-6-oxo-1,6-dihydro-[4,4']bipyrimidinyl-2-yl)-piperazin-1-yl]-benzoic acid tert-butyl ester;
2-[(2R)-4-(4-Chloro-phenyl)-2-methyl-piperazin-1-yl]-1-methyl-1H-[4,4']bipyrimidinyl-6-one;
1-Methyl-2-((2R)-2-methyl-4-quinolin-3-yl-piperazin-1-yl)-1H-[4,4']bipyrimidinyl-6-one;
2-[(2R)-4-(4-Hydroxy-phenyl)-2-methyl-piperazin-1-yl]-1-methyl-1H-[4,4']bipyrimidinyl-6-one;
4-[(3R)-3-Methyl-4-(1-methyl-6-oxo-1,6-dihydro-[4,4']bipyrimidinyl-2-yl)-piperazin-1-yl]-benzoic acid;
4-{(3R)-4-[4-(3-Fluoro-pyridin-4-yl)-1-methyl-6-oxo-1,6-dihydro-pyrimidin-2-yl]-3-methyl-piperazin-1-yl}-benzoic acid methyl ester;
3-{(3R)-4-[4-(3-Fluoro-pyridin-4-yl)-1-methyl-6-oxo-1,6-dihydro-pyrimidin-2-yl]-3-methyl-piperazin-1-yl}-benzoic acid methyl ester;
4-{(3R)-4-[4-(3-Fluoro-pyridin-4-yl)-1-methyl-6-oxo-1,6-dihydro-pyrimidin-2-yl]-3-methyl-piperazin-1-yl}-benzonitrile;
3-{(3R)-4-[4-(3-Fluoro-pyridin-4-yl)-1-methyl-6-oxo-1,6-dihydro-pyrimidin-2-yl]-3-methyl-piperazin-1-yl}-benzonitrile;
2-{(3R)-4-[4-(3-Fluoro-pyridin-4-yl)-1-methyl-6-oxo-1,6-dihydro-pyrimidin-2-yl]-3-methyl-piperazin-1-yl}-benzonitrile;
6-(3-Fluoro-pyridin-4-yl)-3-methyl-2-((2R)-2-methyl-4-pyrimidin-5-yl-piperazin-1-yl)-3H-pyrimidin-4-one;
6-(3-Fluoro-pyridin-4-yl)-3-methyl-2-((3R)-3-methyl-2,3,5,6-tetrahydro-[1,2']bipyrazinyl-4-yl)-3H-pyrimidin-4-one;
6-(3-Fluoro-pyridin-4-yl)-3-methyl-2-((2R)-2-methyl-4-pyridin-4-yl-piperazin-1-yl)-3H-pyrimidin-4-one;
6-(3-Fluoro-pyridin-4-yl)-3-methyl-2-((2R)-2-methyl-4-pyridin-3-yl-piperazin-1-yl)-3H-pyrimidin-4-one;
6-(3-Fluoro-pyridin-4-yl)-3-methyl-2-((2R)-2-methyl-4-pyridin-2-yl-piperazin-1-yl)-3H-pyrimidin-4-one;
4-{(3R)-4-[4-(3-Fluoro-pyridin-4-yl)-1-methyl-6-oxo-1,6-dihydro-pyrimidin-2-yl]-3-methyl-piperazin-1-yl}-benzoic acid tert-butyl ester;
6-(3-Fluoro-pyridin-4-yl)-3-methyl-2-{(2R)-2-methyl-4-[4-(5-methyl-[1,2,4]oxadiazol-3-yl)-phenyl]-piperazin-1-yl}-3H-pyrimidin-4-one;
2-[(2R)-4-(4-Chloro-phenyl)-2-methyl-piperazin-1-yl]-6-(3-fluoro-pyridin-4-yl)-3-methyl-3H-pyrimidin-4-one;
6-(3-Fluoro-pyridin-4-yl)-3-methyl-2-((2R)-2-methyl-4-quinolin-3-yl-piperazin-1-yl)-3H-pyrimidin-4-one;
6-(3-Fluoro-pyridin-4-yl)-3-methyl-2-((2R)-2-methyl-4-quinolin-6-yl-piperazin-1-yl)-3H-pyrimidin-4-one;
6-(3-Fluoro-pyridin-4-yl)-2-[(2R)-4-(4-hydroxy-phenyl)-2-methyl-piperazin-1-yl]-3-methyl-3H-pyrimidin-4-one;
4-{(3R)-4-[4-(3-Fluoro-pyridin-4-yl)-1-methyl-6-oxo-1,6-dihydro-pyrimidin-2-yl]-3-methyl-piperazin-1-yl}-benzoic acid;
4-[(3R)-3-Methyl-4-(1-methyl-6-oxo-4-pyridin-4-yl-1,6-dihydro-pyrimidin-2-yl)-piperazin-1-yl]-benzoic acid methyl ester;
3-[(3R)-3-Methyl-4-(1-methyl-6-oxo-4-pyridin-4-yl-1,6-dihydro-pyrimidin-2-yl)-piperazin-1-yl]-benzoic acid methyl ester;
4-[(3R)-3-Methyl-4-(1-methyl-6-oxo-4-pyridin-4-yl-1,6-dihydro-pyrimidin-2-yl)-piperazin-1-yl]-benzonitrile;
3-[(2R)-3-Methyl-4-(1-methyl-6-oxo-4-pyridin-4-yl-1,6-dihydro-pyrimidin-2-yl)-piperazin-1-yl]-benzonitrile;
3-Methyl-2-((2R)-2-methyl-4-pyridin-4-yl-piperazin-1-yl)-6-pyridin-4-yl-3H-pyrimidin-4-one;
3-Methyl-2-((2R)-2-methyl-4-pyridin-3-yl-piperazin-1-yl)-6-pyridin-4-yl-3H-pyrimidin-4-one;
3-Methyl-2-{(2R)-2-methyl-4-[4-(5-methyl-[1,2,4]oxadiazol-3-yl)-phenyl]-piperazin-1-yl}-6-pyridin-4-yl-3H-pyrimidin-4-one;
2-[(2R)-4-(4-Chloro-phenyl)-2-methyl-piperazin-1-yl]-3-methyl-6-pyridin-4-yl-3H-pyrimidin-4-one;
3-Methyl-2-((2R)-2-methyl-4-quinolin-3-yl-piperazin-1-yl)-6-pyridin-4-yl-3H-pyrimidin-4-one;
3-Methyl-2-((2R)-2-methyl-4-quinolin-6-yl-piperazin-1-yl)-6-pyridin-4-yl-3H-pyrimidin-4-one;
2-[(2R)-4-(4-Hydroxy-phenyl)-2-methyl-piperazin-1-yl]-3-methyl-6-pyridin-4-yl-3H-pyrimidin-4-one;
4-[(3R)-3-Methyl-4-(1-methyl-6-oxo-4-pyridin-4-yl-1,6-dihydro-pyrimidin-2-yl)-piperazin-1-yl]-benzoic acid;

1-Methyl-2-{(2R)-2-methyl-4-[4-(5-propyl-[1,2,4]oxadiazol-3-yl)-phenyl]-piperazin-1-yl}-1H-[4,4']bipyrimidinyl-6-one;

2-{(2R)-4-[4-(5-Methoxymethyl-[1,2,4]oxadiazol-3-yl)-phenyl]-2-methyl-piperazin-1-yl}-1-methyl-1H-[4,4']bipyrimidinyl-6-one;

2-{(2R)-4-[4-(5-tert-Butyl-[1,2,4]oxadiazol-3-yl)-phenyl]-2-methyl-piperazin-1-yl}-1-methyl-1H-[4,4']bipyrimidinyl-6-one;

1-Methyl-2-{(2R)-2-methyl-4-[4-(5-pyridin-2-yl-[1,2,4]oxadiazol-3-yl)-phenyl]-piperazin-1-yl}-1H-[4,4']bipyrimidinyl-6-one;

2-{(2R)-4-[4-(5-Aminomethyl-[1,2,4]oxadiazol-3-yl)-phenyl]-2-methyl-piperazin-1-yl}-1-methyl-1H-[4,4']bipyrimidinyl-6-one;

2-((2R)-4-{4-[5-((1S)-1-Amino-ethyl)-[1,2,4]oxadiazol-3-yl]-phenyl}-2-methyl-piperazin-1-yl)-1-methyl-1H-[4,4']bipyrimidinyl-6-one;

2-((2R)-4-{4-[5-(1-Amino-1-methyl-ethyl)-[1,2,4]oxadiazol-3-yl]-phenyl}-2-methyl-piperazin-1-yl)-1-methyl-1H-[4,4']bipyrimidinyl-6-one;

1-Methyl-2-{(2R)-2-methyl-4-[4-((2RS)-5-pyrrolidin-2-yl-[1,2,4]oxadiazol-3-yl)-phenyl]-piperazin-1-yl}-1H-[4,4']bipyrimidinyl-6-one;

2-[(2R)-4-(4-{5-[(1S)-1-Amino-2-(3H-imidazol-4-yl)-ethyl]-[1,2,4]oxadiazol-3-yl}-phenyl)-2-methyl-piperazin-1-yl]-1-methyl-1H-[4,4']bipyrimidinyl-6-one;

1-Methyl-2-{(2R)-2-methyl-4-[4-(5-phenyl-[1,2,4]oxadiazol-3-yl)-phenyl]-piperazin-1-yl}-1H-[4,4']bipyrimidinyl-6-one;

6-(3-Fluoro-pyridin-4-yl)-3-methyl-2-{(2R)-2-methyl-4-[4-(5-propyl-[1,2,4]oxadiazol-3-yl)-phenyl]-piperazin-1-yl}-3H-pyrimidin-4-one;

6-(3-Fluoro-pyridin-4-yl)-2-{(2R)-4-[4-(5-methoxymethyl-[1,2,4]oxadiazol-3-yl)-phenyl]-2-methyl-piperazin-1-yl}-3-methyl-3H-pyrimidin-4-one;

2-{(2R)-4-[4-(5-tert-Butyl-[1,2,4]oxadiazol-3-yl)-phenyl]-2-methyl-piperazin-1-yl}-6-(3-fluoro-pyridin-4-yl)-3-methyl-3H-pyrimidin-4-one;

6-(3-Fluoro-pyridin-4-yl)-3-methyl-2-{(2R)-2-methyl-4-[4-(5-pyridin-4-yl-[1,2,4]oxadiazol-3-yl)-phenyl]-piperazin-1-yl}-3H-pyrimidin-4-one;

6-(3-Fluoro-pyridin-4-yl)-3-methyl-2-{(2R)-2-methyl-4-[4-(5-pyridin-2-yl-[1,2,4]oxadiazol-3-yl)-phenyl]-piperazin-1-yl}-3H-pyrimidin-4-one;

2-{(2R)-4-[4-(5-Aminomethyl-[1,2,4]oxadiazol-3-yl)-phenyl]-2-methyl-piperazin-1-yl}-6-(3-fluoro-pyridin-4-yl)-3-methyl-3H-pyrimidin-4-one;

2-((2R)-4-{4-[5-((1S)-1-Amino-ethyl)-[1,2,4]oxadiazol-3-yl]-phenyl}-2-methyl-piperazin-1-yl)-6-(3-fluoro-pyridin-4-yl)-3-methyl-3H-pyrimidin-4-one;

2-((2R)-4-{4-[5-(1-Amino-1-methyl-ethyl)-[1,2,4]oxadiazol-3-yl]-phenyl}-2-methyl-piperazin-1-yl)-6-(3-fluoro-pyridin-4-yl)-3-methyl-3H-pyrimidin-4-one;

6-(3-Fluoro-pyridin-4-yl)-3-methyl-2-{(2R)-2-methyl-4-[4-((2RS)-5-pyrrolidin-2-yl-[1,2,4]oxadiazol-3-yl)-phenyl]-piperazin-1-yl}-3H-pyrimidin-4-one;

2-[(2R)-4-(4-{5-[(1S)-1-Amino-2-(3H-imidazol-4-yl)-ethyl]-[1,2,4]oxadiazol-3-yl}-phenyl)-2-methyl-piperazin-1-yl]-6-(3-fluoro-pyridin-4-yl)-3-methyl-3H-pyrimidin-4-one;

6-(3-Fluoro-pyridin-4-yl)-3-methyl-2-{(2R)-2-methyl-4-[4-(5-phenyl-[1,2,4]oxadiazol-3-yl)-phenyl]-piperazin-1-yl}-3H-pyrimidin-4-one;

2-((2R)-4-{4-[5-((1R)-Amino-phenyl-methyl)-[1,2,4]oxadiazol-3-yl]-phenyl}-2-methyl-piperazin-1-yl)-6-(3-fluoro-pyridin-4-yl)-3-methyl-3H-pyrimidin-4-one;

2-((2R)-4-{4-[5-((1R)-1-Amino-ethyl)-[1,2,4]oxadiazol-3-yl]-phenyl}-2-methyl-piperazin-1-yl)-6-(3-fluoro-pyridin-4-yl)-3-methyl-3H-pyrimidin-4-one;

3-Methyl-2-{(2R)-2-methyl-4-[4-(5-propyl-[1,2,4]oxadiazol-3-yl)-phenyl]-piperazin-1-yl}-6-pyridin-4-yl-3H-pyrimidin-4-one;

2-{(2R)-4-[4-(5-Methoxymethyl-[1,2,4]oxadiazol-3-yl)-phenyl]-2-methyl-piperazin-1-yl}-3-methyl-6-pyridin-4-yl-3H-pyrimidin-4-one;

3-Methyl-2-{(2R)-2-methyl-4-[4-(5-pyridin-2-yl-[1,2,4]oxadiazol-3-yl)-phenyl]-piperazin-1-yl}-6-pyridin-4-yl-3H-pyrimidin-4-one;

2-{(2R)-4-[4-(5-Aminomethyl-[1,2,4]oxadiazol-3-yl)-phenyl]-2-methyl-piperazin-1-yl}-3-methyl-6-pyridin-4-yl-3H-pyrimidin-4-one;

2-((2R)-4-{4-[5-((1S)-1-Amino-ethyl)-[1,2,4]oxadiazol-3-yl]-phenyl}-2-methyl-piperazin-1-yl)-3-methyl-6-pyridin-4-yl-3H-pyrimidin-4-one;

2-((2R)-4-{4-[5-(1-Amino-1-methyl-ethyl)-[1,2,4]oxadiazol-3-yl]-phenyl}-2-methyl-piperazin-1-yl)-3-methyl-6-pyridin-4-yl-3H-pyrimidin-4-one;

3-Methyl-2-{(2R)-2-methyl-4-[4-((2RS)-5-pyrrolidin-2-yl-[1,2,4]oxadiazol-3-yl)-phenyl]-piperazin-1-yl}-6-pyridin-4-yl-3H-pyrimidin-4-one;

2-[(2R)-4-(4-{5-[(1S)-1-Amino-2-(3H-imidazol-4-yl)-ethyl]-[1,2,4]oxadiazol-3-yl}-phenyl)-2-methyl-piperazin-1-yl]-3-methyl-6-pyridin-4-yl-3H-pyrimidin-4-one;

2-((2R)-4-{4-[5-((1R)-1-Amino-ethyl)-[1,2,4]oxadiazol-3-yl]-phenyl}-2-methyl-piperazin-1-yl)-3-methyl-6-pyridin-4-yl-3H-pyrimidin-4-one;

3-Methyl-2-{(2R)-2-methyl-4-[4-(5-pyridin-4-yl-[1,2,4]oxadiazol-3-yl)-phenyl]-piperazin-1-yl}-6-pyridin-4-yl-3H-pyrimidin-4-one; and 2-[(2R)-4-(3-Hydroxy-phenyl)-2-methyl-piperazin-1-yl]-3-methyl-6-pyridin-4-yl-3H-pyrimidin-4-one, an optically active isomer thereof, or a pharmaceutically acceptable salt thereof.

29. A medicament comprising as an active ingredient a substance selected from the group consisting of the compound represented by the formula (I) and an optically active isomer thereof, or a pharmaceutically acceptable salt thereof according to any one of the above 1 to 28.

30. A tau protein kinase 1 inhibitor selected from the group consisting of the compound represented by the formula (I) and an optically active isomer thereof, or a pharmaceutically acceptable salt thereof according to any one of the above 1 to 28.

31. The medicament according to the above 29 which is used for preventive and/or therapeutic treatment of a disease caused by tau protein kinase 1 hyperactivity.

32. The medicament according to the above 29 which is used for preventive and/or therapeutic treatment of a neurodegenerative disease.

33. The medicament according to the above 32, wherein the disease is selected from the group consisting of Alzheimer disease, ischemic cerebrovascular accidents, Down syndrome, cerebral bleeding due to cerebral amyloid angiopathy, progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration, frontotemporal dementia, vascular dementia, traumatic injuries, brain and spinal cord trauma, peripheral neuropathies, retinopathies and glaucoma.

34. The medicament according to the above 29, which is used for preventive and/or therapeutic treatment of a disease selected from the group consisting of non-insulin dependent diabetes, obesity, manic depressive illness, schizophrenia, alopecia, breast cancer, non-small cell lung carcinoma, thyroid cancer, T or B-cell leukemia, and a virus-induced tumor.

MODE FOR CARRYING OUT THE INVENTION

Unless otherwise indicated, the following definitions are set forth to illustrate and defined the meaning and scope of the various terms used to describe the invention herein.

The term "$C_1$-$C_6$ alkyl" means alkyl having 1 to 6 carbon atoms which may be either linear or branched, for example, methyl, ethyl, n-propyl, isopropyl, n-butyl, isobutyl, sec-butyl, tert-butyl, n-pentyl, isopentyl, neopentyl, 1,1-dimethylpropyl, n-hexyl, isohexyl.

The term "$C_1$-$C_{12}$ alkyl" means alkyl having 1 to 12 carbon atoms which may be either linear or branched, for example, methyl, ethyl, n-propyl, isopropyl, n-butyl, isobutyl, sec-butyl, tert-butyl, n-pentyl, isopentyl, neopentyl, 1,1-dimethylpropyl, n-hexyl, isohexyl, heptyl, octyl, nonyl, decyl, undecyl or dodecyl.

The term "$C_2$-$C_6$ alkenyl" means alkenyl having 2 to 6 carbon atoms, for example, vinyl, propenyl, butenyl, pentenyl, hexenyl.

The term "$C_2$-$C_6$ alkynyl" means alkynyl group having 2 to 6 carbon atoms, for example, ethynyl, propynl, butynyl, pentynyl, hexynyl.

The term "$C_3$-$C_7$ cycloalkyl" means cycloalkyl having 3 to 7 atoms, for example, cyclopropyl, cyclobutyl, cyclopentyl, cyclohexyl, cycloheptyl.

The term "$C_6$-$C_{10}$ aryl" means a group having 6 to 10 carbon atoms derived from, for example, benzene, naphthalene, indane, indene, tetrahydronaphthalene. The bond position in the cycle is not limited.

The term "heterocyclic group", "heterocycle", and "heterocyclic ring" mean cyclic group derived from, for example, furan, dihydrofuran, tetrahydrofuran, pyran, dihydropyran, tetrahydropyran, benzofuran, dihydrobenzofuran, isobenzofuran, chromene, chroman, isochroman, thiophene, benzothiophene, pyrrole, pyrroline, pyrrolidine, imidazole, imidazoline, imidazolidine, pyrazole, pyrazoline, pyrazolidine, triazole, tetrazole, pyridine, pyridine oxide, piperidine, pyrazine, piperazine, pyrimidine, pyridazine, indole, indoline, isoindole, isoindoline, indazole, benzimidazole, benzotriazole, tetrahydroisoquinoline, benzothiazolinone, benzoxazolinone, purine, quinolizine, quinoline, phthalazine, naphthyridine, quinoxaline, quinazoline, cinnoline, pteridine, oxazole, oxazolidine, isoxazole, isoxazolidine, oxadiazole, thiazole, benzothiazole, thiazolidine, isothiazole, isothiazolidine, benzodioxole, dioxane, benzodioxane, dithian, morpholine, thiomorpholine, phthalimide homopiperidine, homopiperazine. The bond position in the cycle is not limited.

In the specification, when a functional group is defined as "which may be substituted" or "optionally substituted", the number of substituents as well as their types and substituting positions are not particularly limited, and when two or more substituents are present, they may be the same or different.

The substituent in the present specification means, for example, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, $C_6$-$C_{10}$ aryl, heterocycles, $C_1$-$C_6$ alkoxy, $C_3$-$C_6$ alkenyloxy, $C_3$-$C_6$ alkynyloxy, $C_3$-$C_7$ cycloalkyloxy, $C_3$-$C_7$ cycloalkenyloxy, $C_6$-$C_{10}$ aryloxy, heterocycleoxy, halogen (chlorine, bromine, fluorine, iodine), nitro, amino, cyano, hydroxyl, oxo, $C_1$-$C_6$ alkylcarbonyl, $C_2$-$C_6$ alkenylcarbonyl, $C_2$-$C_6$ alkynylcarbonyl, $C_3$-$C_7$ cycloalkylcarbonyl, $C_3$-$C_7$ cycloalkenylcarbonyl, $C_6$-$C_{10}$ arylcarbonyl, heterocyclecarbonyl, $C_1$-$C_6$ alkylsulfonyl, $C_2$-$C_6$ alkenylsulfonyl, $C_2$-$C_6$ alkynylsulfonyl, $C_3$-$C_7$ cycloalkylsulfonyl, $C_3$-$C_7$ cycloalkenylsulfonyl, $C_6$-$C_{10}$ arylsulfonyl, heterocyclesulfonyl, $C_1$-$C_6$ alkoxycarbonyl, $C_3$-$C_6$ alkenyloxycarbonyl, $C_3$-$C_6$ alkynyloxycarbonyl, $C_3$-$C_7$ cycloalkyloxycarbonyl, $C_3$-$C_7$ cycloalkenyloxycarbonyl, $C_6$-$C_{10}$ aryloxycarbonyl, heterocycleoxycarbonyl, amino, $C_1$-$C_6$ alkylamino, $C_3$-$C_6$ alkenylamino, $C_3$-$C_6$ alkynylamino, $C_3$-$C_7$ cycloalkylamino, $C_3$-$C_7$ cycloalkenylamino, $C_6$-$C_{10}$ arylamino, heterocycle-amino, N,N-di-$C_1$-$C_6$ alkylamino, aminocarbonyl, $C_1$-$C_6$ alkylaminocarbonyl, $C_3$-$C_6$ alkenylaminocarbonyl, $C_3$-$C_6$ alkynylaminocarbonyl, $C_3$-$C_7$ cycloalkylaminocarbonyl, $C_3$-$C_7$ cycloalkenylaminocarbonyl, $C_6$-$C_{10}$ arylaminocarbonyl, heterocycle-aminocarbonyl, N,N-di-$C_1$-$C_6$ dialkylaminocarbonyl. The number of substituents as well as their types and substituting positions are not particularly limited, and when two or more substituents are present, they may be the same or different. In the above substituents, every term expressed by "$C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, $C_6$-$C_{10}$ aryl, heterocycle or $C_1$-$C_6$ alkoxy" represents the same meaning as defined in the above. These substituents are also substituted by the substituents described above.

$R^2$ may preferably be a hydrogen atom.

$R^3$ may be preferably hydrogen atom or a $C_1$-$C_3$ alkyl group, more preferably be hydrogen atom or methyl group, further preferably methyl group.

$R^4$ may preferably be a group represented by the formula (II) wherein $A^{14}$ represents a $C_1$-$C_6$ alkyl group, $A^{13}$ represents bond or oxygen atom, $A^{12}$ represents bond or C=O. When at least one of $R^5$ and $R^6$, X and $R^5$, X and $R^6$, and $R^6$ and $R^6$ combine to each other to form a fused or spiro, carbocyclic or heterocyclic ring, together with the ring which contains X, and $R^5$, $R^4$ and $R^6$ bind to, $R^4$ may preferably be hydrogen atom. $R^4$ may also preferably form, with $R^5$, a 1,2,3,4-tetrahydronaphthalene which may be substituted, a chroman ring which may be substituted, a cyclohexane ring which may be substituted, a cyclopentane ring which may be substituted, a tetrahydrofuran ring which may be substituted, together with the two carbon atoms to which $R^4$ and $R^5$ bind to. Alternatively, $R^4$ may preferably combine to $R^6$ to form a $C_2$-$C_4$ methylene group as a bridge.

When X is bond, $R^5$ may preferably form, with $R^6$, a pyrrolidine ring which may be substituted or chroman ring together with the two carbon atoms which have X as bond. Preferable examples of the substituent to the pyrrolidine ring include phenyl group, a methoxy-substituted phenyl group, and oxo group. The substituting position of the pyrrolidine ring may preferably be the nitrogen atom.

$R^5$ may also preferably form, with X, a cyclohexane ring which may be substituted, a pyrrolidine ring which may be substituted, or a 1,2,3,4-tetrahydroisoquinoline ring which may be substituted, together with the carbon atom which $R^5$ binds to.

The symbol p may preferably be 0, and may also preferably be 1, and $R^6$ binds to any one of X, $R^4$ and $R^5$.

When X does not form any ring with $R^4$, $R^5$ or $R^6$, X may preferably be oxygen atom, $CH_2$, or a group represented by the formula (III) wherein $A^9$ represents bond, $A^{10}$ represents bond and $A^{11}$ represents hydrogen atom, a $C_1$-$C_6$ alkyl group which may be substituted, a $C_6$-$C_{10}$ aryl group which may be substituted, or a heterocyclic group which may be substituted. More preferably, X may be an oxygen atom or a group represented by the formula (III) wherein $A^9$ represents bond, $A^{10}$ represents bond and $A^{11}$ represents formula (III-b) wherein $A^{21}$ represents bond and B represents a $C_6$-$C_{10}$ aryl group which may be substituted.

R²⁰ may be preferably a halogen atom, a $C_1$-$C_3$ alkyl group, a $C_1$-$C_3$ alkyloxy group, or a $C_6$-$C_{10}$ aryl group, more preferably a halogen atom, methyl group, or methoxy group.

The symbol q may be preferably 0 to 2, more preferably 0 or 1.

The pharmaceutically acceptable salt of the compound represented by the aforementioned formula (I) may include the salt with inorganic acid such as hydrochloric acid, hydrobromic acid and the like and the salt with organic acid such as acetic acid, propionic acid, tartaric acid, fumaric acid, maleic acid, malic acid, oxalic acid, succinic acid, citric acid, benzoic acid and the like.

In addition to the compound represented by the aforementioned formula (I), an optically active isomer thereof, or a pharmaceutically acceptable salt thereof, their solvates and hydrates also fall within the scope of the present invention. The compound represented by the formula (I) may have one or more asymmetric carbon atoms. As for the stereochemistry of such asymmetric carbon atoms, they may independently be in either of (R) and (S) configuration, and the pyrimidone derivative may exist as stereoisomers such as optical isomers, or diastereoisomers. Any stereoisomers of pure form, any mixtures of stereoisomers, racemates and the like fall within the scope of the present invention Examples of preferred compounds of the present invention are shown in the tables set out below. However, the scope of the present invention is not limited by the following compounds.

TABLE 1

| Compound No. | STRUCTURE |
|---|---|
| B1 | 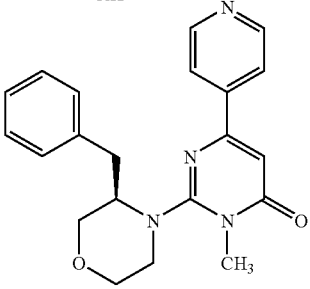 |
| B2 | 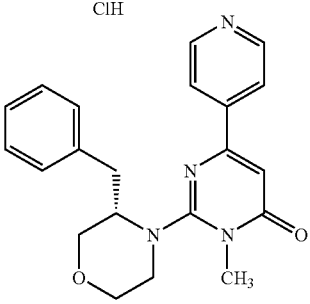 [SMILES: Cl ; Cn1c(N2CCOC[C@@H]2Cc2ccccc2)nc(-c2ccncc2)cc1=O] |
| B3 | 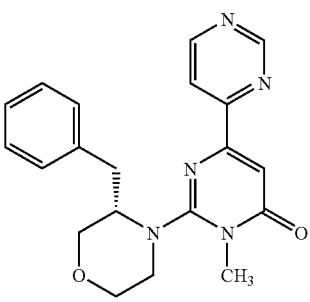 [SMILES: Cn1c(N2CCOC[C@@H]2Cc2ccccc2)nc(-c2ccncn2)cc1=O] |

TABLE 1-continued

| Compound No. | STRUCTURE |
|---|---|
| B4 | 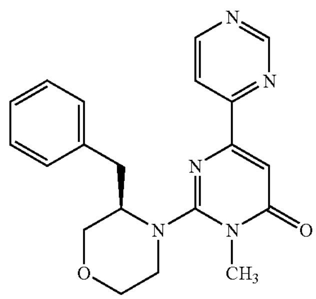 [SMILES: Cn1c(N2CCOC[C@H]2Cc2ccccc2)nc(-c2ccncn2)cc1=O] |
| B5 | 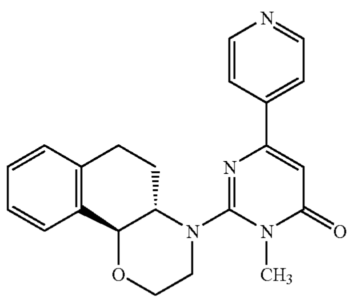 [SMILES: Cn1c(N2CCO[C@H]3c4ccccc4CC[C@@H]32)nc(-c2ccncc2)cc1=O] |
| B6 | 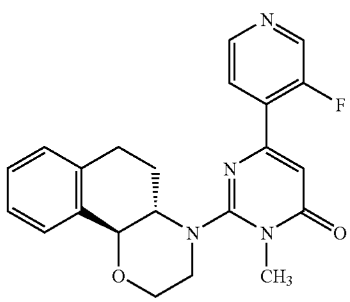 [SMILES: Cn1c(N2CCO[C@H]3c4ccccc4CC[C@@H]32)nc(-c2ccncc2F)cc1=O] |
| B7 | 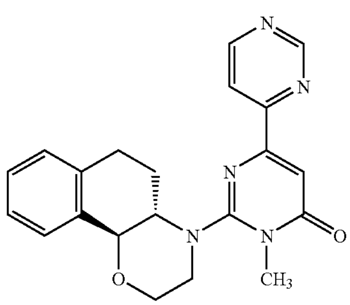 |
| B8 | 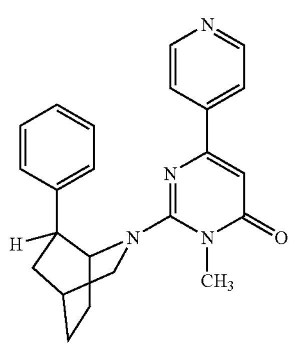 [SMILES: Cn1c(N2CC3CCC2C(c2ccccc2)C3)nc(-c2ccncc2)cc1=O] |

TABLE 1-continued
| Compound No. | STRUCTURE |
|---|---|
| B9 | 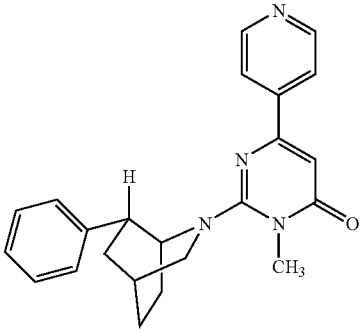 [SMILES: Cn1c(N2CC3CCC2C(c2ccccc2)C3)nc(-c2ccncc2)cc1=O] |
| B10 | 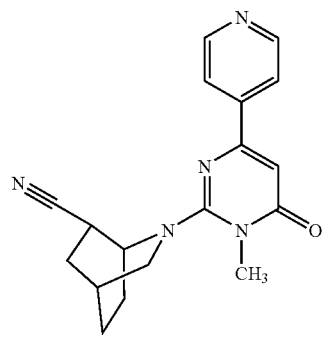 [SMILES: Cn1c(N2CC3CCC2C(C#N)C3)nc(-c2ccncc2)cc1=O] |
| B11 | 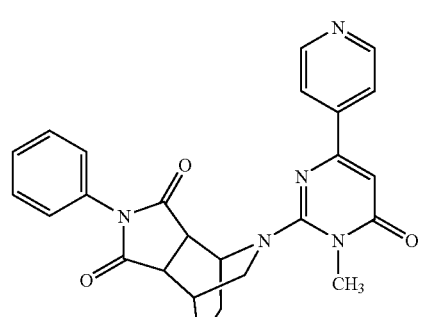 |
| B12 | 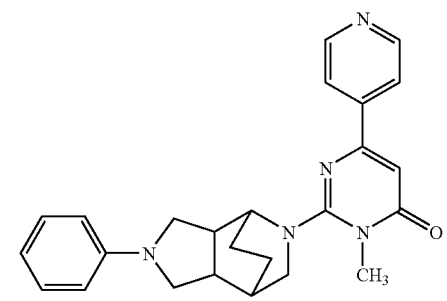 [SMILES: Cn1c(N2CC3CCC2C2CN(c4ccccc4)CC32)nc(-c2ccncc2)cc1=O] |

TABLE 1-continued
| Compound No. | STRUCTURE |
|---|---|
| B13 | 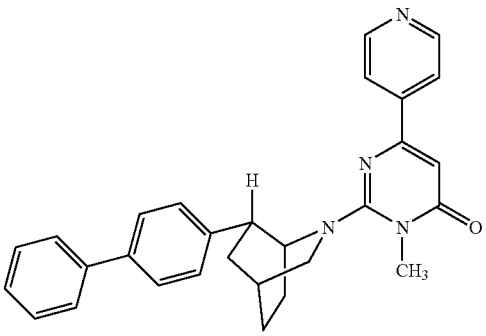 [SMILES: Cn1c(N2CC3CCC2C(c2ccc(-c4ccccc4)cc2)C3)nc(-c2ccncc2)cc1=O] |
| B14 | 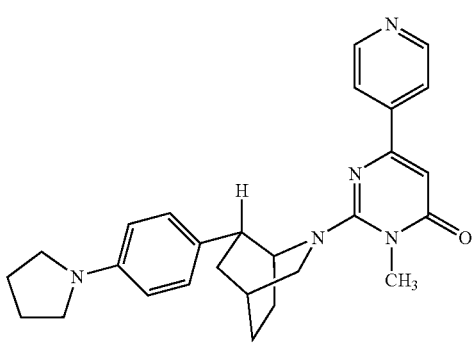 [SMILES: Cn1c(N2CC3CCC2C(c2ccc(N4CCCC4)cc2)C3)nc(-c2ccncc2)cc1=O] |
| B15 | 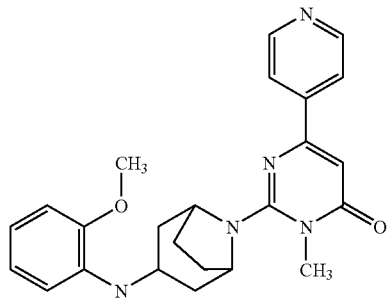 [SMILES: COc1ccccc1NC1CC2CCC(C1)N2c1nc(-c2ccncc2)cc(=O)n1C] |
| B16 | 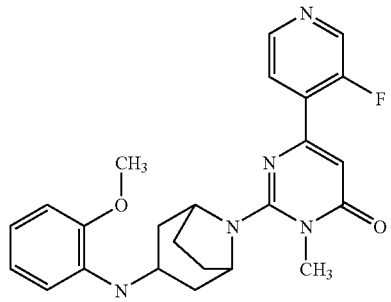 [SMILES: COc1ccccc1NC1CC2CCC(C1)N2c1nc(-c2ccncc2F)cc(=O)n1C] |

TABLE 1-continued

| Compound No. | STRUCTURE |
|---|---|
| B17 | 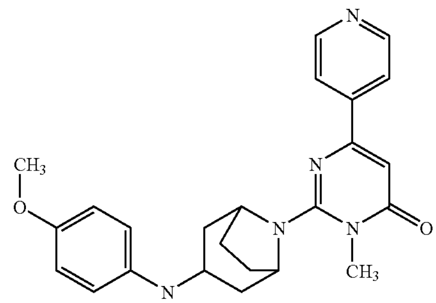 [SMILES: COc1ccc(NC2CC3CCC(C2)N3c2nc(-c3ccncc3)cc(=O)n2C)cc1] |
| B18 | 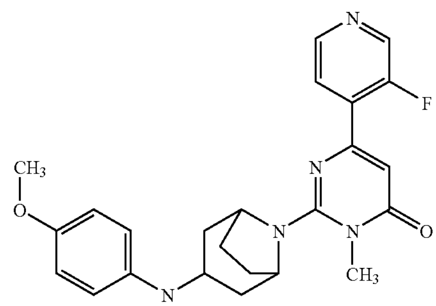 [SMILES: COc1ccc(NC2CC3CCC(C2)N3c2nc(-c3ccncc3F)cc(=O)n2C)cc1] |
| B19 | 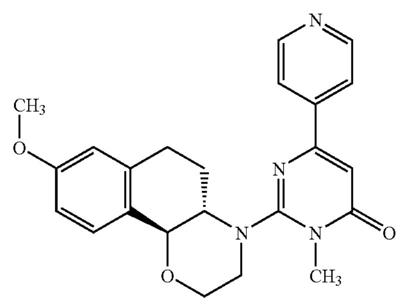 [SMILES: COc1ccc2c(c1)CC[C@H]1[C@H]2OCCN1c1nc(-c2ccncc2)cc(=O)n1C] |
| B20 | 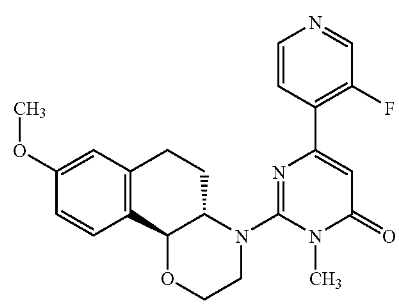 [SMILES: COc1ccc2c(c1)CC[C@H]1[C@H]2OCCN1c1nc(-c2ccncc2F)cc(=O)n1C] |
| B21 | 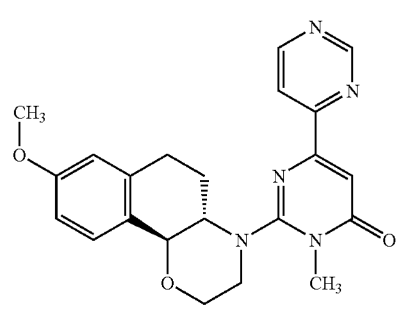 [SMILES: COc1ccc2c(c1)CC[C@H]1[C@H]2OCCN1c1nc(-c2ccncn2)cc(=O)n1C] |

TABLE 1-continued

| Compound No. | STRUCTURE |
|---|---|
| B22 | 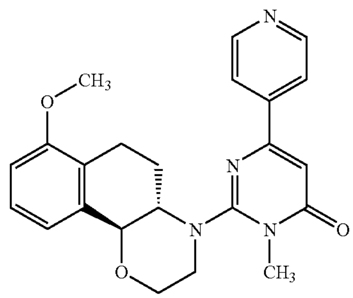 |
| B23 | 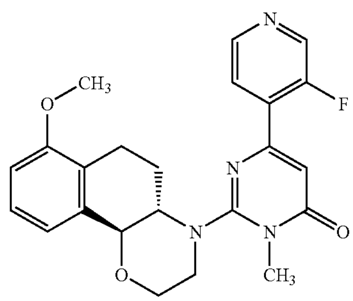 |
| B24 | 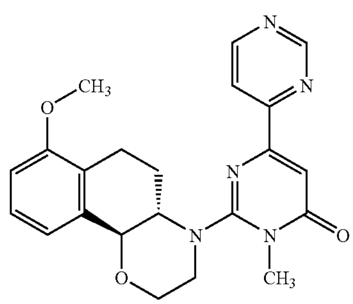 [SMILES: COc1cccc2c1CC[C@H]1[C@H]2OCCN1c1nc(-c2ccncn2)cc(=O)n1C] |
| B25 | 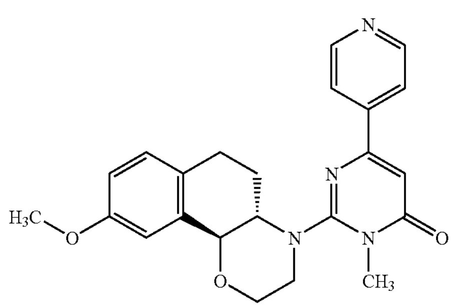 |
| B26 | 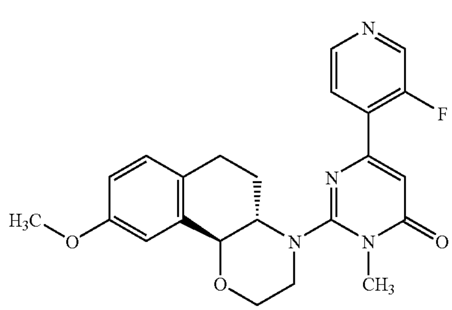 [SMILES: COc1ccc2c(c1)[C@@H]1OCCN(c3nc(-c4ccncc4F)cc(=O)n3C)[C@H]1CC2] |

TABLE 1-continued
| Compound No. | STRUCTURE |
|---|---|
| B27 | 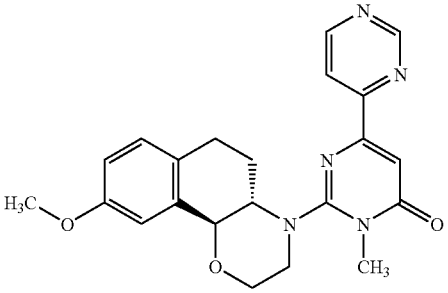 [SMILES: COc1ccc2c(c1)[C@@H]1OCCN(c3nc(-c4ccncn4)cc(=O)n3C)[C@H]1CC2] |
| B28 | 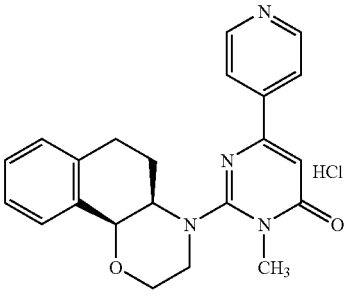 [SMILES: Cn1c(N2CCO[C@H]3c4ccccc4CC[C@H]32)nc(-c2ccncc2)cc1=O ; Cl] |
| B29 | 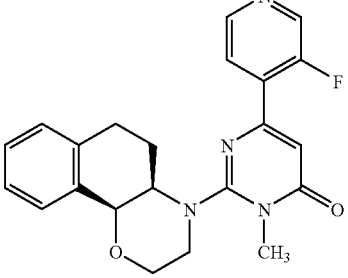 |
| B30 | 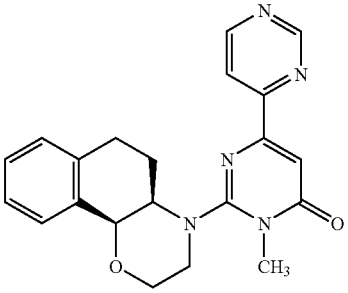 |
| B31 | 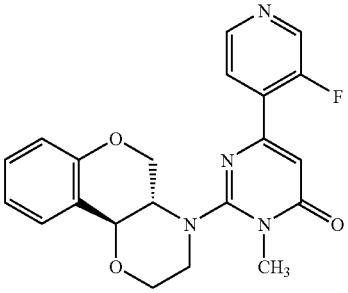 |

TABLE 1-continued

| Compound No. | STRUCTURE |
|---|---|
| B32 | 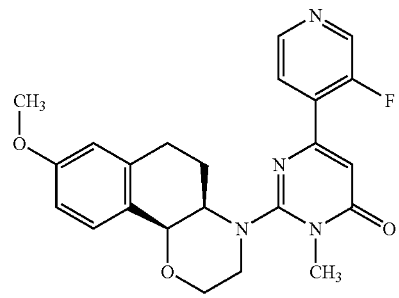 [SMILES: COc1ccc2c(c1)CC[C@@H]1[C@H]2OCCN1c1nc(-c2ccncc2F)cc(=O)n1C] |
| B33 | 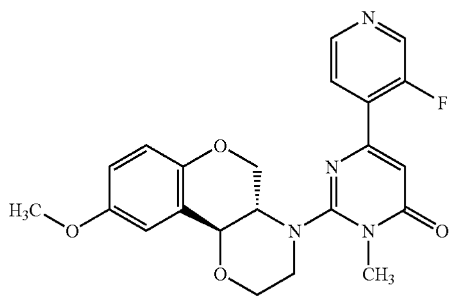 |
| B34 | 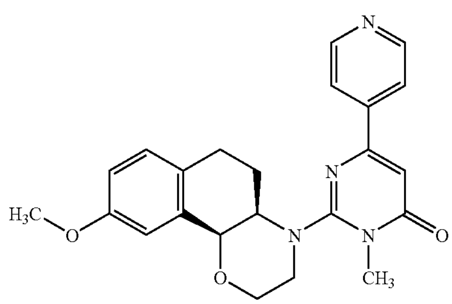 [SMILES: COc1ccc2c(c1)[C@@H]1OCCN(c3nc(-c4ccncn4)cc(=O)n3C)[C@@H]1CC2] |
| B35 | 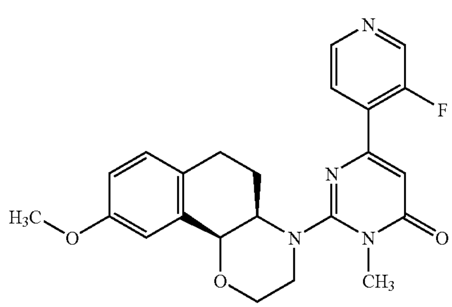 |
| B36 | 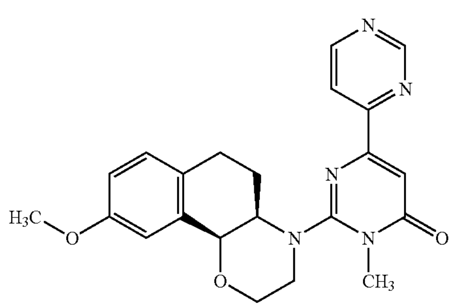 |

TABLE 1-continued
| Compound No. | STRUCTURE |
|---|---|
| B37 | 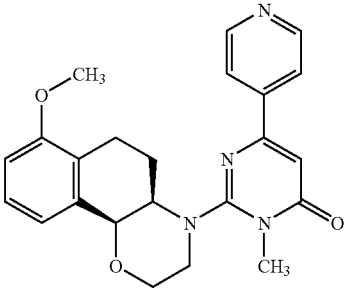 [SMILES: COc1cccc2c1CC[C@@H]1[C@H]2OCCN1c1nc(-c2ccncc2)cc(=O)n1C] |
| B38 | 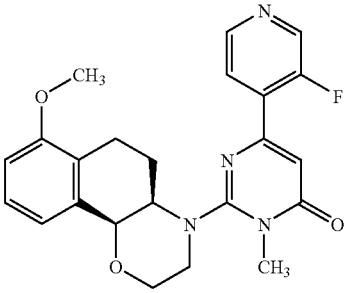 [SMILES: COc1cccc2c1CC[C@@H]1[C@H]2OCCN1c1nc(-c2ccncc2F)cc(=O)n1C] |
| B39 | 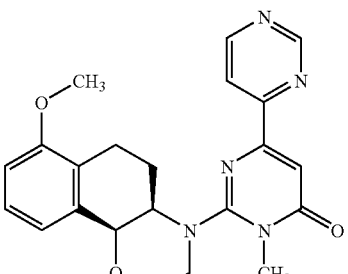 |
| B40 | 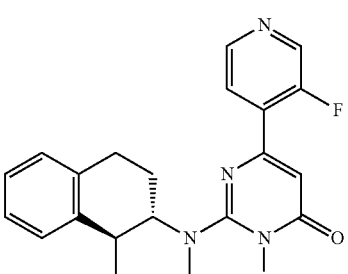 |
| B41 | 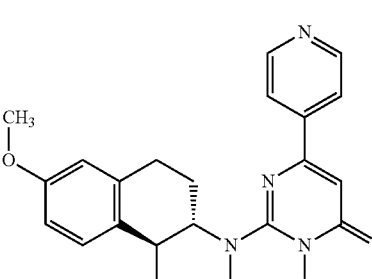 |

TABLE 1-continued
| Compound No. | STRUCTURE |
|---|---|
| B42 | 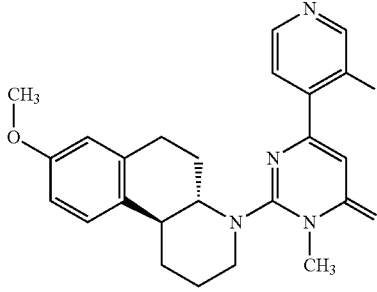 |
| B43 | 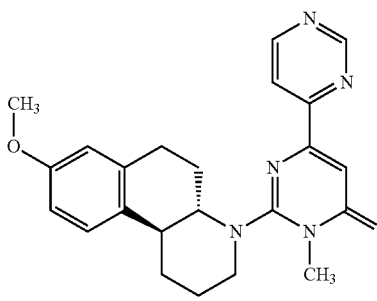 |
| B44 | 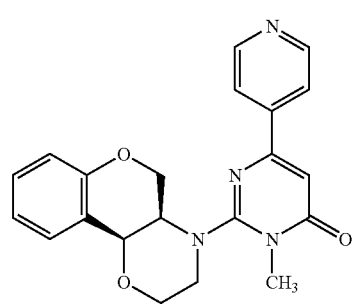 [SMILES: Cn1c(N2CCO[C@H]3c4ccccc4OC[C@H]32)nc(-c2ccncn2)cc1=O] |
| B45 | 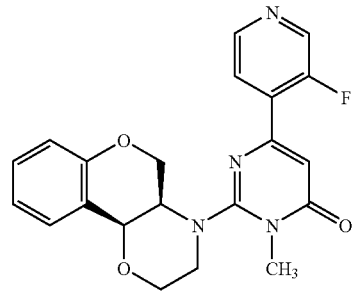 |
| B46 | 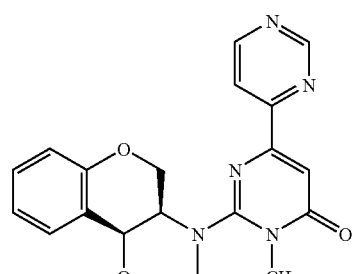 |

TABLE 1-continued
| Compound No. | STRUCTURE |
|---|---|
| B47 | 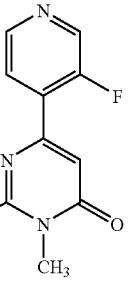 |
| B48 | 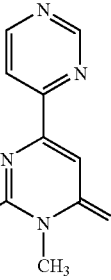 |
| B49 | 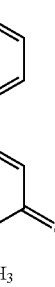 |
| B50 | 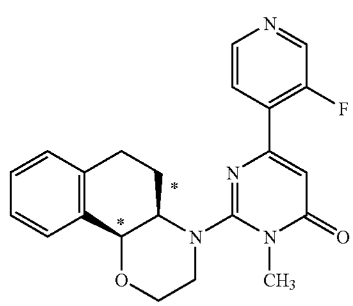 |
| B51 | 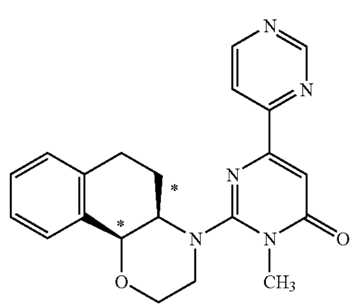 |

TABLE 1-continued

| Compound No. | STRUCTURE |
|---|---|
| B52 | 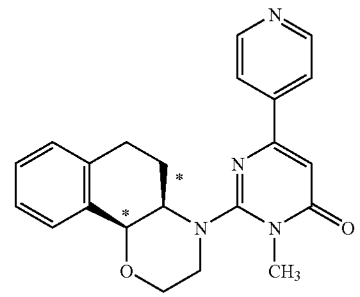 [SMILES: Cn1c(N2CCO[C@H]3c4ccccc4CC[C@H]32)nc(-c2ccncc2)cc1=O] |
| B53 | 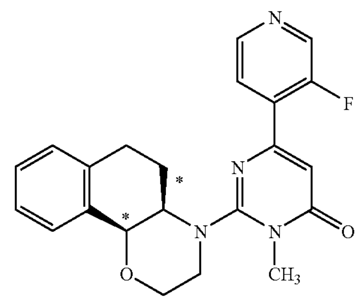 [SMILES: Cn1c(N2CCO[C@H]3c4ccccc4CC[C@H]32)nc(-c2ccncc2F)cc1=O] |
| B54 | 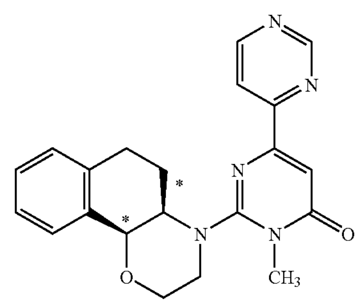 |
| B55 | 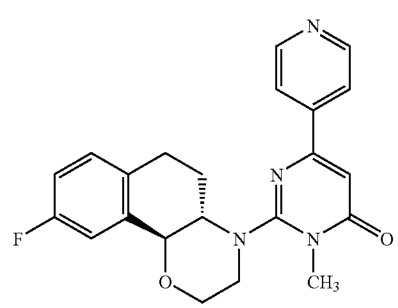 [SMILES: Cn1c(N2CCO[C@H]3c4cc(F)ccc4CC[C@@H]32)nc(-c2ccncc2)cc1=O] |
| B56 | 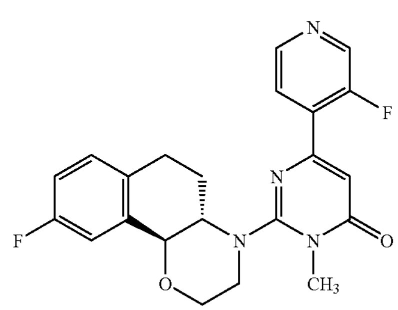 |

TABLE 1-continued
| Compound No. | STRUCTURE |
|---|---|
| B57 | 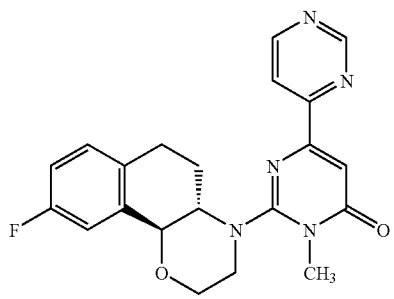 |
| B58 | 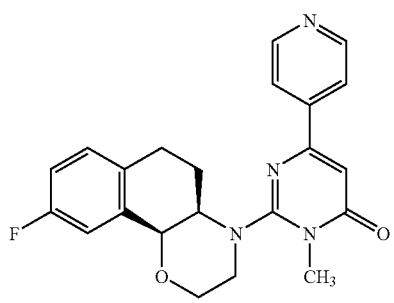 |
| B59 | 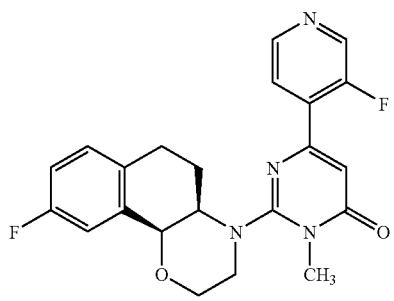 [SMILES: Cn1c(N2CCO[C@H]3c4cc(F)ccc4CC[C@H]32)nc(-c2ccncc2F)cc1=O] |
| B60 | 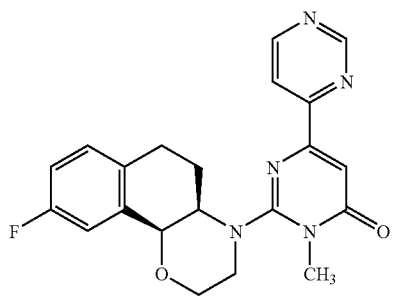 [SMILES: Cn1c(N2CCO[C@H]3c4cc(F)ccc4CC[C@H]32)nc(-c2ccncn2)cc1=O] |
| B61 | 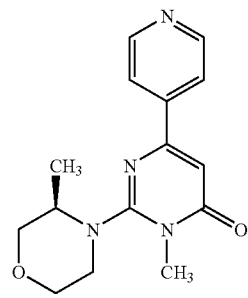 [SMILES: C[C@@H]1COCCN1c1nc(-c2ccncc2)cc(=O)n1C] |

TABLE 1-continued
| Compound No. | STRUCTURE |
|---|---|
| B62 | 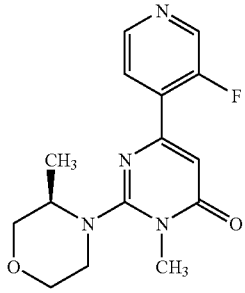 [SMILES: C[C@@H]1COCCN1c1nc(-c2ccncc2F)cc(=O)n1C] |
| B63 | 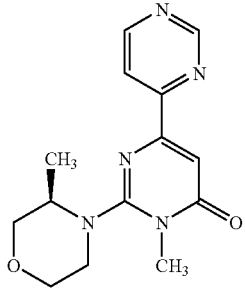 [SMILES: C[C@@H]1COCCN1c1nc(-c2ccncn2)cc(=O)n1C] |
| B64 | 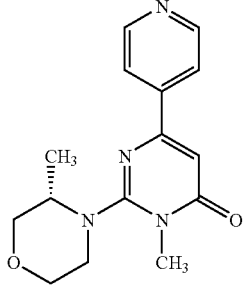 [SMILES: C[C@H]1COCCN1c1nc(-c2ccncc2)cc(=O)n1C] |
| B65 | 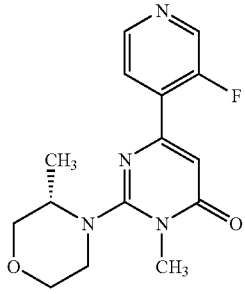 |
| B66 | 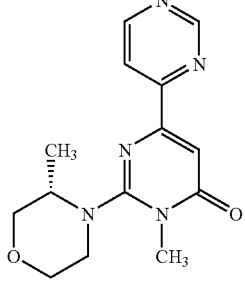 |

TABLE 1-continued
| Compound No. | STRUCTURE |
|---|---|
| B67 | 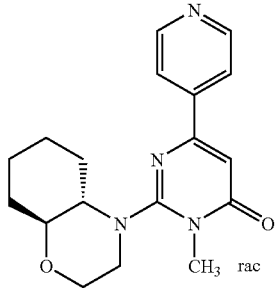 |
| B68 | 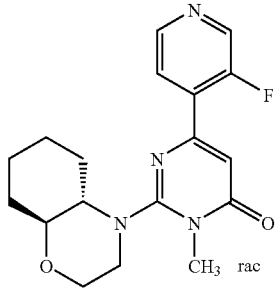 [SMILES: Cn1c(N2CCO[C@H]3CCCC[C@@H]32)nc(-c2ccncc2F)cc1=O] |
| B69 | 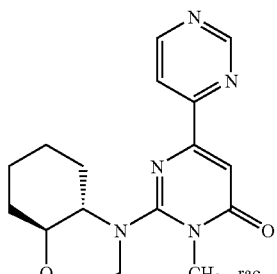 |
| B70 | 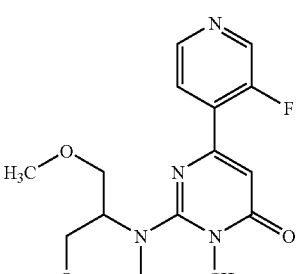 |
| B71 | 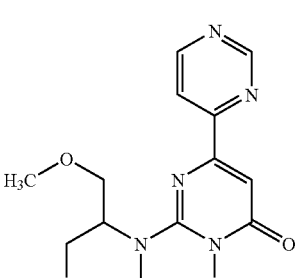 |

TABLE 1-continued

| Compound No. | STRUCTURE |
|---|---|
| B72 | 3-(methoxymethyl)-morpholinyl-pyrimidinone with 4-pyridyl and N-methyl (rac) |
| B73 | 3-ethyl-morpholinyl-pyrimidinone with 4-pyridyl and N-methyl |
| B74 | 3-ethyl-morpholinyl-pyrimidinone with 3-fluoro-4-pyridyl and N-methyl |
| B75 | 3-ethyl-morpholinyl-pyrimidinone with 4-pyrimidinyl and N-methyl |
| B76 | 2-azabicyclo-pyrimidinone with 4-pyridyl and N-methyl |

TABLE 1-continued

| Compound No. | STRUCTURE |
|---|---|
| B77 | 6-(3-fluoropyridin-4-yl)-2-(2-azabicyclo[2.2.1]heptan-2-yl)-3-methylpyrimidin-4(3H)-one |
| B78 | 2-(2-azabicyclo[2.2.1]heptan-2-yl)-3-methyl-6-(pyrimidin-4-yl)pyrimidin-4(3H)-one |
| B79 | (S)-3-isopropyl-4-(3-methyl-4-oxo-6-(pyridin-4-yl)-3,4-dihydropyrimidin-2-yl)morpholine · HCl |
| B80 | (S)-4-(6-(3-fluoropyridin-4-yl)-3-methyl-4-oxo-3,4-dihydropyrimidin-2-yl)-3-isopropylmorpholine · HCl |
| B81 | (S)-3-isopropyl-4-(3-methyl-4-oxo-6-(pyrimidin-4-yl)-3,4-dihydropyrimidin-2-yl)morpholine · HCl |

TABLE 1-continued
| Compound No. | STRUCTURE |
|---|---|
| B82 | 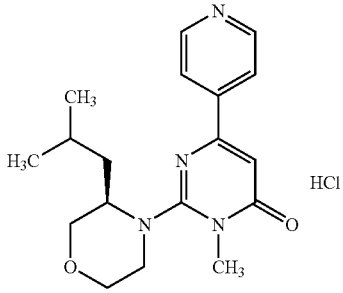 [SMILES: CC(C)C[C@@H]1COCCN1c1nc(-c2ccncc2)cc(=O)n1C ; Cl] HCl |
| B83 | 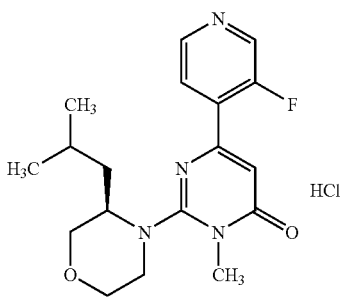 [SMILES: CC(C)C[C@@H]1COCCN1c1nc(-c2ccncc2F)cc(=O)n1C ; Cl] HCl |
| B84 | 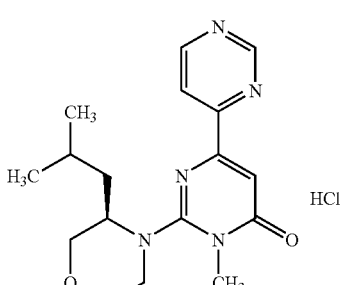 HCl |
| B85 | 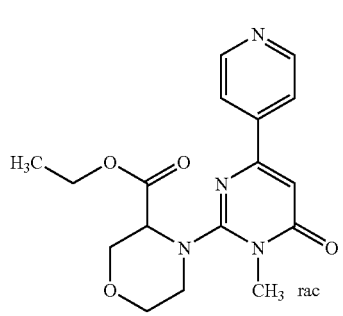 rac |
| B86 | 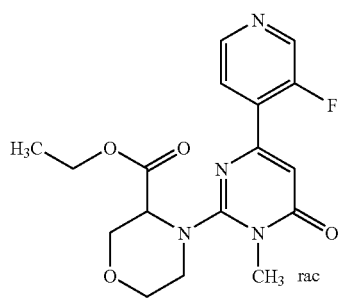 rac |

TABLE 1-continued
| Compound No. | STRUCTURE |
|---|---|
| B87 | 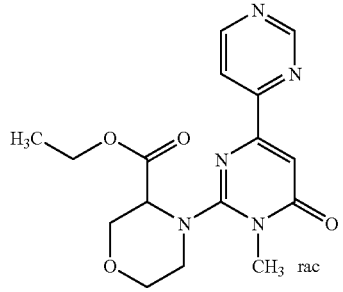 |
| B88 | 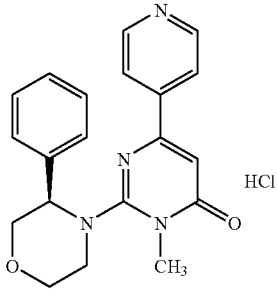 [SMILES: Cn1c(N2CCOC[C@H]2c2ccccc2)nc(-c2ccncc2)cc1=O ; Cl] |
| B89 | 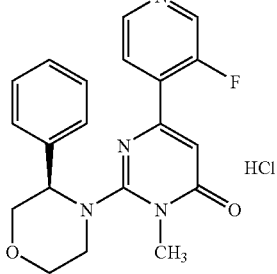 |
| B90 | 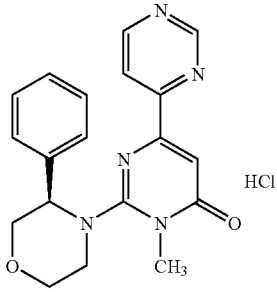 [SMILES: Cn1c(N2CCOC[C@H]2c2ccccc2)nc(-c2ccncn2)cc1=O ; Cl] |
| B91 | 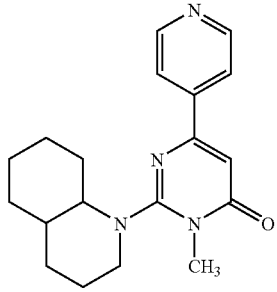 [SMILES: Cn1c(N2CCCC3CCCCC32)nc(-c2ccncn2)cc1=O] |

TABLE 1-continued
| Compound No. | STRUCTURE |
|---|---|
| B92 | 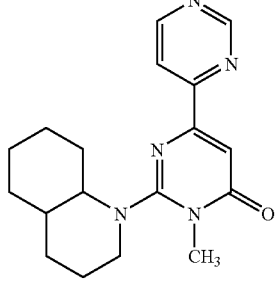 |
| B93 | 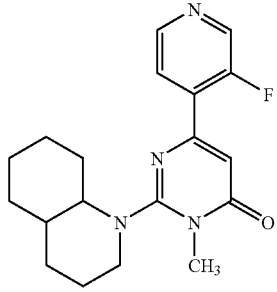 [SMILES: Cn1c(N2CCCC3CCCCC32)nc(-c2ccncc2F)cc1=O] |
| B94 | 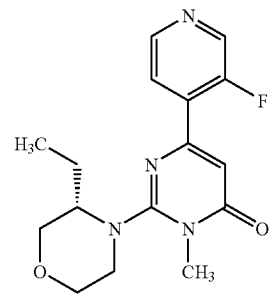 [SMILES: CC[C@H]1COCCN1c1nc(-c2ccncc2F)cc(=O)n1C] |
| B95 | 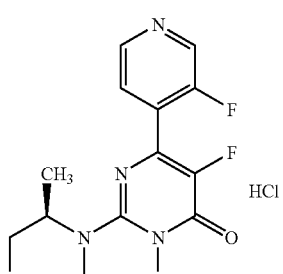 HCl |
| B96 | 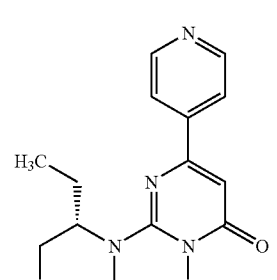 |

TABLE 1-continued

| Compound No. | STRUCTURE |
|---|---|
| B97 | (S)-3-ethylmorpholine linked to 2-position of 3-methyl-6-(pyrimidin-4-yl)pyrimidin-4(3H)-one |
| B98 | (S)-3-methylmorpholine linked to 2-position of 5-fluoro-3-methyl-6-(pyridin-4-yl)pyrimidin-4(3H)-one |
| B99 | (S)-3-methylmorpholine linked to 2-position of 6-(3-chloropyridin-4-yl)-3-methylpyrimidin-4(3H)-one · HCl |
| B100 | (S)-3-methylmorpholine linked to 2-position of 3-methyl-6-(3-methylpyridin-4-yl)pyrimidin-4(3H)-one · HCl |
| B101 | (S)-3-methylmorpholine linked to 2-position of 5-bromo-3-methyl-6-(pyrimidin-4-yl)pyrimidin-4(3H)-one · HCl |

TABLE 1-continued

| Compound No. | STRUCTURE |
|---|---|
| B102 | 6-(3-fluoropyridin-4-yl)-5-bromo-3-methyl-2-[(3S)-3-methylmorpholin-4-yl]pyrimidin-4(3H)-one · HCl |
| B103 | 6-(2,6-diphenylpyridin-4-yl)-3-methyl-2-[(3S)-3-methylmorpholin-4-yl]pyrimidin-4(3H)-one |
| B104 | 6-(3-methoxypyridin-4-yl)-3-methyl-2-[(3S)-3-methylmorpholin-4-yl]pyrimidin-4(3H)-one · HCl |
| B105 | 5-fluoro-3-methyl-2-[(3S)-3-methylmorpholin-4-yl]-6-(pyrimidin-4-yl)pyrimidin-4(3H)-one |
| B106 | 5-bromo-3-methyl-2-[(3S)-3-methylmorpholin-4-yl]-6-(pyrimidin-4-yl)pyrimidin-4(3H)-one · HCl |

TABLE 1-continued
| Compound No. | STRUCTURE |
|---|---|
| B107 | 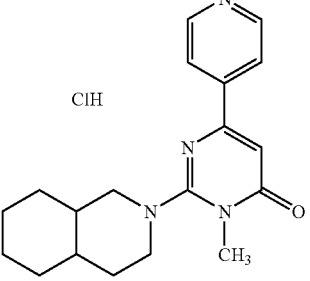 |
| B108 | 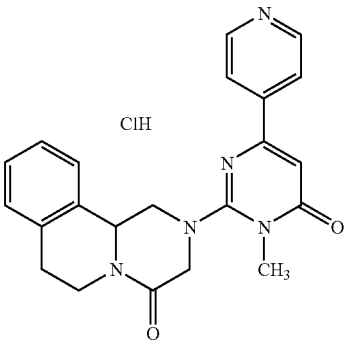 [SMILES: Cn1c(N2CC(=O)N3CCc4ccccc4C3C2)nc(-c2ccncc2)cc1=O ; Cl] |
| B109 | 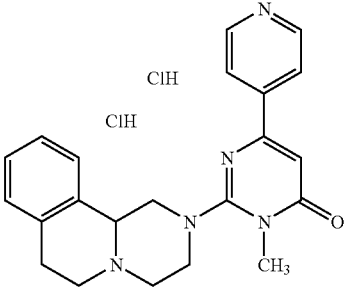 [SMILES: Cn1c(N2CCN3CCc4ccccc4C3C2)nc(-c2ccncc2)cc1=O ; Cl ; Cl] |
| B110 | 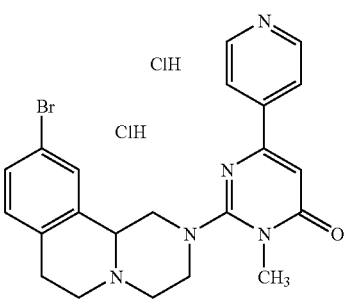 [SMILES: Cn1c(N2CCN3CCc4ccc(Br)cc4C3C2)nc(-c2ccncc2)cc1=O ; Cl ; Cl] |
| B111 | 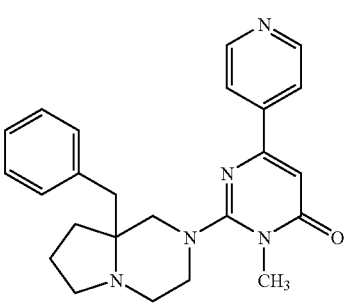 [SMILES: Cn1c(N2CCN3CCCC3(Cc3ccccc3)C2)nc(-c2ccncc2)cc1=O] |

TABLE 1-continued
| Compound No. | STRUCTURE |
|---|---|
| B112 | 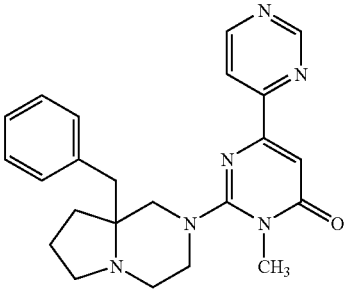 [SMILES: Cn1c(N2CCN3CCCC3(Cc3ccccc3)C2)nc(-c2ccncn2)cc1=O] |
| B113 | 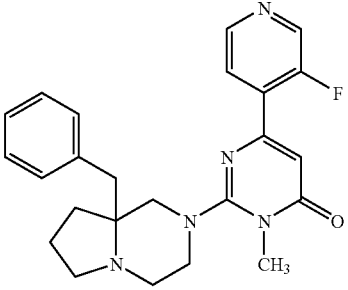 [SMILES: Cn1c(N2CCN3CCCC3(Cc3ccccc3)C2)nc(-c2ccncc2F)cc1=O] |
| B114 | 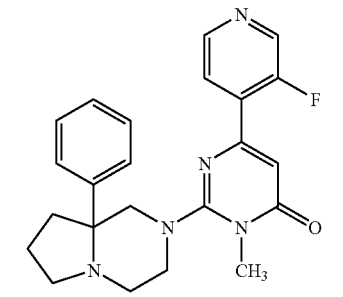 [SMILES: Cn1c(N2CCN3CCCC3(c3ccccc3)C2)nc(-c2ccncc2F)cc1=O] |
| B115 | 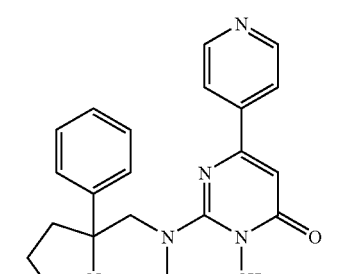 |
| B116 | 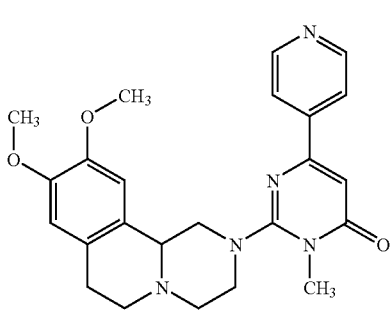 [SMILES: COc1cc2c(cc1OC)C1CN(c3nc(-c4ccncc4)cc(=O)n3C)CCN1CC2] |

TABLE 1-continued
| Compound No. | STRUCTURE |
|---|---|
| B117 | 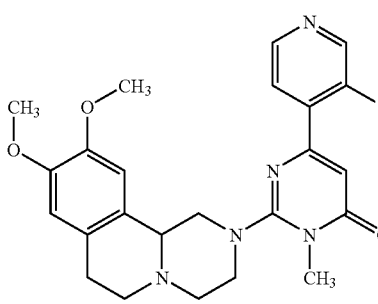 |
| B118 | 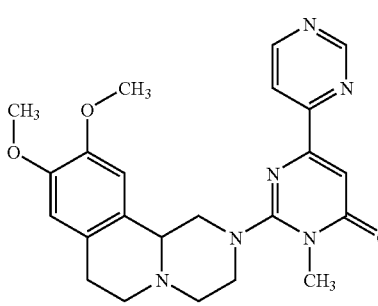 |
| B119 | 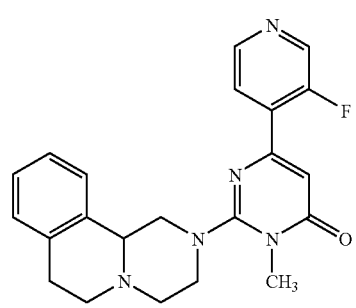 [SMILES: Cn1c(N2CCN3CCc4ccccc4C3C2)nc(-c2ccncc2F)cc1=O] |
| B120 | 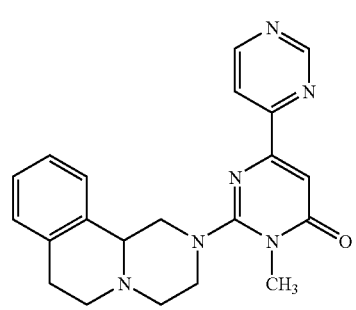 [SMILES: Cn1c(N2CCN3CCc4ccccc4C3C2)nc(-c2ccncn2)cc1=O] |
| B121 | 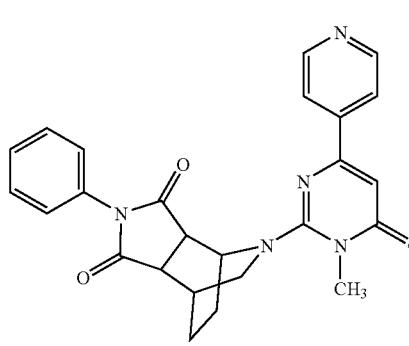 |

TABLE 1-continued

| Compound No. | STRUCTURE |
|---|---|
| B122 | 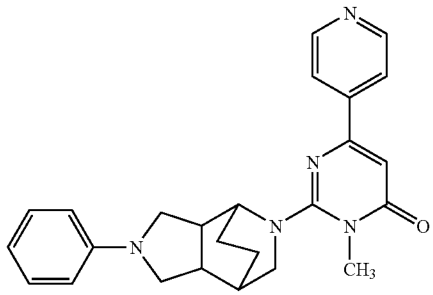 [SMILES: Cn1c(N2CC3CCC2C2CN(c4ccccc4)CC32)nc(-c2ccncc2)cc1=O] |
| B123 | 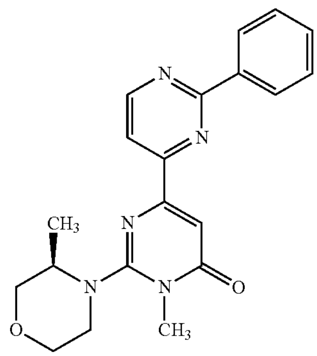 [SMILES: C[C@@H]1COCCN1c1nc(-c2ccnc(-c3ccccc3)n2)cc(=O)n1C] |
| B124 | 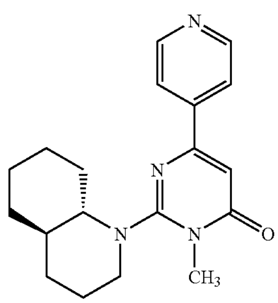 [SMILES: Cn1c(N2CCC[C@H]3CCCC[C@@H]32)nc(-c2ccncc2)cc1=O] |
| B125 | 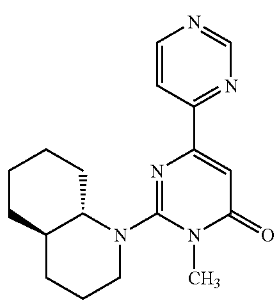 [SMILES: Cn1c(N2CCC[C@H]3CCCC[C@@H]32)nc(-c2ccncn2)cc1=O] |
| B126 | 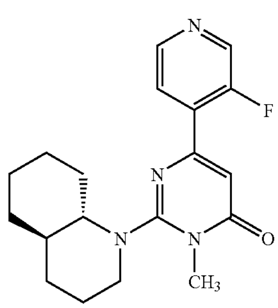 [SMILES: Cn1c(N2CCC[C@H]3CCCC[C@@H]32)nc(-c2ccncc2F)cc1=O] |

TABLE 1-continued

| Compound No. | STRUCTURE |
|---|---|
| B127 | 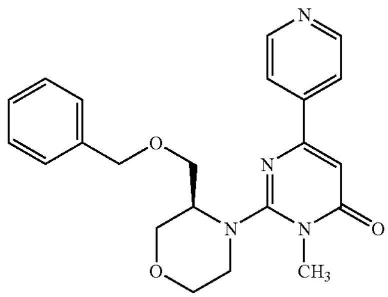 [SMILES: Cn1c(N2CCOC[C@H]2COCc2ccccc2)nc(-c2ccncc2)cc1=O] |
| B128 | 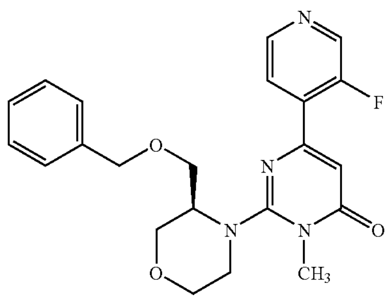 [SMILES: Cn1c(N2CCOC[C@H]2COCc2ccccc2)nc(-c2ccncc2F)cc1=O] |
| B129 | 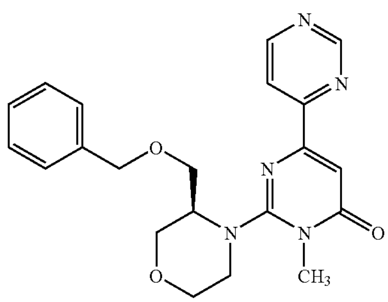 [SMILES: Cn1c(N2CCOC[C@H]2COCc2ccccc2)nc(-c2ccncn2)cc1=O] |
| B130 | 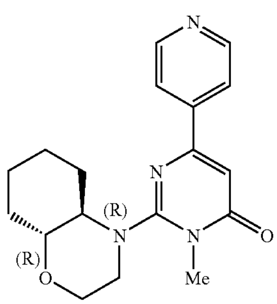 [SMILES: Cn1c(N2CCO[C@@H]3CCCC[C@H]32)nc(-c2ccncc2)cc1=O] |
| B131 | 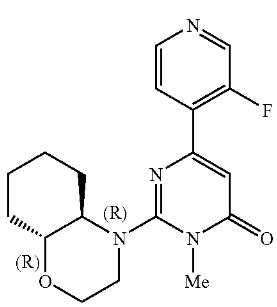 [SMILES: Cn1c(N2CCO[C@@H]3CCCC[C@H]32)nc(-c2ccncc2F)cc1=O] |

TABLE 1-continued

| Compound No. | STRUCTURE |
|---|---|
| B132 | 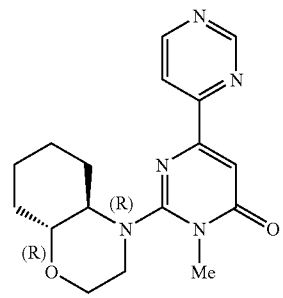 [SMILES: Cn1c(N2CCO[C@@H]3CCCC[C@H]32)nc(-c2ccncn2)cc1=O] |
| B133 | 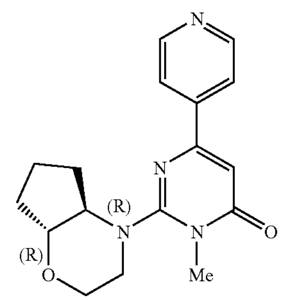 [SMILES: Cn1c(N2CCO[C@@H]3CCC[C@H]32)nc(-c2ccncc2)cc1=O] |
| B134 | 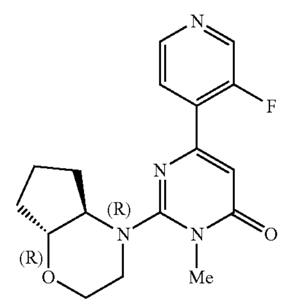 |
| B135 | 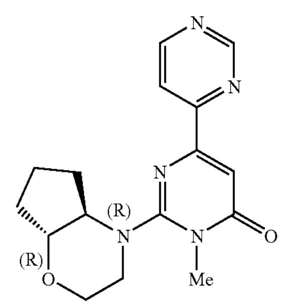 [SMILES: Cn1c(N2CCO[C@@H]3CCC[C@H]32)nc(-c2ccncn2)cc1=O] |
| B136 | 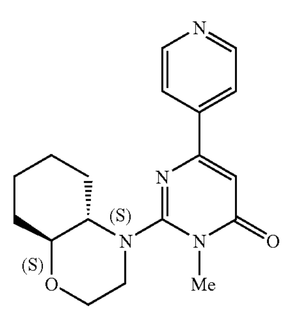 |

TABLE 1-continued

| Compound No. | STRUCTURE |
|---|---|
| B137 | (structure: (4aS,8aS)-octahydrobenzo[b][1,4]oxazine linked to 2-position of 6-(3-fluoropyridin-4-yl)-3-methylpyrimidin-4(3H)-one) |
| B138 | (structure: (4aS,8aS)-octahydrobenzo[b][1,4]oxazine linked to 2-position of 3-methyl-6-(pyrimidin-4-yl)pyrimidin-4(3H)-one) |
| B139 | (structure: trans-2,4-dimethylpiperidine linked to 2-position of 3-methyl-6-(pyrimidin-4-yl)pyrimidin-4(3H)-one, (−)-form) |
| B140 | (structure: trans-2,4-dimethylpiperidine linked to 2-position of 3-methyl-6-(pyrimidin-4-yl)pyrimidin-4(3H)-one, (+)-form) |
| B141 | (structure: 2-cyclobutylmorpholine linked to 2-position of 6-(3-fluoropyridin-4-yl)-3-methylpyrimidin-4(3H)-one, (−)-form) |

TABLE 1-continued
| Compound No. | STRUCTURE |
|---|---|
| B142 | 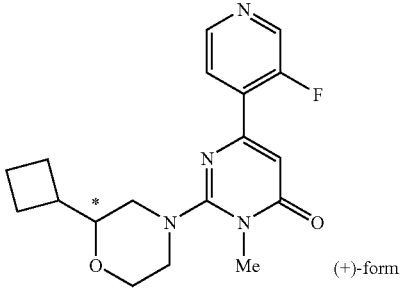 [SMILES: Cn1c(N2CCOC(C3CCC3)C2)nc(-c2ccncc2F)cc1=O] (+)-form |
| B143 | 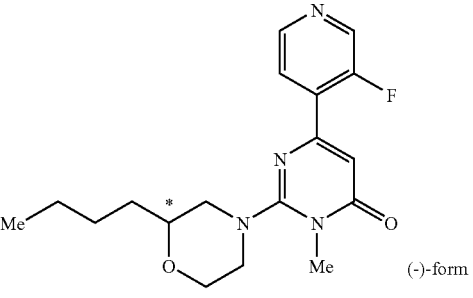 [SMILES: CCCCC1CN(c2nc(-c3ccncc3F)cc(=O)n2C)CCO1] (−)-form |
| B144 | 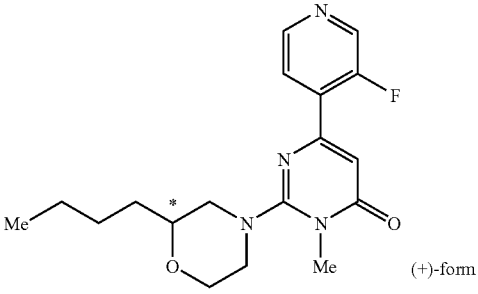 [SMILES: CCCCC1CN(c2nc(-c3ccncc3F)cc(=O)n2C)CCO1] (+)-form |
| B145 | 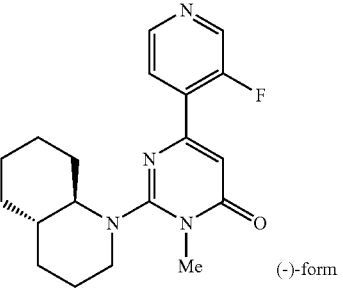 [SMILES: Cn1c(N2CCC[C@@H]3CCCC[C@H]32)nc(-c2ccncc2F)cc1=O] (−)-form |
| B146 | 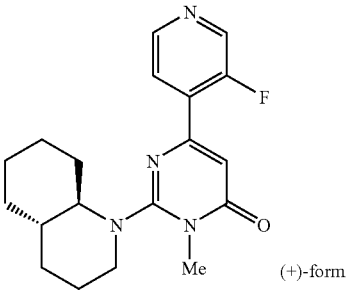 [SMILES: Cn1c(N2CCC[C@@H]3CCCC[C@H]32)nc(-c2ccncc2F)cc1=O] (+)-form |

TABLE 1-continued
| Compound No. | STRUCTURE |
|---|---|
| B147 | 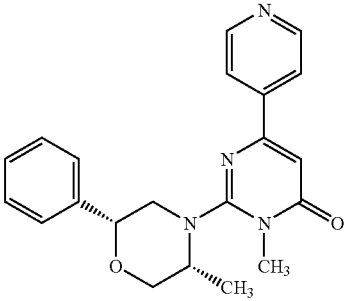 [SMILES: C[C@@H]1CO[C@H](c2ccccc2)CN1c1nc(-c2ccncc2)cc(=O)n1C] |
| B148 | 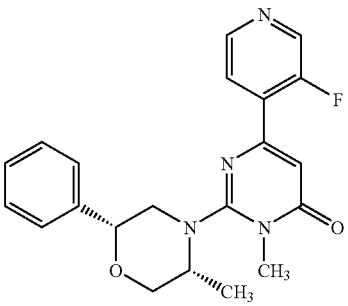 [SMILES: C[C@@H]1CO[C@H](c2ccccc2)CN1c1nc(-c2ccncc2F)cc(=O)n1C] |
| B149 | 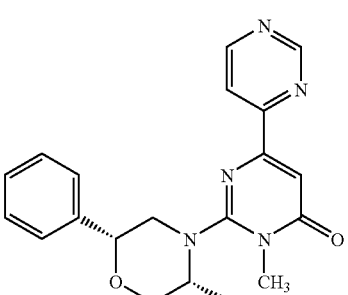 |
| B150 | 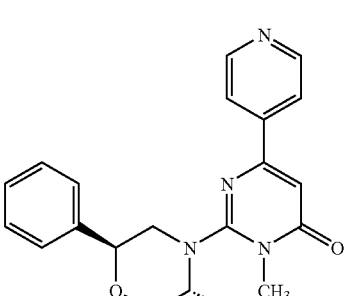 |
| B151 | 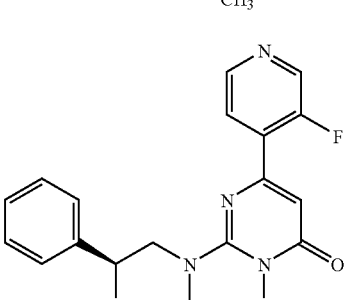 |

TABLE 1-continued
| Compound No. | STRUCTURE |
|---|---|
| B152 | 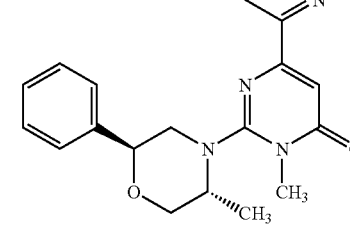 |
| B153 | 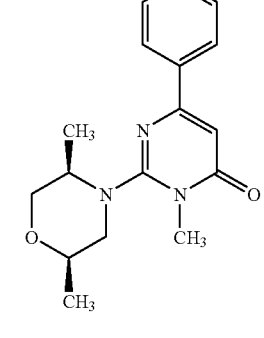 |
| B154 | 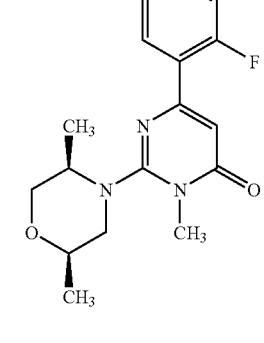 |
| B155 | 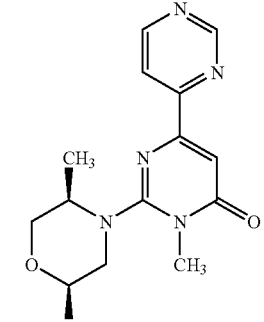 |

TABLE 1-continued
| Compound No. | STRUCTURE |
|---|---|
| B156 | 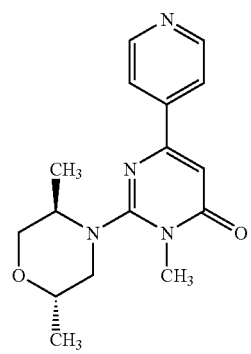 [SMILES: C[C@@H]1CO[C@@H](C)CN1c1nc(-c2ccncc2)cc(=O)n1C] |
| B157 | 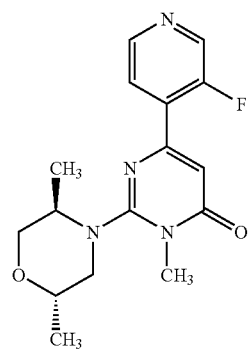 [SMILES: C[C@@H]1CO[C@@H](C)CN1c1nc(-c2ccncc2F)cc(=O)n1C] |
| B158 | 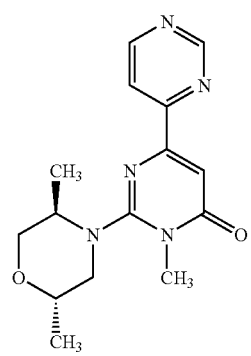 [SMILES: C[C@@H]1CO[C@@H](C)CN1c1nc(-c2ccncn2)cc(=O)n1C] |
| B159 | 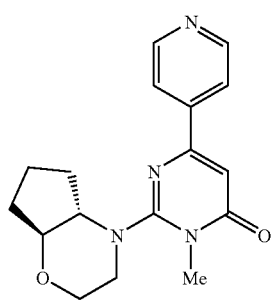 [SMILES: Cn1c(N2CCO[C@H]3CCC[C@@H]32)nc(-c2ccncc2)cc1=O] |

TABLE 1-continued

| Compound No. | STRUCTURE |
|---|---|
| B160 | 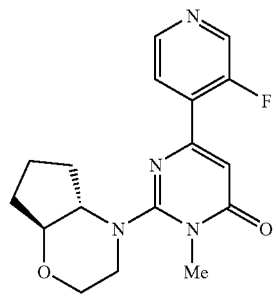 [SMILES: Cn1c(N2CCO[C@H]3CCC[C@@H]32)nc(-c2ccncc2F)cc1=O] |
| B161 | 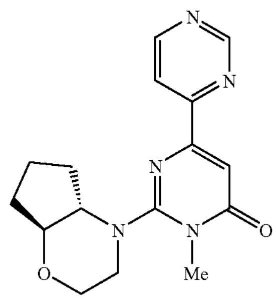 [SMILES: Cn1c(N2CCO[C@H]3CCC[C@@H]32)nc(-c2ccncn2)cc1=O] |
| B162 | 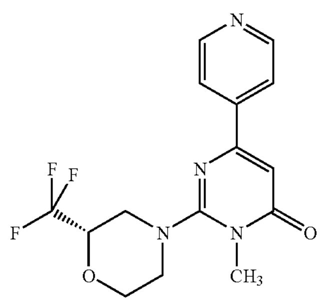 [SMILES: Cn1c(N2CCO[C@H](C(F)(F)F)C2)nc(-c2ccncc2)cc1=O] |
| B163 | 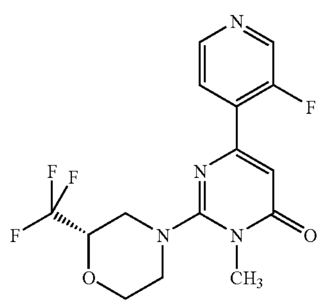 [SMILES: Cn1c(N2CCO[C@H](C(F)(F)F)C2)nc(-c2ccncc2F)cc1=O] |
| B164 | 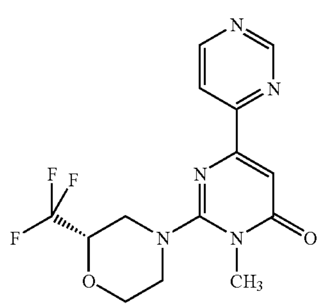 |

TABLE 1-continued

| Compound No. | STRUCTURE |
|---|---|
| B165 | 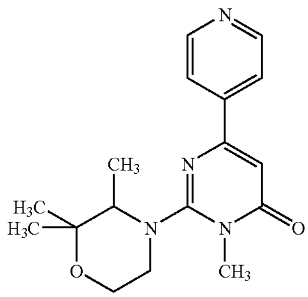 [SMILES: CC1N(c2nc(-c3ccncc3)cc(=O)n2C)CCOC1(C)C] |
| B166 | 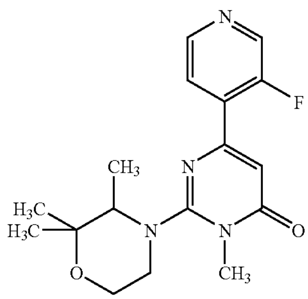 [SMILES: CC1N(c2nc(-c3ccncc3F)cc(=O)n2C)CCOC1(C)C] |
| B167 | 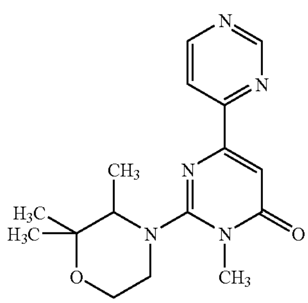 [SMILES: CC1N(c2nc(-c3ccncn3)cc(=O)n2C)CCOC1(C)C] |
| B168 | (rac) |
| B169 | (rac) |

TABLE 1-continued
| Compound No. | STRUCTURE |
|---|---|
| B170 | 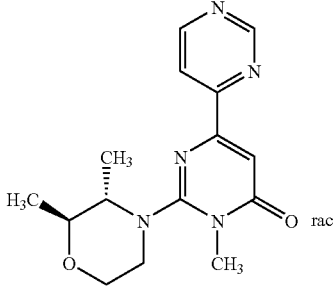 [SMILES: C[C@@H]1OCCN(c2nc(-c3ccncc3)cc(=O)n2C)[C@H]1C] rac |
| B171 | 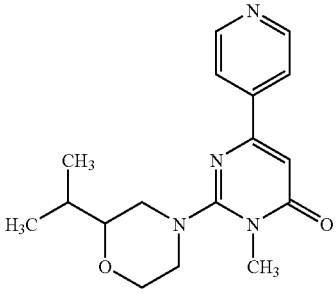 |
| B172 | 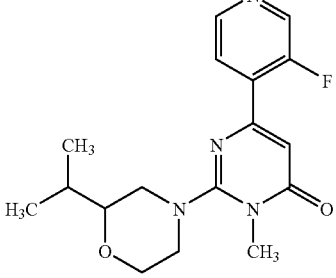 |
| B173 | 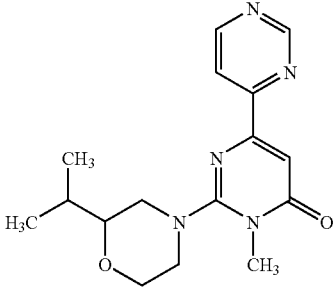 [SMILES: CC(C)C1CN(c2nc(-c3ccncn3)cc(=O)n2C)CCO1] |
| B174 | 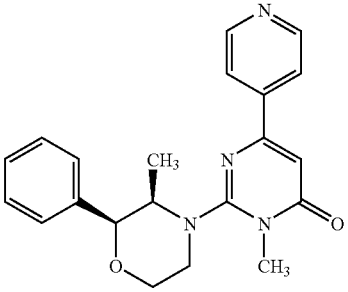 [SMILES: C[C@@H]1[C@H](c2ccccc2)OCCN1c1nc(-c2ccncc2)cc(=O)n1C] |

TABLE 1-continued
| Compound No. | STRUCTURE |
|---|---|
| B175 | 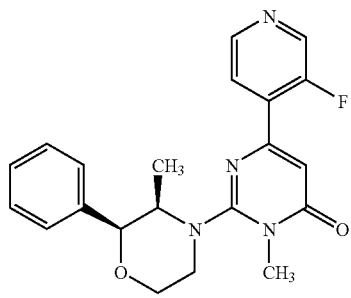 [SMILES: C[C@@H]1[C@H](c2ccccc2)OCCN1c1nc(-c2ccncc2F)cc(=O)n1C] |
| B176 | 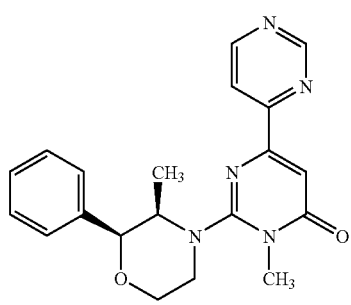 [SMILES: C[C@@H]1[C@H](c2ccccc2)OCCN1c1nc(-c2ccncn2)cc(=O)n1C] |
| B177 | 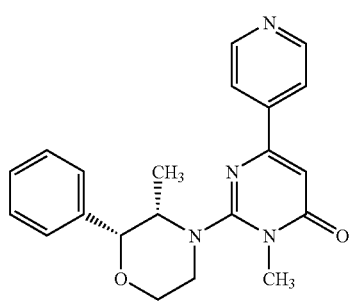 [SMILES: C[C@H]1[C@@H](c2ccccc2)OCCN1c1nc(-c2ccncc2)cc(=O)n1C] |
| B178 | 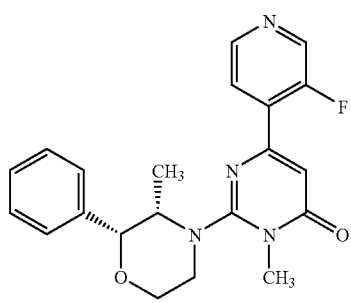 [SMILES: C[C@H]1[C@@H](c2ccccc2)OCCN1c1nc(-c2ccncc2F)cc(=O)n1C] |
| B179 | 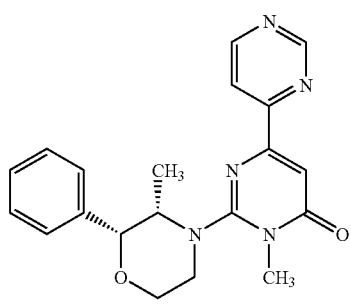 [SMILES: C[C@H]1[C@@H](c2ccccc2)OCCN1c1nc(-c2ccncn2)cc(=O)n1C] |

TABLE 1-continued
| Compound No. | STRUCTURE |
|---|---|
| B180 | 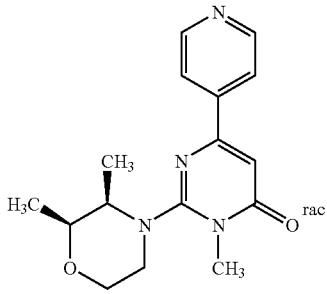 [SMILES: C[C@@H]1OCCN(c2nc(-c3ccncc3)cc(=O)n2C)[C@@H]1C] |
| B181 | 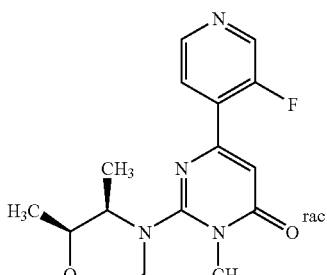 |
| B182 | 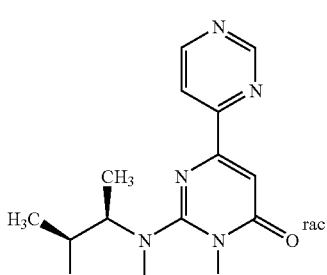 |
| B183 | 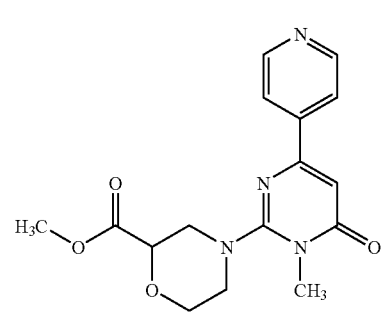 [SMILES: COC(=O)C1CN(c2nc(-c3ccncc3)cc(=O)n2C)CCO1] |
| B184 | 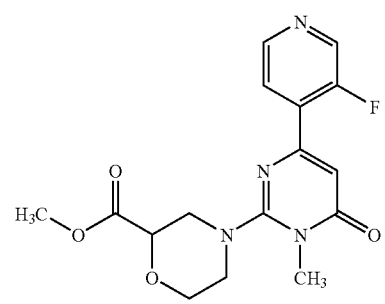 [SMILES: COC(=O)C1CN(c2nc(-c3ccncc3F)cc(=O)n2C)CCO1] |

TABLE 1-continued
| Compound No. | STRUCTURE |
|---|---|
| B185 | 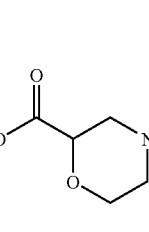 |
| B186 | 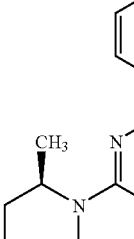 |
| B187 | 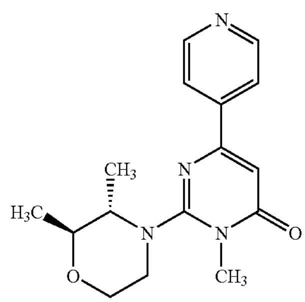 [SMILES: C[C@@H]1OCCN(c2nc(-c3ccncc3)cc(=O)n2C)[C@H]1C] |
| B188 | 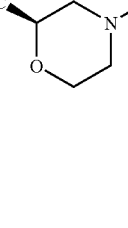 |
| B189 | 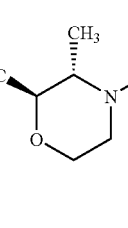 |

TABLE 1-continued
| Compound No. | STRUCTURE | |
|---|---|---|
| B190 | 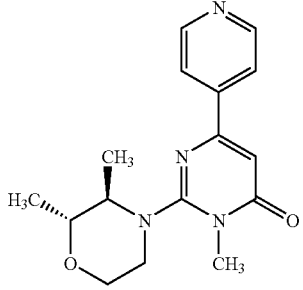 [SMILES: C[C@@H]1[C@@H](C)OCCN1c1nc(-c2ccncc2)cc(=O)n1C] | |
| B191 | 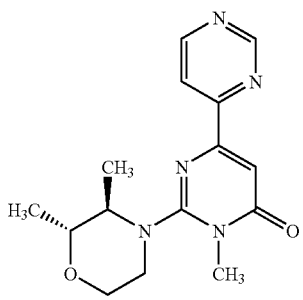 | |
| B192 | 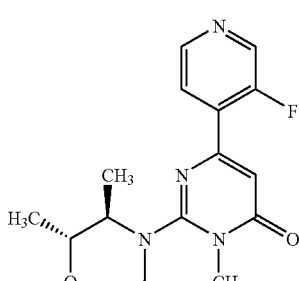 | |
| B193 | 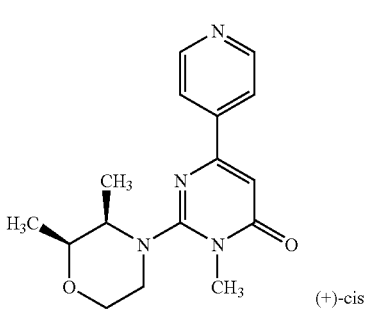 | (+)-cis |
| B194 | 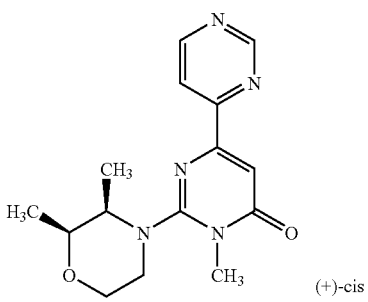 | (+)-cis |

TABLE 1-continued
| Compound No. | STRUCTURE | |
|---|---|---|
| B195 | 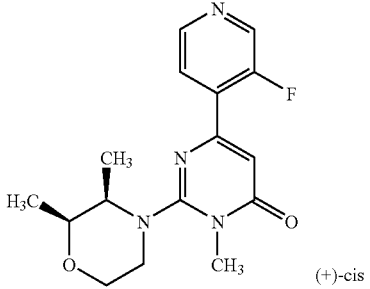 | (+)-cis |
| B196 | 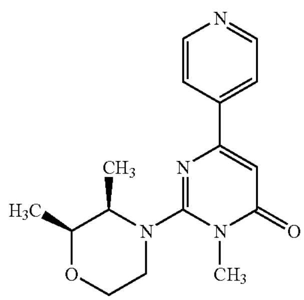 | (−)-cis |
| B197 | 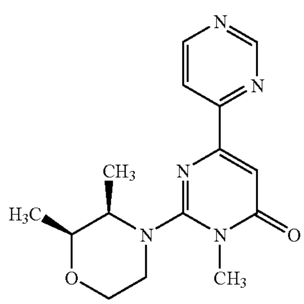 [SMILES: C[C@@H]1[C@@H](C)OCCN1c1nc(-c2ccncn2)cc(=O)n1C] | (−)-cis |
| B198 | 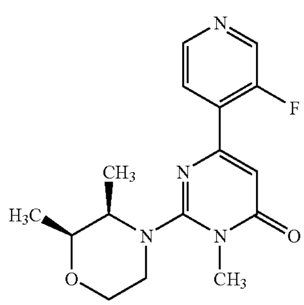 [SMILES: C[C@@H]1[C@@H](C)OCCN1c1nc(-c2ccncc2F)cc(=O)n1C] | (−)-cis |
| B199 | 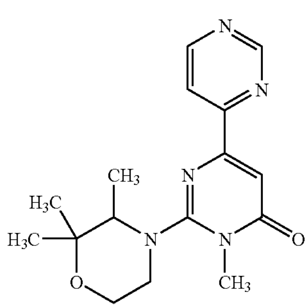 [SMILES: CC1N(c2nc(-c3ccncn3)cc(=O)n2C)CCOC1(C)C] | |

TABLE 1-continued

| Compound No. | STRUCTURE |
|---|---|
| B200 | 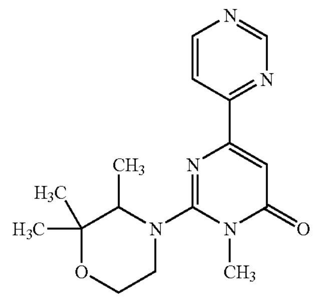 [SMILES: CC1N(c2nc(-c3ccncn3)cc(=O)n2C)CCOC1(C)C] |
| B201 | 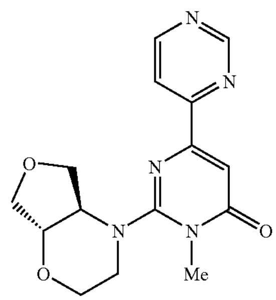 [SMILES: Cn1c(N2CCO[C@@H]3COC[C@H]32)nc(-c2ccncn2)cc1=O] |
| B202 | 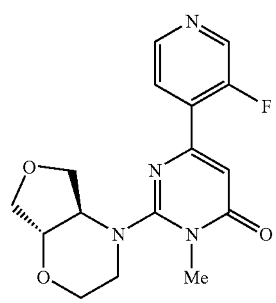 [SMILES: Cn1c(N2CCO[C@@H]3COC[C@H]32)nc(-c2ccncc2F)cc1=O] |
| B203 | 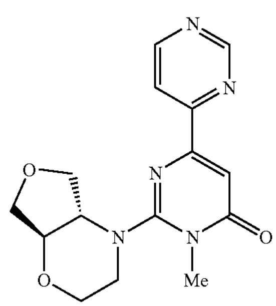 [SMILES: Cn1c(N2CCO[C@H]3COC[C@@H]32)nc(-c2ccncn2)cc1=O] |
| B204 | 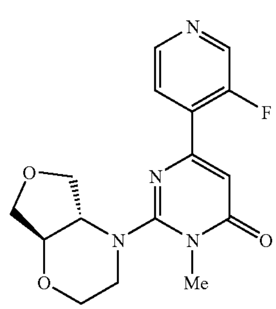 [SMILES: Cn1c(N2CCO[C@H]3COC[C@@H]32)nc(-c2ccncc2F)cc1=O] |

TABLE 1-continued
| Compound No. | STRUCTURE |
|---|---|
| B205 | 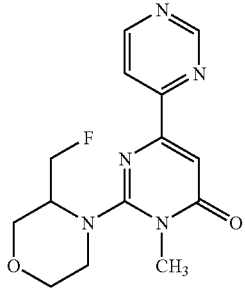 [SMILES: Cn1c(N2CCOCC2CF)nc(-c2ccncn2)cc1=O] |
| B206 | 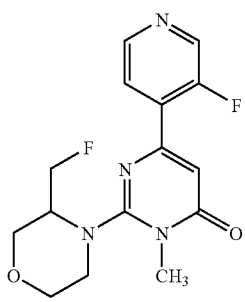 [SMILES: Cn1c(N2CCOCC2CF)nc(-c2ccncc2F)cc1=O] |
| D1 | 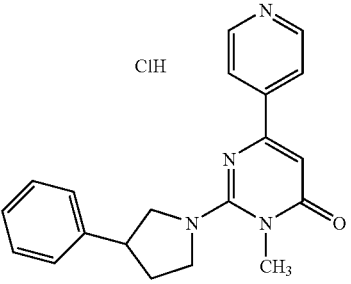 [SMILES: Cn1c(N2CCC(c3ccccc3)C2)nc(-c2ccncc2)cc1=O ; Cl] |
| D2 | 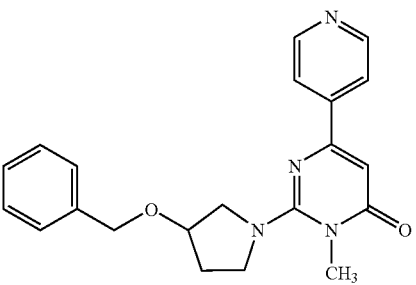 [SMILES: Cn1c(N2CCC(OCc3ccccc3)C2)nc(-c2ccncc2)cc1=O] |
| D3 | 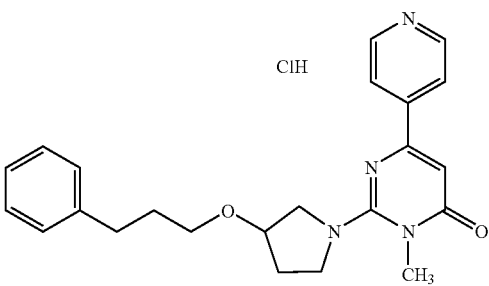 [SMILES: Cn1c(N2CCC(OCCCc3ccccc3)C2)nc(-c2ccncc2)cc1=O ; Cl] |

TABLE 1-continued

| Compound No. | STRUCTURE |
|---|---|
| D4 | 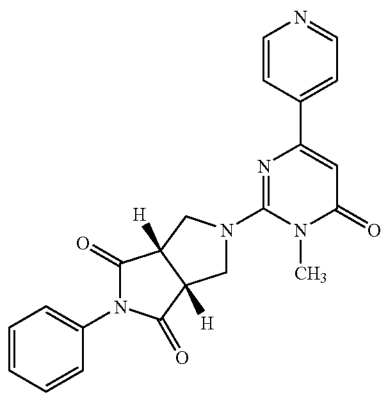 [SMILES: Cn1c(N2C[C@@H]3C(=O)N(c4ccccc4)C(=O)[C@@H]3C2)nc(-c2ccncc2)cc1=O] |
| D5 | 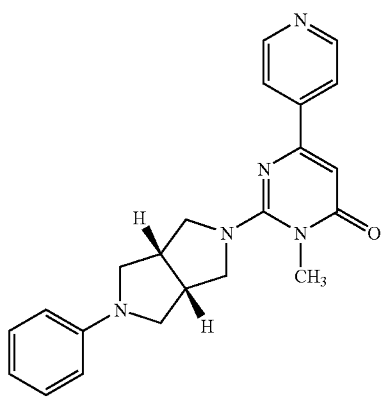 [SMILES: Cn1c(N2C[C@H]3CN(c4ccccc4)C[C@H]3C2)nc(-c2ccncc2)cc1=O] |
| D6 | 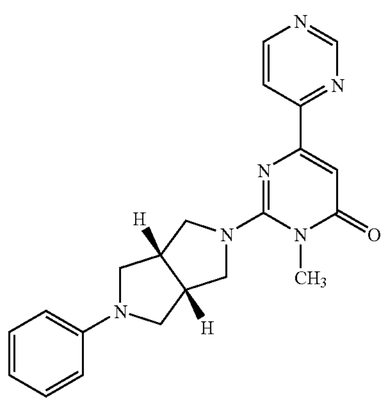 [SMILES: Cn1c(N2C[C@H]3CN(c4ccccc4)C[C@H]3C2)nc(-c2ccncn2)cc1=O] |
| D7 | 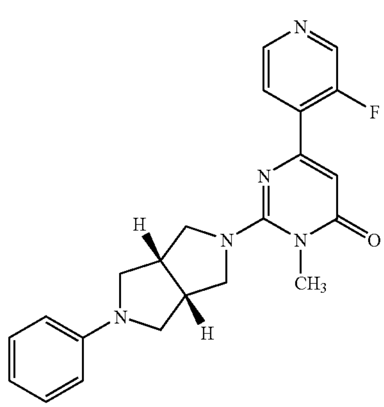 [SMILES: Cn1c(N2C[C@H]3CN(c4ccccc4)C[C@H]3C2)nc(-c2ccncc2F)cc1=O] |

TABLE 1-continued
| Compound No. | STRUCTURE |
|---|---|
| D8 | 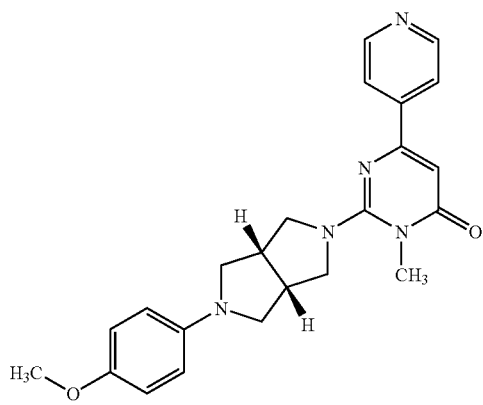 [SMILES: COc1ccc(N2C[C@@H]3CN(c4nc(-c5ccncc5)cc(=O)n4C)C[C@@H]3C2)cc1] |
| D9 | 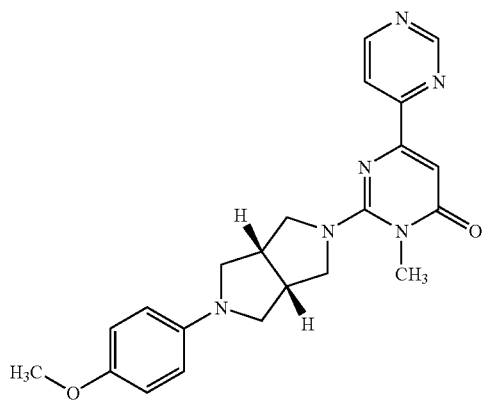 [SMILES: COc1ccc(N2C[C@@H]3CN(c4nc(-c5ccncn5)cc(=O)n4C)C[C@@H]3C2)cc1] |
| D10 | 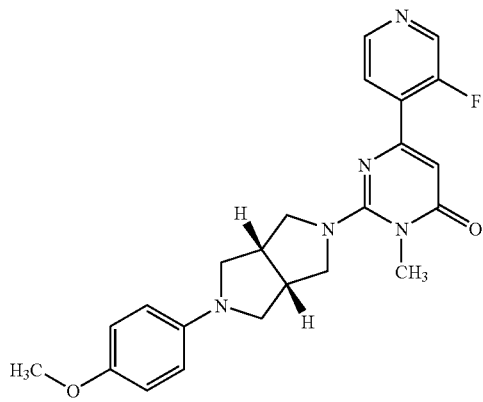 [SMILES: COc1ccc(N2C[C@@H]3CN(c4nc(-c5ccncc5F)cc(=O)n4C)C[C@@H]3C2)cc1] |

TABLE 1-continued
| Compound No. | STRUCTURE |
|---|---|
| D11 | 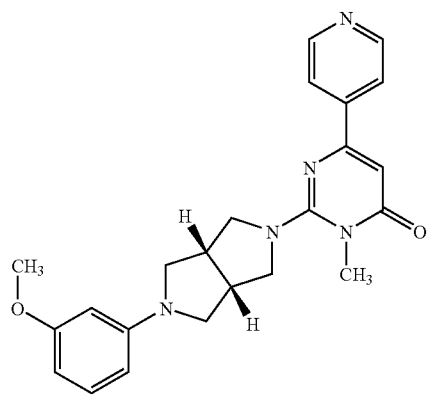 |
| D12 | 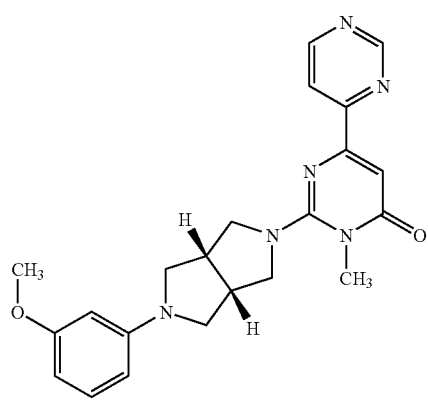 [SMILES: COc1cccc(N2C[C@@H]3CN(c4nc(-c5ccncn5)cc(=O)n4C)C[C@@H]3C2)c1] |
| D13 | 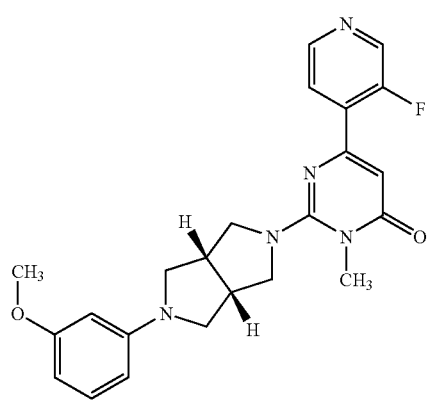 [SMILES: COc1cccc(N2C[C@@H]3CN(c4nc(-c5ccncc5F)cc(=O)n4C)C[C@@H]3C2)c1] |
| D14 | 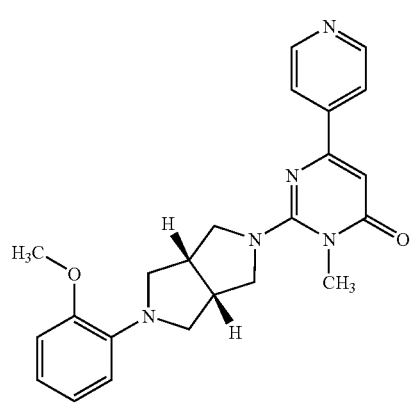 [SMILES: COc1ccccc1N1C[C@@H]2CN(c3nc(-c4ccncc4)cc(=O)n3C)C[C@@H]2C1] |

TABLE 1-continued
| Compound No. | STRUCTURE |
|---|---|
| D15 | 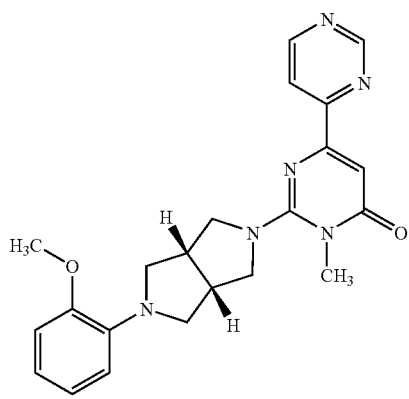 [SMILES: COc1ccccc1N1C[C@@H]2CN(c3nc(-c4ccncn4)cc(=O)n3C)C[C@@H]2C1] |
| D16 | 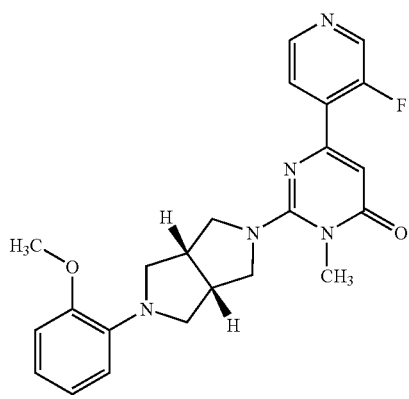 [SMILES: COc1ccccc1N1C[C@@H]2CN(c3nc(-c4ccncc4F)cc(=O)n3C)C[C@@H]2C1] |
| D17 | 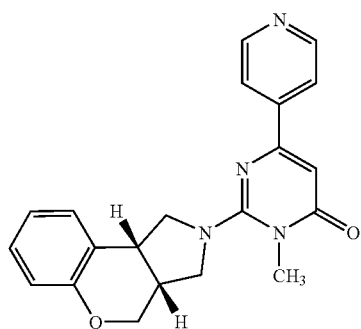 [SMILES: Cn1c(N2C[C@@H]3COc4ccccc4[C@@H]3C2)nc(-c2ccncc2)cc1=O] |
| D18 | 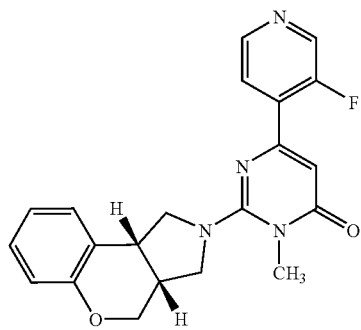 [SMILES: Cn1c(N2C[C@@H]3COc4ccccc4[C@@H]3C2)nc(-c2ccncc2F)cc1=O] |

TABLE 1-continued

| Compound No. | STRUCTURE |
|---|---|
| D19 | 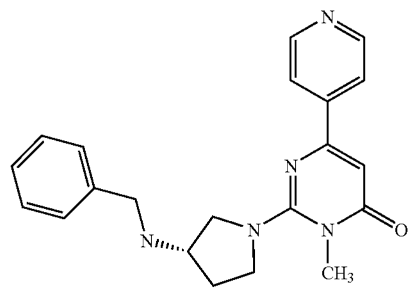 |
| D20 | 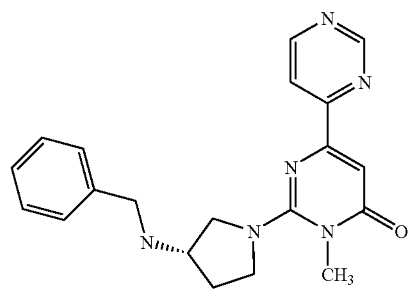 [SMILES: Cn1c(N2CC[C@H](NCc3ccccc3)C2)nc(-c2ccncn2)cc1=O] |
| D21 | 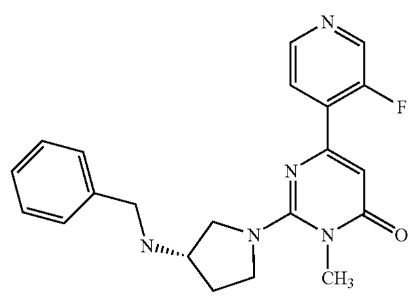 [SMILES: Cn1c(N2CC[C@H](NCc3ccccc3)C2)nc(-c2ccncc2F)cc1=O] |
| D22 | 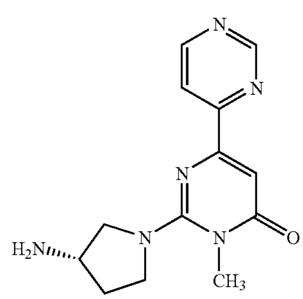 [SMILES: Cn1c(N2CC[C@H](N)C2)nc(-c2ccncn2)cc1=O] |
| D23 | 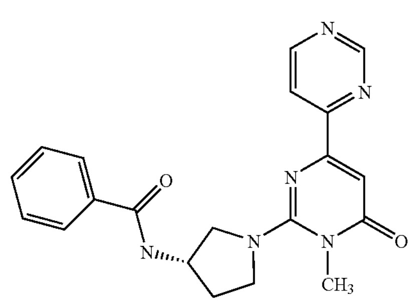 [SMILES: Cn1c(N2CC[C@H](NC(=O)c3ccccc3)C2)nc(-c2ccncn2)cc1=O] |

TABLE 1-continued

| Compound No. | STRUCTURE |
|---|---|
| D24 | 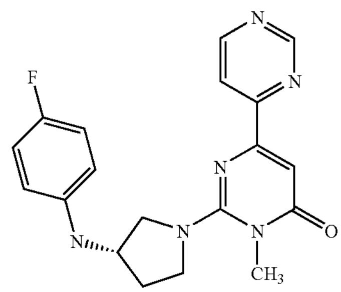 [SMILES: Cn1c(N2CC[C@H](Nc3ccc(F)cc3)C2)nc(-c2ccncn2)cc1=O] |
| D25 | 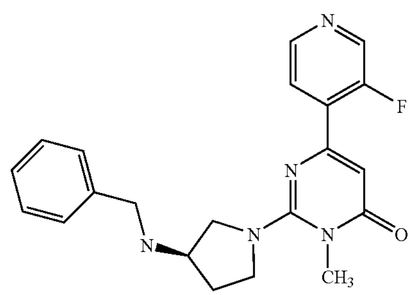 [SMILES: Cn1c(N2CC[C@@H](NCc3ccccc3)C2)nc(-c2ccncc2F)cc1=O] |
| D26 | 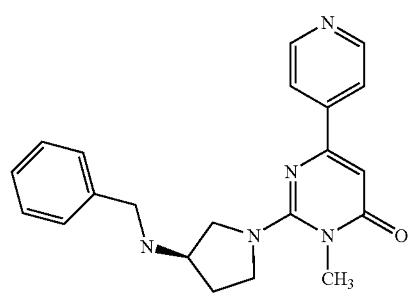 [SMILES: Cn1c(N2CC[C@@H](NCc3ccccc3)C2)nc(-c2ccncc2)cc1=O] |
| D27 | 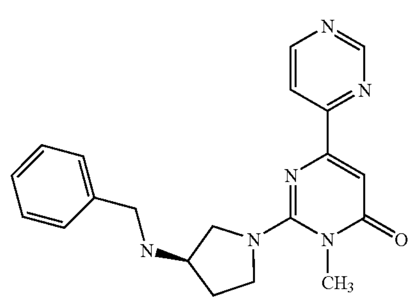 |
| D28 | 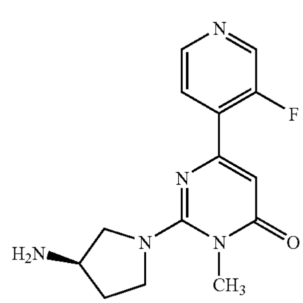 [SMILES: Cn1c(N2CC[C@@H](N)C2)nc(-c2ccncc2F)cc1=O] |

TABLE 1-continued

| Compound No. | STRUCTURE |
|---|---|
| D29 | 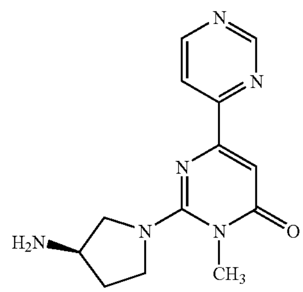 [SMILES: Cn1c(N2CC[C@@H](N)C2)nc(-c2ccncn2)cc1=O] |
| D30 | 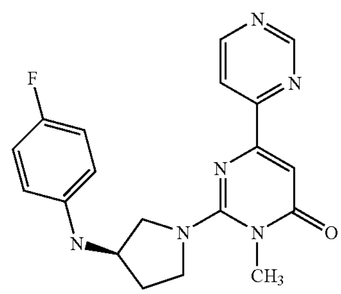 [SMILES: Cn1c(N2CC[C@@H](Nc3ccc(F)cc3)C2)nc(-c2ccncn2)cc1=O] |
| D31 | 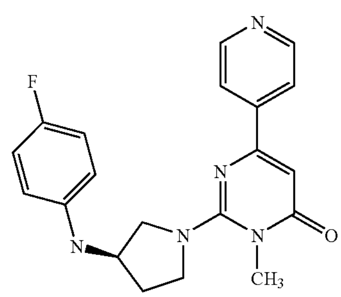 [SMILES: Cn1c(N2CC[C@@H](Nc3ccc(F)cc3)C2)nc(-c2ccncc2)cc1=O] |
| D32 | 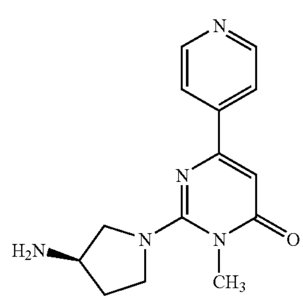 [SMILES: Cn1c(N2CC[C@@H](N)C2)nc(-c2ccncc2)cc1=O] |
| D33 | 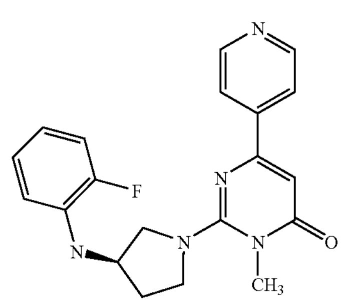 |

TABLE 1-continued
| Compound No. | STRUCTURE |
|---|---|
| D34 | 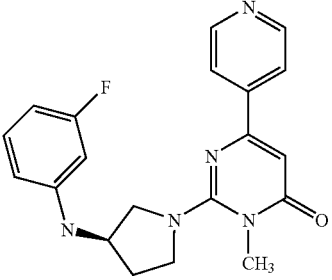 [SMILES: Cn1c(N2CC[C@@H](Nc3cccc(F)c3)C2)nc(-c2ccncc2)cc1=O] |
| D35 | 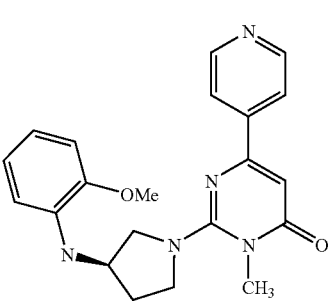 [SMILES: COc1ccccc1N[C@@H]1CCN(c2nc(-c3ccncc3)cc(=O)n2C)C1] |
| D36 | 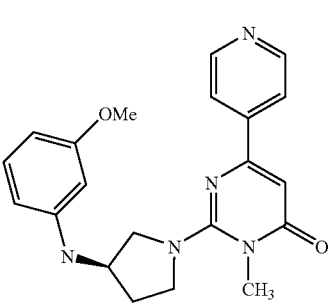 [SMILES: COc1cccc(N[C@@H]2CCN(c3nc(-c4ccncc4)cc(=O)n3C)C2)c1] |
| D37 | 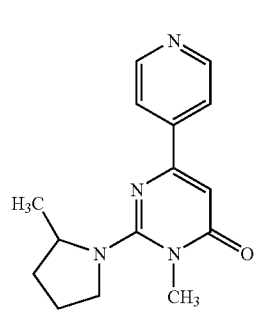 [SMILES: CC1CCCN1c1nc(-c2ccncc2)cc(=O)n1C] |
| D38 | 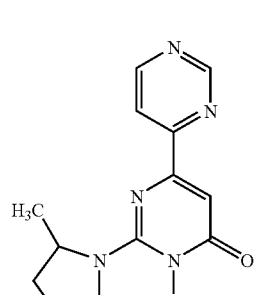 |

TABLE 1-continued
| Compound No. | STRUCTURE |
|---|---|
| D39 | 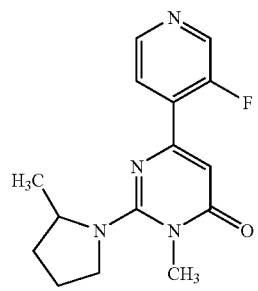 [SMILES: CC1CCCN1c1nc(-c2ccncc2F)cc(=O)n1C] |
| D40 | 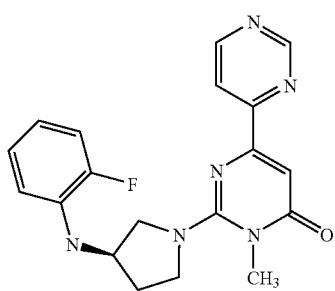 [SMILES: Cn1c(N2CC[C@@H](Nc3ccccc3F)C2)nc(-c2ccncn2)cc1=O] |
| D41 | 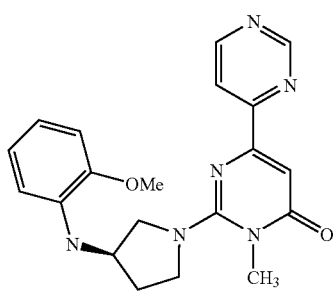 [SMILES: COc1ccccc1N[C@@H]1CCN(c2nc(-c3ccncn3)cc(=O)n2C)C1] |
| D42 | 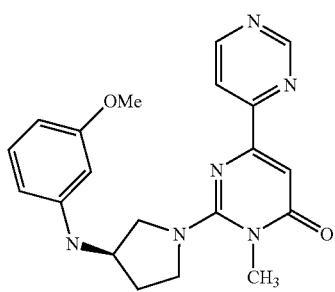 |
| D43 | 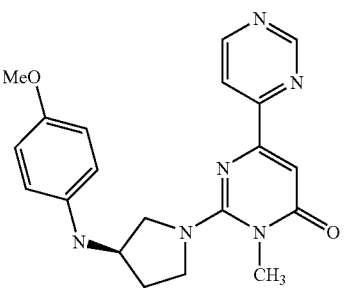 [SMILES: COc1ccc(N[C@@H]2CCN(c3nc(-c4ccncn4)cc(=O)n3C)C2)cc1] |

TABLE 1-continued

| Compound No. | STRUCTURE |
|---|---|
| D44 | 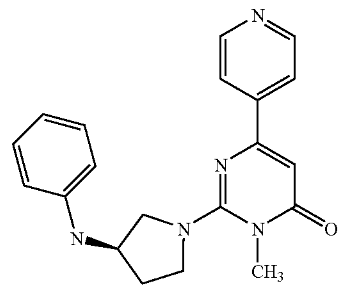 |
| D45 | 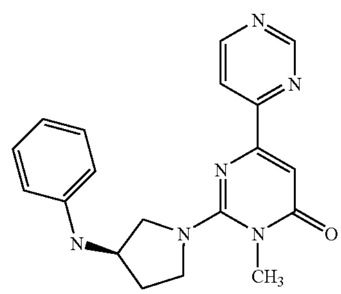 [SMILES: Cn1c(N2CC[C@@H](Nc3ccccc3)C2)nc(-c2ccncn2)cc1=O] |
| D46 | 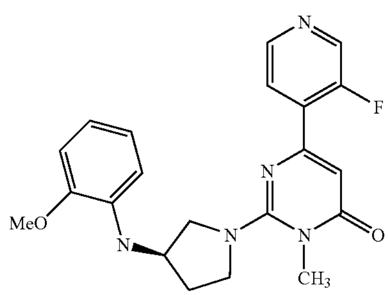 [SMILES: COc1ccccc1N[C@@H]1CCN(c2nc(-c3ccncc3F)cc(=O)n2C)C1] |
| D47 | 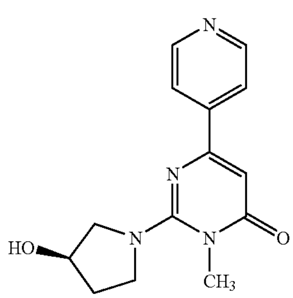 [SMILES: Cn1c(N2CC[C@@H](O)C2)nc(-c2ccncc2)cc1=O] |
| D48 | 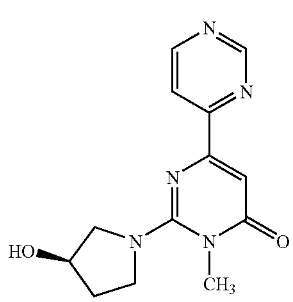 [SMILES: Cn1c(N2CC[C@@H](O)C2)nc(-c2ccncn2)cc1=O] |

TABLE 1-continued
| Compound No. | STRUCTURE |
|---|---|
| D49 | 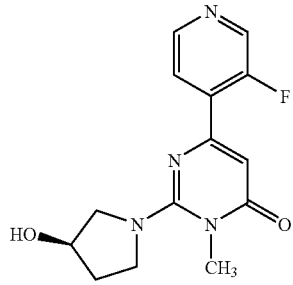 [SMILES: Cn1c(N2CC[C@@H](O)C2)nc(-c2ccncc2F)cc1=O] |
| D50 | 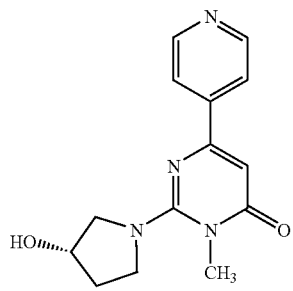 [SMILES: Cn1c(N2CC[C@H](O)C2)nc(-c2ccncc2)cc1=O] |
| D51 | 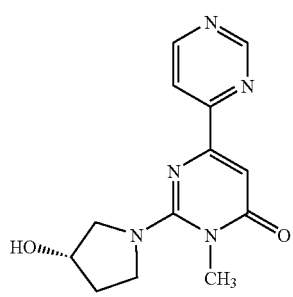 [SMILES: Cn1c(N2CC[C@H](O)C2)nc(-c2ccncn2)cc1=O] |
| D52 | 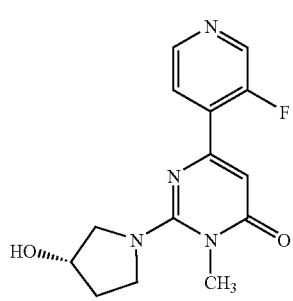 [SMILES: Cn1c(N2CC[C@H](O)C2)nc(-c2ccncc2F)cc1=O] |
| D53 | 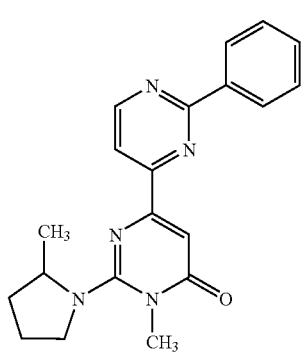 [SMILES: CC1CCCN1c1nc(-c2ccnc(-c3ccccc3)n2)cc(=O)n1C] |

TABLE 1-continued
| Compound No. | STRUCTURE |
|---|---|
| D54 | 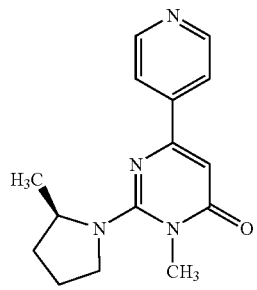 [SMILES: C[C@@H]1CCCN1c1nc(-c2ccncc2)cc(=O)n1C] |
| D55 | 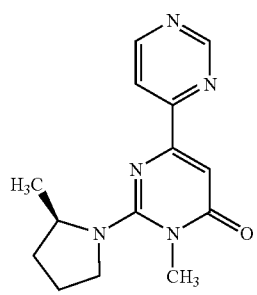 [SMILES: C[C@@H]1CCCN1c1nc(-c2ccncn2)cc(=O)n1C] |
| D56 | 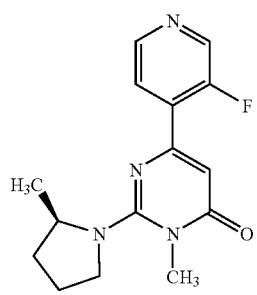 |
| D57 | 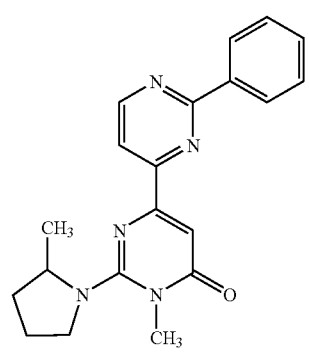 [SMILES: CC1CCCN1c1nc(-c2ccnc(-c3ccccc3)n2)cc(=O)n1C] |
| D58 | 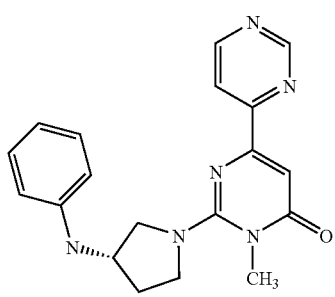 [SMILES: Cn1c(N2CC[C@H](Nc3ccccc3)C2)nc(-c2ccncn2)cc1=O] |

TABLE 1-continued
| Compound No. | STRUCTURE |
|---|---|
| D59 | 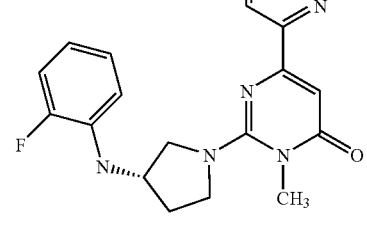 |
| D60 | 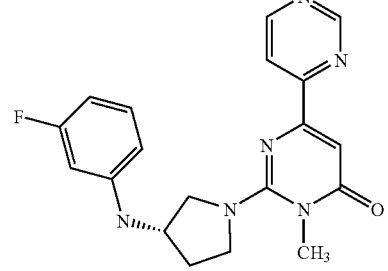 |
| D61 | 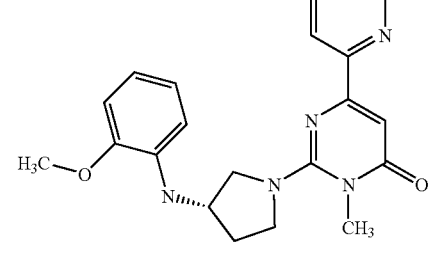 |
| D62 | 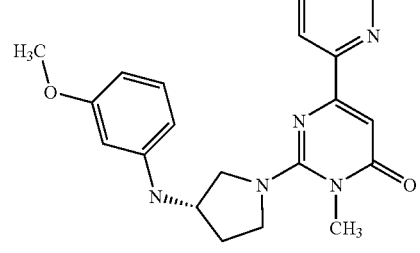 |
| D63 | 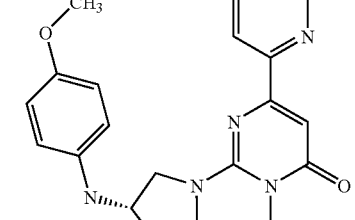 |

TABLE 1-continued

| Compound No. | STRUCTURE |
|---|---|
| D64 | (structure: 2-[(3R)-3-(phenylamino)pyrrolidin-1-yl]-3-methyl-6-(pyridin-4-yl)pyrimidin-4(3H)-one) lp;3p |
| D65 | (structure: 2-[(3R)-3-(2-fluorophenylamino)pyrrolidin-1-yl]-3-methyl-6-(pyridin-4-yl)pyrimidin-4(3H)-one) |
| D66 | (structure: 2-[(3R)-3-(3-fluorophenylamino)pyrrolidin-1-yl]-3-methyl-6-(pyridin-4-yl)pyrimidin-4(3H)-one) |
| D67 | (structure: 2-[(3R)-3-(4-fluorophenylamino)pyrrolidin-1-yl]-3-methyl-6-(pyridin-4-yl)pyrimidin-4(3H)-one) |

TABLE 1-continued
| Compound No. | STRUCTURE |
|---|---|
| D68 | 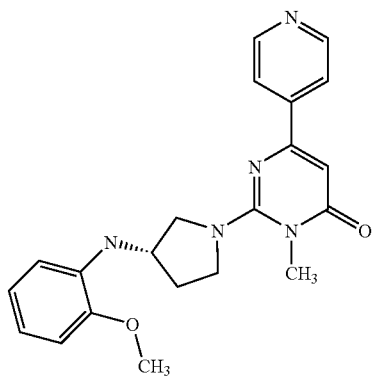 [SMILES: COc1ccccc1N[C@H]1CCN(c2nc(-c3ccncc3)cc(=O)n2C)C1] |
| D69 | 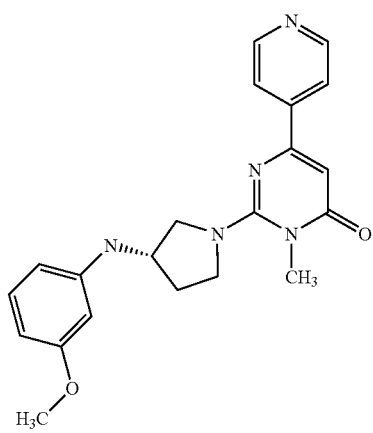 [SMILES: COc1cccc(N[C@H]2CCN(c3nc(-c4ccncc4)cc(=O)n3C)C2)c1] |
| D70 | 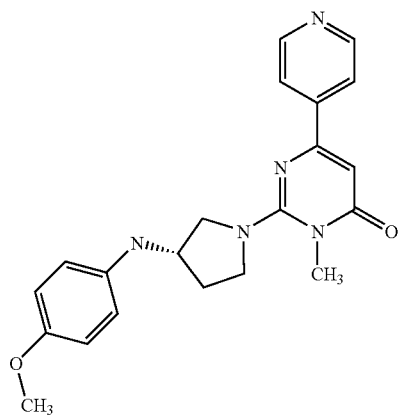 [SMILES: COc1ccc(N[C@H]2CCN(c3nc(-c4ccncc4)cc(=O)n3C)C2)cc1] |
| D71 | 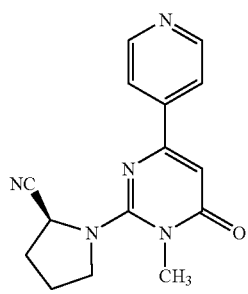 |

TABLE 1-continued

| Compound No. | STRUCTURE |
| --- | --- |
| D72 | 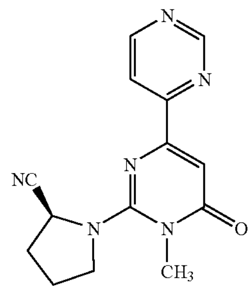 |
| D73 | 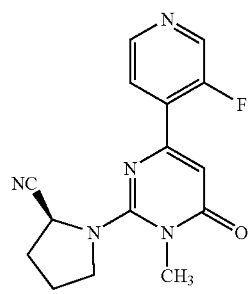 |
| D74 | 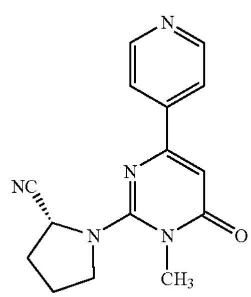 |
| D75 | 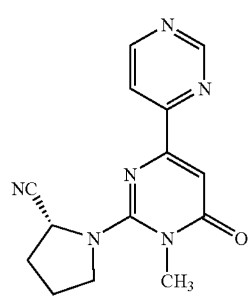 |
| D76 | 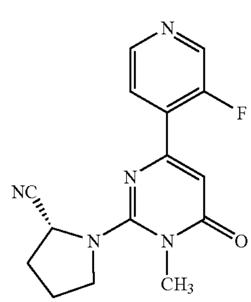 |

TABLE 1-continued
| Compound No. | STRUCTURE |
|---|---|
| D77 | 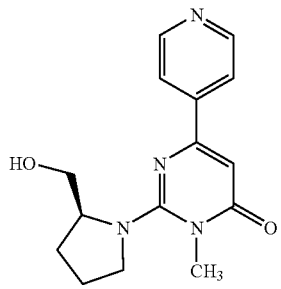 [SMILES: Cn1c(N2CCC[C@H]2CO)nc(-c2ccncc2)cc1=O] |
| D78 | 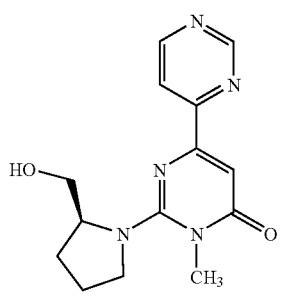 [SMILES: Cn1c(N2CCC[C@H]2CO)nc(-c2ccncn2)cc1=O] |
| D79 | 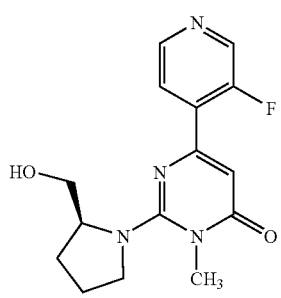 [SMILES: Cn1c(N2CCC[C@H]2CO)nc(-c2ccncc2F)cc1=O] |
| D80 | 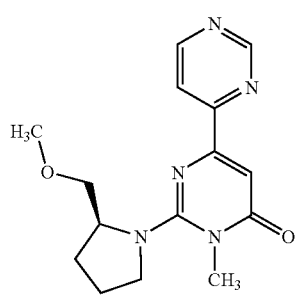 |
| D81 | 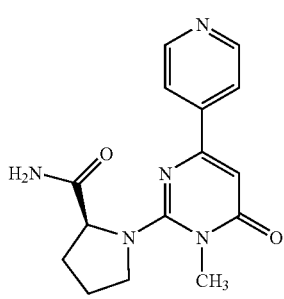 [SMILES: Cn1c(N2CCC[C@H]2C(N)=O)nc(-c2ccncc2)cc1=O] |

TABLE 1-continued
| Compound No. | STRUCTURE |
|---|---|
| D82 | 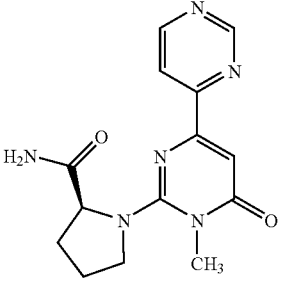 |
| D83 | 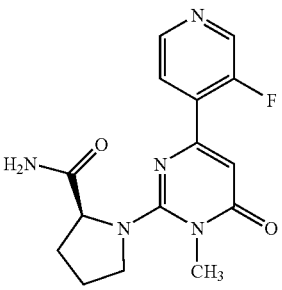 [SMILES: Cn1c(N2CCC[C@H]2C(N)=O)nc(-c2ccncc2F)cc1=O] |
| D84 | 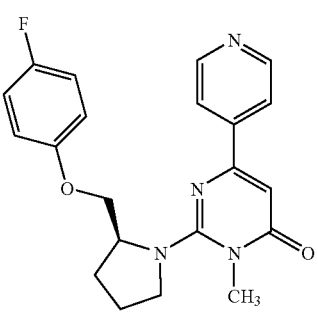 |
| D85 | 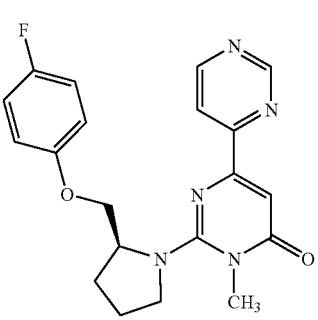 [SMILES: Cn1c(N2CCC[C@H]2COc2ccc(F)cc2)nc(-c2ccncc2)cc1=O] |
| D86 | 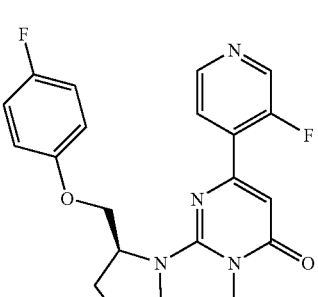 |

TABLE 1-continued
| Compound No. | STRUCTURE |
|---|---|
| D87 | 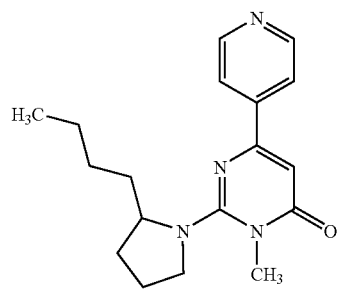 [SMILES: CCCCC1CCCN1c1nc(-c2ccncc2)cc(=O)n1C] |
| D88 | 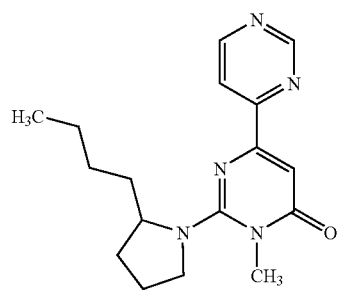 [SMILES: CCCCC1CCCN1c1nc(-c2ccncn2)cc(=O)n1C] |
| D89 | 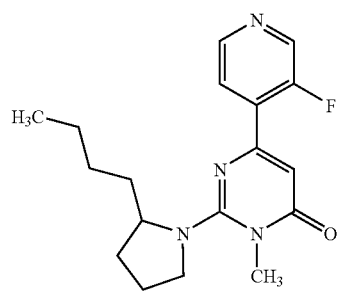 [SMILES: CCCCC1CCCN1c1nc(-c2ccncc2F)cc(=O)n1C] |
| D90 | 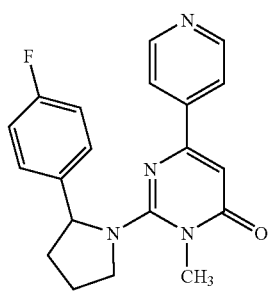 [SMILES: Cn1c(N2CCCC2c2ccc(F)cc2)nc(-c2ccncc2)cc1=O] |
| D91 | 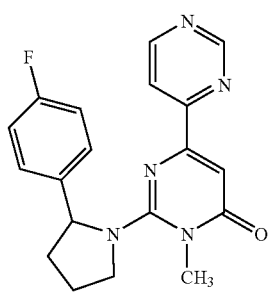 [SMILES: Cn1c(N2CCCC2c2ccc(F)cc2)nc(-c2ccncn2)cc1=O] |

TABLE 1-continued
| Compound No. | STRUCTURE |
|---|---|
| D92 | 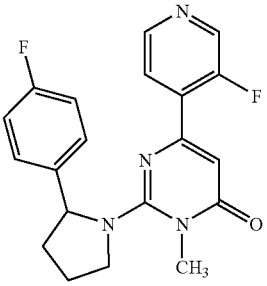 [SMILES: Cn1c(N2CCCC2c2ccc(F)cc2)nc(-c2ccncc2F)cc1=O] |
| D93 | 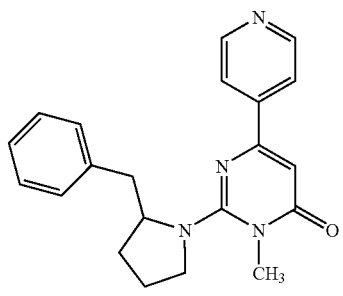 [SMILES: Cn1c(N2CCCC2Cc2ccccc2)nc(-c2ccncc2)cc1=O] |
| D94 | 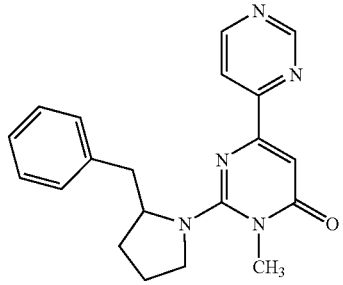 [SMILES: Cn1c(N2CCCC2Cc2ccccc2)nc(-c2ccncn2)cc1=O] |
| D95 | 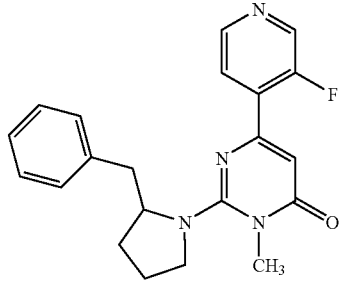 [SMILES: Cn1c(N2CCCC2Cc2ccccc2)nc(-c2ccncc2F)cc1=O] |
| D96 | 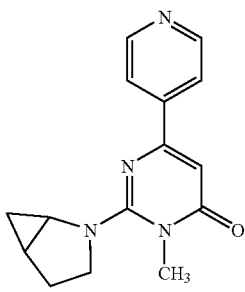 [SMILES: Cn1c(N2CCC3CC32)nc(-c2ccncc2)cc1=O] |

TABLE 1-continued
| Compound No. | STRUCTURE |
|---|---|
| D97 | 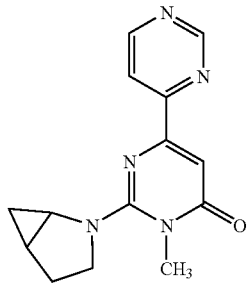 [SMILES: Cn1c(N2CCC3CC32)nc(-c2ccncn2)cc1=O] |
| D98 | 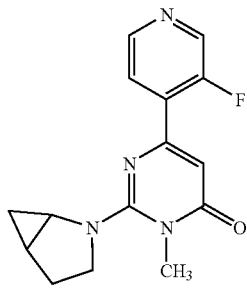 [SMILES: Cn1c(N2CCC3CC32)nc(-c2ccncc2F)cc1=O] |
| D99 | 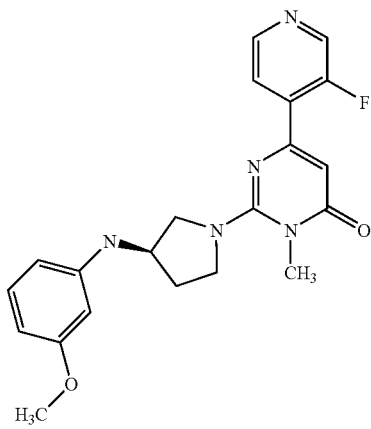 [SMILES: COc1cccc(N[C@@H]2CCN(c3nc(-c4ccncc4F)cc(=O)n3C)C2)c1] |
| D100 | 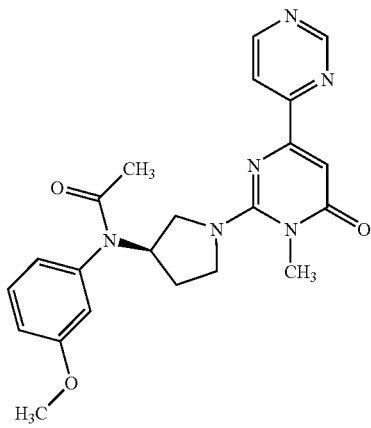 [SMILES: COc1cccc(N(C(C)=O)[C@@H]2CCN(c3nc(-c4ccncn4)cc(=O)n3C)C2)c1] |

161
TABLE 1-continued
| Compound No. | STRUCTURE |
|---|---|
| F1 | 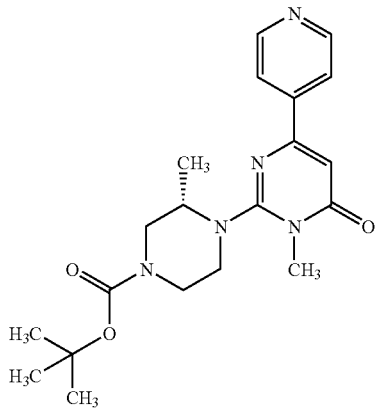 [SMILES: C[C@H]1CN(C(=O)OC(C)(C)C)CCN1c1nc(-c2ccncc2)cc(=O)n1C] |
| F2 | 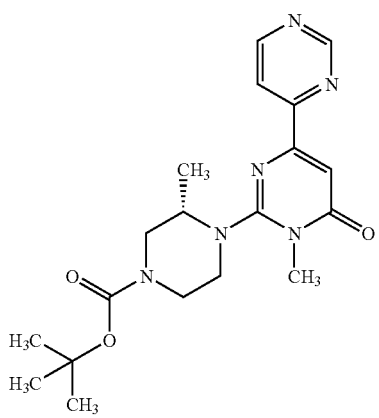 [SMILES: C[C@H]1CN(C(=O)OC(C)(C)C)CCN1c1nc(-c2ccncn2)cc(=O)n1C] |
| F3 | 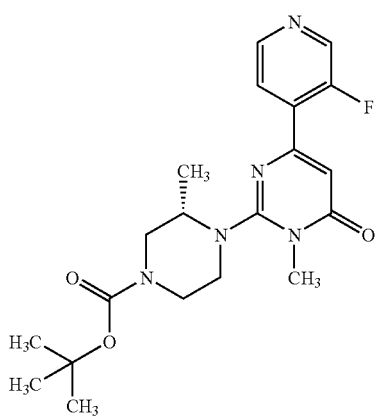 [SMILES: C[C@H]1CN(C(=O)OC(C)(C)C)CCN1c1nc(-c2ccncc2F)cc(=O)n1C] |
| F4 | 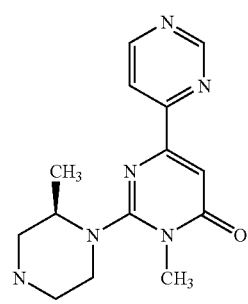 |
162

TABLE 1-continued
| Compound No. | STRUCTURE |
|---|---|
| F5 | 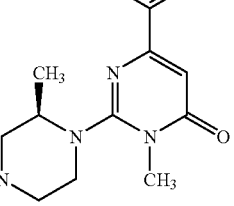 |
| F6 | 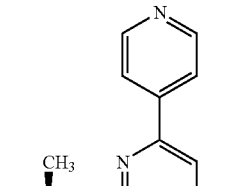 |
| F7 | 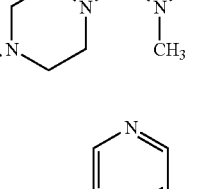 |
| F8 | 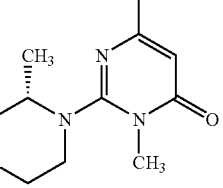 |
| F9 | 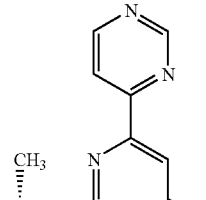 |

TABLE 1-continued
| Compound No. | STRUCTURE |
|---|---|
| F10 | 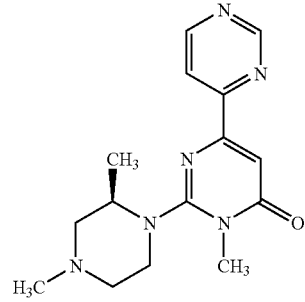 [SMILES: C[C@@H]1CN(C)CCN1c1nc(-c2ccncn2)cc(=O)n1C] |
| F11 | 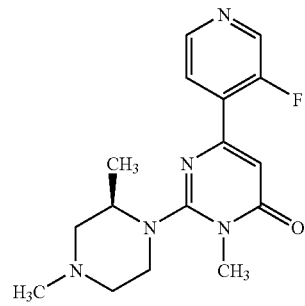 [SMILES: C[C@@H]1CN(C)CCN1c1nc(-c2ccncc2F)cc(=O)n1C] |
| F12 | 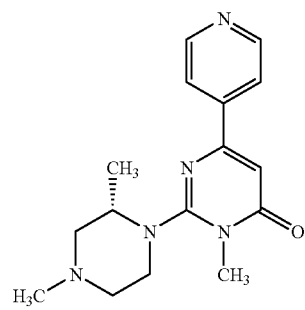 [SMILES: C[C@H]1CN(C)CCN1c1nc(-c2ccncc2)cc(=O)n1C] |
| F13 | 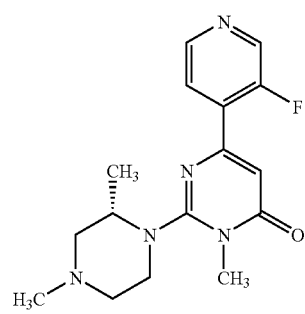 [SMILES: C[C@H]1CN(C)CCN1c1nc(-c2ccncc2F)cc(=O)n1C] |
| F14 | 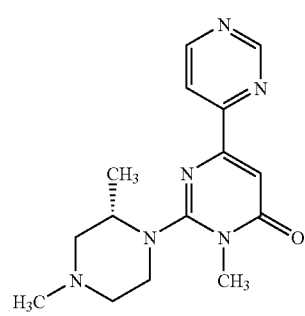 |

TABLE 1-continued
| Compound No. | STRUCTURE |
|---|---|
| F15 | 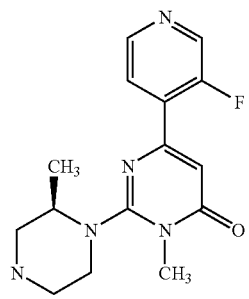 |
| F16 | 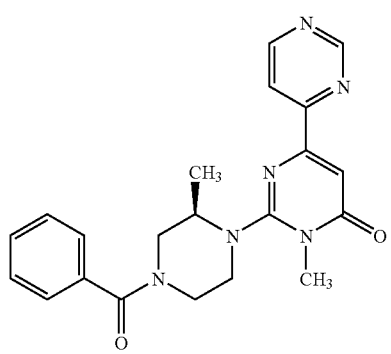 |
| F17 | 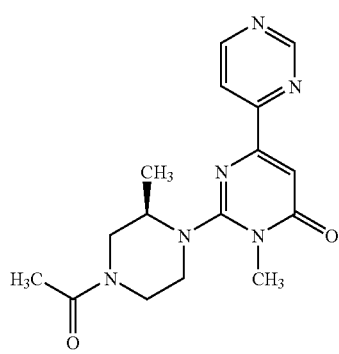 [SMILES: CC(=O)N1CCN(c2nc(-c3ccncn3)cc(=O)n2C)[C@H](C)C1] |
| F18 | 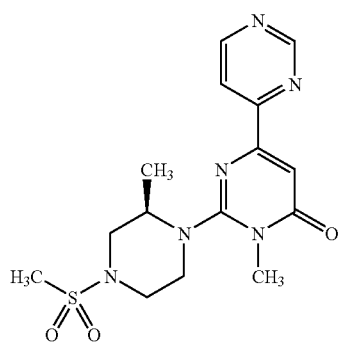 [SMILES: C[C@@H]1CN(S(C)(=O)=O)CCN1c1nc(-c2ccncn2)cc(=O)n1C] |

TABLE 1-continued
| Compound No. | STRUCTURE |
|---|---|
| F19 | 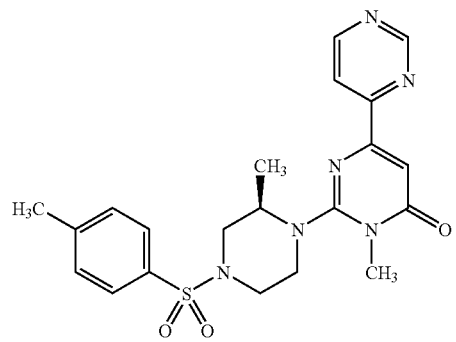 [SMILES: Cc1ccc(S(=O)(=O)N2CCN(c3nc(-c4ccncn4)cc(=O)n3C)[C@H](C)C2)cc1] |
| F20 | 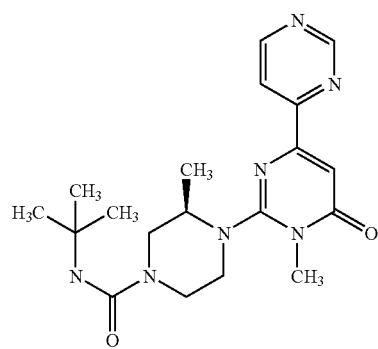 [SMILES: C[C@@H]1CN(C(=O)NC(C)(C)C)CCN1c1nc(-c2ccncn2)cc(=O)n1C] |
| F21 | 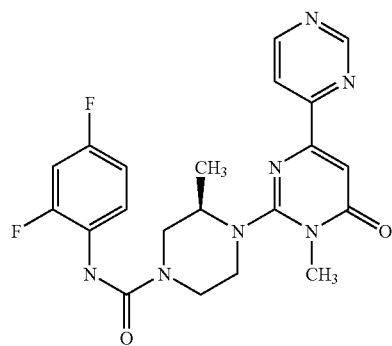 [SMILES: C[C@@H]1CN(C(=O)Nc2ccc(F)cc2F)CCN1c1nc(-c2ccncn2)cc(=O)n1C] |
| F22 | 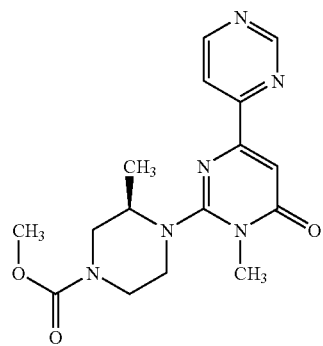 [SMILES: COC(=O)N1CCN(c2nc(-c3ccncn3)cc(=O)n2C)[C@H](C)C1] |

TABLE 1-continued
| Compound No. | STRUCTURE |
|---|---|
| F23 | 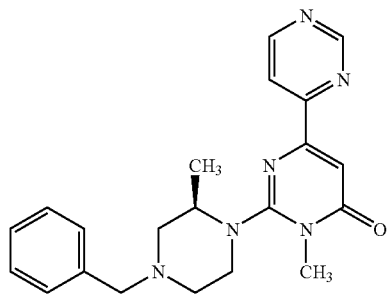 [SMILES: C[C@@H]1CN(Cc2ccccc2)CCN1c1nc(-c2ccncn2)cc(=O)n1C] |
| F24 | 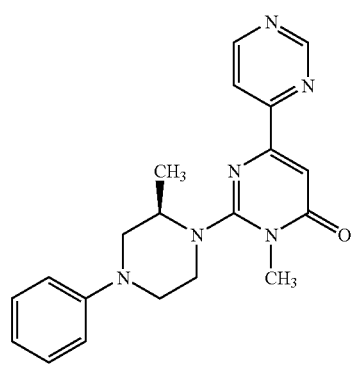 [SMILES: C[C@@H]1CN(c2ccccc2)CCN1c1nc(-c2ccncn2)cc(=O)n1C] |
| F25 | 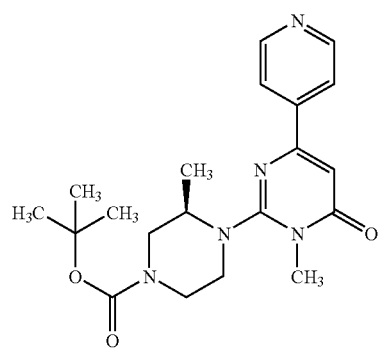 [SMILES: C[C@@H]1CN(C(=O)OC(C)(C)C)CCN1c1nc(-c2ccncc2)cc(=O)n1C] |
| F26 | 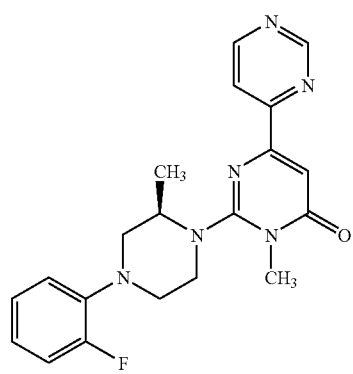 [SMILES: C[C@@H]1CN(c2ccccc2F)CCN1c1nc(-c2ccncn2)cc(=O)n1C] |

TABLE 1-continued
| Compound No. | STRUCTURE |
|---|---|
| F27 | 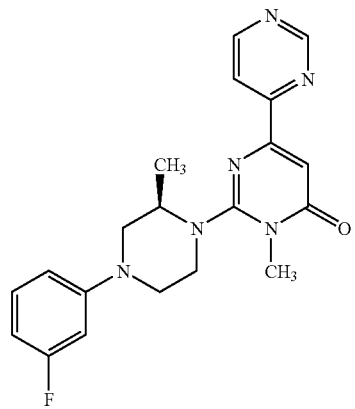 [SMILES: C[C@@H]1CN(c2cccc(F)c2)CCN1c1nc(-c2ccncn2)cc(=O)n1C] |
| F28 | 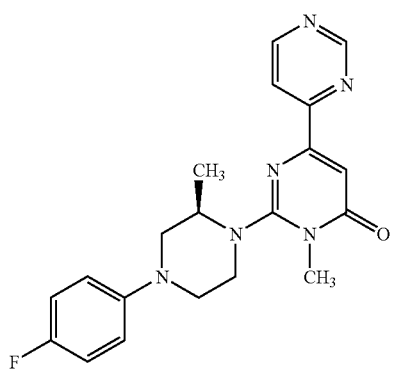 [SMILES: C[C@@H]1CN(c2ccc(F)cc2)CCN1c1nc(-c2ccncn2)cc(=O)n1C] |
| F29 | 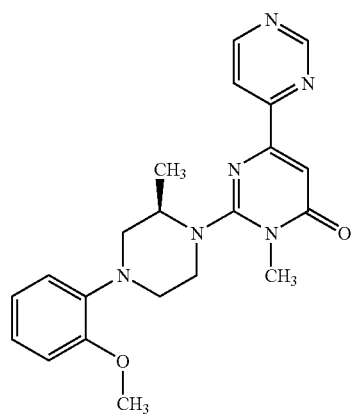 [SMILES: COc1ccccc1N1CCN(c2nc(-c3ccncn3)cc(=O)n2C)[C@H](C)C1] |

TABLE 1-continued
| Compound No. | STRUCTURE |
|---|---|
| F30 | 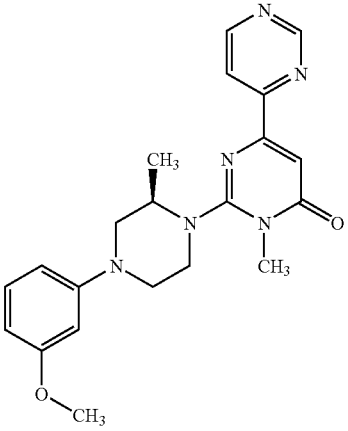 [SMILES: COc1cccc(N2CCN(c3nc(-c4ccncn4)cc(=O)n3C)[C@H](C)C2)c1] |
| F31 | 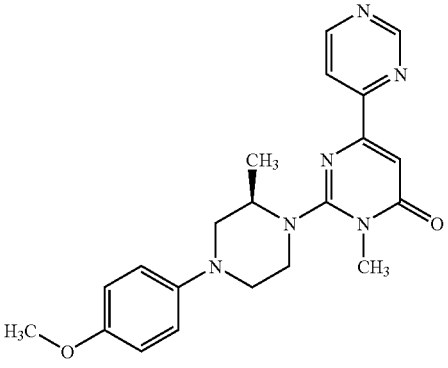 [SMILES: COc1ccc(N2CCN(c3nc(-c4ccncn4)cc(=O)n3C)[C@H](C)C2)cc1] |
| F32 | 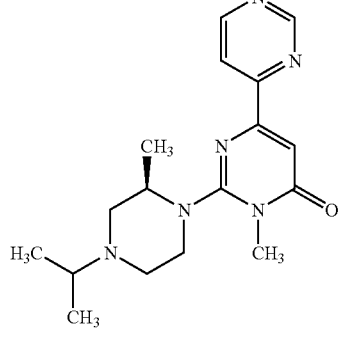 |
| F33 | 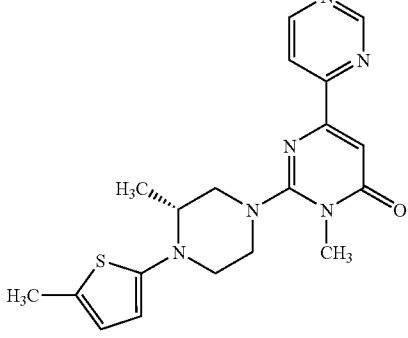 |

TABLE 1-continued
| Compound No. | STRUCTURE |
|---|---|
| F34 | 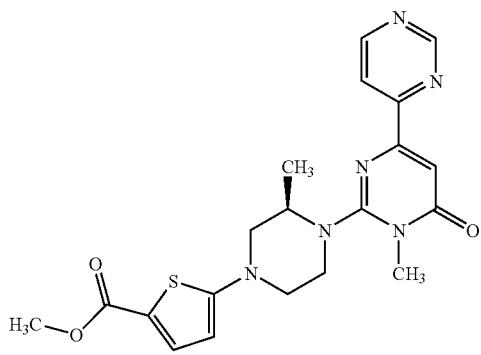 [SMILES: COC(=O)c1ccc(N2CCN(c3nc(-c4ccncn4)cc(=O)n3C)[C@H](C)C2)s1] |
| F35 | 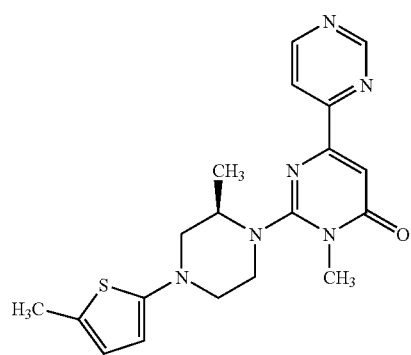 [SMILES: Cc1ccc(N2CCN(c3nc(-c4ccncn4)cc(=O)n3C)[C@H](C)C2)s1] |
| F36 | 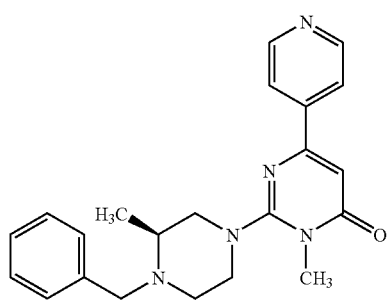 [SMILES: C[C@H]1CN(c2nc(-c3ccncc3)cc(=O)n2C)CCN1Cc1ccccc1] |
| F37 | 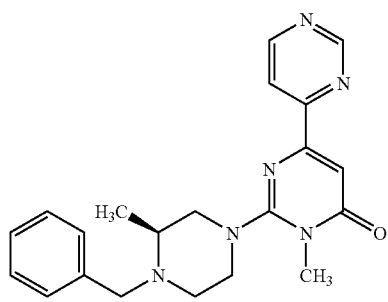 [SMILES: C[C@H]1CN(c2nc(-c3ccncn3)cc(=O)n2C)CCN1Cc1ccccc1] |

TABLE 1-continued
| Compound No. | STRUCTURE |
|---|---|
| F38 | 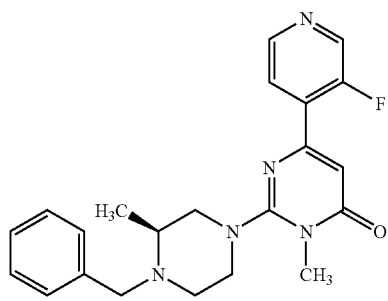 [SMILES: C[C@H]1CN(c2nc(-c3ccncc3F)cc(=O)n2C)CCN1Cc1ccccc1] |
| F39 | 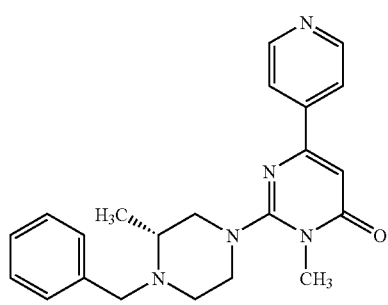 |
| F40 | 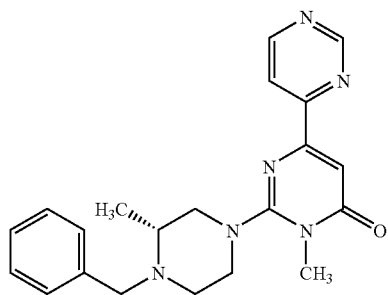 [SMILES: C[C@@H]1CN(c2nc(-c3ccncn3)cc(=O)n2C)CCN1Cc1ccccc1] |
| F41 | 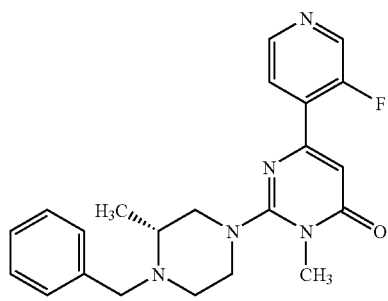 [SMILES: C[C@@H]1CN(c2nc(-c3ccncc3F)cc(=O)n2C)CCN1Cc1ccccc1] |
| F42 | 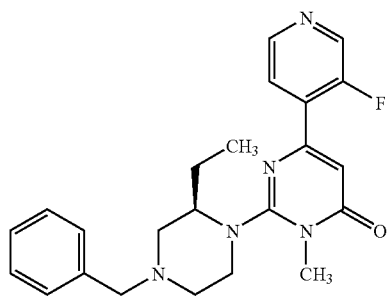 [SMILES: CC[C@@H]1CN(Cc2ccccc2)CCN1c1nc(-c2ccncc2F)cc(=O)n1C] |

TABLE 1-continued
| Compound No. | STRUCTURE |
|---|---|
| F43 | 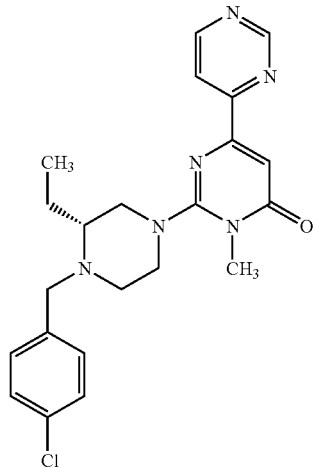 [SMILES: CC[C@@H]1CN(c2nc(-c3ccncn3)cc(=O)n2C)CCN1Cc1ccc(Cl)cc1] |
| F44 | 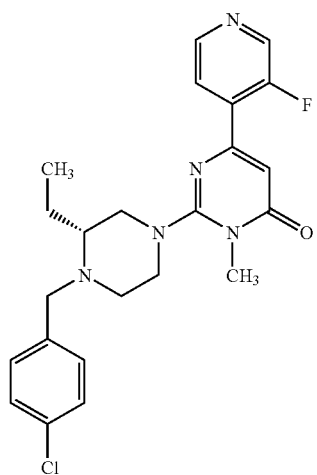 [SMILES: CC[C@@H]1CN(c2nc(-c3ccncc3F)cc(=O)n2C)CCN1Cc1ccc(Cl)cc1] |
| F45 | 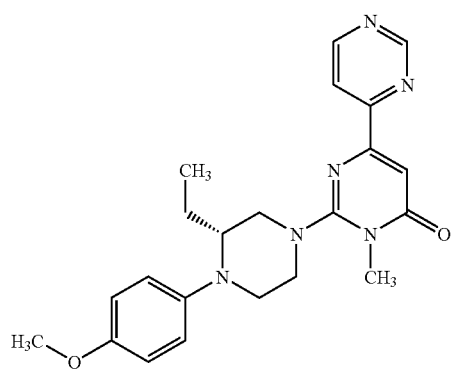 [SMILES: CC[C@@H]1CN(c2nc(-c3ccncn3)cc(=O)n2C)CCN1c1ccc(OC)cc1] |

TABLE 1-continued
| Compound No. | STRUCTURE |
|---|---|
| F46 | 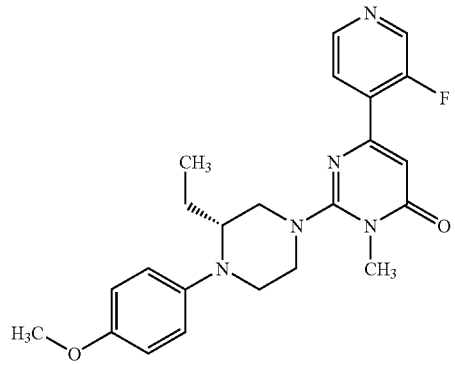 [SMILES: CC[C@@H]1CN(c2nc(-c3ccncc3F)cc(=O)n2C)CCN1c1ccc(OC)cc1] |
| F47 | 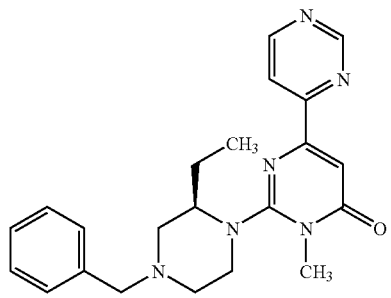 [SMILES: CC[C@@H]1CN(Cc2ccccc2)CCN1c1nc(-c2ccncn2)cc(=O)n1C] |
| F48 | 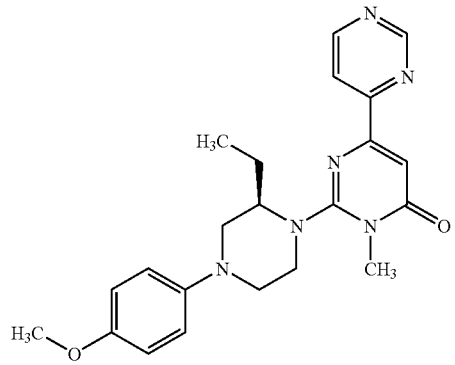 [SMILES: CC[C@@H]1CN(c2ccc(OC)cc2)CCN1c1nc(-c2ccncn2)cc(=O)n1C] |
| F49 | 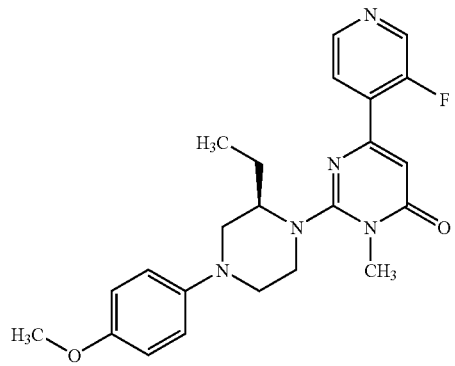 [SMILES: CC[C@@H]1CN(c2ccc(OC)cc2)CCN1c1nc(-c2ccncc2F)cc(=O)n1C] |

TABLE 1-continued
| Compound No. | STRUCTURE |
|---|---|
| F50 | 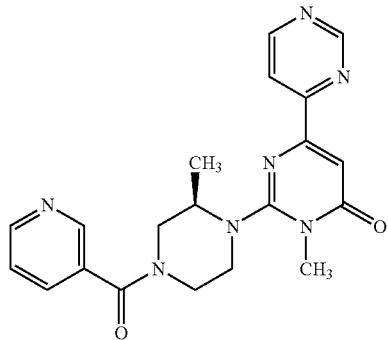 |
| F51 | 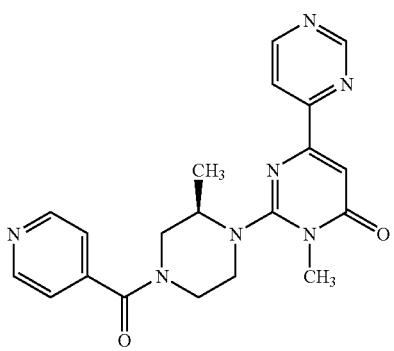 [SMILES: C[C@@H]1CN(C(=O)c2ccncc2)CCN1c1nc(-c2ccncn2)cc(=O)n1C] |
| F52 | 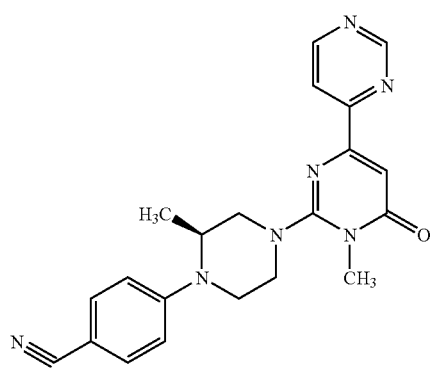 [SMILES: C[C@H]1CN(c2nc(-c3ccncn3)cc(=O)n2C)CCN1c1ccc(C#N)cc1] |
| F53 | 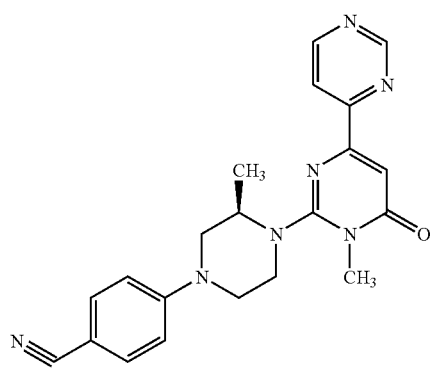 [SMILES: C[C@@H]1CN(c2ccc(C#N)cc2)CCN1c1nc(-c2ccncn2)cc(=O)n1C] |

TABLE 1-continued
| Compound No. | STRUCTURE |
|---|---|
| F54 | 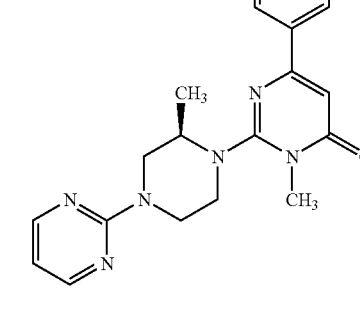 |
| F55 | 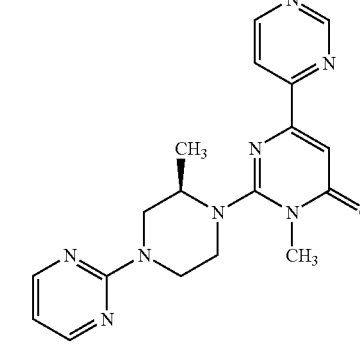 |
| F56 | 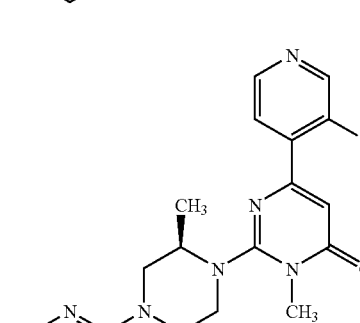 |
| F57 | 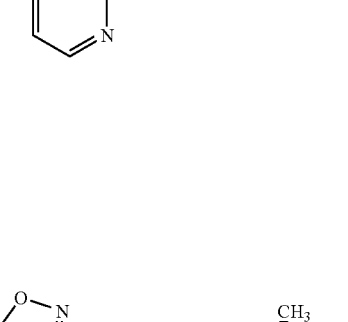 |

TABLE 1-continued
| Compound No. | STRUCTURE |
|---|---|
| F58 | 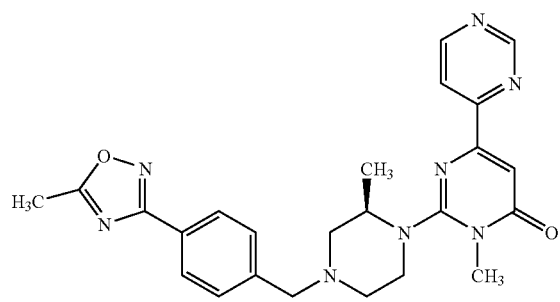 [SMILES: Cc1nc(-c2ccc(CN3CCN(c4nc(-c5ccncn5)cc(=O)n4C)[C@H](C)C3)cc2)no1] |
| F59 | 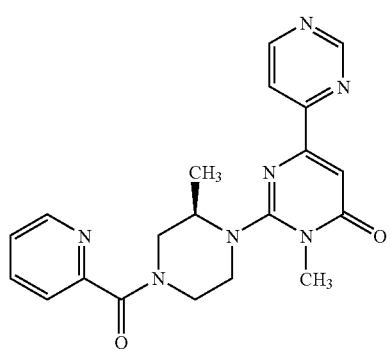 [SMILES: C[C@@H]1CN(C(=O)c2ccccn2)CCN1c1nc(-c2ccncn2)cc(=O)n1C] |
| F60 | 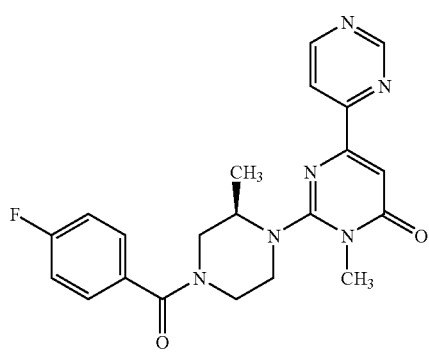 [SMILES: C[C@@H]1CN(C(=O)c2ccc(F)cc2)CCN1c1nc(-c2ccncn2)cc(=O)n1C] |
| F61 | 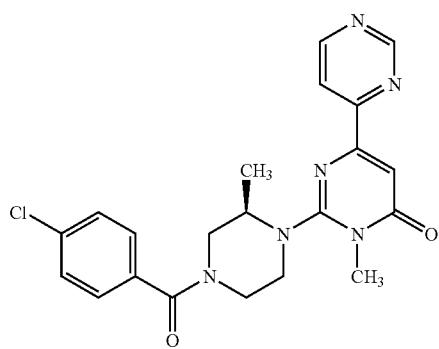 [SMILES: C[C@@H]1CN(C(=O)c2ccc(Cl)cc2)CCN1c1nc(-c2ccncn2)cc(=O)n1C] |

TABLE 1-continued
| Compound No. | STRUCTURE |
|---|---|
| F62 | 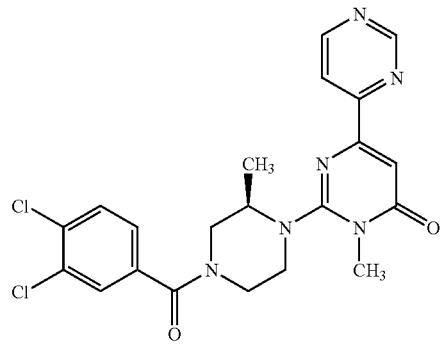 [SMILES: C[C@@H]1CN(C(=O)c2ccc(Cl)c(Cl)c2)CCN1c1nc(-c2ccncn2)cc(=O)n1C] |
| F63 | 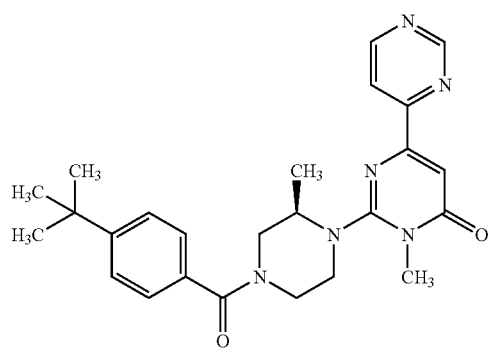 [SMILES: C[C@@H]1CN(C(=O)c2ccc(C(C)(C)C)cc2)CCN1c1nc(-c2ccncn2)cc(=O)n1C] |
| F64 | 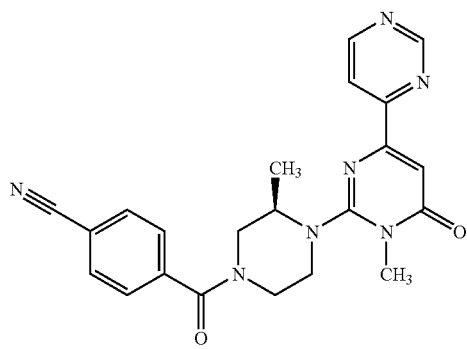 [SMILES: C[C@@H]1CN(C(=O)c2ccc(C#N)cc2)CCN1c1nc(-c2ccncn2)cc(=O)n1C] |
| F65 | 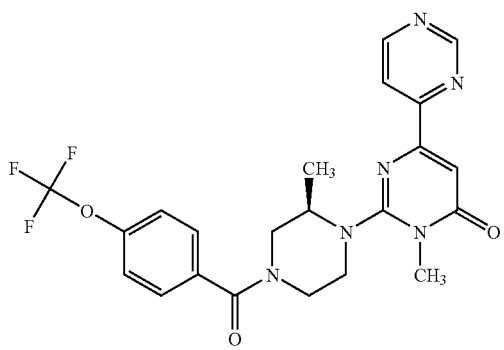 [SMILES: C[C@@H]1CN(C(=O)c2ccc(OC(F)(F)F)cc2)CCN1c1nc(-c2ccncn2)cc(=O)n1C] |

TABLE 1-continued

| Compound No. | STRUCTURE |
|---|---|
| F66 | 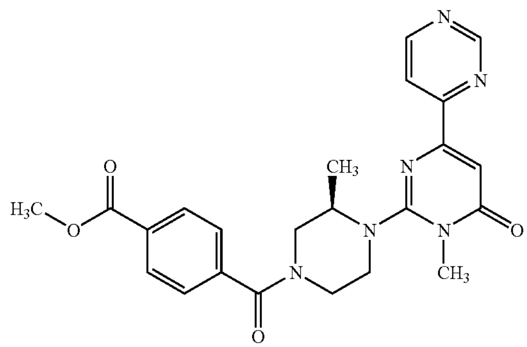 [SMILES: COC(=O)c1ccc(C(=O)N2CCN(c3nc(-c4ccncn4)cc(=O)n3C)[C@H](C)C2)cc1] |
| F67 | 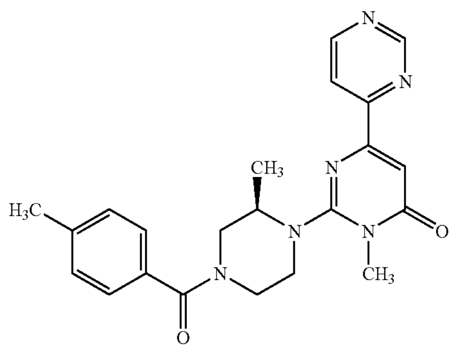 [SMILES: Cc1ccc(C(=O)N2CCN(c3nc(-c4ccncn4)cc(=O)n3C)[C@H](C)C2)cc1] |
| F68 | 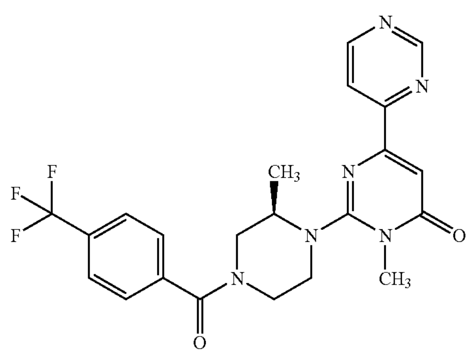 [SMILES: C[C@@H]1CN(C(=O)c2ccc(C(F)(F)F)cc2)CCN1c1nc(-c2ccncn2)cc(=O)n1C] |
| F69 | 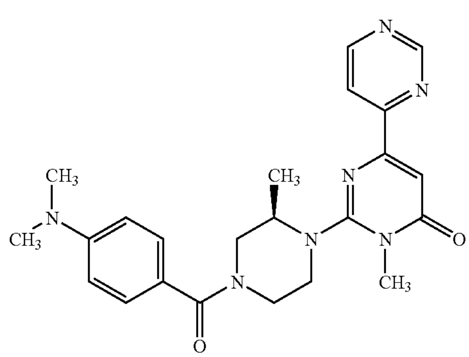 [SMILES: C[C@@H]1CN(C(=O)c2ccc(N(C)C)cc2)CCN1c1nc(-c2ccncn2)cc(=O)n1C] |

TABLE 1-continued
| Compound No. | STRUCTURE |
|---|---|
| F70 | 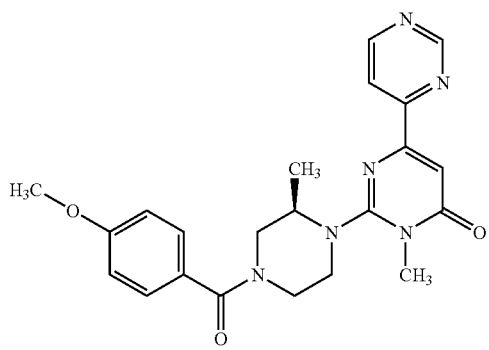 [SMILES: COc1ccc(C(=O)N2CCN(c3nc(-c4ccncn4)cc(=O)n3C)[C@H](C)C2)cc1] |
| F71 | 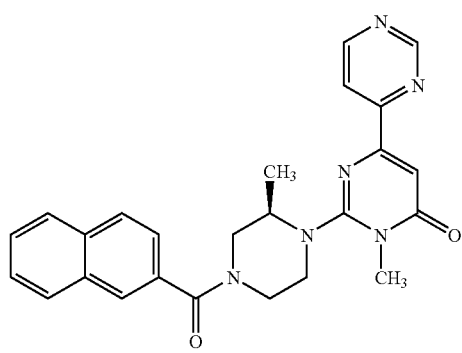 |
| F72 | 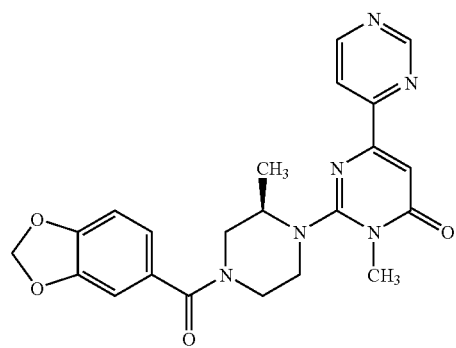 [SMILES: C[C@@H]1CN(C(=O)c2ccc3c(c2)OCO3)CCN1c1nc(-c2ccncn2)cc(=O)n1C] |
| F73 | 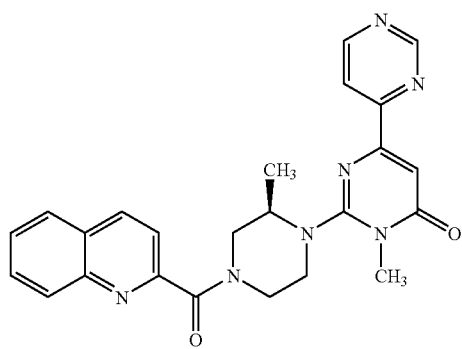 [SMILES: C[C@@H]1CN(C(=O)c2ccc3ccccc3n2)CCN1c1nc(-c2ccncn2)cc(=O)n1C] |

TABLE 1-continued
| Compound No. | STRUCTURE |
|---|---|
| F74 | 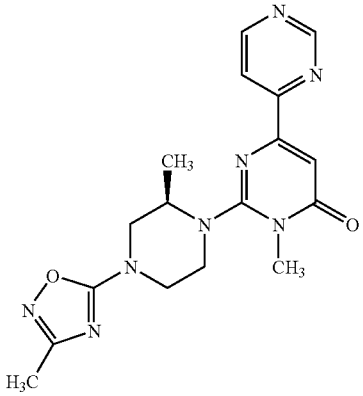 [SMILES: Cc1noc(N2CCN(c3nc(-c4ccncn4)cc(=O)n3C)[C@H](C)C2)n1] |
| F75 | 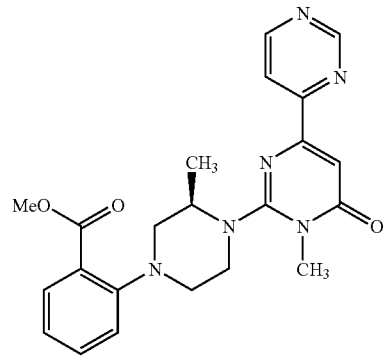 |
| F76 | 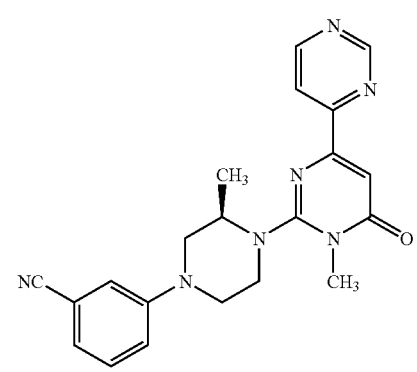 |
| F77 | 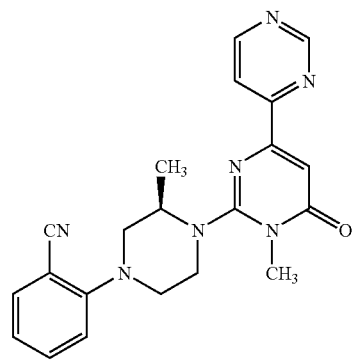 [SMILES: C[C@@H]1CN(c2ccccc2C#N)CCN1c1nc(-c2ccncn2)cc(=O)n1C] |

TABLE 1-continued
| Compound No. | STRUCTURE |
|---|---|
| F78 | 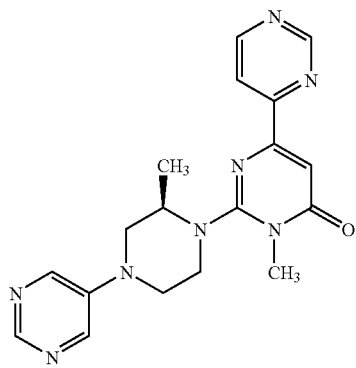 |
| F79 | 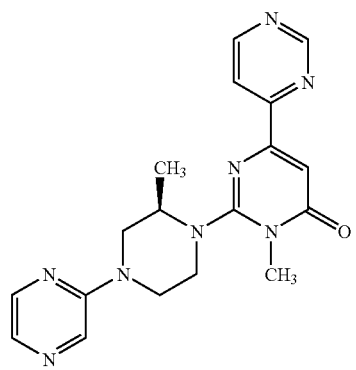 |
| F80 | 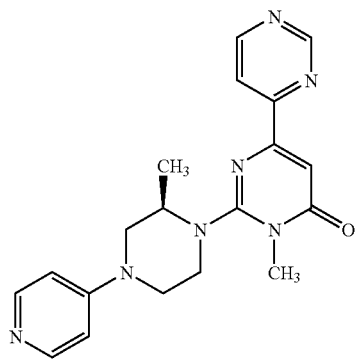 |
| F81 | 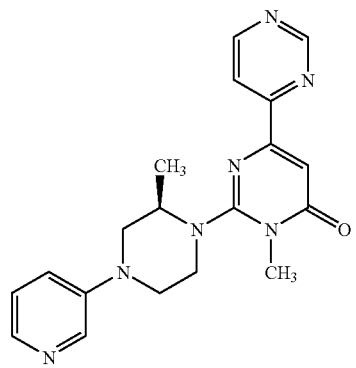 [SMILES: C[C@@H]1CN(c2cccnc2)CCN1c1nc(-c2ccncn2)cc(=O)n1C] |

TABLE 1-continued
| Compound No. | STRUCTURE |
|---|---|
| F82 | 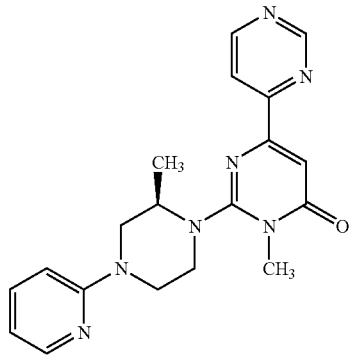 |
| F83 | 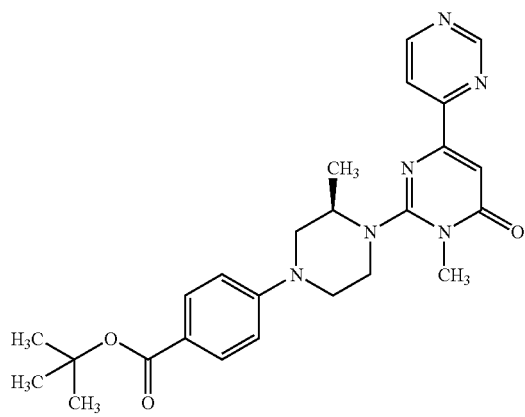 |
| F84 | 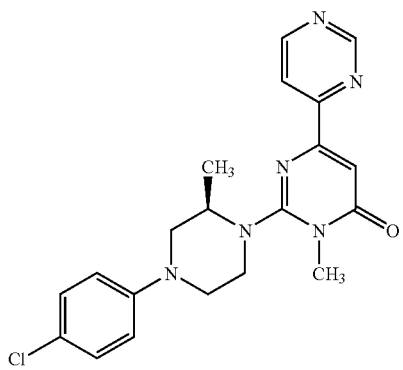 [SMILES: C[C@@H]1CN(c2ccc(Cl)cc2)CCN1c1nc(-c2ccncn2)cc(=O)n1C] |
| F85 | 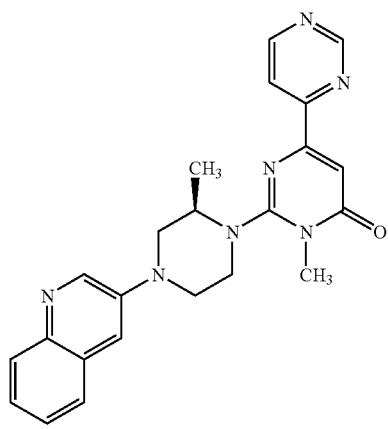 [SMILES: C[C@@H]1CN(c2cnc3ccccc3c2)CCN1c1nc(-c2ccncn2)cc(=O)n1C] |

TABLE 1-continued
| Compound No. | STRUCTURE |
|---|---|
| F86 | 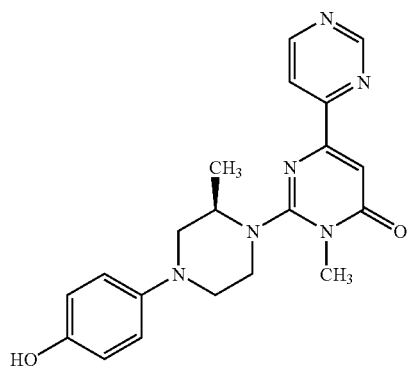 |
| F87 | 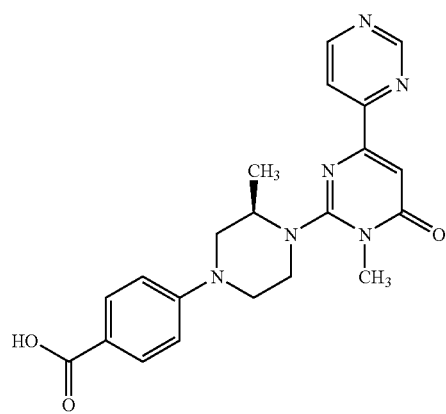 [SMILES: C[C@@H]1CN(c2ccc(C(=O)O)cc2)CCN1c1nc(-c2ccncn2)cc(=O)n1C] |
| F88 | 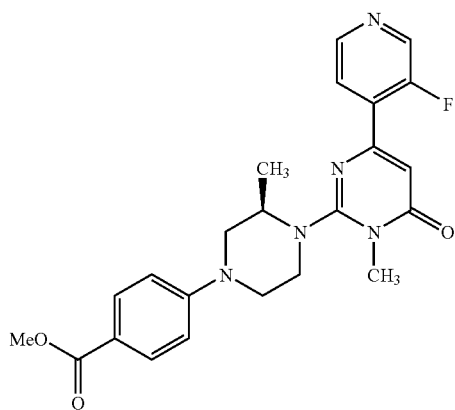 [SMILES: COC(=O)c1ccc(N2CCN(c3nc(-c4ccncc4F)cc(=O)n3C)[C@H](C)C2)cc1] |
| F89 | 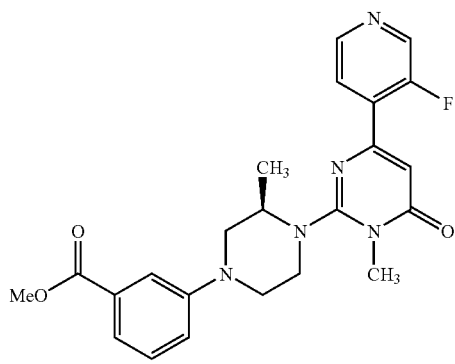 [SMILES: COC(=O)c1cccc(N2CCN(c3nc(-c4ccncc4F)cc(=O)n3C)[C@H](C)C2)c1] |

TABLE 1-continued
| Compound No. | STRUCTURE |
|---|---|
| F90 | 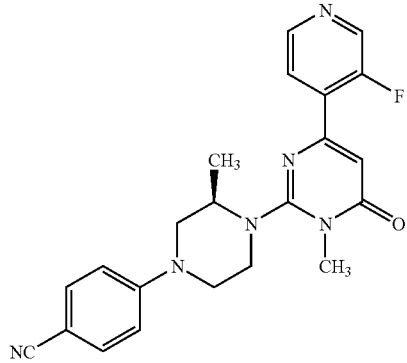 |
| F91 | 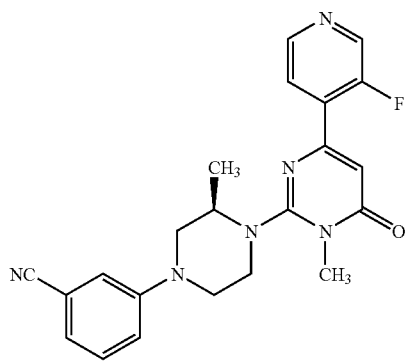 |
| F92 | 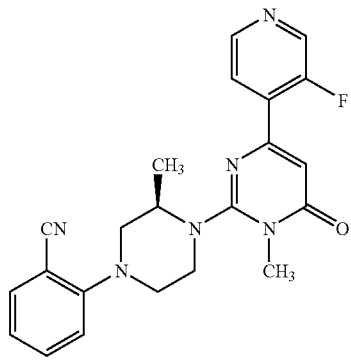 [SMILES: C[C@@H]1CN(c2ccccc2C#N)CCN1c1nc(-c2ccncc2F)cc(=O)n1C] |
| F93 | 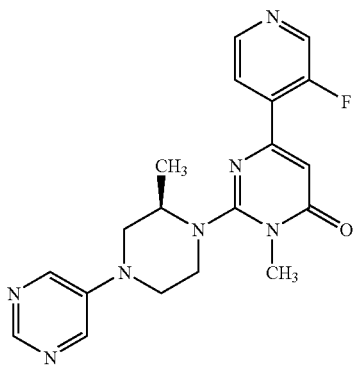 [SMILES: C[C@@H]1CN(c2cncnc2)CCN1c1nc(-c2ccncc2F)cc(=O)n1C] |

TABLE 1-continued
| Compound No. | STRUCTURE |
|---|---|
| F94 | 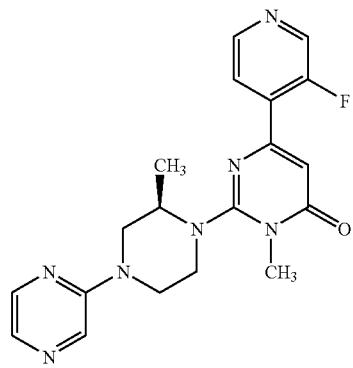 |
| F95 | 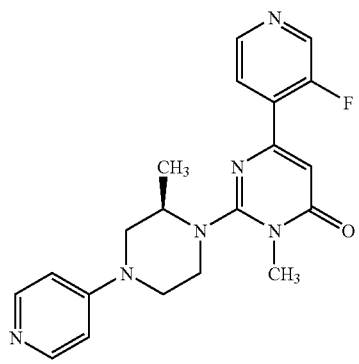 [SMILES: C[C@@H]1CN(c2ccncc2)CCN1c1nc(-c2ccncc2F)cc(=O)n1C] |
| F96 | 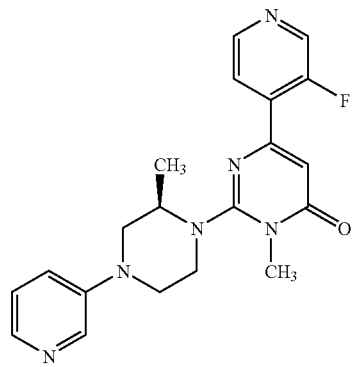 [SMILES: C[C@@H]1CN(c2cccnc2)CCN1c1nc(-c2ccncc2F)cc(=O)n1C] |
| F97 | 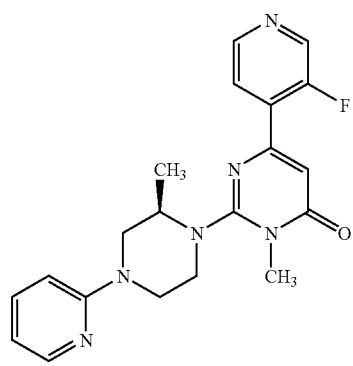 [SMILES: C[C@@H]1CN(c2ccccn2)CCN1c1nc(-c2ccncc2F)cc(=O)n1C] |

TABLE 1-continued
| Compound No. | STRUCTURE |
| --- | --- |
| F98 | 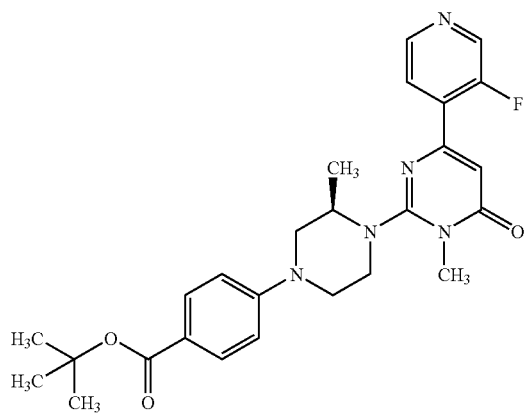 |
| F99 | 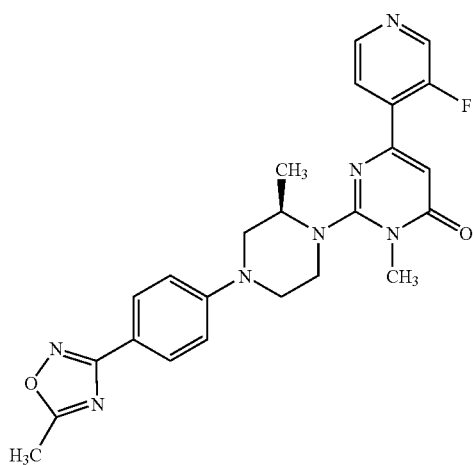 [SMILES: Cc1nc(-c2ccc(N3CCN(c4nc(-c5ccncc5F)cc(=O)n4C)[C@H](C)C3)cc2)no1] |
| F100 | 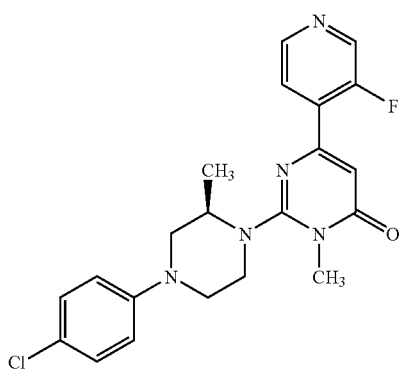 [SMILES: C[C@@H]1CN(c2ccc(Cl)cc2)CCN1c1nc(-c2ccncc2F)cc(=O)n1C] |

TABLE 1-continued
| Compound No. | STRUCTURE |
|---|---|
| F101 | 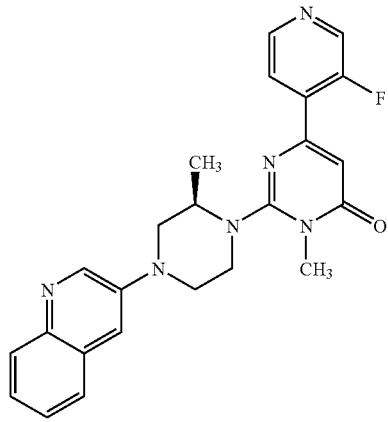 [SMILES: C[C@@H]1CN(c2cnc3ccccc3c2)CCN1c1nc(-c2ccncc2F)cc(=O)n1C] |
| F102 | 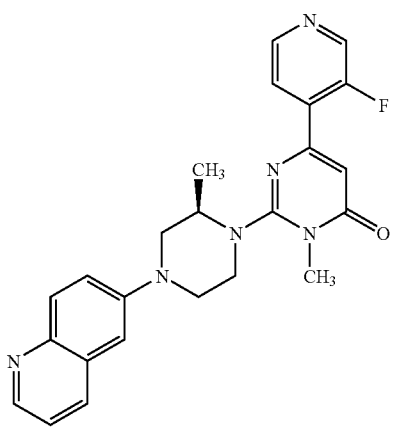 [SMILES: C[C@@H]1CN(c2ccc3ncccc3c2)CCN1c1nc(-c2ccncc2F)cc(=O)n1C] |
| F103 | 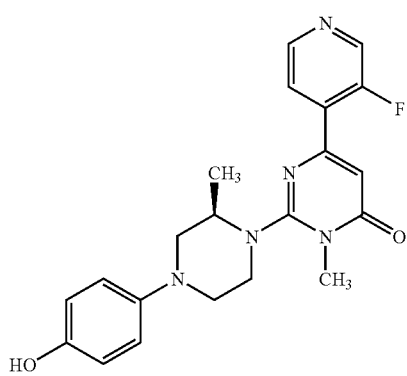 |

TABLE 1-continued
| Compound No. | STRUCTURE |
|---|---|
| F104 | 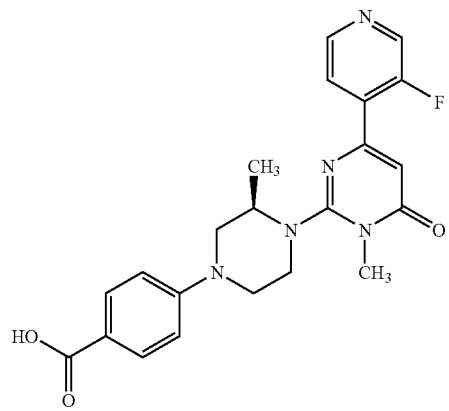 |
| F105 | 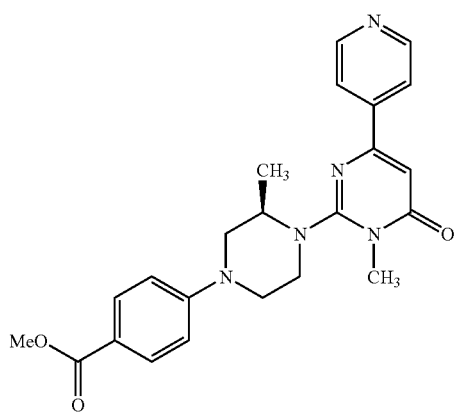 [SMILES: COC(=O)c1ccc(N2CCN(c3nc(-c4ccncc4)cc(=O)n3C)[C@H](C)C2)cc1] |
| F106 | 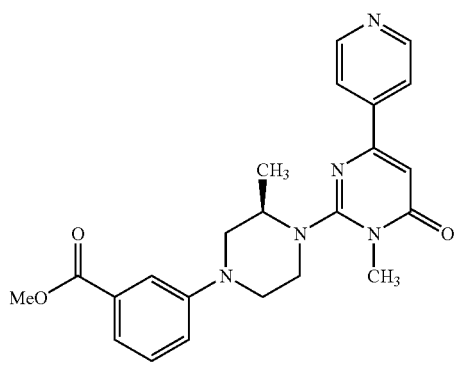 [SMILES: COC(=O)c1cccc(N2CCN(c3nc(-c4ccncc4)cc(=O)n3C)[C@H](C)C2)c1] |
| F107 | 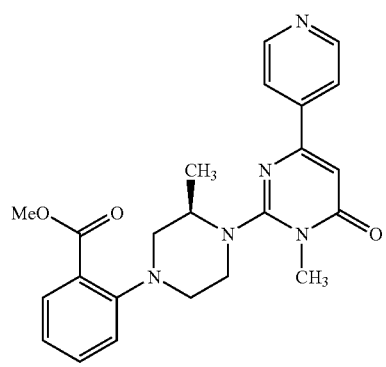 [SMILES: COC(=O)c1ccccc1N1CCN(c2nc(-c3ccncc3)cc(=O)n2C)[C@H](C)C1] |

TABLE 1-continued
| Compound No. | STRUCTURE |
|---|---|
| F108 | 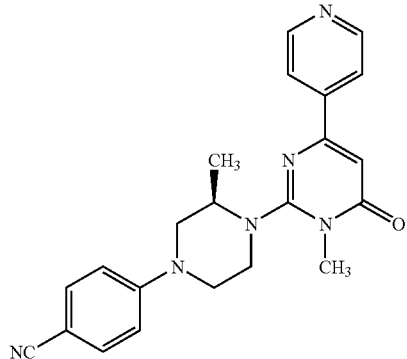 |
| F109 | 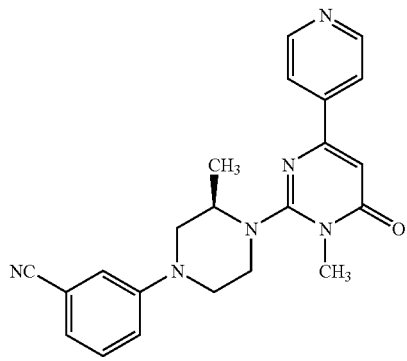 |
| F110 | 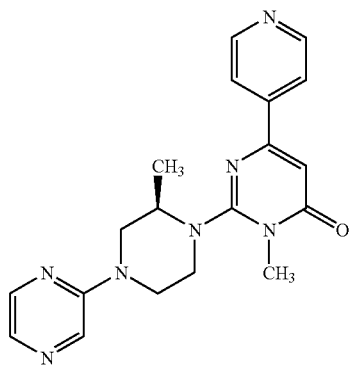 [SMILES: C[C@@H]1CN(c2cnccn2)CCN1c1nc(-c2ccncc2)cc(=O)n1C] |
| F111 | 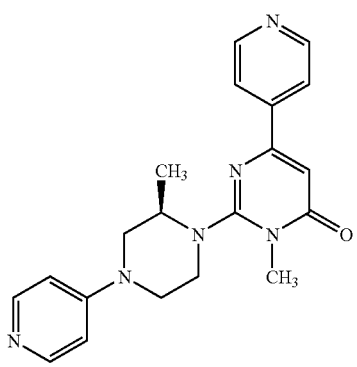 [SMILES: C[C@@H]1CN(c2ccncc2)CCN1c1nc(-c2ccncc2)cc(=O)n1C] |

TABLE 1-continued
| Compound No. | STRUCTURE |
|---|---|
| F112 | 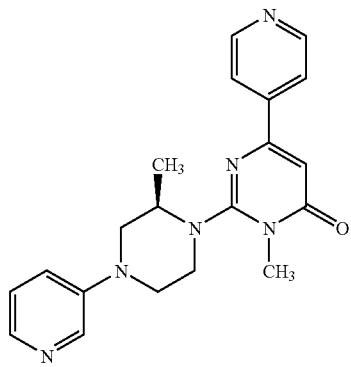 [SMILES: C[C@@H]1CN(c2cccnc2)CCN1c1nc(-c2ccncc2)cc(=O)n1C] |
| F113 | 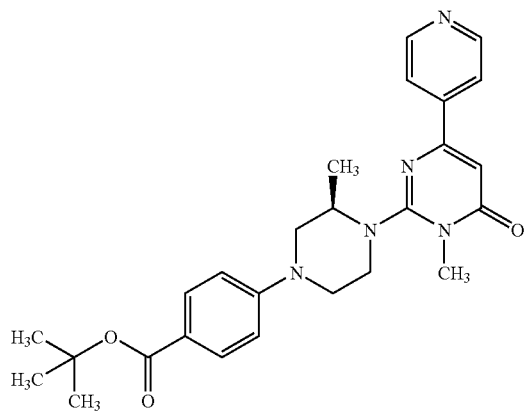 [SMILES: C[C@@H]1CN(c2ccc(C(=O)OC(C)(C)C)cc2)CCN1c1nc(-c2ccncc2)cc(=O)n1C] |
| F114 | 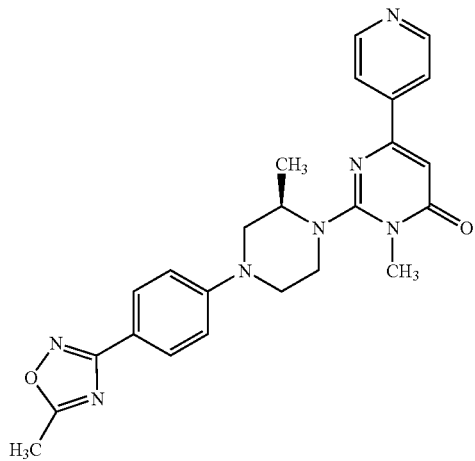 [SMILES: Cc1nc(-c2ccc(N3CCN(c4nc(-c5ccncc5)cc(=O)n4C)[C@H](C)C3)cc2)no1] |

TABLE 1-continued
| Compound No. | STRUCTURE |
|---|---|
| F115 | 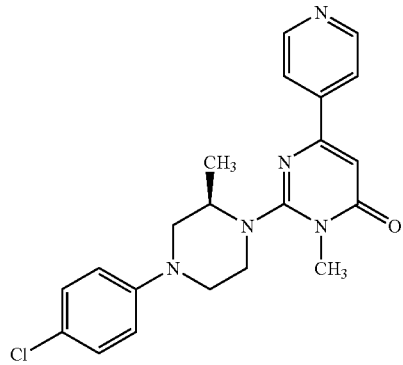 |
| F116 | 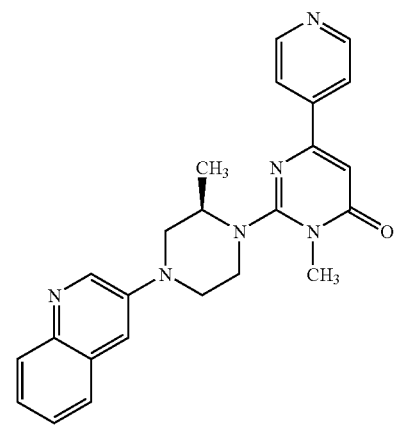 [SMILES: C[C@@H]1CN(c2cnc3ccccc3c2)CCN1c1nc(-c2ccncc2)cc(=O)n1C] |
| F117 | 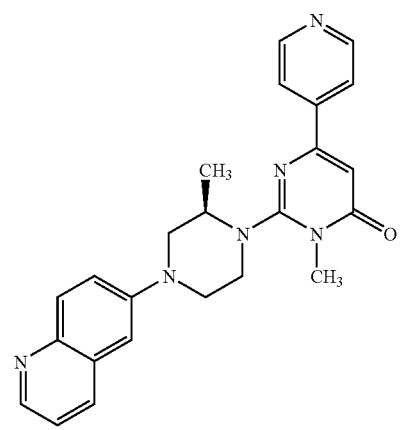 [SMILES: C[C@@H]1CN(c2ccc3ncccc3c2)CCN1c1nc(-c2ccncc2)cc(=O)n1C] |
| F118 | 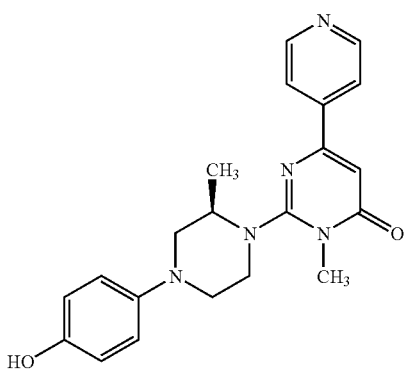 |

TABLE 1-continued
| Compound No. | STRUCTURE |
|---|---|
| F119 | 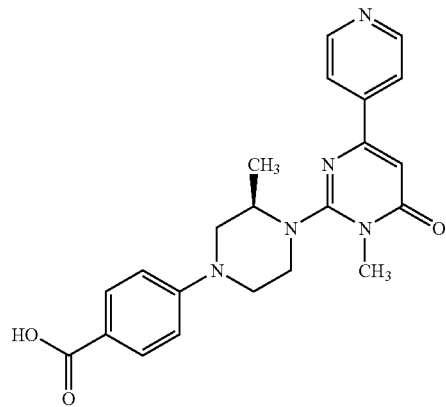 |
| F120 | 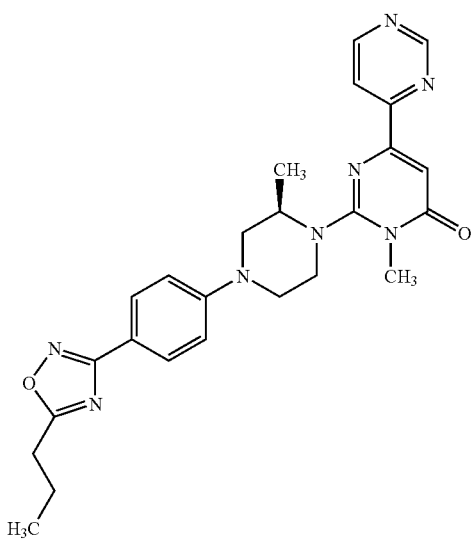 [SMILES: CCCc1nc(-c2ccc(N3CCN(c4nc(-c5ccncn5)cc(=O)n4C)[C@H](C)C3)cc2)no1] |
| F121 | 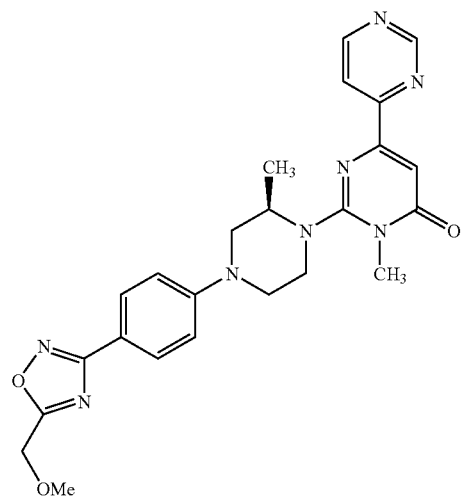 [SMILES: COCc1nc(-c2ccc(N3CCN(c4nc(-c5ccncn5)cc(=O)n4C)[C@H](C)C3)cc2)no1] |

TABLE 1-continued

| Compound No. | STRUCTURE |
|---|---|
| F122 | 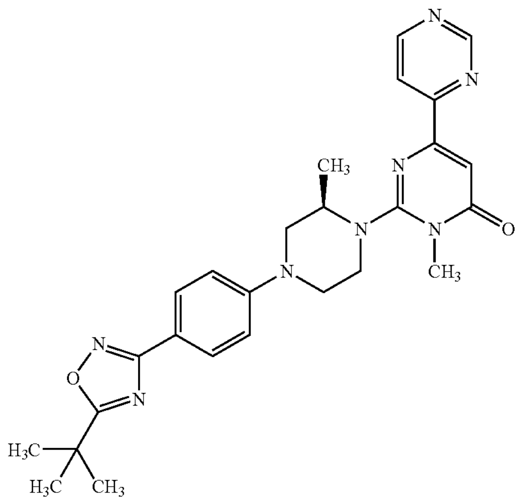 [SMILES: C[C@@H]1CN(c2ccc(-c3noc(C(C)(C)C)n3)cc2)CCN1c1nc(-c2ccncn2)cc(=O)n1C] |
| F123 | 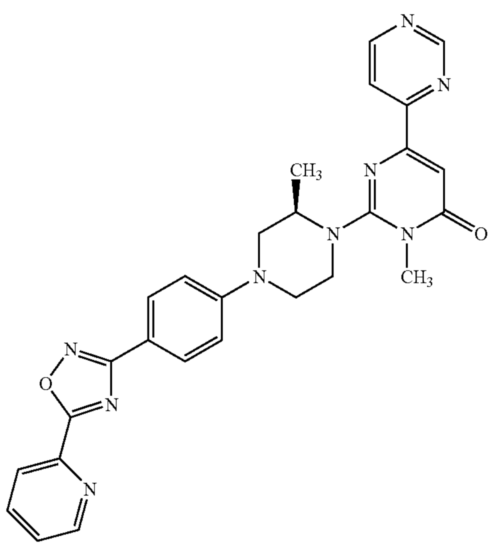 |
| F124 | 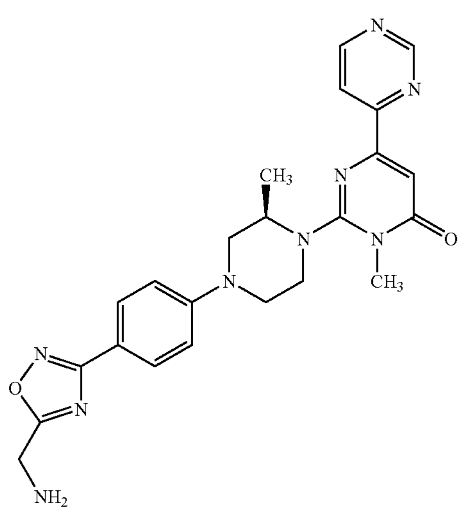 |

TABLE 1-continued
| Compound No. | STRUCTURE |
|---|---|
| F125 | 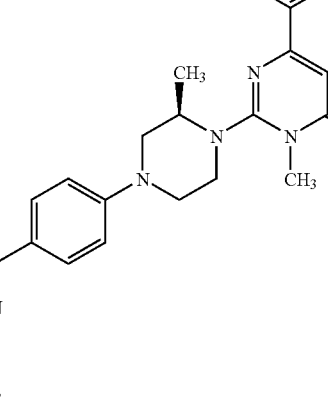 |
| F126 | 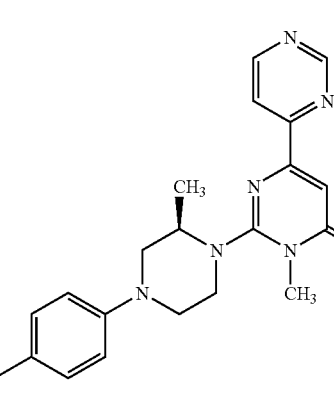 |
| F127 | 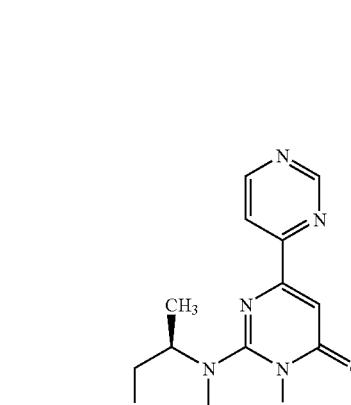 |

TABLE 1-continued
| Compound No. | STRUCTURE |
|---|---|
| F128 | 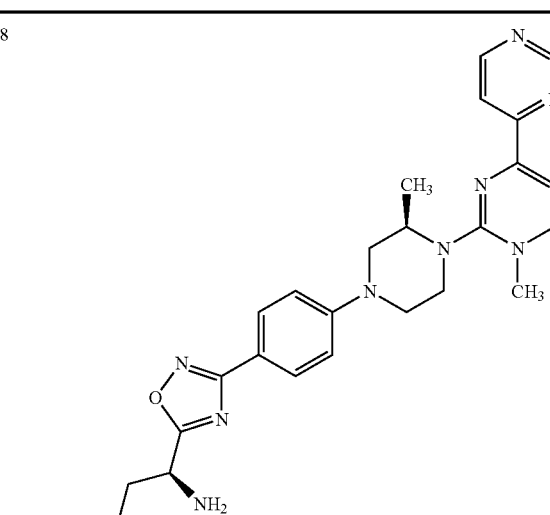 |
| F129 | 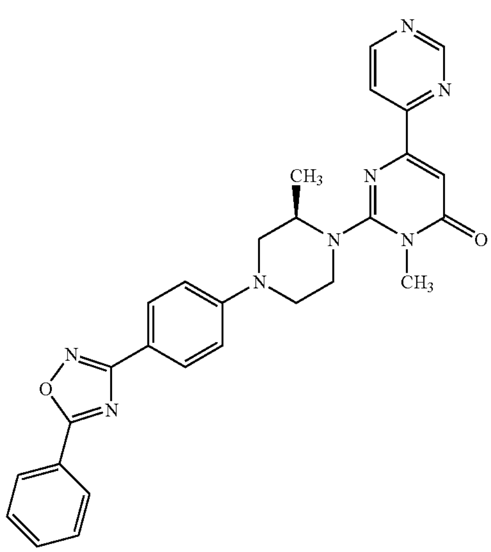 [SMILES: C[C@@H]1CN(c2ccc(-c3noc(-c4ccccn4)n3)cc2)CCN1c1nc(-c2ccncn2)cc(=O)n1C] |

TABLE 1-continued
| Compound No. | STRUCTURE |
|---|---|
| F130 | 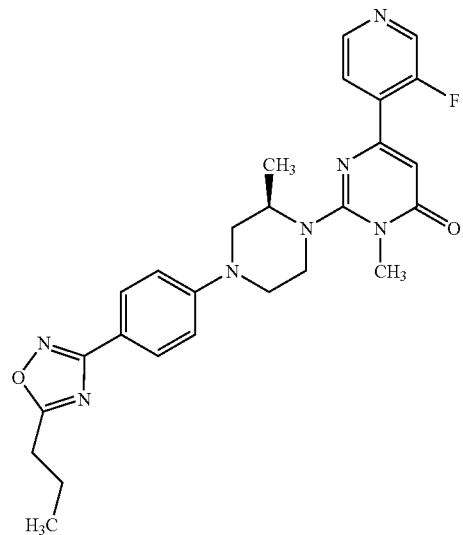 [SMILES: CCCc1nc(-c2ccc(N3CCN(c4nc(-c5ccncc5F)cc(=O)n4C)[C@H](C)C3)cc2)no1] |
| F131 | 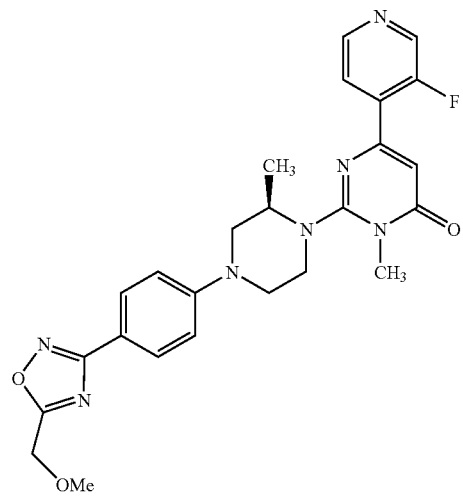 [SMILES: COCc1nc(-c2ccc(N3CCN(c4nc(-c5ccncc5F)cc(=O)n4C)[C@H](C)C3)cc2)no1] |
| F132 | 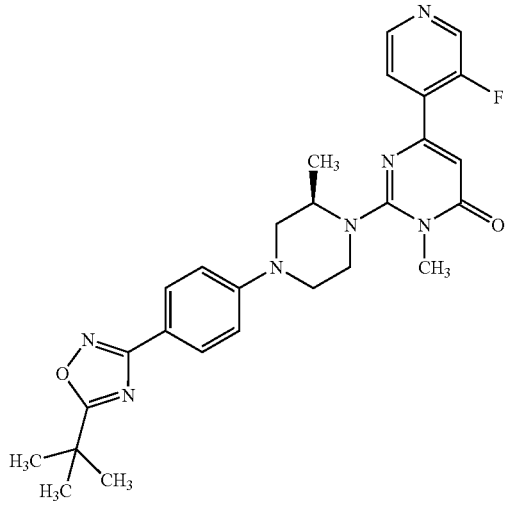 [SMILES: C[C@@H]1CN(c2ccc(-c3noc(C(C)(C)C)n3)cc2)CCN1c1nc(-c2ccncc2F)cc(=O)n1C] |

TABLE 1-continued
| Compound No. | STRUCTURE |
|---|---|
| F133 | 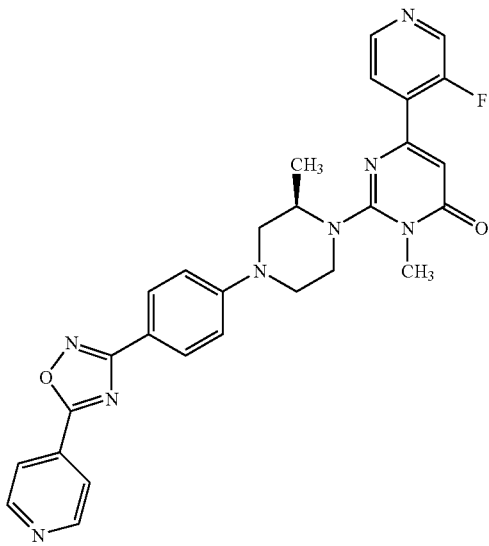 [SMILES: C[C@@H]1CN(c2ccc(-c3noc(-c4ccncc4)n3)cc2)CCN1c1nc(-c2ccncc2F)cc(=O)n1C] |
| F134 | 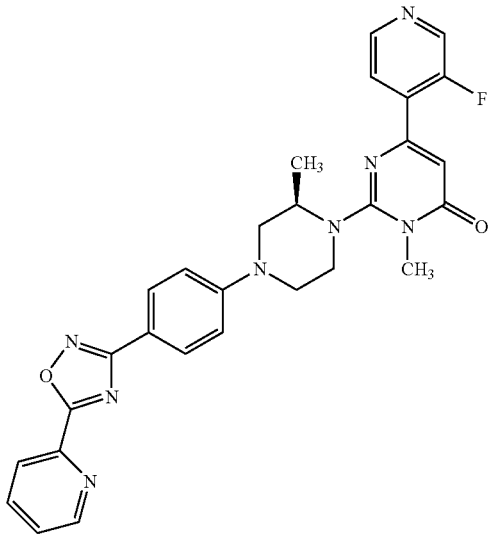 [SMILES: C[C@@H]1CN(c2ccc(-c3noc(-c4ccccn4)n3)cc2)CCN1c1nc(-c2ccncc2F)cc(=O)n1C] |
| F135 | 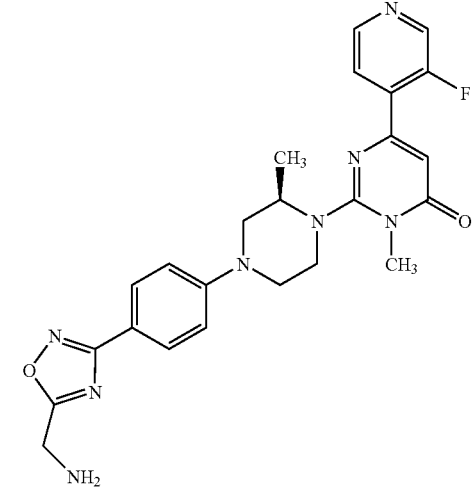 [SMILES: C[C@@H]1CN(c2ccc(-c3noc(CN)n3)cc2)CCN1c1nc(-c2ccncc2F)cc(=O)n1C] |

TABLE 1-continued
| Compound No. | STRUCTURE |
|---|---|
| F136 | 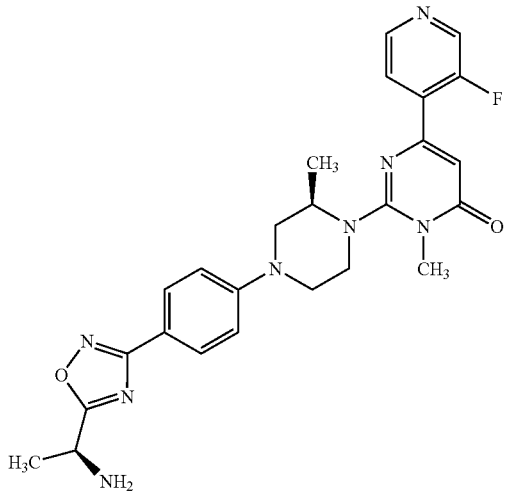 [SMILES: C[C@H](N)c1nc(-c2ccc(N3CCN(c4nc(-c5ccncc5F)cc(=O)n4C)[C@H](C)C3)cc2)no1] |
| F137 | 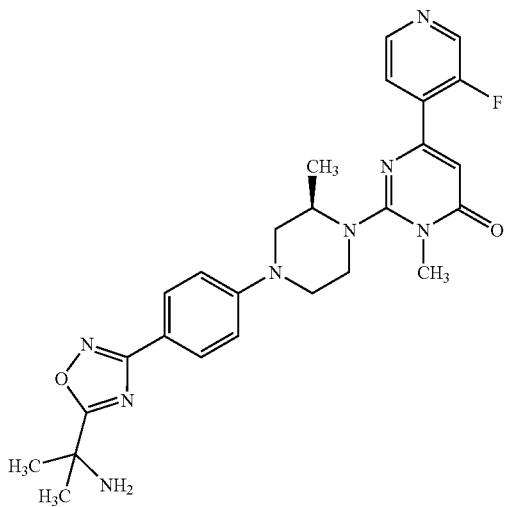 |
| F138 | 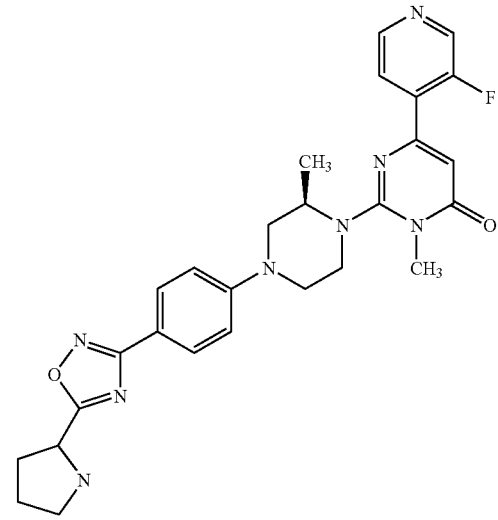 [SMILES: C[C@@H]1CN(c2ccc(-c3noc(C4CCCN4)n3)cc2)CCN1c1nc(-c2ccncc2F)cc(=O)n1C] |

TABLE 1-continued
| Compound No. | STRUCTURE |
|---|---|
| F139 | 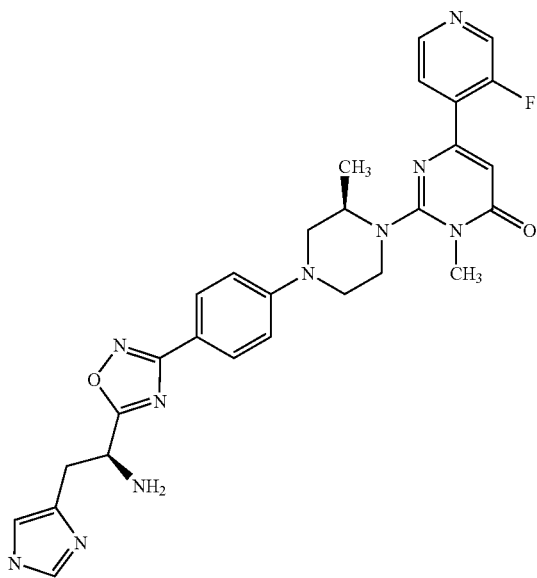 [SMILES: C[C@@H]1CN(c2ccc(-c3noc([C@@H](N)Cc4c[nH]cn4)n3)cc2)CCN1c1nc(-c2ccncc2F)cc(=O)n1C] |
| F140 | 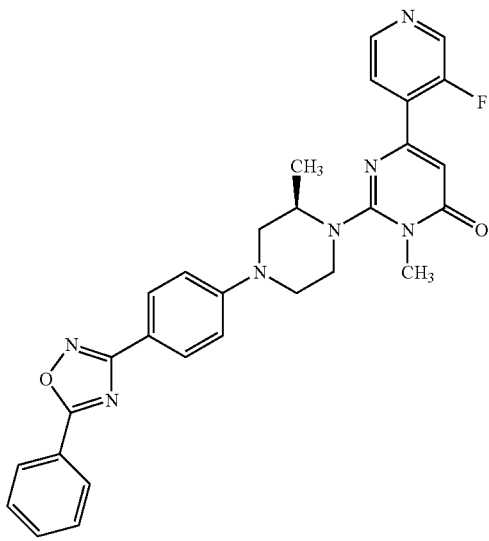 |

TABLE 1-continued
| Compound No. | STRUCTURE |
|---|---|
| F141 | 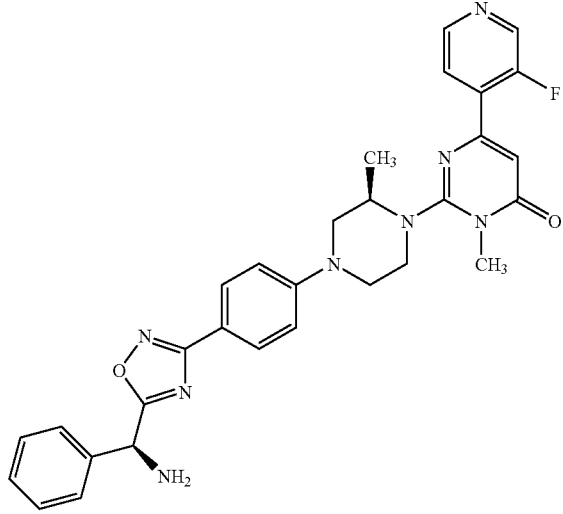 [SMILES: C[C@@H]1CN(c2ccc(-c3noc([C@@H](N)c4ccccc4)n3)cc2)CCN1c1nc(-c2ccncc2F)cc(=O)n1C] |
| F142 | 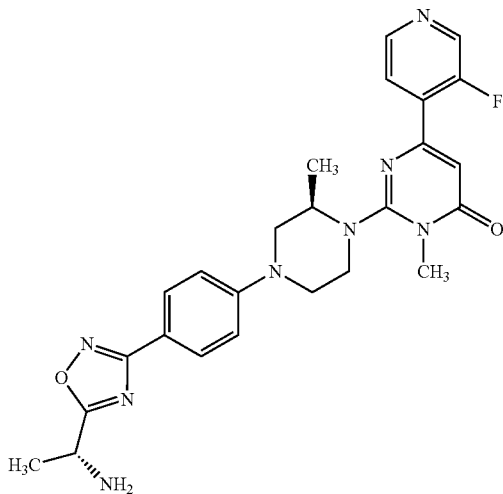 [SMILES: C[C@@H]1CN(c2ccc(-c3noc([C@@H](C)N)n3)cc2)CCN1c1nc(-c2ccncc2F)cc(=O)n1C] |
| F143 | 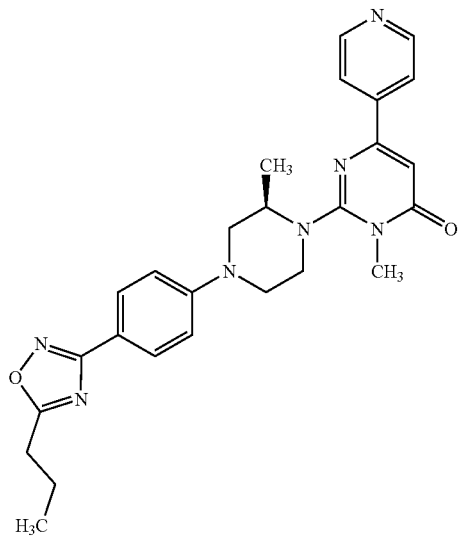 [SMILES: CCCc1nc(-c2ccc(N3CCN(c4nc(-c5ccncc5)cc(=O)n4C)[C@H](C)C3)cc2)no1] |

TABLE 1-continued

| Compound No. | STRUCTURE |
|---|---|
| F144 | (structure) |
| F145 | (structure) |
| F146 | (structure) |

TABLE 1-continued
| Compound No. | STRUCTURE |
|---|---|
| F147 | 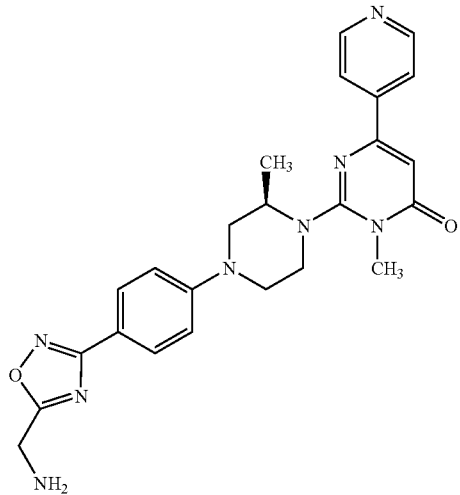 [SMILES: C[C@@H]1CN(c2ccc(-c3noc(CN)n3)cc2)CCN1c1nc(-c2ccncc2)cc(=O)n1C] |
| F148 | 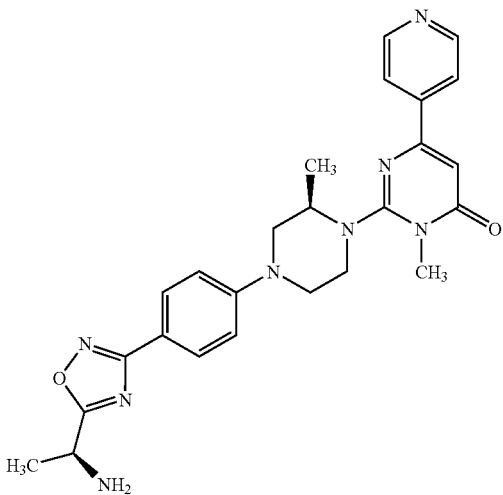 [SMILES: C[C@H](N)c1nc(-c2ccc(N3CCN(c4nc(-c5ccncc5)cc(=O)n4C)[C@H](C)C3)cc2)no1] |
| F149 | 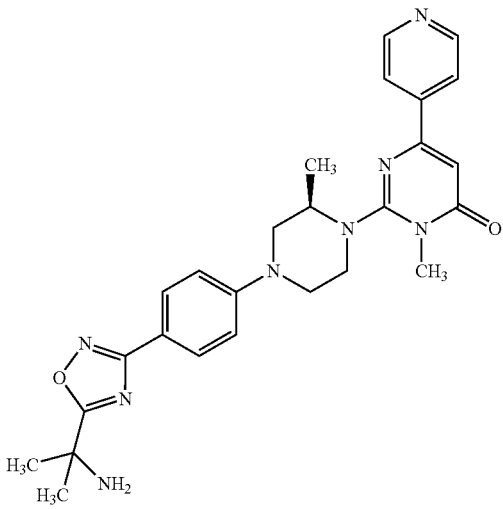 [SMILES: C[C@@H]1CN(c2ccc(-c3noc(C(C)(C)N)n3)cc2)CCN1c1nc(-c2ccncc2)cc(=O)n1C] |

TABLE 1-continued
| Compound No. | STRUCTURE |
|---|---|
| F150 | 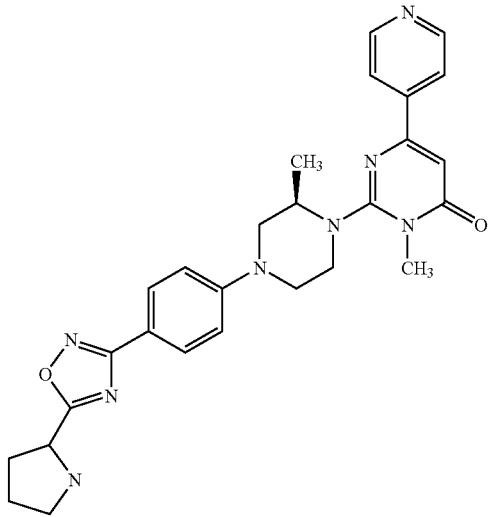 |
| F151 | 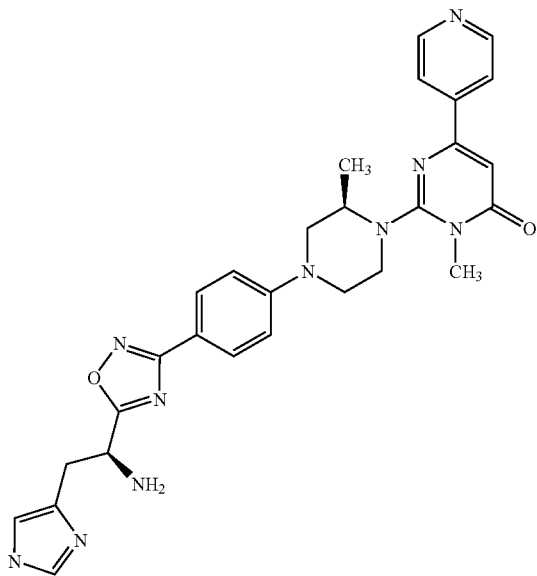 [SMILES: C[C@@H]1CN(c2ccc(-c3noc([C@@H](N)Cc4c[nH]cn4)n3)cc2)CCN1c1nc(-c2ccncc2)cc(=O)n1C] |

TABLE 1-continued
| Compound No. | STRUCTURE |
|---|---|
| F152 | 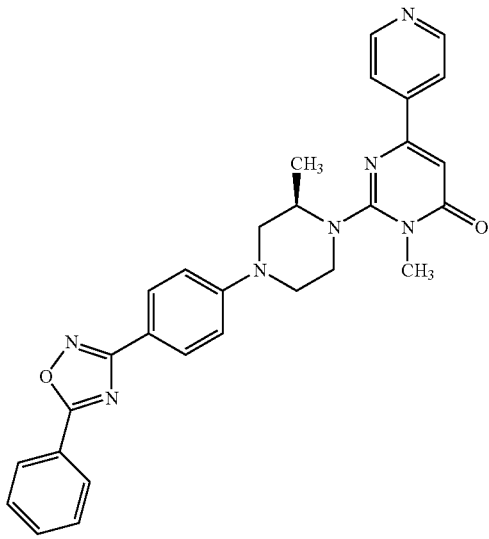 [SMILES: C[C@@H]1CN(c2ccc(-c3noc(-c4ccccc4)n3)cc2)CCN1c1nc(-c2ccncc2)cc(=O)n1C] |
| F153 | 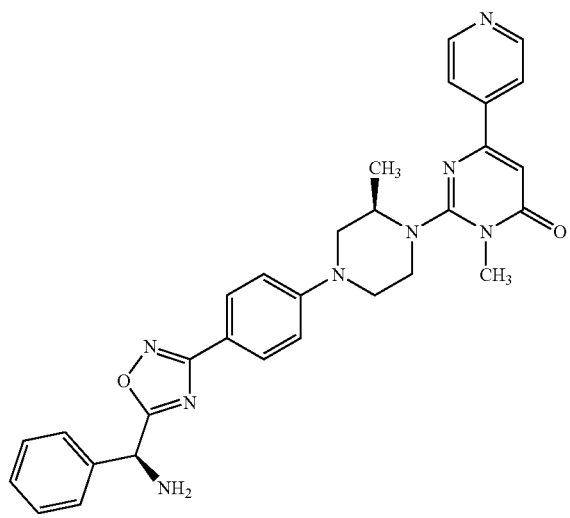 [SMILES: C[C@@H]1CN(c2ccc(-c3noc([C@@H](N)c4ccccc4)n3)cc2)CCN1c1nc(-c2ccncc2)cc(=O)n1C] |
| F154 | 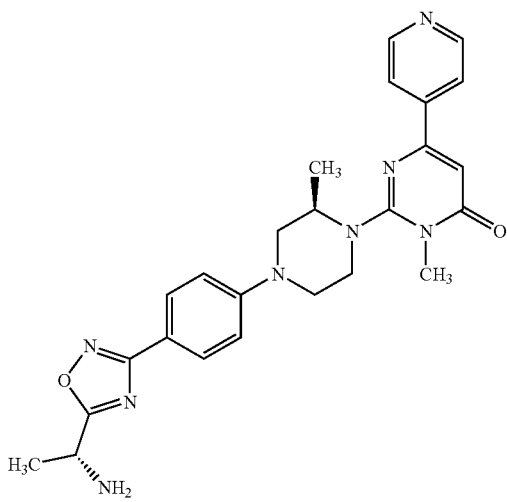 [SMILES: C[C@@H]1CN(c2ccc(-c3noc([C@@H](C)N)n3)cc2)CCN1c1nc(-c2ccncc2)cc(=O)n1C] |

TABLE 1-continued
| Compound No. | STRUCTURE |
|---|---|
| F155 | 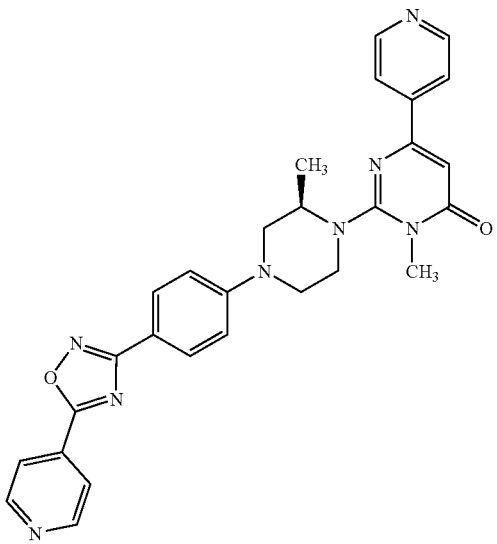 [SMILES: C[C@@H]1CN(c2ccc(-c3noc(-c4ccncc4)n3)cc2)CCN1c1nc(-c2ccncc2)cc(=O)n1C] |
| F156 | 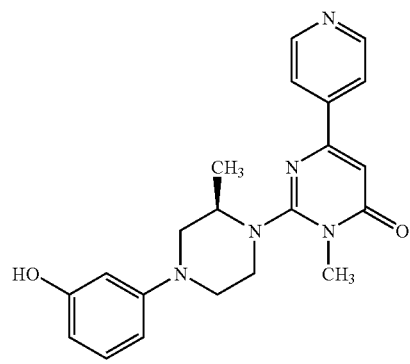 |
| F157 | 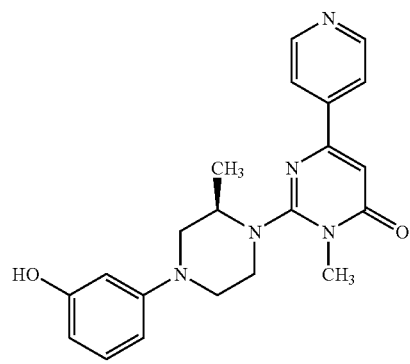 |

TABLE 1-continued

| Compound No. | STRUCTURE |
|---|---|
| F158 | 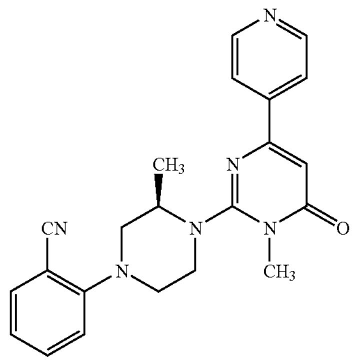 [SMILES: C[C@@H]1CN(c2ccccc2C#N)CCN1c1nc(-c2ccncc2)cc(=O)n1C] |
| F159 | 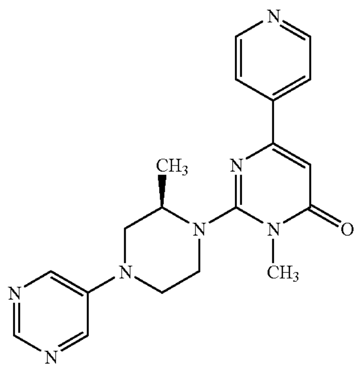 [SMILES: C[C@@H]1CN(c2cncnc2)CCN1c1nc(-c2ccncc2)cc(=O)n1C] |
| F160 | 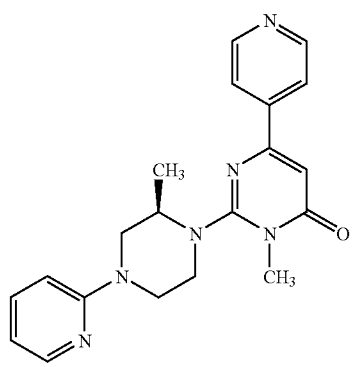 [SMILES: C[C@@H]1CN(c2ccccn2)CCN1c1nc(-c2ccncc2)cc(=O)n1C] |

Particularly preferred compounds of the present invention represented by formula (I) include:

6-(3-Fluoro-pyridin-4-yl)-2-[5-(3-methoxy-phenyl)-(3aRS, 6aSR)-cis-hexahydro-pyrrolo[3,4-c]pyrrol-2-yl]-3-methyl-3H-pyrimidin-4-one;

2-[5-(2-Methoxy-phenyl)-(3aRS,6aSR)-cis-hexahydro-pyrrolo[3,4-c]pyrrol-2-yl]-3-methyl-6-pyridin-4-yl-3H-pyrimidin-4-one;

2-[5-(2-Methoxy-phenyl)-(3aRS,6aSR)-cis-hexahydro-pyrrolo[3,4-c]pyrrol-2-yl]-1-methyl-1H-[4,4']bipyrimidinyl-6-one;

6-(3-Fluoro-pyridin-4-yl)-2-[5-(2-methoxy-phenyl)-(3aRS, 6aSR)-cis-hexahydro-pyrrolo[3,4-c]pyrrol-2-yl]-3-methyl-3H-pyrimidin-4-one;

3-Methyl-6-pyridin-4-yl-2-((3aRS,9bRS)-cis-1,3a,4,9b-tetrahydro-3H-5-oxa-2-aza-cyclopenta[a]naphthalen-2-yl)-3H-pyrimidin-4-one;

6-(3-Fluoro-pyridin-4-yl)-3-methyl-2-((3aRS,9bRS)-cis-1, 3a,4,9b-tetrahydro-3H-5-oxa-2-aza-cyclopenta[a]naphthalen-2-yl)-3H-pyrimidin-4-one;

2-((3S)-3-Benzylamino-pyrrolidin-1-yl)-3-methyl-6-pyridin-4-yl-3H-pyrimidin-4-one;

2-((3S)-3-Benzylamino-pyrrolidin-1-yl)-1-methyl-1H-[4,4'] bipyrimidinyl-6-one;

2-((3S)-3-Benzylamino-pyrrolidin-1-yl)-6-(3-fluoro-pyridin-4-yl)-3-methyl-3H-pyrimidin-4-one;

2-((3S)-3-Amino-pyrrolidin-1-yl)-1-methyl-1H-[4,4']bipyrimidinyl-6-one;

N-[1-(1-Methyl-6-oxo-1,6-dihydro-[4,4']bipyrimidinyl-2-yl)-pyrrolidin-(3S)-3-yl]-benzamide;

2-[(3S)-3-(4-Fluoro-phenylamino)-pyrrolidin-1-yl]-1-methyl-1H-[4,4']bipyrimidinyl-6-one;

2-((3R)-3-Benzylamino-pyrrolidin-1-yl)-6-(3-fluoro-pyridin-4-yl)-3-methyl-3H-pyrimidin-4-one;

2-((3R)-3-Benzylamino-pyrrolidin-1-yl)-3-methyl-6-pyridin-4-yl-3H-pyrimidin-4-one;

2-((3R)-3-Benzylamino-pyrrolidin-1-yl)-1-methyl-1H-[4, 4']bipyrimidinyl-6-one;
2-((3R)-3-Amino-pyrrolidin-1-yl)-6-(3-fluoro-pyridin-4-yl)-3-methyl-3H-pyrimidin-4-one;
2-((3R)-3-Amino-pyrrolidin-1-yl)-1-methyl-1H-[4,4']bipyrimidinyl-6-one;
2-[(3R)-3-(4-Fluoro-phenylamino)-pyrrolidin-1-yl]-1-methyl-1H-[4,4']bipyrimidinyl-6-one;
2-[(3R)-3-(4-Fluoro-phenylamino)-pyrrolidin-1-yl]-3-methyl-6-pyridin-4-yl-3H-pyrimidin-4-one;
2-((3R)-3-Amino-pyrrolidin-1-yl)-3-methyl-6-pyridin-4-yl-3H-pyrimidin-4-one;
2-[(3R)-3-(2-Fluoro-phenylamino)-pyrrolidin-1-yl]-3-methyl-6-pyridin-4-yl-3H-pyrimidin-4-one,
2-[3-((3R)-3-Fluoro-phenylamino)-pyrrolidin-1-yl]-3-methyl-6-pyridin-4-yl-3H-pyrimidin-4-one;
2-[(3R)-3-(2-Methoxy-phenylamino)-pyrrolidin-1-yl]-3-methyl-6-pyridin-4-yl-3H-pyrimidin-4-one;
2-[(3R)-3-(3-Methoxy-phenylamino)-pyrrolidin-1-yl]-3-methyl-6-pyridin-4-yl-3H-pyrimidin-4-one;
3-Methyl-2-(2-methyl-pyrrolidin-1-yl)-6-pyridin-4-yl-3H-pyrimidin-4-one;
1-Methyl-2-(2-methyl-pyrrolidin-1-yl)-1H-[4,4']bipyrimidinyl-6-one;
6-(3-Fluoro-pyridin-4-yl)-3-methyl-2-(2-methyl-pyrrolidin-1-yl)-3H-pyrimidin-4-one;
2-[(3R)-3-(2-Fluoro-phenylamino)-pyrrolidin-1-yl]-1-methyl-1H-[4,4']bipyrimidinyl-6-one;
2-[(3R)-3-(2-Methoxy-phenylamino)-pyrrolidin-1-yl]-1-methyl-1H-[4,4']bipyrimidinyl-6-one;
2-[(3R)-3-(3-Methoxy-phenylamino)-pyrrolidin-1-yl]-1-methyl-1H-[4,4']bipyrimidinyl-6-one;
2-[(3R)-3-(4-Methoxy-phenylamino)-pyrrolidin-1-yl]-1-methyl-1H-[4,4']bipyrimidinyl-6-one;
3-Methyl-2-((3R)-3-phenylamino-pyrrolidin-1-yl)-6-pyridin-4-yl-3H-pyrimidin-4-one;
1-Methyl-2-((3R)-3-phenylamino-pyrrolidin-1-yl)-1H-[4,4']bipyrimidinyl-6-one;
6-(3-Fluoro-pyridin-4-yl)-2-[(3R)-3-(2-methoxy-phenylamino)-pyrrolidin-1-yl]-3-methyl-3H-pyrimidin-4-one;
2-((3S)-3-Benzyl-morpholin-4-yl)-1-methyl-1H-[4,4']bipyrimidinyl-6-one;
2-((4aRS,10bRS)-trans-2,3,4a,5,6,10b-Hexahydro-naphtho[1,2-b][1,4]oxazin-4-yl)-3-methyl-6-pyridin-4-yl-3H-pyrimidin-4-one;
6-(3-Fluoro-pyridin-4-yl)-2-((4aRS,10bRS)-trans-2,3,4a,5,6,10b-hexahydro-naphtho[1,2-b][1,4]oxazin-4-yl)-3-methyl-3H-pyrimidin-4-one;
2-((4aRS,10bRS)-trans-3,4,4a,5,6,10b-Hexahydro-2H-naphtho[1,2-b][1,4]oxazin-4-yl)-3-methyl-6-(pyrimidin-4-yl)-3H-pyrimidin-4-one;
3-Methyl-2-(4-phenyl-4,8-diaza-tricyclo[5.2.2.0$^{2,6}$]undec-8-yl)-6-pyridin-4-yl-3H-pyrimidin-4-one;
3-Methyl-6-pyridin-4-yl-2-[6-(4-pyrrolidin-1-yl-phenyl)-2-aza-bicyclo[2.2.2]oct-2-yl]-3H-pyrimidin-4-one;
2-[3-(2-Methoxy-phenylamino)-8-aza-bicyclo[3.2.1]oct-8-yl]-3-methyl-6-pyridin-4-yl-3H-pyrimidin-4-one;
6-(3-Fluoro-pyridin-4-yl)-2-[3-(2-methoxy-phenylamino)-8-aza-bicyclo[3.2.1]oct-8-yl]-3-methyl-3H-pyrimidin-4-one;
2-[3-(4-Methoxy-phenylamino)-8-aza-bicyclo[3.2.1]oct-8-yl]-3-methyl-6-pyridin-4-yl-3H-pyrimidin-4-one;
6-(3-Fluoro-pyridin-4-yl)-2-[3-(4-methoxy-phenylamino)-8-aza-bicyclo[3.2.1]oct-8-yl]-3-methyl-3H-pyrimidin-4-one;
2-(8-Methoxy-(4aRS,10bRS)-trans-2,3,4a,5,6,10b-hexahydro-naphtho[1,2-b][1,4]oxazin-4-yl)-3-methyl-6-pyridin-4-yl-3H-pyrimidin-4-one;
6-(3-Fluoro-pyridin-4-yl)-2-(8-methoxy-(4aRS,10bRS)-trans-2,3,4a,5,6,10b-hexahydro-naphtho[1,2-b][1,4]oxazin-4-yl)-3-methyl-3H-pyrimidin-4-one;
2-(8-Methoxy-(4aRS,10bRS)-trans-2,3,4a,5,6,10b-hexahydro-naphtho[1,2-b][1,4]oxazin-4-yl)-1-methyl-1H-[4,4']bipyrimidinyl-6-one;
2-(7-Methoxy-(4aRS,10bRS)-trans-2,3,4a,5,6,10b-hexahydro-naphtho[1,2-b][1,4]oxazin-4-yl)-3-methyl-6-pyridin-4-yl-3H-pyrimidin-4-one;
6-(3-Fluoro-pyridin-4-yl)-2-(7-methoxy-(4aRS,10bRS)-trans-2,3,4a,5,6,10b-hexahydro-naphtho[1,2-b][1,4]oxazin-4-yl)-3-methyl-3H-pyrimidin-4-one;
2-(7-Methoxy-(4aRS,10bRS)-trans-2,3,4a,5,6,10b-hexahydro-naphtho[1,2-b][1,4]oxazin-4-yl)-1-methyl-1H-[4,4']bipyrimidinyl-6-one;
2-(9-Methoxy-(4aRS,10bRS)-trans-2,3,4a,5,6,10b-hexahydro-naphtho[1,2-b][1,4]oxazin-4-yl)-3-methyl-6-pyridin-4-yl-3H-pyrimidin-4-one;
6-(3-Fluoro-pyridin-4-yl)-2-(9-methoxy-(4aRS,10bRS)-trans-2,3,4a,5,6,10b-hexahydro-naphtho[1,2-b][1,4]oxazin-4-yl)-3-methyl-3H-pyrimidin-4-one,
2-(9-Methoxy-(4aRS,10bRS)-trans-2,3,4a,5,6,10b-hexahydro-naphtho[1,2-b][1,4]oxazin-4-yl)-1-methyl-1H-[4,4']bipyrimidinyl-6-one;
2-((4aRS,10bSR)-cis-2,3,4a,5,6,10b-Hexahydro-naphtho[1,2-b][1,4]oxazin-4-yl)-3-methyl-6-pyridin-4-yl-3H-pyrimidin-4-one;
6-(3-Fluoro-pyridin-4-yl)-2-((4aRS,10bSR)-cis-2,3,4a,5,6,10b-hexahydro-naphtho[1,2-b][1,4]oxazin-4-yl)-3-methyl-3H-pyrimidin-4-one;
2-((4aRS,10bSR)-cis-2,3,4a,5,6,10b-Hexahydro-naphtho[1,2-b][1,4]oxazin-4-yl)-1-methyl-1H-[4,4']bipyrimidinyl-6-one;
6-(3-Fluoro-pyridin-4-yl)-3-methyl-2-((4aRS,10bRS)-trans-2,3,10,10a-tetrahydro-4-aH-4,9-dioxa-1-aza-phenanthren-1-yl)-3H-pyrimidin-4-one;
6-(3-Fluoro-pyridin-4-yl)-2-(8-methoxy-(4aRS,10bSR)-cis-2,3,4a,5,6,10b-hexahydro-naphtho[1,2-b][1,4]oxazin-4-yl)-3-methyl-3H-pyrimidin-4-one;
6-(3-Fluoro-pyridin-4-yl)-2-(6-methoxy-(4aRS,10aRS)-trans-2,3,10,10a-tetrahydro-4-aH-4,9-dioxa-1-aza-phenanthren-1-yl)-3-methyl-3H-pyrimidin-4-one;
2-(9-Methoxy-(4aRS,10b SR)-cis-2,3,4a,5,6,10b-hexahydro-naphtho[1,2-b][1,4]oxazin-4-yl)-3-methyl-6-pyridin-4-yl-3H-pyrimidin-4-one;
6-(3-Fluoro-pyridin-4-yl)-2-(9-methoxy-(4aRS,10bSR)-cis-2,3,4a,5,6,10b-hexahydro-naphtho[1,2-b][1,4]oxazin-4-yl)-3-methyl-3H-pyrimidin-4-one;
2-(9-Methoxy-(4aRS,10bSR)-cis-2,3,4a,5,6,10b-hexahydro-naphtho[1,2-b][1,4]oxazin-4-yl)-1-methyl-1H-[4,4']bipyrimidinyl-6-one;
2-(7-Methoxy-(4aRS,10bSR)-cis-2,3,4a,5,6,10b-hexahydro-naphtho[1,2-b][1,4]oxazin-4-yl)-3-methyl-6-pyridin-4-yl-3H-pyrimidin-4-one;
6-(3-Fluoro-pyridin-4-yl)-2-(7-methoxy-(4aRS,10bSR)-cis-2,3,4a,5,6,10b-hexahydro-naphtho[1,2-b][1,4]oxazin-4-yl)-3-methyl-3H-pyrimidin-4-one;
2-(7-Methoxy-(4aRS,10bSR)-cis-2,3,4a,5,6,10b-hexahydro-naphtho[1,2-b][1,4]oxazin-4-yl)-1-methyl-1H-[4,4']bipyrimidinyl-6-one;
6-(3-Fluoro-pyridin-4-yl)-2-((4aRS,10aRS)-trans-2,3,4a,5,6,10b-hexahydro-1H-benzo[f]quinolin-4-yl)-3-methyl-3H-pyrimidin-4-one;

2-(8-Methoxy-(4aRS,10aRS)-trans-2,3,4a,5,6,10b-hexahydro-1H-benzo[f]quinolin-4-yl)-3-methyl-6-pyridin-4-yl-3H-pyrimidin-4-one;

6-(3-Fluoro-pyridin-4-yl)-2-(8-methoxy-(4aRS,10aRS)-trans-2,3,4a,5,6,10b-hexahydro-1H-benzo[f]quinolin-4-yl)-3-methyl-3H-pyrimidin-4-one;

2-(8-Methoxy-(4aRS,10aRS)-trans-2,3,4a,5,6,10b-hexahydro-1H-benzo[f]quinolin-4-yl)-1-methyl-1H-[4,4']bipyrimidinyl-6-one;

3-Methyl-6-pyridin-4-yl-2-((4aRS,10aRS)-cis-2,3,10,10a-tetrahydro-4-aH-4,9-dioxa-1-aza-phenanthren-1-yl)-3H-pyrimidin-4-one;

6-(3-Fluoro-pyridin-4-yl)-3-methyl-2-((4aRS,10aRS)-cis-2,3,10,10a-tetrahydro-4-aH-4,9-dioxa-1-aza-phenanthren-1-yl)-3H-pyrimidin-4-one;

1-Methyl-2-((4aRS,10aRS)-cis-2,3,10,10a-tetrahydro-4-aH-4,9-dioxa-1-aza-phenanthren-1-yl)-1H-[4,4']bipyrimidinyl-6-one;

6-(3-Fluoro-pyridin-4-yl)-2-(6-methoxy-(4aRS,10aRS)-cis-2,3,10,10a-tetrahydro-4-aH-4,9-dioxa-1-aza-phenanthren-1-yl)-3-methyl-3H-pyrimidin-4-one;

2-(6-Methoxy-(4aRS,10aRS)-cis-2,3,10,10a-tetrahydro-4-aH-4,9-dioxa-1-aza-phenanthren-1-yl)-1-methyl-1H-[4,4']bipyrimidinyl-6-one;

2-(9-Fluoro-(4aRS,10bRS)-trans-2,3,4a,5,6,10b-hexahydro-naphtho[1,2-b][1,4]oxazin-4-yl)-3-methyl-6-pyridin-4-yl-3H-pyrimidin-4-one;

2-(9-Fluoro-(4aRS,10bRS)-trans-2,3,4a,5,6,10b-hexahydro-naphtho[1,2-b][1,4]oxazin-4-yl)-6-(3-fluoro-pyridin-4-yl)-3-methyl-3H-pyrimidin-4-one;

2-(9-Fluoro-(4aRS,10bRS)-trans-2,3,4a,5,6,10b-hexahydro-naphtho[1,2-b][1,4]oxazin-4-yl)-1-methyl-1H-[4,4']bipyrimidinyl-6-one;

2-(9-Fluoro-(4aRS,10bSR)-cis-2,3,4a,5,6,10b-hexahydro-naphtho[1,2-b][1,4]oxazin-4-yl)-3-methyl-6-pyridin-4-yl-3H-pyrimidin-4-one;

2-(9-Fluoro-(4aRS,10bSR)-cis-2,3,4a,5,6,10b-hexahydro-naphtho[1,2-b][1,4]oxazin-4-yl)-6-(3-fluoro-pyridin-4-yl)-3-methyl-3H-pyrimidin-4-one;

2-(9-Fluoro-(4aRS,10bSR)-cis-2,3,4a,5,6,10b-hexahydro-naphtho[1,2-b][1,4]oxazin-4-yl)-1-methyl-1H-[4,4']bipyrimidinyl-6-one;

3-Methyl-2-((3R)-3-methyl-morpholin-4-yl)-6-pyridin-4-yl-3H-pyrimidin-4-one;

6-(3-Fluoro-pyridin-4-yl)-3-methyl-2-((3R)-3-methyl-morpholin-4-yl)-3H-pyrimidin-4-one;

1-Methyl-2-((3R)-3-methyl-morpholin-4-yl)-1H-[4,4']bipyrimidinyl-6-one;

6-(3-Fluoro-pyridin-4-yl)-3-methyl-2-((3S)-3-methyl-morpholin-4-yl)-3H-pyrimidin-4-one;

3-Methyl-2-(2-methyl-piperidin-1-yl)-6-pyridin-4-yl-3H-pyrimidin-4-one;

1-Methyl-2-(2-methyl-piperidin-1-yl)-1H-[4,4']bipyrimidinyl-6-one;

6-(3-Fluoro-pyridin-4-yl)-3-methyl-2-(2-methyl-piperidin-1-yl)-3H-pyrimidin-4-one;

4-[4-(3-Fluoro-pyridin-4-yl)-1-methyl-6-oxo-1,6-dihydro-pyrimidin-2-yl]-(3R)-3-methyl-piperazine-1-carboxylic acid benzyl ester;

4-[4-(3-Fluoro-pyridin-4-yl)-1-methyl-6-oxo-1,6-dihydro-pyrimidin-2-yl]-(3S)-3-methyl-piperazine-1-carboxylic acid benzyl ester;

6-(3-Fluoro-pyridin-4-yl)-3-methyl-2-((2S)-2-methyl-piperazin-1-yl)-3H-pyrimidin-4-one;

6-(3-Fluoro-pyridin-4-yl)-3-methyl-2-((2R)-2-methyl-piperazin-1-yl)-3H-pyrimidin-4-one;

1-[4-(3-Fluoro-pyridin-4-yl)-1-methyl-6-oxo-1,6-dihydro-pyrimidin-2-yl]-piperidine-2-carboxylic acid ethyl ester;

2-((2SR,4RS)-2,4-Dimethyl-piperidin-1-yl)-6-(3-fluoro-pyridin-4-yl)-3-methyl-3H-pyrimidin-4-one;

2-((2RS,4RS)-2,4-Dimethyl-piperidin-1-yl)-6-(3-fluoro-pyridin-4-yl)-3-methyl-3H-pyrimidin-4-one;

3-Methyl-2-((4aRS,8aRS)-trans-octahydro-benzo[1,4]oxazin-4-yl)-6-pyridin-4-yl-3H-pyrimidin-4-one;

6-(3-Fluoro-pyridin-4-yl)-3-methyl-2-((4aRS,8aRS)-trans-octahydro-benzo[1,4]oxazin-4-yl)-3H-pyrimidin-4-one;

1-Methyl-2-((4aRS,8aRS)-trans-octahydro-benzo[1,4]oxazin-4-yl)-1H-[4,4']bipyrimidinyl-6-one;

2-((3R)-3-Ethyl-morpholin-4-yl)-6-(3-fluoro-pyridin-4-yl)-3-methyl-3H-pyrimidin-4-one;

2-((3R)-3-Ethyl-morpholin-4-yl)-1-methyl-1H-[4,4']bipyrimidinyl-6-one;

2-(8-Aza-bicyclo[3.2.1]oct-8-yl)-6-(3-fluoro-pyridin-4-yl)-3-methyl-3H-pyrimidin-4-one;

2-(8-Aza-bicyclo[3.2.1]oct-8-yl)-1-methyl-1H-[4,4']bipyrimidinyl-6-one;

6-(3-Fluoro-pyridin-4-yl)-2-((3R)-3-isopropyl-morpholin-4-yl)-3-methyl-3H-pyrimidin-4-one;

6-(3-Fluoro-pyridin-4-yl)-2-((3R)-3-isobutyl-morpholin-4-yl)-3-methyl-3H-pyrimidin-4-one;

4-[4-(3-Fluoro-pyridin-4-yl)-1-methyl-6-oxo-1,6-dihydro-pyrimidin-2-yl]-morpholine-3-carboxylic acid ethyl ester;

6-(3-Fluoro-pyridin-4-yl)-3-methyl-2-((3R)-3-phenyl-morpholin-4-yl)-3H-pyrimidin-4-one;

1-Methyl-2-((3R)-3-phenyl-morpholin-4-yl)-1H-[4,4']bipyrimidinyl-6-one;

3-Methyl-2-(octahydro-quinolin-1-yl)-6-pyridin-4-yl-3H-pyrimidin-4-one;

1-Methyl-2-(octahydro-quinolin-1-yl)-1H-[4,4']bipyrimidinyl-6-one;

6-(3-Fluoro-pyridin-4-yl)-3-methyl-2-(octahydro-quinolin-1-yl)-3H-pyrimidin-4-one;

3-Methyl-2-(4-phenyl-4,8-diaza-tricyclo[5.2.2.0$^{2,6}$]undec-8-yl)-6-pyridin-4-yl-3H-pyrimidin-4-one;

3-Methyl-2-((1RS,4SR,6RS)-6-phenyl-2-aza-bicyclo[2.2.2]oct-2-yl)-6-pyridin-4-yl-3H-pyrimidin-4-one;

2-(1,3,4,6,7,11b-Hexahydro-pyrazino[2,1-a]isoquinolin-2-yl)-3-methyl-6-pyridin-4-yl-3H-pyrimidin-4-one;

6-(3-Fluoro-pyridin-4-yl)-2-(1,3,4,6,7,11b-hexahydro-pyrazino[2,1-a]isoquinolin-2-yl)-3-methyl-3H-pyrimidin-4-one;

2-(1,3,4,6,7,11b-Hexahydro-pyrazino[2,1-a]isoquinolin-2-yl)-1-methyl-1H-[4,4']bipyrimidinyl-6-one;

3-Methyl-2-((4aR,8aR)-octahydro-benzo[1,4]oxazin-4-yl)-6-pyridin-4-yl-3H-pyrimidin-4-one;

6-(3-Fluoro-pyridin-4-yl)-3-methyl-2-((4aR,8aR)-octahydro-benzo[1,4]oxazin-4-yl)-3H-pyrimidin-4-one;

1-Methyl-2-((4aR,8aR)-octahydro-benzo[1,4]oxazin-4-yl)-1H-[4,4']bipyrimidinyl-6-one;

2-((4aR,7aR)-Hexahydro-cyclopenta[1,4]oxazin-4-yl)-3-methyl-6-pyridin-4-yl-3H-pyrimidin-4-one;

6-(3-Fluoro-pyridin-4-yl)-2-((4aR,7aR)-hexahydro-cyclopenta[1,4]oxazin-4-yl)-3-methyl-3H-pyrimidin-4-one;

2-((4aR,7aR)-Hexahydro-cyclopenta[1,4]oxazin-4-yl)-1-methyl-1H-[4,4']bipyrimidinyl-6-one;

6-(3-Fluoro-pyridin-4-yl)-3-methyl-2-((3RS)-2,2,3-trimethyl-morpholin-4-yl)-3H-pyrimidin-4-one;

2-((2RS,3RS)-2,3-Dimethyl-morpholin-4-yl)-6-(3-fluoro-pyridin-4-yl)-3-methyl-3H-pyrimidin-4-one;

2-((2RS,3RS)-2,3-Dimethyl-morpholin-4-yl)-1-methyl-1H-[4,4']bipyrimidinyl-6-one;

2-((2RS,3SR)-2,3-Dimethyl-morpholin-4-yl)-6-(3-fluoro-pyridin-4-yl)-3-methyl-3H-pyrimidin-4-one;

2-((2R,3SR)-2,3-Dimethyl-morpholin-4-yl)-6-(3-fluoro-pyridin-4-yl)-3-methyl-3H-pyrimidin-4-one;
2-((2S,3SR)-2,3-Dimethyl-morpholin-4-yl)-6-(3-fluoro-pyridin-4-yl)-3-methyl-3H-pyrimidin-4-one;
2-((2R,3R)-2,3-Dimethyl-morpholin-4-yl)-1-methyl-1H-[4,4']bipyrimidinyl-6-one;
2-((2R,3R)-2,3-Dimethyl-morpholin-4-yl)-6-(3-fluoro-pyridin-4-yl)-3-methyl-3H-pyrimidin-4-one;
1-Methyl-2-((3RS)-2,2,3-trimethyl-morpholin-4-yl)-1H-[4,4']bipyrimidinyl-6-one;
1-Methyl-2-((3R)-2,2,3-trimethyl-morpholin-4-yl)-1H-[4,4']bipyrimidinyl-6-one;
1-Methyl-2-((3S)-2,2,3-trimethyl-morpholin-4-yl)-1H-[4,4']bipyrimidinyl-6-one;
2-(3aS,7aR)-Hexahydro-2,4-dioxa-7-aza-inden-7-yl)-1-methyl-1H-[4,4']bipyrimidinyl-6-one;
6-((3aS,7aR)-3-Fluoro-pyridin-4-yl)-2-(hexahydro-2,4-dioxa-7-aza-inden-7-yl)-3-methyl-3H-pyrimidin-4-one;
2-((3RS)-3-Fluoromethyl-morpholin-4-yl)-1-methyl-1H-[4,4']bipyrimidinyl-6-one;
2-((3R)-3-Fluoromethyl-morpholin-4-yl)-1-methyl-1H-[4,4']bipyrimidinyl-6-one;
2-((3S)-3-Fluoromethyl-morpholin-4-yl)-1-methyl-1H-[4,4']bipyrimidinyl-6-one;
2-((3RS)-3-Fluoromethyl-morpholin-4-yl)-6-(3-fluoro-pyridin-4-yl)-3-methyl-3H-pyrimidin-4-one;
2-((3R)-3-Fluoromethyl-morpholin-4-yl)-6-(3-fluoro-pyridin-4-yl)-3-methyl-3H-pyrimidin-4-one;
2-((3S)-3-Fluoromethyl-morpholin-4-yl)-6-(3-fluoro-pyridin-4-yl)-3-methyl-3H-pyrimidin-4-one;
6-(3-Fluoro-pyridin-4-yl)-3-methyl-2-((4aR,8aR)-octahydro-benzo[1,4]oxazin-4-yl)-3H-pyrimidin-4-one;
1-Methyl-2-((4aR,8aR)-octahydro-benzo[1,4]oxazin-4-yl)-1H-[4,4']bipyrimidinyl-6-one;
6-(3-Fluoro-pyridin-4-yl)-2-((4aR,7aR)-hexahydro-cyclopenta[1,4]oxazin-4-yl)-3-methyl-3H-pyrimidin-4-one;
2-((4aR,7aR)-Hexahydro-cyclopenta[1,4]oxazin-4-yl)-1-methyl-1H-[4,4']bipyrimidinyl-6-one;
6-(3-Fluoro-pyridin-4-yl)-3-methyl-2-((3RS)-2,2,3-trimethyl-morpholin-4-yl)-3H-pyrimidin-4-one;
2-((2RS,3RS)-2,3-Dimethyl-morpholin-4-yl)-6-(3-fluoro-pyridin-4-yl)-3-methyl-3H-pyrimidin-4-one;
2-((2RS,3RS)-2,3-Dimethyl-morpholin-4-yl)-1-methyl-1H-[4,4']bipyrimidinyl-6-one;
2-((2R,3SR)-2,3-Dimethyl-morpholin-4-yl)-6-(3-fluoro-pyridin-4-yl)-3-methyl-3H-pyrimidin-4-one;
2-((2S,3SR)-2,3-Dimethyl-morpholin-4-yl)-6-(3-fluoro-pyridin-4-yl)-3-methyl-3H-pyrimidin-4-one;
2-((2R,3R)-2,3-Dimethyl-morpholin-4-yl)-1-methyl-1H-[4,4']bipyrimidinyl-6-one;
2-((2R,3R)-2,3-Dimethyl-morpholin-4-yl)-6-(3-fluoro-pyridin-4-yl)-3-methyl-3H-pyrimidin-4-one;
1-Methyl-2-((3R)-2,2,3-trimethyl-morpholin-4-yl)-1H-[4,4']bipyrimidinyl-6-one;
1-Methyl-2-((3S)-2,2,3-trimethyl-morpholin-4-yl)-1H-[4,4']bipyrimidinyl-6-one;
2-(3aR,7aS)-Hexahydro-2,4-dioxa-7-aza-inden-7-yl)-1-methyl-1H-[4,4']bipyrimidinyl-6-one;
6-((3aR,7aS)-3-Fluoro-pyridin-4-yl)-2-(hexahydro-2,4-dioxa-7-aza-inden-7-yl)-3-methyl-3H-pyrimidin-4-one;
2-((3RS)-3-Fluoromethyl-morpholin-4-yl)-1-methyl-1H-[4,4']bipyrimidinyl-6-one;
2-((3R)-3-Fluoromethyl-morpholin-4-yl)-1-methyl-1H-[4,4']bipyrimidinyl-6-one;
2-((3S)-3-Fluoromethyl-morpholin-4-yl)-1-methyl-1H-[4,4']bipyrimidinyl-6-one;
2-((3RS)-3-Fluoromethyl-morpholin-4-yl)-6-(3-fluoro-pyridin-4-yl)-3-methyl-3H-pyrimidin-4-one;
2-((3R)-3-Fluoromethyl-morpholin-4-yl)-6-(3-fluoro-pyridin-4-yl)-3-methyl-3H-pyrimidin-4-one;
2-((3S)-3-Fluoromethyl-morpholin-4-yl)-6-(3-fluoro-pyridin-4-yl)-3-methyl-3H-pyrimidin-4-one;
6-(3-Fluoro-pyridin-4-yl)-3-methyl-2-((2R)-2-methyl-pyrrolidin-1-yl)-3H-pyrimidin-4-one;
1-Methyl-2-((4aSR,8aRS)-octahydro-quinolin-1-yl)-1H-[4,4']bipyrimidinyl-6-one;
1-Methyl-2-((4aS,8aR)-octahydro-quinolin-1-yl)-1H-[4,4']bipyrimidinyl-6-one;
1-Methyl-2-((4aR,8aS)-octahydro-quinolin-1-yl)-1H-[4,4']bipyrimidinyl-6-one;
6-(3-Fluoro-pyridin-4-yl)-3-methyl-2-((4aSR,8aRS)-octahydro-quinolin-1-yl)-3H-pyrimidin-4-one;
6-(3-Fluoro-pyridin-4-yl)-3-methyl-2-((4aS,8aR)-octahydro-quinolin-1-yl)-3H-pyrimidin-4-one;
6-(3-Fluoro-pyridin-4-yl)-3-methyl-2-((4aR,8aS)-octahydro-quinolin-1-yl)-3H-pyrimidin-4-one;
2-((2R,4R)-2,4-Dimethyl-piperidin-1-yl)-1-methyl-1H-[4,4']bipyrimidinyl-6-one;
(2S)-2-[4-(3-Fluoro-pyridin-4-yl)-1-methyl-6-oxo-1,6-dihydro-pyrimidin-2-yl]-cyclopentanecarbonitrile;
2-((2RS)-2-Butyl-pyrrolidin-1-yl)-1-methyl-1H-[4,4']bipyrimidinyl-6-one;
2-((2RS)-2-Benzyl-pyrrolidin-1-yl)-1-methyl-1H-[4,4']bipyrimidinyl-6-one;
2-((2RS)-2-Benzyl-pyrrolidin-1-yl)-6-(3-fluoro-pyridin-4-yl)-3-methyl-3H-pyrimidin-4-one;
2-((2R)-2-Benzyl-pyrrolidin-1-yl)-6-(3-fluoro-pyridin-4-yl)-3-methyl-3H-pyrimidin-4-one;
2-((2S)-2-Benzyl-pyrrolidin-1-yl)-6-(3-fluoro-pyridin-4-yl)-3-methyl-3H-pyrimidin-4-one;
6-(3-Fluoro-pyridin-4-yl)-2-[(3R)-3-(3-methoxy-phenylamino)-pyrrolidin-1-yl]-3-methyl-3H-pyrimidin-4-one;
1-Methyl-2-((4aSR,8aRS)-octahydro-quinolin-1-yl)-1H-[4,4']bipyrimidinyl-6-one;
1-Methyl-2-((4aS,8aR)-octahydro-quinolin-1-yl)-1H-[4,4']bipyrimidinyl-6-one;
1-Methyl-2-((4aR,8aS)-octahydro-quinolin-1-yl)-1H-[4,4']bipyrimidinyl-6-one;
6-(3-Fluoro-pyridin-4-yl)-3-methyl-2-((4aSR,8aRS)-octahydro-quinolin-1-yl)-3H-pyrimidin-4-one;
6-(3-Fluoro-pyridin-4-yl)-3-methyl-2-((4aS,8aR)-octahydro-quinolin-1-yl)-3H-pyrimidin-4-one;
6-(3-Fluoro-pyridin-4-yl)-3-methyl-2-((4aR,8aS)-octahydro-quinolin-1-yl)-3H-pyrimidin-4-one;
2-((2R,4R)-2,4-Dimethyl-piperidin-1-yl)-1-methyl-1H-[4,4']bipyrimidinyl-6-one;
(2S)-2-[4-(3-Fluoro-pyridin-4-yl)-1-methyl-6-oxo-1,6-dihydro-pyrimidin-2-yl]-cyclopentanecarbonitrile;
2-((2RS)-2-Benzyl-pyrrolidin-1-yl)-6-(3-fluoro-pyridin-4-yl)-3-methyl-3H-pyrimidin-4-one;
2-((2R)-2-Benzyl-pyrrolidin-1-yl)-6-(3-fluoro-pyridin-4-yl)-3-methyl-3H-pyrimidin-4-one;
2-((2S)-2-Benzyl-pyrrolidin-1-yl)-6-(3-fluoro-pyridin-4-yl)-3-methyl-3H-pyrimidin-4-one;
6-(3-Fluoro-pyridin-4-yl)-2-[(3R)-3-(3-methoxy-phenylamino)-pyrrolidin-1-yl]-3-methyl-3H-pyrimidin-4-one;
2-((2R)-2,4-Dimethyl-piperazin-1-yl)-6-(3-fluoro-pyridin-4-yl)-3-methyl-3H-pyrimidin-4-one;
(3R)-6-(3-Fluoro-pyridin-4-yl)-3-methyl-2-(2-methyl-piperazin-1-yl)-3H-pyrimidin-4-one;
2-((2R)-4-Benzyl-2-methyl-piperazin-1-yl)-1-methyl-1H-[4,4']bipyrimidinyl-6-one;

1-Methyl-2-((2R)-2-methyl-4-phenyl-piperazin-1-yl)-1H-[4,4']bipyrimidinyl-6-one;
2-[(2R)-4-(2-Fluoro-phenyl)-2-methyl-piperazin-1-yl]-1-methyl-1H-[4,4']bipyrimidinyl-6-one;
2-[(2R)-4-(3-Fluoro-phenyl)-2-methyl-piperazin-1-yl]-1-methyl-1H-[4,4']bipyrimidinyl-6-one;
2-[(2R)-4-(4-Fluoro-phenyl)-2-methyl-piperazin-1-yl]-1-methyl-1H-[4,4']bipyrimidinyl-6-one;
2-[(2R)-4-(2-Methoxy-phenyl)-2-methyl-piperazin-1-yl]-1-methyl-1H-[4,4']bipyrimidinyl-6-one;
2-[(2R)-4-(3-Methoxy-phenyl)-2-methyl-piperazin-1-yl]-1-methyl-1H-[4,4']bipyrimidinyl-6-one;
2-[(2R)-4-(4-Methoxy-phenyl)-2-methyl-piperazin-1-yl]-1-methyl-1H-[4,4']bipyrimidinyl-6-one;
2-((2R)-4-Isopropyl-2-methyl-piperazin-1-yl)-1-methyl-1H-[4,4']bipyrimidinyl-6-one;
5-[(3R)-3-Methyl-4-(1-methyl-6-oxo-1,6-dihydro-[4,4']bipyrimidinyl-2-yl)-piperazin-1-yl]-thiophene-2-carboxylic acid ethyl ester;
1-Methyl-2-[(2R)-2-methyl-4-(5-methyl-thiophen-2-yl)-piperazin-1-yl]-1H-[4,4']bipyrimidinyl-6-one;
2-[(2R)-2-Ethyl-4-(4-methoxy-phenyl)-piperazin-1-yl]-1-methyl-1H-[4,4']bipyrimidinyl-6-one;
2-[(2R)-2-Ethyl-4-(4-methoxy-phenyl)-piperazin-1-yl]-6-(3-fluoro-pyridin-4-yl)-3-methyl-3H-pyrimidin-4-one;
1-Methyl-2-[(2R)-2-methyl-4-(pyridine-3-carbonyl)-piperazin-1-yl]-1H-[4,4']bipyrimidinyl-6-one;
4-[(2S)-2-Methyl-4-(1-methyl-6-oxo-1,6-dihydro-[4,4']bipyrimidinyl-2-yl)-piperazin-1-yl]-benzonitrile;
4-[(3R)-3-Methyl-4-(1-methyl-6-oxo-1,6-dihydro-[4,4']bipyrimidinyl-2-yl)-piperazin-1-yl]-benzonitrile;
3-Methyl-2-((2R)-2-methyl-4-pyrimidin-2-yl-piperazin-1-yl)-6-pyridin-4-yl-3H-pyrimidin-4-one;
6-(3-Fluoro-pyridin-4-yl)-3-methyl-2-((2R)-2-methyl-4-pyrimidin-2-yl-piperazin-1-yl)-3H-pyrimidin-4-one;
1-Methyl-2-{(2R)-2-methyl-4-[4-(5-methyl-[1,2,4]oxadiazol-3-yl)-benzoyl]-piperazin-1-yl}-1H-[4,4']bipyrimidinyl-6-one;
1-Methyl-2-{(2R)-2-methyl-4-[4-(5-methyl-[1,2,4]oxadiazol-3-yl)-benzyl]-piperazin-1-yl}-1H-[4,4']bipyrimidinyl-6-one;
1-Methyl-2-[(2R)-2-methyl-4-(pyridine-2-carbonyl)-piperazin-1-yl]-1H-[4,4']bipyrimidinyl-6-one;
2-[(2R)-4-(4-Fluoro-benzoyl)-2-methyl-piperidin-1-yl]-1-methyl-1H-[4,4']bipyrimidinyl-6-one;
2-[(2R)-4-(4-Chloro-benzoyl)-2-methyl-piperidin-1-yl]-1-methyl-1H-[4,4']bipyrimidinyl-6-one;
2-[(2R)-4-(3,4-Dichloro-benzoyl)-2-methyl-piperidin-1-yl]-1-methyl-1H-[4,4']bipyrimidinyl-6-one;
2-[(2R)-4-(4-tert-Butyl-benzoyl)-2-methyl-piperazin-1-yl]-1-methyl-1H-[4,4']bipyrimidinyl-6-one;
4-[(3R)-3-Methyl-4-(1-methyl-6-oxo-1,6-dihydro-[4,4']bipyrimidinyl-2-yl)-piperazine-1-carbonyl]-benzonitrile;
1-Methyl-2-[(2R)-2-methyl-4-(4-trifluoromethoxy-benzoyl)-piperazin-1-yl]-1H-[4,4']bipyrimidinyl-6-one;
4-[(3R)-3-Methyl-4-(1-methyl-6-oxo-1,6-dihydro-[4,4']bipyrimidinyl-2-yl)-piperazine-1-carbonyl]-benzoic acid methyl ester;
1-Methyl-2-[(2R)-2-methyl-4-(4-methyl-benzoyl)-piperazin-1-yl]-1H-[4,4']bipyrimidinyl-6-one;
1-Methyl-2-[(2R)-2-methyl-4-(4-trifluoromethyl-benzoyl)-piperazin-1-yl]-1H-[4,4']bipyrimidinyl-6-one;
2-[(2R)-4-(4-Dimethylamino-benzoyl)-2-methyl-piperazin-1-yl]-1-methyl-1H-[4,4']bipyrimidinyl-6-one;
2-[(2R)-4-(4-Methoxy-benzoyl)-2-methyl-piperazin-1-yl]-1-methyl-1H-[4,4']bipyrimidinyl-6-one;
1-Methyl-2-[(2R)-2-methyl-4-(naphthalene-2-carbonyl)-piperazin-1-yl]-1H-[4,4']bipyrimidinyl-6-one;
2-[(2R)-4-(Benzo[1,3]dioxole-5-carbonyl)-2-methyl-piperazin-1-yl]-1-methyl-1H-[4,4']bipyrimidinyl-6-one;
1-Methyl-2-[(2R)-2-methyl-4-(quinoline-2-carbonyl)-piperazin-1-yl]-1H-[4,4']bipyrimidinyl-6-one;
2-[(3R)-3-Methyl-4-(1-methyl-6-oxo-1,6-dihydro-[4,4']bipyrimidinyl-2-yl)-piperazin-1-yl]-benzoic acid methyl ester;
3-[(3R)-3-Methyl-4-(1-methyl-6-oxo-1,6-dihydro-[4,4']bipyrimidinyl-2-yl)-piperazin-1-yl]-benzonitrile;
2-[(3R)-3-Methyl-4-(1-methyl-6-oxo-1,6-dihydro-[4,4']bipyrimidinyl-2-yl)-piperazin-1-yl]-benzonitrile;
1-Methyl-2-((2R)-2-methyl-4-pyrimidin-5-yl-piperazin-1-yl)-1H-[4,4']bipyrimidinyl-6-one;
1-Methyl-2-((3R)-3-methyl-2,3,5,6-tetrahydro-[1,2']bipyrazinyl-4-yl)-1H-[4,4']bipyrimidinyl-6-one;
1-Methyl-2-((2R)-2-methyl-4-pyridin-4-yl-piperazin-1-yl)-1H-[4,4']bipyrimidinyl-6-one;
1-Methyl-2-((2R)-2-methyl-4-pyridin-3-yl-piperazin-1-yl)-1H-[4,4']bipyrimidinyl-6-one;
1-Methyl-2-((2R)-2-methyl-4-pyridin-2-yl-piperazin-1-yl)-1H-[4,4']bipyrimidinyl-6-one;
4-[(3R)-3-Methyl-4-(1-methyl-6-oxo-1,6-dihydro-[4,4']bipyrimidinyl-2-yl)-piperazin-1-yl]-benzoic acid tert-butyl ester;
2-[(2R)-4-(4-Chloro-phenyl)-2-methyl-piperazin-1-yl]-1-methyl-1H-[4,4']bipyrimidinyl-6-one;
1-Methyl-2-((2R)-2-methyl-4-quinolin-3-yl-piperazin-1-yl)-1H-[4,4']bipyrimidinyl-6-one;
2-[(2R)-4-(4-Hydroxy-phenyl)-2-methyl-piperazin-1-yl]-1-methyl-1H-[4,4']bipyrimidinyl-6-one;
4-[(3R)-3-Methyl-4-(1-methyl-6-oxo-1,6-dihydro-[4,4']bipyrimidinyl-2-yl)-piperazin-1-yl]-benzoic acid;
4-{(3R)-4-[4-(3-Fluoro-pyridin-4-yl)-1-methyl-6-oxo-1,6-dihydro-pyrimidin-2-yl]-3-methyl-piperazin-1-yl}-benzoic acid methyl ester;
3-{(3R)-4-[4-(3-Fluoro-pyridin-4-yl)-1-methyl-6-oxo-1,6-dihydro-pyrimidin-2-yl]-3-methyl-piperazin-1-yl}-benzoic acid methyl ester;
4-{(3R)-4-[4-(3-Fluoro-pyridin-4-yl)-1-methyl-6-oxo-1,6-dihydro-pyrimidin-2-yl]-3-methyl-piperazin-1-yl}-benzonitrile;
3-{(3R)-4-[4-(3-Fluoro-pyridin-4-yl)-1-methyl-6-oxo-1,6-dihydro-pyrimidin-2-yl]-3-methyl-piperazin-1-yl}-benzonitrile;
2-{(3R)-4-[4-(3-Fluoro-pyridin-4-yl)-1-methyl-6-oxo-1,6-dihydro-pyrimidin-2-yl]-3-methyl-piperazin-1-yl}-benzonitrile;
6-(3-Fluoro-pyridin-4-yl)-3-methyl-2-((2R)-2-methyl-4-pyrimidin-5-yl-piperazin-1-yl)-3H-pyrimidin-4-one;
6-(3-Fluoro-pyridin-4-yl)-3-methyl-2-((3R)-3-methyl-2,3,5,6-tetrahydro-[1,2']bipyrazinyl-4-yl)-3H-pyrimidin-4-one;
6-(3-Fluoro-pyridin-4-yl)-3-methyl-2-((2R)-2-methyl-4-pyridin-4-yl-piperazin-1-yl)-3H-pyrimidin-4-one;
6-(3-Fluoro-pyridin-4-yl)-3-methyl-2-((2R)-2-methyl-4-pyridin-3-yl-piperazin-1-yl)-3H-pyrimidin-4-one;
6-(3-Fluoro-pyridin-4-yl)-3-methyl-2-((2R)-2-methyl-4-pyridin-2-yl-piperazin-1-yl)-3H-pyrimidin-4-one;
4-{(3R)-4-[4-(3-Fluoro-pyridin-4-yl)-1-methyl-6-oxo-1,6-dihydro-pyrimidin-2-yl]-3-methyl-piperazin-1-yl}-benzoic acid tert-butyl ester;
6-(3-Fluoro-pyridin-4-yl)-3-methyl-2-{(2R)-2-methyl-4-[4-(5-methyl-[1,2,4]oxadiazol-3-yl)-phenyl]-piperazin-1-yl}-3H-pyrimidin-4-one;
2-[(2R)-4-(4-Chloro-phenyl)-2-methyl-piperazin-1-yl]-6-(3-fluoro-pyridin-4-yl)-3-methyl-3H-pyrimidin-4-one;

6-(3-Fluoro-pyridin-4-yl)-3-methyl-2-((2R)-2-methyl-4-quinolin-3-yl-piperazin-1-yl)-3H-pyrimidin-4-one;

6-(3-Fluoro-pyridin-4-yl)-3-methyl-2-((2R)-2-methyl-4-quinolin-6-yl-piperazin-1-yl)-3H-pyrimidin-4-one;

6-(3-Fluoro-pyridin-4-yl)-2-[(2R)-4-(4-hydroxy-phenyl)-2-methyl-piperazin-1-yl]-3-methyl-3H-pyrimidin-4-one;

4-{(3R)-4-[4-(3-Fluoro-pyridin-4-yl)-1-methyl-6-oxo-1,6-dihydro-pyrimidin-2-yl]-3-methyl-piperazin-1-yl}-benzoic acid;

4-[(3R)-3-Methyl-4-(1-methyl-6-oxo-4-pyridin-4-yl-1,6-dihydro-pyrimidin-2-yl)-piperazin-1-yl]-benzoic acid methyl ester;

3-[(3R)-3-Methyl-4-(1-methyl-6-oxo-4-pyridin-4-yl-1,6-dihydro-pyrimidin-2-yl)-piperazin-1-yl]-benzoic acid methyl ester;

4-[(3R)-3-Methyl-4-(1-methyl-6-oxo-4-pyridin-4-yl-1,6-dihydro-pyrimidin-2-yl)-piperazin-1-yl]-benzonitrile;

3-[(2R)-3-Methyl-4-(1-methyl-6-oxo-4-pyridin-4-yl-1,6-dihydro-pyrimidin-2-yl)-piperazin-1-yl]-benzonitrile;

3-Methyl-2-((3R)-3-methyl-2,3,5,6-tetrahydro-[1,2']bipyrazinyl-4-yl)-6-pyridin-4-yl-3H-pyrimidin-4-one;

3-Methyl-2-((2R)-2-methyl-4-pyridin-4-yl-piperazin-1-yl)-6-pyridin-4-yl-3H-pyrimidin-4-one;

3-Methyl-2-((2R)-2-methyl-4-pyridin-3-yl-piperazin-1-yl)-6-pyridin-4-yl-3H-pyrimidin-4-one;

4-[(3R)-3-Methyl-4-(1-methyl-6-oxo-4-pyridin-4-yl-1,6-dihydro-pyrimidin-2-yl)-piperazin-1-yl]-benzoic acid tert-butyl ester;

3-Methyl-2-{(2R)-2-methyl-4-[4-(5-methyl-[1,2,4]oxadiazol-3-yl)-phenyl]-piperazin-1-yl}-6-pyridin-4-yl-3H-pyrimidin-4-one;

2-[(2R)-4-(4-Chloro-phenyl)-2-methyl-piperazin-1-yl]-3-methyl-6-pyridin-4-yl-3H-pyrimidin-4-one;

3-Methyl-2-((2R)-2-methyl-4-quinolin-3-yl-piperazin-1-yl)-6-pyridin-4-yl-3H-pyrimidin-4-one;

3-Methyl-2-((2R)-2-methyl-4-quinolin-6-yl-piperazin-1-yl)-6-pyridin-4-yl-3H-pyrimidin-4-one;

2-[(2R)-4-(4-Hydroxy-phenyl)-2-methyl-piperazin-1-yl]-3-methyl-6-pyridin-4-yl-3H-pyrimidin-4-one;

4-[(3R)-3-Methyl-4-(1-methyl-6-oxo-4-pyridin-4-yl-1,6-dihydro-pyrimidin-2-yl)-piperazin-1-yl]-benzoic acid;

1-Methyl-2-{(2R)-2-methyl-4-[4-(5-propyl-[1,2,4]oxadiazol-3-yl)-phenyl]-piperazin-1-yl}-1H-[4,4']bipyrimidinyl-6-one;

2-{(2R)-4-[4-(5-Methoxymethyl-[1,2,4]oxadiazol-3-yl)-phenyl]-2-methyl-piperazin-1-yl}-1-methyl-1H-[4,4']bipyrimidinyl-6-one;

2-{(2R)-4-[4-(5-tert-Butyl-[1,2,4]oxadiazol-3-yl)-phenyl]-2-methyl-piperazin-1-yl}-1-methyl-1H-[4,4']bipyrimidinyl-6-one;

1-Methyl-2-{(2R)-2-methyl-4-[4-(5-pyridin-2-yl-[1,2,4]oxadiazol-3-yl)-phenyl]-piperazin-1-yl}-1H-[4,4']bipyrimidinyl-6-one;

2-{(2R)-4-[4-(5-Aminomethyl-[1,2,4]oxadiazol-3-yl)-phenyl]-2-methyl-piperazin-1-yl}-1-methyl-1H-[4,4']bipyrimidinyl-6-one;

2-((2R)-4-{4-[5-((1S)-1-Amino-ethyl)-[1,2,4]oxadiazol-3-yl]-phenyl}-2-methyl-piperazin-1-yl)-1-methyl-1H-[4,4']bipyrimidinyl-6-one;

2-((2R)-4-{4-[5-(1-Amino-1-methyl-ethyl)-[1,2,4]oxadiazol-3-yl]-phenyl}-2-methyl-piperazin-1-yl)-1-methyl-1H-[4,4']bipyrimidinyl-6-one;

1-Methyl-2-{(2R)-2-methyl-4-[4-((2RS)-5-pyrrolidin-2-yl-[1,2,4]oxadiazol-3-yl)-phenyl]-piperazin-1-yl}-1H-[4,4']bipyrimidinyl-6-one;

2-[(2R)-4-(4-{5-[(1S)-1-Amino-2-(3H-imidazol-4-yl)-ethyl]-[1,2,4]oxadiazol-3-yl}-phenyl)-2-methyl-piperazin-1-yl]-1-methyl-1H-[4,4']bipyrimidinyl-6-one;

1-Methyl-2-{(2R)-2-methyl-4-[4-(5-phenyl-[1,2,4]oxadiazol-3-yl)-phenyl]-piperazin-1-yl}-1H-[4,4']bipyrimidinyl-6-one;

6-(3-Fluoro-pyridin-4-yl)-3-methyl-2-{(2R)-2-methyl-4-[4-(5-propyl-[1,2,4]oxadiazol-3-yl)-phenyl]-piperazin-1-yl}-3H-pyrimidin-4-one;

6-(3-Fluoro-pyridin-4-yl)-2-{(2R)-4-[4-(5-methoxymethyl-[1,2,4]oxadiazol-3-yl)-phenyl]-2-methyl-piperazin-1-yl}-3-methyl-3H-pyrimidin-4-one;

2-{(2R)-4-[4-(5-tert-Butyl-[1,2,4]oxadiazol-3-yl)-phenyl]-2-methyl-piperazin-1-yl}-6-(3-fluoro-pyridin-4-yl)-3-methyl-3H-pyrimidin-4-one;

6-(3-Fluoro-pyridin-4-yl)-3-methyl-2-{(2R)-2-methyl-4-[4-(5-pyridin-4-yl-[1,2,4]oxadiazol-3-yl)-phenyl]-piperazin-1-yl}-3H-pyrimidin-4-one;

6-(3-Fluoro-pyridin-4-yl)-3-methyl-2-{(2R)-2-methyl-4-[4-(5-pyridin-2-yl-[1,2,4]oxadiazol-3-yl)-phenyl]-piperazin-1-yl}-3H-pyrimidin-4-one;

2-{(2R)-4-[4-(5-Aminomethyl-[1,2,4]oxadiazol-3-yl)-phenyl]-2-methyl-piperazin-1-yl}-6-(3-fluoro-pyridin-4-yl)-3-methyl-3H-pyrimidin-4-one;

2-((2R)-4-{4-[5-((1S)-1-Amino-ethyl)-[1,2,4]oxadiazol-3-yl]-phenyl}-2-methyl-piperazin-1-yl)-6-(3-fluoro-pyridin-4-yl)-3-methyl-3H-pyrimidin-4-one;

2-((2R)-4-{4-[5-(1-Amino-1-methyl-ethyl)-[1,2,4]oxadiazol-3-yl]-phenyl}-2-methyl-piperazin-1-yl)-6-(3-fluoro-pyridin-4-yl)-3-methyl-3H-pyrimidin-4-one;

6-(3-Fluoro-pyridin-4-yl)-3-methyl-2-{(2R)-2-methyl-4-[4-((2RS)-5-pyrrolidin-2-yl-[1,2,4]oxadiazol-3-yl)-phenyl]-piperazin-1-yl}-3H-pyrimidin-4-one;

2-[(2R)-4-(4-{5-[(1S)-1-Amino-2-(3H-imidazol-4-yl)-ethyl]-[1,2,4]oxadiazol-3-yl}-phenyl)-2-methyl-piperazin-1-yl]-6-(3-fluoro-pyridin-4-yl)-3-methyl-3H-pyrimidin-4-one;

6-(3-Fluoro-pyridin-4-yl)-3-methyl-2-{(2R)-2-methyl-4-[4-(5-phenyl-[1,2,4]oxadiazol-3-yl)-phenyl]-piperazin-1-yl}-3H-pyrimidin-4-one;

2-((2R)-4-{4-[5-((1R)-Amino-phenyl-methyl)-[1,2,4]oxadiazol-3-yl]-phenyl}-2-methyl-piperazin-1-yl)-6-(3-fluoro-pyridin-4-yl)-3-methyl-3H-pyrimidin-4-one;

2-((2R)-4-{4-[5-((1R)-1-Amino-ethyl)-[1,2,4]oxadiazol-3-yl]-phenyl}-2-methyl-piperazin-1-yl)-6-(3-fluoro-pyridin-4-yl)-3-methyl-3H-pyrimidin-4-one;

3-Methyl-2-{(2R)-2-methyl-4-[4-(5-propyl-[1,2,4]oxadiazol-3-yl)-phenyl]-piperazin-1-yl}-6-pyridin-4-yl-3H-pyrimidin-4-one;

2-{(2R)-4-[4-(5-Methoxymethyl-[1,2,4]oxadiazol-3-yl)-phenyl]-2-methyl-piperazin-1-yl}-3-methyl-6-pyridin-4-yl-3H-pyrimidin-4-one;

2-{(2R)-4-[4-(5-tert-Butyl-[1,2,4]oxadiazol-3-yl)-phenyl]-2-methyl-piperazin-1-yl}-3-methyl-6-pyridin-4-yl-3H-pyrimidin-4-one;

3-Methyl-2-{(2R)-2-methyl-4-[4-(5-pyridin-2-yl-[1,2,4]oxadiazol-3-yl)-phenyl]-piperazin-1-yl}-6-pyridin-4-yl-3H-pyrimidin-4-one;

2-{(2R)-4-[4-(5-Aminomethyl-[1,2,4]oxadiazol-3-yl)-phenyl]-2-methyl-piperazin-1-yl}-3-methyl-6-pyridin-4-yl-3H-pyrimidin-4-one;

2-((2R)-4-{4-[5-((1S)-1-Amino-ethyl)-[1,2,4]oxadiazol-3-yl]-phenyl}-2-methyl-piperazin-1-yl)-3-methyl-6-pyridin-4-yl-3H-pyrimidin-4-one;

2-((2R)-4-{4-[5-(1-Amino-1-methyl-ethyl)-[1,2,4]oxadiazol-3-yl]-phenyl}-2-methyl-piperazin-1-yl)-3-methyl-6-pyridin-4-yl-3H-pyrimidin-4-one;

3-Methyl-2-{(2R)-2-methyl-4-[4-((2RS)-5-pyrrolidin-2-yl-[1,2,4]oxadiazol-3-yl)-phenyl]-piperazin-1-yl}-6-pyridin-4-yl-3H-pyrimidin-4-one;
2-[(2R)-4-(4-{5-[(1S)-1-Amino-2-(3H-imidazol-4-yl)-ethyl]-[1,2,4]oxadiazol-3-yl}-phenyl)-2-methyl-piperazin-1-yl]-3-methyl-6-pyridin-4-yl-3H-pyrimidin-4-one;
2-((2R)-4-{4-[5-((1R)-1-Amino-ethyl)-[1,2,4]oxadiazol-3-yl]-phenyl}-2-methyl-piperazin-1-yl)-3-methyl-6-pyridin-4-yl-3H-pyrimidin-4-one;
3-Methyl-2-{(2R)-2-methyl-4-[4-(5-pyridin-4-yl-[1,2,4]oxadiazol-3-yl)-phenyl]-piperazin-1-yl}-6-pyridin-4-yl-3H-pyrimidin-4-one;
2-[(2R)-4-(3-Hydroxy-phenyl)-2-methyl-piperazin-1-yl]-3-methyl-6-pyridin-4-yl-3H-pyrimidin-4-one:
(3R)-6-(3-Fluoro-pyridin-4-yl)-3-methyl-2-(2-methyl-piperazin-1-yl)-3H-pyrimidin-4-one;
2-((2R)-4-Benzyl-2-methyl-piperazin-1-yl)-1-methyl-1H-[4,4']bipyrimidinyl-6-one;
1-Methyl-2-((2R)-2-methyl-4-phenyl-piperazin-1-yl)-1H-[4,4']bipyrimidinyl-6-one;
2-[(2R)-4-(2-Fluoro-phenyl)-2-methyl-piperazin-1-yl]-1-methyl-1H-[4,4']bipyrimidinyl-6-one;
2-[(2R)-4-(3-Fluoro-phenyl)-2-methyl-piperazin-1-yl]-1-methyl-1H-[4,4']bipyrimidinyl-6-one;
2-[(2R)-4-(4-Fluoro-phenyl)-2-methyl-piperazin-1-yl]-1-methyl-1H-[4,4']bipyrimidinyl-6-one;
2-[(2R)-4-(2-Methoxy-phenyl)-2-methyl-piperazin-1-yl]-1-methyl-1H-[4,4']bipyrimidinyl-6-one;
2-[(2R)-4-(3-Methoxy-phenyl)-2-methyl-piperazin-1-yl]-1-methyl-1H-[4,4']bipyrimidinyl-6-one;
2-[(2R)-4-(4-Methoxy-phenyl)-2-methyl-piperazin-1-yl]-1-methyl-1H-[4,4']bipyrimidinyl-6-one;
5-[(3R)-3-Methyl-4-(1-methyl-6-oxo-1,6-dihydro-[4,4']bipyrimidinyl-2-yl)-piperazin-1-yl]-thiophene-2-carboxylic acid ethyl ester;
1-Methyl-2-[(2R)-2-methyl-4-(5-methyl-thiophen-2-yl)-piperazin-1-yl]-1H-[4,4']bipyrimidinyl-6-one;
2-[(2R)-2-Ethyl-4-(4-methoxy-phenyl)-piperazin-1-yl]-1-methyl-1H-[4,4']bipyrimidinyl-6-one;
2-[(2R)-2-Ethyl-4-(4-methoxy-phenyl)-piperazin-1-yl]-6-(3-fluoro-pyridin-4-yl)-3-methyl-3H-pyrimidin-4-one;
4-[(2S)-2-Methyl-4-(1-methyl-6-oxo-1,6-dihydro-[4,4']bipyrimidinyl-2-yl)-piperazin-1-yl]-benzonitrile;
4-[(3R)-3-Methyl-4-(1-methyl-6-oxo-1,6-dihydro-[4,4']bipyrimidinyl-2-yl)-piperazin-1-yl]-benzonitrile;
6-(3-Fluoro-pyridin-4-yl)-3-methyl-2-((2R)-2-methyl-4-pyrimidin-2-yl-piperazin-1-yl)-3H-pyrimidin-4-one;
1-Methyl-2-{(2R)-2-methyl-4-[4-(5-methyl-[1,2,4]oxadiazol-3-yl)-benzoyl]-piperazin-1-yl}-1H-[4,4']bipyrimidinyl-6-one;
1-Methyl-2-{(2R)-2-methyl-4-[4-(5-methyl-[1,2,4]oxadiazol-3-yl)-benzyl]-piperazin-1-yl}-1H-[4,4']bipyrimidinyl-6-one;
2-[(2R)-4-(4-Fluoro-benzoyl)-2-methyl-piperidin-1-yl]-1-methyl-1H-[4,4']bipyrimidinyl-6-one;
2-[(2R)-4-(4-Chloro-benzoyl)-2-methyl-piperidin-1-yl]-1-methyl-1H-[4,4']bipyrimidinyl-6-one;
2-[(2R)-4-(3,4-Dichloro-benzoyl)-2-methyl-piperidin-1-yl]-1-methyl-1H-[4,4']bipyrimidinyl-6-one;
2-[(2R)-4-(4-tert-Butyl-benzoyl)-2-methyl-piperazin-1-yl]-1-methyl-1H-[4,4']bipyrimidinyl-6-one;
4-[(3R)-3-Methyl-4-(1-methyl-6-oxo-1,6-dihydro-[4,4']bipyrimidinyl-2-yl)-piperazine-1-carbonyl]-benzonitrile;
1-Methyl-2-[(2R)-2-methyl-4-(4-trifluoromethoxy-benzoyl)-piperazin-1-yl]-1H-[4,4']bipyrimidinyl-6-one;
4-[(3R)-3-Methyl-4-(1-methyl-6-oxo-1,6-dihydro-[4,4']bipyrimidinyl-2-yl)-piperazine-1-carbonyl]-benzoic acid methyl ester;
1-Methyl-2-[(2R)-2-methyl-4-(4-methyl-benzoyl)-piperazin-1-yl]-1H-[4,4']bipyrimidinyl-6-one;
2-[(2R)-4-(4-Dimethylamino-benzoyl)-2-methyl-piperazin-1-yl]-1-methyl-1H-[4,4']bipyrimidinyl-6-one;
2-[(2R)-4-(4-Methoxy-benzoyl)-2-methyl-piperazin-1-yl]-1-methyl-1H-[4,4']bipyrimidinyl-6-one;
1-Methyl-2-[(2R)-2-methyl-4-(naphthalene-2-carbonyl)-piperazin-1-yl]-1H-[4,4']bipyrimidinyl-6-one;
2-[(2R)-4-(Benzo[1,3]dioxole-5-carbonyl)-2-methyl-piperazin-1-yl]-1-methyl-1H-[4,4']bipyrimidinyl-6-one;
1-Methyl-2-[(2R)-2-methyl-4-(quinoline-2-carbonyl)-piperazin-1-yl]-1H-[4,4']bipyrimidinyl-6-one;
3-[(3R)-3-Methyl-4-(1-methyl-6-oxo-1,6-dihydro-[4,4']bipyrimidinyl-2-yl)-piperazin-1-yl]-benzonitrile;
2-[(3R)-3-Methyl-4-(1-methyl-6-oxo-1,6-dihydro-[4,4']bipyrimidinyl-2-yl)-piperazin-1-yl]-benzonitrile;
1-Methyl-2-((3R)-3-methyl-2,3,5,6-tetrahydro-[1,2']bipyrazinyl-4-yl)-1H-[4,4']bipyrimidinyl-6-one;
1-Methyl-2-((2R)-2-methyl-4-pyridin-4-yl-piperazin-1-yl)-1H-[4,4']bipyrimidinyl-6-one;
1-Methyl-2-((2R)-2-methyl-4-pyridin-3-yl-piperazin-1-yl)-1H-[4,4']bipyrimidinyl-6-one;
1-Methyl-2-((2R)-2-methyl-4-pyridin-2-yl-piperazin-1-yl)-1H-[4,4']bipyrimidinyl-6-one;
4-[(3R)-3-Methyl-4-(1-methyl-6-oxo-1,6-dihydro-[4,4']bipyrimidinyl-2-yl)-piperazin-1-yl]-benzoic acid tert-butyl ester;
2-[(2R)-4-(4-Chloro-phenyl)-2-methyl-piperazin-1-yl]-1-methyl-1H-[4,4']bipyrimidinyl-6-one;
1-Methyl-2-((2R)-2-methyl-4-quinolin-3-yl-piperazin-1-yl)-1H-[4,4']bipyrimidinyl-6-one;
2-[(2R)-4-(4-Hydroxy-phenyl)-2-methyl-piperazin-1-yl]-1-methyl-1H-[4,4']bipyrimidinyl-6-one;
4-[(3R)-3-Methyl-4-(1-methyl-6-oxo-1,6-dihydro-[4,4']bipyrimidinyl-2-yl)-piperazin-1-yl]-benzoic acid;
4-{(3R)-4-[4-(3-Fluoro-pyridin-4-yl)-1-methyl-6-oxo-1,6-dihydro-pyrimidin-2-yl]-3-methyl-piperazin-1-yl}-benzoic acid methyl ester;
3-{(3R)-4-[4-(3-Fluoro-pyridin-4-yl)-1-methyl-6-oxo-1,6-dihydro-pyrimidin-2-yl]-3-methyl-piperazin-1-yl}-benzoic acid methyl ester;
4-{(3R)-4-[4-(3-Fluoro-pyridin-4-yl)-1-methyl-6-oxo-1,6-dihydro-pyrimidin-2-yl]-3-methyl-piperazin-1-yl}-benzonitrile;
3-{(3R)-4-[4-(3-Fluoro-pyridin-4-yl)-1-methyl-6-oxo-1,6-dihydro-pyrimidin-2-yl]-3-methyl-piperazin-1-yl}-benzonitrile;
2-{(3R)-4-[4-(3-Fluoro-pyridin-4-yl)-1-methyl-6-oxo-1,6-dihydro-pyrimidin-2-yl]-3-methyl-piperazin-1-yl}-benzonitrile;
6-(3-Fluoro-pyridin-4-yl)-3-methyl-2-((2R)-2-methyl-4-pyrimidin-5-yl-piperazin-1-yl)-3H-pyrimidin-4-one;
6-(3-Fluoro-pyridin-4-yl)-3-methyl-2-((3R)-3-methyl-2,3,5,6-tetrahydro-[1,2']bipyrazinyl-4-yl)-3H-pyrimidin-4-one;
6-(3-Fluoro-pyridin-4-yl)-3-methyl-2-((2R)-2-methyl-4-pyridin-4-yl-piperazin-1-yl)-3H-pyrimidin-4-one;
6-(3-Fluoro-pyridin-4-yl)-3-methyl-2-((2R)-2-methyl-4-pyridin-3-yl-piperazin-1-yl)-3H-pyrimidin-4-one;
6-(3-Fluoro-pyridin-4-yl)-3-methyl-2-((2R)-2-methyl-4-pyridin-2-yl-piperazin-1-yl)-3H-pyrimidin-4-one;
4-{(3R)-4-[4-(3-Fluoro-pyridin-4-yl)-1-methyl-6-oxo-1,6-dihydro-pyrimidin-2-yl]-3-methyl-piperazin-1-yl}-benzoic acid tert-butyl ester;

6-(3-Fluoro-pyridin-4-yl)-3-methyl-2-{(2R)-2-methyl-4-[4-(5-methyl-[1,2,4]oxadiazol-3-yl)-phenyl]-piperazin-1-yl]-3H-pyrimidin-4-one;

2-[(2R)-4-(4-Chloro-phenyl)-2-methyl-piperazin-1-yl]-6-(3-fluoro-pyridin-4-yl)-3-methyl-3H-pyrimidin-4-one;

6-(3-Fluoro-pyridin-4-yl)-3-methyl-2-((2R)-2-methyl-4-quinolin-3-yl-piperazin-1-yl)-3H-pyrimidin-4-one;

6-(3-Fluoro-pyridin-4-yl)-3-methyl-2-((2R)-2-methyl-4-quinolin-6-yl-piperazin-1-yl)-3H-pyrimidin-4-one;

6-(3-Fluoro-pyridin-4-yl)-2-[(2R)-4-(4-hydroxy-phenyl)-2-methyl-piperazin-1-yl]-3-methyl-3H-pyrimidin-4-one;

4-{(3R)-4-[4-(3-Fluoro-pyridin-4-yl)-1-methyl-6-oxo-1,6-dihydro-pyrimidin-2-yl]-3-methyl-piperazin-1-yl}-benzoic acid;

4-[(3R)-3-Methyl-4-(1-methyl-6-oxo-4-pyridin-4-yl-1,6-dihydro-pyrimidin-2-yl)-piperazin-1-yl]-benzoic acid methyl ester;

3-[(3R)-3-Methyl-4-(1-methyl-6-oxo-4-pyridin-4-yl-1,6-dihydro-pyrimidin-2-yl)-piperazin-1-yl]-benzoic acid methyl ester;

4-[(3R)-3-Methyl-4-(1-methyl-6-oxo-4-pyridin-4-yl-1,6-dihydro-pyrimidin-2-yl)-piperazin-1-yl]-benzonitrile;

3-[(2R)-3-Methyl-4-(1-methyl-6-oxo-4-pyridin-4-yl-1,6-dihydro-pyrimidin-2-yl)-piperazin-1-yl]-benzonitrile;

3-Methyl-2-((2R)-2-methyl-4-pyridin-4-yl-piperazin-1-yl)-6-pyridin-4-yl-3H-pyrimidin-4-one;

3-Methyl-2-((2R)-2-methyl-4-pyridin-3-yl-piperazin-1-yl)-6-pyridin-4-yl-3H-pyrimidin-4-one;

3-Methyl-2-{(2R)-2-methyl-4-[4-(5-methyl-[1,2,4]oxadiazol-3-yl)-phenyl]-piperazin-1-yl}-6-pyridin-4-yl-3H-pyrimidin-4-one;

2-[(2R)-4-(4-Chloro-phenyl)-2-methyl-piperazin-1-yl]-3-methyl-6-pyridin-4-yl-3H-pyrimidin-4-one;

3-Methyl-2-((2R)-2-methyl-4-quinolin-3-yl-piperazin-1-yl)-6-pyridin-4-yl-3H-pyrimidin-4-one;

3-Methyl-2-((2R)-2-methyl-4-quinolin-6-yl-piperazin-1-yl)-6-pyridin-4-yl-3H-pyrimidin-4-one;

2-[(2R)-4-(4-Hydroxy-phenyl)-2-methyl-piperazin-1-yl]-3-methyl-6-pyridin-4-yl-3H-pyrimidin-4-one;

4-[(3R)-3-Methyl-4-(1-methyl-6-oxo-4-pyridin-4-yl-1,6-dihydro-pyrimidin-2-yl)-piperazin-1-yl]-benzoic acid;

1-Methyl-2-{(2R)-2-methyl-4-[4-(5-propyl-[1,2,4]oxadiazol-3-yl)-phenyl]-piperazin-1-yl}-1H-[4,4']bipyrimidinyl-6-one;

2-{(2R)-4-[4-(5-Methoxymethyl-[1,2,4]oxadiazol-3-yl)-phenyl]-2-methyl-piperazin-1-yl}-1-methyl-1H-[4,4']bipyrimidinyl-6-one;

2-{(2R)-4-[4-(5-tert-Butyl-[1,2,4]oxadiazol-3-yl)-phenyl]-2-methyl-piperazin-1-yl}-1-methyl-1H-[4,4']bipyrimidinyl-6-one;

1-Methyl-2-{(2R)-2-methyl-4-[4-(5-pyridin-2-yl-[1,2,4]oxadiazol-3-yl)-phenyl]-piperazin-1-yl}-1H-[4,4']bipyrimidinyl-6-one;

2-{(2R)-4-[4-(5-Aminomethyl-[1,2,4]oxadiazol-3-yl)-phenyl]-2-methyl-piperazin-1-yl}-1-methyl-1H-[4,4']bipyrimidinyl-6-one;

2-((2R)-4-{4-[5-((1S)-1-Amino-ethyl)-[1,2,4]oxadiazol-3-yl]-phenyl}-2-methyl-piperazin-1-yl)-1-methyl-1H-[4,4']bipyrimidinyl-6-one;

2-((2R)-4-{4-[5-(1-Amino-1-methyl-ethyl)-[1,2,4]oxadiazol-3-yl]-phenyl}-2-methyl-piperazin-1-yl)-1-methyl-1H-[4,4']bipyrimidinyl-6-one;

1-Methyl-2-{(2R)-2-methyl-4-[4-((2RS)-5-pyrrolidin-2-yl-[1,2,4]oxadiazol-3-yl)-phenyl]-piperazin-1-yl}-1H-[4,4']bipyrimidinyl-6-one;

2-[(2R)-4-(4-{5-[(1S)-1-Amino-2-(3H-imidazol-4-yl)-ethyl]-[1,2,4]oxadiazol-3-yl}-phenyl)-2-methyl-piperazin-1-yl]-1-methyl-1H-[4,4']bipyrimidinyl-6-one;

1-Methyl-2-{(2R)-2-methyl-4-[4-(5-phenyl-[1,2,4]oxadiazol-3-yl)-phenyl]-piperazin-1-yl}-1H-[4,4']bipyrimidinyl-6-one;

6-(3-Fluoro-pyridin-4-yl)-3-methyl-2-{(2R)-2-methyl-4-[4-(5-propyl-[1,2,4]oxadiazol-3-yl)-phenyl]-piperazin-1-yl}-3H-pyrimidin-4-one;

6-(3-Fluoro-pyridin-4-yl)-2-{(2R)-4-[4-(5-methoxymethyl-[1,2,4]oxadiazol-3-yl)-phenyl]-2-methyl-piperazin-1-yl}-3-methyl-3H-pyrimidin-4-one;

2-{(2R)-4-[4-(5-tert-Butyl-[1,2,4]oxadiazol-3-yl)-phenyl]-2-methyl-piperazin-1-yl}-6-(3-fluoro-pyridin-4-yl)-3-methyl-3H-pyrimidin-4-one;

6-(3-Fluoro-pyridin-4-yl)-3-methyl-2-{(2R)-2-methyl-4-[4-(5-pyridin-4-yl-[1,2,4]oxadiazol-3-yl)-phenyl]-piperazin-1-yl}-3H-pyrimidin-4-one;

6-(3-Fluoro-pyridin-4-yl)-3-methyl-2-{(2R)-2-methyl-4-[4-(5-pyridin-2-yl-[1,2,4]oxadiazol-3-yl)-phenyl]-piperazin-1-yl}-3H-pyrimidin-4-one;

2-{(2R)-4-[4-(5-Aminomethyl-[1,2,4]oxadiazol-3-yl)-phenyl]-2-methyl-piperazin-1-yl}-6-(3-fluoro-pyridin-4-yl)-3-methyl-3H-pyrimidin-4-one;

2-((2R)-4-{4-[5-((1S)-1-Amino-ethyl)-[1,2,4]oxadiazol-3-yl]-phenyl}-2-methyl-piperazin-1-yl)-6-(3-fluoro-pyridin-4-yl)-3-methyl-3H-pyrimidin-4-one;

2-((2R)-4-{4-[5-(1-Amino-1-methyl-ethyl)-[1,2,4]oxadiazol-3-yl]-phenyl}-2-methyl-piperazin-1-yl)-6-(3-fluoro-pyridin-4-yl)-3-methyl-3H-pyrimidin-4-one;

6-(3-Fluoro-pyridin-4-yl)-3-methyl-2-{(2R)-2-methyl-4-[4-((2RS)-5-pyrrolidin-2-yl-[1,2,4]oxadiazol-3-yl)-phenyl]-piperazin-1-yl}-3H-pyrimidin-4-one;

2-[(2R)-4-(4-{5-[(1S)-1-Amino-2-(3H-imidazol-4-yl)-ethyl]-[1,2,4]oxadiazol-3-yl}-phenyl)-2-methyl-piperazin-1-yl]-6-(3-fluoro-pyridin-4-yl)-3-methyl-3H-pyrimidin-4-one;

6-(3-Fluoro-pyridin-4-yl)-3-methyl-2-{(2R)-2-methyl-4-[4-(5-phenyl-[1,2,4]oxadiazol-3-yl)-phenyl]-piperazin-1-yl}-3H-pyrimidin-4-one;

2-((2R)-4-{4-[5-((1R)-Amino-phenyl-methyl)-[1,2,4]oxadiazol-3-yl]-phenyl}-2-methyl-piperazin-1-yl)-6-(3-fluoro-pyridin-4-yl)-3-methyl-3H-pyrimidin-4-one;

2-((2R)-4-{4-[5-((1R)-1-Amino-ethyl)-[1,2,4]oxadiazol-3-yl]-phenyl}-2-methyl-piperazin-1-yl)-6-(3-fluoro-pyridin-4-yl)-3-methyl-3H-pyrimidin-4-one;

3-Methyl-2-{(2R)-2-methyl-4-[4-(5-propyl-[1,2,4]oxadiazol-3-yl)-phenyl]-piperazin-1-yl}-6-pyridin-4-yl-3H-pyrimidin-4-one;

3-Methyl-2-{(2R)-4-[4-(5-Methoxymethyl-[1,2,4]oxadiazol-3-yl)-phenyl]-2-methyl-piperazin-1-yl}-3-methyl-6-pyridin-4-yl-3H-pyrimidin-4-one;

3-Methyl-2-{(2R)-2-methyl-4-[4-(5-pyridin-2-yl-[1,2,4]oxadiazol-3-yl)-phenyl]-piperazin-1-yl}-6-pyridin-4-yl-3H-pyrimidin-4-one;

2-{(2R)-4-[4-(5-Aminomethyl-[1,2,4]oxadiazol-3-yl)-phenyl]-2-methyl-piperazin-1-yl}-3-methyl-6-pyridin-4-yl-3H-pyrimidin-4-one;

2-((2R)-4-{4-[5-((1S)-1-Amino-ethyl)-[1,2,4]oxadiazol-3-yl]-phenyl}-2-methyl-piperazin-1-yl)-3-methyl-6-pyridin-4-yl-3H-pyrimidin-4-one;

2-((2R)-4-{4-[5-(1-Amino-1-methyl-ethyl)-[1,2,4]oxadiazol-3-yl]-phenyl}-2-methyl-piperazin-1-yl)-3-methyl-6-pyridin-4-yl-3H-pyrimidin-4-one;

3-Methyl-2-{(2R)-2-methyl-4-[4-((2RS)-5-pyrrolidin-2-yl-[1,2,4]oxadiazol-3-yl)-phenyl]-piperazin-1-yl}-6-pyridin-4-yl-3H-pyrimidin-4-one;

2-[(2R)-4-(4-{5-[(1S)-1-Amino-2-(3H-imidazol-4-yl)-ethyl]-[1,2,4]oxadiazol-3-yl}-phenyl)-2-methyl-piperazin-1-yl]-3-methyl-6-pyridin-4-yl-3H-pyrimidin-4-one;

2-((2R)-4-{4-[5-((1R)-1-Amino-ethyl)-[1,2,4]oxadiazol-3-yl]-phenyl}-2-methyl-piperazin-1-yl)-3-methyl-6-pyridin-4-yl-3H-pyrimidin-4-one;

3-Methyl-2-{(2R)-2-methyl-4-[4-(5-pyridin-4-yl-[1,2,4]oxadiazol-3-yl)-phenyl]-piperazin-1-yl}-6-pyridin-4-yl-3H-pyrimidin-4-one; and 2-[(2R)-4-(3-Hydroxy-phenyl)-2-methyl-piperazin-1-yl]-3-methyl-6-pyridin-4-yl-3H-pyrimidin-4-one, an optically active isomer thereof, or a pharmaceutically acceptable salt thereof.

Salts of the aforementioned preferred compound, and solvates or hydrates of the aforementioned compounds and salts thereof are also preferred.

The compounds represented by the aforementioned formula (I) can be prepared, for example, according to the method explained below.

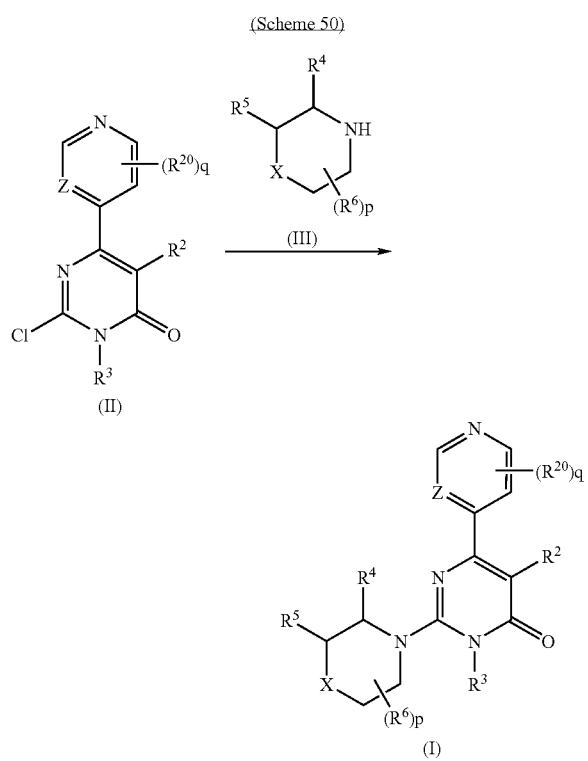

(Scheme 50)

(In the above scheme, definitions of each symbol are the same as those already described.)

The 2-chloropyrimidone represented by the above formula (II) is prepared easily by the method described in the specification of WO2003/027080 and WO2003/037888.

Then the chloride derivative (II) is allowed to react with the amine (III) or salts thereof in the presence of a base such as sodium hydroxide, potassium hydroxide, sodium methoxide, sodium ethoxide, sodium carbonate, sodium hydrogencarbonate, potassium carbonate, triethylamine, diisopropylethylamine, N-methylpiperidine, N-ethylpiperidine, N-methylmorpholine and 1,8-diazabicyclo[5,4,0]undec-7-en for 0.1 to 100 hours at a suitable temperature ranging from 0° C. to 200° C. under nitrogen or argon atmosphere or under ordinary air to afford the desired compound (I). Reaction can also be conducted by microwave with a suitable temperature ranging from 0° C. to 250° C.

Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

Compound (XII), which corresponds to a compound represented by the formula (I) wherein $R^3$ represents hydrogen atom, can be also prepared by following scheme;

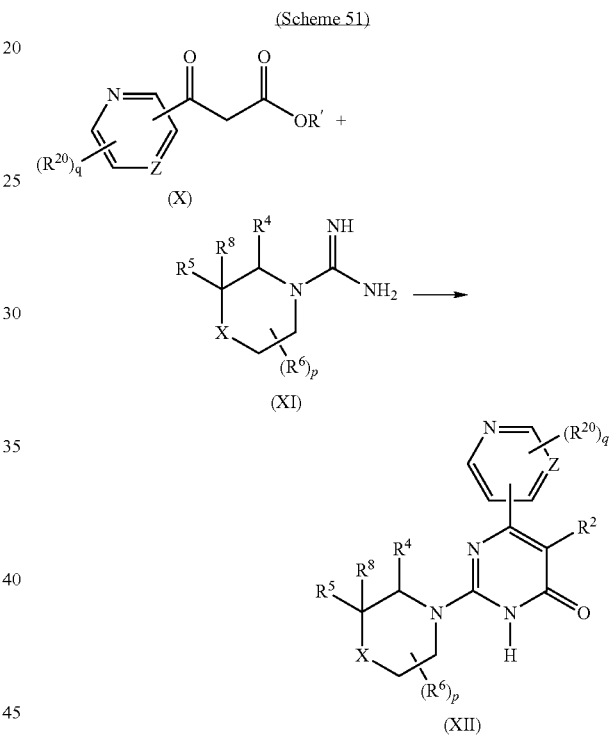

(Scheme 51)

(In the above scheme, R' represents a $C_1$-$C_6$ alkyl which may be substituted, a $C_3$-$C_6$ alkenyl which may be substituted, a $C_6$-$C_{10}$ aryl which may be substituted and a $C_7$-$C_{12}$ aralkyl which may be substituted, and definitions of other symbol are the same as those already described.)

The compound (XII) can be prepared, for example, by the condensation of corresponding 3-substituted 3-oxo-propionic acid ester (X) and amidine or guanidine or salts thereof (XI) in the presence of a base such as sodium hydroxide, potassium hydroxide, sodium methoxide, sodium ethoxide, sodium carbonate, sodium hydrogencarbonate, potassium carbonate, triethylamine, diisopropylethylamine, N-methylpiperidine, N-ethylpiperidine, N-methylmorpholine and 1,8-diazabicyclo[5,4,0]undec-7-en for 1 to 300 hours at a suitable temperature ranging from 0° C. to 200° C. under nitrogen or argon atmosphere or under ordinary air to afford the desired compound (XII).

Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

The compounds of the present invention have inhibitory activity against TPK1, and they inhibit TPK1 activity in neurodegenerative diseases such as Alzheimer disease, thereby suppress the neurotoxicity of Aβ and the formation of PHF and inhibit the nerve cell death. Accordingly, the compounds of the present invention are useful as an active ingredient of a medicament which radically enables preventive and/or therapeutic treatment of Alzheimer disease. In addition, the compounds of the present invention are also useful as an active ingredient of a medicament for preventive and/or therapeutic treatment of ischemic cerebrovascular accidents, Down syndrome, cerebral bleeding due to solitary cerebral amyloid angiopathy, progressive supranuclear palsy, subacute sclerosing panencephalitis, postencephalitic parkinsonism, pugilistic encephalosis, Guam parkinsonism-dementia complex, Lewy body disease, Pick's disease, corticobasal degeneration frontotemporal dementia, vascular dementia, traumatic injuries, brain and spinal cord trauma, peripheral neuropathies, retinopathies and glaucoma, non-insulin dependent diabetes, obesity, manic depressive illness, schizophrenia, alopecia, breast cancer, non-small cell lung carcinoma, thyroid cancer, T or B-cell leukemia, and several virus-induced tumors. As the compound of the present invention has good safety and good pharmacokinetics, the compound has preferable characteristics as a medicament.

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more of pharmaceutical additives. As the active ingredient of the medicament of the present invention, two or more of the aforementioned substance may be used in combination.

A type of the pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like.

Dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 3000 mg (the weight of an active ingredient) to an adult.

EXAMPLES

The present invention will be explained more specifically with reference to examples. However, the scope of the present invention is not limited to the following examples. The compound number in the examples corresponds to that in the table above.

Example 1

2-(1-Methyl-6-oxo-4-pyridin-4-yl-1,6-dihydro-pyrimidin-2-yl)-1,2,3,6,7,11b-hexahydro-pyrazino[2,1-a] isoquinolin-4-one (Compound No. B108)

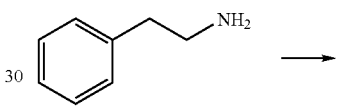

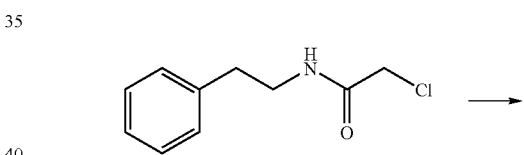

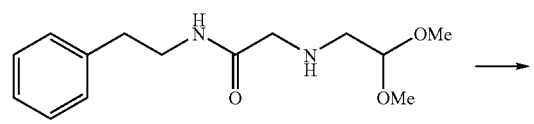

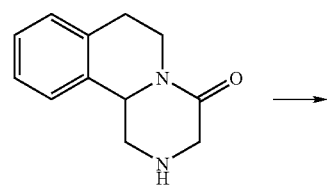

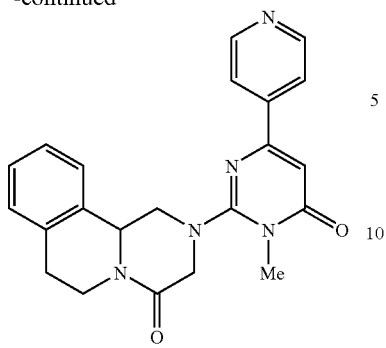

2-Chloro-N-phenethyl-acetamide

Chloroacetylchloride (13.55 g, 120 mmol) was dropped into a solution of 2-phenylethylamine (12.12 g, 100 mmol), sodium bicarbonate (10.6 g, 126 mmol) in dichloromethane (100 ml) under ice cooling and the mixture was stirred for 2 hours. After addition of ice-water, the organic layer was separated and washed with 1N hydrochloric acid and brine. The solvents were removed under reduced pressure and the residue was recrystallized from mixture of water (20 ml) and methanol (30 ml) to afford 2-chloro-N-phenethyl-acetamide (18.33 g, 93%).

2-(2,2-Dimethoxy-ethylamino)-N-phenethyl-acetamide hydrochloride

Aminoacetaldehyde dimethylacetal (20.05 g, 191 mmol) was added to the solution of 2-chloro-N-phenethyl-acetamide (18.33 g, 92.7 mmol) in toluene (92 ml) and refluxed in 2 hours. After ice-cooling and removal of precipitate by filtration, filtrate was washed with water and dried with magnesium sulfate. The solvents were removed under reduced pressure, and 4N hydrogen chloride in ethyl acetate (18 ml) was added to the residue followed by filtration and wash with ethyl acetate and diethyl ether afforded 2-(2,2-dimethoxy-ethylamino)-N-phenethyl-acetamide hydrochloride (8.77 g, 52%).

1,2,3,6,11b-Hexahydro-pyrazino[2,1-a]isoquinolin-4-one 2-(2,2-Dimethoxy-ethylamino)-N-phenethyl-acetamide hydrochloride (8.77 g, 29.0 mmol) was added to the ice-cooled sulfuric acid (8.8 ml) and the mixture was stirred for 3.5 hours at room temperature. Ice-water was added to the solution after cooling by ice and the resulting solution was extracted with dichloromethane after adjusted to pH 12 with 20% aqueous sodium hydroxide. The organic layer was washed with brine and dried with magnesium sulfate, and then the solvents were removed under reduced pressure. Recrystallization of the residue with hexane-ethyl acetate afforded 1,2,3,6,7,11b-hexahydro-pyrazino[2,1-a]isoquinolin-4-one (4.38 g, 75%).

2-(1-Methyl-6-oxo-4-pyridin-4-yl-1,6-dihydro-pyrimidin-2-yl)-1,2,3,6,7,11b-hexahydro-pyrazino[2,1-a]isoquinolin-4-one 2-Chloro-3-methyl-6-pyridin-4-yl-3H-pyrimidin-4-one (332 mg, 1.5 mmol) was added to the solution of 1,2,3,6,7,11b-hexahydro-pyrazino[2,1-a]isoquinolin-4-one (313 mg, 1.55 mmol), triethylamine (0.223 ml, 1.6 mmol) in N,N-dimethylformamide (8 ml) and the mixture was stirred for 4 hour and stood overnight. Ice-water was added to the solution and resulting precipitate was collected by filtration and washed with water and then dried to afford 2-(1-methyl-6-oxo-4-pyridin-4-yl-1,6-dihydro-pyrimidin-2-yl)-1,2,3,6,7,11b-hexahydro-pyrazino[2,1-a]isoquinolin-4-one (555 mg, 96%). Treatment with 4N hydrogen chloride in ethyl acetate yielded corresponding hydrogen chloride salt.

Example 2

2-(1,3,4,6,7,11b-Hexahydro-pyrazino[2,1-a]isoquinolin-2-yl)-3-methyl-6-pyridin-4-yl-3H-pyrimidin-4-one (Compound No. B109)

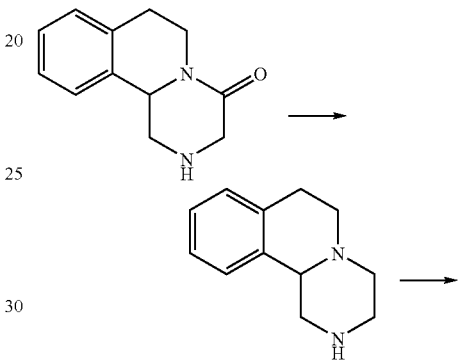

1,3,4,6,7,11b-Hexahydro-2H-pyrazino[2,1-a]isoquinoline 1,2,3,6,7,11b-Hexahydro-pyrazino[2,1-a]isoquinolin-4-one (3.03 g, 15.0 mmol) was added to a solution of lithium aluminum hydride (1.14 g, 30.0 mmol) in tetrahydrofuran (63 ml) and the mixture was refluxed for 6 hours. Water (1.2 ml), 15% aqueous sodium hydroxide (1.2 ml) and water (3.2 ml) were added sequentially to the ice-cooled solution, and filtration of the precipitate and removal of the solvent under reduced pressure afforded 1,3,4,6,7,11b-hexahydro-2H-pyrazino[2,1-a]isoquinoline (2.77 g, 98%).

2-(1,3,4,6,7,11b-Hexahydro-pyrazino[2,1-a] isoquinolin-2-yl)-3-methyl-6-pyridin-4-yl-3H-pyrimidin-4-one 2-Chloro-3-methyl-6-pyridin-4-yl-3H-pyrimidin-4-one (332 mg, 1.5 mmol) was added to the solution of 1,3,4,6,7,11b-hexahydro-2H-pyrazino[2,1-a]isoquinoline (292 mg, 1.55 mmol), triethylamine (0.223 ml, 1.6 mmol) in N,N-dimethylformamide (8 ml) and the mixture was stirred for 6 hours and stood overnight ice-water. After addition of ice-water the solution was partitioned between water and ethyl acetate, and the organic layer was washed with brine and dried with magnesium sulfate. The solvents were removed under reduced pressure and purification by silica gel column chromatography (eluent; dichloromethane/methanol=95/5) afforded title compound (530 mg, 95%). Treatment with 4N hydrogen chloride in ethyl acetate yielded corresponding hydrogen chloride salt (495 mg).

Example 3

2-((4aRS,10bRS)-trans-3,4,4a,5,6,10b-Hexahydro-2H-naphtho[1,2-b][1,4]oxazin-4-yl)-3-methyl-6-(pyrimidin-4-yl)-3H-pyrimidin-4-one (Compound No. B7)

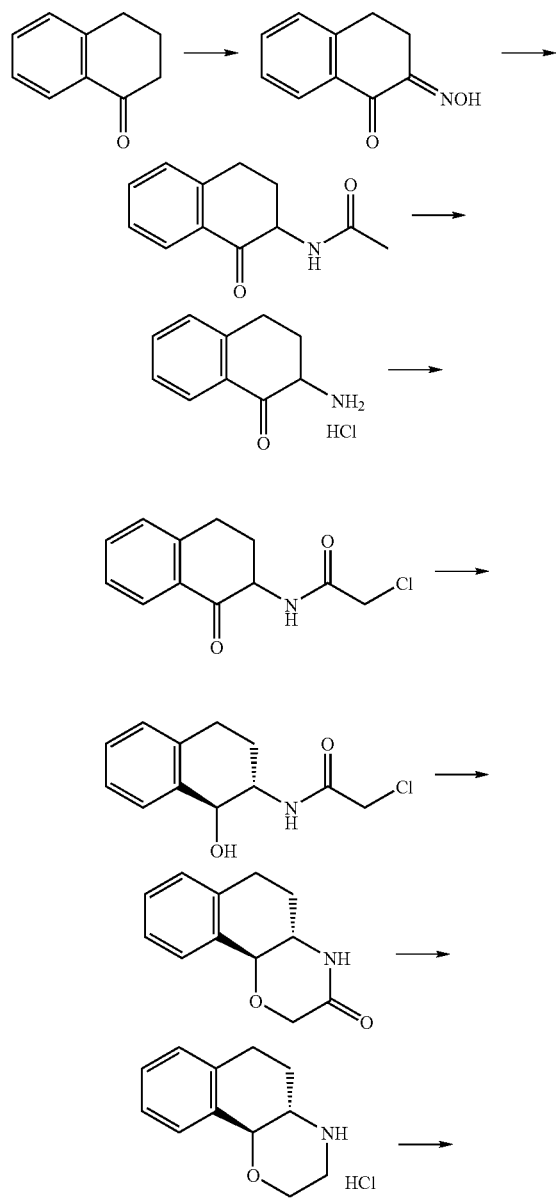

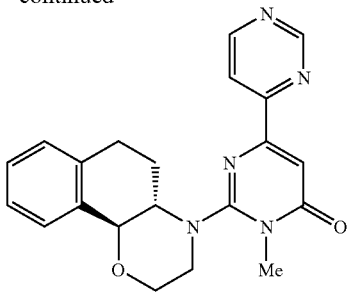

3,4-Dihydro-[1,2]naphthoquinone 2-oxime

Tetralone (25 g, 171 mmol) was added to a solution of potassium tert-butoxide (22 g, 196 mol) and isoamyl nitrite (26 g, 222 mmol) in diethyl ether (200 ml) and tert-butanol (200 ml). The solution was stirred at room temperature for 4 hours and then filtered to collect the potassium salt of the oxime. The solid was dissolved with 1 N aqueous hydrochloric acid (200 ml) and extracted with chloroform and dried over anhydrous magnesium sulfate. After removal of the solvent, the residue was washed with ethyl acetate, and dried to give 3,4-dihydro-[1,2]naphthoquinone 2-oxime (21.5 g, 123 mmol, 72%) as brown crystals.

N-(1-Oxo-1,2,3,4-tetrahydronaphthalen-2-yl)-acetamide

Zinc powder (24 g, 367 mmol) was added to a solution of 3,4-dihydro-[1,2]naphthoquinone 2-oxime (21.5 g, 123 mmol) in acetic acid (200 mw) and acetic anhydride (150 ml), and the solution was stirred at room temperature for 12 hours. After filtration and removal of the solvents under reduced pressure, the residue was partitioned between water and chloroform. The organic layer was washed with brine and dried over anhydrous magnesium sulfate. After removal of the solvent, the residue was washed with ethyl acetate and dried to afford N-(1-oxo-1,2,3,4-tetrahydronaphthalen-2-yl)-acetamide (16.5 g, 81 mmol, 66%) as brown crystals.

2-Amino-3,4-dihydro-2H-naphthalen-1-one Hydrochloride

N-(1-oxo-1,2,3,4-tetrahydronaphthalen-2-yl)-acetamide (16.5 g, 81 mmol) was added to 3N aqueous hydrochloric acid (270 ml) and stirred at 100° C. for 5 hours. After removal of the solvent, the precipitate was filtered, washed with ethanol, and dried to give 2-amino-3,4-dihydro-2H-naphthalen-1-one hydrochloride (16.0 g, 81 mmol, 100%) as white crystals.

2-Chloro-N-(1-oxo-1,2,3,4-tetrahydronaphthalen-2-yl)-acetamide

Chloroacetyl chloride (14 g, 124 mmol) was added to a solution of 2-amino-3,4-dihydro-2H-naphthalen-1-one hydrochloride (16 g, 81 mmol) and triethylamine (41 g, 405 mmol) in tetrahydrofuran (600 ml) and the mixture was stirred for one hour. The solution was partitioned between water and ethyl acetate. The organic layer was washed with brine, dried over magnesium sulfate, and concentrated under reduced pressure. The residue was purified by silica gel column chromatography (eluent; 5-10% methanol in chloroform) to afford 2-chloro-N-(1-oxo-1,2,3,4-tetrahydronaphthalen-2-yl)-acetamide (7.58 g, 31.9 mmol, 39%) as white crystals.

2-Chloro-N-((1RS,2RS)-trans-1-hydroxy-1,2,3,4-tetrahydro-naphthalen-2-yl)-acetamide Sodium borohydride (0.93 g, 24.6 mmol) was added to a solution of 2-chloro-N-(1-oxo-1,2,3,4-tetrahydronaphthalen-2-yl)-acetamide (2.9 μg, 12.2 mmol) in methanol (30 ml). When the reaction was complete (checked by thin layer chromatography), excess reagent was decomposed by the addition of water and pH was adjusted to 5-6 with 3N aqueous hydrochloric acid. The solution was partitioned between water and chloroform. The organic layer was washed with brine, dried over magnesium sulfate, and concentrated under reduced pressure. The residue was purified by silica gel column chromatography (eluent; 5-10% methanol in chloroform) to afford 2-chloro-N-((1RS,2RS)-trans-1-hydroxy-1,2,3,4-tetrahydro-naphthalen-2-yl)-acetamide (2.92 g, 12.2 mmol, 100%) as white crystals.

(4aRS,10bRS)-trans-4-a,5,6,10b-tetrahydro-4H-naphtho[1,2-b][1,4]oxazin-3-one

Sodium hydride (60% dispersion in mineral oil, 1.25 g, 31.3 mmol) was added to a solution of 2-chloro-N-((1RS, 2RS)-trans-1-hydroxy-1,2,3,4-tetrahydro-naphthalen-2-yl)-acetamide (2.92 g, 12.2 mmol) in tetrahydrofuran (30 ml). When the reaction was complete (checked by thin layer chromatography), excess reagent was decomposed by the addition of water and pH was adjusted to 5-6 with 3N aqueous hydrochloric acid. The solution was partitioned between water and chloroform. The organic layer was washed with brine, dried over magnesium sulfate, and concentrated under reduced pressure. The residue was purified by silica gel column chromatography (eluent; 5-10% methanol in chloroform) to afford (4aRS,10bRS)-trans-4-a,5,6,10b-tetrahydro-4H-naphtho[1,2-b][1,4]oxazin-3-one (1.06 g, 5.22 mmol, 43%) as white crystals.

(4aRS,10bRS)-trans-3,4,4a,5,6,10b-Hexahydro-2H-naphtho[1,2-b][1,4]oxazine Hydrochloride Chlorotrimethylsilane (2.85 g, 26.2 mmol) was added to a solution of lithium borohydride (0.29 g, 13.3 mmol) in tetrahydrofuran (20 ml) and the mixture was stirred for 1 hour at room temperature. A solution of (4aRS,10bRS)-trans-4-a,5,6,10b-tetrahydro-4H-naphtho[1,2-b][1,4]oxazin-3-one (1.06 g, 5.22 mmol) in tetrahydrofuran (10 ml) was added to the solution and stirred at room temperature for 1 hour. After careful addition of methanol with ice-cooled solution, pH was adjusted to 12-14 with 6N aqueous potassium hydroxide and the solution was stirred at 80° C. for 2 hours. After cooling, di-tert-butyldicarbonate (1.4 g, 6.41 mmol) was added to a solution at 0° C. and the mixture was stirred for one hour at room temperature. The mixture was partitioned between water and ethyl acetate. The organic layer was washed with brine, dried over magnesium sulfate, and concentrated in vacuo. The residue was purified by silica gel column chromatography (eluent; 5-10% methanol in chloroform) to give tert-butyl (4aRS,10bRS)-trans-3,4,4a,5,6,10b-hexahydro-2H-naphtho[1,2-b][1,4]oxazine-4-carboxylate as colorless oil. Hydrogen chloride (4N) in ethyl acetate solution was added to a solution of the resulting tert-butoxucarbonyl-protected amine in methanol (30 ml). The mixture was stirred for one hour at room temperature and the solvent was evaporated under reduced pressure. The precipitate was filtered, washed with ethyl acetate, and dried to afford (4aRS,10bRS)-trans-3,4,4a,5,6,10b-hexahydro-2H-naphtho[1,2-b][1,4]oxazine hydrochloride (0.7 g, 59%) as white crystals.

2-((4aRS,10bRS)-trans-3,4,4a,5,6,10b-Hexahydro-2H-naphtho[1,2-b][1,4]oxazin-4-yl)-3-methyl-6-(pyrimidin-4-yl)-3H-pyrimidin-4-one A solution of 2-chloro-3-methyl-6-(pyrimidin-4-yl)-3H-pyrimidin-4-one (0.25 g, 1.12 mmol), (4aRS,10bRS)-trans-3,4,4a,5,6,10b-hexahydro-2H-naphtho[1,2-b][1,4]oxazine hydrochloride (0.3 g, 1.33 mmol) and triethylamine (0.4 g, 3.95 mmol) in tetrahydrofuran (15 ml) was stirred for 48 hours at 100° C. The mixture was partitioned between water and chloroform, and the organic layer was washed with brine, dried over magnesium sulfate, and concentrated under reduced pressure. The residue was purified by silica gel column chromatography (eluent; 5-10% methanol in chloroform) to give 2-((4aRS,10bRS)-trans-3,4,4a,5,6,10b-hexahydro-2H-naphtho[1,2-b][1,4]oxazin-4-yl)-3-methyl-6-(pyrimidin-4-yl)-3H-pyrimidin-4-one (72 mg, 0.19 mmol, 16%) as pale white crystals.

Example 4

2-((4aRS,10bSR)-cis-2,3,4a,5,6,10b-Hexahydro-naphtho[1,2-b][1,4]oxazin-4-yl)-1-methyl-1H-[4,4']bipyrimidinyl-6-one (Compound No. B30)

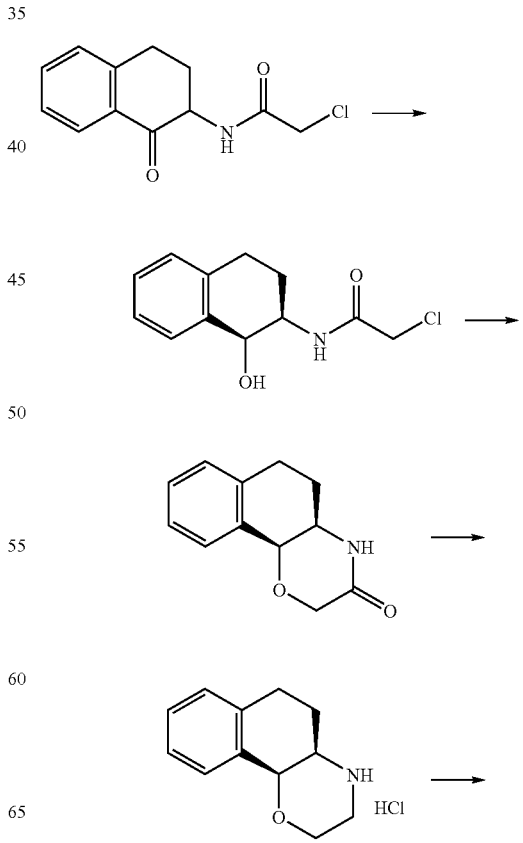

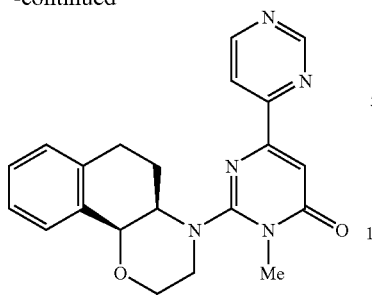

2-Chloro-N-((1RS,2SR)-cis-1-hydroxy-1,2,3,4-tetrahydro-naphthalen-2-yl)-acetamide Lithium tri-sec-butylborohydride (1.0 M solution in tetrahydrofuran, 70 ml, 70 mmol) was added to a solution of 2-chloro-N-(1-oxo-1,2,3,4-tetrahydronaphthalen-2-yl)-acetamide (7.58 g, 31.9 mmol) in tetrahydrofuran (500 ml). When the reaction was complete (checked by thin layer chromatography), excess reagent was decomposed by the addition of water and pH was adjusted to 5-6 with 3N aqueous hydrochloric acid. The residue was partitioned between water and chloroform. The organic layer was washed with brine, dried over magnesium sulfate, and concentrated under reduced pressure. The residue was purified by silica gel column chromatography (eluent; 5-10% methanol in chloroform) to afford 2-chloro-N-((1RS,2SR)-cis-1-hydroxy-1,2,3,4-tetrahydro-naphthalen-2-yl)-acetamide (5.4 g, 22.6 mmol, 71%) as white crystals.

(4aRS,10bSR)-cis-4-a,5,6,10b-Tetrahydro-4H-naphtho[1,2-b][1,4]oxazin-3-one

Sodium hydride (60% dispersion in mineral oil, 2.0 g, 50 mmol) was added to a solution of 2-chloro-N-((1RS,2SR)-cis-1-hydroxy-1,2,3,4-tetrahydro-naphthalen-2-yl)-acetamide (5.42 g, 22.6 mmol) in tetrahydrofuran (500 ml). When the reaction was complete (checked by thin layer chromatography), excess reagent was decomposed by the addition of water and pH was adjusted to 5-6 with 3N aqueous hydrochloric acid. The solution was partitioned between water and chloroform. The organic layer was washed with brine, dried over magnesium sulfate, and concentrated under reduced pressure. The residue was purified by silica gel column chromatography (eluent; 5-10% methanol in chloroform) to afford (4aRS,10bSR)-cis-4-a,5,6,10b-tetrahydro-4H-naphtho[1,2-b][1,4]oxazin-3-one (4.6 g, 22.6 mmol, 100%) as white crystals.

(4aRS,10bSR)-cis-3,4,4a,5,6,10b-Hexahydro-2H-naphtho[1,2-b][1,4]oxazine Hydrochloride Chlorotrimethylsilane (12.3 g, 113 mmol) was added to a solution of lithium borohydride (1.23 g, 56.5 mmol) in tetrahydrofuran (100 ml) and the mixture was stirred for one hour at room temperature. A solution of (4aRS,10bSR)-cis-4-a,5,6,10b-tetrahydro-4H-naphtho[1,2-b][1,4]oxazin-3-one (4.6 g, 22.6 mmol) in tetrahydrofuran (20 ml) was added to the solution and stirred for 1 hour at room temperature. After careful addition of methanol with ice-cooled solution, pH was adjusted to 12-14 with 6N aqueous potassium hydroxide and the solution was stirred at 80° C. for 2 hours. After cooling, di-tert-butyl dicarbonate (6.0 g, 27.5 mmol) was added to a solution at 0° C. and the mixture was stirred for one hour at room temperature. The solution was partitioned between water and ethyl acetate. The organic layer was washed with brine, dried over magnesium sulfate, and concentrated under reduced pressure. The residue was purified by silica gel column chromatography (eluent; 5-10% methanol in chloroform) to afford tert-butyl ((4aRS,10bSR)-cis-3,4,4a,5,6,10b-hexahydro-2H-naphtho[1,2-b][1,4]oxazine-4-carboxylate as colorless oil. Hydrogen chloride (4N) in ethyl acetate was added to a solution of resulting tert-butoxycarbonyl-protected amine in methanol (100 ml). The solution was stirred for one hour at room temperature and the solvent was removed under reduced pressure. The precipitate was filtered, washed with ethyl acetate, and dried to afford (4aRS,10bSR)-cis-3,4,4a,5,6,10b-hexahydro-2H-naphtho[1,2-b][1,4]oxazine hydrochloride (1.56 g, 6.91 mmol, 31%) as white crystals.

2-((4aRS,10bSR)-cis-2,3,4a,5,6,10b-Hexahydro-naphtho[1,2-b][1,4]oxazin-4-yl)-1-methyl-1H-[4,4']bipyrimidinyl-6-one A solution of 2-chloro-3-methyl-6-(pyrimidin-4-yl)-3H-pyrimidin-4-one (0.26 g, 1.17 mmol), (4aRS,10bSR)-cis-3,4,4a,5,6,10b-hexahydro-2H-naphtho[1,2-b][1,4]oxazine hydrochloride (0.4 g, 1.77 mmol) and triethylamine (1.2 g, 11.4 mmol) in tetrahydrofuran (20 ml) was stirred for 48 hours at 100° C. The solution was partitioned between water and chloroform, and the organic layer was washed with brine, dried over magnesium sulfate, and concentrated under reduced pressure. The residue was purified by silica gel column chromatography (eluent; 5-10% methanol in chloroform) to afford 2-((4aRS,10bSR)-cis-2,3,4a,5,6,10b-hexahydro-naphtho[1,2-b][1,4]oxazin-4-yl)-1-methyl-1H-[4,4']bipyrimidinyl-6-one (0.37 g, 85%) as white crystals.

Example 5

6-(3-Fluoro-pyridin-4-yl)-3-methyl-2-((4aRS,10bRS)-trans-2,3,10,10a-tetrahydro-4-aH-4,9-dioxa-1-aza-phenanthren-1-yl)-3H-pyrimidin-4-one (Compound No. B131)

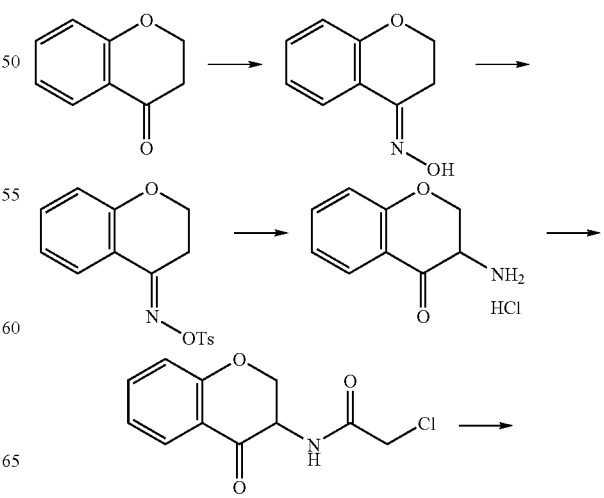

-continued

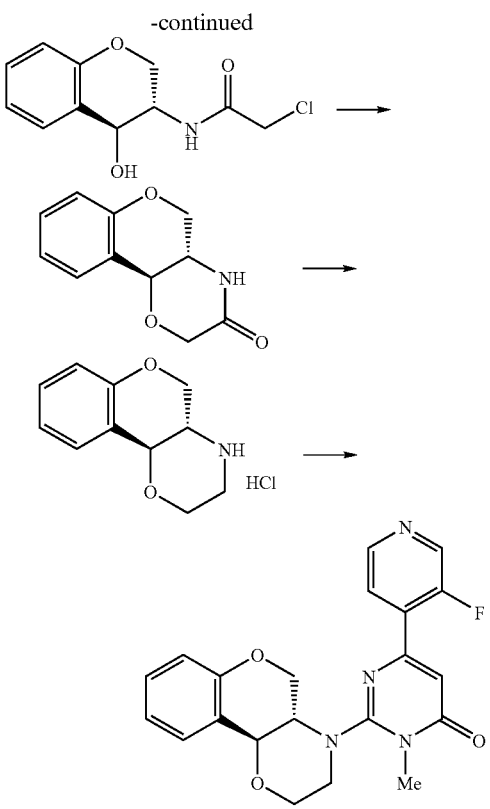

Chroman-4-one Oxime

Chroman-4-one (46.5 g, 314 mmol) was dissolved in pyridine (160 ml) and hydroxylamine hydrochloride (51 g, 734 mmol) was added to this solution. The solution was refluxed for 8 hours and then cooled to room temperature. The solvent was evaporated under reduced pressure and the residue was partitioned between water and chloroform. The organic layer was washed with 1N aqueous hydrochloric acid and brine, dried over magnesium sulfate, and concentrated under reduced pressure. The precipitate was filtered, washed with diisopropylether, and dried to afford chroman-4-one oxime (22.9 g, 275 mmol, 88%) as white crystals.

Chroman-4-one O-p-toluenesulfoxime p-Toluenesulfonyl chloride (52.5 g, 275 mmol) was added to a solution of chroman-4-one oxime (44.9 g, 275 mmol) in pyridine (275 ml) and the mixture was stirred for 12 hours at room temperature. Solvent was evaporated under reduced pressure and the residue was partitioned between water and chloroform. The organic layer was washed with 1N aqueous hydrochloric acid and brine, dried over magnesium sulfate, and concentrated under reduced pressure. The residue was washed with diisopropylether, and dried to afford chroman-4-one O-p-toluenesulfoxime (85.1 g, 268 mmol, 97%) as white crystals.

3-Amino-chroman-4-one Hydrochloride

A solution of potassium ethoxide (23.7 g, 282 mmol) in ethanol (150 ml) was added to a solution of chroman-4-one O-p-toluenesulfoxime (85.1 g, 268 mmol) in toluene (250 ml) and the mixture was stirred for 15 hours at room temperature.

The precipitate (potassium tosylate) was filtered and washed with diethyl ether. The filtrate was added with 37% hydrochloric acid (20 ml) and the solution was stirred for 2 hours at room temperature. After removal of the solvent, the residue was washed with ethanol and dried to afford 3-amino-chroman-4-one hydrochloride (53.5 g, 268 mmol, 100%) as white crystals.

2-Chloro-N-(4-oxo-chroman-3-yl)-acetamide

Chloroacetyl chloride (41.6 g, 368 mmol) was added to a solution of 3-amino-chroman-4-one hydrochloride (67 g, 335 mmol) and triethylamine (102 g, 1.01 mol) in tetrahydrofuran (700 ml) and the mixture was stirred for one hour. The solution was partitioned between water and ethyl acetate. The organic layer was washed with brine, dried over magnesium sulfate, and concentrated under reduced pressure. The residue was purified by silica gel column chromatography (eluent; 5-10% methanol in chloroform) to afford 2-chloro-N-(4-oxo-chroman-3-yl)-acetamide (22.6 g, 94.3 mmol, 28%) as white crystals.

2-Chloro-N-((3RS,4RS)-trans-4-hydroxychroman-3-yl)-acetamide

Sodium borohydride (0.9 g, 23.8 mol) was added to a solution of 2-chloro-N-(4-oxo-chroman-3-yl)-acetamide (3.5 g, 14.6 mmol) in methanol (30 ml). When the reaction was complete (checked by thin layer chromatography), excess reagent was decomposed by the addition of water and pH was adjusted to 5-6 with 3N aqueous hydrochloric acid. The solution was partitioned between water and chloroform. The organic layer was washed with brine, dried over magnesium sulfate, and concentrated under reduced pressure. The residue was purified by silica gel column chromatography (eluent; 5-10% methanol in chloroform) to afford 2-chloro-N-((3RS,4RS)-trans-4-hydroxychroman-3-yl)-acetamide (3.5 g, 14.5 mmol, 99%) as white crystals.

(4aRS,10bRS)-trans-10,10a-Dihydro-1H,4aH-4,9-dioxa-1-aza-phenanthren-2-one

Sodium hydride (60% dispersion in mineral oil, 1.3 g, 32.5 mmol) was added to a solution of 2-chloro-N-((3RS,4RS)-trans-4-hydroxychroman-3-yl)-acetamide (3.5 g, 14.5 mmol) in tetrahydrofuran (300 ml). When the reaction was complete (checked by thin layer chromatography), excess reagent was decomposed by the addition of water and pH was adjusted to 5-6 with 3N aqueous hydrochloric acid. The solution was partitioned between water and chloroform. The organic layer was washed with brine, dried over magnesium sulfate, and concentrated under reduced pressure. The residue was purified by silica gel column chromatography (eluent; 5-10% methanol in chloroform) to afford (4aRS,10bRS)-trans-10,10a-dihydro-1H,4aH-4,9-dioxa-1-aza-phenanthren-2-one (2.68 g, 13.1 mmol, 90%) as white crystals.

(4aRS,10bRS)-trans-2,3,10,10a-Tetrahydro-1H,4aH-4,9-dioxa-1-aza-phenanthrene hydrochloride Chlorotrimethylsilane (7.2 g, 66.3 mmol) was added to a solution of lithium borohydride (0.72 g, 33.1 mmol) in tetrahydrofuran (50 ml) and stirred for 1 hour at room temperature. A solution of (4aRS,10bRS)-trans-10,10a-dihydro-1H,4aH-4,9-dioxa-1-aza-phenanthren-2-one (2.68 g, 13.1 mmol) in tetrahydrofuran (20 ml) was added to the solution and stirred for one hour at room temperature. After careful addition of methanol with ice-cooled solution, pH was adjusted to 12-14 with 6N aqueous potassium hydroxide and the solution was stirred at 80° C. for 2 hours. After cooling, di-tert-butyl dicarbonate (3.5 g, 16.0 mmol) was added to a solution at 0° C. and the solution was stirred for one hour at room temperature. The solution was partitioned between water and ethyl acetate. The organic layer was washed with brine, dried over magnesium sulfate, and concentrated under reduced pressure. The residue was purified by silica gel column chromatography (eluent; 5-10% methanol in chloroform) to afford (4aRS,10bRS)-trans-2,3,10,10a-tetrahydro-4-aH-4,9-dioxa-1-aza-phenanthrene-1-carboxylic acid tert-butyl ester as colorless oil. Hydrogen chloride (4N) in ethyl acetate solution was added to a solution of the resulting tert-butoxycarbonyl-protected amine in methanol (30 ml). The mixture was stirred for one hour at room temperature and the solvent was evaporated under reduced pressure. The residue was filtered, washed with ethyl acetate, and dried to afford (4aRS,10bRS)-trans-2,3,10,10a-tetrahydro-1H,4aH-4,9-dioxa-1-aza-phenanthrene-hydrochloride (0.4 g, 1.76 mmol, 13%) as white crystals.

6-(3-Fluoro-pyridin-4-yl)-3-methyl-2-((4aRS,10bRS)-trans-2,3,10,10a-tetrahydro-4-aH-4,9-dioxa-1-aza-phenanthren-1-yl)-3H-pyrimidin-4-one A solution of 2-chloro-6-(3-fluoropyridin-4-yl)-3-methyl-3H-pyrimidin-4-one (0.16 g, 0.67 mmol), (4aRS,10bRS)-trans-2,3,10,10a-tetrahydro-1H,4aH-4,9-dioxa-1-aza-phenanthrene_hydrochloride (0.2 g, 0.88 mmol) and triethylamine (0.7 g, 1.92 mmol) in tetrahydrofuran (10 ml) was stirred for 48 hours at 100° C. The solution was partitioned between water and chloroform, and the organic layer was washed with brine, dried over magnesium sulfate, and concentrated under reduced pressure. The residue was purified by silica gel column chromatography (eluent; 5-10% methanol in chloroform) to afford 6-(3-Fluoro-pyridin-4-yl)-3-methyl-2-((4aRS,10bRS)-trans-2,3,10,10a-tetrahydro-4-aH-4,9-dioxa-1-aza-phenanthren-1-yl)-3H-pyrimidin-4-one (0.13 g, 0.33 mmol, 49%) as white crystals.

Example 6

6-(3-Fluoro-pyridin-4-yl)-3-methyl-2-((4aRS,10aRS)-cis-2,3,10,10a-tetrahydro-4-aH-4,9-dioxa-1-aza-phenanthren-1-yl)-3H-pyrimidin-4-one (Compound No. B45)

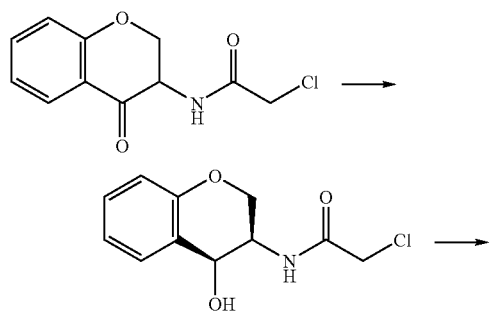

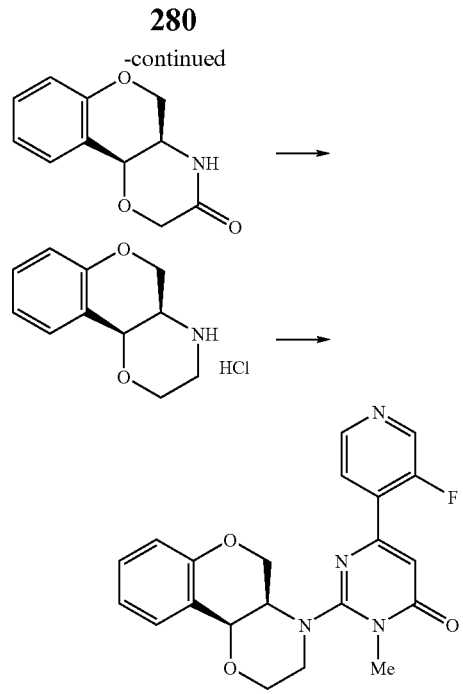

2-Chloro-N-((3RS 4SR)-cis-4-hydroxychroman-3-yl)-acetamide

Lithium tri-sec-butylborohydride (1.0 M solution in tetrahydrofuran, 190 ml, 190 mmol) was added to a solution of 2-chloro-N-(4-oxo-chroman-3-yl)-acetamide (22.6 g, 94.3 mol) in tetrahydrofuran (1000 ml). When the reaction was complete (checked by thin layer chromatography), excess reagent was decomposed by the addition of water and pH was adjusted to 5-6 with 3N aqueous hydrochloric acid. The solution was partitioned between water and chloroform. The organic layer was washed with brine, dried over magnesium sulfate, and concentrated under reduced pressure. The residue was purified by silica gel column chromatography (eluent; 5-10% methanol in chloroform) to afford 2-chloro-N-((3RS,4SR)-cis-4-hydroxychroman-3-yl)-acetamide (19 g, 78.6 mmol, 83%) as white crystals.

(4aRS,10bSR)-cis-10,10a-Dihydro-1H,4aH-4,9-dioxa-1-aza-phenanthren-2-one

Sodium hydride (60% dispersion in mineral oil, 6.3 g, 158 mmol) was added to a solution of 2-chloro-N-((3RS,4SR)-cis-4-hydroxychroman-3-yl)-acetamide (19 g, 78.6 mol) in tatrahydrofuran (1000 ml). When the reaction was complete (checked by thin layer chromatography), excess reagent was decomposed by the addition of water and pH was adjusted to 5-6 with 3N aqueous hydrochloric acid. The solution was partitioned between water and chloroform. The organic layer was washed with brine, dried over magnesium sulfate, and concentrated under reduced pressure. The residue was purified by silica gel column chromatography (eluent; 5-10% methanol in chloroform) to afford (4aRS,10bSR)-cis-10,10a-dihydro-1H,4aH-4,9-dioxa-1-aza-phenanthren-2-one (6.6 g, 32.2 mmol, 41%) as white crystals.

(4aRS,10bSR)-cis-2,3,10,10a-Tetrahydro-1H,4aH-4,9-dioxa-1-aza-phenanthrene

Chlorotrimethylsilane (17.5 g, 161 mmol) was added to a solution of lithium borohydride (1.8 g, 82.6 mmol) in tetrahydrofuran (100 ml) and the mixture was stirred for one hour at room temperature. A solution of (4aRS,10bSR)-cis-10,10a-dihydro-1H,4aH-4,9-dioxa-1-aza-phenanthren-2-one (6.6 g, 32.2 mmol) in tetrahydrofuran (20 ml) was added to the solution and stirred for 1 hour at room temperature. After careful addition of methanol with ice-cooled solution, pH was adjusted to 12-14 with 6N aqueous potassium hydroxide and the solution was stirred for 2 hours at 80° C. After cooling, di-tert-butyl dicarbonate (7.8 g, 35.7 mmol) was added to a solution at 0° C. and the solution was stirred for one hour at room temperature. The solution was partitioned between water and ethyl acetate. The organic layer was washed with brine, dried over magnesium sulfate, and concentrated under reduced pressure. The residue was purified by silica gel column chromatography (eluent; 5-10% methanol in chloroform) to afford (4aRS,10bSR)-cis-2,3,10,10a-tetrahydro-4-aH-4,9-dioxa-1-aza-phenanthrene-1-carboxylic acid tert-butyl ester as colorless oil. Hydrogen chloride (4N) in ethyl acetate solution was added to a solution of the resulting tert-butoxycarbonyl-protected amine in methanol (100 ml). The solution was stirred for one hour at room temperature and the solvent was evaporated under reduced pressure. The precipitate was filtered, washed with ethyl acetate, and dried to afford (4aRS,10bSR)-cis-2,3,10,10a-tetrahydro-1H,4aH-4, 9-dioxa-1-aza-phenanthrene hydrochloride (5.36 g, 23.5 mmol, 73%) as white crystals.

6-(3-Fluoro-pyridin-4-yl)-3-methyl-2-((4aRS, 10aRS)-cis-2,3,10,10a-tetrahydro-4-aH-4,9-dioxa-1-aza-1-phenanthren-1-yl)-3H-pyrimidin-4-one A solution of 2-chloro-6-(3-fluoropyridin-4-yl)-3-methyl-3H-pyrimidin-4-one (0.21 g, 0.88 mmol), (4aRS,10bSR)-cis-2,3,10,10a-tetrahydro-1H,4aH-4,9-dioxa-1-aza-phenanthrene hydrochloride (0.2 g, 0.88 mmol) and triethylamine (0.45 g, 4.45 mmol) in tetrahydrofuran (10 ml) was stirred for 48 hours at 100° C. The solution was partitioned between water and chloroform, and the organic layer was washed with brine, dried over magnesium sulfate, and concentrated under reduced pressure. The residue was purified by silica gel column chromatography (eluent; 5-10% methanol in chloroform) to afford 6-(3-fluoro-pyridin-4-yl)-3-methyl-2-((4aRS,10aRS)-cis-2,3,10,10a-tetrahydro-4-aH-4,9-dioxa-1-aza-phenanthren-1-yl)-3H-pyrimidin-4-one (0.12 g, 0.38 mmol, 34%) as white crystals.

Example 7

6-(3-Fluoro-pyridin-4-yl)-2-((4aRS,10aRS)-trans-2, 3,4a,5,6,10b-hexahydro-1H-benzo[f]quinolin-4-yl)-3-methyl-3H-pyrimidin-4-one (Compound No. B40)

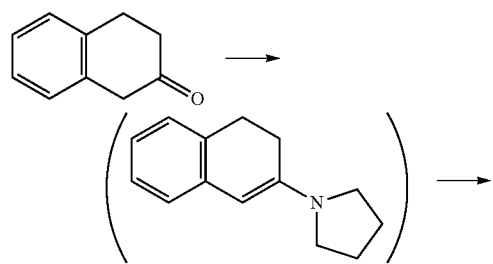

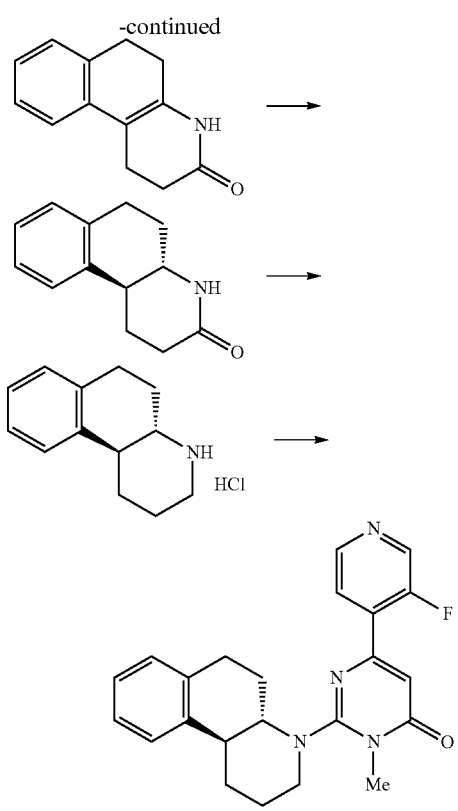

1,4,5,6-Tetrahydro-2H-benzo[f]quinolin-3-one

2-Tetralone (25 g, 171 mmol) was added to a solution of p-toluenesulfonic acid (3.2 g, 16.8 mmol) and pyrrolidine (15 g, 211 mmol) in toluene (250 ml) and the solution was heated under reflux with a Dean-Stark apparatus. When no more water was distilled off, the solvent was removed to afford the enamine as an yellow oil. Acrylamide (46 g, 647 mmol) was added in one portion to the stirred oil, and the resulting mixture was heated at 100° C. for 2 hours. Water (100 ml) was added to the reaction mixture and pH was adjusted to 3-4 with concentrated hydrochloric acid. The solution was extracted with chloroform and the organic layer was washed with brine, dried over magnesium sulfate, and concentrated under reduced pressure. The residue was washed with ethyl acetate, and dried to afford 1,4,5,6-tetrahydro-2H-benzo[f]quinolin-3-one (28 g, 140 mmol, 82%) as white crystals.

(4aRS,10bSR)-trans-1.4.4a,5.6.10b-Hexahydro-2H-benzo[f]quinolin-3-one

A mixture of 1,4,5,6-tetrahydro-2H-benzo[f]quinolin-3-one (10 g, 50.2 mmol) and triethylsilane (17.5 g, 150 mmol) in dichloromethane (100 ml) was stirred for 10 minutes. Trifluoroacetic acid (69 g, 605 mmol) was added dropwise with stirring and the mixture was stirred for 8 hours at room temperature. The mixture was neutralized with saturated aqueous sodium bicarbonate and extracted with chloroform. The organic layer was washed with brine, dried over magnesium sulfate, and concentrated under reduced pressure. The residue was washed with ethyl acetate, and dried to afford (4aRS, 10bSR)-trans-1,4,4a,5,6,10b-hexahydro-2H-benzo[f]quinolin-3-one (7.94 g, 39.5 mmol, 79%) as white crystals.

(4aRS,10bSR)-trans-1,2,3,4,4a,5,6,10b-Octahydro-benzo[f]quinoline Hydrochloride Chlorotrimethylsilane (21.5 g, 198 mmol) was added to a solution of lithium borohydride (2.1 g, 96.4 mmol) in tetrahydrofuran (200 ml) and the mixture was stirred for one hour at room temperature. A solution of (4aRS,10bSR)-trans-1,4,4a,5,6,10b-Hexahydro-2H-benzo[f]quinolin-3-one (7.94 g, 39.5 mmol) in tetrahydrofuran (50 ml) was added to the solution and the mixture was stirred for one hour at room temperature. After careful addition of methanol with ice-cooled solution, pH was adjusted to 12-14 with 6N aqueous potassium hydroxide and the solution was stirred for 2 hours at 80° C. After cooling, di-tert-butyl dicarbonate (10.4 g, 47.7 mmol) was added to a solution at 0° C. and stirred for one hour at room temperature. The solution was partitioned between water and ethyl acetate. The organic layer was washed with brine, dried over magnesium sulfate, and concentrated under reduced pressure. The residue was purified by silica gel column chromatography (eluent; 5-10% methanol in chloroform) to afford tert-butyl (4aRS,10bSR)-trans-1,2,3,4,4a,5,6,10b-octahydro-benzo[f]quinoline-4-carboxylate as colorless oil. Hydrogen chloride (4N) in ethyl acetate solution was added to a solution of resulting tert-butoxycarbonyl-protected amine in methanol (100 ml). The solution was stirred for one hour at room temperature and the solvent was evaporated under reduced pressure. The residue was washed with ethyl acetate, and dried to afford (4aRS,10bSR)-trans-1,2,3,4,4a,5,6,10b-octahydro-benzo[f]quinoline hydrochloride (6.0 g, 26.8 mmol, 68%) as white crystals.

6-(3-Fluoro-pyridin-4-yl)-2-((4aRS,10aRS)-trans-2,3,4a,5,6,10b-hexahydro-1H-benzo[f]quinolin-4-yl)-3-methyl-3H-pyrimidin-4-one A solution of 2-chloro-6-(3-fluoropyridin-4-yl)-3-methyl-3H-pyrimidin-4-one (0.8 g, 3.34 mmol), (4aRS,10bSR)-trans-1,2,3,4,4a,5,6,10b-octahydro-benzo[f]quinoline hydrochloride (1.0 g, 4.47 mmol) and triethylamine (1.7 g, 168 mmol) in tetrahydrofuran (20 ml) was stirred for 48 hours at 100° C. The solution was partitioned between water and chloroform, and the organic layer was washed with brine, dried over magnesium sulfate, and concentrated under reduced pressure. The residue was purified by silica gel column chromatography (eluent; 5-10% methanol in chloroform) to afford 6-(3-fluoro-pyridin-4-yl)-2-((4aRS,10aRS)-trans-2,3,4a,5,6,10b-hexahydro-1H-benzo[f]quinolin-4-yl)-3-methyl-3H-pyrimidin-4-one (0.14 g, 0.36 mmol, 11%) as white crystals.

Example 8

3-Methyl-2-((3R)-3-methylmorpholin-4-yl)-6-(pyrimidin-4-yl)-3H-pyrimidin-4-one (Compound No. B63)

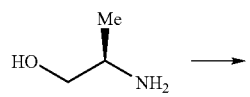

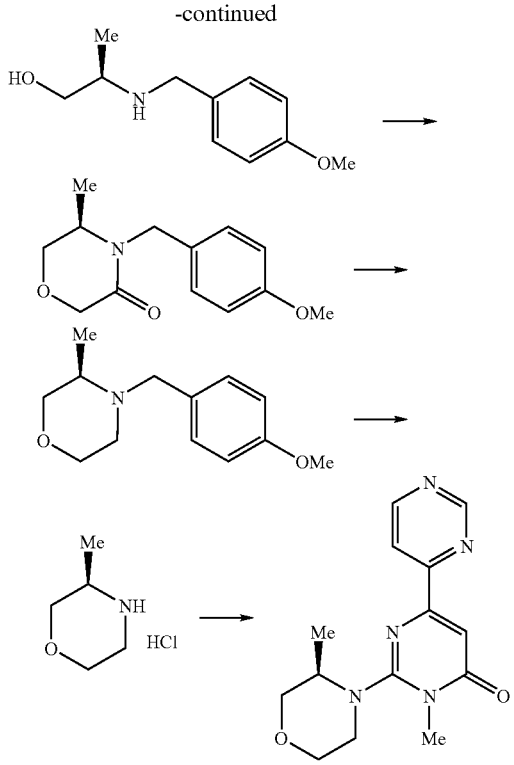

(2R)-2-(4-Methoxybenzylamino)-propan-1-ol

4-Anisaldehyde (18.1 g, 133 mmol) was added to a solution of D-alaninol (10 g, 133 mmol) in methanol (100 ml) with vigorous stirring and the mixture was stirred for 30 minutes. Sodium borohydride (5.0 g, 132 mmol) was added to the ice-cooled solution and stirred for one hour at room temperature. When the reaction was complete (checked by thin layer chromatography), excess reagent was decomposed by the addition of water. The solution was partitioned between water and chloroform. The organic layer was washed with brine, dried over magnesium sulfate. Removal of the solvent under reduced pressure afforded (2R)-2-(4-Methoxybenzylamino)-propan-1-ol (26 g, 133 mmol, 100%) as white crystals.

(5R)-4-(4-Methoxybenzyl)-5-methylmorpholin-3-one

Chloroacetyl chloride (15 g, 133 mmol) was added to a solution of (2R)-2-(4-methoxybenzylamino)-propan-1-ol (26 g, 133 mmol) and triethylamine (15 g, 148 mmol) in tetrahydrofuran (200 ml) and the solution was stirred for one hour. The solution was cooled at 0° C. and sodium hydride (60% dispersion in mineral oil, 5.8 g, 145 mol) was added. When the reaction was complete (checked by thin layer chromatography), excess reagent was decomposed by the addition of water and pH was adjusted to 5-6 with 3N aqueous hydrochloric acid. The solution was partitioned between water and chloroform. The organic layer was washed with brine, dried over magnesium sulfate, and concentrated under reduced pressure. The residue was purified by silica gel column chromatography (eluent; 5-10% methanol in chloroform) to afford (5R)-4-(4-methoxybenzyl)-5-methylmorpholin-3-one (19.6 g, 83.3 mmol, 63%) as colorless oil.

(5R)-4-(4-Methoxybenzyl)-5-methylmorpholine

Chlorotrimethylsilane (37 g, 341 mmol) was added to a solution of lithium borohydride (3.7 g, 170 mmol) in tetrahydrofuran (200 ml) and the mixture was stirred for one hour at room temperature. A solution of (5R)-4-(4-methoxybenzyl)-5-methylmorpholin-3-one (19.6 g, 83.3 mmol) in tetrahydrofuran (20 ml) was added to the solution and the mixture was stirred for one hour at room temperature. After careful addition of methanol with ice-cooled solution, pH was adjusted to 12-14 with 6N aqueous potassium hydroxide and the solution was stirred for 2 hours at 80° C. After cooling, the solution was partitioned between water and ethyl acetate. The organic layer was washed with brine, dried over magnesium sulfate, and concentrated under reduced pressure. The residue was purified by silica gel column chromatography (eluent; 5-10% methanol in chloroform) to afford (5R)-4-(4-methoxybenzyl)-5-methylmorpholine (17.8 g, 80.3 mmol, 96%) as colorless oil.

(3R)-3-Methylmorpholine Hydrochloride

1-Chloroethyl chloroformate (46 g, 322 mmol) was added to a solution of (5R)-4-(4-methoxybenzyl)-5-methylmorpholine (17.8 g, 80.3 mmol) in 1,2-dichloroethane (180 ml) and the mixture was stirred for 6 hours at 80° C. The solvent was evaporated under reduced pressure and a methanol (180 ml) solution of the residue was stirred for one hour at 80° C. The solvent was evaporated under reduced pressure, and the residue was washed with ethyl acetate and dried to afford (3R)-3-methylmorpholine hydrochloride (8.2 g, 59.6 mmol, 74%) as white crystals.

3-Methyl-2-((3R)-3-methylmorpholin-4-yl)-6-(pyrimidin-4-yl)-3H-pyrimidin-4-one A solution of 2-chloro-3-methyl-6-(pyrimidin-4-yl)-3H-pyrimidin-4-one (0.32 g, 1.44 mmol), (3R)-3-methylmorpholine hydrochloride (0.4 g, 2.9 mmol) and triethylamine (0.9 g, 8.9 mmol) in tetrahydrofuran (20 ml) was stirred for 10 hours at 100° C. The solution was partitioned between water and chloroform, and the organic layer was washed with brine, dried over magnesium sulfate, and concentrated under reduced pressure. The residue was purified by silica gel column chromatography (eluent; 5-10% methanol in chloroform) to afford 3-methyl-2-((3R)-3-methylmorpholin-4-yl)-6-(pyrimidin-4-yl)-3H-pyrimidin-4-one (0.31 g, 1.08 mmol, 75%) as white crystals.

Example 9

1-Methyl-2-((4aRS,8aRS)-trans-octahydro-benzo[1,4]oxazin-4-yl)-1H-[4,4']bipyrimidinyl-6-one (Compound No. B69)

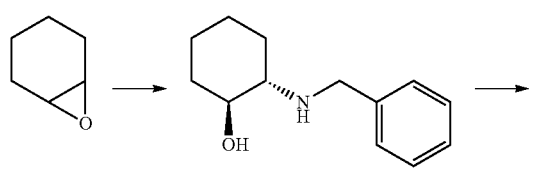

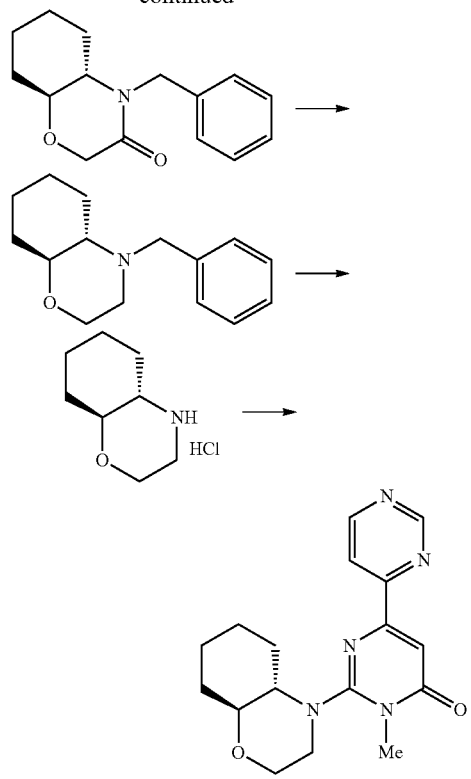

(1RS,2RS)-trans-2-Benzylaminocyclohexanol

A mixture of cyclohexene oxide (20 g, 204 mmol) and benzylamine (44 g, 411 mmol) was heated at 80° C. for 6 hours. An excess benzylamine was removed under reduced pressure and the residue was purified by silica gel column chromatography (eluent; 5-10% methanol in chloroform) to afford (1RS,2RS)-trans-2-benzylaminocyclohexanol (26 g, 127 mmol, 62%) as white crystals.

(4aRS,8bRS)-trans-4-Benzyl-hexahydrobenzo[1,4]oxazin-3-one

Chloroacetyl chloride (15.8 g, 140 mmol) was dropped to a solution of (1RS,2RS)-trans-2-benzylaminocyclohexanol (26 g, 127 mmol) in 1N aqueous sodium hydroxide (200 ml) and dichloromethane (500 ml). The solution was stirred for one hour at room temperature and extracted with chloroform. The organic layer was dried over anhydrous sodium sulfate and the solvent was removed under reduced pressure. The resulting pale brown oil was dissolved into 2-propanol (600 ml), and potassium hydroxide (85% purity, 10.1 g, 153 mmol) was added to the solution and stirred for 10 hours. The solvent was removed under reduced pressure and the residue was partitioned between water and chloroform. The organic layer was washed with 0.5 M hydrochloric acid, saturated sodium hydrogen carbonate, brine and dried over anhydrous magnesium sulfate. Removal of the solvent under reduced pressure afforded (4aRS,8bRS)-trans-4-benzyl-hexahydrobenzo[1,4]oxazin-3-one (31.7 g, 129 mmol, 100%) as a colorless oil.

(4aRS,8bRS)-trans-4-Benzyl-octahydrobenzo[1,4]oxazine

Chlorotrimethylsilane (56 g, 515 mmol) was added to a solution of lithium borohydride (5.6 g, 257 mmol) in tetrahydrofuran (250 ml) and the mixture was stirred for one hour at room temperature. A solution of (4aRS,8bRS)-trans-4-benzyl-hexahydrobenzo[1,4]oxazin-3-one (31.7 g, 129 mmol) in tetrahydrofuran (50 ml) was added to the solution and the mixture was stirred for one hour at room temperature. After careful addition of methanol in ice-cooled solution, pH was adjusted to 12-14 with 6N aqueous potassium hydroxide and the solution was stirred at 80° C. for 2 hours. After cooling, the solution was partitioned between water and ethyl acetate. The organic layer was washed with brine, dried over magnesium sulfate, and concentrated under reduced pressure. The residue was purified by silica gel column chromatography (eluent; 5-10% methanol in chloroform) to afford (4aRS, 8bRS)-trans-4-benzyl-octahydrobenzo[1,4]oxazine (27.5 g, 119 mmol, 92%) as colorless oil.

(4aRS,8bRS)-trans-Octahydrobenzo[1,4]oxazine hydrochloride

1-Chloroethyl chloroformate (5.3 g, 37.1 mmol) was added to a solution of (4aRS,8bRS)-trans-4-benzyl-octahydrobenzo[1,4]oxazine (4.3 g, 18.6 mmol) in 1,2-dichloroethane (50 ml) and the mixture was stirred for 12 hours at room temperature. The solvent was evaporated under reduced pressure, and a methanol (50 ml) solution of the residue was stirred for one hour at 80° C. Solvent was evaporated under reduced pressure, and the residue was washed with ethyl acetate and dried to afford (4aRS,8bRS)-trans-octahydrobenzo[1,4]oxazine hydrochloride (2.37 g, 13.3 mmol, 72%) as white crystals.

1-Methyl-2-((4aRS,8aRS)-trans-octahydro-benzo[1,4]oxazin-4-yl)-1H-[4,4']bipyrimidinyl-6-one A solution of 2-chloro-3-methyl-6-(pyrimidin-4-yl)-3H-pyrimidin-4-one (0.34 g, 1.53 mmol), (4aRS,8bRS)-trans-octahydrobenzo[1,4]oxazine hydrochloride (0.3 g, 1.69 mmol) and triethylamine (0.5 g, 4.94 mmol) in tetrahydrofuran (20 ml) was stirred for 10 hours at 100° C. The solution was partitioned between water and chloroform, and the organic layer was washed with brine, dried over magnesium sulfate, and concentrated under reduced pressure. The residue was purified by silica gel column chromatography (eluent; 5-10% methanol in chloroform) to afford 1-methyl-2-((4aRS, 8aRS)-trans-octahydro-benzo[1,4]oxazin-4-yl)-1H-[4,4']bipyrimidinyl-6-one (0.32 g, 0.98 mmol, 64%) as white crystals.

Example 10

1-Methyl-2-((3R)-3-methyl-morpholin-4-yl)-2'-phenyl-1H-[4,4']bipyrimidinyl-6-one (Compound No. B123)

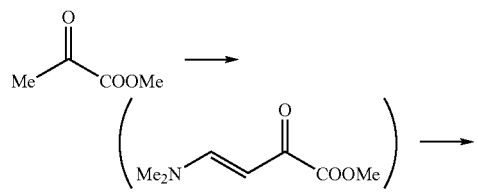

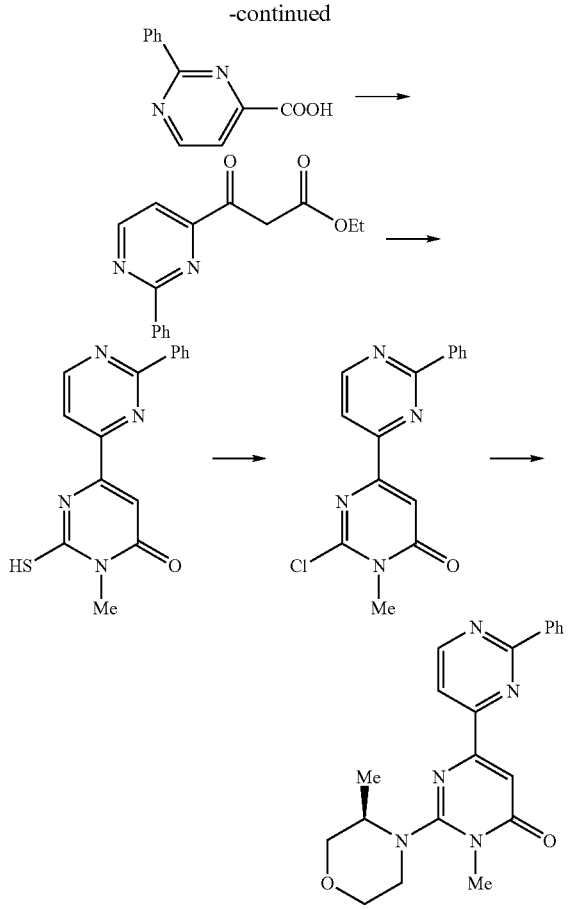

2-Phenyl-pyrimidine-4-carboxylic Acid

A mixture of methyl pyruvate (5.61 g, 55.0 mmol) and dimethylformamide dimethylacetal (6.86 g, 57.6 mmol) was stirred for 2 hours at 80° C., and benzamidine hydrochloride (9.58 g, 61.2 mmol), sodium methoxide (28% in methanol, 23.1 g, 120 mmol) was added to the solution. After reflux for 3 hours, water was added and the organic solvents were removed under reduced pressure. Resulting solids were dissolved in a mixture of water and ethyl acetate, and the remaining insolubles were filtered off. The filtrate was acidified with hydrochloric acid, and extract with ethyl acetate. The organic layer was washed with brine and dried over sodium sulfate. The solvent was removed under reduced pressure, and the residue was dissolved in a mixture of ethanol and aqueous sodium hydroxide to treat with charcoal. After removal of charcoal, the filtrate was acidified with hydrochloric acid, and the removal of ethanol under reduced pressure followed by filtration and dryness afforded 2-phenyl-pyrimidine-4-carboxylic acid (2.51 g, 23%).

3-Oxo-3-(2-phenyl-pyrimidin-4-yl)-propionic Acid Ethyl Ester

A solution of 2-phenyl-pyrimidine-4-carboxylic acid (3.49 g, 17.4 mmol) and 1,1'-carbonyldiimidazole (2.86 g, 17.7 mmol) in tetrahydrofuran (100 ml) was stirred at 60° C. for 20 min. After cooling to room temperature, ethyl potassium malonate (3.28 g, 19.2 mmol) and magnesium chloride (2.48 g, 26.1 mmol) were added and the solution was stirred at 60° C.

for 7 hours. After removal of the solvent, hydrochloric acid was added to adjust pH to 4 to 2, and the resulting solution was partitioned between water and ethyl acetate. The organic layer was washed with brine and dried over sodium sulfate. The solvent was removed under reduced pressure, and the residue was purified with silica gel column chromatography (eluent; hexane/ethyl acetate=2/1) to afford 3-oxo-3-(2-phenyl-pyrimidin-4-yl)-propionic acid ethyl ester (2.74 g, 58%).

2-Mercapto-1-methyl-2'-phenyl-1H-[4,4']bipyrimidinyl-6-one

A solution of 3-oxo-3-(2-phenyl-pyrimidin-4-yl)-propionic acid ethyl ester (2.74 g, 10.1 mmol), N-methylthiourea (1.39 g, 15.5 mmol) and 1,8-diazabicyclo[5,4,0]undec-7-en (1.57 g, 10.3 mmol) in ethanol (30 ml) was heated under reflux for 18 hours. After the solution was acidified by addition of hydrochloric acid, ethanol was removed under reduced pressure, and the resulting solid was filtered, washed with water and dried to afford 2-mercapto-1-methyl-2'-phenyl-1H-[4,4']bipyrimidinyl-6-one (2.78 g, 93%).

2-Chloro-1-methyl-2'-phenyl-1H-[4,4']bipyrimidinyl-6-one

2-Mercapto-1-methyl-2'-phenyl-1H-[4,4']bipyrimidinyl-6-one (2.76 g, 9.33 mmol) in 1,2-dichloroethane (20 ml) and N-methylpyrrolidone (2 ml) was added to a solution of phosphorus oxychloride (3.83 g, 25.0 mmol) and N-methylpyrrolidone (5.22 g, 52.7 mmol) at 50° C. and the mixture was stirred for 20 minutes. The solution was poured into warm water, and sodium bicarbonate (10.2 g, 121 mmol) was added to the solution and the mixture was stirred until no gas was generated. The resulting solution was partitioned between water and dichloromethane, and the organic layer was washed with water and brine and passed through Celite. The solvent was removed under reduced pressure, and the residue was purified with silica gel column chromatography (eluent; hexane/ethyl acetate=2/1 to 1/1) to afford 2-chloro-1-methyl-2'-phenyl-1H-[4,4']bipyrimidinyl-6-one (2.08 g, 75%).

1-Methyl-2-((3R)-3-methyl-morpholin-4-yl)-2'-phenyl-1H-[4,4']bipyrimidinyl-6-one A solution of 2-chloro-1-methyl-2'-phenyl-1H-[4,4']bipyrimidinyl-6-one (149 mg, 0.50 mmol), (3R)-3-Methyl-morpholine hydrochloride (83 mg, 0.82 mmol), and diisopropylethylamine (0.313 ml, 1.8 mmol) in N,N-dimethylformamide (2.0 ml) was stirred at 80° C. Water was added to the solution and the precipitate was filtered, washed with water and diethyl ether, and dried to afford 1-methyl-2-((3R)-3-methyl-morpholin-4-yl)-2'-phenyl-1H-[4,4']bipyrimidinyl-6-one (162 mg, quant.).

Example 11

3-Methyl-2-(3-phenyl-pyrrolidin-1-yl)-6-pyridin-4-yl-3H-pyrimidin-4-one hydrochloride (Compound No. D1)

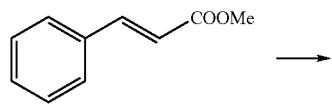

4-Nitro-3-phenyl-butyric Acid Methyl Ester

A solution of methyl cinnamate (4.93 g, 30.4 mmol) and teteramethylguanidine (3.99 g, 34.6 mmol) in nitromethane (30 ml) was stirred for 6 hours at 90° C. After removal of the solvent under reduced pressure, the residue was partitioned between water and ethyl acetate, and the organic layer was washed with water and brine and then dried over sodium sulfate. The organic solvents were removed under reduced pressure, and the residue was purified by silica gel column chromatography (eluent; hexane/ethyl acetate=4/1) to afford 4-nitro-3-phenyl-butyric acid methyl ester (4.02 g, 59%)

1-tert-Butoxycarbonyl-3-phenyl-pyrrolidine

A solution of 4-nitro-3-phenyl-butyric acid methyl ester (4.02 g, 18 mmol) and Raney-Nickel (6 ml, slurry in water) in methanol (30 ml) was stirred under hydrogen atmosphere for 3 hours. After filtration using celite and removal of the solvent under reduced pressure, residue was partitioned between water and ethyl acetate. The organic layer was washed with water and brine, and then dried over sodium sulfate. The solvents were removed under reduced pressure, and the residue was dissolved in toluene (50 ml) and the resulting solution was refluxed for 6 hours. Removal of the solvent afforded crude 4-phenyl-pyrrolidin-2-one. A solution of crude 4-phenyl-pyrrolidin-2-one in tetrahydrofuran (20 ml) was added to a solution of lithium aluminum hydride (1.34 g, 35.3 mmol) and the mixture was refluxed for 6 hours. After quenching the reaction with 20% aqueous sodium hydroxide, a solution of di-tert-butyl dicarbonate (4.14 g, 19 mmol) was added and the

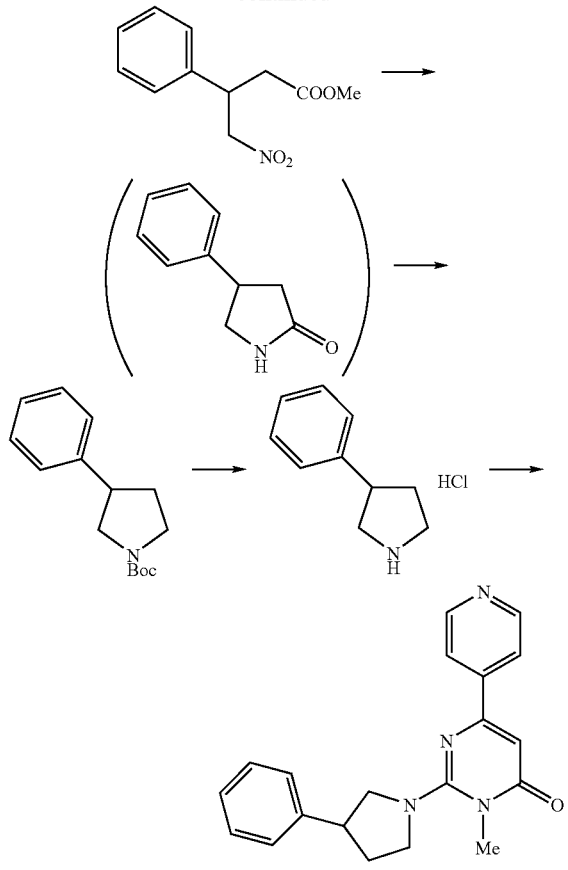

mixture was stirred for 3 hours. Aqueous citric acid and aqueous potassium hydrogen sulfate was added to acidify the solution, and the solution was extracted with toluene. The organic layer was washed with water, aqueous sodium bicarbonate, brine, and dried over sodium sulfate. The solvent was removed under reduced pressure, and the residue was purified with silica gel column chromatography (eluent; hexane/ethyl acetate=9/1) to afford 1-tertbutoxycarbonyl-3-phenyl-pyrrolidine (1.84 g, 42%).

3-phenyl-pyrrolidine

Hydrogen chloride (4N) in ethyl acetate (6 ml) was added to a solution of 1-tertbutoxycarbonyl-3-phenyl-pyrrolidine (1.84 g, 7.4 mmol) in ethyl acetate (2 ml) and the mixture was stirred for 2 hours. After azeotropical removal of the solvent and hydrogen chloride, the residue was partitioned between aqueous potassium carbonate and diethyl ether, and the organic layer was washed with brine, and dried over sodium sulfate. Removal of the solvent afforded 3-phenyl-pyrrolidine (0.95 g, 87%).

3-Methyl-2-(3-phenyl-pyrrolidin-1-yl)-6-pyridin-4-yl-3H-pyrimidin-4-one Hydrochloride A solution of 3-phenyl-pyrrolidine (449 mg, 3.05 mmol), 2-chloro-3-methyl-6-pyridin-4-yl-3H-pyrimidin-4-one (436 mg, 1.97 mmol) and triethylamine (412 mg, 4.07 mmol) was refluxed for one hour. After removal of the solvent, the residue was partitioned between water and ethyl acetate. The solvent was removed under reduced pressure, and the residue was purified by silica gel column chromatography (eluent; ethyl acetate/ethanol=10/1) to afford 3-methyl-2-(3-phenyl-pyrrolidin-1-yl)-6-pyridin-4-yl-3H-pyrimidin-4-one (576 mg, 88%).

Hydrogen chloride (4N) in ethyl acetate (6 ml) was added to a solution of 3-methyl-2-(3-phenyl-pyrrolidin-1-yl)-6-pyridin-4-yl-3H-pyrimidin-4-one (576 mg, 1.73 mmol) in methanol (3 ml) and the mixture was stirred for 15 minutes. Azeotropic removal of the solvents and excess hydrogen chloride afforded 3-methyl-2-(3-phenyl-pyrrolidin-1-yl)-6-pyridin-4-yl-3H-pyrimidin-4-one hydrochloride (621 mg, 97%).

Example 12

2-(3-Benzyloxy-pyrrolidin-1-yl)-3-methyl-6-pyridin-4-yl-3H-pyrimidin-4-one (Compound No. D2)

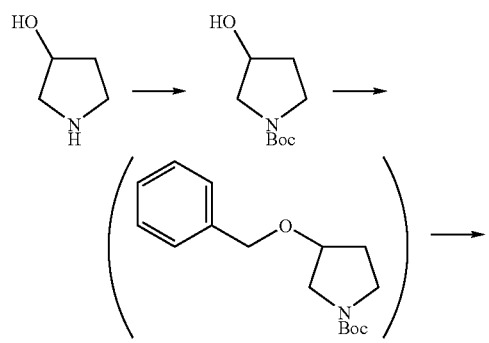

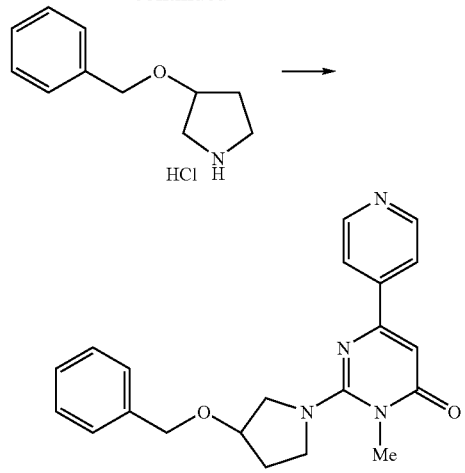

1-(tert-Butoxycarbonyl)-3-hydroxy-pyrrolidine

A solution of di-tert-butyl dicarbonate (14.17 g, 64.9 mmol) in tetrahydrofuran (10 ml) and 10% aqueous potassium carbonate (30 ml) was added to a solution of 3-hydroxy-pyrrolidine (5.38 g, 61.8 mmol) and the mixture was stirred overnight. The solvent was removed under reduced pressure and the residue was partitioned between water and ethyl acetate. The organic layer was washed with brine and dried over sodium sulfate. The solvent was removed under reduced pressure and the residue was purified by silica gel column chromatography (eluent; hexane/ethyl acetate=1/3) to afford 1-(tert-butoxycarbonyl)-3-hydroxy-pyrrolidine (11.43 g, 99%).

3-Benzyloxyyrrolidine

A solution of 1-(tert-butoxycarbonyl)-3-hydroxy-pyrrolidine (430 mg, 2.30 mmol) in N,N-dimethylformamide (3 ml) was added to a solution of sodium hydride (60% dispersion in mineral oil, 137 mg, 3.43 mmol) and the mixture was stirred for one hour. A solution of benzyl bromide (562 mg, 3.29 mmol) in N,N-dimethylformamide (1 ml) was added to the solution and the mixture was stirred overnight. Reaction was quenched with water and the reaction mixture was extracted with diethyl ether. The organic layer was washed with water and dried over sodium sulfate. Removal of solvent afforded crude 3-benzyloxy-1-(tert-butoxycarbonyl)-pyrrolidine (705 mg).

Hydrogen chloride (4N) in ethyl acetate (1.5 ml) was added to a solution of crude 3-benzyloxy-1-(tert-butoxycarbonyl)-pyrrolidine (705 mg) in diethyl ether (3 ml) and the mixture was stirred for 15 minutes. Reaction was quenched with water, and the solution was washed with diethyl ether. After addition of aqueous sodium hydroxide to make the solution basic, the solution was extracted with diethyl ether and the organic layer was washed with brine and dried over sodium sulfate. Removal of the solvent under reduced pressure afforded 3-benzyloxy-pyrrolidine (182 mg, 37%).

2-(3-Benzyloxy-pyrrolidin-1-yl)-3-methyl-6-pyridin-4-yl-3H-pyrimidin-4-one

A solution of 3-benzyloxypyrrolidine (182 mg, 1.03 mmol), 2-chloro-3-methyl-6-pyridin-4-yl-3H-pyrimidin-4-one (181 mg, 0.82 mmol) and triethylamine (387 mmol, 3.83 mmol) was refluxed for 3 hours. After removal of the solvent, the residue was purified by silica gel column chromatography (eluent; dichloromethane/ethanol=10/1) and washed with ethyl acetate to afford 2-(3-benzyloxy-pyrrolidin-1-yl)-3-methyl-6-pyridin-4-yl-3H-pyrimidin-4-one (208 mg, 70%).

Example 13

2-((R)-3-Benzylaminopyrrolidin-1-yl)-3-methyl-6-(pyridin-4-yl)-3H-pyrimidin-4-one (Compound No. D26)

2-((R)-3-Aminopyrrolidin-1-yl)-3-methyl-6-(pyridin-4-yl)-3H-pyrimidin-4-one (Compound No. D32)

2-[(R)-3-(2-Methoxyphenylamino)pyrrolidin-1-yl]-3-methyl-6-(pyridin-4-yl)-3H-pyrimidin-4-one (Compound No. D35)

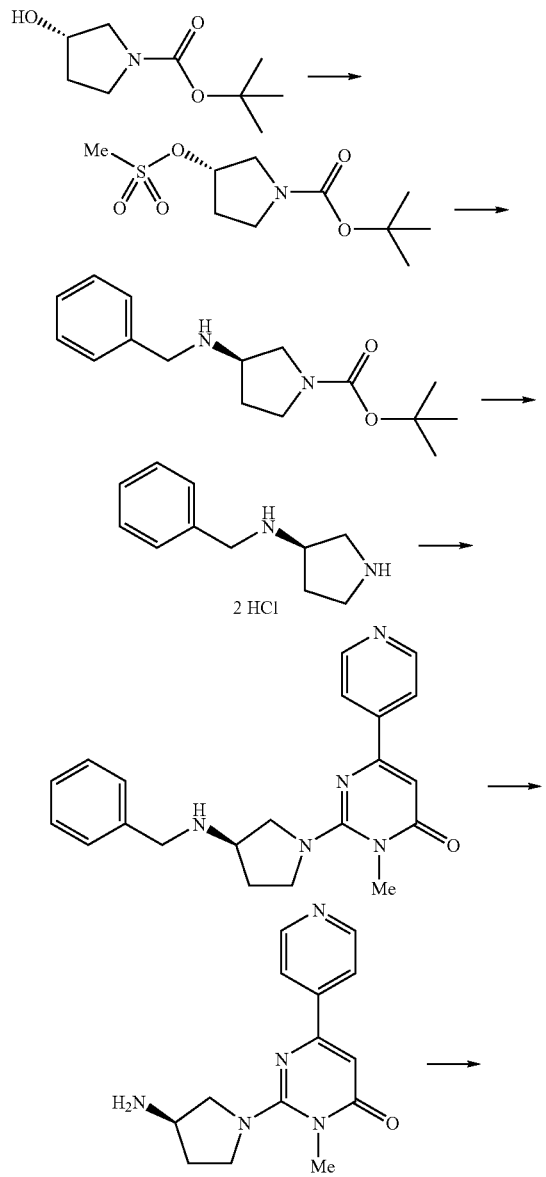

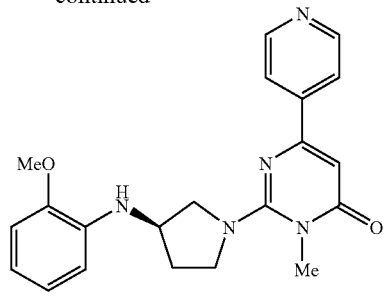

(S)-3-Hydroxyyrrolidine-1-carboxylic Acid Tert-Butyl Ester

A solution of (S)-3-pyrrolidinol (5.0 g, 57 mmol), di-tert-butyl dicarbonate (13.8 g, 63.1 mmol), and triethylamine (19.1 g, 189.4 mmol) in tetrahydrofuran (250 ml) was stirred for 5 hours at room temperature. The solvent was evaporated off under reduced pressure and the obtained residue was purified by silica gel column chromatography (eluent; hexane/ethyl acetate=1/1) to afford (S)-3-hydroxypyrrolidine-1-carboxylic acid tert-butyl ester (11 g, quant.) as colorless oil.

(S)-3-Methanesulfonyloxypyrrolidine-1-carboxylic Acid Tert-Butyl Ester

To a solution of (S)-3-hydroxypyrrolidine-1-carboxylic acid tert-butyl ester (11 g, 57 mmol) and triethylamine (17.3 g, 171 mmol) in tetrahydrofuran (180 ml) was added methanesulfonyl chloride (9.8 g, 85.5 mmol) at 5° C. The mixture was stirred for 3 hours at room temperature, poured into water, and extracted with ethyl acetate. The organic extract was washed with brine and dried over sodium sulfate. The solvent was evaporated under reduced pressure to afford (S)-3-methanesulfonyloxypyrrolidine-1-carboxylic acid tert-butyl ester (16.9 g, quant.) as colorless oil.

(R)-3-Benzylaminopyrrolidine-1-carboxylic Acid Tert-Butyl Ester

A solution of (S)-3-methanesulfonyloxypyrrolidine-1-carboxylic acid tert-butyl ester (16.9 g, 57 mmol) and benzylamine (18.3 g, 171 mmol) was stirred for 4 hours at 95° C. The remaining benzylamine was evaporated off under reduced pressure and the residue was purified by silica gel column chromatography (eluent; ethyl acetate) to afford (R)-3-benzylaminopyrrolidine-1-carboxylic acid tert-butyl ester (15.3 g, 97%) as pale yellow oil.

(R)-Benzylpyrrolidin-3-yl-amine Dihydrochloride

To a solution of (R)-3-benzylaminopyrrolidine-1-carboxylic acid tert-butyl ester (15.3 g, 55.4 mmol) in ethyl acetate (100 ml) was added 12% hydrogen chloride in ethyl acetate (100 ml) at 5° C. The mixture was stirred for 2 hours at room temperature. The precipitated crystals were collected by filtration and washed with ethyl acetate to afford benzylpyrrolidin-3-yl-amine dihydrochloride (6.0 g, 51%) as colorless crystals.

2-((R)-3-Benzylaminopyrrolidin-1-yl)-3-methyl-6-(pyridin-4-yl)-3H-pyrimidin-4-one (Compound No. D26)

A solution of (R)-benzylpyrrolidin-3-yl-amine dihydrochloride (3.0 g, 12 mmol), 2-chloro-3-methyl-6-(pyridin-4- yl)-3H-pyrimidin-4-one (2.6 g, 12 mmol), and triethylamine (6 g, 60 mmol) in tetrahydrofuran (40 ml) was stirred for 12 hours at 95° C. The solvent was evaporated off under reduced pressure and the residue was partitioned between water and dichloromethane. The organic layer was dried over sodium sulfate and the solvent was evaporated under reduced pressure. The obtained residue was purified by silica gel column chromatography (eluent; ethyl acetate) to afford 2-((R)-3-benzylaminopyrrolidin-1-yl)-3-methyl-6-pyridin-4-yl-3H-pyrimidin-4-one (3.2 g, 75%) as pale yellow oil.

2-((R)-3-Aminopyrrolidin-1-yl)-3-methyl-6-(Pyridin-4-yl)-3H-pyrimidin-4-one (Compound No. D32)

To a solution of 2-((R)-3-benzylaminopyrrolidin-1-yl)-3-methyl-6-(pyridin-4-yl)-3H-pyrimidin-4-one (1.6 g, 4.4 mmol) and ammonium formate (0.55 g, 8.9 mmol) in tatrahydrofuran (15 ml), methanol (30 ml) and water (5 ml) was added 10% palladium on charcoal (wet, 160 mg). After stirring for 4 hours at 95° C., palladium on charcoal was removed by filtration. The solvent was evaporated off under reduced pressure and the residue was partitioned between water and dichloromethane. The organic layer was dried over sodium sulfate and the solvent was evaporated under reduced pressure to afford 2-((R)-3-aminopyrrolidin-1-yl)-3-methyl-6-(pyridin-4-yl)-3H-pyrimidin-4-one (1.0 g, 84%) as colorless crystals.

2-[(R)-3-(2-Methoxyphenylamino)pyrrolidin-1-yl]-3-methyl-6-(pyridin-4-yl)-3H-pyrimidin-4-one (Compound No. D35)

A solution of 2-((R)-3-aminopyrrolidin-1-yl)-3-methyl-6-(pyridin-4-yl)-3H-pyrimidin-4-one (0.20 g, 0.74 mmol), 2-bromoanisole (0.13 g, 0.74 mmol), tris(dibenzylideneacetone)dipalladium chloroform complex (0.061 g, 0.059 mmol), sodium tertbutoxide (0.10 g, 1.03 mmol) and 2,2'-bis(diphenylphosphino)-1,1'-binaphthalene (0.11 g, 0.18 mmol) in toluene (12 ml) and dioxane (2 ml) was stirred for 19 hours at 90° C. The solvent was evaporated off under reduced pressure and the residue was partitioned between water and ethyl acetate. The organic layer was dried over sodium sulfate and the solvent was evaporated under reduced pressure. The residue was purified by silica gel column chromatography (eluent; ethyl acetate/methanol=5/1) to afford 2-[(R)-3-(2-methoxyphenylamino)pyrrolidin-1-yl]-3-methyl-6-(pyridin-4-yl)-3H-pyrimidin-4-one (0.083 g, 29%) as colorless crystals.

Example 14

1-Methyl-2-[(2R)-2-methyl-4-(quinoline-2-carbonyl)-piperazin-1-yl]-1H-[4,4']bipyrimidinyl-6-one

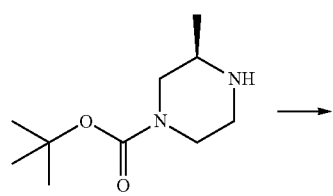

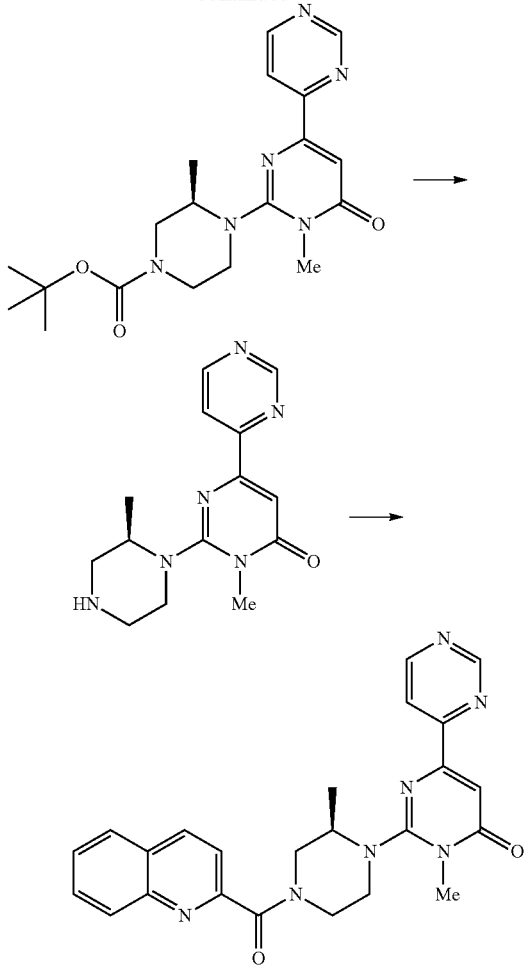

(3R)-3-Methyl-4-(1-methyl-6-oxo-1,6-dihydro-[4,4'] bipyrimidinyl-2-yl)-piperazine-1-carboxylic Acid Tert-Butyl Ester A solution of 2-chloro-3-methyl-6-(pyrimidin-4-yl)-3H-pyrimidin-4-one (5.3 g, 24 mmol), tert-butyl (3R)-3-methylpiperazine-1-carboxylate (5.0 g, 25 mmol) and triethylamine (7.6 g, 75 mmol) in N-methyl-2-pyrrolidone (25 ml) was stirred for 6 hours at 90° C. The solution was partitioned between water and ethyl acetate, and the organic layer was washed with water, brine, dried over sodium sulfate, and concentrated under reduced pressure. The residue was purified by silica gel column chromatography (eluent; ethyl acetate) to afford (3R)-3-methyl-4-(1-methyl-6-oxo-1,6-dihydro-[4,4']bipyrimidinyl-2-yl)-piperazine-1-carboxylic acid tert-butyl ester (6.9 g, 71%).

$^1$H NMR; 1.28 (3H, d, J=7.0 Hz), 1.51 (9H, brs), 3.29-3.52 (4H, m), 3.55 (3H, s), 3.71 (1H, dd, J=3.9, 13.3 Hz), 3.81-4.02 (2H, m), 7.29 (1H, s), 8.16 (1H, dd, J=1.6, 5.5 Hz), 8.88 (1H, d, J=4.7 Hz), 9.25 (1H, s) (CDCl$_3$)
MS; [M$^+$+1]=387

1-Methyl-2-((2R)-2-methyl-piperazin-1-yl)-1H-[4,4'] bipyrimidinyl-6-one

To a solution of (3R)-3-methyl-4-(1-methyl-6-oxo-1,6-dihydro-[4,4']bipyrimidinyl-2-yl)-piperazine-1-carboxylic acid tert-butyl ester (6.9 g, 18 mmol) in ethyl acetate (35 ml) was added hydrogen chloride (4N) in ethyl acetate (35 ml) at room temperature. The mixture was stirred at room temperature for 2 hours and was concentrated under reduced pressure. The residue was partitioned between aqueous sodium hydrogen carbonate and chloroform, and the organic layer was dried over sodium sulfate. The solvent was evaporated under reduced pressure to afford 1-methyl-2-((2R)-2-methyl-piperazin-1-yl)-1H-[4,4']bipyrimidinyl-6-one (4.6 g, 91%).

1H NMR (400 MHz, CDCl$_3$) 1.26 (3H, d, J=6.3 Hz), 2.81 (1H, dd, J=4.7, 11.7 Hz), 3.03-3.06 (2H, m), 3.10-3.18 (2H, m), 3.30-3.38 (1H, m), 3.56 (3H, s), 3.67-3.74 (1H, m), 7.34 (1H, s), 8.17 (1H, dd, J=1.6, 5.5 Hz), 8.88 (1H, d, J=4.7 Hz), 9.28 (1H, d, J=1.6 Hz).

MS; [M$^+$+1]=287

1-Methyl-2-[(2R)-2-methyl-4-(quinoline-2-carbonyl)-piperazin-1-yl]-1H-[4,4']bipyrimidinyl-6-one To a solution of 1-methyl-2-((2R)-2-methyl-piperazin-1-yl)-1H-[4,4']bipyrimidinyl-6-one (0.15 g, 0.52 mmol) and triethylamine (0.15 g, 1.48 mmol) in dichloromethane (2.5 ml) was added quinoline-2-carbonyl chloride (0.11 g, 0.57 mmol) at 0° C. and stirred for one hour at that temperature. The mixture was partitioned between water and dichloromethane, and the organic layer was washed with aqueous sodium hydrogen carbonate, dried over sodium sulfate, and concentrated under reduced pressure. The residue was purified by silica gel column chromatography (eluent; chloroform/methanol=20/1) to afford 1-methyl-2-[(2R)-2-methyl-4-(quinoline-2-carbonyl)-piperazin-1-yl]-1H-[4,4']bipyrimidinyl-6-one (0.18 g, 77%).

Example 15

2-[(3R)-3-Methyl-4-(1-methyl-6-oxo-1,6-dihydro-[4,4']bipyrimidinyl-2-yl)-piperazin-1-yl]-benzonitrile To a stirred solution of 1-methyl-2-((2R)-2-methyl-piperazin-1-yl)-1H-[4,4']bipyrimidinyl-6-one (150 mg, 0.524 mmol) in ethylene glycol dimethyl ether (2.0 ml) was added 2-bromobenzonitrile (143 mg, 0.786 mmol), tris(dibenzylideneacetone)dipalladium (24 mg, 0.026 mmol), 2-dicyclohexylphosphino-2',6'-dimethoxybiphenyl (25 mg, 0.052 mmol) and tripotassium phosphate (167 mg, 0.786 mmol), and the reaction mixture was stirred for 12 hours at 80° C. The reaction was quenched with water, the aqueous layer was extracted with ether. The extract was washed with water and brine, dried over magnesium sulfate, and concentrated in vacuo. The resulting residue was purified with HPLC to afford 2-[(3R)-3-methyl-4-(1-methyl-6-oxo-1,6-dihydro-[4,4']bipyrimidinyl-2-yl)-piperazin-1-yl]-benzonitrile (120 mg, 0.310 mmol, 59%) as pale yellow crystals.

Example 16

2-{(2R)-4-[4-(5-Aminomethyl-[1,2,4]oxadiazol-3-yl)-phenyl]-2-methyl-piperazin-1-yl}-1-methyl-1H-[4,4']bipyrimidinyl-6-one

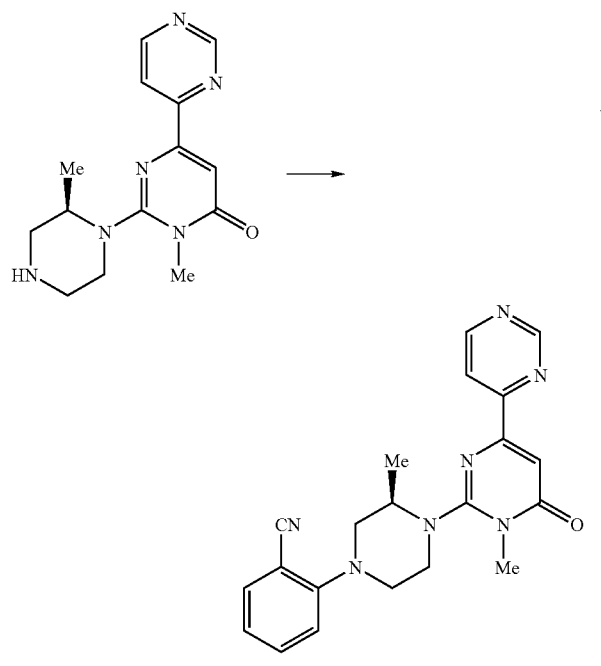

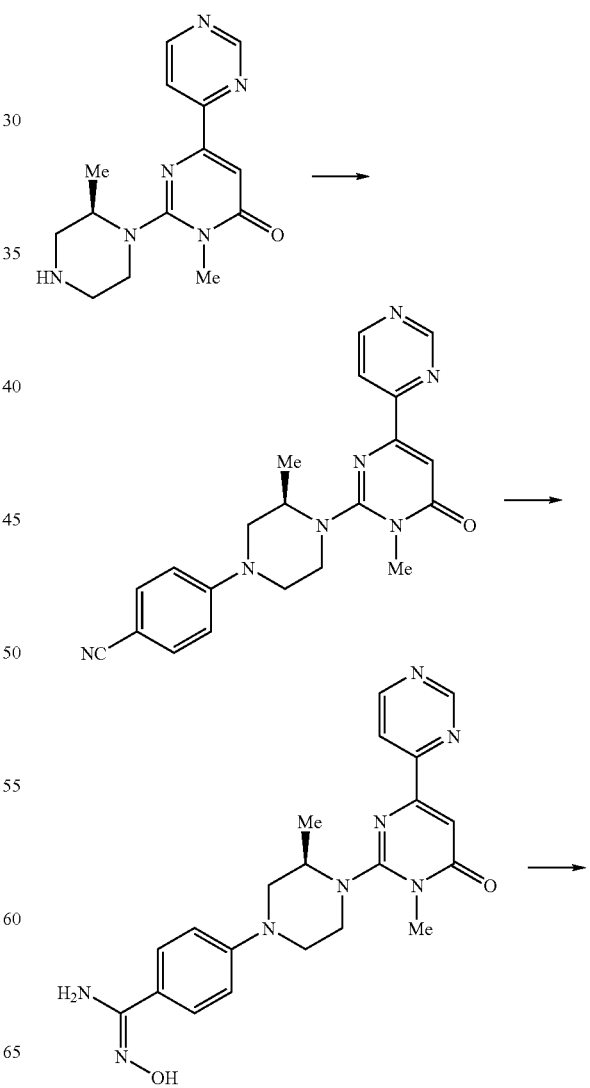

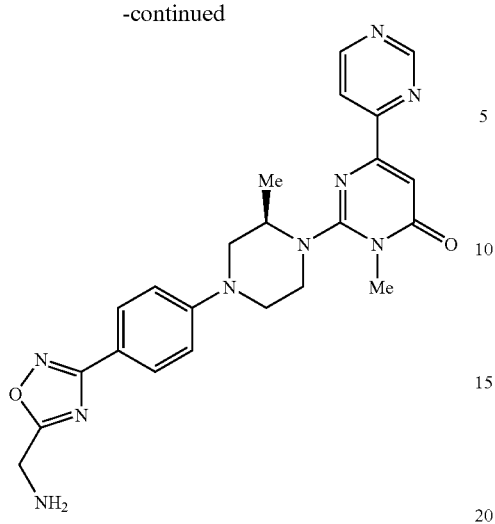

4-[(3R)-3-Methyl-4-(1-methyl-6-oxo-1,6-dihydro-[4,4']bipyrimidinyl-2-yl)-piperazin-1-yl]-benzonitrile To a stirred solution of 1-Methyl-2-((2R)-2-methyl-piperazin-1-yl)-1H-[4,4']bipyrimidinyl-6-one (1.50 g, 5.24 mmol) in dimethyl sulufoxide (10.0 ml) was added 4-fluorobenzonitrile (1.27 g, 10.5 mmol), potassium carbonate (2.90 g, 21.0 mmol), and the reaction mixture was stirred for 12 hours at 120° C. The reaction was quenched with water, the aqueous layer was extracted with ethyl acetate. The extract was washed with water and brine, dried over magnesium sulfate, and concentrated in vacuo. After removal of the solvent, the precipitate was filtered, washed with ether, and dried to give 4-[(3R)-3-Methyl-4-(1-methyl-6-oxo-1,6-dihydro-[4,4']bipyrimidinyl-2-yl)-piperazin-1-yl]-benzonitrile (1.70 g, 4.39 mmol, 84%) as pale yellow crystals.

N-Hydroxy-4-[(3R)-3-methyl-4-(1-methyl-6-oxo-1,6-dihydro-[4,4']bipyrimidinyl-2-yl)-piperazin-1-yl]-benzamidine To a stirred solution of 4-[(3R)-3-methyl-4-(1-methyl-6-oxo-1,6-dihydro-[4,4']bipyrimidinyl-2-yl)-piperazin-1-yl]-benzonitrile (1.50 mg, 3.87 mmol) in ethanol (8.0 ml) and water (4.0 ml) was added hydroxylammonium chloride (807 mg, 11.6 mmol) and sodium carbonate (2.05 g, 19.4 mmol), and the reaction mixture was stirred for 2 hours under reflux. The solution was partitioned between water and chloroform, and the organic layer was washed with water and brine, dried over magnesium sulfate, and concentrated in vacuo. The resulting solid was used for next reaction without further purification.

2-{(2R)-4-[4-(5-aminomethyl-[1,2,4]oxadiazol-3-yl)-phenyl]-2-methyl-piperazin-1-yl}-1-methyl-1H-[4,4']bipyrimidinyl-6-one To a stirred solution of N-tertbutoxycarbonylglycine (94 mg, 0.535 mmol) in N,N-dimethylformamide (2.0 ml) was added [2-(1H-benzotriazole-1-yl)-1,1,3,3-tetramethyluroniumtetrafluoroborate (172 mg, 0.535 mmol), 1-hydroxybenzotriazole hydrate (14 mg, 0.107 mmol) and N,N-diisopropylethylamine (0.31 ml, 1.78 mmol), and the reaction mixture was stirred for 30 minutes at room temperature. After the addition of N-hydroxy-4-[(3R)-3-methyl-4-(1-methyl-6-oxo-1,6-dihydro-[4,4']bipyrimidinyl-2-yl)-piperazin-1-yl]-benzamidine (145 mg, 0.356 mmol), the reaction mixture was stirred for one hour at room temperature, and then heated to 110° C. When the reaction was complete (checked by thin layer chromatography), excess reagent was decomposed by the addition of water and the aqueous layer was extracted with ethyl acetate. The extract was washed with water and brine, dried over magnesium sulfate, and concentrated in vacuo. The resulting residue was treated with trifluoroacetic acid, and the reaction mixture was stirred for 1 hour. After removal of the solvent, the residue was purified with HPLC to afford 2-{(2R)-4-[4-(5-aminomethyl-[1,2,4]oxadiazol-3-yl)-phenyl]-2-methyl-piperazin-1-yl}-1-methyl-1H-[4,4']bipyrimidinyl-6-one (44 mg, 0.096 mmol, 27%) as colorless crystals.

Example 17

1-Methyl-2-{(2R)-2-methyl-4-[4-(5-methyl-[1,2,4]oxadiazol-3-yl)-benzyl]-piperazin-1-yl}-1H-[4,4']bipyrimidinyl-6-one

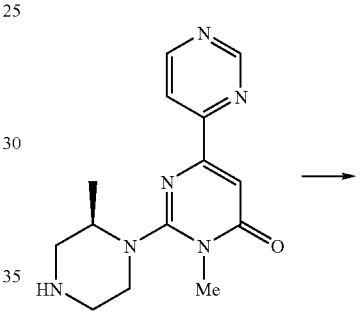

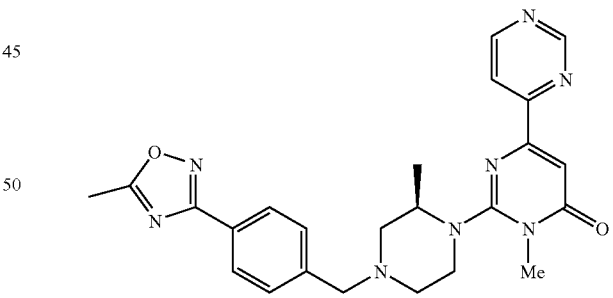

To a solution of 1-methyl-2-((2R)-2-methyl-piperazin-1-yl)-1H-[4,4']bipyrimidinyl-6-one (0.15 g, 0.52 mmol) and potassium carbonate (0.22 g, 1.59 mmol) in N,N-dimethylformamide (1.5 ml) was added 3-[4-(bromomethyl)phenyl]-5-methyl-1,2,4-oxadiazole (0.14 g, 0.55 mmol) at room temperature and the mixture was stirred for 4 hours. The mixture was partitioned between water and dichloromethane, and the organic layer was washed with water, brine, and dried over sodium sulfate, and concentrated under reduced pressure. The residue was purified by silica gel column chromatography (eluent; ethyl acetate) to afford 1-methyl-2-{(2R)-2-methyl-4-[4-(5-methyl-[1,2,4]oxadiazol-3-yl)-benzyl]-piper-azin-1-yl}-1H-[4,4']bipyrimidinyl-6-one (0.15 g, 63%).

Example 18

6-(3-Fluoropyridin-4-yl)-3-methyl-2-((2R,5R)-cis-5-methyl-2-phenylmorpholin-4-yl)-3H-pyrimidin-4-one

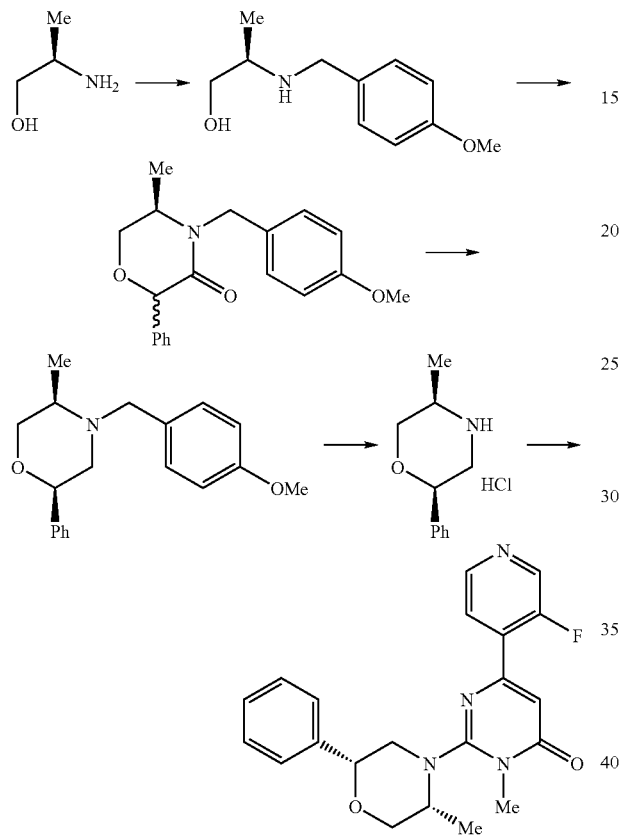

(2R)-2-(4-Methoxybenzylamino)-propan-1-ol

4-Anisaldehyde (5.5 g, 40.4 mmol) was added to a solution of D-alaminol (3.0 g, 39.9 mmol) in methanol (30 ml) with vigorous stirring and the mixture was stirred for 30 minutes. Sodium borohydride (1.52 g, 40.2 mmol) was added to the ice-cooled solution and stirred for 1 hour at room temperature. When the reaction was complete (checked by thin layer chromatography), excess reagent was decomposed by the addition of water. The solution was partitioned between water and chloroform. The organic layer was washed with brine, dried over magnesium sulfate. Removal of the solvent under reduced pressure afforded (2R)-2-(4-methoxybenzylamino)-propan-1-ol (7.79 g, 39.9 mmol, 100%) as white crystals.

(2RS,5R)-4-(4-Methoxybenzyl)-5-methyl-2-phenyl-morpholin-3-one

2-Chloro-2-methylacetyl chloride (8.4 g, 40.0 mmol) was added to a solution of (2R)-2-(4-methoxybenzylamino)-propan-1-ol (7.79 g, 39.9 mmol) and triethylamine (4.5 g, 44.5 mmol) in tetrahydrofuran (100 ml) and the solution was stirred for one hour. The solution was cooled at 0° C. and 28% sodium methoxide in methanol solution (15.4 g, 79.8 mol) was added. When the reaction was complete (checked by thin layer chromatography), excess reagent was decomposed by the addition of water and pH was adjusted to 5-6 with 3N aqueous hydrochloric acid. The solution was partitioned between water and chloroform. The organic layer was washed with brine, dried over magnesium sulfate, and concentrated under reduced pressure. The residue was purified by silica gel column chromatography (eluent; 30-50% ethyl acetate in hexane) to afford (2RS,5R)-4-(4-methoxybenzyl)-5-methyl-2-phenylmorpholin-3-one (12.2 g, 39.1 mmol, 98%) as colorless oil.

(2R,5R)-cis-4-(4-Methoxybenzyl)-5-methyl-2-phenylmorpholine

Chlorotrimethylsilane (17.0 g, 156 mmol) was added to a solution of lithium borohydride (1.7 g, 78.1 mmol) in tetrahydrofuran (100 ml) and the mixture was stirred for one hour at room temperature. A solution of (2RS,5R)-4-(4-methoxybenzyl)-5-methyl-2-phenylmorpholin-3-one (12.2 g, 39.1 mmol) in tetrahydrofuran (20 ml) was added to the solution and the mixture was stirred for one hour at room temperature. After careful addition of methanol with ice-cooled solution, pH was adjusted to 12-14 with 6N aqueous potassium hydroxide and the solution was stirred for 2 hours at 80° C. After cooling, the solution was partitioned between water and ethyl acetate. The organic layer was washed with brine, dried over magnesium sulfate, and concentrated under reduced pressure. The residue was purified by silica gel column chromatography (eluent; 5-10% ethyl acetate in hexane) to afford (2R,5R)-cis-4-(4-methoxybenzyl)-5-methyl-2-phenylmorpholine (6.23 g, 20.9 mmol, 53%) and (2S,5R)-trans-4-(4-methoxybenzyl)-5-methyl-2-phenylmorpholine (3.29 g, 11.1 mmol, 28%) as white crystals.

(2R,5R)-cis-5-Methyl-2-phenylmorpholine Hydrochloride

1-Chloroethyl chloroformate (12.0 g, 83.9 mmol) was added to a solution of (2R,5R)-cis-4-(4-methoxybenzyl)-5-methyl-2-phenylmorpholine (6.23 g, 20.9 mmol) in 1,2-dichloroethane (100 ml) and the mixture was stirred for 6 hours at 80° C. The solvent was evaporated under reduced pressure and a methanol (100 ml) solution of the residue was stirred for one hour at 80° C. The solvent was evaporated under reduced pressure, and the residue was washed with ethyl acetate and dried to afford (2R,5R)-cis-5-methyl-2-phenylmorpholine hydrochloride (2.13 g, 9.97 mmol, 48%) as white crystals.

6-(3-Fluoropyridin-4-yl)-3-methyl-2-((2R,5R)-cis-5-methyl-2-phenylmorpholin-4-yl)-3H-pyrimidin-4-one A solution of 2-chloro-6-(3-fluoropyridin-4-yl)-3-methyl-3H-pyrimidin-4-one (0.45 g, 1.88 mmol), (2R,5R)-5-methyl-2-phenylmorpholine hydrochloride (0.40 g, 1.87 mmol) and triethylamine (0.56 g, 5.53 mmol) in tetrahydrofuran (10 ml) was stirred for 10 hours at 100° C. The solution was partitioned between water and chloroform, and the organic layer was washed with brine, dried over magnesium sulfate, and concentrated under reduced pressure. The residue was purified by silica gel column chromatography (eluent; 5-10% methanol in chloroform) to afford 6-(3-fluoropyridin-4-yl)-

3-methyl-2-((2R,5R)-cis-5-methyl-2-phenylmorpholin-4-yl)-3H-pyrimidin-4-one (0.46 g, 1.21 mmol, 65%) as white crystals.

Example 19

2-((2RS)-2-Benzyl-pyrrolidin-1-yl)-6-(3-fluoro-pyridin-4-yl)-3-methyl-3H-pyrimidin-4-one

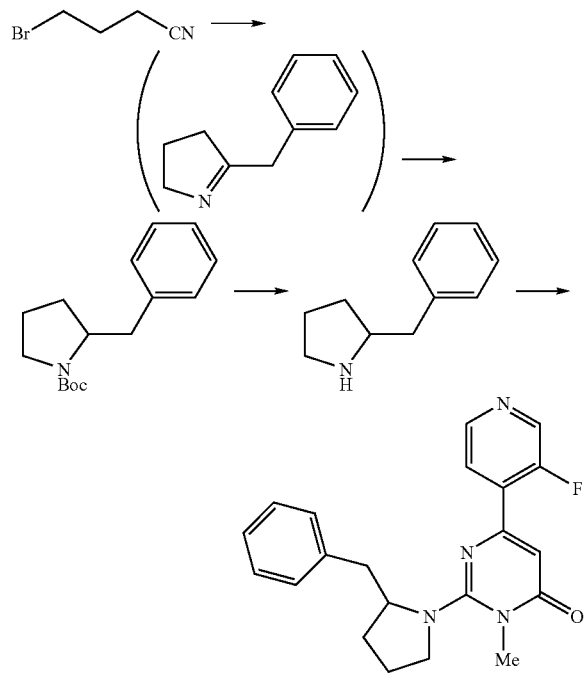

5-Benzyl-3,4-dihydro-2H-pyrrole

5-Benzyl-3,4-dihydro-2H-pyrrole was prepared according to the following literature (Douglas, F. F.; Carol, B. F.; R. Karl, D. *Synlett* 1994, 836).

To a solution of 4-bromobutyronitrile (2.0 g, 13.5 mmol) in toluene (70 ml) was added 1.0 M benzylmagnesium bromide (20.0 ml, 20.0 mmol) in diethyl ether (70 ml) and the mixture was stirred for 2 hours at room temperature. The mixture was partitioned between 0.1N hydrochloric acid and ethyl acetate, and the organic layer was washed with aqueous sodium hydrogen carbonate, dried over sodium sulfate. The solvent was evaporated under reduced pressure to afford 5-benzyl-3,4-dihydro-2H-pyrrole (2.85 g). This compound was used without further purification.

(2RS)-2-Benzyl-pyrrolidine-1-carboxylic Acid Tert-Butyl Ester

Sodium borohydride (1.0 g, 26.4 mmol) was added to a solution of 5-benzyl-3,4-dihydro-2H-pyrrole in methanol (40 ml) and the mixture was stirred at room temperature for 5 hours. The mixture was partitioned between water and chloroform, and the organic layer was washed with brine and concentrated under reduced pressure. Aqueous sodium hydroxide (1N, 30 ml), methanol (30 ml), and di-tert-butyl dicarbonate (3.5 g, 16.0 mmol) was added to the above residue and the mixture was stirred for 4 hours at room temperature. The mixture was partitioned between water and ethyl acetate, and the organic layer was washed with brine, dried over sodium sulfate, and concentrated under reduced pressure. The residue was purified by silica gel column chromatography (eluent; hexane/ethyl acetate=19/1) to afford (2RS)-2-benzyl-pyrrolidine-1-carboxylic acid tert-butyl ester (1.21 g, 34%).

(2RS)-2-Benzyl-pyrrolidine

To a solution of (2RS)-2-benzyl-pyrrolidine-1-carboxylic acid tert-butyl ester (1.21 g, 4.6 mmol) in ethyl acetate (20 ml) was added hydrogen chloride (4N) in ethyl acetate (20 ml) at room temperature. The mixture was stirred at room temperature for 2 hours and was concentrated. The residue was partitioned between aqueous sodium hydrogen carbonate and chloroform, and the organic layer was dried over sodium sulfate. The solvent was evaporated under reduced pressure to afford (2RS)-2-benzyl-pyrrolidine (0.7 g, 93%).

2-((2RS)-2-Benzyl-pyrrolidin-1-yl)-6-(3-fluoro-pyridin-4-yl)-3-methyl-3H-pyrimidin-4-one A solution of 2-chloro-6-(3-fluoropyridin-4-yl)-3-methyl-3H-pyrimidin-4-one (0.24 g, 1.0 mmol), (2RS)-2-benzyl-pyrrolidine (0.20 g, 1.2 mmol) and triethylamine (0.3 g, 3.0 mmol) in tetrahydrofuran (4 ml) was stirred for 5 hours at 40° C. The solution was partitioned between water and ethyl acetate, and the organic layer was washed with brine, dried over sodium sulfate, and concentrated under reduced pressure. The residue was purified by silica gel column chromatography (eluent; chloroform/ethyl acetate=3/2) to afford 2-((2RS)-2-benzyl-pyrrolidin-1-yl)-6-(3-fluoro-pyridin-4-yl)-3-methyl-3H-pyrimidin-4-one (0.29 g, 80%).

Example 20

1-Methyl-2-((4aR,8aR)-trans-octahydro-benzo[1,4]oxazin-4-yl)-1H-[4,4']bipyrimidinyl-6-one

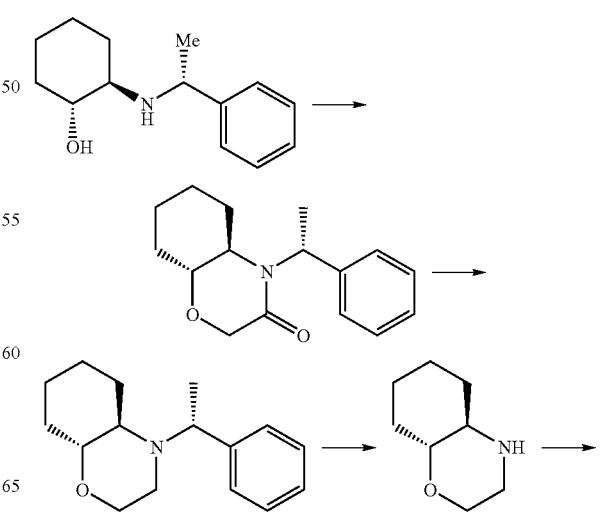

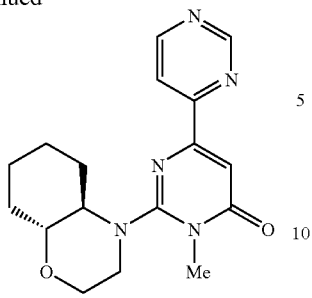

(4aR,8bR)-trans-4-((1R)-1-Phenylethyl)-hexahydrobenzo[1,4]oxazin-3-one (1R,2R)-trans-2-((1R)-1-Phenylethylamino)-cyclohexanol has been reported in the following literature (*J. Org. Chem.*, 50, 4154-4155 (1985)).

Chloroacetyl chloride (5.1 g, 45.2 mmol) was added to a solution of (1R,2R)-trans-2-((1R)-1-phenylethylamino)-cyclohexanol (9.89 g, 45.1 mmol) and triethylamine (5.0 g, 49.1 mmol) in tetrahydrofuran (200 ml) and the solution was stirred for one hour. The solution was cooled at 0° C. and 28% sodium methoxide in methanol solution (17.4 g, 90.2 mol) was added. When the reaction was complete (checked by thin layer chromatography), excess reagent was decomposed by the addition of water and pH was adjusted to 5-6 with 3N aqueous hydrochloric acid. The solution was partitioned between water and chloroform. The organic layer was washed with brine, dried over magnesium sulfate, and concentrated under reduced pressure. The residue was purified by silica gel column chromatography (eluent; 30-50% ethyl acetate in hexane) to afford (4aR,8bR)-trans-4-((1R)-1-phenylethyl)-hexahydrobenzo[1,4]oxazin-3-one (9.84 g, 37.9 mmol, 84%) as white crystals.

(4aR,8bR)-trans-4-((1R)-1-Phenylethyl)-octahydrobenzo[1,4]oxazine

Chlorotrimethylsilane (17 g, 156 mmol) was added to a solution of lithium borohydride (1.7 g, 78.1 mmol) in tetrahydrofuran (100 ml) and the mixture was stirred for one hour at room temperature. A solution of (4aR,8bR)-trans-4-((1R)-1-phenylethyl)-hexahydrobenzo[1,4]oxazin-3-one (9.84 g, 37.9 mmol) in tetrahydrofuran (30 ml) was added to the solution and the mixture was stirred for one hour at room temperature. After careful addition of methanol in ice-cooled solution, pH was adjusted to 12-14 with 6N aqueous potassium hydroxide and the solution was stirred at 80° C. for 2 hours. After cooling, the solution was partitioned between water and ethyl acetate. The organic layer was washed with brine, dried over magnesium sulfate, and concentrated under reduced pressure. The residue was purified by silica gel column chromatography (eluent; 30-50% ethyl acetate in hexane) to afford (4aR,8bR)-trans-4-((1R)-1-phenylethyl)-octahydrobenzo[1,4]oxazine (7.15 g, 29.1 mmol, 77%) as white crystals.

(4aR,8bR)-trans-Octahydrobenzo[1,4]oxazine hydrochloride

1-Chloroethyl chloroformate (17.0 g, 119 mmol) was added to a solution of (4aR,8bR)-trans-4-((1R)-1-phenylethyl)-octahydrobenzo[1,4]oxazine (7.15 g, 29.1 mmol) in 1,2-dichloroethane (70 ml) and the mixture was stirred for 8 hours at 80° C. The solvent was evaporated under reduced pressure, and a methanol (50 ml) solution of the residue was stirred for one hour at 80° C. Solvent was evaporated under reduced pressure, and the residue was washed with ethyl acetate and dried to afford (4aR,8bR)-trans-octahydrobenzo[1,4]oxazine hydrochloride (3.50 g, 19.7 mmol, 68%) as white crystals.

1-Methyl-2-((4aR,8aR)-trans-octahydro-benzo[1,4]oxazin-4-yl)-1H-[4,4']bipyrimidinyl-6-one A solution of 2-chloro-3-methyl-6-(pyrimidin-4-yl)-3H-pyrimidin-4-one (0.46 g, 2.07 mmol), (4aR,8bR)-trans-octahydrobenzo[1,4]oxazine hydrochloride (0.4 g, 2.25 mmol) and triethylamine (0.7 g, 6.92 mmol) in tetrahydrofuran (10 ml) was stirred for 10 hours at 100° C. The solution was partitioned between water and chloroform, and the organic layer was washed with brine, dried over magnesium sulfate, and concentrated under reduced pressure. The residue was purified by silica gel column chromatography (eluent; 5-10% methanol in chloroform) to afford 1-methyl-2-((4aR,8aR)-trans-octahydro-benzo[1,4]oxazin-4-yl)-1H-[4,4']bipyrimidinyl-6-one (0.33 g, 1.01 mmol, 49%) as white crystals.

Example 21

6-((3aS,7aR)-3-fluoro-pyridin-4-yl)-2-(hexahydro-2,4-dioxa-7-aza-inden-7-yl)-3-methyl-3H-pyrimidin-4-one

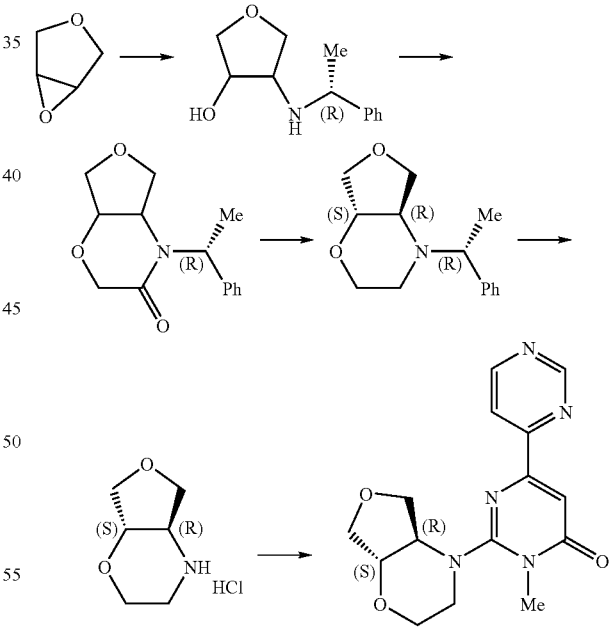

(3RS,4SR)-4-((1R)-1-Phenyl-ethylamino)-tetrahydro-furan-3-ol

To a solution of 3,4-epoxytetrahydrofuran (10 g, 116 mmol) and (R)-phenylethylamine (14.8 ml, 116 mmol) in acetonitrile (100 ml), anhydrous lithium perchlorate (12.3 g, 116 mmol) was added at room temperature and the mixture was refluxed under nitrogen atmosphere for 3 hours. After the reaction mixture was cooled to room temperature, the solution was poured into water and extracted with chloroform. The organic layer was dried over anhydrous sodium sulfate and concentrated. The flash silica gel column chromatography (eluent; 10% methanol in chloroform) was performed to isolate (3RS,4SR)-4-((1R)-1-phenyl-ethylamino)-tetrahydro-furan-3-ol (11 g, 53 mmol, 46%) as partially crystallized yellowish oil.

(3aRS,7aSR)-7-((1R)-1-Phenyl-ethyl)-tetrahydro-2,4-dioxa-7-aza-inden-6-one

Chloroacetyl chloride (0.88 ml, 11 mmol) was added to a solution of (3RS,4SR)-4-((1R)-1-phenyl-ethylamino)-tetrahydro-furan-3-ol (1.9 g, 9.2 mmol) and triethylamine (1.8 ml, 13 mmol) in dichloromethane (30 ml) at 0° C. and the solution was stirred for 2 hours at that temperature. The resulting mixture was poured into water and extracted with chloroform. The combined organic extracts were dried over anhydrous sodium sulfate and concentrated. The crude material was dissolved into 2-propanol (30 ml) at room temperature and 85% potassium hydroxide (1.3 g, 20 mmol) was added to the resulting solution with vigorous stirring at room temperature. After 15 hours, the reaction mixture was poured into water and extracted with ethyl acetate. The combined organic extracts were dried over anhydrous sodium sulfate and concentrated under reduced pressure. The resulting crude material was purified by silica gel column chromatography (eluent; hexane/ethyl acetate=100/0 to 3/1) to yield (3aRS,7aSR)-7-((1R)-1-Phenyl-ethyl)-tetrahydro-2,4-dioxa-7-aza-inden-6-one (1.46 g, 5.9 mmol, 64%) as colorless oil.

(3aS,7aR)-7-((1R)-1-Phenyl-ethyl)-hexahydro-2,4-dioxa-7-aza-indene

To a 0° C. solution of (3aRS,7aSR)-7-((1R)-1-phenyl-ethyl)-tetrahydro-2,4-dioxa-7-aza-inden-6-one (1.46 g, 5.9 mmol) in tetrahydrofuran (20 ml), a 1 M-solution of boran tetrahydrofuran complex in tetrahydrofuran (18 ml, 18 mmol) was added dropwise under nitrogen atmosphere and the resulting mixture was warmed to room temperature. After the reaction mixture was stirred for 15 hours, methanol was added until disappearance of bubbles. The mixture was concentrated under reduced pressure and methanol (10 ml) and 1 N aqueous solution of sodium hydroxide (10 ml) were added to the obtained residue at room temperature. The white slurry was refluxed for 2 hours and cooled to room temperature. After evaporation of methanol, water (30 ml) was added to the residue and extractive workup with ethyl acetate was performed. The organic layer was dried over sodium sulfate and concentrated. (3aS,7aR)-7-((1R)-1-phenyl-ethyl)-hexahydro-2,4-dioxa-7-aza-indene was isolated as a diastereomerically enriched colorless crystalline by silica gel column chromatography (eluent; hexane/ethyl acetate=100/0 to 1/1) of the residue and subsequent recrystallization from ethanol (1.0 g, 4.9 mmol, 73%, 96% de determined by NMR analysis).

(3aS,7aR)-Hexahydro-2,4-dioxa-7-aza-indene Hydrochloride

A solution of (3aS,7aR)-7-((1R)-1-phenyl-ethyl)-hexahydro-2,4-dioxa-7-aza-indene (1.0 g, 4.9 mmol) and 1-chloroethyl chloroformate (2.7 ml, 25 mmol) in 1,2-dichloroethane (15 mL) was refluxed for 15 hours and cooled to room temperature. After the reaction mixture was concentrated under reduced pressure, the resulting residue was dissolved into methanol and the mixture was refluxed for 2 hours. The reaction mixture was cooled to room temperature and concentrated. Ethyl acetate was added to the residue and the precipitated white solid of (3aS,7aR)-hexahydro-2,4-dioxa-7-aza-indene hydrochloride was triturated and collected by filtration (0.74 g, 4.5 mmol, 91%).

6-((3aS,7aR)-3-fluoro-pyridin-4-yl)-2-(hexahydro-2,4-dioxa-7-aza-inden-7-yl)-3-methyl-3H-pyrimidin-4-one A solution of 2-chloro-3-methyl-6-(3-fluoro-pyridin-4-yl)-3H-pyrimidin-4-one (0.55 g, 2.3 mmol), (3aS,7aR)-hexahydro-2,4-dioxa-7-aza-indene hydrochloride (0.37 g, 2.3 mmol) and triethylamine (0.97 ml, 7.0 mmol) in tetrahydrofuran (10 ml) was prepared in a sealed tube and heated to 80° C. After the reaction mixture was stirred for 15 hours at that temperature and cooled to room temperature, the resulting mixture was poured into water. The organic materials were extracted with ethyl acetate and the combined organic phase was dried over sodium sulfate. Subsequent concentration of the mixture and purification of the resulting residue by silica gel column chromatography (eluent; hexane/ethyl acetate=1/2) led to afford 6-((3aS,7aR)-3-fluoro-pyridin-4-yl)-2-(hexahydro-2,4-dioxa-7-aza-inden-7-yl)-3-methyl-3H-pyrimidin-4-one (0.35 g, 1.0 mmol, 45%, $[\alpha]_D^{25}$ −123.8° (c 0.5, $CH_2Cl_2$)) as a white crystalline.

The compounds in the following table were prepared in the same manner as the methods described above. The compound numbers in the following table correspond to those shown in the above-described table of preferred compounds.

TABLE 2

| Compound No. | $^1$H-NMR | MS [M + 1] |
|---|---|---|
| B1 | 2.99 (1H, dd, J = 13.8, 6.6 Hz), 3.27-3.35 (5H, m), 3.55-4.02 (5H, m), 4.22 (1H, m), 6.82 (1H, s), 7.02-7.23 (5H, m), 8.41 (2H, d, J = 6.0 Hz), 8.94 (2H, d, J = 6.0 Hz) (DMSO-d6) | 363 [M + 1] |
| B2 | 2.99 (1H, dd, J = 13.5, 6.6 Hz), 3.22-3.35 (5H, m), 3.59-3.92 (5H, m), 4.22 (1H, m), 6.81 (1H, s), 7.02-7.23 (5H, m), 8.39 (2H, d, J = 6.6 Hz), 8.93 (2H, d, J = 6.6 Hz) (DMSO-d6) | 363 [M + 1] |
| B3 | 3.07-3.27 (3H, m), 3.39 (3H, s), 3.68-4.01 (6H, m),7.11-7.26 (6H, m), 8.13 (1H, d, J = 7.2 Hz), 8.89 (1H, d, J = 5.1 Hz), 9.28 (1H, s) (CDCl$_3$). | 364 [M + 1] |
| B4 | 3.09-3.27 (3H, m), 3.39 (3H, s), 3.68-4.02 (6H, m), 7.11-7.27 (6H, m), 8.13 (1H, dd, J = 5.4, 1.2 Hz), 8.88 (1H, d, J = 5.1 Hz), 9.28 (1H, d, J = 0.9 Hz) (CDCl$_3$). | 364 [M + 1] |
| B5 | 1.56-1.60 (1H, m), 2.20-2.26 (1H, m), 2.79-2.86 (3H, m), 3.50-3.56 (5H, m), 4.02-4.11 (2H, m), 4.59 (1H, dd, J = 1.2 Hz, 10.2 Hz), 7.05 (1H, s), 7.13-7.24 (3H, m), 7.47-7.50 (1H, m), 8.00 (2H, d, J = 4.2 Hz), 8.70 (2H, d, J = 4.2 Hz) (DMSO-d6) | 375 |

TABLE 2-continued

| Compound No. | ¹H-NMR | MS [M + 1] |
|---|---|---|
| B6 | 1.56-1.60 (1H, m), 2.24-2.28 (1H, m), 2.78-2.86 (3H, m), 3.27-3.40 (2H, m), 3.55 (3H, s), 4.02-4.11 (2H, m), 4.58 (1H, dd, J = 1.2 Hz, 10.2 Hz), 6.81 (1H, s), 7.12-7.23 (3H, m), 7.46-7.49 (1H, m), 7.98 (1H, dd, J = 1.2 Hz, 4.2 Hz), 8.58 (1H, d, J = 4.2 Hz), 8.71 (1H, d, J = 1.2 Hz) (DMSO-d6) | 393 |
| B7 | 1.56-1.60 (1H, m), 2.24-2.28 (1H, m), 2.78-2.98 (3H, m), 3.31-3.38 (2H, m), 3.56 (3H, s), 4.03-4.12 (2H, m), 4.60 (1H, dd, J = 1.2 Hz, 10.2 Hz), 7.13-7.24 (4H, m), 7.47-7.50 (1H, m), 8.24 (1H, d, J = 4.2 Hz), 9.00 (1H, d, J = 4.2 Hz), 9.32 (1H, s) (DMSO-d6) | 376 |
| B8 | 1.79 (2H, m), 1.90 (2H, m), 2.10 (1H, m), 2.21 (2H, m), 2.59 (1H, m), 3.27 (2H, m), 3.28 (3H, s), 3.89 (1H, d, J = 10.1 Hz), 4.20 (1H, m), 6.46 (1H, s), 7.17 (1H, m), 7.27 (4H, m), 7.74 (2H, dd, J = 4.5, 1.6 Hz), 8.67 (2H, dd, J = 4.5, 1.6 Hz) (CDCl₃). | 373 |
| B9 | 1.82 (4H, m), 2.06 (3H, m), 2.21 (1H, m), 3.54 (3H, s), 3.58 (1H, m), 3.65 (2H, m), 4.10 (1H, m), 6.57 (1H, s), 7.28 (1H, m), 7.35 (4H, m), 7.80 (2H, dd, J = 4.9, 1.1 Hz), 8.70 (2H, dd, J = 4.9, 1.1 Hz) (CDCl₃). | 373 |
| B10 | 1.82 (2H, m), 2.16 (3H, m), 2.70 (1H, m), 3.05 (1H, d, J = 10.2 Hz), 3.27 (1H, d, J = 9.9 Hz), 3.56 (3H, s), 3.91 (1H, d, J = 9.9 Hz), 4.42 (1H, s), 6.61 (1H, s), 7.76 (2H, d, J = 4.8 Hz), 8.70 (2H, d, J = 4.8 Hz) (CDCl₃). | 322 |
| B11 | 1.83 (2H, m), 1.98 (1H, m), 2.21 (1H, m), 2.71 (1H, m), 3.20 (1H, dd, J = 10.4, 4.0 Hz), 3.51 (1H, d, J = 10.4 Hz), 3.56 (3H, s), 3.79 (1H, dd, J = 10.4, 2.4 Hz), 4.08 (1H, m), 4.67 (1H, m), 6.67 (1H, s), 7.31 (1H, dd, J = 7.6 Hz), 7.45 (1H, t, J = 7.6 Hz), 7.53 (2H, t, J = 7.6 Hz), 7.81 (2H, dd, J = 4.4, 1.6 Hz), 8.73 (2H, dd, J = 4.4, 1.6 Hz) (CDCl₃). | 442 |
| B12 | 1.56 (1H, m), 1.65 (2H, m), 2.99 (2H, m), 2.74 (1H, t, J = 8.6 Hz), 3.15 (1H, t, J = 8.6 Hz), 3.31 (2H, m), 3.48 (1H, m), 3.49 (3H, s), 3.61 (1H, m), 4.12 (1H, m), 6.56 (1H, s), 6.73 (1H, d, J = 8.4 Hz), 6.79 (1H, t, J = 8.4 Hz), 7.31 (2H, t, J = 8.4 Hz), 7.79 (2H, d, J = 6.0 Hz), 8.71 (2H, d, J = 6.0 Hz) (CDCl₃). | 414 |
| B13 | 1.78 (1H, m), 1.90 (1H, m), 2.08 (2H, m), 2.21 (2H, m), 3.56 (3H, s), 3.58 (1H, m), 3.70 (2H, m), 4.15 (1H, s), 6.58 (1H, s), 7.36 (1H, t, J = 7.2 Hz), 7.46 (4H, m), 7.61 (4H, m), 7.82 (2H, dd, J = 4.8, 1.5 Hz), 8.71 (2H, dd, J = 4.8, 1.5 Hz) (CDCl₃). | 449 |
| B14 | 1.60-2.20 (11H, m), 3.30 (4H, m), 3.50 (3H, s), 3.69 (1H, d, J = 9.6 Hz), 4.01 (1H, s), 6.56 (1H, s), 6.58 (2H, d, J = 8.6 Hz), 7.21 (2H, d, J = 8.6 Hz), 7.82 (2H, dd, J = 4.8, 1.5 Hz), 8.69 (2H, dd, J = 4.8, 1.5 Hz) (CDCl₃). | 442 |
| B15 | 1.89-2.07 (6H, m), 2.32-2.40 (2H, m), 3.46 (3H, s), 3.68-3.70 (1H, m), 3.81 (3H, s), 4.38-4.41 (2H, m), 4.78 (1H, d, J = 8.2 Hz), 6.48-6.61 (2H, m), 6.74-6.84 (3H, m), 7.96 (2H, d, J = 4.2 Hz), 8.69 (2H, d, J = 4.2 Hz) (DMSO-d6) | 418 |
| B16 | 1.88-2.07 (6H, m), 2.31-2.38 (2H, m), 3.47 (3H, s), 3.70-3.73 (1H, m), 3.80 (3H, s), 4.36-4.40 (2H, m), 4.78 (1H, d, J = 8.2 Hz), 6.48-6.61 (3H, m), 6.76-6.86 (2H, m), 7.96 (1H, dd, J = 1.2, 4.2 Hz), 8.57 (1H, d, J = 4.2 Hz), 8.69 (1H, d, J = 1.2 Hz) (DMSO-d6) | 436 |
| B17 | 1.84-1.99 (4H, m), 2.15-2.32 (4H, m), 3.46 (3H, s), 3.51-3.53 (1H, m), 3.63 (3H, s), 4.35-4.40 (2H, m), 5.21-5.23 (1H, m), 6.53 (2H, d, J = 7.2 Hz), 6.72-6.75 (3H, m), 7.96 (2H, d, J = 4.2 Hz), 8.69 (2H, d, J = 4.2 Hz) (DMSO-d6) | 418 |
| B18 | 1.82-1.98 (4H, m), 2.15-2.31 (4H, m), 3.46 (3H, s), 3.51-3.53 (1H, m), 3.63 (3H, s), 4.33-4.36 (2H, m), 5.21-5.23 (1H, m), 6.50-6.57 (3H, m), 6.72 (2H, d, J = 7.2 Hz), 7.96 (1H, dd, J = 1.2, 4.2 Hz), 8.57 (1H, d, J = 4.2 Hz), 8.69 (1H, d, J = 1.2 Hz) (DMSO-d6) | 436 |
| B19 | 1.51-1.55 (1H, m), 2.23-2.26 (1H, m), 2.77-2.89 (3H, m), 3.26-3.34 (2H, m), 3.53 (3H, s), 3.73 (3H, s), 3.97-4.08 (2H, m), 4.52 (1H, d, J = 10.2 Hz), 6.71 (1H, d, J = 1.2 Hz), 6.81 (1H, dd, J = 1.2, 7.2 Hz), 7.06 (1H, s), 7.37 (1H, d, J = 7.2 Hz), 8.00 (2H, d, J = 4.2 Hz), 8.70 (2H, d, J = 4.2 Hz) (DMSO-d6) | 405 |
| B20 | 1.52-1.56 (1H, m), 2.23-2.27 (1H, m), 2.76-2.90 (3H, m), 3.23-3.28 (2H, m), 3.54 (3H, s), 3.72 (3H, s), 4.00-4.08 (2H, m), 4.51 (1H, d, J = 10.2 Hz), 6.70 (1H, d, J = 1.2 Hz), 6.77-6.80 (2H, m), 7.36 (1H, d, J = 7.3 Hz), 7.98 (1H, dd, J = 1.2, 4.2 Hz), 8.65 (1H, d, J = 4.2 Hz), 8.72 (1H, d, J = 1.2 Hz) (DMSO-d6) | 423 |
| B21 | 1.52-1.56 (1H, m), 2.23-2.27 (1H, m), 2.76-2.90 (3H, m), 3.30-3.40 (2H, m), 3.55 (3H, s), 3.73 (3H, s), 4.01-4.12 (2H, m), 4.53 (1H, d, J = 10.2 Hz), 6.71 (1H, d, J = 1.2 Hz), 6.80 (1H, dd, J = 1.2, 7.2 Hz), 7.18 (1H, s), 7.38 (1H, d, J = 7.2 Hz), 8.24 (1H, d, J = 4.2 Hz), 9.05 (1H, d, J = 4.2 Hz), 9.31 (1H, s) (DMSO-d6) | 406 |
| B22 | 1.48-1.58 (1H, m), 2.32-2.40 (1H, m), 2.65-2.84 (3H, m), 3.31-3.37 (2H, m), 3.53 (3H, s), 3.79 (3H, s), 4.02-4.13 (2H, m), 4.56 (1H, d, J = 10.2 Hz), 6.88 (1H, d, J = 7.2 Hz), 7.07 (1H, s), 7.11 (1H, d, J = 7.2 Hz), 7.22 (1H, dd, J = 7.1, 7.2 Hz), 8.00 (2H, d, J = 4.2 Hz), 8.71 (2H, d, J = 4.2 Hz) (CDCl₃). | 405 |
| B23 | 1.43-1.50 (1H, m), 2.28-2.34 (1H, m), 2.75-2.80 (3H, m), 3.25-3.35 (2H, m), 3.53 (3H, s), 3.78 (3H, s), 4.01-4.12 (2H, m), 4.55 (1H, d, J = 9.3 Hz), 6.81 (1H, s), 6.88 (1H, d, J = 7.2 Hz), 7.08 (1H, d, | 423 |

TABLE 2-continued

| Compound No. | ¹H-NMR | MS [M + 1] |
|---|---|---|
| | J = 7.2 Hz), 7.21 (1H, dd, J = 7.2 Hz, 7.3 Hz), 7.97 (1H, dd, J = 1.2 Hz, 4.2 Hz), 8.60 (1H, d, J =, 4.2 Hz), 8.73 (1H, d, J = 1.2 Hz) (CDCl₃) | |
| B24 | 1.42-1.52 (1H, m), 2.27-2.39 (1H, m), 2.81-2.96 (3H, m), 3.32-3.40 (2H, m), 3.55 (3H, s), 3.79 (3H, s), 4.02-4.13 (2H, m), 4.57 (1H, d, J = 10.2 Hz), 6.88 (1H, d, J = 7.2 Hz), 7.11 (1H, d, J = 7.2 Hz), 7.19 (1H, s), 7.22 (1H, dd, J = 7.2 Hz 7.3 Hz), 8.23 (1H, dd, J = 1.2 Hz, 4.2 Hz), 9.02 (1H, d, J = 4.2 Hz), 9.31 (1H, d, J = 1.2 Hz) (CDCl₃). | 406 |
| B25 | 1.48-1.58 (1H, m), 2.22-2.26 (1H, m), 2.73-2.88 (3H, m), 3.35-3.39 (2H, m), 3.54 (3H, s), 3.74 (3H, s), 3.98-4.15 (2H, m), 4.54 (1H, d, J = 10.2 Hz), 6.79 (1H, dd, J = 1.2 Hz 7.2 Hz), 7.00-7.07 (3H, m), 8.00 (2H, d, J = 4.2 Hz), 8.70 (2H, d, J = 4.2 Hz) (CDCl₃). | 405 |
| B26 | 1.53-1.56 (1H, m), 2.23-2.27 (1H, m), 2.77-2.86 (3H, m), 3.25-3.36 (2H, m), 3.54 (3H, s), 3.73 (3H, s), 4.01-4.14 (2H, m), 4.54 (1H, d, J = 9.3 Hz), 6.78-6.81 (2H, m), 6.99-7.01 (2H, m), 7.97 (1H, dd, J = 1.2 Hz, 4.2 Hz), 8.58 (1H, d, J = 4.2 Hz), 8.72 (1H, d, J = 1.2 Hz) (CDCl₃) | 423 |
| B27 | 1.50-1.58 (1H, m), 2.22-2.27 (1H, m), 2.73-2.91 (3H, m), 3.37-3.42 (2H, m), 3.55 (3H, s), 3.74 (3H, s), 4.02-4.15 (2H, m), 4.56 (1H, d, J = 10.2 Hz), 6.80 (1H, dd, J = 1.2 Hz 7.2 Hz), 7.01-7.08 (2H, m), 7.19 (1H, s), 8.23 (1H, dd, J = 1.2 Hz, 4.2 Hz), 9.00 (1H, d, J = 4.2 Hz), 9.31 (1H, d, J = 1.2 Hz) (CDCl₃). | 406 |
| B28 | 1.72-1.79 (1H, m), 2.41-2.44 (1H, m), 2.91-2.95 (2H, m), 3.47 (3H, s), 3.52-3.57 (2H, m), 3.93-4.02 (3H, m), 4.65 (1H, d, J = 1.2 Hz), 5.10 (1H, br), 7.03-7.32 (5H, m), 8.54 (2H, d, J = 4.2 Hz), 8.99 (2H, d, J = 4.2 Hz) (DMSO-d6). | 375 |
| B29 | 1.73-1.76 (1H, m), 2.37-2.42 (1H, m), 2.88-2.91 (2H, m), 3.45 (3H, s), 3.45-3.48 (2H, m), 3.90-4.00 (3H, m), 4.63 (1H, d, J =, 1.2 Hz), 6.59 (1H, dd, J = 1.2 Hz, 10.2 Hz), 7.13-7.31 (4H, m), 7.98 (1H, dd, J = 1.2 Hz, 4.2 Hz), 8.57 (1H, d, J = 4.2 Hz), 8.71 (1H, d, J = 1.2 Hz) (CDCl₃). | 393 |
| B30 | 1.72-1.78 (1H, m), 2.42-2.44 (1H, m), 2.90-2.95 (2H, m), 3.46 (3H, s), 3.48-3.53 (2H, m), 3.93-4.03 (3H, m), 4.65 (1H, d, J = 1.2 Hz), 7.00 (1H, s), 7.19-7.31 (4H, m), 8.21 (1H, dd, J = 1.2 Hz, 4.2 Hz), 9.00 (1H, d, J = 4.2 Hz), 9.30 (1H, d, J = 1.2 Hz) (CDCl₃). | 376 |
| B31 | 2.84-2.90 (1H, m), 3.51-3.58 (2H, m), 3.53 (3H, s), 3.88-3.94 (1H, m), 4.06-4.15 (2H, m), 4.64-4.68 (1H, m), 4.78 (1H, d, J = 9.9 Hz), 6.79-6.83 (2H, m), 6.95 (1H, dd, J = 7.2 Hz, 7.3 Hz), 7.21 (1H, dd, J = 7.2 Hz, 7.3 Hz), 7.37 (1H, d, J = 7.2 Hz), 7.95 (1H, dd, J = 1.2 Hz, 4.2 Hz), 8.60 (1H, d, J = 4.2 Hz), 8.74 (1H, d, J = 1.2 Hz) (CDCl₃) | 395 |
| B32 | 1.69-1.72 (1H, m), 2.38-2.42 (1H, m), 2.85-2.88 (2H, m), 3.38-3.44 (2H, m), 3.44 (3H, s), 3.72 (3H, s), 3.87-3.95 (3H, m), 4.57 (1H, d, J = 1.2 Hz), 6.58 (1H, s), 6.68 (1H, d, J = 1.2 Hz), 6.78 (1H, dd, J = 1.2 Hz, 7.2 Hz), 7.20 (1H, d, J = 7.2 Hz), 7.98 (1H, dd, J = 1.2 Hz, 4.2 Hz), 8.56 (1H, d, J = 4.2 Hz), 8.70 (1H, d, J = 1.2 Hz) (CDCl₃) | 423 |
| B33 | 2.87-2.91 (1H, m), 3.50-3.56 (2H, m), 3.52 (3H, s), 3.70 (3H, s), 3.82-3.88 (1H, m), 4.04-4.16 (2H, m), 4.58-4.62 (1H, m), 4.77 (1H, d, J = 9.9 Hz), 6.73-6.81 (3H, m), 6.89 (1H, d, J =, 1.2 Hz), 7.93 (1H, dd, J = 1.2 Hz, 4.2 Hz), 8.60 (1H, d, J = 4.2 Hz), 8.73 (1H, d, J = 1.2 Hz) (CDCl₃) | 425 |
| B34 | 1.69-1.76 (1H, m), 2.39-2.43 (1H, m), 2.80-2.84 (1H, m), 3.44 (3H, s), 3.42-3.53 (2H, m), 3.73 (3H, s), 3.92-3.97 (3H, m), 4.61 (1H, d, J = 1.2 Hz), 6.84-6.87 (3H, m), 7.06 (1H, d, J = 7.2 Hz), 7.98 (2H, d, J = 4.2 Hz), 8.70 (2H, d, J = 4.2 Hz) (CDCl₃). | 405 |
| B35 | 1.70-1.73 (1H, m), 2.34-2.44 (1H, m), 2.78-2.84 (2H, m), 3.44-3.52 (2H, m), 3.44 (3H, s), 3.72 (3H, s), 3.90-3.96 (3H, m), 4.59 (1H, d, J =, 1.2 Hz), 6.58 (1H, s), 6.84-6.88 (2H, m), 7.05 (1H, d, J = 7.3 Hz), 7.98 (1H, dd, J = 1.2 Hz, 4.2 Hz), 8.57 (1H, d, J = 4.2 Hz), 8.71 (1H, d, J = 1.2 Hz) (CDCl₃) | 423 |
| B36 | 1.72-1.78 (1H, m), 2.07-2.10 (1H, m), 2.81-2.84 (2H, m), 3.45 (3H, s), 3.44-3.55 (2H, m), 3.72 (3H, s), 3.92-4.00 (3H, m), 4.62 (1H, d, J = 1.2 Hz), 6.83-6.86 (2H, m), 6.99 (1H, s), 7.06 (1H, d, J = 7.2 Hz), 8.21 (1H, dd, J = 1.2 Hz, 4.2 Hz), 9.01 (1H, d, J = 4.2 Hz), 9.30 (1H, d, J = 1.2 Hz) (CDCl₃). | 406 |
| B37 | 1.72-1.78 (1H, m), 2.38-2.58 (2H, m), 2.89-2.93 (1H, m), 3.43 (3H, s), 3.45-3.53 (2H, m), 3.78 (3H, s), 3.91-3.94 (3H, m), 4.61 (1H, d, J = 1.2 Hz), 6.82 (1H, s), 6.90-6.92 (2H, m), 7.20 (1H, dd, J = 7.2 Hz 7.3 Hz), 7.98 (2H, d, J = 4.2 Hz), 8.69 (2H, d, J = 4.2 Hz) (CDCl₃). | 405 |
| B38 | 1.74-1.78 (1H, m), 2.35-2.40 (2H, m), 2.87-2.93 (1H, m), 3.43 (3H, s), 3.47-3.50 (2H, m), 3.78 (3H, s), 3.89-3.95 (3H, m), 4.60 (1H, d, J =, 1.2 Hz), 6.58 (1H, s), 6.89-6.91 (2H, m), 7.19 (1H, dd, J = 7.2 Hz, 7.3 Hz), 7.99 (1H, dd, J = 1.2 Hz, 4.2 Hz), 8.57 (1H, d, J = 4.2 Hz), 8.71 (1H, d, J = 1.2 Hz) (CDCl₃) | 423 |
| B39 | 1.76-1.80 (1H, m), 2.38-2.61 (2H, m), 2.88-2.94 (1H, m), 3.45 (3H, s), 3.46-3.54 (2H, m), 3.78 (3H, s), 3.91-3.99 (3H, m), 4.62 (1H, d, J = 1.2 Hz), 6.90-6.92 (2H, m), 6.99 (1H, s), 7.20 (1H, dd, J = 7.2 Hz 7.3 Hz), 8.20 (1H, dd, J = 1.2 Hz, 4.2 Hz), 9.01 (1H, d, J = 4.2 Hz), 9.30 (1H, d, J = 1.2 Hz) (CDCl₃). | 406 |

TABLE 2-continued

| Compound No. | ¹H-NMR | MS [M + 1] |
|---|---|---|
| B40 | 1.47-1.51 (2H, m), 1.94-1.98 (2H, m), 2.12-2.17 (1H, m), 2.61-2.98 (5H, m), 3.24-3.28 (2H, m), 3.64 (3H, s), 6.70 (1H, s), 7.11-7.52 (4H, m), 7.92 (1H, dd, J = 1.2 Hz, 4.2 Hz), 8.50 (1H, d, J = 4.2 Hz), 8.55 (1H, d, J = 1.2 Hz) (CDCl₃) | 391 |
| B41 | 1.31-1.34 (1H, m), 1.55-1.65 (1H, m), 1.80-1.90 (2H, m), 2.08-2.10 (1H, m), 2.65-2.88 (5H, m), 3.11-3.15 (1H, m), 3.16-3.20 (1H, m), 3.50 (3H, s), 3.72 (3H, s), 6.67 (1H, d, J = 1.2 Hz), 6.77 (1H, dd, J = 1.2 Hz 7.2 Hz), 7.02 (1H, s), 7.25 (1H, d, J = 7.2 Hz), 7.96 (2H, d, J = 4.2 Hz), 8.68 (2H, d, J = 4.2 Hz) (CDCl₃). | 403 |
| B42 | 1.28-1.32 (1H, m), 1.60-1.64 (1H, m), 1.82-1.85 (2H, m), 2.08-2.11 (1H, m), 2.67-2.86 (5H, m), 3.07-3.13 (1H, m), 3.33-3.36 (1H, m), 3.51 (3H, s), 3.71 (3H, s), 6.67-6.76 (3H, m), 7.24 (1H, d, J = 7.2 Hz), 7.92 (1H, dd, J = 1.2 Hz, 4.2 Hz), 8.57 (1H, d, J = 4.2 Hz), 8.70 (1H, d, J = 1.2 Hz) (CDCl₃) | 421 |
| B43 | 1.28-1.38 (1H, m), 1.55-1.63 (1H, m), 1.78-1.83 (2H, m), 2.00-2.12 (1H, m), 2.65-2.90 (5H, m), 3.14-3.18 (1H, m), 3.28-3.38 (1H, m), 3.51 (3H, s), 3.72 (3H, s), 6.68 (1H, d, J = 1.2 Hz), 6.77 (1H, dd, J = 1.2 Hz 7.2 Hz), 7.15 (1H, s), 7.26 (1H, d, J = 7.2 Hz), 8.16 (1H, dd, J = 1.2 Hz, 4.2 Hz), 8.9 (1H, d, J = 4.2 Hz), 9.31 (1H, d, J = 1.2 Hz) (CDCl₃). | 404 |
| B44 | 3.42-3.48 (2H, m), 3.46 (3H, s), 3.90-3.92 (2H, m), 4.28-4.32 (2H, m), 4.52-4.59 (1H, m), 4.75 (1H, d, J = 1.2 Hz), 6.84-6.86 (2H, m), 6.96 (1H, dd, J = 7.2 Hz 7.3 Hz), 7.23-7.33 (2H, m), 7.96 (2H, d, J = 4.2 Hz), 8.70 (2H, d, J = 4.2 Hz) (CDCl₃). | 377 |
| B45 | 3.29-3.32 (2H, m), 3.44 (3H, s), 3.88-3.90 (2H, m), 4.25-4.34 (2H, m), 4.52-4.59 (1H, m), 4.73 (1H, d, J =, 1.2 Hz), 6.61 (1H, s), 6.84 (1H, d, J = 7.2 Hz), 6.95 (1H, dd, J = 7.2 Hz, 7.3 Hz), 7.23-7.32 (2H, m), 7.96 (1H, dd, J = 1.2 Hz, 4.2 Hz), 8.57 (1H, d, J = 4.2 Hz), 8.71 (1H, d, J = 1.2 Hz) (CDCl₃) | 395 |
| B46 | 3.37-3.41 (2H, m), 3.42 (3H, s), 3.90-3.93 (2H, m), 4.32-4.36 (2H, m), 4.53-4.56 (1H, m), 4.76 (1H, d, J = 1.2 Hz), 6.84-6.98 (2H, m), 7.02 (1H, s), 7.23-7.34 (2H, m), 8.18 (1H, dd, J = 1.2 Hz, 4.2 Hz), 9.01 (1H, d, J = 4.2 Hz), 9.30 (1H, d, J = 1.2 Hz) (CDCl₃). | 378 |
| B47 | 3.25-3.29 (1H, m), 3.38-3.42 (1H, m), 3.51 (3H, s), 3.79 (3H, s), 3.96-4.02 (2H, m), 4.11-4.16 (2H, m), 4.58-4.63 (1H, m), 4.79 (1H, d, J = 1.2 Hz), 6.78-6.90 (4H, m), 7.88 (1H, dd, J = 1.2 Hz, 4.2 Hz), 8.52 (1H, d, J = 4.2 Hz), 8.57 (1H, d, J = 1.2 Hz) (CDCl₃). | 425 |
| B48 | 3.27-3.30 (1H, m), 3.41-3.45 (1H, m), 3.52 (3H, s), 3.80 (3H, s), 3.97-4.04 (2H, m), 4.15-4.20 (2H, m), 4.58-4.65 (1H, m), 4.81 (1H, d, J = 1.2 Hz), 6.79-6.91 (3H, m), 7.39 (1H, s), 8.11 (1H, dd, J = 1.2 Hz, 4.2 Hz), 8.57 (1H, d, J = 4.2 Hz), 9.27 (1H, d, J = 1.2 Hz) (CDCl₃). | 408 |
| B49 | 1.73-1.76 (1H, m), 2.37-2.42 (1H, m), 2.88-2.91 (2H, m), 3.45 (3H, s), 3.45-3.48 (2H, m), 3.90-4.00 (3H, m), 4.63 (1H, d, J =, 1.2 Hz), 6.59 (1H, dd, J = 1.2 Hz, 10.2 Hz), 7.13-7.31 (4H, m), 7.98 (1H, dd, J = 1.2 Hz, 4.2 Hz), 8.57 (1H, d, J = 4.2 Hz), 8.71 (1H, d, J = 1.2 Hz) (CDCl₃) | 393 |
| B50 | 1.72-1.78 (1H, m), 2.42-2.44 (1H, m), 2.90-2.95 (2H, m), 3.46 (3H, s), 3.48-3.53 (2H, m), 3.93-4.03 (3H, m), 4.65 (1H, d, J = 1.2 Hz), 7.00 (1H, s), 7.19-7.31 (4H, m), 8.21 (1H, dd, J = 1.2 Hz, 4.2 Hz), 9.00 (1H, d, J = 4.2 Hz), 9.30 (1H, d, J = 1.2 Hz) (CDCl₃). | 376 |
| B51 | 2.84-2.90 (1H, m), 3.51-3.58 (2H, m), 3.53 (3H, s), 3.88-3.94 (1H, m), 4.06-4.15 (2H, m), 4.64-4.68 (1H, m), 4.78 (1H, d, J = 9.9 Hz), 6.79-6.83 (2H, m), 6.95 (1H, dd, J = 7.2 Hz, 7.3 Hz), 7.21 (1H, dd, J = 7.2 Hz, 7.3 Hz), 7.37 (1H, d, J = 7.2 Hz), 7.95 (1H, dd, J = 1.2 Hz, 4.2 Hz), 8.60 (1H, d, J = 4.2 Hz), 8.74 (1H, d, J = 1.2 Hz) (CDCl₃) | 395 |
| B52 | 1.73-1.76 (1H, m), 2.37-2.42 (1H, m), 2.88-2.91 (2H, m), 3.45 (3H, s), 3.45-3.48 (2H, m), 3.90-4.00 (3H, m), 4.63 (1H, d, J =, 1.2 Hz), 6.59 (1H, dd, J = 1.2 Hz, 10.2 Hz), 7.13-7.31 (4H, m), 7.98 (1H, dd, J = 1.2 Hz, 4.2 Hz), 8.57 (1H, d, J = 4.2 Hz), 8.71 (1H, d, J = 1.2 Hz) (CDCl₃) | 393 |
| B53 | 1.72-1.78 (1H, m), 2.42-2.44 (1H, m), 2.90-2.95 (2H, m), 3.46 (3H, s), 3.48-3.53 (2H, m), 3.93-4.03 (3H, m), 4.65 (1H, d, J = 1.2 Hz), 7.00 (1H, s), 7.19-7.31 (4H, m), 8.21 (1H, dd, J = 1.2 Hz, 4.2 Hz), 9.00 (1H, d, J = 4.2 Hz), 9.30 (1H, d, J = 1.2 Hz) (CDCl₃). | 376 |
| B54 | 2.84-2.90 (1H, m), 3.51-3.58 (2H, m), 3.53 (3H, s), 3.88-3.94 (1H, m), 4.06-4.15 (2H, m), 4.64-4.68 (1H, m), 4.78 (1H, d, J = 9.9 Hz), 6.79-6.83 (2H, m), 6.95 (1H, dd, J = 7.2 Hz, 7.3 Hz), 7.21 (1H, dd, J = 7.2 Hz, 7.3 Hz), 7.37 (1H, d, J = 7.2 Hz), 7.95 (1H, dd, J = 1.2 Hz, 4.2 Hz), 8.60 (1H, d, J = 4.2 Hz), 8.74 (1H, d, J = 1.2 Hz) (CDCl₃) | 395 |
| B55 | 1.58-1.62 (1H, m), 2.30-2.34 (1H, m), 2.87-3.18 (4H, m), 3.49-3.56 (1H, m), 3.66 (3H, s), 4.07-4.11 (1H, m), 4.19-4.23 (1H, m), 4.55 (1H, d, J = 10.2 Hz), 6.84 (1H, s), 6.91-7.10 (2H, m), 7.30 (1H, d, J = 1.2 Hz), 7.80 (2H, d, J = 4.2 Hz), 8.73 (2H, d, J = 4.2 Hz) (CDCl₃). | 393 |
| B56 | 1.55-1.62 (1H, m), 2.29-2.33 (1H, m), 2.87-3.18 (4H, m), 3.46-3.52 (1H, m), 3.66 (3H, s), 4.04-4.10 (1H, m), 4.19-4.24 (1H, m), 4.54 (1H, dd, J = 1.2 Hz, 10.2 Hz), 6.90-7.10 (3H, m), 7.29 (1H, d, J = 1.2 Hz), 7.92 (1H, dd, J = 1.2 Hz, 4.2 Hz), 8.52 (1H, d, J = 4.2 Hz), 8.58 (1H, d, J = 1.2 Hz) (CDCl₃). | 411 |

TABLE 2-continued

| Compound No. | ¹H-NMR | MS [M + 1] |
|---|---|---|
| B57 | 1.58-1.62 (1H, m), 2.28-2.38 (1H, m), 2.89-3.18 (4H, m), 3.49-3.54 (1H, m), 3.67 (3H, s), 4.08-4.12 (1H, m), 4.20-4.24 (1H, m), 4.56 (1H, d, J = 10.2 Hz), 6.91-7.10 (2H, m), 7.30 (1H, d, J = 1.2 Hz), 7.50 (1H, s), 8.13 (1H, dd, J = 1.2 Hz, 4.2 Hz), 8.88 (1H, d, J = 4.2 Hz), 9.29 (1H, d, J = 1.2 Hz) (CDCl₃). | 394 |
| B58 | 1.78-1.82 (1H, m), 2.60-2.93 (3H, m), 3.33-3.38 (1H, m), 3.55 (3H, s), 3.60-3.66 (1H, m), 3.88-3.92 (1H, m), 4.02-4.06 (2H, m), 4.66 (1H, d, J = 1.2 Hz), 6.70 (1H, s), 6.96-7.14 (3H, m), 7.80 (2H, d, J = 4.2 Hz), 8.73 (2H, d, J = 4.2 Hz) (CDCl₃). | 393 |
| B59 | 1.77-1.81 (1H, m), 2.57-2.98 (3H, m), 3.31-3.35 (1H, m), 3.55-3.65 (4H, m), 3.84-3.89 (1H, m), 4.02-4.05 (2H, m), 4.66 (1H, d, J = 1.2 Hz), 6.88 (1H, s), 6.99-7.14 (3H, m), 7.93 (1H, dd, J = 1.2 Hz, 4.2 Hz), 8.52 (1H, d, J = 4.2 Hz), 8.56 (1H, d, J = 1.2 Hz) (CDCl₃). | 411 |
| B60 | 1.77-1.80 (1H, m), 2.58-2.98 (3H, m), 3.31-3.36 (1H, m), 3.56 (3H, s), 3.60-3.69 (1H, m), 3.87-3.91 (1H, m), 3.98-4.05 (2H, m), 4.67 (1H, d, J = 1.2 Hz), 6.97-7.14 (3H, m), 7.36 (1H, s), 8.13 (1H, dd, J = 1.2 Hz, 4.2 Hz), 8.88 (1H, d, J = 4.2 Hz), 9.29 (1H, d, J = 1.2 Hz) (CDCl₃). | 394 |
| B61 | 1.29 (3H, d, J = 7.2 Hz), 3.12-3.22 (1H, m), 3.42-3.48 (1H, m), 3.55 (3H, s), 3.60-3.64 (1H, m), 3.68-3.92 (4H, m), 6.71 (1H, s), 7.81 (2H, d, J = 4.2 Hz), 8.72 (2H, d, J = 4.2 Hz) (CDCl₃). | 287 |
| B62 | 1.27 (3H, t, J = 7.2 Hz), 3.10-3.17 (1H, m), 3.40-3.46 (1H, m), 3.55 (3H, s), 3.60-3.63 (1H, m), 3.68-3.72 (1H, m), 3.83-3.91 (3H, m), 6.90 (1H, s), 7.97 (1H, dd, J = 1.2 Hz, 4.2 Hz), 8.52 (1H, d, J = 4.2 Hz), 8.54 (1H, d, J = 1.2 Hz) (CDCl₃). | 305 |
| B63 | 1.26 (3H, d, J = 7.2 Hz), 3.10-3.18 (1H, m), 3.38-3.52 (1H, m), 3.56 (3H, s), 3.59-3.64 (1H, m), 3.68-3.72 (1H, m), 3.85-3.92 (3H, m), 7.37 (1H, s), 8.16 (1H, d, J = 4.2 Hz), 8.87 (1H, d, J = 4.2 Hz), 9.28 (1H, s) (CDCl₃). | 288 |
| B64 | 1.29 (3H, d, J = 7.2 Hz), 3.12-3.22 (1H, m), 3.42-3.48 (1H, m), 3.55 (3H, s), 3.60-3.64 (1H, m), 3.68-3.92 (4H, m), 6.71 (1H, s), 7.81 (2H, d, J = 4.2 Hz), 8.72 (2H, d, J = 4.2 Hz) (CDCl₃). | 287 |
| B65 | 1.27 (3H, t, J = 7.2 Hz), 3.10-3.17 (1H, m), 3.40-3.46 (1H, m), 3.55 (3H, s), 3.60-3.63 (1H, m), 3.68-3.72 (1H, m), 3.83-3.91 (3H, m), 6.90 (1H, s), 7.97 (1H, dd, J = 1.2 Hz, 4.2 Hz), 8.52 (1H, d, J = 4.2 Hz), 8.54 (1H, d, J = 1.2 Hz) (CDCl₃). | 305 |
| B66 | 1.26 (3H, d, J = 7.2 Hz), 3.10-3.18 (1H, m), 3.38-3.52 (1H, m), 3.56 (3H, s), 3.59-3.64 (1H, m), 3.68-3.72 (1H, m), 3.85-3.92 (3H, m), 7.37 (1H, s), 8.16 (1H, d, J = 4.2 Hz), 8.87 (1H, d, J = 4.2 Hz), 9.28 (1H, s) (CDCl₃). | 288 |
| B67 | 0.96-1.08 (1H, m), 1.35-1.56 (3H, m), 1.68-1.76 (1H, m), 1.79-1.83 (1H, m), 1.94-2.00 (1H, m), 2.11-2.16 (1H, m), 3.00-3.02 (2H, m), 3.16-3.20 (1H, m), 3.36-3.40 (1H, m), 3.61 (3H, s), 3.86-4.00 (2H, m), 6.81 (1H, s), 7.81 (2H, d, J = 4.2 Hz), 8.74 (2H, d, J = 4.2 Hz) (CDCl₃). | 327 |
| B68 | 0.96-1.04 (1H, m), 1.34-1.55 (3H, m), 1.66-1.74 (1H, m), 1.80-1.84 (1H, m), 1.94-2.00 (1H, m), 2.06-2.16 (1H, m), 2.98-3.02 (2H, m), 3.13-3.16 (1H, m), 3.37-3.40 (1H, m), 3.61 (3H, s), 3.87-4.01 (2H, m), 7.00 (1H, s), 7.95 (1H, dd, J = 1.2 Hz, 4.2 Hz), 8.51-8.61 (2H, m) (CDCl₃). | 345 |
| B69 | 0.98-1.06 (1H, m), 1.34-1.58 (3H, m), 1.66-1.72 (1H, m), 1.80-1.84 (1H, m), 1.98-2.02 (1H, m), 2.06-2.12 (1H, m), 2.98-3.02 (2H, m), 3.12-3.16 (1H, m), 3.33-3.39 (1H, m), 3.62 (3H, s), 3.82-3.98 (2H, m), 7.47 (1H, s), 8.16 (1H, d, J = 4.2 Hz), 8.90 (1H, d, J = 4.2 Hz), 9.29 (1H, s) (CDCl₃). | 328 |
| B70 | 3.24-3.27 (1H, m), 3.26 (3H, s), 3.53 (3H, s), 3.52-3.55 (1H, m), 3.68-3.96 (7H, m), 6.85 (1H, s), 7.94 (1H, dd, J = 1.2 Hz, 4.2 Hz), 8.51 (1H, d, J = 4.2 Hz), 8.56 (1H, d, J = 1.2 Hz) (CDCl₃). | 335 |
| B71 | 3.26 (3H, s), 3.26-3.28 (1H, m), 3.54 (3H, s), 3.55-3.99 (8H, m), 7.33 (1H, s), 8.14 (1H, d, J = 4.2 Hz), 8.87 (1H, d, J = 4.2 Hz), 9.28 (1H, s) (CDCl₃). | 318 |
| B72 | 3.27 (3H, s), 3.27-3.30 (1H, m), 3.53 (3H, s), 3.58-3.60 (1H, m), 3.79-3.97 (7H, m), 6.67 (1H, s), 7.98 (2H, d, J = 4.2 Hz), 8.71 (2H, d, J = 4.2 Hz) (CDCl₃). | 317 |
| B73 | 0.92 (3H, t, J = 7.2 Hz), 1.77-1.92 (2H, m), 3.23-3.28 (1H, m), 3.53 (3H, s), 3.52-3.56 (2H, m), 3.76-3.93 (4H, m), 6.67 (1H, s), 7.80 (2H, d, J = 4.2 Hz), 8.72 (2H, d, J = 4.2 Hz) (CDCl₃). | 301 |
| B74 | 0.92 (3H, t, J = 7.2 Hz), 1.76-1.92 (2H, m), 3.21-3.25 (1H, m), 3.48-3.52 (2H, m), 3.53 (3H, s), 3.76-3.92 (4H, m), 6.85 (1H, s), 7.94 (1H, dd, J = 1.2 Hz, 4.2 Hz), 8.51 (1H, d, J = 4.2 Hz), 8.55 (1H, d, J = 1.2 Hz) (CDCl₃). | 319 |
| B75 | 0.91 (3H, t, J = 7.2 Hz), 1.72-1.91 (2H, m), 3.22-3.26 (1H, m), 3.50-3.52 (2H, m), 3.53 (3H, s), 3.77-3.93 (4H, m), 7.33 (1H, s), 8.15 (1H, d, J = 4.2 Hz), 8.87 (1H, d, J = 4.2 Hz), 9.28 (1H, s) (CDCl₃). | 302 |
| B76 | 1.60-2.11 (10H, m), 3.57 (3H, s), 4.28-4.31 (2H, m), 6.60 (1H, s), 7.80 (2H, d, J = 4.2 Hz), 8.71 (2H, d, J = 4.2 Hz) (CDCl₃). | 297 |
| B77 | 1.60-2.10 (10H, m), 3.57 (3H, s), 4.25-4.27 (2H, m), 6.78 (1H, s), 7.96, 8.50 (1H, d, J = 4.2 Hz), 8.59 (1H, d, J = 1.2 Hz) (CDCl₃). | 315 |

TABLE 2-continued

| Compound No. | $^1$H-NMR | MS [M + 1] |
|---|---|---|
| B78 | 1.60-2.11 (10H, m), 3.58 (3H, s), 4.28-4.29 (2H, m), 7.24 (1H, s), 8.15 (1H, d, J = 4.2 Hz), 8.85 (1H, d, J = 4.2 Hz), 9.26 (1H, s) (CDCl$_3$). | 298 |
| B79 | 0.82 (3H, d, J = 6.8 Hz), 0.96 (3H, d, J = 6.8 Hz), 2.46-2.48 (1H, m), 3.40 (3H, s), 3.36-3.53 (5H, m), 3.77-3.80 (2H, m), 3.92-3.96 (1H, m), 4.36 (1H, br), 7.00 (1H, s), 8.57 (2H, d, J = 4.2 Hz), 8.96 (2H, d, J = 4.2 Hz) (DMSO-d6). | 315 |
| B80 | 0.82 (3H, d, J = 6.8 Hz), 0.95 (3H, d, J = 6.8 Hz), 2.38-2.42 (1H, m), 3.39 (3H, s), 3.38-3.52 (4H, m), 3.76-3.80 (2H, m), 3.92-3.96 (1H, m), 6.51 (1H, s), 6.81 (1H, br), 8.00 (1H, dd, J = 1.2 Hz, 4.2 Hz), 8.50 (1H, d, J = 4.2 Hz), 8.75 (1H, d, J = 1.2 Hz) (DMSO-d6). | 333 |
| B81 | 0.83 (3H, d, J = 6.8 Hz), 0.96 (3H, d, J = 6.8 Hz), 2.42-2.46 (1H, m), 3.40 (3H, s), 3.40-3.55 (4H, m), 3.77-3.82 (2H, m), 3.95-3.97 (1H, m), 6.57 (1H, br), 6.91 (1H, s), 8.22 (1H, d, J = 4.2 Hz), 9.01 (1H, d, J = 4.2 Hz), 9.30 (1H, s) (DMSO-d6). | 316 |
| B82 | 0.79 (3H, d, J = 7.0 Hz), 0.85 (3H, d, J = 7.0 Hz), 1.54-1.67 (3H, m), 3.33-3.40 (2H, m), 3.40 (3H, s), 3.50-3.92 (6H, m), 6.99 (1H, s), 8.41 (2H, d, J = 4.2 Hz), 8.92 (2H, d, J = 4.2 Hz) (DMSO-d6). | 329 |
| B83 | 0.80 (3H, d, J = 7.0 Hz), 0.85 (3H, d, J = 7.0 Hz), 1.52-1.63 (3H, m), 3.39 (3H, s), 3.33-4.04 (7H, m), 5.68 (1H, br), 6.54 (1H, s), 7.98 (1H, dd, J = 1.2 Hz, 4.2 Hz), 8.58 (1H, d, J = 4.2 Hz), 8.73 (1H, d, J = 1.2 Hz) (DMSO-d6). | 347 |
| B84 | 0.79 (3H, d, J = 7.0 Hz), 0.86 (3H, d, J = 7.0 Hz), 1.55-1.68 (3H, m), 3.35-3.37 (1H, m), 3.40 (3H, s), 3.53-3.90 (6H, m), 4.97 (1H, br), 6.95 (1H, s), 8.21 (1H, d, J = 4.2 Hz), 9.01 (1H, d, J = 4.2 Hz), 9.30 (1H, s) (DMSO-d6). | 330 |
| B85 | 1.23 (3H, d, J = 7.2 Hz), 3.19-3.25 (1H, m), 3.59 (3H, s), 3.65-3.82 (1H, m), 3.85-3.95 (2H, m), 4.07-4.21 (4H, m), 4.42-4.45 (1H, m), 6.70 (1H, s), 7.74 (2H, d, J = 4.2 Hz), 8.70 (2H, d, J = 4.2 Hz) (CDCl$_3$). | 345 |
| B86 | 1.22 (3H, d, J = 7.2 Hz), 3.20-3.28 (1H, m), 3.59 (3H, s), 3.62-3.78 (1H, m), 3.84-3.90 (2H, m), 4.07-4.20 (4H, m), 4.38-4.40 (1H, m), 6.90 (1H, s), 7.87 (1H, dd, J = 1.2 Hz, 4.2 Hz), 8.50 (1H, d, J = 4.2 Hz), 8.58 (1H, d, J = 1.2 Hz) (CDCl$_3$). | 363 |
| B87 | 1.23 (3H, d, J = 7.2 Hz), 3.12-3.20 (1H, m), 3.60 (3H, s), 3.62-3.72 (1H, m), 3.82-3.92 (2H, m), 4.08-4.18 (4H, m), 4.39-4.42 (1H, m), 7.36 (1H, d, J = 4.2 Hz), 8.86 (1H, d, J = 4.2 Hz), 9.27 (1H, s) (CDCl$_3$). | 346 |
| B88 | 2.94-3.00 (1H, m), 3.36-3.40 (1H, m), 3.49-3.53 (1H, m), 3.61 (3H, s), 3.64-3.65 (1H, m), 3.87-3.94 (3H, m), 4.73 (1H, dd, J = 1.2 Hz 10.2 Hz), 7.07 (1H, s), 7.15-7.26 (3H, m), 7.42-7.45 (2H, m), 8.26 (2H, d, J = 4.2 Hz), 8.90 (2H, d, J = 4.2 Hz) (DMSO-d6). | 349 |
| B89 | 2.94-3.00 (1H, m), 3.28-3.32 (1H, m), 3.58-3.60 (1H, m), 3.61 (3H, s), 3.86-3.90 (3H, m), 4.63 (1H, dd, J = 1.2 Hz 10.2 Hz), 6.58 (1H, s), 7.20-7.31 (3H, m), 7.38-7.42 (2H, m), 7.57 (1H, dd, J = 1.2 Hz, 4.2 Hz), 8.52 (1H, d, J = 4.2 Hz), 8.66 (1H, d, J = 1.2 Hz) (DMSO-d6). | 367 |
| B90 | 2.94-2.98 (1H, m), 3.34-3.38 (1H, m), 3.44-3.48 (1H, m), 3.60 (3H, s), 3.63-3.66N, 3.85-3.90 (3H, m), 4.71 (1H, dd, J = 1.2 Hz 10.2 Hz), 6.96 (1H, s), 7.11-7.22 (3H, m), 7.22-7.27 (2H, m), 7.98 (1H, d, J = 4.2 Hz), 8.98 (1H, d, J = 4.2 Hz), 9.23 (1H, s) (DMSO-d6). | 350 |
| B91 | 1.49-2.66 (15H, m), 3.26 (1H, td, J = 3.6 and 10.8 Hz), 3.43-3.50 (1H, m), 3.50 (3H, s), 3.63 (1H, m), 6.60 (1H, s), 7.80 (2H, d, J = 6.0 Hz), 8.70 (2H, d, J = 6.3 Hz) (CDCl$_3$) | 325 |
| B92 | 1.26-2.05 (15H, m), 3.25 (1H, td, J = 3.6 and 10.8 Hz), 3.26-3.51 (1H, m), 3.51 (3H, s), 3.64 (1H, m), 7.25 (1H, s), 8.15 (1H, dd, J = 1.2 and 6.0 Hz), 8.86 (1H, d, J = 5.1 Hz), 9.27 (1H, d, J = 1.2 Hz) (CDCl$_3$) | 326 |
| B93 | 1.41-2.06 (15H, m), 3.23 (1H, td, J = 3.6 and 10.8 Hz), 3.40 (1H, m), 3.50 (3H, s), 3.56-3.62 (1H, m), 6.72 (1H, s), 7.96 (1H, dd, J = 1.2 and 6.6 Hz), 8.51 (1H, d, J = 4.8 Hz), 8.54 (1H, d, J = 3.0 Hz) (CDCl$_3$) | 343 |
| B94 | 0.92 (3H, t, J = 7.2 Hz), 1.76-1.92 (2H, m), 3.21-3.25 (1H, m), 3.48-3.52 (2H, m), 3.53 (3H, s), 3.76-3.92 (4H, m), 6.85 (1H, s), 7.94 (1H, dd, J = 1.2 Hz, 4.2 Hz), 8.51 (1H, d, J = 4.2 Hz), 8.55 (1H, d, J = 1.2 Hz) (CDCl$_3$). | 319 |
| B95 | 1.15 (3H, d, J = 6.8 Hz), 2.98-3.04 (1H, m), 3.30-3.36 (1H, m), 3.48 (3H, s), 3.68-3.79 (5H, m), 4.82 (1H, br), 7.70 (1H, dd, J = 1.2 Hz, 4.2 Hz), 8.61 (1H, d, J = 4.2 Hz), 8.77 (1H, d, J = 1.2 Hz) (DMSO-d6). | 323 |
| B96 | 0.92 (3H, t, J = 7.2 Hz), 1.77-1.92 (2H, m), 3.23-3.28 (1H, m), 3.53 (3H, s), 3.52-3.56 (2H, m), 3.76-3.93 (4H, m), 6.67 (1H, s), 7.80 (2H, d, J = 4.2 Hz), 8.72 (2H, d, J = 4.2 Hz) (CDCl$_3$). | 301 |
| B97 | 0.91 (3H, t, J = 7.2 Hz), 1.72-1.91 (2H, m), 3.22-3.26 (1H, m), 3.50-3.52 (2H, m), 3.53 (3H, s), 3.77-3.93 (4H, m), 7.33 (1H, s), 8.15 (1H, d, J = 4.2 Hz), 8.87 (1H, d, J = 4.2 Hz), 9.28 (1H, s) (CDCl$_3$). | 302 |
| B98 | 1.21 (3H, d, J = 6.8 Hz), 3.04-3.12 (1H, m), 3.28-3.38 (1H, m), 3.55-3.65 (2H, m), 3.60 (3H, s), 3.85-3.92 (3H, m), 7.91 (2H, d, J = 4.2 Hz), 8.76 (2H, d, J = 4.2 Hz) (CDCl$_3$). | 305 |

TABLE 2-continued

| Compound No. | ¹H-NMR | MS [M + 1] |
|---|---|---|
| B99 | 1.18 (3H, d, J = 6.8 Hz), 3.10-3.14 (1H, m), 3.26-3.49 (2H, m), 3.36 (3H, s), 3.56-3.76 (5H, m), 6.43 (1H, s), 7.65 (1H, d, J = 4.2 Hz), 8.63 (1H, d, J = 4.2 Hz), 8.74 (1H, s) (DMSO-d6). | 321 |
| B100 | 1.18 (3H, d, J = 6.8 Hz), 2.50 (3H, s), 3.08-3.13 (1H, m), 3.37-3.54 (2H, m), 3.44 (3H, s), 3.64-3.79 (4H, m), 4.35 (1H, br), 6.43 (1H, s), 7.95 (1H, d, J = 4.2 Hz), 8.78 (1H, d, J = 4.2 Hz), 8.84 (1H, s) (DMSO-d6). | 301 |
| B101 | 1.22 (3H, d, J = 6.8 Hz), 3.16-3.20 (1H, m), 3.36-3.62 (2H, m), 3.48 (3H, s), 3.62-3.80 (4H, m), 4.90 (1H, br), 8.08 (2H, d, J = 4.2 Hz), 8.92 (2H, d, J = 4.2 Hz) (DMSO-d6). | 366 |
| B102 | 1.19 (3H, d, J = 6.8 Hz), 3.09-3.13 (1H, m), 3.32-3.36, 3.50 (3H, s), 3.52-3.56 (1H, m), 3.63-3.73 (4H, m), 5.52 (1H, br), 7.59 (1H, dd, J = 1.2 Hz, 4.2 Hz), 8.59 (1H, d, J = 4.2 Hz), 8.75 (1H, d, J = 1.2 Hz) (DMSO-d6). | 384 |
| B103 | 1.31 (3H, d, J = 6.8 Hz), 3.18-3.22 (1H, m), 3.58 (3H, s), 3.52-3.66 (2H, m), 3.76-3.80 (1H, m), 3.88-3.96 (3H, m), 6.84 (1H, s), 7.44-7.56 (5H, m), 8.18-8.20 (7H, m) (CDCl₃). | 439 |
| B104 | 1.18 (3H, d, J = 6.8 Hz), 3.16-3.18 (1H, m), 3.45 (3H, s), 3.51-3.55 (2H, m), 3.68-3.82 (4H, m), 4.12 (3H, s), 5.93 (1H, br), 6.91 (1H, s), 8.36 (1H, d, J = 4.2 Hz), 8.59 (1H, d, J = 4.2 Hz), 8.80 (1H, d, J = 4.2 Hz) (DMSO-d6). | 317 |
| B105 | 1.19 (3H, d, J = 6.8 Hz), 3.08-3.13 (1H, m), 3.32-3.40 (1H, m), 3.63 (3H, s), 3.63-3.66 (2H, m), 3.83-3.91 (3H, m), 7.97 (1H, dd, J = 1.2 Hz, 4.2 Hz), 8.91 (1H, d, J = 4.2 Hz), 9.40 (1H, d, J = 1.2 Hz) (CDCl₃). | 306 |
| B106 | 1.20 (3H, d, J = 6.8 Hz), 3.12-3.16 (1H, m), 3.34-3.38 (2H, m), 3.48 (3H, s), 3.64-3.78 (4H, m), 4.76 (1H, br), 7.81 (1H, dd, J = 1.2 Hz, 4.2 Hz), 9.00 (1H, d, J = 4.2 Hz), 9.34 (1H, d, J = 1.2 Hz) (DMSO-d6). | 367 |
| B107 | 1.0-1.6 (m, 7H); 1.6-1.9 (m, 5H); 2.70 (t, 1H); 3.04 (dt, 1H); 3.53 (s, 3H); 3.75 (bd, 1H); 3.85 (bd, 1H); 6.95 (s, 1H); 8.69 (d, 2H); 8.94 (d, 2H) (CD₃OD) | 325 |
| B108 | 2.4-3.1 (m, 3H); 3.57 (dd, 1H); 3.67 (s, 3H); 4.23 (q, 2H); 4.53 (dd, 1H); 4.7-4.8 (m, 1H); 5.20 (dd, 2H); 6.99 (s, 1H); 7.1-7.4 (m, 4H); 8.65 (d, 2H); 8.95 (d, 2H) (CD₃OD) | 388 |
| B109 | 3.1-3.3 (m, 2H); 3.4-4.1 (m, 9H); 3.64 (s, 3H); 4.7-5.1 (m, H); 7.14 (bs, 1H); 7.3-7.6 (m, 4H); 8.72 (d, 2H); 8.97 (d, 2H) (CD₃OD) | 374 |
| B110 | 2.6-2.8 (m, 3H); 3.0-3.2 (m, 4H); 3.35 (dt, 1H); 3.59 (bd, 2H); 3.61 (s, 3H); 4.11 (dt, 1H); 6.70 (s, 1H); 7.04 (d, 1H); 7.32 (s, 1H); 7.33 (d, 1H); 7.82 (d, 2H); 8.72 (d, 2H) (CD₃OD) | 453 |
| B111 | 1.44 (1H, m), 1.82 (2H, m), 1.98 (1H, m), 2.78 (1H, d, J = 13.2 Hz), 3.02 (5H, m), 3.23 (1H, m), 3.33 (1H, d, J = 13.2 Hz), 3.42 (1H, m), 3.50 (1H, m), 3.57 (3H, s), 6.68 (1H, s), 7.04 (1H, d, J = 7.6 Hz), 7.19 (3H, m), 7.77 (2H, dd, J = 3.6, 1.5 Hz), 8.70 (2H, dd, J = 3.6, 1.5 Hz) (CDCl₃) | 402 |
| B112 | 1.44 (1H, m), 1.84 (2H, m), 1.97 (1H, m), 2.99 (1H, d, J = 14.8 Hz), 3.07 (4H, m), 3.22 (1H, m), 3.32 (1H, d, J = 13.2 Hz), 3.40 (1H, m), 3.50 (1H, m), 3.58 (3H, s), 7.03 (2H, d, J = 8.0 Hz), 7.18 (3H, m), 7.34 (1H, s), 8.11 (1H, d, J = 4.8 Hz), 8.85 (1H, d, J = 4.8 Hz), 9.28 (1H, s) (CDCl₃) | 403 |
| B113 | 1.44 (1H, m), 1.82 (2H, m), 1.95 (1H, m), 2.78 (1H, d, J = 13.1 Hz), 3.05 (5H, m), 3.20 (1H, m), 3.31 (1H, d, J = 13.1 Hz), 3.40 (1H, m), 3.47 (1H, m), 3.57 (3H, s), 6.86 (1H, s), 7.04 (2H, d, J = 7.8 Hz), 7.19 (3H, m), 7.90 (1H, dd, J = 4.8, 3.2 Hz), 8.49 (1H, d, J = 4.8 Hz), 8.55 (1H, d, J = 3.0 Hz) (CDCl₃) | 420 |
| B114 | 1.88 (2H, m), 2.00 (2H, m), 2.97 (1H, m), 3.06 (1H, m), 3.17 (2H, m), 3.28 (s, 3H), 3.29 (2H, m), 3.46 (1H, d, J = 13.2 Hz), 3.80 (1H, d, J = 13.2 Hz), 6.78 (1H, s), 7.20 (1H, t, J = 7.5 Hz), 7.32 (2H, t, J = 7.5 Hz), 7.52 (2H, t, J = 7.5 Hz), 7.95 (1H, dd, J = 5.1, 3.3 Hz), 8.53 (1H, d, J = 5.1 Hz), 8.55 (1H, d, J = 3.3 Hz) (CDCl₃) | 406 |
| B115 | 2.02 (1H, m), 2.22 (1H, m), 2.37 (1H, m), 2.60 (1H, m), 3.36 (3H, s), 4.80-3.35 (6H, m), 3.87 (1H, d, J = 14.4 Hz), 4.00 (1H, d, J = 14.4 Hz), 6.99 (1H, s), 7.35 (1H, t, J = 7.6 Hz), 7.41 (2H, t, J = 7.6 Hz), 7.84 (2H, d, J = 7.6 Hz), 8.37 (2H, d, J = 6.8 Hz), 8.91 (2H, d, J = 6.8 Hz), 11.57 (1H, br s) (DMSO-d6) | 388 |
| B116 | 2.47-2.61 (3H, m), 2.76-2.98 (4H, m), 3.16-3.22 (1H, m), 3.44-3.48 (1H, m), 3.50 (3H, s), 3.60-3.63 (1H, m), 3.66 (3H, s), 3.71 (3H, s), 4.26 (1H, d, J = 10.2 Hz), 6.71 (1H, s), 6.84 (1H, s), 6.85 (1H, s), 8.00 (2H, d, J = 4.2 Hz), 8.69 (2H, d, J = 4.2 Hz) (CDCl₃). | 434 |
| B117 | 2.46-2.62 (3H, m), 2.75-2.79 (1H, m), 2.91-2.98 (3H, m), 3.14-3.18 (1H, m), 3.42-3.45 (1H, m), 3.50 (3H, s), 3.70-3.72 (1H, m), 3.72 (3H, s), 3.74 (3H, s), 4.26 (1H, dd, J = 1.2 Hz, 12.6 Hz), 6.60 (1H, s), 6.70 (1H, s), 6.82 (1H, s), 8.02 (1H, dd, J = 1.2 Hz, 4.2 Hz), 8.56 (1H, d, J = 4.2 Hz), 8.70 (1H, d, J = 1.2 Hz) (CDCl₃) | 452 |
| B118 | 2.47-2.61 (3H, m), 2.82-3.00 (4H, m), 3.21-3.29 (1H, m), 3.45-3.48 (1H, m), 3.52 (3H, s), 3.69-3.71 (1H, m), 3.73 (3H, s), 3.76 (3H, s), 4.26 (1H, d, J = 10.2 Hz), 6.72 (1H, s), 6.86 (1H, s), 7.01 (1H, s), | 435 |

TABLE 2-continued

| Compound No. | ¹H-NMR | MS [M + 1] |
|---|---|---|
| | 8.25 (1H, dd, J = 1.2 Hz, 4.2 Hz), 9.00 (1H, d, J = 4.2 Hz), 9.30 (1H, d, J = 1.2 Hz) (CDCl₃). | |
| B119 | 2.56-2.83 (4H, m), 2.97-3.16 (4H, m), 3.51 (3H, s), 3.52-3.54 (1H, m), 3.67-3.70 (1H, m), 4.24 (1H, dd, J = 1.2 Hz, 12.6 Hz), 6.60 (1H, s), 7.12-7.19 (3H, m), 7.35 (1H, dd, J = 7.2 Hz, 7.3 Hz), 8.01 (1H, dd, J = 1.2 Hz, 4.2 Hz), 8.57 (1H, d, J = 4.2 Hz), 8.71 (1H, d, J = 1.2 Hz) (CDCl₃) | 392 |
| B120 | 2.58-2.76 (3H, m), 2.83-2.90 (1H, m), 2.96-3.05 (3H, m), 3.12-3.22 (1H, m), 3.52 (3H, s), 3.52-3.56 (1H, m), 3.70-3.74 (1H, m), 4.26 (1H, d, J = 10.2 Hz), 7.01 (1H, s), 7.13-7.20 (3H, m), 7.39 (1H, dd, J = 7.2 Hz 7.3 Hz), 8.24 (1H, dd, J = 1.2 Hz, 4.2 Hz), 9.01 (1H, d, J = 4.2 Hz), 9.30 (1H, d, J = 1.2 Hz) (CDCl₃). | 375 |
| B121 | 1.83 (2H, m), 1.98 (1H, m), 2.21 (1H, m), 2.71 (1H, m), 3.20 (1, dd, J = 10.4, 4.0, 1H), 3.51 (1H, d, J = 10.4 Hz), 3.56 (3H, s), 3.71 (1H, dd, J = 10.4, 2.4 Hz), 4.08 (1H, m), 4.67 (1H, m), 6.67 (1H, s), 7.31 (1H, d, J = 7.6 Hz), 7.45 (1H, t, J = 7.6 Hz), 7.53 (2H, t, J = 7.6 Hz), 7.81 (2H, dd, J = 4.4, 1.6 Hz), 8.73 (2H, dd, J = 4.4, 1.6 Hz) (CDCl₃) | 442 |
| B122 | 1.56 (1H, m), 1.65 (2H, m), 1.99 (2H, m), 2.10 (2H, m), 2.74 (1H, t, J = 8.6 Hz), 3.15 (1H, t, J = 8.6 Hz), 3.31 (2H, t, J = 10.5 Hz), 3.48 (1H, m), 3.49 (3H, s), 3.61 (1H, m), 4.12 (1H, m), 6.56 (1H, s), 6.73 (1H, d, J = 8.4 Hz), 6.79 (1H, t, J = 8.4 Hz), 7.31 (2H, d, J = 8.4 Hz), 7.79 (2H, d, J = 6.0 Hz), 8.71 (2H, d, J = 6.0 Hz) (CDCl₃) | 414 |
| B123 | 1.28 (3H, d, J = 6.6 Hz), 3.20 (1H, m), 3.44 (1H, m), 3.58 (3H, s), 3.62-3.64 (1H, m), 3.74 (1H, m), 3.87-3.94 (3H, m), 7.49-7.53 (3H, m), 7.59 (1H, s), 8.02 (1H, d, J = 5.1 Hz), 8.55 (1H, dd, J = 6.3, 2.4 Hz), 8.95 (1H, d, J = 5.1 Hz) (CDCl₃). | 364 |
| B124 | 1.16-1.24 (6H, m), 1.72-1.78 (6H, m), 2.20 (1H, m), 2.69 (1H, m), 2.91 (1H, td, J = 10.2, 3.0 Hz), 3.10 (1H, d, J = 12.6 Hz), 3.59 (3H, s), 6.78 (1H, s), 7.80 (2H, d, J = 6.0 Hz), 8.74 (2H, d, J = 6.0 Hz) (CDCl₃) | 325 |
| B125 | 1.16-1.24 (6H, m), 1.72-1.78 (6H, m), 2.20 (1H, m), 2.69 (1H, m), 2.91 (1H, td, J = 10.2, 3.0 Hz), 3.10 (1H, d, J = 12.6 Hz), 3.59 (3H, s), 7.20 (1H, s), 8.14 (1H, d, J = 5.4 Hz), 8.85 (1H, d, J = 5.1 Hz), 9.27 (1H, s) (CDCl₃) | 326 |
| B126 | 1.16-1.24 (6H, m), 1.72-1.78 (6H, m), 2.20 (1H, m), 2.69 (1H, m), 2.91 (1H, td, J = 10.2, 3.0 Hz), 3.10 (1H, d, J = 12.6 Hz), 3.59 (3H, s), 6.96 (1H, s), 7.94 (1H, dd, J = 6.6, 5.1 Hz), 8.53 (1H, d, J = 5.1 Hz), 8.56 (1H, d, J = 3.0 Hz) (CDCl₃) | 343 |
| B127 | 3.28-3.32 (1H, m), 3.51-3.55 (1H, m), 3.51 (3H, s), 3.73-3.77 (2H, m), 3.85-3.97 (5H, m), 4.41 (2H, q, J = 12.0 Hz), 6.61 (1H, s), 7.14-7.26 (5H, m), 7.71 (2H, d, J = 4.8 Hz), 8.71 (2H, d, J = 4.2 Hz) (CDCl₃). | 393 |
| B128 | 3.24-3.28 (1H, m), 3.49-3.52 (1H, m), 3.51 (3H, s), 3.72-3.78 (2H, m), 3.86-3.96 (5H, m), 4.41 (2H, q, J = 12.0 Hz), 6.79 (1H, s), 7.14-7.19 (2H, m), 7.22-7.26 (3H, m), 7.90 (1H, dd, J = 2.4 Hz, 5.4 Hz), 8.49 (1H, d, J = 5.4 Hz), 8.55 (1H, d, J = 2.4 Hz) (CDCl₃). | 411 |
| B129 | 3.34-3.41 (1H, m), 3.61 (3H, s), 3.52-3.67 (4H, m), 3.82-3.96 (5H, m), 4.38 (2H, q, J = 12.0 Hz), 6.91 (1H, s), 7.10-7.18 (5H, m), 8.21 (1H, J = 1.2 Hz, 4.2 Hz), 9.00 (1H, d, J = 4.2 Hz), 9.30 (1H, d, J = 1.2 Hz) (DMSO-d6). | 394 |
| B130 | 0.96-1.08 (1H, m), 1.35-1.56 (3H, m), 1.68-1.76 (1H, m), 1.79-1.83 (1H, m), 1.94-2.00 (1H, m), 2.11-2.16 (1H, m), 3.00-3.02 (2H, m), 3.16-3.20 (1H, m), 3.36-3.40 (1H, m), 3.61 (3H, s), 3.86-4.00 (2H, m), 6.81 (1H, s), 7.81 (2H, d, J = 4.2 Hz), 8.74 (2H, d, J = 4.2 Hz) (CDCl₃). | 327 |
| B131 | 0.96-1.04 (1H, m), 1.34-1.55 (3H, m), 1.66-1.74 (1H, m), 1.80-1.84 (1H, m), 1.94-2.00 (1H, m), 2.06-2.16 (1H, m), 2.98-3.02 (2H, m), 3.13-3.16 (1H, m), 3.37-3.40 (1H, m), 3.61 (3H, s), 3.87-4.01 (2H, m), 7.00 (1H, s), 7.95 (1H, dd, J = 2.4 Hz, 5.4 Hz), 8.51-8.61 (2H, m) (CDCl₃). | 345 |
| B132 | 0.98-1.06 (1H, m), 1.34-1.58 (3H, m), 1.66-1.72 (1H, m), 1.80-1.84 (1H, m), 1.98-2.02 (1H, m), 2.06-2.12 (1H, m), 2.98-3.02 (2H, m), 3.12-3.16 (1H, m), 3.33-3.39 (1H, m), 3.62 (3H, s), 3.82-3.98 (2H, m), 7.47 (1H, s), 8.16 (1H, d, J = 4.2 Hz), 8.90 (1H, d, J = 4.2 Hz), 9.29 (1H, s) (CDCl₃) | 328 |
| B133 | 1.22-1.32 (1H, m), 1.67-2.03 (4H, m), 2.26-2.41 (1H, m), 2.81-2.92 (1H, m), 3.17-3.23 (2H, m), 3.50-3.52 (1H, m), 3.59 (3H, s), 3.90-3.95 (1H, m), 4.06-4.11 (1H, m), 6.76 (1H, s), 7.80 (2H, d, J = 4.8 Hz), 8.74 (2H, d, J = 4.8 Hz) (CDCl₃) | 313 |
| B134 | 1.20-1.38 (1H, m), 1.59-1.77 (3H, m9, 1.92-1.99 (1H, m), 2.24-2.38 (1H, m), 2.81-2.89 (1H, m), 3.12-3.22 (2H, m), 3.46-3.51 (1H, m), 3.59 (3H, s), 3.90-3.95 (1H, m), 4.04-4.10 (1H, m), 6.94 (1H, s), 7.95 (1H, dd, J = 2.4 Hz, 5.4 Hz), 8.54-8.57 (2H, m) (CDCl₃). | 331 |
| B135 | 1.18-1.30 (1H, m), 1.71-1.77 (3H, m), 1.98-2.03 (1H, m), 2.28-2.38 (1H, m), 2.82-2.90 (1H, m), 3.16-3.23 (2H, m), 3.51-3.55 (1H, m), 3.60 (3H, s), 3.86-3.94 (1H, m), 4.06-4.10 (1H, m), 7.42 (1H, s), 8.16 (1H, dd, J = 1.2 Hz, 4.2 Hz), 8.91 (1H, d, J = 4.2 Hz), 9.29 (1H, d, J = 1.2 Hz) (CDCl₃). | 314 |
| B136 | 0.96-1.08 (1H, m), 1.35-1.56 (3H, m), 1.68-1.76 (1H, m), 1.79-1.83 (1H, m), 1.94-2.00 (1H, m), 2.11-2.16 (1H, m), 3.00-3.02 (2H, m), 3.16-3.20 (1H, m), 3.36-3.40 (1H, m), 3.61 (3H, s), 3.86-4.00 (2H, m), 6.81 (1H, s), 7.81 (2H, d, J = 4.2 Hz), 8.74 (2H, d, J = 4.2 Hz) (CDCl₃). | 327 |

TABLE 2-continued

| Compound No. | $^1$H-NMR | MS [M + 1] |
|---|---|---|
| B137 | 0.96-1.04 (1H, m), 1.34-1.55 (3H, m), 1.66-1.74 (1H, m), 1.80-1.84 (1H, m), 1.94-2.00 (1H, m), 2.06-2.16 (1H, m), 2.98-3.02 (2H, m), 3.13-3.16 (1H, m), 3.37-3.40 (1H, m), 3.61 (3H, s), 3.87-4.01 (2H, m), 7.00 (1H, s), 7.95 (1H, dd, J = 2.4 Hz, 5.4 Hz), 8.51-8.61 (2H, m) (CDCl$_3$). | 345 |
| B138 | 0.98-1.06 (1H, m), 1.34-1.58 (3H, m), 1.66-1.72 (1H, m), 1.80-1.84 (1H, m), 1.98-2.02 (1H, m), 2.06-2.12 (1H, m), 2.98-3.02 (2H, m), 3.12-3.16 (1H, m), 3.33-3.39 (1H, m), 3.62 (3H, s), 3.82-3.98 (2H, m), 7.47 (1H, s), 8.16 (1H, d, J = 4.2 Hz), 8.90 (1H, d, J = 4.2 Hz), 9.29 (1H, s) (CDCl$_3$). | 328 |
| B139 | 1.01 (3H, d, J = 6.0 Hz), 1.13 (3H, d, J = 5.4 Hz), 1.18 (1H, m), 1.32 (1H, d, J = 12 Hz), 1.79 (2H, t, J = 15.0 Hz), 2.67 (1H, t, J = 12.3 Hz), 3.13 (1H, dd, J = 12.0, 2.4 Hz), 3.40 (1H, m), 3.59 (3H, s), 7.42 (1H, s), 8.19 (1H, d, J = 4.5 Hz), 8.88 (1H, d, J = 5.1 Hz), 9.28 (1H, s) (CDCl$_3$) | 300 |
| B140 | 1.01 (3H, d, J = 5.4 Hz), 1.13 (3H, d, J = 5.4 Hz), 1.25 (1H, m), 1.35 (1H, d, J = 12 Hz), 1.79 (2H, t, J = 15.7 Hz), 2.67 (1H, t, J = 12.3 Hz), 3.13 (1H, d, J = 11.7 Hz), 3.40 (1H, m), 3.59 (3H, s), 7.41 (1H, s), 8.19 (1H, s), 8.89 (1H, d, J = 4.4 Hz), 9.27 (1H, s) (CDCl$_3$) | 300 |
| B141 | 1.88-2.03 (5H, m), 2.43 (1H, m), 2.70 (1H, dd, J = 12.9, 9.3 Hz), 3.14 (1H, t, J = 12.2 Hz), 3.38-3.61 (4H, m), 3.53 (3H, s), 3.80 (1H, t, J = 11.6 Hz), 4.02 (1H, d, J = 11.1 Hz), 6.86 (1H, s), 7.96 (1H, dd, J = 4.8, 6.3 Hz), 8.52 (1H, d, J = 4.8 Hz), 8.54 (1H, d, J = 2.7 Hz) (CDCl$_3$) | 345 |
| B142 | 1.88-2.02 (5H, m), 2.42 (1H, m), 2.70 (1H, dd, J = 12.9, 9.3 Hz), 3.15 (1H, t, J = 12.2 Hz), 3.38-3.61 (4H, m), 3.53 (3H, s), 3.80 (1H, t, J = 11.6 Hz), 4.02 (1H, d, J = 11.1 Hz), 6.86 (1H, s), 7.96 (1H, s), 8.52 (1H, m), 8.55 (1H, s) (CDCl$_3$) | 345 |
| B143 | 0.93 (3H, t, J = 6.6 Hz), 1.35-1.60 (5H, m), 2.83 (1H, dd, J = 10.5, 12.9 Hz), 3.16 (1H, m), 3.41-3.48 (3H, m), 3.52 (3H, s), 3.64 (1H, m), 3.80 (1H, td, J = 11.4, 2.1 Hz), 3.99 (1H, dd, J = 11.1, 1.5 Hz), 6.86 (1H, s), 7.96 (1H, dd, J = 6.3, 5.4 Hz), 8.52 (1H, d, J = 5.1 Hz), 8.55 (1H, d, J = 3.3 Hz) (CDCl$_3$) | 347 |
| B144 | 1H NMR (300 MHz, CDCl3) 0.93 (3H, t, J = 6.9 Hz), 1.36-1.61 (5H, m), 2.83 (1H, dd, J = 10.8, 12.6 Hz), 3.16 (1H, t, J = 12.3 Hz), 3.41-3.48 (3H, m), 3.52 (3H, s), 3.64 (1H, m), 3.80 (1H, t, J = 11.7 Hz), 3.99 (1H, dd, J = 11.1, 1.5 Hz), 6.86 (1H, s), 7.96 (1H, dd, J = 6.3, 5.4 Hz), 8.52 (1H, d, J = 5.1 Hz), 8.55 (1H, d, J = 3.3 Hz). | 347 |
| B145 | 1.15-1.78 (12H, m), 2.02 (1H, m), 2.65 (1H, m), 2.87 (1H, m), 3.10 (1H, d, J = 12.9 Hz), 3.59 (3H, s), 6.96 (1H, s), 7.93 (1H, dd, J = 6.3, 5.4 Hz), 8.53 (1H, d, J = 4.8 Hz), 8.56 (1H, d, J = 3.3 Hz) (CDCl$_3$) | 343 |
| B146 | 1.15-1.78 (12H, m), 2.02 (1H, d, J = 12.6 Hz), 2.68 (1H, m), 2.87 (1H, m), 3.10 (1H, d, J = 12.6 Hz), 3.59 (3H, s), 6.96 (1H, s), 7.93 (1H, dd, J = 6.6 Hz, 5.4 Hz), 8.53 (1H, d, J = 4.8 Hz), 8.56 (1H, d, J = 3.3 Hz) (CDCl$_3$) | 343 |
| B147 | 1.50 (3H, d, J = 6.8 Hz), 3.47-3.54 (2H, m), 3.54 (3H, s), 3.78-3.85 (1H, m), 3.92-3.96 (1H, m), 4.08-4.11 (1H, m), 4.78 (1H, dd, J = 1.2 Hz, 10.2 Hz), 6.77 (1H, s), 7.36-7.47 (5H, m), 7.79 (2H, d, J = 4.8 Hz), 8.72 (2H, d, J = 4.8 Hz) (CDCl$_3$). | 363 |
| B148 | 1.50 (3H, d, J = 6.8 Hz), 3.41-3.50 (2H, m), 3.50 (3H, s), 3.74-3.80 (1H, m), 3.91-3.96 (1H, m), 4.06-4.11 (1H, m), 4.77 (1H, dd, J = 1.2 Hz, 10.2 Hz), 6.86 (1H, s), 7.38-7.50 (5H, m), 7.91 (1H, dd, J = 2.4 Hz, 5.4 Hz), 8.51 (1H, d, J = 5.4 Hz), 8.55 (1H, d, J = 2.4 Hz) (CDCl$_3$). | 381 |
| B149 | 1.49 (3H, d, J = 6.8 Hz), 3.48-3.51 (2H, m), 3.56 (3H, s), 3.79-3.81 (1H, m), 3.93-3.96 (1H, m), 4.09-4.13 (1H, m), 4.76 (1H, dd, J = 1.2 Hz, 10.2 Hz), 7.26 (1H, s), 7.36-7.52 (5H, m), 8.12 (1H, dd, J = 1.2 Hz, 4.2 Hz), 8.86 (1H, d, J = 4.2 Hz), 9.27 (1H, s) (CDCl$_3$). | 364 |
| B150 | 1.12 (3H, d, J = 6.8 Hz), 2.82-2.90 (1H, m), 3.16-3.22 (1H, m), 3.61-3.75 (2H, m), 3.67 (3H, s), 4.11-4.15 (1H, m), 4.72 (1H, dd, J = 1.2 Hz, 10.2 Hz), 6.80 (1H, s), 7.26-7.40 (5H, m), 7.82 (2H, d, J = 4.8 Hz), 8.73 (2H, d, J = 4.8 Hz) (CDCl$_3$). | 363 |
| B151 | 1.11 (3H, d, J = 6.8 Hz), 2.81-2.88 (1H, m), 3.16-3.22 (1H, m), 3.60-3.73 (2H, m), 3.67 (3H, s), 4.10-4.14 (1H, m), 4.72 (1H, dd, J = 1.2 Hz, 10.2 Hz), 6.98 (1H, s), 7.26-7.40 (5H, m), 7.98 (1H, dd, J = 2.4 Hz, 5.4 Hz), 8.54-8.58 (2H, m) (CDCl$_3$). | 381 |
| B152 | 1.10 (3H, d, J = 6.8 Hz), 2.82-2.89 (1H, m), 3.17-3.22 (1H, m), 3.62-3.75 (2H, m), 3.68 (3H, s), 4.11-4.16 (1H, m), 4.74 (1H, dd, J = 1.2 Hz, 10.2 Hz), 7.23-7.45 (6H, m), 8.20 (1H, dd, J = 1.2 Hz, 4.2 Hz), 8.90 (1H, d, J = 4.2 Hz), 9.28 (1H, s) (CDCl$_3$). | 364 |
| B153 | 1.28 (3H, d, J = 6.8 Hz), 1.37 (3H, d, J = 6.8 Hz), 3.19-3.30 (2H, m), 3.51 (3H, s), 3.74-3.82 (3H, m), 3.95 (1H, dd, J = 1.2 Hz, 10.2 Hz), 6.65 (1H, s), 7.78 (2H, d, J = 4.8 Hz), 8.72 (2H, d, J = 4.2 Hz) (CDCl$_3$). | 301 |
| B154 | 1.27 (3H, d, J = 6.8 Hz), 1.36 (3H, d, J = 6.8 Hz), 3.20-3.32 (2H, m), 3.51 (3H, s), 3.71-3.81 (3H, m), 3.94 (1H, dd, J = 1.2 Hz, 10.2 Hz), 6.83 (1H, s), 7.93 (1H, dd, J = 2.4 Hz, 5.4 Hz), 8.52-8.56 (2H, m) (CDCl$_3$). | 319 |
| B155 | 1.28 (3H, d, J = 6.8 Hz), 1.36 (3H, d, J = 6.8 Hz), 3.19-3.32 (2H, m), 3.52 (3H, s), 3.72-3.83 (3H, m), 3.95 (1H, dd, J = 1.2 Hz, 10.2 Hz), 7.30 (1H, s), 8.13 (1H, dd, J = 1.2 Hz, 4.2 Hz), 8.87 (1H, d, J = 4.2 Hz), 9.28 (1H, s) (CDCl$_3$). | 302 |

TABLE 2-continued

| Compound No. | $^1$H-NMR | MS [M + 1] |
|---|---|---|
| B156 | 1.05 (3H, d, J = 6.8 Hz), 1.23 (3H, d, J = 6.8 Hz), 2.54-2.62 (1H, m), 3.00-3.04 (1H, m), 3.46-3.50 (1H, m), 3.59-62 (1H, m), 3.60 (3H, s), 3.80-3.83 (1H, m), 3.94 (1H, dd, J = 1.2 Hz, 10.2 Hz), 6.80 (1H, s), 7.81 (2H, d, J = 4.8 Hz), 8.74 (2H, d, J = 4.2 Hz) (CDCl$_3$). | 301 |
| B157 | 1.04 (3H, d, J = 6.8 Hz), 1.22 (3H, d, J = 6.8 Hz), 2.52-2.60 (1H, m), 2.97-3.00 (1H, m), 3.41-3.57 (2H, m), 3.57 (3H, s), 3.78-3.86 (1H, m), 3.95 (1H, dd, J = 1.2 Hz, 10.2 Hz), 6.99 (1H, s), 7.96 (1H, dd, J = 2.4 Hz, 5.4 Hz), 8.51-8.58 (2H, m) (CDCl$_3$). | 319 |
| B158 | 1.04 (3H, d, J = 6.8 Hz), 1.22 (3H, d, J = 6.8 Hz), 2.53-2.60 (1H, m), 3.00-3.05 (1H, m), 3.46-3.51 (1H, m), 3.57-61 (1H, m), 3.61 (3H, s), 3.80-3.86 (1H, m), 3.93 (1H, dd, J = 1.2 Hz, 10.2 Hz), 7.46 (1H, s), 8.17 (1H, dd, J = 1.2 Hz, 4.2 Hz), 8.90 (1H, d, J = 4.2 Hz), 9.29 (1H, s) (CDCl$_3$). | 302 |
| B159 | 1.22-1.32 (1H, m), 1.67-2.03 (4H, m), 2.26-2.41 (1H, m), 2.81-2.92 (1H, m), 3.17-3.23 (2H, m), 3.50-3.52 (1H, m), 3.59 (3H, s), 3.90-3.95 (1H, m), 4.06-4.11 (1H, m), 6.76 (1H, s), 7.80 (2H, d, J = 4.8 Hz), 8.74 (2H, d, J = 4.8 Hz) (CDCl$_3$). | 313 |
| B160 | 1.20-1.38 (1H, m), 1.59-1.77 (3H, m9, 1.92-1.99 (1H, m), 2.24-2.38 (1H, m), 2.81-2.89 (1H, m), 3.12-3.22 (2H, m), 3.46-3.51 (1H, m), 3.59 (3H, s), 3.90-3.95 (1H, m), 4.04-4.10 (1H, m), 6.94 (1H, s), 7.95 (1H, dd, J = 2.4 Hz, 5.4 Hz), 8.54-8.57 (2H, m) (CDCl$_3$). | 331 |
| B161 | 1.18-1.30 (1H, m), 1.71-1.77 (3H, m), 1.98-2.03 (1H, m), 2.28-2.38 (1H, m), 2.82-2.90 (1H, m), 3.16-3.23 (2H, m), 3.51-3.55 (1H, m), 3.60 (3H, s), 3.86-3.94 (1H, m), 4.06-4.10 (1H, m), 7.42 (1H, s), 8.16 (1H, dd, J = 1.2 Hz, 4.2 Hz), 8.91 (1H, d, J = 4.2 Hz), 9.29 (1H, d, J = 1.2 Hz) (CDCl$_3$). | 314 |
| B162 | 3.23-3.32 (2H, m), 3.42-3.47 (1H, m), 3.55 (3H, s), 3.75-3.90 (2H, m), 4.13-4.26 (2H, m), 6.74 (1H, s), 7.78 (2H, d, J = 4.8 Hz), 8.75 (2H, d, J = 4.8 Hz) (CDCl$_3$). | 341 |
| B163 | 3.21-3.30 (2H, m), 3.41-3.46 (1H, m), 3.55 (3H, s), 3.71-3.76 (2H, m), 3.86-3.96 (1H, m), 4.13-4.23 (1H, m), 6.92 (1H, s), 7.91 (1H, dd, J = 2.4 Hz, 5.4 Hz), 8.50-8.58 (2H, m) (CDCl$_3$). | 359 |
| B164 | 3.23-3.30 (2H, m), 3.40-3.46 (1H, m), 3.55 (3H, s), 3.73-3.78 (2H, m), 3.86-3.94 (1H, m), 4.13-4.26 (1H, m), 7.46 (1H, s), 8.11 (1H, dd, J = 1.2 Hz, 4.2 Hz), 8.91 (1H, d, J = 4.2 Hz), 9.29 (1H, d, J = 1.2 Hz) (CDCl$_3$). | 342 |
| B165 | 1.22 (3H, s), 1.28 (3H, d, J = 6.8 Hz), 1.46 (3H, s), 3.29-3.34 (1H, m), 3.41-3.50 (2H, m), 3.54 (3H, s), 3.80-3.84 (1H, m), 4.02-4.07 (1H, m), 6.66 (1H, s), 7.79 (2H, d, J = 4.8 Hz), 8.72 (2H, d, J = 4.8 Hz) (CDCl$_3$). | 315 |
| B166 | 1.22 (3H, s), 1.27 (3H, d, J = 6.8 Hz), 1.46 (3H, s), 3.25-3.29 (1H, m), 3.39-3.47 (2H, m), 3.54 (3H, s), 3.78-3.84 (1H, m), 4.01-4.08 (1H, m), 6.85 (1H, s), 7.96 (1H, dd, J = 2.4 Hz, 5.4 Hz), 8.52 (1H, d, J = 5.4 Hz), 8.56 (1H, d, J = 2.4 Hz) (CDCl$_3$). | 333 |
| B167 | 1.23 (3H, s), 1.26 (3H, d, J = 6.8 Hz), 1.46 (3H, s), 3.26-3.31 (1H, m), 3.41-3.49 (2H, m), 3.56 (3H, s), 3.81-3.86 (1H, m), 4.02-4.07 (1H, m), 7.32 (1H, s), 8.17 (1H, dd, J = 1.2 Hz, 4.2 Hz), 8.89 (1H, d, J = 4.2 Hz), 9.28 (1H, d, J = 1.2 Hz) (CDCl$_3$). | 316 |
| B168 | 1.12 (3H, d, J = 6.8 Hz), 1.33 (3H, d, J = 6.8 Hz), 3.02-3.07 (2H, m), 3.33-3.37 (1H, m), 3.51-3.54 (1H, m), 3.59 (3H, s), 3.81-3.86 (1H, m), 3.97-4.00 (1H, m), 6.79 (1H, s), 7.81 (2H, d, J = 4.8 Hz), 8.74 (2H, d, J = 4.8 Hz) (CDCl$_3$). | 301 |
| B169 | 1.11 (3H, d, J = 6.8 Hz), 1.32 (3H, d, J = 6.8 Hz), 3.01-3.07 (2H, m), 3.28-3.33 (1H, m), 3.51-3.55 (1H, m), 3.60 (3H, s), 3.81-3.86 (1H, m), 3.96-4.00 (1H, m), 6.98 (1H, s), 7.96 (1H, dd, J = 2.4 Hz, 5.4 Hz), 8.51-8.58 (2H, m) (CDCl$_3$). | 319 |
| B170 | 1.10 (3H, d, J = 6.8 Hz), 1.33 (3H, d, J = 6.8 Hz), 3.01-3.07 (2H, m), 3.31-3.36 (1H, m), 3.51-3.54 (1H, m), 3.61 (3H, s), 3.80-3.85 (1H, m), 3.97-4.01 (1H, m), 7.45 (1H, s), 8.17 (1H, dd, J = 1.2 Hz, 4.2 Hz), 8.89 (1H, d, J = 4.2 Hz), 9.29 (1H, d, J = 1.2 Hz) (CDCl$_3$). | 302 |
| B171 | 0.99 (3H, d, J = 6.8 Hz), 1.03 (3H, d, J = 6.8 Hz), 1.74-1.80 (1H, m), 2.83-2.91 (1H, m), 3.14-3.21 (1H, m), 3.36-3.47 (2H, m), 3.54-3.58 (1H, m), 3.53 (3H, s), 3.74-3.81 (1H, m), 4.03 (1H, dd, J = 1.2 Hz, 10.2 Hz), 6.83 (1H, s), 7.79 (2H, d, J = 4.8 Hz), 8.72 (2H, d, J = 4.8 Hz) (CDCl$_3$). | 315 |
| B172 | 0.98 (3H, d, J = 6.8 Hz), 1.02 (3H, d, J = 6.8 Hz), 1.75-1.80 (1H, m), 2.81-2.89 (1H, m), 3.13-3.19 (1H, m), 3.33-3.44 (2H, m), 3.51-3.55 (1H, m), 3.53 (3H, s), 3.74-3.80 (1H, m), 4.03 (1H, dd, J = 1.2 Hz, 10.2 Hz), 6.87 (1H, s), 7.96 (1H, dd, J = 2.4 Hz, 5.4 Hz), 8.53 (1H, d, J = 5.4 Hz), 8.56 (1H, d, J = 2.4 Hz) (CDCl$_3$). | 333 |
| B173 | 0.99 (3H, d, J = 6.8 Hz), 1.03 (3H, d, J = 6.8 Hz), 1.72-1.86 (1H, m), 2.82-2.86 (1H, m), 3.15-3.20 (1H, m), 3.36-3.45 (2H, m), 3.51-3.55 (1H, m), 3.54 (3H, s), 3.76-3.81 (1H, m), 4.03 (1H, dd, J = 1.2 Hz, 10.2 Hz), 7.33 (1H, s), 8.16 (1H, dd, J = 1.2 Hz, 4.2 Hz), 8.88 (1H, d, J = 4.2 Hz), 9.29 (1H, d, J = 1.2 Hz) (CDCl$_3$). | 316 |
| B174 | 1.20 (3H, d, J = 6.8 Hz), 3.12-3.14 (1H, m), 3.64 (3H, s), 3.70-3.75 (1H, m), 3.89-3.93 (1H, m), 4.18-4.31 (2H, m), 4.56 (1H, d, J = 3.0 Hz), 6.59 (1H, s), 7.25-7.30 (3H, m), 7.36-7.41 (2H, m), 7.57 (2H, d, J = 4.8 Hz), 8.63 (2H, d, J = 4.8 Hz) (CDCl$_3$). | 363 |

TABLE 2-continued

| Compound No. | ¹H-NMR | MS [M + 1] |
|---|---|---|
| B175 | 1.19 (3H, d, J = 6.8 Hz), 3.06-3.10 (1H, m), 3.66 (3H, s), 3.64-3.69 (1H, m), 3.89-3.93 (1H, m), 4.19-4.30 (2H, m), 4.52 (1H, d, J = 3.0 Hz), 6.77 (1H, s), 7.25-7.30 (3H, m), 7.35-7.39 (2H, m), 7.56 (1H, dd, J = 2.4 Hz, 5.4 Hz), 8.41 (1H, d, J = 5.4 Hz), 8.49 (1H, d, J = 2.4 Hz) (CDCl₃). | 381 |
| B176 | 1.20 (3H, d, J = 6.8 Hz), 3.10-3.14 (1H, m), 3.66 (3H, s), 3.64-3.73 (1H, m), 3.90-3.95 (1H, m), 4.19-4.32 (2H, m), 4.53 (1H, d, J = 3.0 Hz), 7.23-7.26 (4H, m), 7.34-7.39 (2H, m), 7.85 (1H, dd, J = 1.2 Hz, 4.2 Hz), 8.78 (1H, d, J = 4.2 Hz), 9.21 (1H, d, J = 1.2 Hz) (CDCl₃). | 364 |
| B177 | 1.20 (3H, d, J = 6.8 Hz), 3.12-3.14 (1H, m), 3.64 (3H, s), 3.70-3.75 (1H, m), 3.89-3.93 (1H, m), 4.18-4.31 (2H, m), 4.56 (1H, d, J = 3.0 Hz), 6.59 (1H, s), 7.25-7.30 (3H, m), 7.36-7.41 (2H, m), 7.57 (2H, d, J = 4.8 Hz), 8.63 (2H, d, J = 4.8 Hz) (CDCl₃). | 363 |
| B178 | 1.19 (3H, d, J = 6.8 Hz), 3.06-3.10 (1H, m), 3.66 (3H, s), 3.64-3.69 (1H, m), 3.89-3.93 (1H, m), 4.19-4.30 (2H, m), 4.52 (1H, d, J = 3.0 Hz), 6.77 (1H, s), 7.25-7.30 (3H, m), 7.35-7.39 (2H, m), 7.56 (1H, dd, J = 2.4 Hz, 5.4 Hz), 8.41 (1H, d, J = 5.4 Hz), 8.49 (1H, d, J = 2.4 Hz) (CDCl₃). | 381 |
| B179 | 1.20 (3H, d, J = 6.8 Hz), 3.10-3.14 (1H, m), 3.66 (3H, s), 3.64-3.73 (1H, m), 3.90-3.95 (1H, m), 4.19-4.32 (2H, m), 4.53 (1H, d, J = 3.0 Hz), 7.23-7.26 (4H, m), 7.34-7.39 (2H, m), 7.85 (1H, dd, J = 1.2 Hz, 4.2 Hz), 8.78 (1H, d, J = 4.2 Hz), 9.21 (1H, d, J = 1.2 Hz) (CDCl₃). | 364 |
| B180 | 1.16 (3H, d, J = 6.8 Hz), 1.26 (3H, d, J = 6.8 Hz), 3.29-3.34 (1H, m), 3.51 (3H, s), 3.51-3.61 (2H, m), 3.86-3.97 (3H, m), 6.65 (1H, s), 7.78 (2H, d, J = 4.8 Hz), 8.71 (2H, d, J = 4.8 Hz) (CDCl₃). | 301 |
| B181 | 1.16 (3H, d, J = 6.8 Hz), 1.25 (3H, d, J = 6.8 Hz), 3.24-3.30 (1H, m), 3.51 (3H, s), 3.50-3.58 (2H, m), 3.84-3.96 (3H, m), 6.83 (1H, s), 7.93 (1H, dd, J = 2.4 Hz, 5.4 Hz), 8.52 (1H, d, J = 5.4 Hz), 8.55 (1H, d, J = 2.4 Hz) (CDCl₃). | 319 |
| B182 | 1.17 (3H, d, J = 6.8 Hz), 1.24 (3H, d, J = 6.8 Hz), 3.27-3.31 (1H, m), 3.52 (3H, s), 3.52-3.61 (2H, m), 3.86-4.00 (3H, m), 7.30 (1H, s), 8.14 (1H, dd, J = 1.2 Hz, 4.2 Hz), 8.87 (1H, d, J = 4.2 Hz), 9.27 (1H, s) (CDCl₃). | 302 |
| B183 | 3.38-3.46 (1H, m), 3.54-3.60 (2H, m), 3.58 (3H, s), 3.88 (3H, s), 3.93-4.20 (4H, m), 4.71 (1H, dd, J = 1.2 Hz, 10.2 Hz), 7.29 (1H, s), 8.66 (2H, d, J = 4.2 Hz), 9.14 (2H, d, J = 4.2 Hz) (DMSO-d6). | 331 |
| B184 | 3.27-3.40 (3H, m), 3.55 (3H, s), 3.72-3.77 (1H, m), 3.84 (3H, s), 3.85-3.88 (1H, m), 4.17-4.21 (1H, m), 4.45 (1H, dd, J = 1.2 Hz, 10.2 Hz), 6.91 (1H, s), 7.95 (1H, dd, J = 2.4 Hz, 5.4 Hz), 8.52-8.57 (2H, m) (CDCl₃). | 349 |
| B185 | 3.29-3.41 (3H, m), 3.56 (3H, s), 3.76-3.89 (2H, m), 3.85 (3H, s), 4.18-4.22 (1H, m), 4.47 (1H, dd, J = 1.2 Hz, 10.2 Hz), 7.38 (1H, s), 8.16 (1H, dd, J = 1.2 Hz, 4.2 Hz), 8.89 (1H, d, J = 4.2 Hz), 9.29 (1H, d, J = 1.2 Hz) (CDCl₃). | 332 |
| B186 | 1.11 (3H, d, J = 6.4 Hz), 1.99 (3H, s), 2.96 (1H, dt, J = 3.9, 13.0 Hz), 3.28-3.34 (1H, m), 3.43-3.47 (1H, m), 3.45 (3H, s), 3.56-3.60 (1H, m), 3.66-3.78 (3H, m), 7.50 (2H, d, J = 5.7 Hz), 8.69 (2H, d, J = 5.6 Hz) (DMSO-d6) | 301 |
| B187 | 1H NMR (400 MHz, CDCl3) 1.12 (3H, d, J = 6.3 Hz), 1.33 (3H, d, J = 6.3 Hz), 3.00-3.10 (2H, m), 3.32-3.38 (1H, m), 3.50-3.58 (1H, m), 3.60 (3H, s), 3.78-3.85 (1H, m), 3.96-4.01 (1H, m), 6.79 (1H, s), 7.81 (2H, d, J = 6.3 Hz), 8.74 (2H, d, J = 6.3 Hz) | 301 |
| B188 | 1.11 (3H, d, J = 6.3 Hz), 1.34 (3H, d, J = 6.3 Hz), 2.98-3.10 (2H, m), 3.30-3.37 (1H, m), 3.50-3.57 (1H, m), 3.61 (3H, s), 3.79-3.85 (1H, m), 3.96-4.01 (1H, m), 7.45 (1H, s), 8.18 (1H, dd, J = 1.6, 4.7 Hz), 8.91 (1H, d, J = 5.5 Hz), 9.29 (1H, d, J = 1.6 Hz) (CDCl₃) | 302 |
| B189 | 1.11 (3H, d, J = 6.3 Hz), 1.33 (3H, d, J = 6.3 Hz), 2.98-3.09 (2H, m), 3.28-3.34 (1H, m), 3.49-3.56 (1H, m), 3.60 (3H, s), 3.78-3.84 (1H, m), 3.96-4.01 (1H, m), 6.98 (1H, s), 7.96 (1H, dd, J = 4.7, 6.3 Hz), 8.55 (1H, d, J = 4.7 Hz), 8.57 (1H, d, J = 3.1 Hz) (CDCl₃) | 319 |
| B190 | 1.12 (3H, d, J = 6.3 Hz), 1.33 (3H, d, J = 6.3 Hz), 3.00-3.10 (2H, m), 3.32-3.38 (1H, m), 3.50-3.58 (1H, m), 3.60 (3H, s), 3.78-3.85 (1H, m), 3.96-4.01 (1H, m), 6.79 (1H, s), 7.81 (2H, d, J = 6.3 Hz), 8.74 (2H, d, J = 6.3 Hz) (CDCl₃) | 301 |
| B191 | 1.11 (3H, d, J = 6.3 Hz), 1.34 (3H, d, J = 6.3 Hz), 2.98-3.10 (2H, m), 3.30-3.37 (1H, m), 3.50-3.57 (1H, m), 3.61 (3H, s), 3.79-3.85 (1H, m), 3.96-4.01 (1H, m), 7.45 (1H, s), 8.18 (1H, dd, J = 1.6, 4.7 Hz), 8.91 (1H, d, J = 5.5 Hz), 9.29 (1H, d, J = 1.6 Hz) (CDCl₃) | 302 |
| B192 | 1.11 (3H, d, J = 6.3 Hz), 1.33 (3H, d, J = 6.3 Hz), 2.98-3.09 (2H, m), 3.28-3.34 (1H, m), 3.49-3.56 (1H, m), 3.60 (3H, s), 3.78-3.84 (1H, m), 3.96-4.01 (1H, m), 6.98 (1H, s), 7.96 (1H, dd, J = 4.7, 6.3 Hz), 8.55 (1H, d, J = 4.7 Hz), 8.57 (1H, d, J = 3.1 Hz) (CDCl₃) | 319 |
| B193 | 1.17 (3H, d, J = 6.3 Hz), 1.26 (3H, d, J = 6.3 Hz), 3.30-3.34 (1H, m), 3.51-3.60 (5H, m), 3.84-4.00 (3H, m), 6.65 (1H, s), 7.79 (2H, d, J = 6.3 Hz), 8.72 (2H, d, J = 6.3 Hz) (CDCl₃) | 301 |
| B194 | 1.18 (3H, d, J = 7.0 Hz), 1.25 (3H, d, J = 7.0 Hz), 3.27-3.31 (1H, m), 3.52-3.60 (5H, m), 3.84-4.01 (3H, m), 7.30 (1H, s), 8.14 (1H, d, J = 4.7 Hz), 8.88 (1H, d, J = 4.7 Hz), 9.28 (1H, s) (CDCl₃) | 302 |
| B195 | 1.17 (3H, d, J = 7.0 Hz), 1.25 (3H, d, J = 7.0 Hz), 3.25-3.30 (1H, m), 3.50-3.58 (5H, m), 3.82-3.99 (3H, m), 6.83 (1H, s), 7.94 (1H, dd, J = 5.5, 7.0 Hz), 8.52 (1H, d, J = 5.5 Hz), 8.55 (1H, d, J = 3.1 Hz) (CDCl₃) | 319 |

TABLE 2-continued

| Compound No. | ¹H-NMR | MS [M + 1] |
|---|---|---|
| B196 | 1.17 (3H, d, J = 6.3 Hz), 1.26 (3H, d, J = 6.3 Hz), 3.30-3.34 (1H, m), 3.51-3.60 (5H, m), 3.84-4.00 (3H, m), 6.65 (1H, s), 7.79 (2H, d, J = 6.3 Hz), 8.72 (2H, d, J = 6.3 Hz) (CDCl₃) | 301 |
| B197 | 1.18 (3H, d, J = 7.0 Hz), 1.25 (3H, d, J = 7.0 Hz), 3.27-3.31 (1H, m), 3.52-3.60 (5H, m), 3.84-4.01 (3H, m), 7.30 (1H, s), 8.14 (1H, d, J = 4.7 Hz), 8.88 (1H, d, J = 4.7 Hz), 9.28 (1H, s) (CDCl₃) | 302 |
| B198 | 1.17 (3H, d, J = 7.0 Hz), 1.25 (3H, d, J = 7.0 Hz), 3.25-3.30 (1H, m), 3.50-3.58 (5H, m), 3.82-3.99 (3H, m), 6.83 (1H, s), 7.94 (1H, dd, J = 5.5, 7.0 Hz), 8.52 (1H, d, J = 5.5 Hz), 8.55 (1H, d, J = 3.1 Hz) (CDCl₃) | 319 |
| B199 | 1.12 (3H, s), 1.21 (3H, d, J = 6.4 Hz), 1.36 (3H, s), 3.41-3.44 (2H, m), 3.46 (3H, s), 3.64-3.70 (2H, m), 3.94 (1H, dt, J = 7.3, 11.7 Hz), 6.96 (1H, s), 8.23 (1H, dd, J = 1.2, 4.8 Hz), 9.01 (1H, d, J = 5.0 Hz), 9.30 (1H, s) (DMSO-d6) | 316 |
| B200 | 1.12 (3H, s), 1.21 (3H, d, J = 6.4 Hz), 1.36 (3H, s), 3.36-3.38 (2H, m), 3.44 (3H, s), 3.64-3.70 (2H, m), 3.94 (1H, dt, J = 7.3, 11.8 Hz), 6.95 (1H, s), 8.23 (1H, dd, J = 1.2, 5.4 Hz), 9.01 (1H, d, J = 5.3 Hz), 9.30 (1H, s) (DMSO-d6) | 315 |
| B201 | 2.81 (1H, dt, J = 3.1, 12.3 Hz), 3.45-3.52 (3H, m), 3.49 (3H, s), 3.59-3.63 (2H, m), 3.84-3.99 (3H, m), 4.07 (1H, dd, J = 2.2, 11.8 Hz), 4.43-4.50 (1H, m), 7.09 (1H, s), 8.22 (1H, dd, J = 1.0, 5.8 Hz), 9.04 (1H, d, J = 5.3 Hz), 9.31 (1H, d, J = 1.0 Hz) (DMSO-d6) | 316 |
| B202 | 2.80 (1H, dt, J = 3.1, 12.3 Hz), 3.37-3.50 (2H, m), 3.48 (3H, s), 3.56-3.60 (2H, m), 3.82-3.60 (2H, m), 3.82-3.97 (3H, m), 4.06 (1H, dd, J = 2.2, 11.7 Hz), 4.38 (1H, t, J = 7.0 Hz), 6.67 (1H, s), 7.95 (1H, dd, J = 5.0, 6.8 Hz), 8.61 (1H, d, J = 4.8 Hz), 8.72 (1H, d, J = 3.1 Hz) (DMSO-d6) | 333 |
| B203 | 2.81 (1H, dt, J = 3.2, 12.3 Hz), 3.03-3.07 (1H, m), 3.54-3.52 (5H, m), 3.59-3.63 (3H, m), 3.84-3.99 (3H, m), 4.07 (1H, dd, J = 2.2, 11.8 Hz), 4.43-4.50 (1H, m), 7.09 (1H, s), 8.22 (1H, dd, J = 1.2, 5.4 Hz), 9.04 (1H, d, J = 5.1 Hz), 9.31 (1H, s) (DMSO-d6) | 316 |
| B204 | 2.80 (1H, dt, J = 3.2, 12.4 Hz), 3.37-3.50 (2H, m), 3.56-3.60 (2H, m), 3.83-3.97 (3H, m), 4.06 (1H, dd, J = 2.1, 11.8 Hz), 4.38 (1H, t, J = 7.0 Hz), 6.67 (1H, s), 7.95 (1H, dd, J = 5.2, 6.8 Hz), 8.61 (1H, d, J = 5.0 Hz), 8.72 (1H, d, J = 3.1 Hz) (DMSO-d6) | 333 |
| B205 | 3.38-3.42 (1H, m), 3.42 (3H, s), 3.56-3.68 (2H, m), 3.85 (3H, br), 4.20 (1H, br), 4.73 (1H, ddd, J = 5.6, 9.4, 46.0 Hz), 4.90 (1H, dt, J = 8.6, 48.0 Hz), 6.98 (1H, s), 8.24 (1H, d, J = 5.2 Hz), 9.01 (1H, d, J = 5.0 Hz), 9.30 (1H, s) (DMSO-d6) | 306 |
| B206 | 3.38-3.42 (1H, m), 3.42 (3H, s), 3.55 (1H, dt, J = 2.3, 10.9 Hz), 3.83-3.85 (3H, m), 4.15 (1H, br), 4.70 (1H, ddd, J = 5.6, 9.5, 45.7 Hz), 4.88 (1H, dt, J = 8.1, 9.4, 47.6 Hz), 6.58 (1H, s), 7.99 (1H, dd, J = 5.2, 6.8 Hz), 8.57 (1H, d, J = 5.5 Hz), 8.71 (1H, d, J = 3.1 Hz) (DMSO-d6) | 323 |
| D1 | 2.01-2.15 (1H, m), 2.26-2.37 (1H, m), 3.38-3.51 (2H, m), 3.46 (3H, s), 3.69-3.77 (2H, m), 3.88-4.02 (2H, m), 6.85 (1H, s), 7.25-7.30 (1H, m), 7.34-7.41 (4H, m), 8.45 (2H, d, J = 6.3 Hz), 8.90 (2H, d, J = 6.5 Hz) (DMSO-d6) | 333 |
| D2 | 1.99-2.18 (2H, m), 3.40 (3H, s), 3.60-3.66 (2H, m), 3.80-3.89 (2H, m), 4.20-4.28 (2H, m), 4.55 (2H, s), 6.61 (1H, s), 7.25-7.33 (5H, m), 7.97 (2H, dd, J = 1.5, 4.6 Hz), 8.67 (2H, dd, J = 1.4, 4.6 Hz) (DMSO-d6) | 363 |
| D3 | 1.71-1.82 (2H, m), 1.93-2.09 (2H, m), 2.57-2.62 (2H, m), 3.38-3.47 (2H, m), 3.43 (3H, s), 3.53-3.57 (1H, m), 3.60-3.68 (1H, m), 3.79-3.90 (2H, m), 4.10-4.18 (1H, m), 6.91 (1H, s), 7.12-7.16 (3H, m), 7.21-7.26 (2H, m), 8.56 (2H, d, J = 6.6 Hz), 8.97 (2H, d, J = 6.4 Hz) (DMSO-d6) | 391 |
| D4 | 3.53 (3H, s), 3.64 (4H, m), 4.35 (2H, m), 6.72 (1H, s), 7.07 (2H, m), 7.32 (3H, m), 7.71 (2H, dd, J = 4.8, 1.2 Hz), 8.65 (2H, dd, J = 4.8, 1.2 Hz) (CDCl₃) | 402 |
| D5 | 3.15 (2H, m), 3.35 (2H, dd, J = 9.6, 3.2 Hz), 3.51 (3H, s), 3.59 (4H, m), 3.93 (2H, dd, J = 10.8, 6.8 Hz), 6.57 (1H, s), 6.61 (2H, d, J = 8.0 Hz), 6.75 (1H, t, J = 8.0 Hz), 7.26 (2H, t, J = 8.0 Hz), 7.79 (2H, dd, J = 4.8, 1.2 Hz), 8.70 (2H, dd, J = 4.8, 1.2 Hz) (CDCl₃) | 374 |
| D6 | 3.16 (2H, m), 3.34 (2H, dd, J = 9.8, 3.6 Hz), 3.52 (3H, s), 3.59 (4H, m), 3.92 (2H, dd, J = 10.9, 7.1 Hz), 6.61 (2H, d, J = 8.0 Hz), 6.75 (1H, t, J = 8.0 Hz), 7.21 (1H, s), 7.26 (2H, t, J = 8.0 Hz), 8.14 (1H, d, J = 5.0 Hz), 8.84 (1H, d, J = 5.0 Hz), 9.26 (1H, s) (CDCl₃) | 375 |
| D7 | 3.15 (2H, m), 3.34 (2H, dd, J = 10.0, 3.6 Hz), 3.52 (3H, s), 3.57 (4H, m), 3.91 (2H, dd, J = 10.4, 7.2 Hz), 6.61 (2H, d, J = 8.0 Hz), 6.75 (1H, t, J = 8.0 Hz), 7.26 (2H, t, J = 8.0 Hz), 7.94 (1H, dd, J = 4.4, 3.2 Hz), 8.49 (1H, d, J = 4.4 Hz), 8.53 (1H, d, J = 3.2 Hz) (CDCl₃) | 392 |
| D8 | 3.14 (2H, m), 3.29 (2H, m), 3.49 (2H, m), 3.52 (3H, s), 3.56 (2H, m), 3.76 (3H, s), 3.90 (2H, m), 6.57 (1H, s), 6.58 (2H, d, J = 8.8 Hz), 6.86 (2H, d J = 8.8 Hz), 7.78 (2H, dd, J = 4.4, 1.2 Hz), 8.69 (2H, dd, J = 4.4, 1.2 Hz) (CDCl₃) | 404 |
| D9 | 3.14 (2H, m), 3.28 (2H, m), 3.48 (2H, m), 3.52 (3H, s), 3.55 (2H, m), 3.76 (3H, s), 3.89 (1H, m), 6.60 (2H, d, J = 8.0 Hz), 6.86 (2H, d, J = 8.0 Hz), 7.21 (1H, s), 8.14 (1H, d, J = 5.2 Hz), 8.84 (1H, d, J = 5.2 Hz), 9.26 (1H, s) (CDCl₃) | 405 |
| D10 | 3.12 (2H, m), 3.27 (2H, m), 3.48 (2H, m), 3.52 (3H, s), 3.54 (2H, m), 3.76 (3H, s), 3.87 (2H, m), 6.58 (2H, d, J = 9.2 Hz), 6.75 (1H, s), | 422 |

TABLE 2-continued

| Compound No. | $^1$H-NMR | MS [M + 1] |
|---|---|---|
| | 6.86 (2H, d, J = 9.2 Hz), 7.94 (1H, dd, J = 4.8, 3.2 Hz), 8.49 (1H, d, J = 4.8 Hz), 8.53 (1H, d, J = 3.2 Hz) (CDCl$_3$) | |
| D11 | 3.14 (2H, m), 3.33 (2H, m), 3.51 (3H, s), 3.58 (4H, m), 3.80 (3H, s), 3.92 (2H, m), 6.15 (1H, t, J = 2.4 Hz), 6.23 (1H, dd, J = 8.2, 2.4 Hz), 6.32 (1H, dd, J = 8.2, 2.4 Hz), 6.57 (1H, s), 7.16 (1H, t, J = 8.2 Hz), 7.78 (2H, dd, J = 4.4, 1.6 Hz), 8.69 (2H, dd, J = 4.4, 1.6 Hz) (CDCl$_3$) | 404 |
| D12 | 3.15 (2H, m), 3.33 (2H, m), 3.52 (3H, s), 3.58 (4H, m), 3.80 (3H, s), 3.91 (2H, m), 6.16 (1H, t, J = 2.4 Hz), 6.24 (1H, dd, J = 8.2, 2.4 Hz), 6.32 (1H, dd, J = 8.2, 2.4 Hz), 7.16 (1H, t, J = 8.2 Hz), 7.21 (1H, s), 8.13 (1H, d, J = 5.2 Hz), 8.84 (1H, d, J = 5.2 Hz), 9.26 (1H, s) (CDCl$_3$) | 405 |
| D13 | 3.13 (2H, m), 3.32 (2H, m), 3.51 (3H, s), 3.56 (4H, m), 3.80 (3H, s), 3.89 (2H, m), 6.15 (1H, t, J = 2.0 Hz), 6.23 (1H, dd, J = 8.2, 2.0 Hz), 6.74 (1H, s), 7.16 (1H, t, J = 8.2 Hz), 7.93 (1H, dd, J = 5.2, 2.8 Hz), 8.49 (1H, d, J = 5.2 Hz), 8.53 (1H, d, J = 2.8 Hz) (CDCl$_3$) | 422 |
| D14 | 3.07 (2H, m), 3.28 (2H, m), 3.46 (2H, m), 3.53 (2H, m), 3.56 (3H, s), 3.80 (2H, m), 3.85 (3H, s), 6.59 (1H, s), 6.79 (1H, m), 6.89 (3H, m), 7.80 (2H, d, J = 4.8 Hz), 8.70 (2H, d, J = 4.8 Hz) (CDCl$_3$) | 404 |
| D15 | 3.07 (2H, m), 3.28 (2H, m), 3.48 (2H, m), 3.52 (2H, m), 3.55 (3H, s), 3.79 (2H, m), 3.85 (3H, s), 6.80 (1H, m), 6.92 (3H, m), 7.24 (1H, s), 8.16 (1H, dd, J = 4.8, 0.8 Hz), 8.85 (1H, d, J = 4.8 Hz), 9.26 (1H, d, J = 0.8 Hz) (CDCl$_3$) | 405 |
| D16 | 3.07 (2H, m), 3.27 (2H, m), 3.45 (2H, m), 3.50 (2H, m), 3.55 (3H, s), 3.78 (2H, m), 3.85 (3H, s), 6.77 (1H, s), 6.79 (1H, m), 6.90 (3H, m), 7.96 (1H, dd, J = 4.8, 3.2 Hz), 8.49 (1H, d, J = 4.8 Hz), 8.54 (1H, d, J = 3.2 Hz) (CDCl$_3$) | 422 |
| D17 | 2.86 (1H, m), 3.49 (3H, s), 3.51-3.59 (2H, m), 3.79 (1H, m), 3.98 (1H, m), 4.05-4.10 (2H, m), 4.24 (1H, m), 6.55 (1H, s), 6.91 (1H, d, J = 8.4 Hz), 6.96 (1H, dd, J = 8.0, 6.8 Hz), 7.16-7.21 (2H, m), 7.78 (2H, dd, J = 4.8, 1.2 Hz), 8.69 (2H, dd, J = 4.8, 1.2 Hz) (CDCl$_3$) | 361 |
| D18 | 2.86 (1H, m), 3.49 (3H, s), 3.49-3.59 (2H, m), 3.75 (1H, m), 3.97-4.07 (2H, m), 4.23 (1H, m), 6.72 (1H, s), 6.91 (1H, d, J = 8.4 Hz), 6.96 (1H, m), 7.16-7.26 (2H, m), 7.93 (1H, dd, J = 6.8, 5.2 Hz), 8.49 (1H, d, J = 4.8 Hz), 8.53 (1H, d, J = 3.2 Hz) (CDCl$_3$) | 379 |
| D19 | 1.86-1.93 (1H, m), 2.15-2.21 (1H, m), 3.42-3.51 (2H, m), 3.50 (3H, s), 3.65-3.81 (3H, m), 3.86 (2H, d, J = 5.1 Hz), 6.53 (1H, s), 7.24-7.34 (5H, m), 7.80 (2H, d, J = 6.0 Hz), 8.69 (2H, d, J = 6.0 Hz) (CDCl$_3$) | 362 |
| D20 | 1.87-1.93 (1H, m), 2.15-2.21 (1H, m), 3.41-3.55 (2H, m), 3.49 (3H, s), 3.46-3.81 (3H, m), 3.86 (2H, d, J = 5.4 Hz), 7.16 (1H, s), 7.26-7.34 (5H, m), 8.14 (1H, dd, J = 5.4 Hz and 1.5 Hz), 8.84 (1H, d, J = 5.1 Hz), 9.26 (1H, d, J = 0.9 Hz) (CDCl$_3$) | 363 |
| D21 | 1.86-1.92 (1H, m), 2.14-2.18 (1H, m), 3.39-3.54 (2H, m), 3.48 (3H, s), 3.65-3.81 (3H, m), 3.85 (2H, d, J = 5.7 Hz), 6.70 (1H, s), 7.24-7.39 (5H, m), 7.95 (1H, dd, J = 5.1 Hz and 6.6 Hz), 8.49 (1H, d, J = 5.1 Hz), 8.53 (1H, d, J = 3.0 Hz) (CDCl$_3$) | 380 |
| D22 | 1.70 (2H, br.s), 1.81-1.83 (1H, m), 2.18-2.20 (1H, m), 3.33-3.36 (1H, m), 3.52 (3H, s), 3.66-3.86 (4H, m), 7.17 (1H, s), 8.16 (1H, dd, J = 5.4 Hz and 1.5 Hz), 8.84 (1H, d, J = 5.1 Hz), 9.26 (1H, d, J = 1.2 Hz) (CDCl$_3$) | 273 |
| D23 | 2.21-2.25 (1H, m), 2.36-2.42 (1H, m), 3.53 (3H, s), 3.71-3.81 (2H, m), 3.81 (2H, d, J = 3.0 Hz), 4.78 (1H, dd, J = 5.4 Hz and 5.1 Hz), 6.94 (1H, br.d, J = 6.0 Hz), 7.14 (1H, s), 7.26-7.35 (2H, m), 7.44 (1H, dd, J = 7.2 Hz and 7.2 Hz), 7.73 (2H, dd, J = 7.3 Hz and 1.5 Hz), 8.09 (1H, dd, J = 5.4 Hz and 1.5 Hz), 8.79 (1H, d, J = 5.1 Hz), 9.19 (1H, d, J = 1.2 Hz) (CDCl$_3$) | 377 |
| D24 | 2.04-2.07 (1H, m), 2.31-2.35 (1H, m), 3.53 (3H, s), 3.59 (1H, dd, J = 11.1 Hz and 4.2 Hz), 3.70-3.83 (3H, m), 3.96 (1H, dd, J = 11.1 Hz ans 5.4 Hz), 4.13 (1H, m), 6.55-6.59 (2H, m), 6.92 (2H, dd, J = 5.7 Hz and 6.0 Hz), 7.20 (1H, s), 8.12 (1H, dd, J = 5.4 Hz and 1.5 Hz), 8.84 (1H, d, J = 5.4 Hz), 9.27 (1H, d, J = 1.5 Hz) (CDCl$_3$) | 367 |
| D25 | 1.88-1.92 (1H, m), 2.14-2.19 (1H, m), 3.40-3.51 (2H, m), 3.48 (3H, s), 3.62-3.85 (3H, m), 3.90 (2H, d, J = 13.2 Hz), 6.71 (1H, s), 7.29-7.37 (5H, m), 7.96 (1H, dd, J = 6.6 Hz and 5.1 Hz), 8.48 (1H, d, J = 5.1 Hz), 8.53 (1H, d, J = 3.3 Hz) (CDCl$_3$) | 380 |
| D26 | 1.88-1.92 (1H, m), 2.14-2.19 (1H, m), 3.42-3.51 (2H, m), 3.48 (3H, s), 3.62-3.85 (3H, m), 3.86 (2H, d, J = 13.2 Hz), 6.52 (1H, s), 7.28-7.37 (5H, m), 7.79 (2H, d, J = 6.0 Hz), 8.69 (2H, d, J = 6.0 Hz) (CDCl$_3$) | 362 |
| D27 | 1.87-1.93 (1H, m), 2.04-2.22 (1H, m), 3.41-3.52 (2H, m), 3.49 (3H, s), 3.65-3.81 (3H, m), 3.86 (2H, d, J = 13.2 Hz), 7.16 (1H, s), 7.22-7.40 (5H, m), 8.18 (1H, dd, J = 5.4 Hz and 1.5 Hz), 8.84 (1H, d, J = 5.1 Hz), 9.26 (1H, d, J = 0.9 Hz) (CDCl$_3$) | 363 |
| D28 | 1.54 (2H, br.s), 1.78-1.84 (1H, m), 2.15-2.21 (1H, m), 3.32-3.35 (1H, m), 3.52 (3H, s), 3.68-3.87 (4H, m), 6.71 (1H, s), 7.98 (1H, dd, J = 5.1 Hz and 6.6 Hz), 8.49 (1H, d, J = 5.1 Hz), 8.53 (1H, d, J = 3.0 Hz) (CDCl$_3$) | 290 |

TABLE 2-continued

| Compound No. | $^1$H-NMR | MS [M + 1] |
|---|---|---|
| D29 | 1.76 (2H, br.s), 1.79-1.85 (1H, m), 2.17-2.20 (1H, m), 3.31-3.35 (1H, m), 3.53 (3H, s), 3.70-3.86 (4H, m), 7.17 (1H, s), 8.16 (1H, dd, J = 5.4 Hz and 1.5 Hz), 8.84 (1H, d, J = 5.1 Hz), 9.26 (1H, d, J = 1.2 Hz) (CDCl$_3$) | 273 |
| D30 | 2.05-2.09 (1H, m), 2.32-2.37 (1H, m), 3.53 (3H, s), 3.57 (1H, dd, J = 11.1 Hz and 4.2 Hz), 3.72-3.79 (3H, m), 3.96 (1H, dd, J = 11.1 Hz ans 5.4 Hz), 4.21 (1H, m), 6.55-6.59 (2H, m), 6.92 (2H, dd, J = 5.7 Hz and 6.0 Hz), 7.20 (1H, s), 8.12 (1H, dd, J = 5.4 Hz and 1.5 Hz), 8.85 (1H, d, J = 5.4 Hz), 9.27 (1H, d, J1.5 Hz) (CDCl$_3$) | 367 |
| D31 | 2.05-2.09 (1H, m), 2.32-2.37 (1H, m), 3.52 (3H, s), 3.57 (1H, dd, J = 11.1 Hz and 4.2 Hz), 3.71-3.82 (3H, m), 3.97 (1H, dd, J = 11.1 Hz ans 5.4 Hz), 4.21 (1H, m), 6.54-6.59 (2H, m), 6.57 (1H, s), 6.92 (2H, dd, J = 5.7 Hz and 6.0 Hz), 7.79 (2H, d, J = 6.0 Hz), 8.70 (2H, d, J = 6.0 Hz) (CDCl$_3$) | 366 |
| D32 | 1.33 (2H, br.s), 1.70-1.84 (1H, m), 2.16-2.22 (1H, m), 3.40-3.48 (1H, m), 3.52 (3H, s), 3.70-3.85 (4H, m), 6.54 (1H, s), 7.81 (2H, d, J = 6.0 Hz), 8.69 (2H, d, J = 6.0 Hz) (CDCl$_3$) | 272 |
| D33 | 2.08-2.14 (1H, m), 2.33-2.39 (1H, m), 3.53 (3H, s), 3.65 (1H, dd, J = 10.8 Hz and 3.6 Hz), 3.72-3.75 (2H, m), 3.99 (1H, dd, J = 11.1 Hz and 5.7 Hz), 4.14-4.19 (2H, m), 6.58 (1H, s), 6.69-6.77 (2H, m), 6.96-7.03 (2H, m), 7.80 (2H, d, J = 6.0 Hz), 8.70 (2H, d, J = 6.0 Hz) (CDCl$_3$) | 366 |
| D34 | 2.07-2.11 (1H, m), 2.32-2.38 (1H, m), 3.53 (3H, s), 3.60 (1H, dd, J = 11.4 Hz and 3.6 Hz), 3.70-3.80 (2H, m), 3.97 (1H, dd, J = 10.8 Hz and 5.4 Hz), 4.30-4.20 (2H, m), 6.30-6.40 (3H, m), 6.58 (1H, s), 7.09-7.15 (1H, m), 7.78 (2H, d, J = 6.0 Hz), 8.70 (2H, d, J = 6.0 Hz) (CDCl$_3$) | 366 |
| D35 | 2.08-2.15 (1H, m), 2.32-2.38 (1H, m), 3.53 (3H, s), 3.64 (1H, dd, J = 11.4 Hz and 4.8 Hz), 3.72-3.84 (3H, m), 3.78 (3H, s), 3.97 (1H, dd, J = 11.1 Hz and 5.4 Hz), 4.18 (1H, m), 4.46 (1H, d, J = 6.9 Hz), 6.57 (1H, s), 6.65 (1H, d, J = 7.2 Hz), 6.73-6.80 (2H, m), 6.89 (1H, t, J = 7.2 Hz), 7.80 (2H, d, J = 6.0 Hz), 8.70 (2H, d, J = 6.0 Hz) (CDCl$_3$) | 378 |
| D36 | 2.04-2.10 (1H, m), 2.31-2.36 (1H, m), 3.52 (3H, s), 3.58 (1H, dd, J = 11.1 Hz and 4.2 Hz), 3.70-3.99 (4H, m), 3.78 (3H, s), 4.16 (1H, m), 6.18 (1H, d, J = 2.0 Hz), 6.25 (1H, dd, J = 9.8 Hz and 1.9 Hz), 6.34 (1H, dd, J = 8.2 Hz and 2.0 Hz), 6.56 (1H, s), 7.11 (1H, dd, J = 8.1 Hz and 8.2 Hz), 7.78 (2H, d, J = 6.0 Hz), 8.70 (2H, d, J = 6.0 Hz) (CDCl$_3$) | 378 |
| D37 | 1.32 (3H, d, J = 6.0 Hz), 1.61-1.85 (2H, m), 2.00-2.05 (1H, m), 2.23-2.27 (1H, m), 3.32 (1H, t, J = 9.3 Hz), 3.48 (3H, s), 3.71 (1H, td, J = 9.6 Hz and 3.6 Hz), 4.42 (1H, td, J = 5.9 Hz and 6.3 Hz), 6.56 (1H, s), 7.80 (2H, d, J = 6.4 Hz), 8.70 (2H, d, J = 6.0 Hz) (CDCl$_3$) | 271 |
| D38 | 1.31 (3H, d, J = 6.0 Hz), 1.62-1.85 (2H, m), 2.01-2.05 (1H, m), 2.24-2.28 (1H, m), 3.21 (1H, t, J = 9.3 Hz), 3.49 (3H, s), 3.69 (1H, td, J = 9.6 Hz and 3.6 Hz), 4.41 (1H, td, J = 5.9 Hz and 6.3 Hz), 7.20 (1H, s), 8.14 (1H, dd, J = 5.4 Hz), 8.86 (1H, d, J = 5.1 Hz), 9.27 (1H, s) (CDCl$_3$) | 272 |
| D39 | 1.30 (3H, d, J = 6.0 Hz), 1.61-1.71 (2H, m), 2.00-2.05 (1H, m), 2.21-2.26 (1H, m), 3.32 (1H, t, J = 9.3 Hz), 3.49 (3H, s), 3.71 (1H, td, J = 9.6 Hz and 3.6 Hz), 4.36 (1H, td, J = 5.9 Hz and 6.3 Hz), 6.73 (1H, d, J = 0.9 Hz), 7.94 (1H, dd, J = 5.4 Hz), 8.50 (1H, dd, J = 0.9 Hz and 5.1 Hz), 8.54 (1H, s) (CDCl$_3$) | 289 |
| D40 | 2.10-2.15 (1H, m), 2.34-2.40 (1H, m), 3.55 (3H, s), 3.65 (1H, dd, J = 10.8 Hz and 3.6 Hz), 3.72-3.83 (2H, m), 3.97 (1H, dd, J = 11.1 Hz and 5.7 Hz), 4.16-4.20 (2H, m), 6.69-6.77 (2H, m), 6.96-7.03 (2H, m), 7.22 (1H, s), 8.13 (1H, d, J = 5.4 Hz), 8.86 (1H, d, J = 5.1 Hz), 9.27 (1H, s) (CDCl$_3$) | 367 |
| D41 | 2.08-2.15 (1H, m), 2.32-2.38 (1H, m), 3.54 (3H, s), 3.64 (1H, dd, J = 11.4 Hz and 4.8 Hz), 3.72-3.84 (3H, m), 3.78 (3H, s), 3.97 (1H, dd, J = 11.1 Hz and 5.4 Hz), 4.19 (1H, m), 4.46 (1H, d, J = 6.9 Hz), 6.65 (1H, d, J = 7.2 Hz), 6.72-6.80 (2H, m), 6.89 (1H, t, J = 7.2 Hz), 7.20 (1H, s), 8.15 (1H, d, J = 5.4 Hz), 8.85 (1H, d, J = 5.1 Hz), 9.27 (1H, s) (CDCl$_3$) | 379 |
| D42 | 2.04-2.11 (1H, m), 2.31-2.37 (1H, m), 3.53 (3H, s), 3.59 (1H, dd, J = 11.1 Hz and 4.2 Hz), 3.70-3.99 (4H, m), 3.78 (3H, s), 4.17 (1H, m), 6.18 (1H, d, J = 2.0 Hz), 6.24 (1H, dd, J = 9.8 Hz and 1.9 Hz), 6.33 (1H, dd, J = 8.2 Hz and 2.0 Hz), 7.11 (1H, dd, J = 8.1 Hz and 8.2 Hz), 7.20 (1H, s), 8.14 (1H, d, J = 5.4 Hz), 8.86 (1H, d, J = 5.1 Hz), 9.27 (1H, s) (CDCl$_3$) | 379 |
| D43 | 2.04-2.08 (1H, m), 2.30-2.36 (1H, m), 3.53 (3H, s), 3.56 (1H, dd, J = 11.1 Hz and 4.2 Hz), 3.72-3.79 (3H, m), 3.76 (3H, s), 3.96 (1H, dd, J = 11.1 Hz ans 5.4 Hz), 4.12 (1H, m), 6.60 (2H, d, J = 9.0 Hz), 6.80 (2H, d, J = 9.0 Hz), 7.20 (1H, s), 8.12 (1H, d, J = 5.4 Hz), 8.86 (1H, d, J = 5.1 Hz), 9.27 (1H, s) (CDCl$_3$) | 379 |
| D44 | 2.02-2.11 (1H, m), 2.32-2.38 (1H, m), 3.53 (3H, s), 3.57 (1H, dd, J = 11.4 Hz and 3.9 Hz), 3.72-3.87 (3H, m), 3.98 (1H, dd, J = 10.9 Hz and 5.6 Hz), 4.20 (1H, m), 6.57 (1H, s), 6.63 (2H, d, J = 8.2 Hz), 6.77 (2H, dd, J = 7.40 Hz and 7.4 Hz), 7.21 (2H, dd, J = 8.1 Hz and 7.6 Hz), 7.79 (2H, d, J = 5.8 Hz), 8.70 (2H, d, J = 5.8 Hz) (CDCl$_3$) | 348 |
| D45 | 2.07-2.12 (1H, m), 2.33-2.39 (1H, m), 3.54 (3H, s), 3.60 (1H, dd, J = 11.4 Hz and 3.9 Hz), 3.72-3.86 (3H, m), 3.97 (1H, dd, J = 10.9 Hz and 5.6 Hz), 4.20 (1H, m), 6.63 (2H, d, J = 8.2 Hz), 6.78 (1H, dd, J = 7.4 Hz | 349 |

TABLE 2-continued

| Compound No. | $^1$H-NMR | MS [M + 1] |
|---|---|---|
| | and 7.4 Hz), 7.21 (2H, dd, J = 8.1 Hz and 7.6 Hz), 7.24 (1H, s), 8.13 (1H, d, J = 5.4 Hz), 8.86 (1H, d, J = 5.1 Hz), 9.27 (1H, s) (CDCl$_3$) | |
| D46 | 2.08-2.14 (1H, m), 2.32-2.38 (1H, m), 3.53 (3H, s), 3.64 (1H, dd, J = 11.4 Hz and 4.8 Hz), 3.72-3.84 (3H, m), 3.78 (3H, s), 3.95 (1H, dd, J = 11.1 Hz and 5.4 Hz), 4.19 (1H, m), 6.65 (1H, d, J = 7.2 Hz), 6.72-6.80 (3H, m), 6.90 (1H, t, J = 7.2 Hz), 7.96 (1H, dd, J = 5.1 Hz and 6.6 Hz), 8.50 (1H, d, J = 5.4 Hz), 8.54 (1H, d, J = 3.0 Hz) (CDCl$_3$) | 396 |
| D47 | 2.05-2.15 (2H, m), 2.78 (1H, m), 3.48-3.63 (2H, m), 3.53 (3H, s), 3.87 (1H, dd, J = 11.4 Hz and 4.20 Hz), 4.00 (1H, dd, J = 18.3 Hz and 8.4 Hz), 4.63 (1H, br.s), 6.52 (1H, s), 7.76 (2H, d, J = 6.0 Hz), 8.66 (2H, d, J = 6.0 Hz) (CDCl$_3$) | 273 |
| D48 | 2.08-2.15 (2H, m), 3.08 (1H, m), 3.55-3.62 (2H, m), 3.51 (3H, s), 3.85 (1H, dd, J = 11.4 Hz and 4.20 Hz), 3.98 (1H, dd, J = 18.3 Hz and 8.4 Hz), 4.63 (1H, br.s), 7.10 (1H, s), 8.09 (1H, d, J = 5.2 Hz), 8.78 (1H, d, J = 5.2 Hz), 9.21 (1H, s) (CDCl$_3$) | 274 |
| D49 | 2.07-2.13 (2H, m), 2.46 (1H, m), 3.53 (3H, s), 3.56-3.61 (2H, m), 3.84 (1H, dd, J = 11.7 Hz and 4.2 Hz), 3.92-4.17 (1H, m), 4.62 (1H, br.s), 6.95 (1H, s), 7.95 (1H, dd, J = 6.6 Hz and 5.1 Hz), 8.46 (1H, dd, J = 5.1 Hz and 0.9 Hz), 8.51 (1H, d, J = 3.0 Hz) (CDCl$_3$) | 291 |
| D50 | 2.05-2.15 (2H, m), 2.78 (1H, m), 3.48-3.63 (2H, m), 3.53 (3H, s), 3.87 (1H, dd, J = 11.4 Hz and 4.20 Hz), 4.00 (1H, dd, J = 18.3 Hz and 8.4 Hz), 4.63 (1H, br.s), 6.52 (1H, s), 7.76 (2H, d, J = 6.0 Hz), 8.66 (2H, d, J = 6.0 Hz) (CDCl$_3$) | 273 |
| D51 | 2.08-2.15 (2H, m), 3.08 (1H, m), 3.55-3.62 (2H, m), 3.51 (3H, s), 3.85 (1H, dd, J = 11.4 Hz and 4.20 Hz), 3.98 (1H, dd, J = 18.3 Hz and 8.4 Hz), 4.63 (1H, br.s), 7.10 (1H, s), 8.09 (1H, d, J = 5.2 Hz), 8.78 (1H, d, J = 5.2 Hz), 9.21 (1H, s) (CDCl$_3$) | 274 |
| D52 | 2.07-2.13 (2H, m), 2.46 (1H, m), 3.53 (3H, s), 3.56-3.61 (2H, m), 3.84 (1H, dd, J = 11.7 Hz and 4.2 Hz), 3.92-4.17 (1H, m), 4.62 (1H, br.s), 6.95 (1H, s), 7.95 (1H, dd, J = 6.6 Hz and 5.1 Hz), 8.46 (1H, dd, J = 5.1 Hz and 0.9 Hz), 8.51 (1H, d, J = 3.0 Hz) (CDCl$_3$) | 291 |
| D53 | 1.34 (3H, d, J = 6.0 Hz), 1.65 (1H, m), 1.86 (1H, m), 2.03 (1H, m), 2.25 (1H, m), 3.33 (1H, m), 3.52 (3H, s), 3.72 (1H, ddd, J = 10.5, 10.5, 3.3 Hz), 4.44 (1H, m), 7.43 (1H, s), 7.50-7.52 (3H, m), 8.02 (1H, d, J = 5.4 Hz), 8.56 (1H, dd, J = 5.7, 2.1 Hz), 8.93 (1H, d, J = 4.8 Hz) (CDCl$_3$). | 348 |
| D54 | 1.32 (3H, d, J = 6.0 Hz), 1.61-1.63 (1H, m), 1.68-1.70 (1H, m), 1.83-1.85 (1H, m), 1.96-2.05 (1H, m), 3.32 (1H, t, J = 8.8 Hz), 3.49 (3H, s), 3.70 (1H, dt, J = 6.3, 10.1 Hz), 4.41 (1H, dt, J = 4.7, 11.5 Hz), 6.56 (1H, s), 7.80 (2H, d, J = 6.0 Hz), 8.70 (2H, d, J = 6.0 Hz) (CDCl$_3$) | 271 |
| D55 | 1.32 (3H, d, J = 6.0 Hz), 1.61-1.63 (1H, m), 1.68-1.70 (1H, m), 1.83-1.85 (1H, m), 1.96-2.05 (1H, m), 3.32 (1H, t, J = 8.8 Hz), 3.49 (3H, s), 3.70 (1H, dt, J = 6.3, 10.1 Hz), 4.41 (1H, dt, J = 4.7, 11.5 Hz), 7.20 (1H, s), 8.14 (1H, d, J = 5.4 Hz), 8.85 (1H, d, J = 5.1 Hz), 9.27 (1H, s) (CDCl$_3$) | 272 |
| D56 | 1.32 (3H, d, J = 6.0 Hz), 1.61-1.63 (1H, m), 1.68-1.70 (1H, m), 1.83-1.85 (1H, m), 1.96-2.05 (1H, m), 3.32 (1H, t, J = 8.8 Hz), 3.49 (3H, s), 3.70 (1H, dt, J = 6.3, 10.1 Hz), 4.41 (1H, dt, J = 4.7, 11.5 Hz), 7.27 (1H, s), 7.95 (1H, dd, J = 6.3, 5.1 Hz), 8.50 (1H, d, J = 5.1 Hz), 8.54 (1H, d, J = 3.3 Hz) (CDCl$_3$) | 289 |
| D57 | 1.34 (3H, d, J = 6.0 Hz), 1.65-2.28 (4H, m), 3.33 (1H, m), 3.52 (3H, s), 3.71 (1H, m), 4.44 (1H, m), 7.43 (1H, s), 7.51 (3H, m), 8.02 (1H, d, J = 5.1 Hz), 8.56 (2H, m), 8.93 (1H, d, J = 5.1 Hz) (CDCl$_3$) | 347 |
| D58 | 2.08 (1H, dt, J = 12.8, 5.5 Hz), 2.34 (1H, dt, J = 12.8, 5.5 Hz), 3.53 (3H, s), 3.71-3.80 (2H, m), 3.88 1H, d, J = 6.3 Hz), 3.97 (1H, dd, J = 10.9, 5.6 Hz), 4.20 (1H, m), 6.64 (2H, d, J = 8.0 Hz), 6.77 (1H, dd, J = 7.2, 7.4 Hz), 7.19-7.26 (3H, m), 8.12 (1H, d, J = 5.2 Hz), 8.84 (1H, d, J = 5.1 Hz), 9.26 (1H, s) (CDCl$_3$) | 349 |
| D59 | 2.12 (1H, dt, J = 12.8, 5.5 Hz), 2.38 (1H, dt, J = 12.8, 5.5 Hz), 3.55 (3H, s), 3.64-3.80 (3H, m), 3.97 (1H, dd, J = 11.1, 5.7 Hz), 4.18 (1H, m), 6.69-6.77 (2H, m), 6.96-7.07 (2H, m), 7.21 (1H, s), 8.13 (1H, dd, J = 5.1, 1.2 Hz), 8.85 (1H, d, J = 5.1 Hz), 9.27 (1H, s) (CDCl$_3$) | 367 |
| D60 | 2.09 (1H, dt, J = 12.8, 5.5 Hz), 2.38 (1H, dt, J = 12.8, 5.5 Hz), 3.53 (3H, s), 3.59-3.84 (3H, m), 3.98 (1H, dd, J = 11.1, 5.7 Hz), 4.15 (2H, m), 6.31-6.47 (2H, m), 7.09-7.17 (2H, m), 7.21 (1H, s), 8.12 (1H, dd, J = 5.1, 1.2 Hz), 8.85 (1H, d, J = 5.1 Hz), 9.26 (1H, s) (CDCl$_3$) | 367 |
| D61 | 2.12 (1H, dt, J = 12.8, 5.5 Hz), 2.36 (1H, dt, J = 12.8, 5.5 Hz), 3.54 (3H, s), 3.64-3.82 (3H, m), 3.78 (3H, s), 3.83 (1H, dd, J = 11.1, 5.4 Hz), 4.18 (1H, dd, J = 5.4, 10.8 Hz), 4.46 (1H, d, J = 6.6 Hz), 6.65 (1H, d, J = 7.8 Hz), 6.70-6.80 (2H, m), 6.90 (1H, dd, J = 7.5, 7.5 Hz), 7.20 (1H, s), 8.14 (1H, d, J = 5.1 Hz), 8.84 (1H, d, J = 4.8 Hz), 9.27 (1H, s) (CDCl$_3$) | 379 |
| D62 | 2.08 (1H, dt, J = 12.8, 5.5 Hz), 2.35 (1H, dt, J = 12.8, 5.5 Hz), 3.35 (3H, s), 3.59 (1H, dd, J = 10.9, 4.0 Hz), 3.72-3.82 (2H, m), 3.77 (3H, s), 3.90-3.99 (2H, m), 4.19 (1H, m), 6.19 (1H, s), 6.24 (1H, dd, J = 9.8, 1.8 Hz), 6.33 (1H, dd, J = 8.1, 1.9 Hz), 7.11 (1H, dd, J = 8.0, 8.1 Hz), 7.19 (1H, s), 8.11 (1H, d, J = 5.2 Hz), 8.84 (1H, d, J = 5.1 Hz), 9.20 (1H, s) (CDCl$_3$) | 379 |

TABLE 2-continued

| Compound No. | $^1$H-NMR | MS [M + 1] |
|---|---|---|
| D63 | 2.04 (1H, dt, J = 12.8, 5.5 Hz), 2.32 (1H, dt, J = 12.8, 5.5 Hz), 3.53 (3H, s), 3.58-3.93 (5H, m), 3.76 (3H, s), 4.19 (1H, m), 6.66 (2H, dd, J = 6.8 Hz), 6.81 (2H, d, J = 6.8 Hz), 7.19 (1H, s), 8.12 (1H, d, J = 5.2 Hz), 8.84 (1H, d, J = 5.1 Hz), 9.27 (1H, s) (CDCl$_3$) | 379 |
| D64 | 2.08 (1H, dt, J = 12.8, 5.5 Hz), 2.34 (1H, dt, J = 12.8, 5.5 Hz), 3.52 (3H, s), 3.60 (1H, dd, J = 11.0, 4.2 Hz), 3.74-3.88 (3H, m), 3.98 (1H, dd, J = 11.0, 5.3 Hz), 4.19 (2H, m), 6.56 (1H, s), 6.67 (2H, dd, J = 7.4, 7.4 Hz), 7.21 (2H, dd, J = 8.0, 7.6 Hz), 7.79 (2H, d, J = 5.9 Hz), 8.70 (2H, d, J = 6.0 Hz) (CDCl$_3$) | 348 |
| D65 | 2.10 (1H, dt, J = 12.9, 5.4 Hz), 2.37 (1H, dt, J = 12.9, 5.4 Hz), 3.53 (3H, s), 3.65 (1H, dd, J = 11.1, 3.9 Hz), 3.72-3.83 (2H, m), 3.99 (1H, dd, J = 10.7, 5.3 Hz), 4.14-4.20 (2H, m), 6.58 (1H, m), 6.69-6.77 (2H, m), 6.96-7.07 (2H, m), 7.79 (2H, d, J = 6.0 Hz), 8.70 (2H, d, J = 5.7 Hz) (CDCl$_3$) | 366 |
| D66 | 2.08 (1H, dt, J = 12.9, 5.4 Hz), 2.35 (1H, dt, J = 12.9, 5.4 Hz), 3.53 (3H, s), 3.65 (1H, dd, J = 11.1, 3.9 Hz), 3.70-3.83 (2H, m), 3.99 (1H, dd, J = 10.7, 5.3 Hz), 4.07-4.14 (2H, m), 6.30-6.45 (3H, m), 6.58 (1H, s), 7.12 (1H, dd, J = 8.0, 15.0 Hz), 7.79 (2H, d, J = 6.0 Hz), 8.70 (2H, d, J = 5.7 Hz) (CDCl$_3$) | 366 |
| D67 | 2.06 (1H, dt, J = 12.9, 5.4 Hz), 2.35 (1H, dt, J = 12.9, 5.4 Hz), 3.53 (3H, s), 3.65 (1H, dd, J = 11.1, 3.9 Hz), 3.72-3.84 (3H, m), 3.99 (1H, dd, J = 10.7, 5.3 Hz), 4.12 (1H, m), 6.54-6.59 (3H, m), 6.93 (2H, dd, J = 9.0, 8.4 Hz), 7.79 (2H, d, J = 6.0 Hz), 8.70 (2H, d, J = 5.7 Hz) (CDCl$_3$) | 366 |
| D68 | 2.12 (1H, dt, J = 12.8, 5.5 Hz), 2.35 (1H, dt, J = 12.8, 5.5 Hz), 3.54 (3H, s), 3.63-3.83 (3H, m), 3.77 (3H, s), 3.97 (1H, dd, J = 11.1, 5.4 Hz), 4.17 (1H, m), 4.47 (1H, d, J = 6.3 Hz), 6.56 (1H, s), 6.64 (1H, d, J = 7.5 Hz), 6.70-6.80 (2H, m), 6.89 (1H, dd, J = 7.0, 7.5 Hz), 7.79 (2H, d, J = 6.1 Hz), 8.70 (1H, d, J = 5.9 Hz) (CDCl$_3$) | 378 |
| D69 | 2.12 (1H, dt, J = 12.8, 5.5 Hz), 2.36 (1H, dt, J = 12.8, 5.5 Hz), 3.54 (3H, s), 3.64-3.82 (3H, m), 3.78 (3H, s), 3.97 (1H, dd, J = 11.1, 5.4 Hz), 4.18 (1H, dd, J = 10.8, 5.4 Hz), 4.46 (1H, d, J = 6.6 Hz), 6.17 (1H, m), 6.24 (1H, dd, J = 7.9, 1.9 Hz), 6.34 (1H, dd, J = 8.1, 2.1 Hz), 6.57 (1H, s), 7.11 (1H, dd, J = 8.0, 8.2 Hz), 7.79 (2H, d, J = 6.1 Hz), 8.70 (1H, d, J = 5.9 Hz) (CDCl$_3$) | 378 |
| D70 | 2.03 (1H, dt, J = 12.8, 5.5 Hz), 2.36 (1H, dt, J = 12.8, 5.5 Hz), 3.52 (3H, s), 3.51-3.59 (2H, m), 3.70-3.84 (2H, m), 3.76 (3H, s), 6.56 (1H, s), 6.60 (2H, dd, J = 6.8 Hz), 6.81 (2H, dd, J = 6.8 Hz), 7.79 (2H, d, J = 6.1 Hz), 8.70 (1H, d, J = 5.9 Hz) (CDCl$_3$) | 378 |
| D71 | 2.01-2.11 (1H, m), 2.29-2.40 (2H, m), 2.49 (1H, m), 3.49 (1H, m), 3.56 (3H, s), 3.79 (1H, q, J = 7.7 Hz), 5.08 (1H, t, J = 7.1 Hz), 6.64 (1H, s), 7.81 (2H, d, J = 5.8 Hz), 8.71 (2H, d, J = 5.7 Hz) (CDCl$_3$) | 282 |
| D72 | 2.01-2.11 (1H, m), 2.29-2.40 (2H, m), 2.49 (1H, m), 3.49 (1H, m), 3.56 (3H, s), 3.79 (1H, q, J = 7.7 Hz), 5.08 (1H, t, J = 7.1 Hz), 7.30 (1H, s), 8.20 (1H, d, J = 5.4 Hz), 8.89 (1H, d, J = 5.1 Hz), 9.28 (1H, s) (CDCl$_3$) | 283 |
| D73 | 2.01-2.11 (1H, m), 2.29-2.40 (2H, m), 2.49 (1H, m), 3.49 (1H, m), 3.56 (3H, s), 3.79 (1H, q, J = 7.7 Hz), 5.08 (1H, t, J = 7.1 Hz), 6.83 (1H, s), 8.00 (1H, dd, J = 5.4, 6.6 Hz), 8.53 (1H, s), 8.55 (1H, d, J = 3.6 Hz) (CDCl$_3$) | 300 |
| D74 | 2.01-2.11 (1H, m), 2.29-2.40 (2H, m), 2.49 (1H, m), 3.49 (1H, m), 3.56 (3H, s), 3.79 (1H, q, J = 7.7 Hz), 5.08 (1H, t, J = 7.1 Hz), 6.64 (1H, s), 7.81 (2H, d, J = 5.8 Hz), 8.71 (2H, d, J = 5.7 Hz) (CDCl$_3$) | 282 |
| D75 | 2.01-2.11 (1H, m), 2.29-2.40 (2H, m), 2.49 (1H, m), 3.49 (1H, m), 3.56 (3H, s), 3.79 (1H, q, J = 7.7 Hz), 5.08 (1H, t, J = 7.1 Hz), 7.30 (1H, s), 8.20 (1H, d, J = 5.4 Hz), 8.89 (1H, d, J = 5.1 Hz), 9.28 (1H, s) (CDCl$_3$) | 283 |
| D76 | 2.01-2.11 (1H, m), 2.29-2.40 (2H, m), 2.49 (1H, m), 3.49 (1H, m), 3.56 (3H, s), 3.79 (1H, q, J = 7.7 Hz), 5.08 (1H, t, J = 7.1 Hz), 6.83 (1H, s), 8.00 (1H, dd, J = 5.4, 6.6 Hz), 8.53 (1H, s), 8.55 (1H, d, J = 3.6 Hz) (CDCl$_3$) | 300 |
| D77 | 1.83-1.88 (2H, m), 2.07 (1H, m), 2.23 (1H, m), 3.06 (1H, t, J = 5.4 Hz), 3.41 (1H, dd, J = 7.2, 9.9 Hz), 3.50 (3H, s), 3.70-3.79 (2H, m), 3.86-3.91 (1H, m), 4.71 (1H, m), 6.53 (1H, s), 7.74 (2H, d, J = 6.3 Hz), 8.69 (2H, d, J = 6.3 Hz) (CDCl$_3$) | 287 |
| D78 | 1.83-1.88 (2H, m), 2.07 (1H, m), 2.23 (1H, m), 3.06 (1H, t, J = 5.4 Hz), 3.41 (1H, dd, J = 7.2, 9.9 Hz), 3.50 (3H, s), 3.70-3.79 (2H, m), 3.86-3.91 (1H, m), 4.71 (1H, m), 7.11 (1H, s), 8.02 (1H, d, J = 4.5 Hz), 8.86 (1H, d, J = 4.5 Hz), 9.29 (1H, s) (CDCl$_3$) | 288 |
| D79 | 1.83-1.88 (2H, m), 2.07 (1H, m), 2.23 (1H, m), 2.73 (1H, t, J = 5.5 Hz), 3.41 (1H, dd, J = 7.2, 7.9 Hz), 3.50 (3H, s), 3.70-3.79 (2H, m), 3.86-3.91 (1H, m), 4.71 (1H, m), 6.67 (1H, s), 7.83 (1H, dd, J = 6.3, 5.1 Hz), 8.50 (1H, d, J = 5.1 Hz), 8.54 (1H, d, J = 3.6 Hz) (CDCl$_3$) | 305 |
| D80 | 1.87-1.89 (2H, m), 2.09 (1H, m), 2.27 (1H, m), 3.32 (1H, d, J = 10.9 Hz), 3.49 (3H, s), 3.70 (3H, s), 3.71 (1H, m), 4.34 (2H, m), 4.85 (1H, m), 7.23 (1H, s), 8.15 (1H, d, J = 4.7 Hz), 8.86 (1H, d, J = 4.8 Hz), 9.27 (1H, s) (CDCl$_3$) | 302 |

TABLE 2-continued

| Compound No. | ¹H-NMR | MS [M + 1] |
|---|---|---|
| D81 | 1.75-1.88 (2H, m), 2.03 (1H, m), 2.28 (1H, m), 3.49 (3H, s), 3.68 (1H, dd, J = 16.0, 7.2 Hz), 3.80 (1H, dd, J = 15.8, 9.2 Hz), 4.59 (1H, dd, J = 8.9, 6.9 Hz), 6.63 (1H, s), 7.00 (1H, br.s), 7.51 (1H, br.s), 7.97 (2H, d, J = 6.2 Hz), 8.64 (2H, d, J = 6.2 Hz) (DMSO-d6) | 300 |
| D82 | 1.75-1.88 (2H, m), 2.03 (1H, m), 2.28 (1H, m), 3.49 (3H, s), 3.68 (1H, dd, J = 16.0, 7.2 Hz), 3.80 (1H, dd, J = 15.8, 9.2 Hz), 4.59 (1H, dd, J = 8.9, 6.9 Hz), 6.82 (1H, s), 7.00 (1H, br.s), 7.54 (1H, br.s), 8.21 (1H, d, J = 5.2 Hz), 8.97 (1H, d, J = 5.2 Hz), 9.27 (1H, s) (DMSO-d6) | 301 |
| D83 | 1.75-1.88 (2H, m), 2.01 (1H, m), 2.27 (1H, m), 3.47 (3H, s), 3.68 (1H, dd, J = 16.0, 7.2 Hz), 3.80 (1H, dd, J = 15.8, 9.2 Hz), 4.59 (1H, dd, J = 8.9, 6.9 Hz), 6.43 (1H, s), 7.00 (1H, br.s), 7.48 (1H, br.s), 8.03 (1H, dd, J = 6.6, 5.1 Hz), 8.52 (1H, d, J = 5.1 Hz), 8.67 (1H, d, J = 3.3 Hz) (DMSO-d6) | 318 |
| D84 | 1.92-2.11 (3H, m), 2.35 (1H, m), 3.38 (1H, dd, J = 8.1, 9.0 Hz), 3.44 (3H, s), 3.69 (1H, dd, J = 6.0, 9.4 Hz), 4.07 (1H, dd, J = 9.9, 5.7 Hz), 4.17 (1H, dd, J = 9.9, 3.6 Hz), 4.91 (1H, m), 6.56 (1H, s), 6.78-6.94 (4H, m), 7.74 (2H, d, J = 6.0 Hz), 8.69 (2H, d, J = 6.0 Hz) (CDCl₃) | 381 |
| D85 | 1.92-2.11 (3H, m), 2.35 (1H, m), 3.38 (1H, dd, J = 8.1, 9.0 Hz), 3.45 (3H, s), 3.69 (1H, dd, J = 6.0, 9.9 Hz), 4.07 (1H, dd, J = 9.9, 5.7 Hz), 4.17 (1H, dd, J = 9.9, 3.6 Hz), 4.90 (1H, m), 6.78-6.54 (4H, m), 7.21 (1H, s), 8.00 (1H, d, J = 6.6 Hz), 8.82 (1H, d, J = 5.4 Hz), 9.26 (1H, s) (CDCl₃) | 382 |
| D86 | 1.92-2.11 (3H, m), 2.35 (1H, m), 3.38 (1H, dd, J = 8.1, 9.0 Hz), 3.45 (3H, s), 3.69 (1H, dd, J = 6.0, 9.9 Hz), 4.07 (1H, dd, J = 9.9, 5.7 Hz), 4.17 (1H, dd, J = 9.9, 3.6 Hz), 4.85 (1H, m), 6.70 (1H, s), 6.78-6.93 (4H, m), 782 (1H, dd, J = 6.6, 5.0 Hz), 8.46 (1H, d, J = 5.1 Hz), 8.54 (1H, d, J = 3.0 Hz) (CDCl₃) | 399 |
| D87 | 0.90 (3H, t, J = 7.0 Hz), 1.31-1.44 (5H, m), 1.60-1.70 (1H, m), 1.75-1.93 (2H, m), 1.99-2.06 (1H, m), 2.22-2.30 (1H, m), 3.31 (1H, dd, J = 8.6, 8.6 Hz), 3.48 (3H, s), 3.61-3.68 (1H, m), 4.39-4.46 (1H, m), 6.56 (1H, s), 7.79 (2H, d, J = 6.3 Hz), 8.70 (2H, d, J = 6.3 Hz) (CDCl₃) | 313 |
| D88 | 0.90 (3H, t, J = 7.0 Hz), 1.31-1.45 (5H, m), 1.61-1.70 (1H, m), 1.75-1.92 (2H, m), 2.00-2.06 (1H, m), 2.23-2.30 (1H, m), 3.31 (1H, dd, J = 8.6, 8.6 Hz), 3.49 (3H, s), 3.62-3.68 (1H, m), 4.37-4.45 (1H, m), 7.19 (1H, s), 8.12 (1H, dd, J = 1.6, 5.5 Hz), 8.86 (1H, d, J = 5.5 Hz), 9.27 (1H, d, J = 1.6 Hz) (CDCl₃) | 314 |
| D89 | 0.90 (3H, t, J = 7.0 Hz), 1.30-1.43 (5H, m), 1.59-1.69 (1H, m), 1.74-1.92 (2H, m), 1.99-2.06 (1H, m), 2.21-2.29 (1H, m), 3.31 (1H, dd, J = 8.6, 8.6 Hz), 3.48 (3H, s), 3.60-3.67 (1H, m), 4.33-4.40 (1H, m), 6.73 (1H, s), 7.93 (1H, dd, J = 5.5, 6.3 Hz), 8.49 (1H, d, J = 5.5 Hz), 8.54 (1H, d, J = 3.1 Hz) (CDCl₃) | 331 |
| D90 | 1.85-2.08 (2H, m), 2.14-2.22 (1H, m), 2.43-2.50 (1H, m), 3.47-3.55 (4H, m), 3.92-3.98 (1H, m), 5.37 (1H, dd, J = 6.3, 10.2 Hz), 6.49 (1H, s), 6.98-7.02 (2H, m), 7.32-7.36 (2H, m), 7.62 (2H, d, J = 6.3 Hz), 8.66 (2H, d, J = 6.3 Hz) (CDCl₃) | 351 |
| D91 | 1.85-2.08 (2H, m), 2.15-2.22 (1H, m), 2.44-2.51 (1H, m), 3.49-3.54 (1H, m), 3.56 (3H, s), 3.92-3.99 (1H, m), 5.36 (1H, dd, J = 6.3, 10.2 Hz), 6.97-7.03 (2H, m), 7.14 (1H, s), 7.30-7.35 (2H, m), 7.89 (1H, dd, J = 1.6, 5.5 Hz), 8.81 (1H, d, J = 5.5 Hz), 9.21 (1H, d, J = 1.6 Hz) (CDCl₃) | 352 |
| D92 | 1.85-2.07 (2H, m), 2.15-2.21 (1H, m), 2.43-2.49 (1H, m), 3.49-3.54 (1H, m), 3.55 (3H, s), 3.91-3.98 (1H, m), 5.31 (1H, dd, J = 6.3, 10.2 Hz), 6.68 (1H, s), 6.98-7.04 (2H, m), 7.30-7.34 (2H, m), 7.63 (1H, dd, J = 5.5, 6.3 Hz), 8.44 (1H, d, J = 5.5 Hz), 8.50 (1H, d, J = 3.1 Hz) (CDCl₃) | 369 |
| D93 | 1.69-1.84 (2H, m), 1.93-2.01 (1H, m), 2.05-2.13 (1H, m), 2.76 (1H, dd, J = 7.8, 13.3 Hz), 3.21 (1H, dd, J = 3.9, 13.3 Hz), 3.29-3.33 (1H, m), 3.47 (3H, s), 3.54-3.61 (1H, m), 4.66-4.74 (1H, m), 6.58 (1H, s), 7.17-7.30 (5H, m), 7.84 (2H, d, J = 6.3 Hz), 8.73 (2H, d, J = 6.3 Hz) (CDCl₃) | 347 |
| D94 | 1.69-1.84 (2H, m), 1.93-2.01 (1H, m), 2.07-2.16 (1H, m), 2.80 (1H, dd, J = 7.8, 13.3 Hz), 3.17 (1H, dd, J = 3.9, 13.3 Hz), 3.28-3.33 (1H, m), 3.47 (3H, s), 3.54-3.60 (1H, m), 4.66-4.73 (1H, m), 7.16-7.30 (6H, m), 8.18 (1H, dd, J = 1.6, 5.5 Hz), 8.89 (1H, d, J = 5.5 Hz), 9.29 (1H, s) (CDCl₃) | 348 |
| D95 | 1.68-1.83 (2H, m), 1.92-2.01 (1H, m), 2.04-2.13 (1H, m), 2.74 (1H, dd, J = 7.8, 13.3 Hz), 3.19 (1H, dd, J = 3.9, 13.3 Hz), 3.29-3.33 (1H, m), 3.47 (3H, s), 3.54-3.61 (1H, m), 4.60-4.67 (1H, m), 6.74 (1H, s), 7.15-7.30 (5H, m), 7.99 (1H, dd, J = 5.5, 7.0 Hz), 8.53 (1H, d, J = 5.5 Hz), 8.57 (1H, d, J = 3.1 Hz) (CDCl₃) | 365 |
| D96 | 0.74-0.79 (1H, m), 0.92-0.98 (1H, m), 1.78-1.85 (1H, m), 1.97-2.04 (1H, m), 2.22-2.32 (1H, m), 3.37-3.48 (2H, m), 3.65 (3H, s), 3.98-4.05 (1H, m), 6.57 (1H, s), 7.81 (2H, d, J = 4.7 Hz), 8.70 (2H, d, J = 4.7 Hz) (CDCl₃) | 269 |
| D97 | 0.74-0.78 (1H, m), 0.92-0.97 (1H, m), 1.78-1.85 (1H, m), 1.98-2.04 (1H, m), 2.23-2.32 (1H, m), 3.36-3.46 (2H, m), 3.65 (3H, s), 3.96-4.03 (1H, m), 7.20 (1H, s), 8.16 (1H, dd, J = 1.6, 4.7 Hz), 8.85 (1H, d, J = 5.5 Hz), 9.27 (1H, s) (CDCl₃) | 270 |

TABLE 2-continued

| Compound No. | ¹H-NMR | MS [M + 1] |
|---|---|---|
| D98 | 0.74-0.77 (1H, m), 0.92-0.97 (1H, m), 1.78-1.85 (1H, m), 1.96-2.03 (1H, m), 2.23-2.30 (1H, m), 3.36-3.44 (2H, m), 3.65 (3H, s), 3.94-4.00 (1H, m), 6.75 (1H, s), 7.97 (1H, dd, J = 4.7, 7.0 Hz), 8.49 (1H, d, J = 4.7 Hz), 8.53 (1H, d, J = 3.1 Hz) (CDCl₃) | 287 |
| D99 | 2.08 (1H, dt, J = 12.8, 5.5 Hz), 2.33 (1H, dt, J = 12.8, 5.5 Hz), 3.54 (3H, s), 3.64-3.82 (3H, m), 3.78 (3H, s), 3.97 (1H, dd, J = 11.1, 5.4 Hz), 4.18 (1H, dd, J = 10.8, 5.4 Hz), 6.17 (1H, m), 6.24 (1H, dd, J = 7.9, 1.9 Hz), 6.34 (1H, dd, J = 8.1, 2.1 Hz), 6.76 (1H, s), 7.11 (1H, dd, J = 8.0, 8.2 Hz), 7.94 (1H, dd, J = 6.9, 5.1 Hz), 8.49 (1H, d, J = 5.1 Hz), 8.54 (1H, d, J = 3.0 Hz) (CDCl₃) | 396 |
| D100 | 1.14 (3H, d, J = 6.3 Hz), 1.85 (3H, s), 1.90 (1H, m), 2.20 (1H, m), 3.39 (1H, m), 3.55-3.65 (2H, m), 3.78 (3H, s), 3.91 (1H, dd, J = 10.8, 6.9 Hz), 5.25 (1H, d, J = 7.2 Hz), 6.71 (1H, d, J = 1.8 Hz), 6.76 (1H, d, J = 7.8 Hz), 6.93 (1H, dd, J = 8.4, 2.7 Hz), 7.16 (1H, s), 7.35 (1H, t, J = 8.1 Hz), 8.09 (1H, d, J = 5.1 Hz), 8.86 (1H, d, J = 5.1 Hz), 9.26 (1H, s) (CDCl₃) | 421 |
| F1 | 1.26 (3H, d, J = 6.6 Hz), 1.50 (9H, s), 3.24-3.83 (7H, m), 3.53 (3H, s), 6.70 (1H, s), 7.79 (2H, d, J = 6.0 Hz), 8.72 (2H, d, J = 6.0 Hz) (CDCl₃) | 386 |
| F2 | 1.26 (3H, d, J = 6.6 Hz), 1.50 (9H, s), 3.24-3.83 (7H, m), 3.55 (3H, s), 7.42 (1H, s), 8.14 (1H, d, J = 5.4 Hz), 8.87 (1H, d, J = 5.1 Hz), 9.28 (1H, s) (CDCl₃) | 387 |
| F3 | 1.26 (3H, d, J = 6.6 Hz), 1.50 (9H, s), 3.24-3.83 (7H, m), 3.55 (3H, s), 6.81 (1H, s), 7.93 (1H, dd, J = 6.5, 5.1 Hz), 8.51 (1H, d, J = 5.1 Hz), 8.55 (1H, d, J = 3.1 Hz) (CDCl₃) | 404 |
| F4 | 1.26 (3H, d, J = 6.6 Hz), 2.80 (1H, dd, J = 13.2, 5.1 Hz), 3.02-3.18 (3H, m), 3.30-3.33 (1H, m), 3.30-3.36 (1H, m), 3.55 (3H, s), 3.71 (1H, m), 7.34 (1H, s), 8.16 (1H, dd, J = 5.2 Hz), 8.87 (1H, d, J = 5.1 Hz), 9.28 (1H, s) (CDCl₃) | 287 |
| F5 | 1.27 (3H, d, J = 6.4 Hz), 2.80 (1H, dd, J = 13.2, 5.1 Hz), 3.03-3.06 (2H, m), 3.12-3.18 (2H, m), 3.30-3.36 (1H, m), 3.55 (3H, s), 3.73 (1H, m), 6.69 (1H, s), 7.80 (2H, d, J = 6.3 Hz), 8.70 (2H, d, J = 6.0 Hz) (CDCl₃) | 286 |
| F6 | 1.29 (3H, t, J = 6.6 Hz), 2.32 (3H, s), 2.43-2.65 (4H, m), 3.27-3.29 (1H, m), 3.37-3.41 (1H, m), 3.53 (3H, s), 3.82 (1H, m), 6.89 (1H, s), 7.80 (2H, d, J = 6.0 Hz), 8.71 (2H, d, J = 6.0 Hz) (CDCl₃) | 300 |
| F7 | 1.27 (3H, d, J = 6.4 Hz), 2.80 (1H, dd, J = 13.2, 5.1 Hz), 3.03-3.06 (2H, m), 3.12-3.18 (2H, m), 3.30-3.36 (1H, m), 3.55 (3H, s), 3.73 (1H, m), 6.69 (1H, s), 7.80 (2H, d, J = 6.3 Hz), 8.70 (2H, d, J = 6.0 Hz) (CDCl₃) | 286 |
| F8 | 1.26 (3H, d, J = 6.6 Hz), 2.80 (1H, dd, J = 13.2, 5.1 Hz), 3.02-3.18 (3H, m), 3.30-3.33 (1H, m), 3.31-3.35 (1H, m), 3.55 (3H, s), 3.71 (1H, m), 7.34 (1H, s), 8.16 (1H, dd, J = 5.2 Hz), 8.87 (1H, d, J = 5.1 Hz), 9.28 (1H, s) (CDCl₃) | 287 |
| F9 | 1.26 (3H, d, J = 6.3 Hz), 2.80 (1H, dd, J = 12.3, 5.1 Hz), 3.02-3.17 (4H, m), 3.30-3.34 (1H, m), 3.55 (3H, m), 3.70 (1H, m), 6.88 (1H, s), 7.97 (1H, dd, J = 6.6, 5.1 Hz), 8.52 (1H, d, J = 5.1 Hz), 8.55 (1H, d, J = 3.0 Hz) (CDCl₃) | 304 |
| F10 | 1.28 (3H, d, J = 6.3 Hz), 2.32 (3H, s), 2.43-2.63 (4H, m), 3.24 (1H, m), 3.35-3.39 (1H, m), 3.80 (3H, s), 3.81 (1H, m), 7.33 (1H, s), 8.16 (1H, d, J = 4.8 Hz), 8.87 (1H, d, J = 5.1 Hz), 9.27 (1H, s) (CDCl₃) | 301 |
| F11 | 1.28 (3H, d, J = 6.3 Hz), 2.32 (3H, s), 2.42-2.64 (4H, m), 3.23-3.26 (1H, m), 3.35-3.39 (1H, m), 3.53 (3H, s), 3.80 (1H, m), 6.88 (1H, s), 7.97 (1H, dd, J = 6.6, 5.1 Hz), 8.52 (1H, d, J = 5.1 Hz), 8.55 (1H, d, J = 3.0 Hz) (CDCl₃) | 318 |
| F12 | 1.29 (3H, t, J = 6.6 Hz), 2.32 (3H, s), 2.43-2.65 (4H, m), 3.27-3.29 (1H, m), 3.37-3.41 (1H, m), 3.53 (3H, s), 3.82 (1H, m), 6.89 (1H, s), 7.80 (2H, d, J = 6.0 Hz), 8.71 (2H, d, J = 6.0 Hz) (CDCl₃) | 300 |
| F13 | 1.28 (3H, d, J = 6.3 Hz), 2.32 (3H, s), 2.42-2.64 (4H, m), 3.23-3.26 (1H, m), 3.35-3.39 (1H, m), 3.53 (3H, s), 3.80 (1H, m), 6.88 (1H, s), 7.97 (1H, dd, J = 6.6, 5.1 Hz), 8.52 (1H, d, J = 5.1 Hz), 8.55 (1H, d, J = 3.0 Hz) (CDCl₃) | 318 |
| F14 | 1.28 (3H, d, J = 6.3 Hz), 2.33 (3H, s), 2.43-2.63 (4H, m), 3.24 (1H, m), 3.35-3.39 (1H, m), 3.80 (3H, s), 3.81 (1H, m), 7.33 (1H, s), 8.16 (1H, d, J = 4.8 Hz), 8.87 (1H, d, J = 5.1 Hz), 9.27 (1H, s) (CDCl₃) | 301 |
| F15 | 1.26 (3H, d, J = 6.3 Hz), 2.80 (1H, dd, J = 12.3, 5.1 Hz), 3.02-3.17 (4H, m), 3.30-3.34 (1H, m), 3.55 (3H, m), 3.70 (1H, m), 6.88 (1H, s), 7.97 (1H, dd, J = 6.6, 5.1 Hz), 8.52 (1H, d, J = 5.1 Hz), 8.55 (1H, d, J = 3.0 Hz) (CDCl₃) | 304 |
| F16 | 1.26 (3H, d, J = 6.6 Hz), 3.31-3.70 (7H, m), 3.56 (3H, s), 7.32 (1H, s), 7.45 (5H, m), 8.11 (1H, d, J = 5.2 Hz), 8.89 (1H, d, J = 5.1 Hz), 9.29 (1H, s) (CDCl₃) | 391 |
| F17 | 1.22 (1.5H, d, J = 6.6 Hz), 1.29 (1.5H, d, J = 6.3 Hz), 2.15 (1.5H, s), 2.19 (1.5H, s), 3.28-4.26 (7H, m), 3.56 (3H, s), 7.27 (1H, s), 8.12 (1H, d, J = 5.2 Hz), 8.88 (1H, d, J = 5.1 Hz), 9.27 (1H, s) (CDCl₃) | 329 |

TABLE 2-continued

| Compound No. | ¹H-NMR | MS [M + 1] |
|---|---|---|
| F18 | 1.37 (3H, d, J = 6.6 Hz), 2.85 (3H, s), 3.58 (3H, s), 3.27-3.90 (6H, m), 4.12 (1H, m), 7.27 (1H, s), 8.11 (1H, d, J = 5.2 Hz), 8.89 (1H, d, J = 5.1 Hz), 9.29 (1H, s) (CDCl₃) | 365 |
| F19 | 1.33 (3H, d, J = 6.6 Hz), 2.43 (3H, s), 2.95-3.03 (2H, m), 3.20-3.50 (4H, m), 3.45 (3H, s), 3.85 (1H, m), 7.21 (1H, s), 7.35 (2H, d, J = 8.2 Hz), 7.66 (2H, d, J = 8.2 Hz), 8.12 (1H, d, J = 5.4 Hz), 8.87 (1H, d, J = 4.9 Hz), 9.27 (1H, s) (CDCl₃) | 441 |
| F20 | 1.26 (3H, d, J = 6.6 Hz), 1.38 (3H, s), 3.24-3.54 (5H, m), 3.54 (3H, s), 3.66 (1H, m), 3.82 (1H, m), 4.31 (1H, br.s), 7.36 (1H, s), 8.13 (1H, d, J = 5.4 Hz), 8.87 (1H, d, J = 4.9 Hz), 9.28 (1H, s) (CDCl₃) | 386 |
| F21 | 1.32 (3H, d, J = 6.6 Hz), 3.37-3.67 (5H, m), 3.57 (3H, s), 3.86-3.92 (2H, m), 6.45 (1H, br.s), 6.83-6.91 (2H, m), 7.38 (1H, s), 7.95-8.03 (1H, m), 8.13 (1H, d, J = 5.4 Hz), 8.88 (1H, d, J = 4.9 Hz), 9.29 (1H, s) (CDCl₃) | 442 |
| F22 | 1.25 (3H, d, J = 6.9 Hz), 3.22-3.83 (7H, m), 3.50 (3H, s), 3.70 (3H, s), 7.36 (1H, s), 8.13 (1H, d, J = 5.4 Hz), 8.88 (1H, d, J = 4.9 Hz), 9.28 (1H, s) (CDCl₃) | 345 |
| F23 | 1.28 (3H, d, J = 6.3 Hz), 2.47-2.61 (3H, m), 2.69 (1H, m), 3.27 (1H, m), 3.39-3.61 (3H, m), 3.53 (3H, s), 3.81 (1H, m), 7.26-7.36 (6H, m), 8.10 (1H, d, J = 5.4 Hz), 8.86 (1H, d, J = 5.1 Hz), 8.27 (1H, s) (CDCl₃) | 377 |
| F24 | 1.38 (1H, d, J = 6.4 Hz), 3.22-3.26 (1H, m), 3.28 (1H, d, J = 4.3 Hz), 3.31-3.48 (3H, m), 3.53-3.58 (1H, m), 3.59 (3H, s), 3.91-4.00 (1H, m), 6.91-6.98 (3H, m), 7.31 (2H, dd, J = 8.3, 7.3 Hz), 7.37 (1H, s), 8.18 (1H, d, J = 5.2 Hz), 8.88 (1H, d, J = 5.2 Hz), 9.29 (1H, d, J = 1.2 Hz) (CDCl₃) | 363 |
| F25 | 1.25 (3H, d, J = 6.3 Hz), 1.49 (9H, s), 3.25-3.91 (7H, m), 3.53 (3H, s), 6.67 (1H, s), 7.97 (2H, d, J = 6.2 Hz), 8.72 (1H, d, J = 6.2 Hz) (CDCl₃) | 386 |
| F26 | 1.42 (3H, d, J = 6.0 Hz), 3.23-3.57 (5H, m), 3.41-3.57 (1H, m), 3.59 (3H, s), 3.96 (1H, m), 6.98-7.10 (4H, m), 7.36 (1H, s), 8.20 (1H, d, J = 5.2 Hz), 8.88 (1H, d, J = 5.0 Hz), 9.29 (1H, s) (CDCl₃) | 381 |
| F27 | 1.37 (3H, d, J = 6.5 Hz), 3.23-3.57 (5H, m), 3.41-3.57 (1H, m), 3.59 (3H, s), 3.96 (1H, m), 6.59-6.65 (2H, m), 6.71 (1H, dd, J = 8.1, 2.4 Hz), 7.22-7.26 (1H, m), 7.27 (1H, s), 8.18 (1H, d, J = 5.2 Hz), 8.88 (1H, d, J = 5.0 Hz), 9.28 (1H, s) (CDCl₃) | 381 |
| F28 | 1.38 (3H, d, J = 6.5 Hz), 3.16-3.42 (5H, m), 3.41-3.57 (1H, m), 3.59 (3H, s), 3.94 (1H, m), 6.90-7.04 (4H, m), 7.37 (1H, s), 8.18 (1H, d, J = 5.2 Hz), 8.88 (1H, d, J = 5.0 Hz), 9.28 (1H, s) (CDCl₃) | 381 |
| F29 | 1.40 (3H, d, J = 6.3 Hz), 3.18 (2H, d, J = 3.9 Hz), 3.22-3.24 (2H, m), 3.42 (1H, dt, J = 12.6, 3.9 Hz), 3.55 (1H, m), 3.59 (3H, s), 3.90 (3H, s), 3.93 (1H, m), 6.89-7.08 (4H, m), 7.36 (1H, s), 8.20 (1H, d, J = 4.8 Hz), 8.88 (1H, d, J = 5.1 Hz), 9.29 (1H, s) (CDCl₃) | 393 |
| F30 | 1.36 (3H, d, J = 6.6 Hz), 3.33-3.55 (7H, m), 3.59 (3H, s), 3.82 (3H, s), 6.46 (1H, m), 6.49 (1H, s), 6.57 (1H, d, J = 9.6 Hz), 7.22 (1H, dd, J = 8.7, 7.5 Hz), 7.37 (1H, s), 8.20 (1H, d, J = 4.8 Hz), 8.88 (1H, d, J = 5.1 Hz), 9.29 (1H, s) (CDCl₃) | 393 |
| F31 | 1.38 (3H, d, J = 6.3 Hz), 3.22-3.55 (6H, m), 3.59 (3H, s), 3.79 (3H, s), 3.94 (1H, m), 6.86-6.98 (4H, m), 7.36 (1H, s), 8.19 (1H, d, J = 4.8 Hz), 8.88 (1H, d, J = 5.1 Hz), 9.28 (1H, s) (CDCl₃) | 393 |
| F32 | 1.23-1.29 (9H, m), 3.23-3.50 (4H, m), 3.55 (3H, s), 3.67-4.16 (3H, m), 4.90 (1H, q, J = 6.3 Hz), 7.36 (1H, s), 8.13 (1H, d, J = 5.1 Hz), 8.88 (1H, d, J = 5.1 Hz), 9.62 (1H, s) (CDCl₃) | 329 |
| F33 | 1.14 (3H, d, J = 6.5 Hz), 2.41 (3H, s), 3.15-3.19 (2H, m), 3.28-3.32 (2H, m), 3.44-3.48 (3H, m), 3.58 (3H, s), 6.24 (1H, d, J = 3.6 Hz), 6.46 (1H, d, J = 3.9 Hz), 7.34 (1H, s), 8.19 (1H, d, J = 5.5 Hz), 8.88 (1H, d, J = 5.1 Hz), 9.28 (1H, s) (CDCl₃) | 383 |
| F34 | 1.35 (3H, t, J = 6.9 Hz), 1.59 (3H, s), 3.31-3.56 (6H, m), 3.58 (3H, s), 3.92 (1H, m), 4.32 (2H, q, J = 6.9 Hz), 6.11 (1H, d, J = 4.2 Hz), 7.39 (1H, s), 7.58 (1H, d, J = 4.2 Hz), 8.14 (1H, d, J = 5.1 Hz), 8.89 (1H, d, J = 5.1 Hz), 9.28 (1H, s) (CDCl₃) | 427 |
| F35 | 1.35 (3H, d, J = 6.5 Hz), 2.38 (3H, s), 3.08-3.39 (5H, m), 3.50-3.53 (1H, m), 3.57 (3H, s), 3.90 (1H, s), 6.00 (1H, d, J = 3.6 Hz), 6.43 (1H, d, J = 3.8 Hz), 7.36 (1H, s), 8.17 (1H, d, J = 5.3 Hz), 8.88 (1H, d, J = 5.1 Hz), 9.28 (1H, s) (CDCl₃) | 383 |
| F36 | 1.26 (3H, d, J = 6.3 Hz), 2.32-2.38 (1H, m), 2.68-2.75 (1H, m), 2.82-2.87 (1H, m), 2.97-3.02 (1H, m), 3.14-3.21 (1H, m), 3.25 (1H, d, J = 13.3 Hz), 3.39-3.49 (2H, m), 3.51 (3H, s), 4.11 (1H, d, J = 13.3 Hz), 6.65 (1H, s), 7.26-7.37 (5H, m), 7.80 (2H, d, J = 6.3 Hz), 8.71 (2H, d, J = 6.3 Hz) (CDCl₃) | 376 |
| F37 | 1.26 (3H, d, J = 6.3 Hz), 2.32-2.38 (1H, m), 2.68-2.76 (1H, m), 2.82-2.87 (1H, m), 2.96-3.02 (1H, m), 3.13-3.20 (1H, m), 3.25 (1H, d, J = 13.3 Hz), 3.37-3.48 (2H, m), 3.52 (3H, s), 4.11 (1H, d, J = 13.3 Hz), 7.26-7.37 (6H, m), 8.16 (1H, dd, J = 1.6, 5.5 Hz), 8.87 (1H, d, J = 5.5 Hz), 9.27 (1H, s) (CDCl₃) | 377 |
| F38 | 1.25 (3H, d, J = 6.3 Hz), 2.31-2.37 (1H, m), 2.66-2.75 (1H, m), 2.81-2.86 (1H, m), 2.95-3.00 (1H, m), 3.12-3.18 (1H, m), 3.25 (1H, d, | 394 |

TABLE 2-continued

| Compound No. | $^1$H-NMR | MS [M + 1] |
|---|---|---|
|  | J = 13.3 Hz), 3.36-3.46 (2H, m), 3.51 (3H, s), 4.10 (1H, d, J = 13.3 Hz), 6.84 (1H, s), 7.25-7.36 (5H, m), 7.97 (1H, dd, J = 5.5, 7.0 Hz), 8.51 (1H, d, J = 5.5 Hz), 8.54 (1H, d, J = 3.1 Hz) (CDCl$_3$) |  |
| F39 | 1.26 (3H, d, J = 6.3 Hz), 2.32-2.38 (1H, m), 2.68-2.75 (1H, m), 2.82-2.87 (1H, m), 2.97-3.02 (1H, m), 3.14-3.21 (1H, m), 3.25 (1H, d, J = 13.3 Hz), 3.39-3.49 (2H, m), 3.51 (3H, s), 4.11 (1H, d, J = 13.3 Hz), 6.65 (1H, s), 7.26-7.37 (5H, m), 7.80 (2H, d, J = 6.3 Hz), 8.71 (2H, d, J = 6.3 Hz) (CDCl$_3$) | 376 |
| F40 | 1.26 (3H, d, J = 6.3 Hz), 2.32-2.38 (1H, m), 2.68-2.76 (1H, m), 2.82-2.87 (1H, m), 2.96-3.02 (1H, m), 3.13-3.20 (1H, m), 3.25 (1H, d, J = 13.3 Hz), 3.37-3.48 (2H, m), 3.52 (3H, s), 4.11 (1H, d, J = 13.3 Hz), 7.26-7.37 (6H, m), 8.16 (1H, dd, J = 1.6, 5.5 Hz), 8.87 (1H, d, J = 5.5 Hz), 9.27 (1H, s) (CDCl$_3$) | 377 |
| F41 | 1.25 (3H, d, J = 6.3 Hz), 2.31-2.37 (1H, m), 2.66-2.75 (1H, m), 2.81-2.86 (1H, m), 2.95-3.00 (1H, m), 3.12-3.18 (1H, m), 3.25 (1H, d, J = 13.3 Hz), 3.36-3.46 (2H, m), 3.51 (3H, s), 4.10 (1H, d, J = 13.3 Hz), 6.84 (1H, s), 7.25-7.36 (5H, m), 7.97 (1H, dd, J = 5.5, 7.0 Hz), 8.51 (1H, d, J = 5.5 Hz), 8.54 (1H, d, J = 3.1 Hz) (CDCl$_3$) | 394 |
| F42 | 0.80 (3H, t, J = 7.5 Hz), 1.74-1.80 (1H, m), 1.90-1.99 (1H, m), 2.37 (1H, dt, J = 3.1, 11.0 Hz), 2.45 (1H, dd, J = 3.2, 11.4 Hz), 2.72-2.81 (2H, m), 3.32-3.36 (1H, m), 3.44-3.53 (5H, m), 3.59-3.62 (2H, m), 6.81 (1H, s), 7.24-7.36 (5H, m), 7.96 (1H, dd, J = 5.2, 6.5 Hz), 8.50 (1H, d, J = 4.9 Hz), 8.54 (1H, d, J = 3.1 Hz) (CDCl3) | 408 |
| F43 | 0.94 (3H, t, J = 7.5 Hz), 1.58-1.67 (1H, m), 1.71-1.78 (1H, m), 2.29-2.34 (1H, m), 2.73-2.76 (1H, m), 3.04 (1H, dd, J = 8.5, 12.8 Hz), 4.01 (1H, d, J = 13.8 Hz), 6.97 (1H, s), 7.36-7.42 (4H, m), 8.22 (1H, dd, J = 1.3, 5.8 Hz), 9.01 (1H, d, J = 5.3 Hz), 9.30 (1H, s) (DMSO-d6) | 425 |
| F44 | 0.92 (3H, t, J = 7.4 Hz), 1.54-1.65 (1H, m), 1.69-1.76 (1H, m), 2.30 (1H, dt, J = 2.4, 10.6 Hz), 2.71-2.75 (1H, m), 3.01 (1H, dd, J = 8.5, 12.7 Hz), 3.09 (1H, t, J = 9.9 Hz), 3.28 (1H, d, J = 13.8 Hz), 3.52 (1H, d, J = 12.2 Hz), 3.99 (1H, d, J = 13.8 Hz), 6.56 (1H, s), 7.38 (4H, m), 7.99 (1H, dd, J = 5.2, 6.7 Hz), 8.57 (1H, d, J = 4.8 Hz), 8.70 (1H, d, J = 3.0 Hz) (DMSO-d6) | 442 |
| F45 | 1H NMR (400 MHz, DMSO-d6) 0.81 (3H, t, J = 7.5 Hz), 1.34-1.39 (1H, m), 1.52-1.59 (1H, m), 3.19-3.21 (2H, m), 3.23-3.31 (1H, m), 3.42-3.56 (7H, m), 3.57-3.61 (1H, m), 3.70 (1H, s), 6.86 (2H, d, J = 9.0 Hz), 6.96 (2H, d, J = 9.0 Hz), 7.00 (1H, s), 8.27 (1H, dd, J = 1.3, 4.6 Hz), 9.03 (1H, d, J = 4.9 Hz), 9.31 (1H, d, J = 1.1 Hz) | 407 |
| F46 | 0.86 (3H, t, J = 7.5 Hz), 1.49-1.52 (2H, m), 3.15-3.20 (1H, m), 3.24-3.39 (4H, m), 3.49-3.55 (2H, m), 3.59 (3H, s), 3.80 (3H, s), 6.87 (2H, d, J = 9.0 Hz), 6.98 (2H, d, J = 8.8 Hz), 8.01 (1H, dd, J = 5.2, 6.5 Hz), 8.53 (1H, d, J = 4.8 Hz), 8.56 (1H, d, J = 3.1 Hz) (DMSO-d6) | 424 |
| F47 | 0.75 (3H, t, J = 7.5 Hz), 1.74-1.91 (2H, m), 2.24-2.30 (1H, m), 2.37 (1H, dd, J = 3.2, 11.5 Hz), 2.69 (1H, d, J = 11.3 Hz), 2.77 (1H, d, J = 11.3 Hz), 3.39 (3H, s), 3.43 (1H, d, J = 13.2 Hz), 3.44-3.46 (3H, m), 3.59 (1H, d, J = 13.2 Hz), 3.77 (1H, br), 6.93 (1H, s), 7.24-7.30 (1H, m), 7.32-7.35 (4H, m), 8.20 (1H, dd, J = 1.2, 5.3 Hz), 9.00 (1H, d, J = 4.9 Hz), 9.30 (1H, d, J = 1.2 Hz) (DMSO-d6) | 391 |
| F48 | 0.89 (3H, t, J = 7.5 Hz), 1.80-1.94 (2H, m), 2.28-2.88 (1H, m), 3.05 (1H, dd, J = 3.2, 11.9 Hz), 3.33-3.40 (2H, m), 3.45 (3H, s), 3.56-3.57 (2H, m), 3.88-3.92 (1H, m), 6.85 (2H, d, J = 8.9 Hz), 6.94 (2H, d, J = 8.9 Hz), 8.23 (1H, dd, J = 1.2, 5.9 Hz), 9.02 (1H, d, J = 5.3 Hz), 9.30 (1H, d, J = 1.2 Hz) (DMSO-d6) | 407 |
| F49 | 0.88 (3H, t, J = 7.5 Hz), 1.76-1.92 (2H, m), 2.79-2.86 (1H, m), 3.02 (1H, dd, J = 3.2, 12.0 Hz), 3.31-3.39 (2H, m), 3.45 (3H, s), 3.51-3.53 (2H, m), 3.69 (3H, s), 3.84-3.88 (1H, m), 6.56 (1H, s), 6.84 (2H, d, J = 9.1 Hz), 6.93 (2H, d, J = 9.1 Hz), 7.98 (1H, dd, J = 5.2, 6.7 Hz), 8.58 (1H, d, J = 4.8 Hz), 8.70 (1H, d, J = 3.0 Hz) (DMSO-d6) | 424 |
| F50 | 1.19-1.39 (3H, m), 3.27-3.61 (5H, m), 3.62-3.97 (4H, m), 4.06-4.41 (1H, m), 7.39 (1H, s), 7.42 (1H, dd, J = 4.7, 7.8 Hz), 7.80-7.83 (1H, m), 8.11 (1H, dd, J = 1.6, 4.7 Hz), 8.71-8.73 (2H, m), 8.89 (1H, d, J = 4.7 Hz), 9.29 (1H, d, J = 1.6 Hz) (CDCl$_3$) | 392 |
| F51 | 1.21-1.34 (3H, m), 3.25-3.41 (2H, m), 3.49-3.72 (6H, m), 3.75-3.94 (1H, m), 4.12-4.39 (1H, m), 7.32-7.35 (2H, m), 7.39 (1H, s), 8.10 (1H, d, J = 4.7 Hz), 8.75 (1H, d, J = 4.7 Hz), 8.89 (1H, d, J = 5.5 Hz), 9.29 (1H, s) (CDCl$_3$) | 392 |
| F52 | 1.30 (3H, d, J = 7.0 Hz), 3.19-3.25 (1H, m), 3.39-3.48 (2H, m), 3.55-3.59 (1H, m), 3.62-3.67 (4H, m), 3.74-3.79 (1H, m), 4.25-4.32 (1H, m), 6.89 (2H, d, J = 8.6 Hz), 7.38 (1H, s), 7.55 (2H, d, J = 8.6 Hz), 8.17 (1H, dd, J = 1.6, 5.5 Hz), 8.89 (1H, d, J = 5.5 Hz), 9.29 (1H, s) (CDCl$_3$) | 388 |
| F53 | 1.35 (3H, d, J = 6.3 Hz), 3.39-3.45 (3H, m), 3.49-3.58 (2H, m), 3.59-3.63 (4H, m), 3.95-4.02 (1H, m), 6.91 (2H, d, J = 9.4 Hz), 7.38 (1H, s), 7.55 (2H, d, J = 9.4 Hz), 8.14 (1H, dd, J = 1.6, 5.5 Hz), 8.88 (1H, d, J = 5.5 Hz), 9.29 (1H, d, J = 1.6 Hz) (CDCl$_3$) | 388 |
| F54 | 1.28 (3H, d, J = 6.3 Hz), 3.34-3.39 (1H, m), 3.45-3.53 (1H, m), 3.59 (3H, s), 3.67-3.74 (1H, m), 3.77-3.81 (1H, m), 3.88-3.95 (1H, m), 4.14-4.19 (1H, m), 4.33-4.39 (1H, m), 6.55 (1H, t, J = 4.7 Hz), | 364 |

TABLE 2-continued

| Compound No. | $^1$H-NMR | MS [M + 1] |
|---|---|---|
| | 6.71 (1H, s), 7.81 (2H, d, J = 6.3 Hz), 8.34 (2H, d, J = 4.7 Hz), 8.72 (2H, d, J = 6.3 Hz) (CDCl$_3$) | |
| F55 | 1.28 (3H, d, J = 6.3 Hz), 3.31-3.37 (1H, m), 3.45-3.51 (1H, m), 3.60 (3H, s), 3.69-3.76 (1H, m), 3.79-3.83 (1H, m), 3.87-3.93 (1H, m), 4.13-4.18 (1H, m), 4.32-4.37 (1H, m), 6.56 (1H, t, J = 4.7 Hz), 7.36 (1H, s), 8.16 (1H, dd, J = 1.6, 5.5 Hz), 8.35 (2H, d, J = 4.7 Hz), 8.87 (1H, d, J = 5.5 Hz), 9.28 (1H, d, J = 1.6 Hz) (CDCl$_3$) | 365 |
| F56 | 1.27 (3H, d, J = 6.3 Hz), 3.31-3.36 (1H, m), 3.43-3.50 (1H, m), 3.59 (3H, s), 3.67-3.73 (1H, m), 3.77-3.82 (1H, m), 3.85-3.92 (1H, m), 4.13-4.18 (1H, m), 4.32-4.37 (1H, m), 6.55 (1H, t, J = 4.7 Hz), 6.90 (1H, s), 7.96 (1H, dd, J = 4.7, 6.3 Hz), 8.34 (1H, d, J = 4.7 Hz), 8.51 (1H, d, J = 5.5 Hz), 8.55 (1H, d, J = 3.1 Hz) (CDCl$_3$) | 382 |
| F57 | 1.19-1.36 (3H, m), 2.69 (3H, s), 3.27-3.59 (6H, m), 3.60-3.94 (3H, m), 4.09-4.37 (1H, m), 7.38 (1H, s), 7.57 (2H, d, J = 7.8 Hz), 8.11 (1H, dd, J = 1.6, 5.5 Hz), 8.16 (2H, d, J = 7.8 Hz), 8.88 (1H, d, J = 5.5 Hz), 9.29 (1H, d, J = 1.6 Hz) (CDCl$_3$) | 473 |
| F58 | 1.30 (3H, d, J = 6.3 Hz), 2.49-2.63 (2H, m), 2.67 (3H, s), 2.71-2.76 (1H, m), 3.24-3.30 (1H, m), 3.42-3.48 (1H, m), 3.54 (3H, s), 3.56 (1H, d, J = 13.3 Hz), 3.64 (1H, d, J = 13.3 Hz), 3.78-3.85 (1H, m), 7.33 (1H, s), 7.48 (2H, d, J = 8.6 Hz), 8.04 (2H, d, J = 8.6 Hz), 8.17 (1H, dd, J = 1.6, 4.7 Hz), 8.87 (1H, d, J = 4.7 Hz), 8.87 (1H, d, J = 4.7 Hz), 9.28 (1H, s) (CDCl$_3$) | 459 |
| F59 | 1.22-1.37 (3H, m), 3.29-3.43 (1H, m), 3.50-3.59 (4H, m), 3.63-3.90 (3H, m), 3.92-4.08 (1H, m), 4.16-4.39 (1H, m), 7.37-7.41 (2H, m), 7.75 (1H, d, J = 7.8 Hz), 7.85 (1H, dt, J = 1.6, 7.8 Hz), 8.14 (1H, dd, J = 1.6, 4.7 Hz), 8.62 (1H, d, J = 4.7 Hz), 8.88 (1H, dd, J = 3.1, 5.5 Hz), 9.29 (1H, d, J = 1.6 Hz) (CDCl$_3$) | 392 |
| F60 | 1.22-1.31 (3H, m), 3.27-3.51 (2H, m), 3.56 (3H, s), 3.58-3.89 (4H, m), 3.97-4.42 (1H, m), 7.12-7.16 (2H, m), 7.38 (1H, s), 7.45-7.49 (2H, m), 8.12 (1H, dd, J = 1.6, 5.5 Hz), 8.89 (1H, d, J = 4.7 Hz), 9.29 (1H, d, J = 1.6 Hz) (CDCl$_3$) | 409 |
| F61 | 1.11-1.27 (3H, m), 3.31-3.63 (8H, m), 3.91-4.31 (2H, m), 7.01 (1H, s), 7.47-7.57 (4H, m), 8.23 (1H, d, J = 5.5 Hz), 9.00 (1H, d, J = 5.5 Hz), 9.31 (1H, brs) (DMSO-d6) | 425 |
| F62 | 1.11-1.29 (3H, m), 3.33-3.64 (8H, m), 3.92-4.29 (2H, m), 7.01 (1H, s), 7.42-7.50 (1H, m), 7.72-7.78 (2H, m), 8.22 (1H, d, J = 4.7 Hz), 9.00 (1H, d, J = 4.7 Hz), 9.30 (1H, brs) (DMSO-d6) | 459 |
| F63 | 1.12-1.31 (12H, m), 3.35-3.65 (8H, m), 3.93-4.35 (2H, m), 7.00 (1H, s), 7.37-7.40 (2H, m), 7.49 (2H, d, J = 8.6 Hz), 8.24 (1H, d, J = 5.5 Hz), 8.99 (1H, d, J = 5.5 Hz), 9.30 (1H, d, J = 1.6 Hz) (DMSO-d6) | 447 |
| F64 | 1.21-1.34 (3H, m), 3.26-3.46 (2H, m), 3.51-3.96 (7H, m), 4.09-4.38 (1H, m), 7.38 (1H, s), 7.56 (2H, d, J = 7.8 Hz), 7.77 (2H, d, J = 7.8 Hz), 8.10 (1H, dd, J = 1.6, 5.5 Hz), 8.88 (1H, d, J = 5.5 Hz), 9.29 (1H, d, J = 1.6 Hz) (CDCl$_3$) | 416 |
| F65 | 1.12-1.29 (3H, m), 3.30-3.61 (8H, m), 3.94-4.32 (2H, m), 7.00 (1H, s), 7.46-7.49 (2H, m), 7.57-7.64 (2H, m), 8.24 (1H, d, J = 5.5 Hz), 9.00 (1H, d, J = 5.5 Hz), 9.31 (1H, brs) (DMSO-d6) | 475 |
| F66 | 1.12-1.29 (3H, m), 3.27-3.62 (8H, m), 3.89 (3H, s), 3.91-4.34 (2H, m), 7.00 (1H, s), 7.56-7.63 (2H, m), 8.04 (2H, d, J = 7.8 Hz), 8.23 (1H, brs), 9.00 (1H, brs), 9.30 (1H, brs) (DMSO-d6) | 449 |
| F67 | 1.11-1.29 (3H, m), 2.35 (3H, s), 3.37-3.65 (8H, m), 3.89-4.34 (2H, m), 7.00 (1H, s), 7.27 (2H, d, J = 7.8 Hz), 7.31-7.37 (2H, m), 8.23 (1H, d, J = 4.7 Hz), 9.00 (1H, d, J = 4.7 Hz), 9.30 (1H, d, J = 1.6 Hz) (DMSO-d6) | 405 |
| F68 | 1.13-1.32 (3H, m), 3.28-3.62 (8H, m), 3.94-4.35 (2H, m), 7.00 (1H, s), 7.66-7.72 (2H, m), 7.86 (2H, d, J = 6.3 Hz), 8.22 (1H, brs), 9.00 (1H, brs), 9.30 (1H, brs) (DMSO-d6) | 459 |
| F69 | 1.19 (3H, d, J = 7.0 Hz), 2.96 (6H, s), 3.32-3.56 (7H, m), 3.72-4.03 (3H, m), 6.72 (2H, d, J = 8.6 Hz), 7.00 (1H, s), 7.32 (2H, d, J = 8.6 Hz), 8.22 (1H, dd, J = 1.6, 4.7 Hz), 8.99 (1H, d, J = 5.5 Hz), 9.30 (1H, d, J = 1.6 Hz) (DMSO-d6) | 434 |
| F70 | 1.16-1.29 (3H, m), 3.33-3.61 (8H, m), 3.79-4.07 (5H, m), 6.99-7.02 (3H, m), 7.42 (2H, d, J = 8.6 Hz), 8.23 (1H, dd, J = 1.6, 5.5 Hz), 9.00 (1H, d, J = 5.5 Hz), 9.30 (1H, d, J = 1.6 Hz) (DMSO-d6) | 421 |
| F71 | 1.12-1.36 (3H, m), 3.34-3.71 (8H, m), 3.90-4.39 (2H, m), 7.01 (1H, s), 7.55-7.63 (3H, m), 7.98-8.05 (4H, m), 8.23 (1H, d, J = 4.7 Hz), 8.98 (1H, d, J = 3.1 Hz), 9.30 (1H, d, J = 1.6 Hz) (DMSO-d6) | 441 |
| F72 | 1.13-1.25 (3H, m), 3.32-3.60 (8H, m), 3.94-4.15 (2H, m), 6.09 (2H, s), 6.95-7.02 (4H, m), 8.23 (1H, dd, J = 1.6, 4.7 Hz), 9.00 (1H, d, J = 4.7 Hz), 9.30 (1H, d, J = 1.6 Hz) (DMSO-d6) | 435 |
| F73 | 1.21-1.34 (3H, m), 3.30-3.83 (8H, m), 3.95-4.44 (2H, m), 7.01 (1H, d, J = 1.6 Hz), 7.69-7.76 (2H, m), 7.84-7.88 (1H, m), 8.04-8.10 (2H, m), 8.22-8.26 (1H, m), 8.54 (1H, d, J = 8.6 Hz), 8.97-9.01 (1H, m), 9.30 (1H, brs) (DMSO-d6) | 442 |

TABLE 2-continued

| Compound No. | $^1$H-NMR | MS [M + 1] |
|---|---|---|
| F74 | 1.32 (3H, t, J = 7.0 Hz), 2.52 (3H, d, J = 2.4 Hz), 3.38-3.46 (1H, m), 3.49-3.59 (4H, m), 3.61-3.75 (1H, m), 3.84-3.97 (2H, m), 4.08-4.41 (2H, m), 7.40 (1H, s), 8.11 (1H, d, J = 5.5 Hz), 8.89 (1H, d, J = 5.5 Hz), 9.29 (1H, brs) (CDCl$_3$) | 369 |
| F75 | 1.35 (3H, d, J = 6.4 Hz), 2.94-3.13 (2H, m), 3.13-3.33 (2H, m), 3.45 (3H, s), 3.33-3.65 (3H, m), 3.85 (3H, s), 4.05-4.08 (1H, m), 7.00 (1H, s), 7.07 (1H, t, J = 7.6 Hz), 7.17 (1H, d, J = 8.1 Hz), 7.41-7.57 (1H, m), 7.59 (1H, dd, J = 7.7, 1.2 Hz), 8.26 (1H, d, J = 5.1 Hz), 9.02 (1H, d, J = 5.1 Hz), 9.31 (1H, s) (DMSO-d6) | 421 |
| F76 | 1.31 (3H, d, J = 6.4 Hz), 3.20-3.25 (2H, m), 3.29-3.40 (2H, m), 3.47 (3H, s), 3.50-3.67 (2H, m), 3.99-4.13 (1H, m), 7.02 (1H, s), 7.19 (1H, d, J = 7.5 Hz), 7.33 (1H, dd, J = 8.5, 2.2 Hz), 7.42 (2H, t, J = 8.0 Hz), 8.24 (1H, d, J = 5.2 Hz), 9.02 (1H, d, J = 5.2 Hz), 9.31 (1H, s) (DMSO-d6) | 388 |
| F77 | 1.42 (3H, d, J = 6.5 Hz), 3.10-3.43 (5H, m), 3.47 (3H, s), 3.52-3.75 (2H, m), 4.06-3.22 (1H, m), 7.02 (1H, s), 7.15 (1H, t, J = 7.5 Hz), 7.25 (1H, d, J = 8.3 Hz), 7.56-7.71 (1H, m), 7.75 (1H, dd, J = 6.5, 1.2 Hz), 8.27 (1H, d, J = 3.9 Hz), 9.02 (1H, d, J = 5.1 Hz), 9.31 (1H, s) (DMSO-d6) | 388 |
| F78 | 1.32 (3H, d, J = 6.4 Hz), 3.20-3.34 (4H, m), 3.47 (3H, s), 3.52-3.67 (2H, m), 4.00-4.22 (1H, m), 8.02 (1H, m), 8.22 (1H, d, J = 7.6 Hz), 8.34 (1H, s), 8.57 (1H, s), 8.62 (1H, s), 9.03 (1H, d, J = 7.6 Hz), 9.32 (1H, d, J = 5.0 Hz) (DMSO-d6) | 365 |
| F79 | 1.25 (3H, d, J = 6.5 Hz), 3.32-3.67 (4H, m), 3.48 (3H, s), 3.77-4.28 (3H, m), 7.02 (1H, s), 7.87 (1H, d, J = 2.6 Hz), 8.11 (1H, d, J = 1.5 Hz), 8.23 (1H, d, J = 5.1 Hz), 8.41 (1H, d, J = 1.2 Hz), 9.02 (1H, d, J = 5.2 Hz), 9.31 (1H, s) (DMSO-d6) | 365 |
| F80 | 1.23 (3H, d, J = 6.4 Hz), 3.47 (3H, s), 3.52-3.72 (4H, m), 3.80-3.85 (1H, m), 4.03-4.05 (1H, m), 4.11-4.13 (1H, m), 4.17 (1H, m), 7.02 (1H, s), 7.29 (2H, d, J = 6.8 Hz), 8.21 (1H, d, J = 5.0 Hz), 8.31 (2H, d, J = 7.0 Hz), 9.02 (1H, d, J = 5.1 Hz), 9.31 (1H, s) (DMSO-d6) | 364 |
| F81 | 1.31 (3H, d, J = 6.4 Hz), 3.34-3.71 (5H, m), 3.48 (3H, s), 3.76-3.79 (1H, m), 4.10-4.14 (1H, m), 7.03 (1H, s), 7.82 (1H, dd, J = 8.9, 5.2 Hz), 8.08 (1H, dd, J = 8.9, 2.4 Hz), 8.21-8.25 (2H, m), 8.54 (1H, d, J = 2.7 Hz), 9.03 (1H, d, J = 5.2 Hz), 9.31 (1H, s) (DMSO-d6) | 364 |
| F82 | 1.26 (3H, d, J = 6.5 Hz), 3.48 (3H, s), 3.52-3.58 (3H, m), 3.69 (1H, dd, J = 13.1, 3.1), 3.89 (1H, dd, J = 13.4, 4.0 Hz), 4.07-3.95 (1H, m), 4.18-4.13 (1H, m), 6.87 (1H, t, J = 6.3 Hz), 7.03 (1H, s), 7.26 (1H, d, J = 9.0 Hz), 7.87 (1H, t, J = 7.4 Hz), 8.10 (1H, dd, J = 8.4, 1.3 Hz), 8.22 (1H, d, J = 3.9 Hz), 9.02 (1H, d, J = 5.2 Hz), 9.31 (1H, s) (DMSO-d6) | 364 |
| F83 | 1.28 (3H, d, J = 6.4 Hz), 1.52 (11H, s), 3.42-3.44 (2H, m), 3.47 (3H, s), 3.51-3.60 (2H, m), 3.60-3.74 (2H, m), 3.97-4.16 (1H, m), 7.01 (2H, d, J = 8.7 Hz), 7.02 (1H, s), 7.76 (2H, d, J = 8.9 Hz), 8.23 (1H, d, J = 5.1 Hz), 9.02 (1H, d, J = 5.2 Hz), 9.31 (1H, s) (DMSO-d6) | 463 |
| F84 | 1.31 (3H, d, J = 6.5 Hz), 3.11-3.14 (2H, m), 3.24 (1H, dd, J = 12.1, 3.4 Hz), 3.34 (1H, dd, J = 12.1, 4.2 Hz), 3.46 (3H, s), 3.50-3.60 (2H, m), 3.94-4.14 (1H, m), 7.01 (2H, d, J = 7.4 Hz) 7.02 (1H, s), 7.27 (2H, d, J = 9.0 Hz), 8.23 (1H, d, J = 5.1 Hz), 9.02 (1H, d, J = 5.1 Hz), 9.31 (1H, s) (DMSO-d6) | 397 |
| F85 | 1.39 (3H, d, J = 6.5 Hz), 3.45-3.50 (1H, m), 3.51 (3H, s), 3.59-3.72 (4H, m), 3.69-3.78 (1H, m), 4.11-4.15 (1H, m), 7.04 (1H, s), 7.65 (2H, d, J = 5.2 Hz), 7.89-8.10 (3H, m), 8.24 (1H, d, J = 5.1 Hz), 9.03 (1H, d, J = 5.1 Hz), 9.10 (1H, d, J = 2.6 Hz), 9.32 (1H, s) (DMSO-d6) | 414 |
| F86 | 1.33 (3H, t, J = 6.4 Hz), 3.04-3.39 (4H, m), 3.45 (3H, s), 3.48-3.55 (2H, m), 4.02-4.10 (1H, m), 6.71 (2H, d, J = 8.8 Hz), 6.88-6.93 (2H, m), 7.02 (1H, s), 8.24 (1H, d, J = 5.1 Hz), 9.02 (1H, d, J = 5.1 Hz), 9.31 (1H, s) (DMSO-d6) | 379 |
| F87 | 1.30 (3H, t, J = 6.5 Hz), 3.27-3.45 (3H, m), 3.48 (3H, m), 3.52-3.60 (2H, m), 3.66-3.72 (1H, m), 4.10-4.06 (1H, m), 7.03-7.01 (3H, m), 7.80 (2H, d, J = 8.9 Hz), 8.23 (1H, d, J = 3.9 Hz), 9.02 (1H, d, J = 5.1 Hz), 9.31 (1H, s) (DMSO-d6) | 407 |
| F88 | 1.26 (3H, d, J = 6.5 Hz), 3.27-3.42 (3H, m), 3.46 (3H, s), 3.51-3.58 (2H, m), 3.68-3.72 (1H, m), 3.78 (3H, m), 3.97-4.10 (1H, m), 6.61 (1H, s), 7.02 (2H, d, J = 9.0 Hz), 7.81 (2H, d, J = 8.9 Hz), 7.99 (1H, t, J = 6.7 Hz), 8.58 (1H, d, J = 5.0 Hz), 8.71 (1H, d, J = 3.0 Hz) (DMSO-d6) | 438 |
| F89 | 1.32 (3H, d, J = 6.4 Hz), 3.10-3.20 (1H, m), 3.25-3.31 (1H, m), 3.33-3.39 (2H, m), 3.47 (3H, m), 3.49-3.61 (2H, m), 3.85 (3H, s), 3.96-4.10 (1H, m), 6.62 (1H, s), 7.26-7.31 (1H, m), 7.38-7.42 (2H, m), 7.50 (1H, s), 8.00 (1H, dd, J = 6.7, 5.1 Hz), 8.59 (1H, d, J = 4.9 Hz), 8.72 (1H, d, J = 3.0 Hz) (DMSO-d6) | 438 |
| F90 | 1.24 (3H, d, J = 6.4 Hz), 3.41-3.61 (8H, m), 3.70-3.74 (1H, m), 4.02-4.05 (1H, m), 6.61 (1H, d, J = 1.0 Hz), 7.06 (2H, d, J = 8.9 Hz), 7.60 (2H, d, J = 8.9 Hz), 7.97 (1H, d, J = 5.0, 6.4 Hz), 8.58 (1H, d, J = 5.0 Hz), 8.71 (1H, d, J = 3.0 Hz) (DMSO-d6) | 405 |

TABLE 2-continued

| Compound No. | $^1$H-NMR | MS [M + 1] |
|---|---|---|
| F91 | 1.31 (3H, d, J = 6.4 Hz), 3.22-3.26 (1H, m), 3.28-3.68 (7H, m), 3.96-4.11 (1H, m), 6.63 (1H, s), 7.20 (1H, d, J = 7.5 Hz), 7.33-7.48 (2H, m), 7.55 (1H, t, J = 8.0 Hz), 7.88-7.96 (1H, m), 8.01 (1H, t, J = 5.9 Hz), 8.61 (1H, d, J = 4.7 Hz), 8.72 (1H, s) (DMSO-d6) | 405 |
| F92 | 1.40 (3H, d, J = 6.5 Hz), 3.14-3.43 (3H, m), 3.46 (3H, s), 3.49-3.66 (2H, m), 4.03-4.11 (3H, m), 6.62 (1H, s), 7.41 (1H, t, J = 7.5 Hz), 7.24 (1H, d, J = 8.3 Hz), 7.60-7.66 (1H, m), 7.04 (1H, dd, J = 7.7, 1.2 Hz), 8.03 (1H, dd, J = 6.8, 5.1 Hz), 8.59 (1H, d, J = 5.0 Hz), 8.72 (1H, d, J = 3.0 Hz) (DMSO-d6) | 405 |
| F93 | 1.30 (3H, d, J = 6.4 Hz), 3.20-3.30 (1H, m), 3.31-3.61 (7H, m), 3.65-3.70 (1H, m), 4.00-4.05 (1H, m), 6.62 (1H, s), 7.98-8.01 (1H, m), 8.35 (1H, s), 7.88-8.05 (5H, m), 8.47-8.79 (1H, m) (DMSO-d6) | 382 |
| F94 | 1.23 (3H, d, J = 6.5 Hz), 3.29-3.52 (2H, m), 3.47 (3H, m), 3.53-3.59 (1H, m), 3.94 (1H, dd, J = 13.0, 4.1 Hz), 3.99-4.18 (2H, m), 6.61 (1H, s), 7.86 (1H, d, J = 2.6 Hz), 8.00 (1H, dd, J = 6.8, 5.3 Hz), 8.08-8.13 (1H, m), 8.40 (1H, s), 8.58 (1H, d, J = 4.9 Hz), 8.71 (1H, d, J = 3.1 Hz) (DMSO-d6) | 382 |
| F95 | 1H NMR (400 MHz, DMSO-d6) d 3.46 (3H, s), 3.56-3.68 (3H, m), 3.80 (1H, dd, J = 13.7, 3.3 Hz), 3.98 (1H, dd, J = 13.7, 4.6 Hz), 4.08-4.12 (2H, m), 6.63 (1H, s), 7.25 (2H, d, J = 7.2 Hz), 7.97 (1H, dd, J = 6.7, 5.3 Hz), 8.27 (2H, d, J = 7.4 Hz), 8.58 (1H, d, J = 5.0 Hz), 8.72 (1H, d, J = 3.0 Hz) (DMSO-d6) | 381 |
| F96 | 1.29 (3H, d, J = 6.4 Hz), 3.37-3.42 (1H, m), 3.48 (3H, s), 3.53-3.68 (4H, m), 3.76 (1H, d, J = 12.3 Hz), 4.06-4.09 (1H, m), 6.63 (1H, s), 7.81 (1H, dd, J = 8.9, 5.2 Hz), 7.92-8.03 (1H, m), 8.07 (1H, dd, J = 8.9, 2.1 Hz), 8.23 (1H, d, J = 5.2 Hz), 8.54 (1H, d, J = 2.4 Hz), 8.59 (1H, d, J = 4.8 Hz), 8.72 (1H, d, J = 3.0 Hz) (DMSO-d6) | 381 |
| F97 | 1.25 (3H, d, J = 6.5 Hz), 3.47 (3H, s), 3.51-3.63 (3H, m), 3.67 (1H, dd, J = 13.3, 3.2 Hz), 3.88 (1H, dd, J = 13.3, 4.7 Hz), 3.98-4.03 (1H, m), 4.11-4.17 (1H, m), 6.85 (1H, t, J = 6.3 Hz), 6.98 (1H, s), 7.23 (1H, d, J = 9.0 Hz), 7.84 (1H, t, J = 7.3 Hz), 8.05-8.14 (1H, m), 8.20 (2H, d, J = 6.3 Hz), 8.82 (2H, d, J = 6.3 Hz) (DMSO-d6) | 381 |
| F98 | 1.25 (3H, d, J = 6.4 Hz), 3.52 (9H, s), 3.27-3.29 (1H, m), 3.33-3.58 (7H, m), 3.62-3.69 (2H, m), 4.00-4.05 (1H, m), 6.63 (1H, s), 7.00 (2H, d, J = 9.0 Hz), 7.76 (2H, d, J = 7.6 Hz), 7.99 (1H, dd, J = 6.8, 5.4 Hz), 8.59 (1H, d, J = 4.9 Hz), 8.71 (1H, d, J = 3.0 Hz) (DMSO-d6) | 480 |
| F99 | 1.29 (3H, d, J = 6.4 Hz), 2.63 (3H, s), 3.18-3.31 (1H, m), 3.33-3.59 (7H, m), 3.61-3.72 (1H, m), 3.98-4.11 (1H, m), 6.62 (1H, s), 7.11 (2H, d, J = 9.0 Hz), 7.84 (2H, d, J = 8.9 Hz), 8.00 (1H, dd, J = 6.7, 5.1 Hz), 8.59 (1H, d, J = 5.0 Hz), 8.72 (1H, d, J = 3.0 Hz) (DMSO-d6) | 462 |
| F100 | 1.30 (3H, d, J = 6.4 Hz), 3.06.3.13 (1H, m), 3.23 (1H, dd, J = 12.2, 3.3 Hz), 3.33 (1H, dd, J = 12.2, 4.3 Hz), 3.36-3.58 (7H, m), 3.91-4.09 (1H, m), 6.62 (1H, s), 7.00 (2H, d, J = 9.0 Hz), 7.26 (2H, d, J = 9.0 Hz), 7.94-8.07 (1H, m), 8.60 (1H, d, J = 4.9 Hz), 8.73 (1H, d, J = 2.2 Hz) (DMSO-d6) | 414 |
| F101 | 1.36 (3H, d, J = 6.5 Hz), 3.40-3.55 (1H, m), 3.43-3.56 (5H, m), 3.60-3.65 (2H, m), 3.75 (1H, d, J = 12.2 Hz), 4.01-4.18 (1H, m), 6.64 (1H, s), 7.60-7.65 (2H, m), 7.87-8.10 (4H, m), 8.60 (1H, d, J = 5.0 Hz), 8.72 (1H, d, J = 3.0 Hz), 9.09 (1H, d, J = 2.8 Hz) (DMSO-d6) | 431 |
| F102 | 1.33 (3H, d, J = 6.5 Hz), 3.27-3.43 (1H, m), 3.50 (3H, s), 3.55-3.70 (2H, m), 3.77 (1H, d, J = 12.2 Hz), 4.02-4.19 (1H, m), 7.48 (1H, d, J = 2.4 Hz), 7.79 (1H, dd, J = 8.4 Hz), 7.88-8.02 (2H, m), 8.05 (1H, d, J = 9.4 Hz), 8.59 (1H, d, J = 5.0 Hz), 8.67 (1H, d, J = 8.3 Hz), 8.72 (1H, d, J = 3.0 Hz), 8.89 (1H, d, J = 3.8 Hz) (DMSO-d6) | 431 |
| F103 | 1.31 (3H, d, J = 6.1 Hz), 3.05-3.09 (1H, m), 3.11-3.18 (1H, m), 3.25-3.42 (3H, m), 3.46 (3H, s), 3.50-3.55 (1H, m), 3.98-3.99 (1H, m), 6.63 (1H, s), 6.71 (1H, d, J = 8.8 Hz), 6.94-6.99 (3H, m), 7.56 (1H, d, J = 9.0 Hz), 7.99 (1H, dd, J = 6.5, 5.1 Hz), 8.59 (1H, d, J = 4.9 Hz), 8.72 (1H, d, J = 3.0 Hz) (DMSO-d6) | 396 |
| F104 | 1.27 (3H, d, J = 6.5 Hz), 3.16-3.35 (1H, m), 3.40-3.44 (2H, m), 3.46 (3H, s), 3.50-3.55 (2H, m), 3.56-3.70 (1H, m), 4.02-4.05 (1H, m), 6.62 (1H, s), 7.01 (2H, d, J = 9.0 Hz), 7.80 (2H, d, J = 8.9 Hz), 7.99 (1H, dd, J = 6.8, 5.3 Hz), 8.59 (1H, d, J = 4.9 Hz), 8.71 (1H, d, J = 3.0 Hz) (DMSO-d6) | 424 |
| F105 | 1.28 (3H, d, J = 6.4 Hz), 3.43-3.46 (1H, m), 3.47 (3H, s), 3.53-3.60 (3H, m), 3.69-6.72 (1H, m), 3.78 (3H, s), 4.06-4.10 (1H, m), 6.99 (1H, s), 7.03 (2H, d, J = 9.1 Hz), 7.82 (2H, d, J = 9.0 Hz), 8.25 (2H, d, J = 6.4 Hz) 8.84 (2H, d, J = 6.4 Hz) (DMSO-d6) | 420 |
| F106 | 1.33 (3H, d, J = 6.4 Hz), 3.15-3.27 (1H, m), 3.30 (1H, dd, J = 12.0, 5.1 Hz), 3.35-3.42 (2H, m), 3.47 (3H, s), 3.55-3.60 (2H, m), 3.85 (3H, s), 4.06-4.09 (1H, m), 7.00 (1H, s), 7.23-7.35 (1H, m), 7.37-7.43 (2H, m), 7.51 (1H, s), 8.27 (2H, d, J = 6.4 Hz), 8.85 (2H, d, J = 6.3 Hz) (DMSO-d6) | 420 |
| F107 | 1.34 (3H, d, J = 6.5 Hz), 3.03-3.10 (1H, m), 3.12-3.27 (2H, m), 3.46 (3H, s), 3.49-3.52 (1H, m), 3.53-3.65 (1H, m), 3.85 (3H, s), 4.06-4.08 (1H, m), 7.00 (1H, s), 7.07 (1H, t, J = 13.4 Hz), 7.17 (1HJ, d, J = 8.1 Hz), | 420 |

TABLE 2-continued

| Compound No. | ¹H-NMR | MS [M + 1] |
|---|---|---|
| | 7.48 (1H, dd, J = 12.1, 3.1 Hz), 7.59 (1H, dd, J = 7.7, 1.3 Hz), 8.32 (2H, d, J = 6.5 Hz), 8.87 (2H, d, J = 6.4 Hz) (DMSO-d6) | |
| F108 | 1.25 (3H, d, J = 6.4 Hz), 3.30-3.37 (1H, m), 3.45 (3H, s), 3.47-3.60 (4H, m), 3.71-3.74 (1H, m), 4.03-4.07 (1H, m), 6.87 (1H, s), 7.07 (2H, d, J = 8.8 Hz), 7.61 (2H, d, J = 8.8 Hz), 7.98-8.00 (2H, m), 8.69-8.71 (2H, m) (DMSO-d6) | 387 |
| F109 | 1.30 (3H, d, J = 6.5 Hz), 3.09-3.29 (1H, m), 3.36 (1H, dd, J = 12.3, 3.3 Hz), 3.48-3.42 (4H, m), 3.51-3.61 (3H, m), 4.03-4.06 (1H, m), 6.96 (1H, s), 7.19 (1H, d, J = 7.5 Hz), 7.34 (1H, dd, J = 8.4, 2.2 Hz), 7.40-7.44 (2H, m), 8.18 (1H, d, J = 6.3 Hz), 8.80 (2H, d, J = 6.3 Hz) (DMSO-d6) | 387 |
| F110 | 1.24 (3H, d, J = 6.5 Hz), 3.40-3.53 (6H, m), 3.58 (1H, dd, J = 13.1, 3.1 Hz), 3.9, 8.30 5 (1H, dd, J = 13.1, 4.1 Hz), 4.06-4.13 (2H, m), 6.99 (1H, s), 7.86 (1H, d, J = 2.6 Hz), 8.11-5.2 (1H, d, J = 2.5 Hz), 8.24 (1H, d, J = 6.4 Hz), 8.41 (1H, s), 8.83 (2H, t, J = 5.3 Hz) (DMSO-d6) | 364 |
| F111 | 1.22 (3H, d, J = 6.4 Hz), 3.46 (3H, s), 3.57-3.65 (4H, m), 3.82 (1H, d, J = 13.1 Hz), 3.99 (1H, d, J = 13.6 Hz), 4.12-4.18 (1H, m), 6.96 (1H, s), 7.28 (2H, d, J = 6.8 Hz), 8.15 (2H, d, J = 5.2 Hz), 8.30 (2H, d, J = 7.1 Hz), 8.80 (2H, d, J = 5.1 Hz) (DMSO-d6) | 363 |
| F112 | 1.31 (1H, d, J = 6.5 Hz), 3.31-3.72 (8H, m), 3.79 (1H, d, J = 12.4 Hz), 4.10-4.14 (1H, m), 6.98 (1H, s), 7.84 (1H, dd, J = 8.9, 5.3 Hz), 8.11 (1H, dd, J = 8.9, 2.5 Hz), 8.21 (1H, d, J = 6.3 Hz), 8.25 (1H, d, J = 5.2 Hz), 8.57 (1H, d, J = 2.7 Hz), 8.83 (2H, d, J = 6.2 Hz) (DMSO-d6) | 363 |
| F113 | 1.28 (2H, d, J = 6.4 Hz), 1.52 (9H, s), 3.21-3.36 (1H, m), 3.41-3.46 (1H, m), 3.47 (3H, s), 3.53-3.57 (3H, m), 3.69 (1H, d, J = 12.4 Hz), 4.06-4.08 (1H, m), 7.00 (1H, s), 7.01 (2H, d, J = 9.1 Hz), 7.76 (1H, d, J = 8.9 Hz), 8.27 (2H, d, J = 6.4 Hz), 8.85 (2H, d, J = 6.3 Hz) (DMSO-d6) | 462 |
| F114 | 1.31 (3H, d, J = 6.4 Hz), 2.63 (3H, s), 3.15-3.33 (1H, m), 3.40 (1H, dd, J = 12.4, 3.2 Hz), 3.47 (3H, s), 3.49-3.62 (3H, m), 3.67 (1H, d, J = 12.3 Hz), 4.07-4.09 (1H, m), 7.00 (1H, s), 7.11 (2H, d, J = 8.9 Hz), 7.85 (2H, d, J = 8.9 Hz), 8.29 (2H, t, J = 6.2 Hz), 8.85 (2H, d, J = 6.3 Hz) (DMSO-d6) | 444 |
| F115 | 1.31 (2H, d, J = 6.4 Hz), 3.09-3.14 (1H, m), 3.24 (1H, dd, J = 12.1, 3.1 Hz), 3.34 (1H, dd, J = 12.1, 4.2 Hz), 3.43-3.57 (6H, m), 4.02-4.06 (1H, m), 6.97 (s, 1H), 7.00 (2H, d, J = 9.0 Hz), 7.27 (2H, d, J = 9.0 Hz), 8.22 (2H, d, J = 6.3 Hz), 8.83 (2H, d, J = 6.2 Hz) (DMSO-d6) | 396 |
| F116 | 1.37 (3H, d, J = 6.5 Hz), 3.34-3.39 (1H, m), 3.45-3.52 (4H, m), 3.55-3.67 (3H, m), 3.72-3.75 (1H, m), 4.11-4.13 (1H, m), 6.99 (1H, s), 7.55-7.67 (2H, m), 7.86-8.03 (3H, m), 8.21 (2H, d, J = 6.3 Hz), 8.82 (2H, d, J = 6.3 Hz), 9.05 (1H, d, J = 2.7 Hz) (DMSO-d6) | 413 |
| F117 | 1.33 (3H, d, J = 6.5 Hz), 3.27-3.45 (1H, m), 3.49 (3H, s), 3.51-3.57 (2H, m), 3.60-3.66 (2H, m), 3.78 (1H, d, J = 12.2 Hz), 4.11-4.14 (1H, m), 6.96 (1H, s), 7.49 (1H, d, J = 2.5 Hz), 7.80 (1H, dd, J = 8.4, 5.0 Hz), 7.96 (1H, dd, J = 9.5, 2.6 Hz), 8.05 (1H, d, J = 9.4 Hz), 8.16 (2H, d, J = 6.3 Hz), 8.68 (1H, d, J = 8.4 Hz), 8.79 (2H, d, J = 6.3 Hz), 8.89 (1H, d, J = 3.7 Hz) (DMSO-d6) | 413 |
| F118 | 1.33 (1H, d, J = 6.4 Hz), 3.29-3.35 (2H, m), 3.45 (3H, s), 3.47-3.50 (2H, m), 3.51-3.55 (2H, m), 4.00-4.03 (1H, m), 6.69 (1H, d, J = 8.9 Hz), 6.70 (1H, d, J = 8.8 Hz), 6.96 (1H, s), 8.18 (2H, d, J = 6.2 Hz), 8.80 (2H, d, J = 6.2 Hz) (DMSO-d6) | 378 |
| F119 | 1.28 (2H, d, J = 6.4 Hz), 3.27-3.32 (1H, m), 3.42-3.46 (5H, m), 3.53-3.57 (2H, m), 3.64-3.71 (1H, m), 4.06-4.07 (1H, m), 6.96 (1H, s), 7.01 (2H, d, J = 8.7 Hz), 7.80 (2H, d, J = 8.7 Hz), 8.18 (2H, d, J = 5.8 Hz), 8.80 (2H, d, J = 5.7 Hz) (DMSO-d6) | 406 |
| F120 | 0.98 (3H, t, J = 7.4 Hz), 1.31 (3H, d, J = 6.4 Hz), 1.80 (2H, m), 2.94 (2H, t, J = 7.4 Hz), 3.25-3.31 (1H, m), 3.40 (1H, dd, J = 12.5, 3.2 Hz), 3.47-3.61 (2H, m), 3.65-3.68 (1H, m), 3.96-4.18 (1H, m), 7.02 (1H, s), 7.12 (2H, d, J = 9.0 Hz), 7.86 (2H, d, J = 8.9 Hz), 8.24 (1H, d, J = 5.1 Hz), 9.02 (1H, d, J = 5.2 Hz), 9.31 (1H, s) (DMSO-d6) | 473 |
| F121 | 1.31 (3H, d, J = 6.5 Hz), 3.27-3.33 (1H, m), 3.42 (3H, s), 3.49 (3H, s), 3.50-3.63 (4H, m), 3.66-3.69 (1H, m), 4.07-4.11 (1H, m), 4.79 (3H, s), 7.02 (1H, s), 7.13 (2H, d, J = 9.0 Hz), 7.88 (2H, d, J = 8.9 Hz), 8.24 (1H, d, J = 5.1 Hz), 9.02 (1H, d, J = 5.2 Hz), 9.31 (1H, s) (DMSO-d6) | 475 |
| F122 | 1.30 (3H, t, J = 6.4 Hz), 1.43 (9H, s), 3.21-3.34 (3H, m), 3.48 (3H, s), 3.50-3.73 (3H, m), 4.05-4.10 (1H, m), 7.02 (1H, s), 7.11 (2H, d, J = 9.0 Hz), 7.85 (2H, d, J = 8.9 Hz), 8.24 (1H, d, J = 3.9 Hz), 9.02 (1H, d, J = 5.2 Hz), 9.31 (1H, s) (DMSO-d6) | 487 |
| F123 | 1.32 (3H, d, J = 6.5 Hz), 3.29-3.34 (1H, m), 3.42-3.51 (5H, m), 3.53-3.61 (2H, m), 3.65-3.76 (1H, m), 4.08-4.12 (1H, m), 7.03 (1H, s), 7.17 (2H, d, J = 9.0 Hz), 7.74 (1H, dd, J = 7.2, 4.7 Hz), 7.97 (2H, d, J = 8.9 Hz), 8.13 (1H, t, J = 7.8 Hz), 8.25 (1H, d, J = 5.1 Hz), 8.33 (1H, d, J = 7.8 Hz), 8.85 (1H, d, J = 4.0 Hz), 9.03 (1H, d, J = 5.2 Hz), 9.31 (1H, s) (DMSO-d6) | 508 |

TABLE 2-continued

| Compound No. | ¹H-NMR | MS [M + 1] |
|---|---|---|
| F124 | 1.31 (3H, d, J = 6.3 Hz), 3.28-3.34 (2H, m), 3.41-3.55 (5H, m), 3.58-3.61 (2H, m), 3.68-3.71 (1H, m), 4.11-4.08 (1H, m), 4.58 (2H, s), 7.03 (1H, s), 7.16 (2H, d, J = 9.0 Hz), 7.89 (2H, d, J = 8.9 Hz), 8.24 (1H, d, J = 5.1 Hz), 8.87 (2H, s), 9.02 (1H, d, J = 5.1 Hz), 9.31 (1H, s) (DMSO-d6) | 460 |
| F125 | 1.32 (3H, d, J = 6.5 Hz), 1.67 (3H, d, J = 7.0 Hz), 3.19-3.38 (1H, m), 3.42-3.51 (5H, m), 3.54-3.62 (2H, m), 3.68-3.71 (1H, m), 4.08-4.12 (1H, m), 4.99 (1H, q, J = 6.9 Hz), 7.03 (1H, s), 7.16 (2H, d, J = 9.0 Hz), 7.89 (2H, d, J = 8.9 Hz), 8.24 (1H, d, J = 5.1 Hz), 8.95 (2H< s), 9.02 (1H, d, J = 5.2 Hz), 9.31 (1H, s) (DMSO-d6) | 474 |
| F126 | 1.32 (2H, t, J = 7.4 Hz), 1.77 (6H, s), 3.29-3.34 (1H, m), 3.42-3.51 (5H, m), 3.54-3.59 (2H, m), 3.68-3.71 (1H, m), 4.09-4.12 (1H, m), 7.03 (1H, s), 7.16 (2H, d, J = 9.0 Hz), 7.89 (2H, d, J = 8.9 Hz), 8.24 (1H, d, J = 3.9 Hz), 9.02 (1H, d, J = 5.0 Hz), 9.11 (2H, s), 9.31 (1H, s) (DMSO-d6) | 488 |
| F127 | 1.32 (3H, d, J = 6.4 Hz), 1.95-2.22 (2H, m), 2.22-2.42 (2H, m), 2.43-2.65 (2H, m), 3.28-3.36 (1H, m), 3.37-3.61 (7H, m), 3.68-3.71 (1H, m), 4.08-4.11 (1H, m), 5.15 (1H, t, J = 7.9 Hz), 7.03 (1H, s), 7.15 (2H, d, J = 9.0 Hz), 7.89 (2H, d, J = 8.9 Hz), 8.24 (1H, d, J = 5.1 Hz), 9.02 (1H, d, J = 5.2 Hz), 9.31 (1H, s) (DMSO-d6) | 500 |
| F128 | 1.31 (3H, d, J = 6.5 Hz), 3.29-3.33 (1H, m), 3.42-3.51 (5H, m), 3.53-3.62 (2H, m), 3.69 (1H, d, J = 12.3 Hz), 4.09-4.11 (1H, m), 5.24 (1H, t, J = 7.3 Hz), 7.03 (1H, s), 7.15 (2H, d, J = 9.0 Hz), 7.52 (1H, s), 7.86 (2H, d, J = 8.9 Hz), 8.24 (1H, d, J = 5.1 Hz), 8.94-9.08 (2H, m), 9.32 (1H, s) (DMSO-d6) | 540 |
| F129 | 1.39 (3H, d, J = 6.4 Hz), 3.39-3.48 (4H, m), 3.57-3.59 (2H, m), 3.61 (3H, s), 3.95-4.10 (1H, m), 7.03 (2H, d, J = 8.8 Hz), 7.38 (1H, s), 7.54-7.62 (3H, m), 8.10 (2H, d, J = 6.9 Hz), 8.17-8.23 (3H, m), 8.89 (1H, d, J = 5.3 Hz), 9.29 (1H, s) (CDCl₃) | 507 |
| F130 | 0.98 (2H, t, J = 7.4 Hz), 1.29 (3H, d, J = 6.4 Hz), 1.80 (2H, m, J = 7.4 Hz), 2.93 (2H, t, J = 7.4 Hz), 3.22-3.29 (1H, m), 3.32-3.59 (7H, m), 3.59-3.72 (1H, m), 3.63-3.66 (1H, m), 4.02-4.18 (1H, m), 6.62 (1H, s), 7.10 (2H, d, J = 9.0 Hz), 7.85 (2H, d, J = 8.9 Hz), 8.00 (1H, dd, J = 6.7, 5.4 Hz), 8.59 (1H, d, J = 5.0 Hz), 8.71 (1H, d, J = 3.0 Hz) (DMSO-d6) | 490 |
| F131 | 1.30 (3H, d, J = 6.5 Hz), 3.24-3.30 (1H, m), 3.38-3.47 (5H, m), 3.48 (3H, s), 3.51-3.54 (2H, m), 3.65-3.68 (1H, m), 4.03-4.06 (1H, m), 4.80 (2H, s), 6.62 (1H, s), 7.12 (2H, d, J = 9.0 Hz), 7.87 (2H, d, J = 8.9 Hz), 8.00 (1H, dd, J = 6.8, 5.1 Hz), 8.59 (1H, d, J = 4.9 Hz), 8.71 (1H, d, J = 3.1 Hz) (DMSO-d6) | 492 |
| F132 | 1.29 (3H, t, J = 6.6 Hz), 1.44 (6H, s), 3.33-3.60 (7H, m), 3.22-3.29 (1H, m), 3.37-3.57 (7H, m), 3.63-3.66 (1H, m), 4.03-4.06 (1H, m), 6.62 (1H, s), 7.10 (2H, d, J = 9.0 Hz), 7.85 (2H, d, J = 8.9 Hz), 7.99 (1H, dd, J = 6.8, 5.2 Hz), 8.59 (1H, d, J = 5.0 Hz), 8.71 (1H, d, J = 3.0 Hz) (DMSO-d6) | 504 |
| F133 | 1.30 (3H, d, J = 6.4 Hz), 3.26-3.32 (1H, m), 3.37-3.44 (2H, m), 3.47 (3H, s), 3.53-3.59 (2H, m), 3.69 (2H, d, J = 12.3 Hz), 4.04-4.06 (1H, m), 6.62 (1H, s), 7.16 (2H, d, J = 9.0 Hz), 7.87-8.04 (3H, m), 8.07-8.14 (2H, m), 8.59 (1H, d, J = 5.1 Hz), 8.72 (1H, d, J = 3.0 Hz), 8.92 (2H, dd, J = 4.5 Hz) (DMSO-d6) | 525 |
| F134 | 1.30 (3H, d, J = 6.5 Hz), 3.26-3.32 (1H, m), 3.37-3.44 (2H, m), 3.47 (3H, s), 3.53-3.59 (2H, m), 3.69 (2H, d, J = 12.3 Hz), 4.04-4.06 (1H, m), 6.62 (1H, s), 7.16 (2H, d, J = 9.0 Hz), 7.73 (1H, dd, J = 7.6 Hz), 7.89-8.05 (3H, m), 8.13 (1H, t, J = 7.8 Hz), 8.33 (1H, d, J = 6.4 Hz), 8.59 (1H, d, J = 4.9 Hz), 8.72 (1H, d, J = 3.1 Hz), 8.85 (1H, d, J = 4.4 Hz) (DMSO-d6) | 525 |
| F135 | 1.29 (1H, d, J = 6.4 Hz), 3.26-3.32 (1H, m), 3.41-3.69 (7H, m), 4.03-4.06 (1H, m), 4.57 (2H, s), 6.62 (1H, s), 7.15 (1H, d, J = 9.0 Hz), 7.88 (1H, d, J = 8.9 Hz), 7.98 (1H, dd, J = 6.7, 5.0 Hz), 8.59 (1H, d, J = 4.9 Hz), 8.71 (1H, d, J = 4.8 Hz), 8.78 (2H, brs) (DMSO-d6) | 477 |
| F136 | 1.30 (3H, d, J = 6.5 Hz), 1.66 (3H, d, J = 7.0 Hz), 3.26-3.31 (1H, m), 3.39-3.44 (2H, m), 3.47 (3H, s), 3.53-3.59 (2H, m), 3.67-3.70 (1H, m), 4.04-4.07 (1H, m), 4.99 (1H, q, J = 6.9 Hz), 6.62 (1H, s), 7.15 (2H, d, J = 9.0 Hz), 7.88 (1H, d, J = 8.9 Hz), 7.99 (1H, dd, J = 6.8, 5.0 Hz), 8.59 (1H, d, J = 4.9 Hz), 8.72 (1H, d, J = 3.2 Hz), 8.93 (2H, brs) (DMSO-d6) | 491 |
| F137 | 1.30 (3H, d, J = 6.4 Hz), 1.76 (6H, s), 3.26-3.32 (2H, m), 3.41-3.44 (2H, m), 3.47 (3H, s), 3.53-3.56 (2H, m), 3.67-3.70 (1H, m), 4.02-4.06 (1H, m), 6.62 (1H, s), 7.15 (1H, d, J = 9.0 Hz), 7.88 (1H, d, J = 9.0 Hz), 7.99 (1H, dd, J = 6.7, 5.0 Hz), 8.59 (1H, d, J = 5.0 Hz), 8.72 (1H, d, J = 3.0 Hz), 9.07 (2H, brs) (DMSO-d6) | 505 |
| F138 | 1.30 (3H, d, J = 6.5 Hz), 1.96-2.22 (2H, m), 2.23-2.41 (2H, m), 2.42-2.62 (2H, m), 3.26-3.31 (1H, m), 3.36-3.39 (2H, m), 3.42-3.46 (2H, m), 3.47 (3H, s), 3.55-3.66 (1H, m), 4.04-4.06 (1H, m), 5.15 (1H, t, J = 7.9 Hz), 6.62 (1H, s), 7.14 (2H, d, J = 9.0 Hz), 7.88 (2H, d, J = 8.9 Hz), 7.99 (1H, dd, J = 6.7, 5.2 Hz), 8.59 (1H, d, J = 5.0 Hz), 8.72 (1H, d, J = 3.0 Hz) (DMSO-d6) | 517 |

TABLE 2-continued

| Compound No. | $^1$H-NMR | MS [M + 1] |
|---|---|---|
| F139 | 1.29 (3H, d, J = 6.4 Hz), 3.26-3.31 (1H, m), 3.38-3.66 (8H, m), 4.03-4.06 (1H, m), 5.23 (1H, t, J = 7.3 Hz), 6.62 (1H, s), 7.14 (2H, d, J = 9.0 Hz), 7.53 (1H, s), 7.86 (2H, d, J = 8.9 Hz), 7.98 (1H, dd, J = 6.8, 5.4 Hz), 8.59 (1H, d, J = 5.9 Hz), 8.72 (1H, d, J = 3.0 Hz), 9.01 (1H, s) (DMSO-d6) | 557 |
| F140 | 1.30 (3H, d, J = 6.4 Hz), 3.26-3.32 (1H, m), 3.41-3.43 (2H, m), 3.47 (3H, s), 3.52-3.59 (2H, m), 3.67-3.70 (1H, m), 4.04-4.07 (1H, m), 6.62 (1H, s), 7.15 (2H, d, J = 9.0 Hz), 7.65-7.68 (2H, m), 7.72-7.76 (1H, m), 7.95 (2H, d, J = 9.0 Hz), 7.99 (1H, d, J = 6.8, 5.3 Hz), 8.18 (2H, d, J = 7.1 Hz), 8.59 (1H, d, J = 4.8 Hz), 8.72 (1H, d, J = 3.0 Hz) (DMSO-d6) | 524 |
| F141 | 1.29 (3H, d, J = 6.4 Hz), 3.26-3.32 (1H, m), 3.38-3.44 (2H, m), 3.47 (3H, s), 3.53-3.57 (2H, m), 3.67-3.70 (1H, m), 4.04-4.07 (1H, m), 6.29 (1H, s), 6.62 (1H, s), 7.52-7.56 (3H, m), 7.60-7.61 (1H, m), 7.62-7.63 (1H, m), 7.88 (1H, d, J = 8.9 Hz), 7.99 (1H, dd, J = 6.7, 5.1 Hz), 8.59 (1H, d, J = 4.9 Hz), 8.72 (1H, d, J = 3.0 Hz), 9.52 (1H, brs) (DMSO-d6) | 553 |
| F142 | 1.30 (3H, d, J = 6.4 Hz), 3.17-3.61 (9H, m), 4.02-4.06 (1H, m), 6.62 (1H, s), 7.12 (2H, d, J = 9.0 Hz), 7.88 (2H, d, J = 8.9 Hz), 7.99 (1H, dd, J = 6.7, 5.4 Hz), 8.11 (2H, brs), 8.59 (1H, d, J = 4.9 Hz), 8.71 (1H, d, J = 3.0 Hz) (DMSO-d6) | 491 |
| F143 | 1.00 (3H, d, J = 6.4 Hz), 1.31 (3H, d, J = 6.5 Hz), 1.80 (2H, m), 2.94 (3H, t, J = 7.4 Hz), 3.20-3.35 (1H, m), 3.38-3.60 (7H, m), 3.65-3.68 (1H, m), 3.98-4.18 (1H, m), 6.98 (1H, s), 7.12 (2H, d, J = 9.0 Hz), 7.86 (2H, d, J = 8.9 Hz), 8.24 (2H, d, J = 6.4 Hz), 8.83 (2H, d, J = 6.3 Hz) (DMSO-d6) | 472 |
| F144 | 1.31 (2H, d, J = 6.4 Hz), 3.26-3.32 (1H, m), 3.39-3.49 (2H, m), 3.43 (3H, s), 3.47 (3H, s), 3.53-3.60 (2H, m), 3.67-3.72 (1H, m), 4.07-4.10 (1H, m), 4.80 (2H, s), 6.99 (1H, s), 7.13 (2H, d, J = 9.0 Hz), 7.88 (2H, d, J = 8.9 Hz), 8.25 (2H, d, J = 6.4 Hz), 8.84 (2H, d, J = 6.3 Hz) (DMSO-d6) | 474 |
| F145 | 1.31 (3H, d, J = 6.4 Hz), 1.41 (9H, s), 3.26-3.30 (1H, s), 3.39-3.42 (2H, m), 3.47 (4H, m), 3.50-3.78 (4H, m), 4.01-4.20 (1H, m), 6.99 (1H, s), 7.11 (2H, d, J = 9.0 Hz), 7.86 (2H, d, J = 8.9 Hz), 8.25 (2H, d, J = 6.4 Hz), 8.84 (2H, d, J = 6.4 Hz) (DMSO-d6) | 486 |
| F146 | 1.32 (3H, d, J = 6.4 Hz), 3.23-3.38 (1H, m), 3.43-3.50 (5H, m), 3.54-3.59 (2H, m), 3.64-3.77 (1H, m), 4.08-4.17 (1H, m), 6.96 (1H, s), 7.17 (2H, d, J = 9.0 Hz), 7.74 (1H, dd, J = 7.2, 4.8 Hz), 7.97 (2H, d, J = 8.9 Hz), 8.12 (1H, dt, J = 7.8, 1.5 Hz), 8.18 (2H, d, J = 6.1 Hz, 2H), 8.33 (1H, d, J = 7.9 Hz), 8.80 (2H, d, J = 6.2 Hz), 8.85 (1H, d, J = 4.4 Hz) (DMSO-d6) | 507 |
| F147 | 1.31 (3H, d, J = 6.4 Hz), 3.28-3.35 (1H, m), 3.41-3.49 (5H, m), 3.53-3.61 (2H, m), 3.68-3.71 (1H, m), 4.07-4.10 (1H, m), 4.58 (2H, s), 6.94 (1H, s), 7.16 (2H, d, J = 9.0 Hz), 7.90 (2H, d, J = 8.7 Hz), 8.15 (2H, d, J = 6.3 Hz), 8.79 (2H, d, J = 6.1 Hz), 8.86 (2H, brs) (DMSO-d6) | 459 |
| F148 | 1.31 (3H, d, J = 6.4 Hz), 1.66 (3H, d, J = 6.1 Hz), 3.28-3.33 (1H, m), 3.37-3.45 (2H, m), 3.47 (3H, s), 3.53-3.60 (2H, m), 3.67-3.70 (1H, m), 4.06-4.09 (1H, m), 4.96-5.04 (1H, m), 6.93 (1H, s), 7.15 (1H, d, J = 9.0 Hz), 7.45 (2H, d, J = 7.4 Hz), 7.89 (2H, d, J = 8.9 Hz), 8.10 (2H, d, J = 6.2 Hz), 8.76 (2H, d, J = 6.2 Hz), 8.88 (2H, brs) (DMSO-d6) | 473 |
| F149 | 1.30 (1H, d, J = 6.4 Hz), 1.76 (6H, s), 3.28-3.33 (1H, m), 3.42-3.49 (5H, m), 3.53-3.57 (2H, m), 3.67-3.70 (1H, m), 4.07-4.10 (1H, m), 6.93 (1H, s), 7.15 (2H, d, J = 9.0 Hz), 7.89 (2H, d, J = 8.9 Hz), 8.11 (2H, d, J = 8.9 Hz), 8.77 (2H, d, J = 6.2 Hz), 9.06 (1H, brs) (DMSO-d6) | 487 |
| F150 | 1.30 (2H, d, J = 6.4 Hz), 1.90-2.20 (2H, m), 2.21-2.38 (2H, m), 2.48-2.56 (2H, m), 3.28-3.47 (6H, m), 2.53-2.57 (2H, m), 3.68-3.71 (1H, m), 4.06-4.10 (1H, m), 5.14 (1H, t, J = 7.9 Hz), 6.94 (1H, s), 7.15 (2H, d, J = 9.0 Hz), 7.89 (2H, d, J = 8.9 Hz), 8.13 (2H, d, J = 6.2 Hz), 8.78 (2H, d, J = 6.2 Hz) (DMSO-d6) | 499 |
| F151 | 1.30 (3H, d, J = 6.5 Hz), 2.69 (1H, s), 3.17-3.37 (1H, m), 3.37-3.63 (11H, m), 3.63-3.79 (1H, m), 3.97-4.15 (1H, m), 5.25 (1H, t, J = 7.4 Hz), 6.94 (1H, s), 7.15 (2H, d, J = 9.0 Hz), 7.54 (1H, s), 7.86 (2h, d, J = 8.9 Hz), 8.12 (2H, d, J = 6.2 Hz), 8.77 (2H, d, J = 6.2 Hz), 9.04 (1H, s) (DMSO-d6) | 539 |
| F152 | 1.32 (2H, d, J = 6.4 Hz), 3.32 (1H, d, J = 9.4 Hz), 3.36-3.64 (7H, m), 3.70 (1H, d, J = 12.2 Hz), 4.02-4.21 (1H, m), 6.98 (1H, s), 7.16 (1H, d, J = 9.0 Hz), 7.70 (2H, td, J = 8.5, 7.2 Hz), 7.96 (1H, d, J = 8.9 Hz), 8.20 (2H, dd, J = 13.7 Hz), 8.82 (1H, d, J = 6.3 Hz) (DMSO-d6) | 506 |
| F153 | 1.30 (1H, d, J = 6.4 Hz), 3.31 (1H, s), 3.38-3.364 (6H, m), 3.64-3.78 (1H, m), 4.07 (1H, s), 6.29 (1H, s), 6.93 (1H, s), 7.16 (1H, d, J = 9.0 Hz), 7.44-7.71 (2H, m), 7.89 (1H, d, J = 8.9 Hz), 8.12 (1H, d, J = 6.2 Hz), 8.77 (1H, d, J = 6.2 Hz), 9.25-9.62 (1H, m) (DMSO-d6) | 535 |

TABLE 2-continued

| Compound No. | $^1$H-NMR | MS [M + 1] |
|---|---|---|
| F154 | 1.30 (1H, d, J = 6.4 Hz), 3.31 (1H, s), 3.38-3.64 (6H, m), 3.64-3.78 (1H, m), 4.07 (1H, s), 6.29 (1H, s), 6.93 (1H, s), 7.16 (1H, d, J = 9.0 Hz), 7.44-7.71 (2H, m), 7.89 (1H, d, J = 8.9 Hz), 8.12 (1H, d, J = 6.2 Hz), 8.77 (1H, d, J = 6.2 Hz), 9.25-9.62 (1H, m) (DMSO-d6) | 473 |
| F155 | 1.32 (3H, d, J = 6.4 Hz), 3.29-3.34 (1H, m), 3.42-3.56 (5H, m), 3.57-3.62 (2H, m), 3.70-3.73 (1H, m), 4.09-4.12 (1H, m), 7.00 (1H, s), 7.17 (2H, d, J = 9.0 Hz), 7.96 (2H, d, J = 8.9 Hz), 8.10 (2H, d, J = 6.1 Hz), 8.29 (2H, t, J = 11.1 Hz), 8.85 (2H, d, J = 6.3 Hz), 8.92 (2H, d, J = 6.0 Hz) (DMSO-d6) | 507 |
| F156 | 1.30 (3H, d, J = 6.4 Hz), 3.04-3.10 (1H, m), 3.16-3.20 (1H, m), 3.26-3.30 (1H, m), 3.37-3.42 (1H, m), 3.46 (3H, s), 3.49-3.55 (2H, m), 4.02-4.05 (1H, m), 4.25 (1H, dd, J = 1.8, 7.9 Hz), 6.34-6.36 (1H, m), 6.43 (1H, dd, J = 1.8, 7.9 Hz), 6.98-7.03 (2H, m), 8.24 (2H, d, J = 6.1 Hz), 8.83 (2H, d, J = 6.1 Hz) (DMSO-d6) | 492 |
| F157 | 1.30 (3H, d, J = 6.4 Hz), 3.04-3.10 (1H, m), 3.16-3.20 (1H, m), 3.26-3.30 (1H, m), 3.37-3.42 (1H, m), 3.46 (3H, s), 3.49-3.55 (2H, m), 4.02-4.05 (1H, m), 4.25 (1H, dd, J = 1.8, 7.9 Hz), 6.34-6.36 (1H, m), 6.43 (1H, dd, J = 1.8, 7.9 Hz), 6.98-7.03 (2H, m), 8.24 (2H, d, J = 6.1 Hz), 8.83 (2H, d, J = 6.1 Hz) (DMSO-d6) | 378 |
| F158 | 1.41 (3H, d. J = 6.6 Hz), 3.18-3.42 (4H, m), 3.46 (3H, s), 4.12-4.14 (1H, m), 6.99 (1H, s), 7.15 (1H, t, J = 7.4 Hz), 7.24 (1H, d, J = 8.3 Hz), 7.62-7.66 (1H, m), 7.74-7.76 (1H, m), 8.26 (2H, d, J = 6.3 Hz), 8.83 (2H, d, J = 6.3 Hz) (DMSO-d6) | 387 |
| F159 | 1.31 (3H, d, J = 6.4 Hz), 3.23-3.29 (1H, m), 3.37-3.41 (1H, m), 3.45 (1H, s), 3.48-3.68 (4H, m), 4.05-4.08 (1H, m), 6.99 (1H, s), 8.24-8.25 (2H, m), 8.57 (2H, s), 8.62 (1H, s), 8.84 (2H, d, J = 6.2 Hz) (DMSO-d6) | 364 |
| F160 | 1.26 (3H, d, J = 6.4 Hz), 3.47 (3H, s), 3.51-3.56 (3H, m), 3.67-3.72 (1H, m), 3.87-3.92 (1H, m), 4.01-4.04 (1H, m), 4.13-4.17 (1H, m), 6.87 (1H, t, J = 6.3 Hz), 6.99 (1H, s), 7.26 (1H, d, J = 9.0 Hz), 7.85-7.89 (1H, m), 8.10-8.12 (1H, m), 8.23 (2H, d, J = 6.4 Hz), 8.84 (2H, d, J = 6.4 Hz) (DMSO-d6) | 363 |

Experiment 1

Inhibitory Activity of the Medicament of the Present Invention Against P-GS1 Phosphorylation by Bovine Cerebral TPK1

A mixture containing 100 mM MES-sodium hydroxide (pH 6.5), 1 mM magnesium acetate, 0.5 mM EGTA, 5 mM β-mercaptoethanol, 0.02% Tween 20, 10% glycerol, 12 μg/ml P-GS1, 41.7 μM [γ-$^{32}$P] ATP (68 kBq/ml), bovine cerebral TPK1 and a compound shown in Table (a final mixture contained 1.7% DMSO deriving from a solution of a test compound prepared in the presence of 10% DMSO) was used as a reaction system. The phosphorylation was started by adding ATP, and the reaction was conducted at 25° C. for 2 hours, and then stopped by adding 21% perchloric acid on ice cooling. The reaction mixture was centrifuged at 12,000 rpm for 5 minutes and adsorbed on P81 paper (Whatmann), and then the paper was washed four times with 75 mM phosphoric acid, three times with water and once with acetone. The paper was dried, and the residual radioactivity was measured using a liquid scintillation counter. The results are shown in the table below. The test compound markedly inhibited the P-GS1 phosphorylation by TPK1. The results strongly suggest that the medicaments of the present invention inhibit the TPK1 activity, thereby suppress the Aβ neurotoxicity and the PHF formation, and that the medicaments of the present invention are effective for preventive and/or therapeutic treatment of Alzheimer disease and the above-mentioned diseases.

TABLE 3

| Compound No. | IC$_{50}$ (nM) |
|---|---|
| B6 | 1.7 |
| B9 | 1.2 |
| B16 | 2.8 |
| B20 | 1.1 |
| B37 | 1.5 |
| B46 | 2.5 |
| B62 | 7 |
| B69 | 4 |
| B77 | 9.8 |
| B109 | 14 |
| D16 | 14 |
| D42 | 7.9 |
| D95 | 5.6 |
| F24 | 1.4 |
| F56 | 2.2 |
| F69 | 2.4 |
| F148 | 2.6 |

Experiment 2

Inhibitory Activity on Tau Phosphorylation In Vivo

Test compound was administered to male CD-1 mice of 5-6 weeks weighing 25-35 g (Charles River Japan, inc.) at 1, 3, 10, 30 mg/kg p.o. (0.5% Tween/H$_2$O suspension) and after 1 h, mice were decapitated and cortex was promptly removed, followed by being frozen in liquid N2. Cortex was directly homogenized with 2.3% SDS homogenization buffer (62.5 mM Tris-HCl, 2.3% SDS, 1 mM each of EDTA, EGTA and DTT, protease inhibitor cocktail (sigma P2714) containing 0.2 μM 4-(2-Aminoethyl)benzenesulfonyl fluoride (AEBSF), 13 μM bestatin, 1.4 μM E-64, 0.1 mM leupeptin, 30 nM aprotinin, pH 6.8) and centrifuged at 15000×g for 15 min at 4° C. Protein concentrations were determined using DC protein assay kit (BIO-RAD). Supernatants were diluted with sample buffer (62.5 mM Tris-HCl, 25% glycerol, 2% SDS, 0.01% Bromophenol Blue, pH6.8) to adjust the protein concentrations around 0.5-2 mg/mg and then boiled for 5 min. 10 µg of samples were applied on 10% SDS-PAGE mini slab gels and transferred onto PVDF membranes. Membranes were incubated with PBS containing 5% non-fat milk for 1 h at r.t. and then probed with pS396 anti-body (BIOSOURCE) over night at 4° C. Anti-rabbit IgG HRP-conjugated anti-body (Promega) was used as secondary anti-body. Membranes were visualized by ECL kit (Amerasham Bioscience) and detected by LAS1000 (Fuji Photo Film).

Solubility Example (1). Preparation
1-1. The First Solution Prescribed in Degradation Test Method of Japanese Pharmacopoeia 14 (JP-14)
To 2.0 g of sodium chloride, 7.0 mL of hydrochloric acid and water were added and the solution was adjusted to 1000 mL. This solution was clear and colorless, with pH of approximately 1.2.
1-2. The Second Solution Prescribed in Degradation Test Method of JP 14
To 250 mL of 0.2 mol/L potassium dihydrogen phosphate test solution, 118 mL of 0.2 mol/L sodium hydroxide test solution and water were added and the solution was adjusted to 1000 mL. This solution was clear and colorless, with pH of approximately 6.8.
1-3. Diluted McIlvaine buffer (pH 4.0)
Disodium hydrogen phosphate solution (0.05 mol/L) and 0.0025 mol/L citric acid solution were mixed and the mixture was adjusted to pH4.0 to prepare a diluted McIlvaine buffer.
3-4. Artificial Intestinal Solutions
Two artificial intestinal fluid formulations were used: fasted-state simulated intestinal fluid (FaSSIF) and fed-state simulated intestinal fluid (FeSSIF) (Pharm. Res., Vol. 15, No. 5, 1998, p 698-705). In order to prepare these solutions, the test reagents were combined as shown in Table 4, the mixture was added with water, and the preparations were homogenized by supersonic vibration. After confirming that the emulsifications were homogeneous, the pH was adjusted by adding 1 mol/L sodium hydroxide solution and the volume of solution was adjusted by adding appropriate amount of water.

TABLE 4

Compositions of simulated intestinal fluid

| FaSSIF | | FeSSIF | |
|---|---|---|---|
| pH | 6.5 | pH | 5 |
| Osmolality | 270 mOsmol | Osmolality | 635 mOsmol |
| Sodium taurocholate | 3 mM | Sodium taurocholate | 15 mM |
| Lecithin | 0.75 mM | Lecithin | 3.75 mM |
| KH2PO4 | 3.9 g | Acetic acid | 8.65 g |
| KCl | 7.7 g | KCl | 15.2 g |
| NaOH | pH 6.5 | NaOH | pH 5.0 |
| Water | 1 L | Water | 1 L |

(2) Determination of the Appropriate Quantitative Measurement Method
For the purpose of rapid qualitative measurement, the rapid analysis method (conditions described in more detail below) using semi-micro columns was developed to produce evenly symmetrical, discrete test compounds peaks separated from solvent shock peaks.

[HPLC conditions]
Detector: Photodiode array
Wavelength: UV235 nm
Column: inertsil ODS-3 5 µm 3.0 mm I.D.×75 mm
Column temperature: 40° C.
Mobile phase: A, 0.1% trifluoroacetic acid solution
B, 0.1% trifluoroacetic acid/acetonitrile solution
A:B=65:35 (isocratic elution)
Flow rate: 0.50 mL/min
Injection volume: 5 µL
(3) Determination of the Appropriate Solubility Measurement Method
After the potential of test material to be adsorbed on various type of filters was examined, solubility measurements were conducted by removing insoluble components by filtration.
(4) Measurement Procedures of Sample Solubility to JP-14 First Solution, JP-14 Second Solution, McIlvaine Buffer (pH=4.0), Water, and Artificial Intestinal Fluids (Fasted-State and Fed-State)
The test liquid (70 mL) was added to a 200 mL conical flask which was warmed to 37° C. in water bath. Approximately 70 mg of each test material was directly added to the flask, dispersed by supersonic vibration for 5 minutes, then stirred at approximately 600 rpm (confirmed by tachometer readings) using a magnetic stir rod of approximately 5 cm long. At the pre-determined sampling times after the solubility measurement started, 5 mL of the test solution was taken and filtered through the membrane filter (DISMIC-25HP) having a pore size of 0.45 µm or less. 500 µL of the filtered solution was precisely measured after the initial 2.0 mL was discarded. Acetonitrile of 500 µL was precisely measured and added to this filtered solution to make a test solution for HPLC.
Separately, approximately 5 mg of the test compound was weighed precisely and the solvent such as acetonitrile or 50% acetonitrile/water solution was added to make a standard solution in a concentration of approximately 50 µg/mL. Peak areas of $A_T$ and $A_S$ were measured by the liquid chromatography under the conditions above-mentioned for 5 µL aliquots of the test solution and the standard solution, respectively, and, from which the solubility of test materials was determined using a one-point standard calibration method.

Formulation Example (1) Tablets
The ingredients below were mixed by an ordinary method and compressed by using a conventional apparatus.

| Compound of Example 1 | 30 mg |
|---|---|
| Crystalline cellulose | 60 mg |
| Corn starch | 100 mg |
| Lactose | 200 mg |
| Magnesium stearate | 4 mg |

(2) Soft Capsules
The ingredients below were mixed by an ordinary method and filled in soft capsules.

| Compound of Example 1 | 30 mg |
|---|---|
| Olive oil | 300 mg |
| Lecithin | 20 mg |

Industrial Applicability

The compounds of the present invention have TPK1 inhibitory activity and are useful as an active ingredient of a medicament for preventive and/or therapeutic treatment of diseases caused by abnormal advance of TPK1 such as neurodegenerative diseases (e.g. Alzheimer disease) and the above-mentioned diseases.

The invention claimed is:

1. A compound represented by the formula (I), an optically active isomer thereof, or a pharmaceutically acceptable salt thereof:

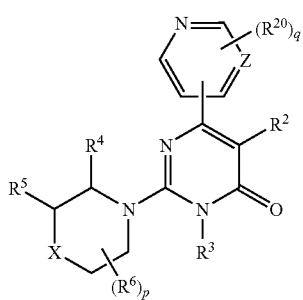

(I)

wherein each symbol is defined as below:
 $R^4$ represents a group represented by the following formula (II):

wherein
 $A^{14}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, or a heterocyclic group which may be substituted;
 $A^{13}$ represents bond, or oxygen atom;
 $A^{12}$ represents bond, or a $C_1$-$C_3$ methylene group, and $A^{14}$ and $A^{13}$ may combine to each other to form a 5 to 7 membered heterocyclic ring;
 X represents oxygen atom;
 $R^5$ represents a hydrogen atom, a $C_1$-$C_6$ alkyl group which may be substituted, or a group represented by the following formula (IV):

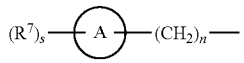

(IV)

wherein n represents 0 or integer of 1 to 3,
A represents a $C_6$-$C_{10}$ aryl group,
 $R^7$ may be the same or different and represents a halogen atom, or a group represented by the following formula (IV-a):

(IV-a)

wherein $C^4$ represents hydrogen atom (except when all of $C^3$, $C^2$, and $C^1$ represent bond), a $C_1$-$C_6$ alkyl group which may be substituted, a $C_6$-$C_{10}$ aryl group which may be substituted, a heterocyclic group which may be substituted,
 $C^3$ represents bond, or oxygen atom,
 $C^2$ represents bond, or C=O,
 $C^1$ represents bond;

s represents 0 or an integer of 1 to 5,
 $R^6$ may be the same or different and represents a halogen atom, nitro group, cyano group, or a group represented by the following formula (V):

(V)

wherein $B^{14}$ represents hydrogen atom(except when all of $B^{13}$, $B^{12}$, and $B^{11}$ represent bond), a $C_1$-$C_6$ alkyl group which may be substituted, a heterocyclic group which may be substituted,
 $B^{13}$ represents bond,
 $B^{12}$ represents bond,
 $B^{11}$ represents bond;
p represents an integer of 0 to 6;
Z represents nitrogen atom, C—H or C—$R^{20}$;
 $R^{20}$ may be the same or different and represents a halogen atom, or a group represented by the following formula (VI):

(VI)

wherein $D^4$ represents a $C_1$-$C_6$ alkyl group which may be substituted,
 $D^3$ represents bond, or oxygen atom,
 $D^2$ represents bond,
 $D^1$ represents bond,
q represents 0 or an integer of 1 to 3;
 $R^2$ represents hydrogen atom, a halogen atom or a $C_1$-$C_6$ alkyl group which may be ubstituted;
 $R^3$ represents a $C_1$-$C_{12}$ alkyl group;
any one or more of $R^5$ and $R^6$, $R^5$ and $R^4$, $R^6$ and $R^4$, and $R^6$ and $R^6$ may combine to each other to form a fused, carbocyclic or heterocyclic ring, together with the ring which contains X, and $R^5$, $R^4$ and $R^6$ bind to;
and each symbol satisfies the following proviso (1):
(1) when $R^4$ is a hydrogen atom, at least one of $R^5$ and $R^6$, and $R^6$ and $R^6$ combine to each other to form a fused carbocyclic or heterocyclic ring, together with the ring which contains X, and $R^5$, $R^4$ and $R^6$ bind to.

2. The compound, an optically active isomer thereof, or a pharmaceutical acceptable salt thereof according to claim 1, wherein the formula (VI), (V), and (IV-a) each independently represents a group represented by the following formula (IIa):

(IIa)

$R^{20b}$ represents hydrogen atom(except when $Q^{20a}$ represents bond), a $C_1$-$C_{12}$ alkyl group, a $C_6$-$C_{10}$ aryl-$C_1$-$C_{12}$ alkyl group, and each of said groups may be substituted with a halogen atom, cyano group, nitro group, hydroxyl group, a $C_1$-$C_{12}$ alkyloxy, a $C_6$-$C_{10}$ aryloxy, amino group, a $C_1$-$C_{12}$ alkylamino group, a $C_3$-$C_{12}$ cycloalkylamino group, a di($C_1$-$C_{12}$ alkyl) amino group, or a heterocyclic group;
 $Q^{20a}$ represents bond, or oxygen atom;
X is oxygen atom;
n in the formula (IV) is 0 or 1;
A in the formula (IV) is phenyl group, naphthyl group, a heteroaryl group; and
when any one or more of $R^5$ and $R^6$, $R^5$ and $R^4$, $R^6$ and $R^4$, and $R^6$ and $R^6$ combine to each other to form a fused, carbocyclic or heterocyclic ring, together with the ring which contains X, and $R^5$, $R^4$ and $R^6$ bind to, the one or more of $R^5$ and $R^6$, $R^5$ and $R^4$, $R^6$ and $R^4$, and $R^6$ and $R^6$ are a part of an optionally substituted 5 to 7 membered ring optionally containing 1 or 2 hetero atoms selected from the group consisting of nitrogen atoms oxygen atoms and sulfur atoms, and said 5 to 7 membered ring may be substituted and/or be condensed with a $C_6$-$C_{10}$ aryl group which may be substituted or a heterocyclic group which may be substituted.

3. The compound, an optically active isomer thereof, or a pharmaceutical acceptable salt thereof according to claim 1, wherein $R^3$ is methyl group.

4. A compound selected from the group consisting of:
2-((3S)-3-Benzyl-morpholin-4-yl)-1-methyl-1H-[4,4']bipyrimidinyl-6-one;
2-((4aRS,10bRS)-trans-2,3,4a,5,6,10b-Hexahydro-naphtho[1,2-b][1,4]oxazin-4-yl)-3-methyl-6-pyridin-4-yl-3H-pyrimidin-4-one;
6-(3-Fluoro-pyridin-4-yl)-2-((4aRS,10bRS)-trans-2,3,4a,5,6,10b-hexahydro-naphtho [1,2-b][1,4]oxazin-4-yl)-3-methyl-3H-pyrimidin-4-one;
2-((4aRS,10bRS)-trans-3,4,4a,5,6,10b-Hexahydro-2H-naphtho[1,2-b][1,4]oxazin-4-yl) -3-methyl-6-(pyrimidin-4-yl)-3H-pyrimidin-4-one;
2-(8-Methoxy-(4aRS,10bRS)-trans-2,3,4a,5,6,10b-hexahydro-naphtho[1,2-b][1,4]oxazin-4-yl)-3-methyl-6-pyridin-4-yl-3H-pyrimidin-4-one;
6-(3-Fluoro-pyridin-4-yl)-2-(8-methoxy-(4aRS,10bRS)-trans-2,3,4a,5,6,10b-hexahydro-naphtho[1,2-b][1,4]oxazin-4-yl)-3-methyl-3H-pyrimidin-4-one;
2-(8-Methoxy-(4aRS,10bRS)-trans-2,3,4a,5,6,10b-hexahydro-naphtho[1,2-b][1,4]oxazin-4-yl)-1-methyl-1H-[4,4']bipyrimidinyl-6-one;
2-(7-Methoxy-(4aRS,10bRS)-trans-2,3,4a,5,6,10b-hexahydro-naphtho[1,2-b][1,4]oxazin-4-yl)-3-methyl-6-pyridin-4-yl-3H-pyrimidin-4-one;
6-(3-Fluoro-pyridin-4-yl)-2-(7-methoxy-(4aRS,10bRS)-trans-2,3,4a,5,6,10b-hexahydro-naphtho[1,2-b][1,4]oxazin-4-yl)-3-methyl-3H-pyrimidin-4-one;
2-(7-Methoxy-(4aRS,10bRS)-trans-2,3,4a,5,6,10b-hexahydro-naphtho[1,2-b][1,4]oxazin-4-yl)-1-methyl-1H-[4,4']bipyrimidinyl-6-one;
2-(9-Methoxy-(4aRS,10bRS)-trans-2,3,4a,5,6,10b-hexahydro-naphtho[1,2-b][1,4]oxazin-4-yl)-3-methyl-6-pyridin-4-yl-3H-pyrimidin-4-one;
6-(3-Fluoro-pyridin-4-yl)-2-(9-methoxy-(4aRS,10bRS)-trans-2,3,4a,5,6,10b-hexahydro-naphtho[1,2-b][1,4]oxazin-4-yl)-3-methyl-3H-pyrimidin-4-one,
2-(9-Methoxy-(4aRS,10bRS)-trans-2,3,4a,5,6,10b-hexahydro-naphtho[1,2-b][1,4]oxazin-4-yl)-1-methyl-1H-[4,4']bipyrimidinyl-6-one;
2-((4aRS,10bSR)-cis-2,3,4a,5,6,10b-Hexahydro-naphtho[1,2-b][1,4]oxazin-4-yl)-3-methyl-6-pyridin-4-yl-3H-pyrimidin-4-one;
6-(3-Fluoro-pyridin-4-yl)-2-((4aRS,10bSR)-cis-2,3,4a,5,6,10b-hexahydro-naphtho[1,2-b][1,4]oxazin-4-yl)-3-methyl-3H-pyrimidin-4-one;
2-((4aRS,10bSR)-cis-2,3,4a,5,6,10b-Hexahydro-naphtho[1,2-b][1,4]oxazin-4-yl)-1-methyl-1H-[4,4']bipyrimidinyl-6-one;
6-(3-Fluoro-pyridin-4-yl)-3-methyl-2-((4aRS,10bRS)-trans-2,3,10,10a-tetrahydro-4aH-4,9-dioxa-1-aza-phenanthren-1-yl)-3H-pyrimidin-4-one;
6-(3-Fluoro-pyridin-4-yl)-2-(8-methoxy-(4aRS,10bSR)-cis-2,3,4a,5,6,10b-hexahydro-naphtho[1,2-b][1,4]oxazin-4-yl)-3-methyl-3H-pyrimidin-4-one;
6-(3-Fluoro-pyridin-4-yl)-2-(6-methoxy-(4aRS,10aRS)-trans-2,3,10,10a-tetrahydro-4aH-4,9-dioxa-1-aza-phenanthren-1-yl)-3-methyl-3H-pyrimidin-4-one;
2-(9-Methoxy-(4aRS,10bSR)-cis-2,3,4a,5,6,10b-hexahydro-naphtho[1,2-b][1,4]oxazin-4-yl)-3-methyl-6-pyridin-4-yl-3H-pyrimidin-4-one;
6-(3-Fluoro-pyridin-4-yl)-2-(9-methoxy-(4aRS,10bSR)-cis-2,3,4a,5,6,10b-hexahydro-naphtho[1,2-b][1,4]oxazin-4-yl)-3-methyl-3H-pyrimidin-4-one;
2-(9-Methoxy-(4aRS,10bSR)-cis-2,3,4a,5,6,10b-hexahydro-naphtho[1,2-b][1,4]oxazin-4-yl)-1-methyl-1H-[4,4']bipyrimidinyl-6-one;
2-(7-Methoxy-(4aRS,10bSR)-cis-2,3,4a,5,6,10b-hexahydro-naphtho[1,2-b][1,4]oxazin-4-yl)-3-methyl-6-pyridin-4-yl-3H-pyrimidin-4-one;
6-(3-Fluoro-pyridin-4-yl)-2-(7-methoxy-(4aRS,10bSR)-cis-2,3,4a,5,6,10b-hexahydro-naphtho[1,2-b][1,4]oxazin-4-yl)-3-methyl-3H-pyrimidin-4-one;
2-(7-Methoxy-(4aRS,10bSR)-cis-2,3,4a,5,6,10b-hexahydro-naphtho[1,2-b][1,4]oxazin-4-yl)-1-methyl-1H-[4,4']bipyrimidinyl-6-one;
3-Methyl-6-pyridin-4-yl-2-((4aRS,10aRS)-cis-2,3,10,10a-tetrahydro-4aH-4,9-dioxa-1-aza-phenanthren-1-yl)-3H-pyrimidin-4-one;
6-(3-Fluoro-pyridin-4-yl)-3-methyl-2-((4aRS,10aRS)-cis-2,3,10,10a-tetrahydro-4aH-4,9-dioxa-1-aza-phenanthren-1-yl)-3H-pyrimidin-4-one;
1-Methyl-2-((4aRS,10aRS)-cis-2,3,10,10a-tetrahydro-4aH-4,9-dioxa-1-aza-phenanthren-1-yl)-1H-[4,4']bipyrimidinyl-6-one;
6-(3-Fluoro-pyridin-4-yl)-2-(6-methoxy-(4aRS,10aRS)-cis-2,3,10,10a-tetrahydro-4aH-4,9-dioxa-1-aza-phenanthren-1-yl)-3-methyl-3H-pyrimidin-4-one;
2-(6-Methoxy-(4aRS,10aRS)-cis-2,3,10,10a-tetrahydro-4aH-4,9-dioxa-1-aza-phenanthren-1-yl)-1-methyl-1H-[4,4']bipyrimidinyl-6-one;
2-(9-Fluoro-(4aRS,10bRS)-trans-2,3,4a,5,6,10b-hexahydro-naphtho[1,2-b][1,4]oxazin-4-yl)-3-methyl-6-pyridin-4-yl-3H-pyrimidin-4-one;
2-(9-Fluoro-(4aRS,10bRS)-trans-2,3,4a,5,6,10b-hexahydro-naphtho[1,2-b][1,4]oxazin-4-yl)-6-(3-fluoro-pyridin-4-yl)-3-methyl-3H-pyrimidin-4-one;
2-(9-Fluoro-(4aRS,10bRS)-trans-2,3,4a,5,6,10b-hexahydro-naphtho[1,2-b][1,4]oxazin-4-yl)-1-methyl-1H-[4,4']bipyrimidinyl-6-one;
2-(9-Fluoro-(4aRS,10bSR)-cis-2,3,4a,5,6,10b-hexahydro-naphtho[1,2-b][1,4]oxazin-4-yl)-3-methyl-6-pyridin-4-yl-3H-pyrimidin-4-one;
2-(9-Fluoro-(4aRS,10bSR)-cis-2,3,4a,5,6,10b-hexahydro-naphtho[1,2-b][1,4]oxazin-4-yl)-6-(3-fluoro-pyridin-4-yl)-3-methyl-3H-pyrimidin-4-one;
2-(9-Fluoro-(4aRS,10bSR)-cis-2,3,4a,5,6,10b-hexahydro-naphtho[1,2-b][1,4]oxazin-4-yl)-1-methyl-1H-[4,4']bipyrimidinyl-6-one;
3-Methyl-2-((3R)-3-methyl-morpholin-4-yl)-6-pyridin-4-yl-3H-pyrimidin-4-one;
6-(3-Fluoro-pyridin-4-yl)-3-methyl-2-((3R)-3-methyl-morpholin-4-yl)-3H-pyrimidin-4-one;
1-Methyl-2-((3R)-3-methyl-morpholin-4-yl)-1H-[4,4']bipyrimidinyl-6-one;
6-(3-Fluoro-pyridin-4-yl)-3-methyl-2-((3S)-3-methyl-morpholin-4-yl)-3H-pyrimidin-4-one;
3-Methyl-2-((4aRS,8aRS)-trans-octahydro-benzo[1,4]oxazin-4-yl)-6-pyridin-4-yl-3H-pyrimidin-4-one;
6-(3-Fluoro-pyridin-4-yl)-3-methyl-2-((4aRS,8aRS)-trans-octahydro-benzo[1,4]oxazin-4-yl)-3H-pyrimidin-4-one;
1-Methyl-2-((4aRS,8aRS)-trans-octahydro-benzo[1,4]oxazin-4-yl)-1H-[4,4']bipyrimidinyl-6-one;
2-((3R)-3-Ethyl-morpholin-4-yl)-6-(3-fluoro-pyridin-4-yl)-3-methyl-3H-pyrimidin-4-one;
2-((3R)-3-Ethyl-morpholin-4-yl)-1-methyl-1H-[4,4']bipyrimidinyl-6-one;

6-(3-Fluoro-pyridin-4-yl)-2-((3R)-3-isopropyl-morpholin-4-yl)-3-methyl-3H-pyrimidin-4-one; and 6-(3-Fluoro-pyridin-4-yl)-2-((3R)-3-isobutyl-morpholin-4-yl)-3-methyl-3H-pyrimidin-4-one; and an optically active isomer thereof, or a pharmaceutically acceptable salt thereof.

5. A medicament composition comprising as an active ingredient a substance selected from the compound represented by the formula (I), an optically active isomer thereof, or a pharmaceutically acceptable salt thereof according to claim 1.

6. A tau protein kinase 1 inhibitor composition comprising as an active ingredient a substance selected from the compound represented by the formula (I), an optically active isomer thereof, or a pharmaceutically acceptable salt thereof according to claim 1.

7. A medicament composition comprising as an active ingredient the compound according to claim 4, an optically active isomer thereof, or a pharmaceutically acceptable salt thereof.

8. A tau protein kinase 1 inhibitor composition comprising as an active ingredient the compound according to claim 4, an optically active isomer thereof, or a pharmaceutically acceptable salt thereof.

\* \* \* \* \*

UNITED STATES PATENT AND TRADEMARK OFFICE
CERTIFICATE OF CORRECTION

PATENT NO. : 8,569,294 B2  Page 1 of 1
APPLICATION NO. : 12/282396
DATED : October 29, 2013
INVENTOR(S) : Fukunaga et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1032 days.

Signed and Sealed this
Twenty-second Day of September, 2015

Michelle K. Lee
*Director of the United States Patent and Trademark Office*